United States Patent
Mita et al.

(10) Patent No.: US 7,947,715 B2
(45) Date of Patent: May 24, 2011

(54) ISOXAZOLINE COMPOUND AND PESTICIDE

(75) Inventors: Takeshi Mita, Funabashi (JP);
Kazushige Maeda, Funabashi (JP);
Mitsuaki Komoda, Minamisaitama-gun (JP); Eitatsu Ikeda, Funabashi (JP);
Ken-ichi Toyama, Funabashi (JP);
Motoyoshi Iwasa, Funabashi (JP)

(73) Assignee: Nissan Chemical Industries, Ltd., Tokyo (JP)

( * ) Notice: Subject to any disclaimer, the term of this patent is extended or adjusted under 35 U.S.C. 154(b) by 0 days.

(21) Appl. No.: 12/230,780

(22) Filed: Sep. 4, 2008

(65) Prior Publication Data

US 2009/0156643 A1 Jun. 18, 2009

Related U.S. Application Data

(63) Continuation-in-part of application No. PCT/JP2007/055325, filed on Mar. 12, 2007.

(30) Foreign Application Priority Data

Mar. 10, 2006 (JP) .................. 2006-065097

(51) Int. Cl.
*A01N 43/40* (2006.01)
(52) U.S. Cl. ...... 514/340; 514/378; 548/240; 546/272.1
(58) Field of Classification Search ........... 514/340, 514/378; 548/240; 546/272.1
See application file for complete search history.

(56) References Cited

FOREIGN PATENT DOCUMENTS

| WO | WO 95/24398 A1 | 9/1995 |
|---|---|---|
| WO | WO 97/23212 A1 | 7/1997 |
| WO | WO 97/48395 A1 | 12/1997 |
| WO | WO 99/14210 A1 | 3/1999 |
| WO | WO 2004/018410 A1 | 3/2004 |
| WO | WO 2005/051932 | * 6/2005 |
| WO | WO 2005/085216 A1 | 9/2005 |
| WO | WO 2007/026965 | * 3/2007 |
| WO | WO 2008/122375 | 10/2008 |

OTHER PUBLICATIONS

Raw machine translaiton of WO 2005/051932.*
Kawase et al.; "Chemistry of Amine-Boranes. Part 5. Reduction of Oximes, *O*-Acyl-oximes, and *O*-Alkyl-oximes with Pyridine-Borane in Acid;" *J. Chem. Soc.*; 1979; pp. 643-645.

* cited by examiner

*Primary Examiner* — Yong Chu
*Assistant Examiner* — Valerie Rodriguez-Garcia
(74) *Attorney, Agent, or Firm* — Oliff & Berridge, PLC

(57) ABSTRACT

There is provided a novel pesticide, particularly an insecticide or an acaricide. A substituted isoxazoline compound of formula (1) or a salt thereof:

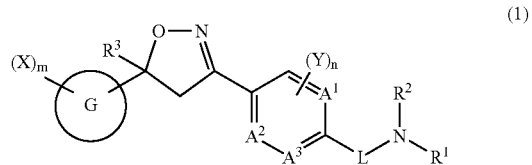

(1)

wherein $A^1$, $A^2$ and $A^3$ independently of one another are carbon atom or nitrogen atom, G is benzene ring, etc., L is $-CH_2-$, $-C(CH_3)-$, $-CH(CN)-$, etc., X is halogen atom, $C_1$-$C_6$haloalkyl, etc., Y is halogen atom, $C_1$-$C_6$alkyl, etc., $R^1$ is $-C(O)R^{1a}$, $-C(O)OR^{1a}$, $-C(O)NHR^{1a}$, etc., $R^2$ is hydrogen atom, $C_1$-$C_6$haloalkyl, $-C_1$-$C_4$alkoxy $C_1$-$C_4$alkyl, cyano $C_1$-$C_6$alkyl, $C_3$-$C_6$alkenyl, $C_3$-$C_6$alkynyl, $-C(O)R^{15}$, $-C(O)OR^{15}$, etc., $R^3$ is $C_1$-$C_6$haloalkyl, etc., m is an integer of 0 to 5, n is an integer of 0 to 4. The pesticide containing these compounds.

9 Claims, No Drawings

ISOXAZOLINE COMPOUND AND PESTICIDE

TECHNICAL FIELD

The present invention relates to a novel substituted isoxazoline compound and the salt thereof, and a pesticide characterized by containing the compound as an active ingredient. The pesticide in the present invention means a pest controlling agent applied for harmful arthropods in agricultural and horticultural field or livestock farming and hygienic field (endo-parasiticides and ecto-parasiticides for mammals or birds as domestic animals or pets, or hygienic pest- or unpleasant pest-controlling agents for domestic or business use). In addition, agricultural chemicals in the present invention mean insecticides, acaricides, nematicides, herbicides and fungicides, and the like in agricultural and horticultural field.

BACKGROUND ART

Conventionally, as to substituted isoxazoline compounds, it is known that 4-(5-substituted-5-substituted aryl-4,5-dihydroisoxazol-3-yl)benzamide compounds show pesticidal activity, particularly insecticidal and acaricidal activity (see, Patent Document 1). However, there is no disclosure on substituted 4-(5-substituted-5-substituted aryl-4,5-dihydroisoxazol-3-yl)benzyl amine compounds according to the present invention.

In addition, it is known that 3-(5-substituted carbamoylmethyl-5-substituted alkyl-4,5-dihydroisoxazol-3-yl)benzyl amine derivatives have platelet glycoprotein IIb/IIIa fibrinogen receptor complex competitive activity or factor Xa inhibition activity or the like, and can be used as a thrombolysis agent or a therapeutic agent of thrombo-embolic disorder (see, for example Patent Documents 2 and 3). Further, it is known that other specific substituted isoxazoline compound can be used as a production intermediate of HIV protease inhibitors or as a production intermediate of insecticides (see, for example Patent Documents 4 and 5). However, there is no disclosure on substituted 4-(5-substituted-5-substituted aryl-4,5-dihydroisoxazol-3-yl)benzyl amine compounds according to the present invention, and further the usefulness thereof as a pesticide is not known at all.

On the other hand, as to substituted benzaldoxime compounds, 4-alkoxy substituted benzaldoxime derivatives (see, Patent Document 6) and 4-hydroxyiminomethyl-N,N-dimethyl benzamide (see, Non-patent Document 1) and the like are known. However, 4-(substituted aminoalkyl) substituted benzaldoxime derivatives that can be used as a production intermediate of the pesticides according to the present invention are not described in any documents and thus novel compounds.

Patent Document 1: WO 2005/085216 Pamphlet
Patent Document 2: WO 97/023212 Pamphlet
Patent Document 3: WO 97/048395 Pamphlet
Patent Document 4: WO 99/014210 Pamphlet
Patent Document 5: WO 2004/018410 Pamphlet
Patent Document 6: WO 95/024398 Pamphlet
Non-patent Document 1: J. Chem. Soc. Perkin Trans. 1, 1979, p. 643

DISCLOSURE OF INVENTION

Problems to be Solved by the Invention

The development of pesticides for controlling several pests such as agricultural and horticultural pests, forestall pests, or hygienic pests, etc. expands, and a number of different agents have been practically utilized to the present.

However, recently, pests acquire resistance by the use of pesticides such as insecticides or fungicides over long term, and thus control by the insecticides or fungicides that have been conventionally used becomes difficult. In addition, a part of known pesticides has a high toxicity, or some of them start to disturb native ecosystems due to long-term persistency. Under the circumstances, it is expected all the time to develop a novel pesticide having not only a high pest controlling activity but also a low toxicity and a low persistency.

Means for Solving the Problems

The inventors have eagerly investigated in order to solve the above-mentioned problems, and as a result of it, they found that novel substituted isoxazoline compounds of formula (I) are extremely useful compounds having excellent pest controlling activity, particularly insecticidal activity and acaricidal activity, and having little adverse affect on non-targeted beings such as mammals, fishes and useful insects, etc. Thus, the present invention has been accomplished.

That is, the present invention relates to the following aspects (1) to (10):
(1) A substituted isoxazoline compound of formula (1) or a salt thereof:

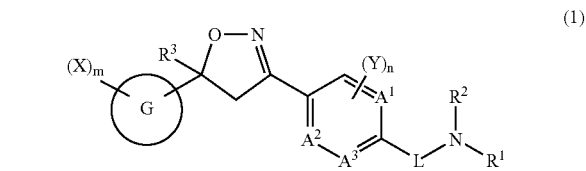

(1)

wherein $A^1$, $A^2$ and $A^3$ independently of one another are carbon atom or nitrogen atom, G is benzene ring, nitrogen-containing 6-membered aromatic heterocyclic ring, furan ring, thiophene ring, or 5-membered aromatic heterocyclic ring containing two or more hetero atoms selected from oxygen atom, sulfur atom and nitrogen atom, L is —C($R^{2a}$)($R^{2b}$)—, —N($R^{2c}$)—, —C($R^{2a}$)($R^{2b}$)CH$_2$—, —C($R^{2a}$)($R^{2b}$)N($R^{2c}$)— or —CH$_2$C($R^{2a}$)($R^{2b}$)—, X is halogen atom, cyano, nitro, azido, —SCN, —SF$_5$, C$_1$-C$_6$alkyl, C$_1$-C$_6$alkyl arbitrarily substituted with $R^4$, C$_3$-C$_8$cycloalkyl, C$_3$-C$_8$cycloalkyl arbitrarily substituted with $R^4$, E-1 to E-49, C$_2$-C$_6$alkenyl, C$_2$-C$_6$alkenyl arbitrarily substituted with $R^4$, C$_3$-C$_8$cycloalkenyl, C$_3$-C$_8$halocycloalkenyl, C$_2$-C$_6$alkynyl, C$_2$-C$_6$alkynyl arbitrarily substituted with $R^4$, —OH, —O$R^5$, —OSO$_2R^5$, —SH, —S(O)$_rR^5$, —NH$_2$, —N($R^7$)$R^6$, —N=CHO$R^8$, —N=C($R^9$)O$R^8$, —CHO, —C(O)$R^9$, —C(O)O$R^9$, —C(O)S$R^9$, —C(O)NH$_2$, —C(O)N($R^{10}$)$R^9$, —C(S)O$R^9$, —C(S)S$R^9$, —C(S)NH$_2$, —C(S)N($R^{10}$)$R^9$, —CH=NO$R^{11}$, —C($R^9$)=NO$R^{11}$, M-5, M-20, M-40 to M-43, M-46 to M-48, —S(O)$_2$O$R^9$, —S(O)$_2$NH$_2$, —S(O)$_2$N($R^{10}$)$R^9$, —Si($R^{12a}$)($R^{2b}$)$R^2$, phenyl, phenyl substituted with (Z)$_{p1}$, or D-1 to D-65, when m is an integer of 2 or more, each X may be identical with or different from each other, further, when two Xs are adjacent, the adjacent two Xs may form 5-membered or 6-membered ring together with carbon atoms to which the two Xs are bonded by forming —CH$_2$CH$_2$CH$_2$—, —CH$_2$CH$_2$O—, —CH$_2$OCH$_2$—, —OCH$_2$O—, —CH$_2$CH$_2$S—, —CH$_2$SCH$_2$—, —CH$_2$CH$_2$N($R^{13}$)—, —CH$_2$N($R^{13}$)CH$_2$—, —CH$_2$CH$_2$CH$_2$CH$_2$—, —CH₂CH₂CH₂O—, —CH₂CH₂OCH₂—, —CH₂OCH₂O—, —OCH₂CH₂O—, —OCH₂CH₂S—, —CH₂CH₂CH=CH—, —OCH=CH—, —SCH=CH—, —N(R¹³)CH=CH—, —OCH=N—, —SCH=N—, —N(R¹³)CH=N—, —N(R¹³)N=CH—, —CH=CHCH=CH—, —OCH₂CH=CH—, —N=CHCH=CH—, —N=CHCH=N— or —N=CHN=CH—, in this case, hydrogen atoms bonded to each carbon atom forming the ring may be arbitrarily substituted with Z, further when the hydrogen atoms are substituted with two or more Zs at the same time, each Z may be identical with or different from each other, Y is halogen atom, cyano, nitro, azido, —SCN, —SF₅, C₁-C₆alkyl, C₁-C₆alkyl arbitrarily substituted with R⁴, C₃-C₈cycloalkyl, C₃-C₈cycloalkyl arbitrarily substituted with R⁴, E-1 to E-49, C₂-C₆alkynyl, C₂-C₆alkynyl arbitrarily substituted with R⁴, —OH, —OR⁵, —OSO₂R⁵, —SH, —S(O)ᵣR⁵, —NH₂, —N(R⁷)R⁶, —N(R⁷)C(O)R⁹ᵃ, —N(R⁷)C(O)OR⁹ᵃ, —N(R⁷)C(O)SR⁹ᵃ, —N(R⁷)C(S)OR⁹ᵃ, —N(R⁷)C(S)SR⁹ᵃ, —N(R⁷)S(O)₂R⁹ᵃ, —N=CHOR⁸, —N=C(R⁹)OR⁸, —C(O)NH₂, —C(O)N(R¹⁰)R⁹, —C(S)NH₂, —C(S)N(R¹⁰)R⁹, —Si(R¹²ᵃ)(R¹²ᵇ)R¹², phenyl, phenyl substituted with (Z)ₚ₁, or D-1 to D-65, when n is an integer of 2 or more, each Y may be identical with or different from each other, further, when two Ys are adjacent, the adjacent two Ys may form 5-membered or 6-membered ring together with carbon atoms to which the two Ys are bonded by forming —CH₂CH₂CH₂—, —CH₂CH₂O—, —CH₂OCH₂—, —OCH₂O—, —CH₂CH₂S—, —CH₂SCH₂—, —SCH₂S—, —CH₂CH₂CH₂CH₂—, —CH₂CH₂CH₂O—, —CH₂CH₂OCH₂—, —CH₂OCH₂O—, —OCH₂CH₂O—, —OCH₂CH₂S—, —SCH₂CH₂S—, —OCH=N— or —SCH=N—, in this case, hydrogen atoms bonded to each carbon atom forming the ring may be arbitrarily substituted with Z, further when the hydrogen atoms are substituted with two or more Zs at the same time, each Z may be identical with or different from each other, R¹ is hydrogen atom, —CHO, —C(=W¹)R¹ᵃ, C(=W¹)—W²—R¹ᵃ, —C(=W¹)NH₂, —C(=W¹)N(R¹ᵇ)R¹ᵃ, —C(=W¹)N(R¹ᵇ)OR¹ᵃ, —C(=W¹)NHC(O)R¹ᵃ, —C(=W¹)NHSO₂R¹ᵃ, —C(=W¹)CH=NOR¹ᵃ, —S(O)₂R¹ᵃ, —S(O)₂NH₂ or —S(O)₂N(R¹ᵇ)R¹ᵃ, W¹ and W² independently of each other are oxygen atom or sulfur atom, R¹ᵃ is C₁-C₁₂alkyl, C₁-C₁₂alkyl arbitrarily substituted with R¹⁴, C₃-C₁₂cycloalkyl, C₃-C₁₂cyloalkyl arbitrarily substituted with R¹⁴, E-1 to E-49, C₂-C₁₂alkenyl, C₂-C₁₂alkenyl arbitrarily substituted with R¹⁴, C₃-C₁₂cycloalkenyl, C₃-C₁₂halocycloalkenyl, C₂-C₁₂alkynyl, C₂-C₁₂alkynyl arbitrarily substituted with R¹⁴ phenyl, phenyl substituted with (Z)ₚ₁, or D-1 to D-65, R¹ᵇ is hydrogen atom, C₁-C₆alkyl, C₁-C₆haloalkyl, C₃-C₆cycloalkyl C₁-C₄alkyl, C₁-C₆alkoxy C₁-C₄alkyl, C₁-C₆alkylthio C₁-C₄alkyl, cyano C₁-C₆alkyl, phenyl C₁-C₄alkyl, phenyl C₁-C₄alkyl substituted with (Z)ₚ₁, C₃-C₆alkenyl or C₃-C₆alkynyl, or R¹ᵇ together with R¹ᵃ may form 3- to 7-membered ring together with the nitrogen atom bonding them by forming C₂-C₆alkylene chain, in this case, the alkylene chain may contain one oxygen atom, sulfur atom or nitrogen atom, and may be arbitrarily substituted with halogen atom, C₁-C₆alkyl, C₁-C₆alkoxy, —CHO, C₁-C₆alkylcarbonyl or C₁-C₆alkoxycarbonyl, R² is hydrogen atom, C₁-C₁₂alkyl, C₁-C₁₂haloalkyl, C₁-C₆alkyl arbitrarily substituted with R¹⁴ᵃ, C₃-C₁₂cycloalkyl, C₃-C₁₂alkenyl, C₃-C₁₂haloalkenyl, C₃-C₁₂alkynyl, C₃-C₁₂haloalkynyl, —C(O)R¹⁵, —C(O)OR¹⁵, —C(O)SR¹⁵, —CONH₂, —C(O)N(R¹⁶)R¹⁵, —C(O)C(O)OR¹⁵, —C(S)OR¹⁵, —C(S)SR¹⁵, —C(S)NH₂, —C(S)N(R¹⁶)R¹⁵, C₁-C₁₂alkoxy, —SR¹⁵, —S(O)₂R¹⁵, —SN(R¹⁸)R¹⁷, phenyl or phenyl substituted with (Z)ₚ₁, or R² together with R¹ may form 5- to 7-membered ring together with the nitrogen atom bonding them by forming C₄-C₆alkylene chain, in this case, the alkylene chain may contain one oxygen atom, sulfur atom or nitrogen atom, and may be arbitrarily substituted with C₁-C₆alkyl, C₁-C₆haloalkyl, —CHO, C₁-C₆alkylcarbonyl, C₁-C₆haloalkylcarbonyl, C₁-C₆alkoxycarbonyl, C₁-C₆haloalkoxycarbonyl, C₁-C₆alkylaminocarbonyl, C₁-C₆haloalkylaminocarbonyl, phenyl, phenyl substituted with (Z)ₚ₁, D-52, D-55, oxo or thioxo, or further when substituent Y is present on an adjacent position, R² together with Y may form 5- or 6-membered ring together with the atoms to which the R² and Y are bonded by forming —CH₂—, —CH₂CH₂—, —CH₂O—, —CH₂S— or —CH₂N(R⁶)—, R²ᵃ is hydrogen atom, cyano, C₁-C₆alkyl, C₁-C₆haloalkyl, C₃-C₆cycloalkyl, C₁-C₆alkoxycarbonyl, —C(O)NH₂, —C(S)NH₂ or phenyl, R²ᵇ is hydrogen atom or C₁-C₆alkyl, or R²ᵇ together with R²ᵃ may form 3- to 6-membered ring with the carbon atom bonding them by forming C₂-C₅alkylene chain, in this case, the alkylene chain may contain one oxygen atom, sulfur atom or nitrogen atom, R²ᶜ is hydrogen atom, C₁-C₆alkyl, C₁-C₆haloalkyl, C₁-C₆alkylcarbonyl, C₁-C₆haloalkylcarbonyl, C₃-C₆cycloalkylcarbonyl, C₃-C₆halocycloalkylcarbonyl, C₁-C₆alkoxycarbonyl or C₁-C₆haloalkoxycarbony, R³ is halogen atom, cyano, C₁-C₆alkyl, C₁-C₆alkyl arbitrarily substituted with R⁴, C₃-C₈cycloalkyl, C₃-C₈cycloalkyl arbitrarily substituted with R⁴, E-1 to E-49, C₃-C₆alkenyl, C₂-C₆alkenyl arbitrarily substituted with R⁴, C₃-C₆alkynyl, C₂-C₆alkynyl arbitrarily substituted with R⁴, —OR⁵, —S(O)ᵣR⁵, —N(R¹⁰)R⁹, —N(R¹⁰)R⁹ᵃ, —CHO, —C(O)R⁹, —C(O)OR⁹, —C(O)SR⁹, —C(O)NH₂, —C(O)N(R¹⁰)R⁹, —C(S)OR⁹, —C(S)SR⁹, —C(S)NH₂, —C(S)N(R¹⁰)R⁹, —CH=NOR¹¹, —C(R⁹)=NOR¹¹, M-5, M-20, M-48, —Si(R¹²ᵃ)(R¹²ᵇ)R¹², —P(O)(OR¹⁹)₂, phenyl, phenyl substituted with (Z)ₚ₁ or D-1 to D-65, D-1 to D-65 are aromatic heterocyclic rings of the following formulae, respectively

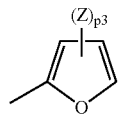

D-1

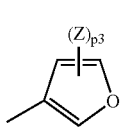

D-2

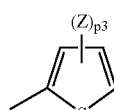

D-3

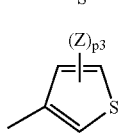

D-4

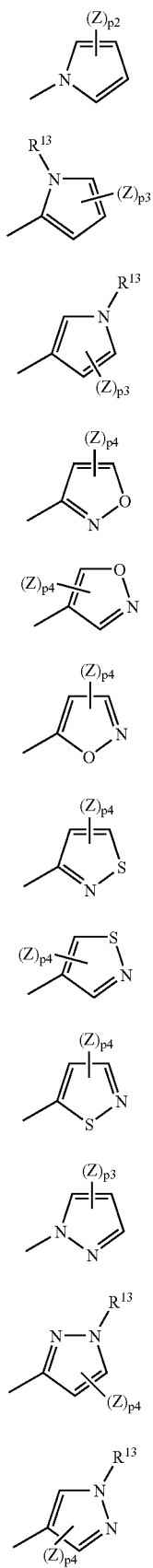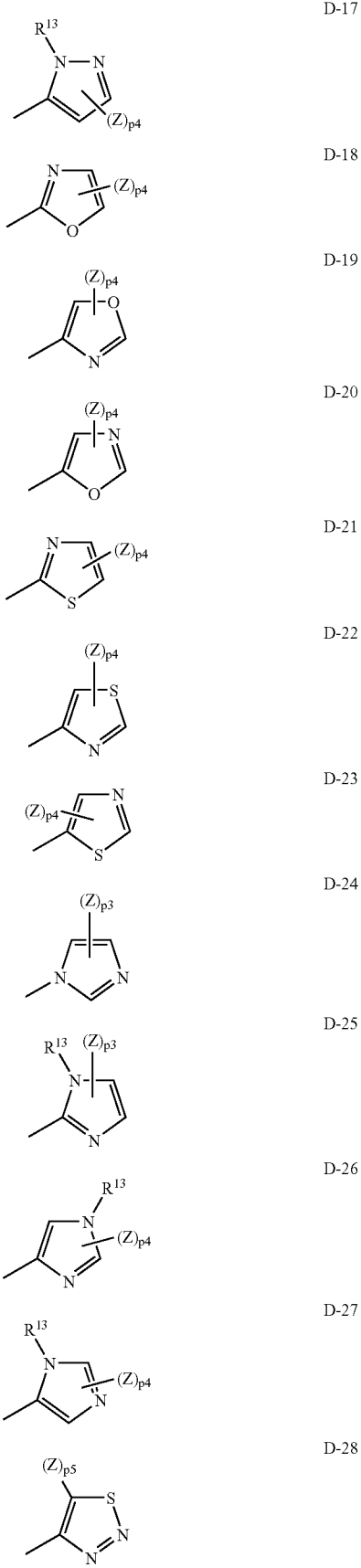

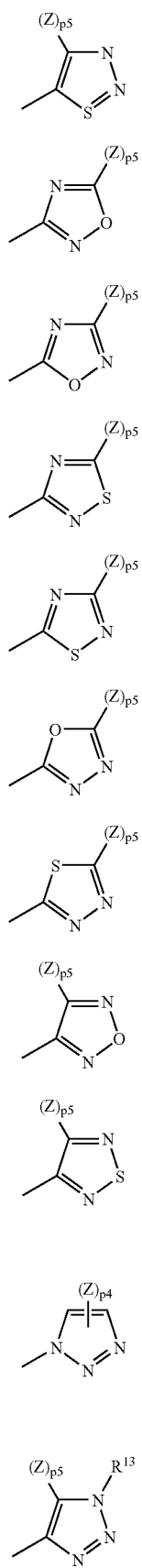
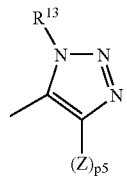
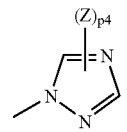
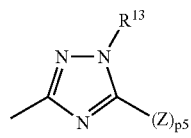
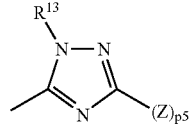
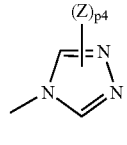
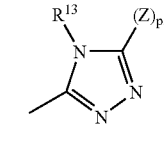
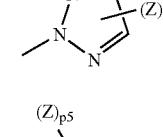
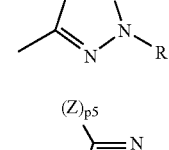
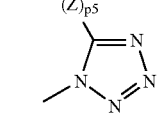
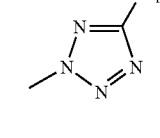
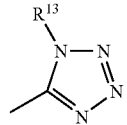

-continued

D-51 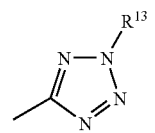

D-52 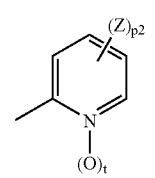

D-53

D-54 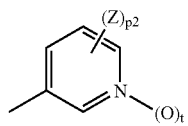

D-55 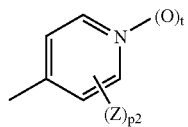

D-56 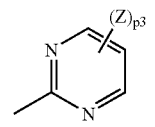

D-57 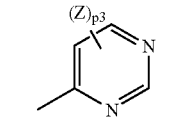

D-58 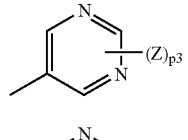

D-59 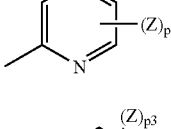

D-60 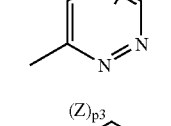

D-61 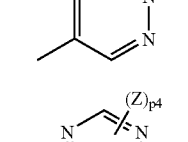

D-62 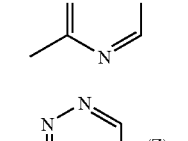

-continued

D-63 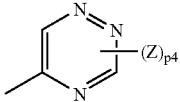

D-64 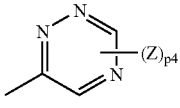

D-65 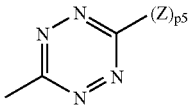

Z is halogen atom, cyano, nitro, $C_1$-$C_6$alkyl, $C_1$-$C_6$haloalkyl, $C_1$-$C_4$alkoxy $C_1$-$C_4$alkyl, $C_1$-$C_4$haloalkoxy $C_1$-$C_4$alkyl, $C_1$-$C_4$alkylthio $C_1$-$C_4$alkyl, $C_1$-$C_4$haloalkylthio $C_1$-$C_4$alkyl, $C_1$-$C_4$alkylsulfinyl $C_1$-$C_4$alkyl, $C_1$-$C_4$haloalkylsulfinyl $C_1$-$C_4$alkyl, $C_1$-$C_4$alkylsulfonyl $C_1$-$C_4$alkyl, $C_1$-$C_4$haloalkylsulfonyl $C_1$-$C_4$alkyl, $C_3$-$C_6$cycloalkyl, $C_3$-$C_6$halocycloalkyl, —OH, $C_1$-$C_6$alkoxy, $C_1$-$C_6$haloalkoxy, $C_1$-$C_6$alkylsulfonyloxy, $C_1$-$C_6$haloalkylsulfonyloxy, $C_1$-$C_6$alkylthio, $C_1$-$C_6$haloalkylthio, $C_1$-$C_6$alkylsulfinyl, $C_1$-$C_6$haloalkylsulfinyl, $C_1$-$C_6$alkylsulfonyl, $C_1$-$C_6$haloalkylsulfonyl, —$NH_2$, $C_1$-$C_6$alkylamino, di($C_1$-$C_6$alkyl)amino, $C_1$-$C_6$alkoxycarbonyl, $C_1$-$C_6$haloalkoxycarbonyl, —C(O)$NH_2$, $C_1$-$C_6$alkylaminocarbonyl, $C_1$-$C_6$haloalkylaminocarbonyl, di($C_1$-$C_6$alkyl)aminocarbonyl, —C(S)$NH_2$, —S(O)$_2NH_2$, $C_1$-$C_6$alkylaminosulfonyl, di($C_1$-$C_6$alkyl)aminosulfonyl, phenyl or phenyl arbitrarily substituted with halogen atom, when p1, p2, p3 or p4 is an integer of 2 or more, each Z may be identical with or different from each other, further, when two Zs are adjacent, the adjacent two Zs may form 5-membered or 6-membered ring together with carbon atoms to which the two Zs are bonded by forming —$CH_2CH_2CH_2$—, —$CH_2CH_2O$—, —$CH_2OCH_2$—, —$OCH_2O$—, —$CH_2CH_2S$—, —$CH_2SCH_2$—, —$CH_2CH_2CH_2CH_2$—, —$CH_2CH_2CH_2O$—, —$CH_2CH_2OCH_2$—, —$CH_2OCH_2O$—, —$OCH_2CH_2O$—, —$CH_2CH_2CH_2S$—, —$OCH_2CH_2S$— or —CH=CH—CH=CH—, in this case, hydrogen atoms bonded to each carbon atom forming the ring may be arbitrarily substituted with halogen atom, cyano, nitro, $C_1$-$C_4$alkyl, $C_1$-$C_4$haloalkyl, $C_1$-$C_4$alkoxy or $C_1$-$C_4$alkylthio, E-1 to E-49 are saturated heterocyclic rings of the following formulae, respectively E-1 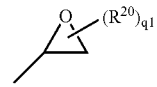

E-2 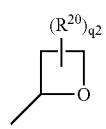

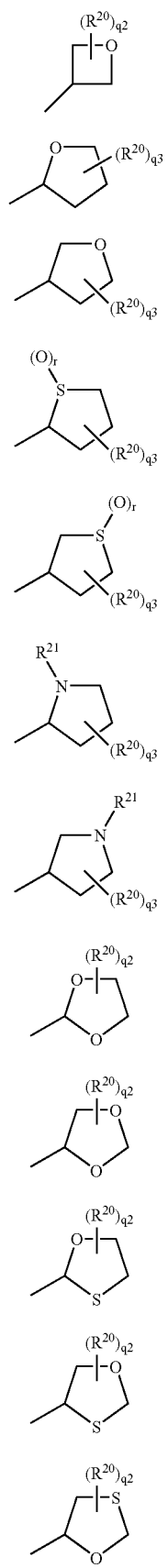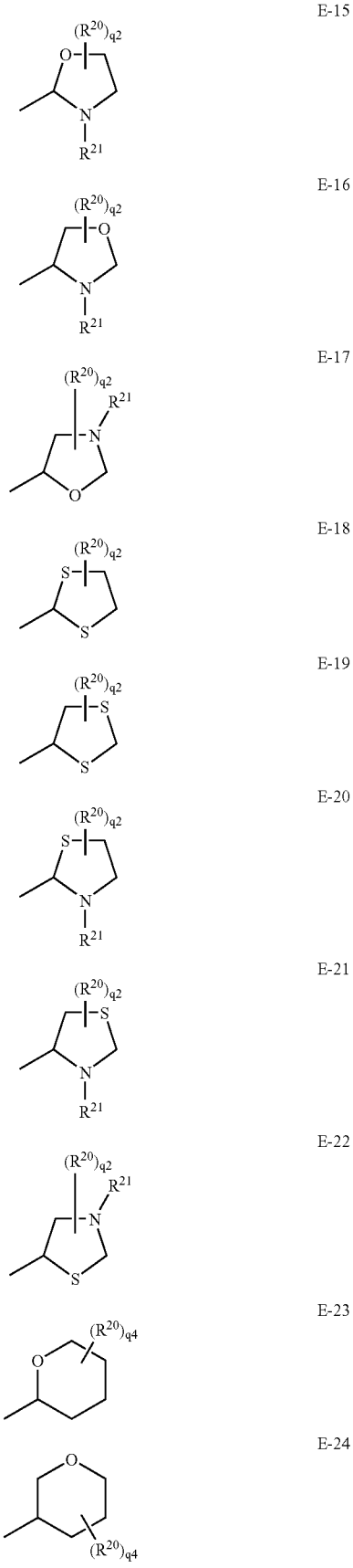

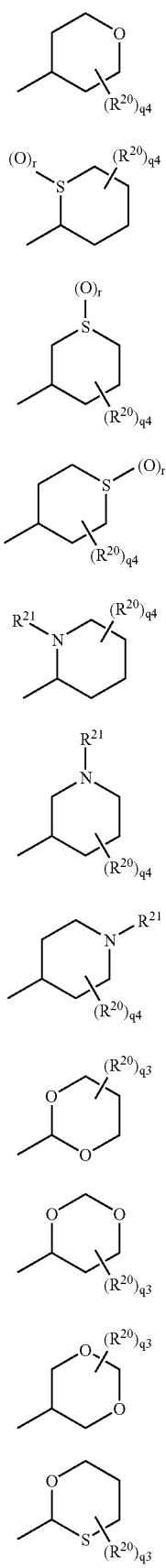
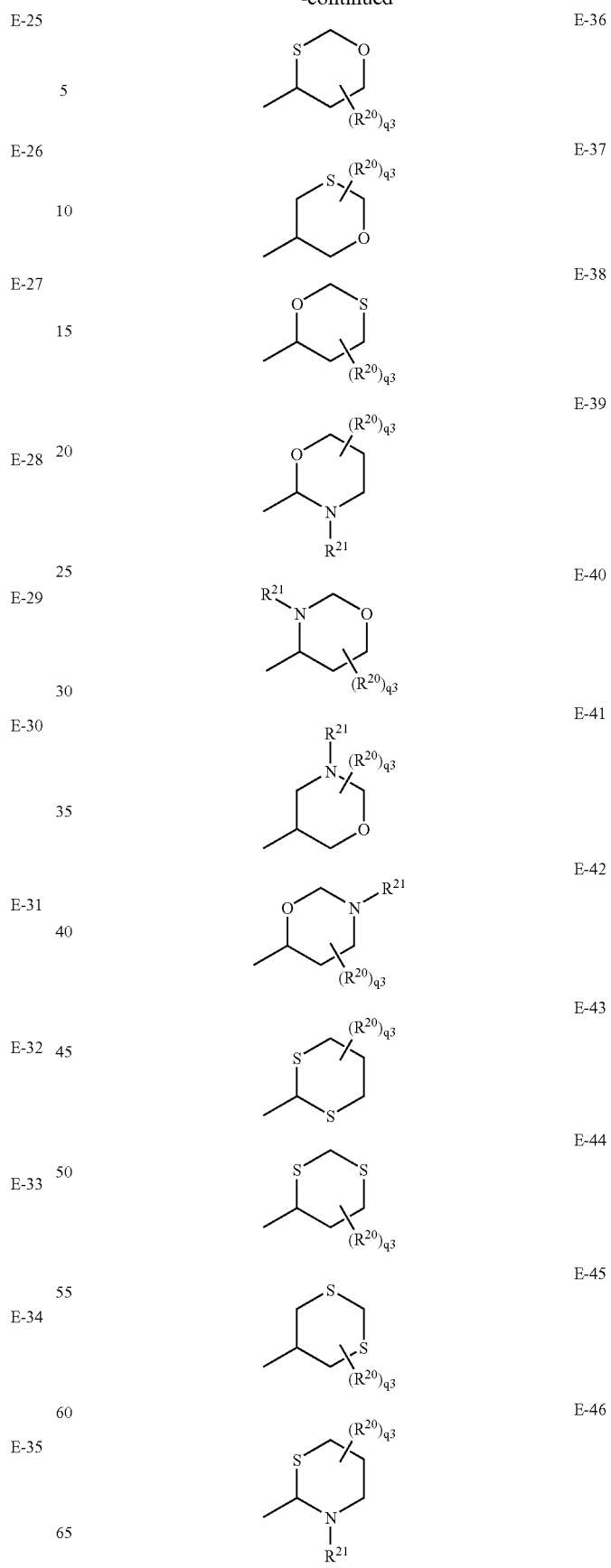

-continued

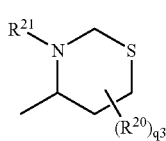
E-47

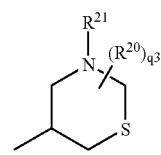
E-48

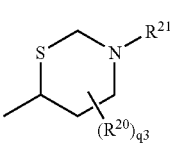
E-49

$R^4$ is halogen atom, cyano, $C_3$-$C_6$cycloalkyl, $C_3$-$C_8$halocycloalkyl, E-1 to E-49, —OH, —OR$^5$, —SH, —S(O)$_r$R$^5$, —N(R$^7$)R$^6$, —N(R$^7$)C(O)R$^{9a}$, —N(R$^7$)C(O)OR$^{9a}$, —N(R$^7$)C(O)SR$^{9a}$, —N(R$^7$)C(S)OR$^{9a}$, —N(R$^7$)C(S)SR$^{9a}$, —N(R$^7$)S(O)$_2$R$^{9a}$, —C(O)OR$^9$, —C(O)N(R$^{10}$)R$^9$, —Si(R$^{12a}$)(R$^{12b}$)R$^{12}$, phenyl, phenyl substituted with (Z)$_{p1}$, or D-1 to D-65, $R^5$ is $C_1$-$C_6$alkyl, $C_1$-$C_6$alkyl arbitrarily substituted with R$^{22}$, $C_3$-$C_8$cycloalkyl, $C_3$-$C_8$cycloalkyl arbitrarily substituted with R$^{22}$, E-3 to E-9, E-23 to E-31, E-34, E-45, $C_2$-$C_6$alkenyl, $C_2$-$C_6$alkenyl arbitrarily substituted with R$^{22}$, $C_3$-$C_8$cycloalkenyl, $C_3$-$C_8$halocycloalkenyl, $C_3$-$C_6$alkynyl, $C_3$-$C_6$alkynyl arbitrarily substituted with R$^{22}$, $C_1$-$C_6$alkylcarbonyl, $C_1$-$C_6$alkoxycarbonyl, phenyl, phenyl substituted with (Z)$_{p1}$, D-1 to D-4, D-6 to D-13, D-15 to D-23, D-25 to D-37, D-39, D-40, D-42, D-43, D-45, D-47, D-50 to D-64 or D-65, $R^6$ is $C_1$-$C_6$alkyl, $C_1$-$C_6$alkyl arbitrarily substituted with R$^{22}$, $C_3$-$C_6$cycloalkyl, $C_3$-$C_8$halocycloalkyl, $C_3$-$C_6$alkenyl, $C_3$-$C_6$haloalkenyl, $C_3$-$C_6$alkynyl, $C_3$-$C_6$haloalkynyl, —CHO, —C(O)R$^9$, —C(O)OR$^9$, —C(O)SR$^9$, —C(O)NH$_2$, —C(O)N(R$^{10}$)R$^9$, —C(S)OR$^9$, —C(S)SR$^9$, —C(S)NH$_2$, —C(S)N(R$^{10}$)R$^9$, —C(O)C(O)R$^9$, —C(O)C(O)OR$^9$, —OH, —S(O)$_2$R$^9$, —S(O)$_2$N(R$^{10}$)R$^9$, —P(O)(OR$^{19}$)$_2$ or —P(S)(OR$^{19}$)$_2$, $R^7$ is hydrogen atom, $C_1$-$C_6$alkyl, $C_1$-$C_6$alkyl arbitrarily substituted with R$^{22}$, $C_3$-$C_8$cycloalkyl, $C_3$-$C_6$alkenyl, $C_3$-$C_6$haloalkenyl, $C_3$-$C_6$alkynyl, $C_3$-$C_6$haloalkynyl, —CHO, $C_1$-$C_6$alkylcarbonyl, $C_1$-$C_6$haloalkylcarbonyl or $C_1$-$C_6$alkoxycarbonyl, or R$^7$ together with R$^6$ may form 3- to 7-membered ring together with the nitrogen atom bonding them by forming $C_2$-$C_6$alkylene chain, in this case, the alkylene chain may contain one oxygen atom, sulfur atom or nitrogen atom, and may be arbitrarily substituted with halogen atom, $C_1$-$C_6$alkyl, $C_1$-$C_6$haloalkyl, oxo or thioxo, $R^8$ is $C_1$-$C_6$alkyl, $C_1$-$C_6$haloalkyl, $C_3$-$C_6$alkenyl, phenyl or phenyl substituted with (Z)$_{p1}$, $R^9$ is $C_1$-$C_6$alkyl, $C_1$-$C_6$alkyl arbitrarily substituted with R$^{22}$, $C_3$-$C_8$cycloalkyl, $C_3$-$C_8$halocycloalkyl, E-1 to E-49, $C_3$-$C_6$alkenyl, $C_3$-$C_6$haloalkenyl, $C_3$-$C_6$alkynyl or $C_3$-$C_6$haloalkynyl, $R^{9a}$ is phenyl, phenyl substituted with (Z)$_{p1}$ or D-1 to D-65, $R^{10}$ is hydrogen atom, $C_1$-$C_6$alkyl, $C_1$-$C_6$haloalkyl, $C_3$-$C_6$cycloalkyl $C_1$-$C_4$alkyl, $C_1$-$C_6$alkoxy $C_1$-$C_4$alkyl, $C_1$-$C_6$alkylthio $C_1$-$C_4$alkyl, cyano $C_1$-$C_6$alkyl, $C_3$-$C_6$alkenyl or $C_3$-$C_6$alkynyl, or R$^{10}$ together with R$^9$ may form 3- to 7-membered ring with the nitrogen atom bonding them by forming $C_2$-$C_6$alkylene chain, in this case, the alkylene chain may contain one oxygen atom, sulfur atom or nitrogen atom, and may be arbitrarily substituted with halogen atom, $C_1$-$C_6$alkyl, $C_1$-$C_6$alkoxy, —CHO, $C_1$-$C_6$alkylcarbonyl or $C_1$-$C_6$alkoxycarbonyl, $R^{11}$ is hydrogen atom, $C_1$-$C_6$alkyl, $C_1$-$C_6$haloalkyl, phenyl $C_1$-$C_4$alkyl, phenyl $C_1$-$C_4$alkyl substituted with (Z)$_{p1}$, $C_3$-$C_6$alkenyl, $C_3$-$C_6$haloalkenyl, $C_3$-$C_6$alkynyl or $C_3$-$C_6$haloalkynyl, $R^{12}$ is $C_1$-$C_6$alkyl, $C_1$-$C_6$haloalkyl, $C_1$-$C_6$alkoxy, phenyl or phenyl substituted with (Z)$_{p1}$, $R^{12a}$ and $R^{12b}$ independently of each other are $C_1$-$C_6$alkyl, $C_1$-$C_6$haloalkyl or $C_1$-$C_6$alkoxy, $R^{13}$ is hydrogen atom, $C_1$-$C_6$alkyl, $C_1$-$C_6$haloalkyl, $C_1$-$C_6$alkoxycarbonyl $C_1$-$C_4$alkyl, $C_1$-$C_6$haloalkoxycarbonyl $C_1$-$C_4$alkyl, phenyl $C_1$-$C_4$alkyl, phenyl $C_1$-$C_4$alkyl substituted with (Z)$_{p1}$, $C_2$-$C_6$alkenyl, $C_2$-$C_6$haloalkenyl, $C_3$-$C_6$alkynyl, $C_3$-$C_6$haloalkynyl, $C_1$-$C_6$alkoxy, $C_1$-$C_6$alkoxycarbonyl, $C_1$-$C_6$haloalkoxycarbonyl, phenyl or phenyl substituted with (Z)$_{p1}$, further, in case where Z is present in an adjacent position of $R^{13}$, $R^{13}$ together with Z may form 6-membered ring together with the atom bonding them by forming —CH$_2$CH$_2$CH$_2$CH$_2$—, —CH=CH—CH=CH—, —N=CH—CH=CH—, —CH=N—CH=CH—, —CH=CH—N=CH— or —CH=CH—CH=N—, in this case, hydrogen atoms bonded to each carbon atom forming the ring may be arbitrarily substituted with halogen atom, $C_1$-$C_4$alkyl or $C_1$-$C_4$haloalkyl, $R^{14}$ is halogen atom, cyano, nitro, $C_3$-$C_8$cycloalkyl, $C_3$-$C_8$halocycloalkyl, E-4 to E-7, E-9 to E-11, E-11, E-18, E-23 to E-28, E-30 to E-32, E-43, $C_5$-$C_8$cycloalkenyl, $C_5$-$C_8$halocycloalkenyl, —OR$^{23}$, —N(R$^{24}$)R$^{23}$, —S(O)$_r$R$^{25}$, —C(O)R$^{26}$, —CH=NOR$^{28}$, —C(R$^{26}$)=NOR$^{28}$, —C(O)OR$^{26}$, —C(O)SR$^{26}$, —C(O)NH$_2$, —C(O)N(R$^{27}$)R$^{26}$, —C(O)C(O)OR$^{26}$, —C(S)OR$^{26}$, —C(S)SR$^{26}$, —C(S)NH$_2$, —C(S)N(R$^{27}$)R$^{26}$, —SO$_2$NH$_2$, —SO$_2$N(R$^{27}$)R$^{26}$, —C(=NR$^{27}$)OR$^{26}$, —C(=NR$^{27}$)SR$^{26}$, —C(=NR$^{27}$)N(R$^{27a}$)R$^{26a}$, —C(=NOR$^{28}$)N(R$^{27a}$)R$^{26a}$, M1 to M-48, —Si(R$^{12a}$)(R$^{12b}$)R$^{12}$, phenyl, phenyl substituted with (Z)$_{p1}$, naphthyl or D-1 to D-65, M-1 to M-48 are partially saturated heterocyclic rings of the following formulae, respectively

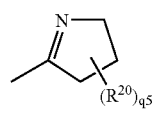
M-1

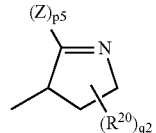
M-2

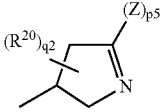
M-3

-continued
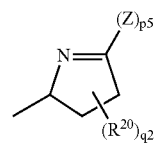 M-4
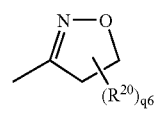 M-5
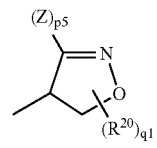 M-6
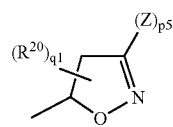 M-7
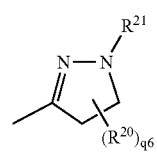 M-8
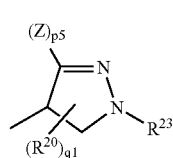 M-9
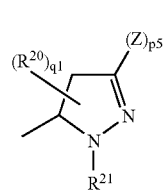 M-10
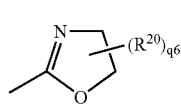 M-11
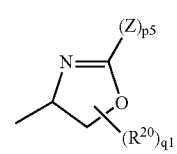 M-12
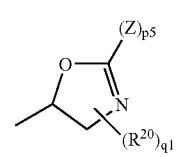 M-13
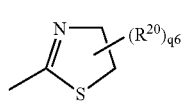 M-14
-continued
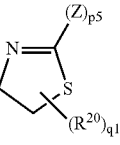 M-15
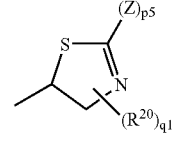 M-16
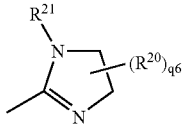 M-17
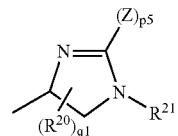 M-18
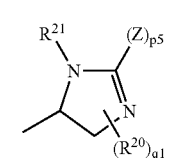 M-19
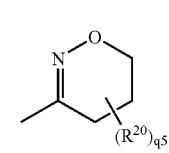 M-20
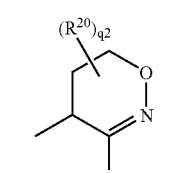 M-21
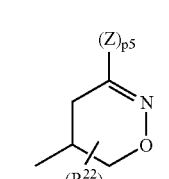 M-22
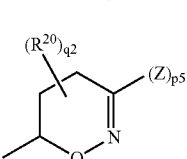 M-23
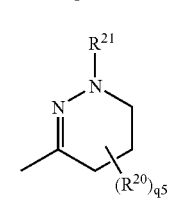 M-24

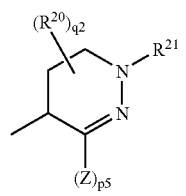 M-25
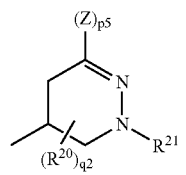 M-26
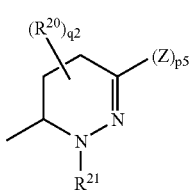 M-27
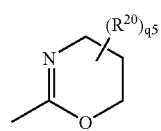 M-28
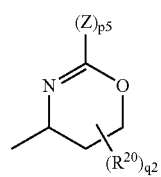 M-29
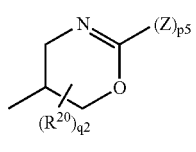 M-30
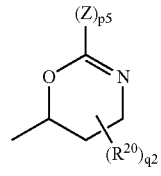 M-31
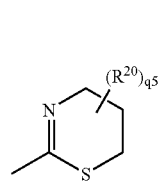 M-32
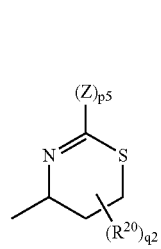 M-33
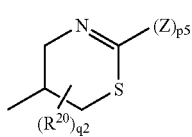 M-34
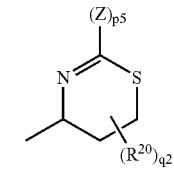 M-35
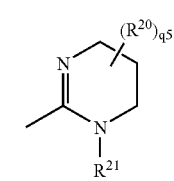 M-36
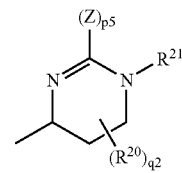 M-37
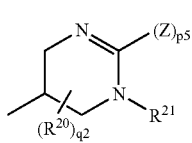 M-38
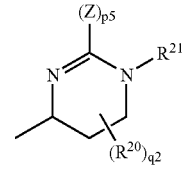 M-39
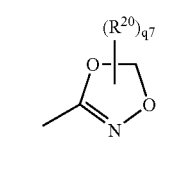 M-40
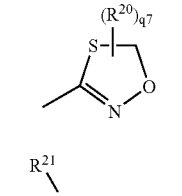 M-41
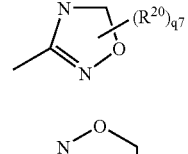 M-42
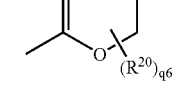 M-43

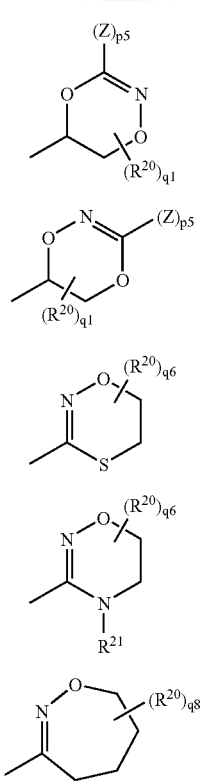

$R^{14a}$ is cyano, nitro, $C_3$-$C_6$cycloalkyl, —$OR^{23}$—$N(R^{24})R^{23}$, —$S(O)R^{25}$—CHO, —$C(O)R^{26}$, —$C(O)OR^{26}$, —$C(O)SR^{26}$, —$C(O)NH_2$, —$C(O)C(O)OR^{26}$, —$C(S)OR^{26}$, —$C(S)SR^{26}$, —$C(S)NH_2$, $Si(R^{12a})(R^{12b})R^{12}$, —$P(O)(OR^{19})_2$, —$P(S)(OR^{19})_2$, phenyl or phenyl substituted with $(Z)_{p1}$, $R^{15}$ is $C_1$-$C_6$alkyl, $C_1$-$C_6$alkyl arbitrarily substituted with $R^{29}$, $C_3$-$C_8$cycloalkyl, $C_3$-$C_8$halocycloalkyl, E-1 to E-49, $C_2$-$C_6$alkenyl, $C_2$-$C_6$haloalkenyl, $C_3$-$C_8$cycloalkenyl, $C_3$-$C_8$halocycloalkenyl, $C_2$-$C_6$alkynyl, $C_2$-$C_6$haloalkynyl, phenyl, phenyl substituted with $(Z)_{p1}$, naphthyl or D-1 to D-65, $R^{16}$ is hydrogen atom, $C_1$-$C_6$alkyl, $C_1$-$C_6$haloalkyl, $C_3$-$C_6$alkenyl or $C_3$-$C_6$alkynyl, or $R^{16}$ together with $R^{15}$ may form 5- to 6-membered ring with the nitrogen atom bonding them by forming $C_4$-$C_5$alkylene chain, in this case, the alkylene chain may contain one oxygen atom or sulfur atom, $R^{17}$ is $C_1$-$C_{12}$alkyl, $C_1$-$C_6$alkoxy $C_1$-$C_6$alkyl, $C_1$-$C_6$alkoxycarbonyl $C_1$-$C_6$alkyl, phenyl $C_1$-$C_6$alkyl, phenyl $C_1$-$C_6$alkyl substituted with $(Z)_{p1}$, $C_1$-$C_{12}$alkoxycarbonyl, —C(O)ON=C(CH$_3$)SCH$_3$ or —C(O)ON=C(SCH$_3$)C(O)N(CH$_3$)$_2$, $R^{18}$ is $C_1$-$C_{12}$alkyl, phenyl $C_1$-$C_6$alkyl or phenyl $C_1$-$C_6$alkyl substituted with $(Z)_{p1}$, or $R^{18}$ together with $R^{17}$ may form 5- to 6-membered ring with the nitrogen atom bonding them by forming $C_4$-$C_5$alkylene chain, in this case, the alkylene chain may contain one oxygen atom or sulfur atom, and may be arbitrarily substituted with $C_1$-$C_4$alkyl or $C_1$-$C_4$alkoxy, $R^{19}$ is $C_1$-$C_6$alkyl or $C_1$-$C_6$haloalkyl, $R^{20}$ is halogen atom, $C_1$-$C_6$alkyl or $C_1$-$C_6$haloalkyl, when q1 to q8 are an integer of 2 or more, each $R^{20}$ may be identical with or different from each other, further, when two $R^{20}$s are present on the same carbon atom, the two $R^{20}$s together may form oxo or thioxo, $R^{21}$ is hydrogen atom, $C_1$-$C_6$alkyl, $C_1$-$C_6$haloalkyl, —CHO, —$C(O)R^{30}$, —$C(O)OR^{30}$, —$C(O)SR^{30}$, —$C(O)NH_2$, —$C(O)N(R^{31})R^{30}$ or —$S(O)_2R^{30}$, $R^{22}$ is halogen atom, cyano, $C_3$-$C_8$cycloalkyl, $C_3$-$C_8$halocycloalkyl, E-1 to E-49, $C_1$-$C_6$alkoxy, $C_1$-$C_6$haloalkoxy, $C_1$-$C_6$alkylthio, $C_1$-$C_6$haloalkylthio, $C_1$-$C_6$alkylsulfonyl, $C_1$-$C_6$haloalkylsulfonyl, $C_1$-$C_6$alkylamino, di($C_1$-$C_6$alkyl)amino, —CHO, $C_1$-$C_6$alkylcarbonyl, $C_1$-$C_6$haloalkylcarbonyl, $C_1$-$C_6$alkoxycarbonyl, $C_1$-$C_6$haloalkoxycarbonyl, $C_1$-$C_6$alkylaminocarbonyl, di($C_1$-$C_6$alkyl)aminocarbonyl, phenyl, phenyl substituted with $(Z)_{p1}$, or D-1 to D-65, $R^{23}$ is hydrogen atom, $C_1$-$C_6$alkyl, $C_1$-$C_6$alkyl arbitrarily substituted with $R^{29}$, $C_3$-$C_6$alkenyl, $C_3$-$C_6$alkynyl, —$C(O)R^{30}$, —$C(O)OR^{30}$, —$C(O)SR^{30}$, —$C(O)NH_2$, —$C(O)N(R^{31})R^{30}$, —$C(S)R^{30}$, —$C(S)OR^{30}$, —$C(S)SR^{30}$, —$C(S)NH_2$, —$C(S)N(R^{31})R^{30}$, —$S(O)_2R^{30}$, —$S(O)_2N(R^{31})R^{30}$, tri($C_1$-$C_4$alkyl) silyl, di($C_1$-$C_6$alkyl) thiophosphoryl, phenyl or phenyl substituted with $(Z)_{p1}$, $R^{24}$ is hydrogen atom, $C_1$-$C_6$alkyl, $C_1$-$C_6$haloalkyl, $C_3$-$C_6$alkenyl or $C_3$-$C_6$alkynyl, or $R^{24}$ together with $R^{23}$ may form 4- to 6-membered ring with the nitrogen atom bonding them by forming $C_3$-$C_5$alkylene chain, in this case, the alkylene chain may contain one oxygen atom, sulfur atom or nitrogen atom, $R^{25}$ is $C_1$-$C_6$alkyl, $C_1$-$C_6$alkyl arbitrarily substituted with $R^{29}$, —$C(O)R^{30}$, —$C(O)NH_2$, —$C(O)N(R^{31})R^{30}$, —$C(S)OR^{30}$, —$C(S)NH_2$, —$C(S)N(R^{31})R^{30}$, $C_1$-$C_6$alkylthio, phenyl, phenyl substituted with $(Z)_{p1}$, D-21, D-35, D-52 or D-55, $R^{26}$ and $R^{26a}$ independently of each other are $C_1$-$C_6$alkyl, $C_1$-$C_6$alkyl arbitrarily substituted with $R^{29}$, $C_3$-$C_6$cycloalkyl, $C_3$-$C_6$halocycloalkyl, E-4, E-5, E-7, E-23, $C_2$-$C_6$alkenyl, $C_2$-$C_6$haloalkenyl, $C_2$-$C_6$alkynyl, $C_2$-$C_6$haloalkynyl, phenyl, phenyl substituted with $(Z)_{p1}$, D-1 to D-4, D-21 to D-23, D-52 to D-56, D-58 or D-59, $R^{27}$ and $R^{27a}$ independently of each other are hydrogen atom, $C_1$-$C_6$alkyl, $C_1$-$C_4$alkoxy $C_1$-$C_4$alkyl, $C_1$-$C_4$alkylthio $C_1$-$C_4$alkyl, cyano $C_1$-$C_6$alkyl, $C_3$-$C_6$alkenyl or $C_3$-$C_6$alkynyl, or $R^{27}$ together with $R^{26}$ may form 3- to 6-membered ring with the nitrogen atom bonding them by forming $C_2$-$C_5$alkylene chain, in this case, the alkylene chain may contain one oxygen atom, sulfur atom or nitrogen atom, $R^{28}$ is $C_1$-$C_8$alkyl, $C_1$-$C_8$alkyl arbitrarily substituted with $R^{29}$, $C_3$-$C_8$cycloalkyl, $C_3$-$C_8$alkenyl, $C_3$-$C_8$alkenyl arbitrarily substituted with $R^{29}$, $C_3$-$C_8$alkynyl or $C_3$-$C_8$alkynyl arbitrarily substituted with $R^{29}$, $R^{29}$ is halogen atom, cyano, $C_3$-$C_8$cycloalkyl, $C_3$-$C_8$halocycloalkyl, E-4 to E-7, —OH, —$OR^{30}$, —$S(O)_rR^{30}$, —$C(O)OR^{30}$, —$C(O)NH_2$, —$C(O)N(R^{31})R^{30}$, tri($C_1$-$C_4$alkyl) silyl, phenyl, phenyl substituted with $(Z)_{p1}$, D-1 to D-4, D-21 to D-23, D-52, D-53 or D-54, $R^{30}$ is $C_1$-$C_6$alkyl, $C_1$-$C_6$haloalkyl, $C_1$-$C_4$alkyl arbitrarily substituted with $R^{32}$, $C_3$-$C_6$cycloalkyl, $C_3$-$C_6$halocycloalkyl, $C_2$-$C_6$alkenyl, $C_2$-$C_6$alkynyl, phenyl, or phenyl substituted with $(Z)_{p1}$, $R^{31}$ is hydrogen atom, $C_1$-$C_6$alkyl, $C_1$-$C_6$haloalkyl, $C_3$-$C_6$alkenyl or $C_3$-$C_6$alkynyl, or $R^{31}$ together with $R^{30}$ may form 3- to 6-membered ring with the nitrogen atom bonding them by forming $C_2$-$C_5$alkylene chain, in this case, the alkylene chain may contain one oxygen atom or sulfur atom, $R^{32}$ is $C_3$-$C_6$cycloalkyl, $C_1$-$C_4$alkoxy, $C_1$-$C_4$alkylthio, $C_1$-$C_4$alkylsulfonyl, phenyl or phenyl substituted with $(Z)_{p1}$, m is an integer of 0 to 5,
n is an integer of 0 to 4,
p1 is an integer of 1 to 5,
p2 is an integer of 0 to 4,
p3 is an integer of 0 to 3,
p4 is an integer of 0 to 2,
p5 is an integer of 0 or 1,
q1 is an integer of 0 to 3, q2 is an integer of 0 to 5,
q3 is an integer of 0 to 7,
q4 is an integer of 0 to 9,
q5 is an integer of 0 to 6,
q6 is an integer of 0 to 4,
q7 is an integer of 0 to 2,
q8 is an integer of 0 to 8,
r is an integer of 0 to 2, and
t is an integer of 0 or 1.

(2) The substituted isoxazoline compound or the salt thereof as set forth in (1), wherein
G is an aromatic 6-membered ring shown in any one of G-1, G-3 or G-4 or an aromatic 5-membered ring shown in any one of G-13, G-14, G-17, G-18, G-20, G-21 or G-22

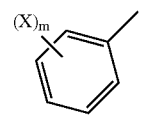
G-1

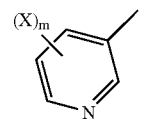
G-3

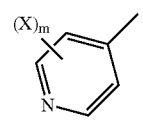
G-4

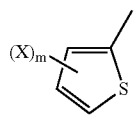
G-13

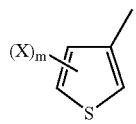
G-14

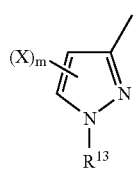
G-17

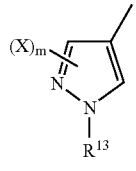
G-18

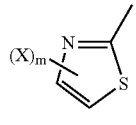
G-20

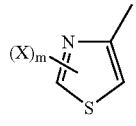
G-21

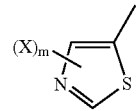
G-22

L is —CH($R^{2a}$)—, —N($R^{2c}$)—, —CH($R^{2a}$)CH$_2$— or —CH($R^{2a}$)N($R^{2c}$)—,

X is halogen atom, cyano, nitro, —SF$_5$, C$_1$-C$_6$alkyl, C$_1$-C$_6$alkyl arbitrarily substituted with R$^4$, C$_3$-C$_8$cycloalkyl, C$_3$-C$_8$haloycloalkyl, C$_2$-C$_6$alkenyl, C$_2$-C$_6$halolkenyl, C$_2$-C$_6$alkynyl, C$_2$-C$_6$halolkynyl, —OH, —OR$^5$, —OSO$_2$R$^5$—S(O)$_r$R$^5$ or tri(C$_1$-C$_6$alkyl)silyl, when m is an integer of 2 or 3, each X may be identical with or different from each other, further, when two Xs are adjacent, the adjacent two Xs may form 5-membered or 6-membered ring together with carbon atoms to which the two Xs are bonded by forming —CF$_2$OCF$_2$—, —OCF$_2$O—, —CF$_2$OCF$_2$O— or —OCF$_2$CF$_2$O—, Y is halogen atom, cyano, nitro, C$_1$-C$_6$alkyl, C$_1$-C$_6$alkyl arbitrarily substituted with R$^4$, C$_2$-C$_6$alkynyl, tri(C$_1$-C$_6$alkyl)silylethynyl, —OR$^5$, —OSO$_2$R$^5$, S(O)$_r$R$^5$, —NH$_2$, —N(R$^7$)R$^6$, —N=C(R$^9$)OR$^8$, —C(O)NH$_2$ or —C(S)NH$_2$, when n is 2, each Y may be identical with or different from each other, R$^1$ is hydrogen atom, —C(O)R$^{1a}$, —C(S)R$^{1a}$, —C(O)OR$^{1a}$, —C(O)SR$^{1a}$, —C(S)OR$^{1a}$, —C(S)SR$^{1a}$, C(O)N(R$^{1b}$)R$^{1a}$, —C(O)N(R$^{1b}$)OR$^{1a}$, —C(S)N(R$^{1b}$)R$^{1a}$ or S(O)$_2$R$^{1a}$, R$^{1a}$ is C$_1$-C$_6$alkyl, C$_1$-C$_6$haloalkyl, C$_1$-C$_4$alkyl arbitrarily substituted with R$^{14}$, C$_3$-C$_8$cycloalkyl, C$_3$-C$_6$halocycloalkyl, cyano C$_3$-C$_6$cycloalkyl, phenyl C$_3$-C$_6$cycloalkyl, E-4 to E-7, C$_2$-C$_6$alkenyl, C$_2$-C$_6$haloalkenyl, C$_2$-C$_6$alkynyl, C$_2$-C$_6$haloalkynyl, phenyl, phenyl substituted with (Z)$_{p1}$, D-1 to D-4, D-15 to D-17, D-21 to D-24, D-52 to D-58 or D-59, R$^{1b}$ is hydrogen atom or C$_1$-C$_6$alkyl, or R$^{1b}$ together with R$^{1a}$ may form 3- to 7-membered ring together with the nitrogen atom bonding them by forming C$_2$-C$_6$alkylene chain, in this case, the alkylene chain may contain one oxygen atom or sulfur atom, R$^2$ is hydrogen atom, C$_1$-C$_6$alkyl, C$_1$-C$_6$haloalkyl, C$_1$-C$_4$alkyl arbitrarily substituted with R$^{14a}$, C$_3$-C$_6$cycloalkyl, C$_3$-C$_6$alkenyl, C$_3$-C$_6$alkynyl, —C(O)R$^{15}$, —C(O)OR$^{15}$, —C(O)SR$^{15}$, —C(O)C(O)OR$^{15}$, —C(S)OR$^{15}$, —C(S)SR$^{15}$, C$_1$-C$_6$alkoxy, C$_1$-C$_6$haloalkylthio or —SN(R$^{18}$)R$^{17}$, or R$^2$ together with R$^1$ may form 5- to 7-membered ring together with the nitrogen atom bonding them by forming C$_4$-C$_6$alkylene chain, in this case, the alkylene chain may contain one oxygen atom, sulfur atom or nitrogen atom, and may be arbitrarily substituted with C$_1$-C$_6$alkyl, oxo or thioxo, R$^{2a}$ is hydrogen atom, cyano, C$_1$-C$_6$alkyl, C$_1$-C$_6$haloalkyl, C$_3$-C$_6$cycloalkyl, —C(O)NH$_2$ or —C(S)NH$_2$, R$^{2c}$ is hydrogen atom, C$_1$-C$_6$alkyl, C$_1$-C$_6$alkylcarbonyl, C$_1$-C$_6$haloalkylcarbonyl or C$_3$-C$_6$cycloalkylcarbonyl, R$^3$ is C$_1$-C$_6$alkyl, C$_1$-C$_6$haloalkyl, C$_1$-C$_4$alkoxy C$_1$-C$_4$haloalkyl, C$_1$-C$_4$haloalkoxy C$_1$-C$_4$haloalkyl, C$_1$-C$_4$alkylthio C$_1$-C$_4$haloalkyl, C$_1$-C$_4$haloalkylthio C$_1$-C$_4$haloalkyl, cyano C$_1$-C$_6$haloalkyl, C$_3$-C$_6$cycloalkyl or C$_3$-C$_6$halocycloalkyl, Z is halogen atom, cyano, nitro, C$_1$-C$_6$alkyl, C$_1$-C$_6$haloalkyl, C$_1$-C$_6$alkoxy, C$_1$-C$_6$haloalkoxy, C$_1$-C$_6$alkylsulfonyloxy, C$_1$-C$_6$haloalkylsulfonyloxy, C$_1$-C$_6$alkylthio, C$_1$-C$_6$haloalkylthio, C$_1$-C$_6$alkylsulfinyl, C$_1$-C$_6$haloalkylsulfinyl, C$_1$-C$_6$alkylsulfonyl, C$_1$-C$_6$haloalkylsulfonyl, —C(O)NH$_2$, —C(S)NH$_2$ or —S(O)₂NH₂, when p1, p2, p3 or p4 is an integer of 2 or more, each Z may be identical with or different from each other, further, when two Zs are adjacent, the adjacent two Zs may form 5-membered or 6-membered ring together with carbon atoms to which the two Zs are bonded by forming —OCH₂O— or —OCH₂CH₂O—, in this case, hydrogen atoms bonded to each carbon atom forming the ring may be arbitrarily substituted with halogen atom, $R^4$ is halogen atom, —OH, $C_1$-$C_6$alkoxy, $C_1$-$C_6$haloalkoxy, $C_1$-$C_6$alkylthio, $C_1$-$C_6$haloalkylthio, $C_1$-$C_6$alkylsulfinyl, $C_1$-$C_6$haloalkylsulfinyl, $C_1$-$C_6$alkylsulfonyl or $C_1$-$C_6$haloalkylsulfonyl, $R^5$ is $C_1$-$C_6$alkyl, $C_1$-$C_6$haloalkyl, $C_1$-$C_4$haloalkoxy $C_1$-$C_4$haloalkyl, $C_2$-$C_6$alkenyl, $C_2$-$C_6$haloalkenyl, $C_3$-$C_6$alkynyl, $C_3$-$C_6$haloalkynyl or $C_1$-$C_6$alkoxycarbonyl, $R^6$ is $C_1$-$C_6$alkyl, $C_1$-$C_6$haloalkyl, —CHO, —C(O)$R^9$, —C(O)O$R^9$, —C(O)S$R^9$, —C(S)O$R^9$, —C(S)S$R^9$ or —S(O)₂$R^9$, $R^7$ is hydrogen atom, $C_1$-$C_6$alkyl or $C_1$-$C_6$haloalkyl, $R^8$ is $C_1$-$C_6$alkyl, $R^9$ is $C_1$-$C_6$alkyl, $C_1$-$C_6$haloalkyl, $C_3$-$C_6$cycloalkyl or $C_3$-$C_6$halocycloalkyl, $R^{13}$ is $C_1$-$C_6$alkyl or $C_1$-$C_6$haloalkyl, $R^{14}$ is cyano, $C_3$-$C_6$cycloalkyl, $C_1$-$C_6$alkoxy, phenoxy, —NHC(O)$R^{30}$, —NHC(O)O$R^{30}$, $C_1$-$C_6$alkylthio, $C_1$-$C_6$alkylsulfinyl, $C_1$-$C_6$alkylsulfonyl, $C_1$-$C_6$alkoxycarbonyl, $C_5$-$C_6$cycloalkenyl, phenyl, phenyl substituted with $(Z)_{p1}$, D-21, D-22, D-52, D-53 or D-54, $R^{14a}$ is cyano, $C_3$-$C_6$cycloalkyl, —O$R^{23}$, $C_1$-$C_6$alkylthio, $C_1$-$C_6$alkylsulfonyl or phenyl, $R^{15}$ is $C_1$-$C_6$alkyl, $C_1$-$C_6$haloalkyl, $C_1$-$C_4$alkoxy $C_1$-$C_4$alkyl, $C_1$-$C_4$alkylthio $C_1$-$C_4$alkyl, $C_1$-$C_4$alkylsulfinyl $C_1$-$C_4$alkyl, $C_1$-$C_4$alkylsulfonyl $C_1$-$C_4$alkyl, $C_3$-$C_6$cycloalkyl, $C_2$-$C_6$alkenyl, $C_2$-$C_6$alkynyl or phenyl, $R^{17}$ is $C_1$-$C_6$alkyl, $C_1$-$C_6$alkoxycarbonyl $C_1$-$C_4$alkyl or $C_1$-$C_6$alkoxycarbonyl, $R^{18}$ is $C_1$-$C_6$alkyl or benzyl, $R^{23}$ is $C_1$-$C_6$alkyl, $C_1$-$C_6$haloalkyl, —C(O)$R^{30}$ or —C(O)O$R^{30}$, $R^{30}$ is $C_1$-$C_6$alkyl, $C_3$-$C_6$cycloalkyl or phenyl, m is an integer of 1 to 3, n is an integer of 0 to 2, and q3 is 0.

(3) The substituted isoxazoline compound or the salt thereof as set forth in (2), wherein $A^1$ is carbon atom or nitrogen atom, $A^2$ and $A^3$ are carbon atoms, G is G-1, L is —CH₂—, —CH(CH₃)—, —CH(CF₃)— or —CH(CN)—, X is halogen atom, cyano, nitro, —SF₅, $C_1$-$C_6$alkyl, $C_1$-$C_6$haloalkyl, hydroxy $C_1$-$C_6$haloalkyl, $C_1$-$C_6$alkoxy $C_1$-$C_6$haloalkyl, $C_3$-$C_8$halocycloalkyl, —O$R^5$, —OSO₂$R^5$ or —S(O)$_r$$R^5$, when m is 2 or 3, each X may be identical with or different from each other, Y is halogen atom, cyano, nitro, $C_1$-$C_6$alkyl, $C_1$-$C_6$haloalkyl, $C_1$-$C_4$alkyl arbitrarily substituted with $R^4$, $C_3$-$C_6$alkynyl, —O$R^5$, —S$R^5$, —NH₂, —N($R^7$)$R^6$ or —C(S)NH₂, $R^1$ is hydrogen atom, —C(O)$R^{1a}$, —C(S)$R^{1a}$, —C(O)O$R^{1a}$, —C(S)O$R^{1a}$, C(O)N($R^{1b}$)$R^{1a}$ or —C(O)N($R^{1b}$)O$R^{1a}$, $R^{1a}$ is $C_1$-$C_6$alkyl, $C_1$-$C_6$haloalkyl, $C_1$-$C_4$alkyl substituted with $R^{14}$, $C_3$-$C_6$cycloalkyl, $C_3$-$C_6$halocycloalkyl, cyano $C_3$-$C_6$cycloalkyl, E-4, E-5, E-7, $C_2$-$C_6$alkenyl, $C_2$-$C_6$alkynyl, phenyl or phenyl substituted with $(Z)_{p1}$, $R^{1b}$ is hydrogen atom or $C_1$-$C_6$alkyl, $R^2$ is hydrogen atom, $C_1$-$C_6$alkyl, $C_1$-$C_4$alkyl substituted with $R^{14a}$, $C_3$-$C_6$alkynyl, —C(O)$R^{15}$, —C(O)O$R^{15}$, $C_1$-$C_6$alkoxy or $C_1$-$C_6$haloalkylthio, $R^3$ is $C_1$-$C_6$haloalkyl or $C_3$-$C_8$halocycloalkyl, $R^4$ is —OH, $C_1$-$C_4$alkoxy or $C_1$-$C_4$alkylthio $R^5$ is $C_1$-$C_6$alkyl, $C_1$-$C_6$haloalkyl or $C_1$-$C_4$haloalkoxy $C_1$-$C_4$haloalkyl, $R^6$ is $C_1$-$C_6$alkyl, —CHO, $C_1$-$C_6$alkylcarbonyl, $C_1$-$C_6$haloalkylcarbonyl, $C_1$-$C_6$alkoxycarbonyl, $C_1$-$C_6$alkylthiocarbonyl, $C_1$-$C_6$alkoxythiocarbonyl, $C_1$-$C_6$alkyldithiocarbonyl, $C_1$-$C_6$alkylsulfonyl or $C_1$-$C_6$haloalkylsulfonyl, $R^7$ is hydrogen atom or $C_1$-$C_6$alkyl $R^{14}$ is $C_3$-$C_4$cycloalkyl, $C_1$-$C_4$alkoxy, $C_1$-$C_4$alkylthio, $C_1$-$C_4$alkylsulfinyl or $C_1$-$C_4$alkylsulfonyl, $R^{14a}$ is cyano, $C_3$-$C_4$cycloalkyl or —O$R^{23}$, $R^{15}$ is $C_1$-$C_6$alkyl, $C_1$-$C_6$haloalkyl, $C_1$-$C_4$alkoxy $C_1$-$C_4$alkyl, $C_1$-$C_4$alkylthio $C_1$-$C_4$alkyl, $C_3$-$C_6$cycloalkyl, or $C_3$-$C_6$alkenyl, $R^{23}$ is $C_1$-$C_6$alkyl, $C_1$-$C_6$haloalkyl, $C_1$-$C_6$alkylcarbonyl, $C_3$-$C_6$cycloalkylcarbonyl, $C_1$-$C_6$alkoxycarbonyl or phenylcarbonyl, and n is an integer of 0 or 1.

(4) The substituted isoxazoline compound or the salt thereof as set forth in (3), wherein L is —CH₂—, —CH(CH₃)— or —CH(CN)—, X is halogen atom, cyano, nitro, $C_1$-$C_4$alkyl, $C_1$-$C_4$haloalkyl, —O$R^5$ or —S(O)$_r$$R^5$, when m is 2 or 3, each X may be identical with or different from each other, Y is halogen atom, cyano, nitro, $C_1$-$C_4$alkyl, $C_1$-$C_4$haloalkyl, —O$R^5$, —S$R^5$, —NH₂ or —N($R^7$)$R^6$, $R^1$ is —C(O)$R^{1a}$ or —C(O)NH$R^{1a}$, $R^{1a}$ is $C_1$-$C_4$alkyl, $C_1$-$C_4$haloalkyl, $C_1$-$C_2$alkyl substituted with $R^{14}$, $C_3$-$C_4$cycloalkyl, $C_3$-$C_4$halocycloalkyl, $C_3$-$C_4$alkynyl, phenyl or phenyl substituted with $(Z)_{p1}$, $R^2$ is hydrogen atom, $C_1$-$C_4$alkyl, $C_1$-$C_2$alkyl substituted with $R^{14a}$, $C_3$-$C_4$alkynyl, $C_1$-$C_4$alkylcarbonyl or $C_1$-$C_4$alkoxycarbonyl, $R^3$ is $C_1$-$C_4$haloalkyl, $R^5$ is $C_1$-$C_4$alkyl or $C_1$-$C_4$haloalkyl, $R^6$ is $C_1$-$C_4$alkyl, —CHO, $C_1$-$C_4$alkylcarbonyl or $C_1$-$C_4$alkoxycarbonyl, $R^{14}$ is $C_3$-$C_4$cycloalkyl, $C_1$-$C_4$alkylthio, $C_1$-$C_4$alkylsulfinyl or $C_1$-$C_4$alkylsulfonyl, $R^{14a}$ is cyano or —O$R^{23}$, and $R^{23}$ is $C_1$-$C_4$alkyl, $C_1$-$C_4$haloalkyl, $C_1$-$C_4$alkylcarbonyl or $C_1$-$C_4$alkoxycarbonyl.

(5) The substituted isoxazoline compound or the salt thereof as set forth in (4), wherein $A^1$ is carbon atom, X is halogen atom or $C_1$-$C_4$haloalkyl, when m is 2 or 3, each X may be identical with or different from each other, Y is halogen atom, $C_1$-$C_4$alkyl or $C_1$-$C_4$haloalkyl, $R^1$ is —C(O)$R^{1a}$, $R^{1a}$ is $C_1$-$C_4$alkyl, $C_1$-$C_4$haloalkyl, $C_3$-$C_4$cycloalkyl or $C_3$-$C_4$alkynyl, $R^2$ is hydrogen atom or $C_1$-$C_4$alkyl, and $R^3$ is —CF₃ or —CF₂Cl.

(6) Substituted benzaldoxime compound of formula (2) or a salt thereof:

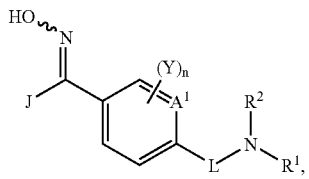

(2)

wherein
$A^1$ is carbon atom or nitrogen atom,
J is hydrogen atom or halogen atom,
L is —$CH_2$—, —$CH(CH_3)$—, —$CH(CF_3)$— or —$CH(CN)$—,
Y is halogen atom, cyano, nitro, $C_1$-$C_6$alkyl, $C_1$-$C_6$haloalkyl, $C_1$-$C_4$alkyl arbitrarily substituted with $R^4$, —$OR^5$ or —$N(R^7)R^6$,
$R^1$ is —$C(O)R^{1a}$, —$C(O)OR^{1a}$, —$C(O)N(R^{1b})R^{1a}$ or —$C(O)N(R^{1b})OR^{1a}$,
$R^{1a}$ is $C_1$-$C_6$alkyl, $C_1$-$C_6$haloalkyl, $C_1$-$C_4$alkyl substituted with $R^{14}$, $C_3$-$C_6$cyloalkyl, $C_3$-$C_6$halocyloalkyl, cyano $C_3$-$C_6$cycloalkyl, E-4, E-5, $C_2$-$C_6$alkenyl, $C_2$-$C_6$alkynyl, phenyl or phenyl substituted with $(Z)_{p1}$,
$R^{1b}$ is hydrogen atom or $C_1$-$C_6$alkyl,
$R^2$ is hydrogen atom, $C_1$-$C_6$alkyl, $C_1$-$C_4$alkyl substituted with $R^{14a}$, $C_3$-$C_6$alkynyl, —$C(O)R^{15}$, —$C(O)OR^{15}$ or $C_1$-$C_6$alkoxy,
Z is halogen atom, cyano, nitro, $C_1$-$C_6$alkyl, $C_1$-$C_6$haloalkyl, $C_1$-$C_6$alkoxy, $C_1$-$C_6$haloalkoxy, $C_1$-$C_6$alkylsulfonyloxy, $C_1$-$C_6$haloalkylsulfonyloxy, $C_1$-$C_6$alkylsulfonyl, $C_1$-$C_6$haloalkylsulfonyl or —$C(O)NH_2$, when p1 is an integer of 2 or more, each Z may be identical with or different from each other,
E-4 and E-5 are saturated heterocyclic rings of the following formulae, respectively,

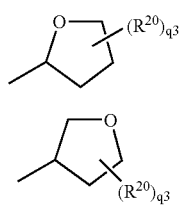

E-4

E-5

$R^4$ is $C_1$-$C_4$alkoxy,
$R^5$ is $C_1$-$C_6$alkyl, $C_1$-$C_6$haloalkyl or $C_1$-$C_4$haloalkoxy $C_1$-$C_4$haloalkyl,
$R^6$ is —CHO, $C_1$-$C_6$alkylcarbonyl, $C_1$-$C_6$haloalkylcarbonyl, $C_1$-$C_6$alkoxycarbonyl, $C_1$-$C_6$alkylsulfonyl or $C_1$-$C_6$haloalkylsulfonyl,
$R^7$ is hydrogen atom or $C_1$-$C_6$alkyl,
$R^{14}$ is $C_3$-$C_4$cycloalkyl, $C_1$-$C_4$alkoxy or $C_1$-$C_4$alkylsulfonyl,
$R^{14a}$ is cyano, $C_3$-$C_4$cycloalkyl or —$OR^{23}$,
$R^{15}$ is $C_1$-$C_6$alkyl, $C_1$-$C_6$haloalkyl, $C_1$-$C_4$alkoxy $C_1$-$C_4$alkyl, $C_3$-$C_6$cycloalkyl or $C_3$-$C_6$alkenyl,
$R^{23}$ is $C_1$-$C_6$alkyl, $C_1$-$C_6$haloalkyl, $C_1$-$C_6$alkylcarbonyl, $C_3$-$C_6$cycloalkylcarbonyl, $C_1$-$C_6$alkoxycarbonyl or phenylcarbonyl, n is an integer of 0 or 1,
p1 is an integer of 1 to 5, and
q3 is 0.
(7) A pesticide containing as an active ingredient one or more selected from the substituted isoxazoline compound and the salt thereof as set forth in (1) to (5).
(8) An agrochemical containing as an active ingredient one or more selected from the substituted isoxazoline compound and the salt thereof as set forth in (1) to (5).
(9) An endo- or ecto-parasiticide for mammals or birds containing as an active ingredient one or more selected from the substituted isoxazoline compound and the salt thereof as set forth in (1) to (5).
(10) An insecticide or acaricide containing as an active ingredient one or more selected from the substituted isoxazoline compound and the salt thereof as set forth in (1) to (5).

EFFECT OF THE INVENTION

The compound according to the present invention has an excellent insecticidal and acaricidal activity for many agricultural insect pests, spider mites, endo- or ecto-parasiticide for mammals or birds, and exerts a control effect sufficient for pest insects that acquire resistance against exiting insecticides. Further, the compound has little adverse affect on mammals, fishes and beneficial insects, and has a low persistency and a low impact on the environment. Therefore, the present invention can provide a useful and novel pesticide.

BEST MODE FOR CARRYING OUT THE INVENTION

Active compounds used as the pesticide in the present invention are the compounds in the above-mentioned items (1) to (5), and the compounds in the above-mentioned item (6) are generally novel production intermediates used for the production of these active compounds.

In the compounds included in the present invention, some compounds have geometrical isomers of E-form and Z-form depending on the kind of substituents. The present invention includes these E-forms, Z-forms and mixtures containing E-form and Z-form in an arbitrary proportion. In addition, the compounds included in the present invention have optically active forms resulting from the presence of 1 or more asymmetric carbon atoms, and the present invention includes all optically active forms or racemates.

The compounds included in the present invention can be converted to acid addition salts for example salts of hydrohalide acid such as hydrofluoric acid, hydrochloric acid, hydrobromic acid, hydriodic acid or the like, salts of inorganic acids such as nitric acid, sulfuric acid, phosphoric acid, chloric acid, perchloric acid or the like, salts of sulfonic acid such as methansulfonic acid, ethansulfonic acid, trufluoromethansulfonic acid, benzene sulfonic acid, p-toluene sulfonic acid or the like, salts of carboxylic acid such as formic acid, acetic acid, propionic acid, trifluoroacetic acid, fumaric acid, tartaric acid, oxalic acid, maleic acid, malic acid, succinic acid, benzoic acid, mandelic acid, ascorbic acid, lactic acid, gluconic acid, citric acid or the like, or salts of amino acid such as glutamic acid, aspartic acid or the like, according to a conventional method.

The compounds included in the present invention can be converted to metal salts for example salts of alkali metal such as lithium, sodium, potassium, salts of alkaline earth metal such as calcium, barium, magnesium, or salts of aluminum, according to a conventional method.

Hereinafter, concrete examples of each substituent shown in the specification are described. In the specification, "n-" means normal, "i-" means iso, "s-" means secondary, and "t-" means tertiary, and "Ph" means phenyl.

Halogen atom in the compounds of the present invention includes fluorine atom, chlorine atom, bromine atom and iodine atom. In the interim, the indication of "halo" in the specification also means these halogen atoms.

In the specification, the indication of "$C_a$-$C_b$alkyl" means straight-chain or branched-chain hydrocarbon groups having carbon atom number of a to b, and includes for example methyl, ethyl, n-propyl, i-propyl, n-butyl, i-butyl, s-butyl, t-butyl, n-pentyl, 1-methylbutyl, 2-methylbutyl, 3-methylbutyl, 1-ethylpropyl, 1,1-dimethylpropyl, 1,2-dimethylpropyl, 2,2-dimethylpropyl, n-hexyl, 1-methylpentyl, 2-methylpentyl, 1,1-dimethylbutyl, 1,3-dimethylbutyl, heptyl, octyl, nonyl, decyl, undecyl, dodecyl and the like. It is selected from the scope of the indicated carbon atom number.

In the specification, the indication of "$C_a$-$C_b$haloalkyl" means straight-chain or branched-chain hydrocarbon groups having carbon atom number of a to b that a hydrogen atom (hydrogen atoms) bonded to carbon atom is (are) arbitrarily substituted with a halogen atom (halogen atoms). In this case, if it is substituted with two or more halogen atoms, these halogen atoms may be identical with or different from each other. Concrete examples thereof are for example fluoromethyl, chloromethyl, bromomethyl, iodomethyl, difluoromethyl, chlorofluoromethyl, dichloromethyl, bromofluoromethyl, trifluoromethyl, chlorodifluoromethyl, dichlorofluoromethyl, trichloromethyl, bromodifluoromethyl, bromochlorofluoromethyl, dibromofluoromethyl, 2-fluoroethyl, 2-chloroethyl, 2-bromoethyl, 2,2-difluoroethyl, 2-chloro-2-fluoroethyl, 2,2-dichloroethyl, 2-bromo-2-fluoroethyl, 2,2,2-trifluoroethyl, 2-chloro-2,2-difluoroethyl, 2,2-dichloro-2-fluoroethyl, 2,2,2-trichloroethyl, 2-bromo-2,2-difluoroethyl, 2-bromo-2-chloro-2-fluoroethyl, 2-bromo-2,2-dichloroethyl, 1,1,2,2-tetrafluoroethyl, pentafluoroethyl, 1-chloro-1,2,2,2-tetrafluoroethyl, 2-chloro-1,2,2,2-tetrafluoroethyl, 1,2-dichloro-1,2,2-trifluoroethyl, 2-bromo-1,1,2,2-tetrafluoroethyl, 2-fluoropropyl, 2-chloropropyl, 2-bromopropyl, 2-chloro-2-fluoropropyl, 2,3-dichloropropyl, 2-bromo-3-fluoropropyl, 3-bromo-2-chloropropyl, 2,3-dibromopropyl, 3,3,3-trifluoropropyl, 3-bromo-3,3-difluoropropyl, 2,2,3,3-tetrafluoropropyl, 2-chloro-3,3,3-trifluoropropyl, 2,2,3,3,3-pentafluoropropyl, 1,1,2,3,3,3-hexafluoropropyl, heptafluoropropyl, 2,3-dichloro-1,1,2,3,3-pentafluoropropyl, 2-fluoro-1-methylethyl, 2-chloro-1-methylethyl, 2-bromo-1-methylethyl, 2,2,2-trifluoro-1-(trifluoromethyl)ethyl, 1,2,2,2-tetrafluoro-1-(trifluoromethyl)ethyl, 2,2,3,3,4,4-hexafluorobutyl, 2,2,3,4,4,4-hexafluorobutyl, 2,2,3,3,4,4,4-heptafluorobutyl, 1,1,2,2,3,3,4,4-octafluorobutyl, nonafluorobutyl, 4-chloro-1,1,2,2,3,3,4,4-octafluorobutyl, 2-fluoro-2-methylpropyl, 2-chloro-1,1-dimethylethyl, 2-bromo-1,1-dimethylethyl, 5-chloro-2,2,3,4,4,5,5-heptafluoropentyl, tridecafluorohexyl, and the like. It is selected from the scope of the indicated carbon atom number.

In the specification, the indication of "$C_a$-$C_b$cycloalkyl" means cyclic hydrocarbon groups having carbon atom number of a to b, and can form 3-membered to 6-membered single ring or conjugated ring structure. In addition, each ring may be arbitrarily substituted alkyl group in the scope of the indicated carbon atom number. Concrete examples thereof are for example cyclopropyl, 1-methylcyclopropyl, 2-methylcyclopropyl, 2,2-dimethylcyclopropyl, 2,2,3,3-tetramethylcyclopropyl, cyclobutyl, cyclopentyl, 2-methylcyclopentyl, 3-methylcyclopentyl, cyclohexyl, 2-methylcyclohexyl, 3-methylcyclohexyl, 4-methylcyclohexyl, bicyclo[2.2.1]heptan-2-yl and the like. It is selected from the scope of the indicated carbon atom number.

In the specification, the indication of "$C_a$-$C_b$halocycloalkyl" means cyclic hydrocarbon groups having carbon atom number of a to b that a hydrogen atom (hydrogen atoms) bonded to carbon atom is (are) arbitrarily substituted with a halogen atom (halogen atoms), and can form 3-membered to 6-membered single ring or conjugated ring structure. In addition, each ring may be arbitrarily substituted alkyl group in the scope of the indicated carbon atom number. The substitution for halogen atom may be in the ring structure moiety, the side chain moiety or both of them. Further, if it is substituted with two or more halogen atoms, these halogen atoms may be identical with or different from each other. Concrete examples thereof are for example 2,2-difluorocyclopropyl, 2,2-dichlorocyclopropyl, 2,2-dibromocyclopropyl, 2,2-difluoro-1-methylcyclopropyl, 2,2-dichloro-1-methylcyclopropyl, 2,2-dibromo-1-methylcyclopropyl, 2,2,3,3-tetrafluorocyclobutyl, 2-(trifluoromethyl)cyclohexyl, 3-(trifluoromethyl)cyclohexyl, 4-(trifluoromethyl)cyclohexyl and the like. It is selected from the scope of the indicated carbon atom number.

In the specification, the indication of "$C_a$-$C_b$alkenyl" means straight-chain or branched-chain unsaturated hydrocarbon groups having carbon atom number of a to b and having 1 or more double bonds. Concrete examples thereof are for example vinyl, 1-propenyl, 2-propenyl, 1-methylethenyl, 2-butenyl, 1-methyl-2-propenyl, 2-methyl-2-propenyl, 2-pentenyl, 2-methyl-2-butenyl, 3-methyl-2-butenyl, 2-ethyl-2-propenyl, 1,1-dimethyl-2-propenyl, 2-hexenyl, 2-methyl-2-pentenyl, 2,4-dimethyl-2,6-heptadienyl, 3,7-dimethyl-2,6-octadienyl, and the like. It is selected from the scope of the indicated carbon atom number.

In the specification, the indication of "$C_a$-$C_b$haloalkenyl" means straight-chain or branched-chain unsaturated hydrocarbon groups having carbon atom number of a to b and having 1 or more double bonds, which a hydrogen atom (hydrogen atoms) bonded to carbon atom is (are) arbitrarily substituted with a halogen atom (halogen atoms). In this case, if it is substituted with two or more halogen atoms, these halogen atoms may be identical with or different from each other. Concrete examples thereof are for example 2,2-dichlorovinyl, 2-fluoro-2-propenyl, 2-chloro-2-propenyl, 3-chloro-2-propenyl, 2-bromo-2-propenyl, 3-bromo-2-propenyl, 3,3-difluoro-2-propenyl, 2,3-dichloro-2-propenyl, 3,3-dichloro-2-propenyl, 2,3-dibromo-2-propenyl, 2,3,3-trifluoro-2-propenyl, 2,3,3-trichloro-2-propenyl, 1-(trifluoromethyl)ethenyl, 3-chloro-2-butenyl, 3-bromo-2-butenyl, 4,4-difluoro-3-butenyl, 3,4,4-trifluoro-3-butenyl, 3-chloro-4,4,4-trifluoro-2-butenyl, 3-bromo-2-methyl-2-propenyl, and the like. It is selected from the scope of the indicated carbon atom number.

In the specification, the indication of "$C_a$-$C_b$cycloalkenyl" means cyclic unsaturated hydrocarbon groups having carbon atom number of a to b and having 1 or more double bonds, and can form 3-membered to 6-membered single ring or conjugated ring structure. In addition, each ring may be arbitrarily substituted alkyl group in the scope of the indicated carbon atom number, and further the double bond may be either endo- or exo-form. Concrete examples thereof are for example 2-cyclopenten-1-yl, 3-cyclopenten-1-yl, 2-cyclohexen-1-yl, 3-cyclohexen-1-yl, bicyclo[2.2.1]-5-hepten-2-yl and the like. It is selected from the scope of the indicated carbon atom number.

In the specification, the indication of "$C_a$-$C_b$halocycloalkenyl" means cyclic unsaturated hydrocarbon groups having carbon atom number of a to b and having 1 or more double bonds, which a hydrogen atom (hydrogen atoms) bonded to carbon atom is (are) arbitrarily substituted with a halogen atom (halogen atoms), and can form 3-membered to 6-membered single ring or conjugated ring structure. In addition, each ring may be arbitrarily substituted alkyl group in the scope of the indicated carbon atom number, and further the double bond may be either endo- or exo-form. The substitution for halogen atom may be in the ring structure moiety, the side chain moiety or both of them. Further, if it is substituted with two or more halogen atoms, these halogen atoms may be identical with or different from each other. Concrete examples thereof are for example 2-chlorobicyclo[2.2.1]-5-hepten-2-yl and the like. It is selected from the scope of the indicated carbon atom number.

In the specification, the indication of "$C_a$-$C_b$alkynyl" means straight-chain or branched-chain unsaturated hydrocarbon groups having carbon atom number of a to b and having 1 or more triple bonds. Concrete examples thereof are for example ethynyl, 1-propynyl, 2-propynyl, 2-butynyl, 1-methyl-2-propynyl, 2-pentynyl, 1-methyl-2-butynyl, 1,1-dimethyl-2-propynyl, 2-hexynyl, and the like. It is selected from the scope of the indicated carbon atom number.

In the specification, the indication of "$C_a$-$C_b$halolkynyl" means straight-chain or branched-chain unsaturated hydrocarbon groups having carbon atom number of a to b and having 1 or more triple bonds, which a hydrogen atom (hydrogen atoms) bonded to carbon atom is (are) arbitrarily substituted with a halogen atom (halogen atoms). In this case, if it is substituted with two or more halogen atoms, these halogen atoms may be identical with or different from each other. Concrete examples thereof are for example 2-chloroethynyl, 2-bromoethynyl, 2-iodoethynyl, 3-chloro-2-propynyl, 3-bromo-2-propynyl, 3-iodo-2-propynyl, and the like. It is selected from the scope of the indicated carbon atom number.

In the specification, the indication of "$C_a$-$C_b$alkoxy" means alkyl-O— groups wherein the alkyl has carbon atom number of a to b, and includes for example methoxy, ethoxy, n-propyloxy, i-propyloxy, n-butyloxy, i-butyloxy, s-butyloxy, t-butyloxy, n-pentyloxy, n-hexyloxy and the like. It is selected from the scope of the indicated carbon atom number.

In the specification, the indication of "$C_a$-$C_b$haloalkoxy" means haloalkyl-O— groups wherein the haloalkyl has carbon atom number of a to b, and includes for example difluoromethoxy, trifluoromethoxy, chlorodifluoromethoxy, bromodifluoromethoxy, 2-fluoroethoxy, 2-chloroethoxy, 2,2,2-trifluoroethoxy, 1,1,2,2-tetrafluoroethoxy, 2-chloro-1,1,2-trifluoroethoxy, 2-bromo-1,1,2-trifluoroethoxy, pentafluoroethoxy, 2,2-dichloro-1,1,2-trifluoroethoxy, 2,2,2-trichloro-1,1-difluoroethoxy, 2-bromo-1,1,2,2-tetrafluoroethoxy, 2,2,3,3-tetrafluoropropyloxy, 1,1,2,3,3,3-hexafluoropropyloxy, 2,2,2-trifluoro-1-(trifluoromethyl)ethoxy, heptafluoropropyloxy, 2-bromo-1,1,2,3,3,3-hexafluoropropyloxy, and the like. It is selected from the scope of the indicated carbon atom number.

In the specification, the indication of "$C_a$-$C_b$alkylthio" means alkyl-S— groups wherein the alkyl has carbon atom number of a to b, and includes for example methylthio, ethylthio, n-propylthio, i-propylthio, n-butylthio, i-butylthio, s-butylthio, t-butylthio, n-pentylthio, n-hexylthio and the like. It is selected from the scope of the indicated carbon atom number.

In the specification, the indication of "$C_a$-$C_b$haloalkylthio" means haloalkyl-S— groups wherein the haloalkyl has carbon atom number of a to b, and includes for example difluoromethylthio, trifluoromethylthio, chlorodifluoromethylthio, bromodifluoromethylthio, 2,2,2-trifluoroethylthio, 1,1,2,2-tetrafluoroethylthio, 2-chloro-1,1,2-trifluoroethylthio, pentafluoroethylthio, 2-bromo-1,1,2,2-tetrafluoroethylthio, 1,1,2,3,3,3-hexafluoropropylthio, heptafluoropropylthio, 1,2,2,2-tetrafluoro-1-(trifluoromethyl)ethylthio, nonafluorobutylthio, and the like. It is selected from the scope of the indicated carbon atom number.

In the specification, the indication of "$C_a$-$C_b$alkylsulfinyl" means alkyl-S(O)— groups wherein the alkyl has carbon atom number of a to b, and includes for example methylsulfinyl, ethylsulfinyl, n-propylsulfinyl, i-propylsulfinyl, n-butylsulfinyl, i-butylsulfinyl, s-butylsulfinyl, t-butylsulfinyl, and the like. It is selected from the scope of the indicated carbon atom number.

In the specification, the indication of "$C_a$-$C_b$haloalkylsulfinyl" means haloalkyl-S(O)— groups wherein the haloalkyl has carbon atom number of a to b, and includes for example difluoromethylsulfinyl, trifluoromethylsulfinyl, chlorodifluoromethylsulfinyl, bromodifluoromethylsulfinyl, 2,2,2-trifluoroethylsulfinyl, 2-bromo-1,1,2,2-tetrafluoroethylsulfinyl, 1,2,2,2-tetrafluoro-1-(trifluoromethyl)ethylsulfinyl, nonafluorobutylsulfinyl, and the like. It is selected from the scope of the indicated carbon atom number.

In the specification, the indication of "$C_a$-$C_b$alkylsulfonyl" means alkyl-$SO_2$— groups wherein the alkyl has carbon atom number of a to b, and includes for example methylsulfonyl, ethylsulfonyl, n-propylsulfonyl, i-propylsulfonyl, n-butylsulfonyl, i-butylsulfonyl, s-butylsulfonyl, t-butylsulfonyl, n-pentylsulfonyl, n-hexylsulfonyl, and the like. It is selected from the scope of the indicated carbon atom number.

In the specification, the indication of "$C_a$-$C_b$haloalkylsulfonyl" means haloalkyl-$SO_2$— groups wherein the haloalkyl has carbon atom number of a to b, and includes for example difluoromethylsulfonyl, trifluoromethylsulfonyl, chlorodifluoromethylsulfonyl, bromodifluoromethylsulfonyl, 2,2,2-trifluoroethylsulfonyl, 1,1,2,2-tetrafluoroethylsulfonyl, 2-chloro-1,1,2-trifluoroethylsulfonyl, 2-bromo-1,1,2,2-tetrafluoroethylsulfonyl, and the like. It is selected from the scope of the indicated carbon atom number.

In the specification, the indication of "$C_a$-$C_b$alkylamino" means amino groups, which either hydrogen atom is substituted with the above-mentioned alkyl group having carbon atom number of a to b, and includes for example methylamino, ethylamino, n-propylamino, i-propylamino, n-butylamino, i-butylamino, t-butylamino, and the like. It is selected from the scope of the indicated carbon atom number.

In the specification, the indication of "di($C_a$-$C_b$alkyl)amino" means amino groups, which both hydrogen atoms are substituted with the above-mentioned alkyl groups having carbon atom number of a to b that may be identical with or different from each other, and includes for example dimethylamino, ethyl(methyl)amino, diethylamino, n-propyl(methyl)amino, i-propyl(methyl)amino, di(n-propyl)amino, n-butyl(methyl)amino, i-butyl(methyl)amino, t-butyl(methyl)amino, and the like. It is selected from the scope of the indicated carbon atom number.

In the specification, the indication of "$C_a$-$C_b$alkylcarbonyl" means alkyl-C(O)— groups wherein the alkyl has carbon atom number of a to b, and includes for example acetyl, propionyl, butyryl, isobutyryl, valeryl, isovaleryl, 2-methylbutanoyl, pivaloyl, hexanoyl, heptanoyl, and the like. It is selected from the scope of the indicated carbon atom number.

In the specification, the indication of "$C_a$-$C_b$haloalkylcarbonyl" means haloalkyl-C(O)— groups wherein the haloalkyl has carbon atom number of a to b, and includes for example fluoroacetyl, chloroacetyl, difluoroacetyl, dichloroacetyl, trifluoroacetyl, chlorodifluoroacetyl, bromodifluoroacetyl, trichloroacetyl, pentafluoropropionyl, heptafluorobutanoyl, 3-chloro-2,2-dimethylpropanoyl, and the like. It is selected from the scope of the indicated carbon atom number.

In the specification, the indication of "$C_a$-$C_b$alkoxycarbonyl" means alkyl-O—C(O)— groups wherein the alkyl has carbon atom number of a to b, and includes for example methoxycarbonyl, ethoxycarbonyl, n-propyloxycarbonyl, 1-propyloxycarbonyl, n-butoxycarbonyl, i-butoxycarbonyl, t-butoxycarbonyl, and the like. It is selected from the scope of the indicated carbon atom number.

In the specification, the indication of "$C_a$-$C_b$haloalkoxycarbonyl" means haloalkyl-O—C(O)— groups wherein the haloalkyl has carbon atom number of a to b, and includes for example 2-chloroethoxycarbonyl, 2,2-difluoroethoxycarbonyl, 2,2,2-trifluoroethoxycarbonyl, 2,2,2-trichloroethoxycarbonyl, and the like. It is selected from the scope of the indicated carbon atom number.

In the specification, the indication of "$C_a$-$C_b$alkylthiocarbonyl" means alkyl-S—C(O)— groups wherein the alkyl has carbon atom number of a to b, and includes for example methylthio-C(O)—, ethylthio-C(O)—, n-propylthio-C(O)—, i-propylthio-C(O)—, n-butylthio-C(O)—, i-butylthio-C(O)—, t-butylthio-C(O)—, and the like. It is selected from the scope of the indicated carbon atom number.

In the specification, the indication of "$C_a$-$C_b$alkoxythiocarbonyl" means alkyl-O—C(S)— groups wherein the alkyl has carbon atom number of a to b, and includes for example methoxy-C(S)—, ethoxy-C(S)—, n-propyloxy-C(S)—, i-propyloxy-C(S)—, and the like. It is selected from the scope of the indicated carbon atom number.

In the specification, the indication of "$C_a$-$C_b$alkyldithiocarbonyl" means alkyl-S—C(S)— groups wherein the alkyl has carbon atom number of a to b, and includes for example methylthio-C(S)—, ethylthio-C(S)—, n-propylthio-C(S)—, i-propylthio-C(S)—, and the like. It is selected from the scope of the indicated carbon atom number.

In the specification, the indication of "$C_a$-$C_b$alkylaminocarbonyl" means carbamoyl groups, which either hydrogen atom is substituted with the above-mentioned alkyl group having carbon atom number of a to b, and includes for example methylcarbamoyl, ethylcarbamoyl, n-propylcarbamoyl, i-propylcarbamoyl, n-butylcarbamoyl, i-butylcarbamoyl, s-butylcarbamoyl, t-butylcarbamoyl, and the like. It is selected from the scope of the indicated carbon atom number.

In the specification, the indication of "$C_a$-$C_b$haloalkylaminocarbonyl" means carbamoyl groups, which either hydrogen atom is substituted with the above-mentioned haloalkyl group having carbon atom number of a to b, and includes for example 2-fluoroethylcarbamoyl, 2-chloroethylcarbamoyl, 2,2-difluoroethylcarbamoyl, 2,2,2-trifluoroethylcarbamoyl, and the like. It is selected from the scope of the indicated carbon atom number.

In the specification, the indication of "di($C_a$-$C_b$alkyl)aminocarbonyl" means carbamoyl groups, which both hydrogen atoms are substituted with the above-mentioned alkyl group having carbon atom number of a to b that may be identical with or different from each other, and includes for example N,N-dimethylcarbamoyl, N-ethyl-N-methylcarbamoyl, N,N-diethylcarbamoyl, N,N-di-n-propylcarbamoyl, N,N-di-n-butylcarbamoyl, and the like. It is selected from the scope of the indicated carbon atom number.

In the specification, the indication of "$C_a$-$C_b$alkylaminosulfonyl" means sulfamoyl groups, which either hydrogen atom is substituted with the above-mentioned alkyl group having carbon atom number of a to b, and includes for example methylsulfamoyl, ethylsulfamoyl, n-propylsulfamoyl, i-propylsulfamoyl, n-butylsulfamoyl, i-butylsulfamoyl, s-butylsulfamoyl, t-butylsulfamoyl, and the like. It is selected from the scope of the indicated carbon atom number.

In the specification, the indication of "di($C_a$-$C_b$alkyl)aminosulfonyl" means sulfamoyl groups, which both hydrogen atoms are substituted with the above-mentioned alkyl group having carbon atom number of a to b that may be identical with or different from each other, and includes for example N,N-dimethylsulfamoyl, N-ethyl-N-methylsulfamoyl, N,N-diethylsulfamoyl, N,N-di-n-propylsulfamoyl, N,N-di-n-butylsulfamoyl, and the like. It is selected from the scope of the indicated carbon atom number.

In the specification, the indication of "tri($C_a$-$C_b$alkyl)silyl" means silyl groups substituted with the above-mentioned alkyl group having carbon atom number of a to b that may be identical with or different from each other, and includes for example trimethylsilyl, triethylsilyl, tri(n-propyl)silyl, ethyldimethylsilyl, n-propyldimethylsilyl, n-butyldimethylsilyl, i-butyldimethylsilyl, t-butyldimethylsilyl, and the like. It is selected from the scope of the indicated carbon atom number.

In the specification, the indication of "di($C_a$-$C_b$alkyl)thiophosphoryl" means thiophosphoryl groups substituted with the above-mentioned alkyl group having carbon atom number of a to b that may be identical with or different from each other, and includes for example $(CH_3O)_2P(S)$—, $(CH_3CH_2O)_2P(S)$—, and the like. It is selected from the scope of the indicated carbon atom number.

In the specification, the indication of "$C_a$-$C_b$alkylsulfonyloxy" means alkylsulfonyl-O— groups wherein the alkyl has carbon atom number of a to b, and includes for example methylsulfonyloxy, ethylsulfonyloxy, n-propylsulfonyloxy, i-propylsulfonyloxy, and the like. It is selected from the scope of the indicated carbon atom number.

In the specification, the indication of "$C_a$-$C_b$haloalkylsulfonyloxy" means haloalkylsulfonyl-O— groups wherein the haloalkyl has carbon atom number of a to b, and includes for example difluoromethylsulfonyloxy, triflubromethylsulfonyloxy, chlorodifluoromethylsulfonyloxy, bromodifluoromethanesulfonyloxy, and the like. It is selected from the scope of the indicated carbon atom number.

In the specification, the indication of "$C_a$-$C_b$cycloalkyl $C_d$-$C_e$alkyl", "$C_a$-$C_b$alkoxy $C_d$-$C_e$alkyl", "$C_a$-$C_b$haloalkoxy $C_d$-$C_e$alkyl", "$C_a$-$C_b$alkylthio $C_d$-$C_e$alkyl", "$C_a$-$C_b$haloalkylthio $C_d$-$C_e$alkyl", "$C_a$-$C_b$alkylsulfinyl $C_d$-$C_e$alkyl", "$C_a$-$C_b$haloalkylsulfinyl $C_d$-$C_e$alkyl", "$C_a$-$C_b$alkylsulfonyl $C_d$-$C_e$alkyl", "$C_a$-$C_b$haloalkylsulfonyl $C_d$-$C_e$alkyl", "cyano $C_d$-$C_e$alkyl", "$C_a$-$C_b$alkoxycarbonyl $C_d$-$C_e$alkyl", "$C_a$-$C_b$haloalkoxycarbonyl $C_d$-$C_e$alkyl", "phenyl $C_d$-$C_e$alkyl", or "phenyl $C_d$-$C_e$alkyl substituted with $(Z)_{p1}$" means alkyl groups having carbon atom number of d to e, which a hydrogen atom (hydrogen atoms) bonded to carbon atom is (are) arbitrarily substituted with the $C_a$-$C_b$cycloalkyl, $C_a$-$C_b$alkoxy, $C_a$-$C_b$haloalkoxy, $C_a$-$C_b$alkylthio, $C_a$-$C_b$haloalkylthio, $C_a$-$C_b$alkylsulfinyl, $C_a$-$C_b$haloalkylsulfinyl, $C_a$-$C_b$alkylsulfonyl, $C_a$-$C_b$haloalkylsulfonyl, $C_a$-$C_b$alkoxycarbonyl, $C_a$-$C_b$haloalkoxycarbonyl, cyano, phenyl, or phenyl substituted with $(Z)_{p1}$ that has the meaning mentioned above, respectively. It is selected from the scope of the indicated carbon atom number.

In the specification, the indication of "$C_a$-$C_b$alkyl arbitrarily substituted with $R^4$", "$C_a$-$C_b$alkyl arbitrarily substituted with $R^{14}$", "$C_a$-$C_b$alkyl arbitrarily substituted with $R^{14a}$", "$C_a$-$C_b$alkyl arbitrarily substituted with $R^{22}$", "$C_a$-$C_b$alkyl arbitrarily substituted with $R^{29}$" or "$C_a$-$C_b$alkyl arbitrarily substituted with $R^{32}$" means straight-chain or branched-chain hydrocarbon groups having carbon atom number of a to b, which a hydrogen atom (hydrogen atoms) bonded to carbon atom is (are) arbitrarily substituted with $R^4$, $R^{14}$, $R^{14a}$, $R^{22}$, $R^{29}$ or $R^{32}$. It is selected from the scope of the indicated carbon atom number.

In this case, when two or more substituents $R^4$, $R^{14}$, $R^{14a}$, $R^{22}$, $R^{29}$ or $R^{32}$ are present on the $C_a$-$C_b$alkyl, respective $R^4$, $R^{14}$, $R^{14a}$, $R^{22}$, $R^{29}$ or $R^{32}$ may be identical with or different from each other.

In the specification, the indication of "hydroxy $C_d$-$C_e$haloalkyl", "$C_a$-$C_b$alkoxy $C_d$-$C_e$haloalkyl", "$C_a$-$C_b$haloalkoxy $C_d$-$C_e$haloalkyl", "$C_a$-$C_b$alkylthio $C_d$-$C_e$haloalkyl", "$C_a$-$C_b$haloalkylthio $C_d$-$C_e$haloalkyl" or "cyano $C_d$-$C_e$haloalkyl" means the haloalkyl having carbon atom number of d to e, which a hydrogen atom (hydrogen atoms) or a halogen atom (halogen atoms) bonded to carbon atom is (are) arbitrarily substituted with the $C_a$-$C_b$alkoxy, $C_a$-$C_b$haloalkoxy, $C_a$-$C_b$alkylthio, $C_a$-$C_b$haloalkylthio, hydroxy or cyano. It is selected from the scope of the indicated carbon atom number.

In the specification, the indication of "$C_a$-$C_b$cycloalkyl arbitrarily substituted with $R^4$", "$C_a$-$C_b$cycloalkyl arbitrarily substituted with $R^{14}$" or "$C_a$-$C_b$cycloalkyl arbitrarily substituted with $R^{22}$" means the cycloalkyl groups having carbon atom number of a to b, which a hydrogen atom (hydrogen atoms) bonded to carbon atom is (are) arbitrarily substituted with $R^4$, $R^{14}$ or $R^{22}$. The substitution for $R^4$, $R^{14}$ or $R^{22}$ may be in the ring structure moiety, the side chain moiety or both of them. In this case, when two or more substituents $R^4$, $R^{14}$ or $R^{22}$ are present on the $C_a$-$C_b$cycloalkyl, respective $R^4$, $R^{14}$ or $R^{22}$ may be identical with or different from each other.

In the specification, the indication of "$C_a$-$C_b$alkenyl arbitrarily substituted with $R^4$", "$C_a$-$C_b$alkenyl arbitrarily substituted with $R^{14}$" or "$C_a$-$C_b$alkenyl arbitrarily substituted with $R^{22}$" means the alkenyl groups having carbon atom number of a to b, which a hydrogen atom (hydrogen atoms) bonded to carbon atom is (are) arbitrarily substituted with $R^4$, $R^{14}$ or $R^{22}$. It is selected from the scope of the indicated carbon atom number. In this case, when two or more substituents $R^4$, $R^{14}$ or $R^{22}$ are present on the $C_a$-$C_b$alkenyl, respective $R^4$, $R^{14}$ or $R^{22}$ may be identical with or different from each other.

In the specification, the indication of "$C_a$-$C_b$alkynyl arbitrarily substituted with $R^4$", "$C_a$-$C_b$alkynyl arbitrarily substituted with $R^{14}$" or "$C_a$-$C_b$alkynyl arbitrarily substituted with $R^{22}$" means the alkynyl groups having carbon atom number of a to b, which a hydrogen atom (hydrogen atoms) bonded to carbon atom is (are) arbitrarily substituted with $R^4$, $R^{14}$ or $R^{22}$. It is selected from the scope of the indicated carbon atom number. In this case, when two or more substituents $R^4$, $R^{14}$ or $R^{22}$ are present on the $C_a$-$C_b$alkenyl, respective $R^4$, $R^{14}$ or $R^{22}$ may be identical with or different from each other.

In the specification, the indication of "$C_a$-$C_b$alkoxy $C_d$-$C_e$alkoxy" means the $C_d$-$C_e$alkoxy, which a hydrogen atom (hydrogen atoms) bonded to carbon atom is (are) arbitrarily substituted with $C_a$-$C_b$alkoxy. It is selected from the scope of the indicated carbon atom number.

In the specification, concrete examples of the indication of "$R^{1b}$ together with $R^{1a}$ may form 3- to 7-membered ring together with the nitrogen atom bonding them by forming $C_2$-$C_6$ alkylene chain, in this case, the alkylene chain may contain one oxygen atom, sulfur atom or nitrogen atom", "$R^{10}$ together with $R^9$ may form 3- to 7-membered ring with the nitrogen atom bonding them by forming $C_2$-$C_6$alkylene chain, in this case, the alkylene chain may contain one oxygen atom, sulfur atom or nitrogen atom", "$R^{16}$ together with $R^{15}$ may form 5- to 6-membered ring with the nitrogen atom bonding them by forming $C_4$-$C_5$alkylene chain, in this case, the alkylene chain may contain one oxygen atom or sulfur atom", "$R^{18}$ together with $R^{17}$ may form 5- to 6-membered ring with the nitrogen atom bonding them by forming $C_4$-$C_5$alkylene chain, in this case, the alkylene chain may contain one oxygen atom or sulfur atom", "$R^{24}$ together with $R^{23}$ may form 4- to 6-membered ring with the nitrogen atom bonding them by forming $C_3$-$C_5$alkylene chain, in this case, the alkylene chain may contain one oxygen atom, sulfur atom or nitrogen atom", "$R^{27}$ together with $R^{26}$ may form 3- to 6-membered ring with the nitrogen atom bonding them by forming $C_2$-$C_5$alkylene chain, in this case, the alkylene chain may contain one oxygen atom, sulfur atom or nitrogen atom", and "$R^{31}$ together with $R^{30}$ may form 3- to 6-membered ring with the nitrogen atom bonding them by forming $C_2$-$C_5$alkylene chain, in this case, the alkylene chain may contain one oxygen atom or sulfur atom", are for example aziridine ring, azetidine ring, pyrrolidine ring, oxazolidine ring, thiazoridine ring, imidazolidine ring, piperidine ring, morpholine ring, thiomorpholine ring, piperazine ring, homopiperidine ring, heptamethyleneimine ring, and the like. It is selected from the scope of the indicated carbon atom number.

In the specification, concrete examples of the indication of "$R^2$ together with $R^1$ may form 5- to 7-membered ring with the nitrogen atom bonding them by forming $C_4$-$C_6$alkylene chain, in this case, the alkylene chain may contain one oxygen atom, sulfur atom or nitrogen atom", and may be substituted with oxo or thioxo", and "$R^7$ together with $R^6$ may form 3- to 7-membered ring with the nitrogen atom bonding them by forming $C_2$-$C_6$alkylene chain, in this case, the alkylene chain may contain one oxygen atom, sulfur atom or nitrogen atom", and may be substituted with oxo or thioxo", are for example aziridine ring, azetidine ring, azetidin-2-one ring, pyrrolidine ring, pyrrolidin-2-one ring, oxazolidine ring, oxazolidin-2-one ring, oxazolidin-2-thione ring, thiazoridine ring, thiazoridin-2-one ring, thiazoridin-2-thione ring, imidazolidine ring, imidazolidin-2-one ring, imidazolidin-2-thione ring, piperidine ring, piperidin-2-one ring, piperidin-2-thione ring, 2H-3,4,5,6-tetrahydro-1,3-oxadin-2-one ring, 2H-3,4,5,6-tetrahydro-1,3-oxadin-2-thione ring, morpholine ring, 2H-3,4,5,6-tetrahydro-1,3-thiadin-2-one ring, 2H-3,4,5,6-tetrahydro-1,3-thiadin-2-thione ring, thiomorpholine ring, perhydropyrimidin-2-one ring, piperazine ring, homopiperidine ring, homopiperidin-2-one ring, heptamethyleneimine ring, and the like. It is selected from the scope of the indicated carbon atom number.

In the specification, concrete examples of the indication of "$R^{2b}$ together with $R^{2a}$ may form 3- to 6-membered ring with the carbon atom bonding them by forming $C_2$-$C_5$alkylene chain, in this case, the alkylene chain may contain one oxygen atom, sulfur atom or nitrogen atom" are for example cyclopropane ring, cyclobutane ring, cyclopentane ring, tetrahydrofuran ring, tetrahydrothiophene ring, pyrrolidine ring, cyclohexane ring, tetrahydropyran ring, tetrahydrothiopyran ring, piperidine ring, cycloheptane ring, oxepane ring, thiepane ring, azepane ring, and the like. It is selected from the scope of the indicated carbon atom number.

In the compounds included in the present invention, the combination of the atoms of $A^1$, $A^2$ and $A^3$ includes for example the following groups.

That is, A-I: $A^1$, $A^2$ and $A^3$ are carbon atoms.
A-II: $A^1$ is nitrogen atom, $A^2$ and $A^3$ are carbon atoms.
A-III: nitrogen atom, $A^1$ and $A^3$ are carbon atoms.
A-IV: $A^1$ and $A^3$ are nitrogen atoms, $A^2$ is carbon atom.
A-V: $A^1$ and $A^2$ are nitrogen atoms, $A^3$ is carbon atom.
A-V: $A^2$ and $A^3$ are nitrogen atoms, $A^1$ is carbon atom.

In the compounds included in the present invention, the substituent shown in G includes aromatic 6-membered and 5-membered rings. Among them, aromatic 6-membered rings shown in G-1, G-3 and G-4 and aromatic 5-membered rings shown in any one of G-13, G-14, G-17, G-18, G-20, G-21 and G-22 are preferable, and aromatic 6-membered ring shown in G-1 is particularly preferable.

In the compounds included in the present invention, the substituent L includes for example the following groups.
That is, L-I: —$CH_2$—.
L-II: —$CH(CH_3)$— and —$CH(CN)$—.
L-III: —$CH(CH_3)$—, —$CH(CF_3)$— and —$CH(CN)$—.
L-IV: —$CH(R^{2a})$— (wherein $R^{2a}$ is cyano, $C_1$-$C_6$alkyl, $C_1$-$C_6$haloalkyl, $C_3$-$C_6$cycloalkyl, —$C(O)NH_2$ or —$C(S)NH_2$).
L-V: —$CH(R^{2a})CH_2$— (wherein $R^{2a}$ is hydrogen atom, cyano or $C_1$-$C_6$alkyl).
L-VI: —$N(R^{2c})$— and —$CH(R^{2a})N(R^{2c})$—(wherein $R^{2a}$ is hydrogen atom, cyano or $C_1$-$C_6$alkyl, $R^{2c}$ is hydrogen atom, $C_1$-$C_6$alkyl, $C_1$-$C_6$alkylcarbonyl, $C_1$-$C_6$haloalkylcarbonyl or $C_3$-$C_6$cycloalkylcarbonyl).

In the compounds included in the present invention, the substituent L preferably includes the region shown by L-I to L-V, among them, the region shown by L-I to L-III is more preferable, and further the region shown by L-I and L-II is particularly preferable.

In the compounds included in the present invention, the substituent X includes for example the following groups. In each case mentioned below, when m is an integer of 2 or more, Xs may be identical with or different from each other.
That is, X-I: halogen atom and $C_1$-$C_4$haloalkyl.
X-II: halogen atom, cyano, nitro, $C_1$-$C_4$alkyl, $C_1$-$C_4$haloalkyl, —$OR^5$, and —$S(O)_rR^5$ (wherein $R^5$ is $C_1$-$C_4$alkyl or $C_1$-$C_4$haloalkyl, and r is an integer of 0 to 2).
X-III: halogen atom, cyano, nitro, —$SF_5$, $C_1$-$C_6$alkyl, $C_1$-$C_6$haloalkyl, hydroxy $C_1$-$C_6$haloalkyl, $C_1$-$C_6$alkoxy $C_1$-$C_6$haloalkyl, $C_3$-$C_8$halocycloalkyl, —$OR^5$, —$OSO_2R^5$, and —$S(O)_rR^5$ (wherein $R^5$ is $C_1$-$C_6$alkyl, $C_1$-$C_6$haloalkyl or $C_1$-$C_3$haloalkoxy $C_1$-$C_3$haloalkyl, and r is an integer of 0 to 2).
X-IV: halogen atom, $C_1$-$C_6$haloalkyl, $C_1$-$C_6$haloalkyl arbitrarily substituted with $R^4$ (wherein $R^4$ is —OH, $C_1$-$C_6$alkoxy or $C_1$-$C_6$haloalkoxy), $C_3$-$C_8$halocycloalkyl, $C_2$-$C_6$haloalkenyl, $C_2$-$C_6$haloalkynyl, —$OR^5$, —$OSO_2R^5$ and —$S(O)_rR^5$ (wherein $R^5$ is $C_1$-$C_6$haloalkyl, $C_1$-$C_3$haloalkoxy $C_1$-$C_3$haloalkyl, $C_2$-$C_6$haloalkenyl or $C_3$-$C_6$haloalkynyl, and r is an integer of 0 to 2).
X-V: halogen atom, $C_1$-$C_6$alkyl, $C_1$-$C_6$haloalkyl, $C_1$-$C_6$alkyl arbitrarily substituted with $R^4$ (wherein $R^4$ is $C_1$-$C_6$alkoxy, $C_1$-$C_6$haloalkoxy, $C_1$-$C_6$alkylthio, $C_1$-$C_6$haloalkylthio, $C_1$-$C_6$alkylsulfinyl, $C_1$-$C_6$alkylsulfonyl or $C_1$-$C_6$haloalkylsulfonyl), $C_3$-$C_8$cycloalkyl, $C_2$-$C_6$alkenyl, $C_2$-$C_6$alkynyl, —OH, —$OR^5$, —$OSO_2R^5$ and $S(O)_rR^5$ (wherein $R^5$ is $C_1$-$C_6$alkyl, $C_2$-$C_6$alkenyl, $C_3$-$C_6$alkynyl, or $C_1$-$C_6$alkoxycarbonyl, and r is an integer of 0 to 2).
X-VI: halogen atom, $C_1$-$C_6$haloalkyl, cyano, nitro, —$SF_5$ and tri($C_1$-$C_6$alkyl)silyl.
X-VII: m is 2, two adjacent Xs form 5- or 6-membered ring with the carbon atoms to which the two Xs are bonded by forming —$CF_2OCF_2$—, —$OCF_2O$—, —$CF_2OCF_2O$— or —$OCF_2CF_2O$—.

In the compounds included in the present invention, m indicating the number of substituent X is an integer of 0 to 5. Among them, m is preferably 1, 2 and 3.

In the compounds included in the present invention, the substituent Y includes for example the following groups. In each case mentioned below, when n is an integer of 2 or more, Ys may be identical with or different from each other.
That is, Y-I: halogen atom, $C_1$-$C_4$alkyl and $C_1$-$C_4$haloalkyl.
Y-I: halogen atom, cyano, nitro, $C_1$-$C_4$alkyl, $C_1$-$C_4$haloalkyl, —$OR^5$, —$SR^5$ (wherein $R^5$ is $C_1$-$C_4$alkyl or $C_1$-$C_4$haloalkyl), —$NH_2$ and —$N(R^7)R^6$ (wherein $R^6$ is $C_1$-$C_4$alkyl, —CHO, $C_1$-$C_4$alkylcarbonyl or $C_1$-$C_4$alkoxycarbonyl, and $R^7$ is hydrogen atom or $C_1$-$C_4$alkyl).
Y-II: halogen atom, cyano, nitro, $C_1$-$C_6$alkyl, $C_1$-$C_6$haloalkyl, $C_1$-$C_4$alkyl arbitrarily substituted with $R^4$ (wherein $R^4$ is —OH, $C_1$-$C_4$alkoxy or $C_1$-$C_4$alkylthio), $C_3$-$C_6$alkynyl, —$OR^5$, —$SR^5$ (wherein $R^5$ is $C_1$-$C_6$alkyl or $C_1$-$C_6$haloalkyl), —$NH_2$, —$N(R^7)R^6$ (wherein $R^6$ is $C_1$-$C_6$alkyl, —CHO, $C_1$-$C_6$alkylcarbonyl, $C_1$-$C_6$haloalkylcarbonyl, $C_1$-$C_6$alkoxycarbonyl, $C_1$-$C_6$alkylthiocarbonyl, $C_1$-$C_6$alkoxythiocarbonyl, $C_1$-$C_6$alkyldithiocarbonyl, $C_1$-$C_6$alkylsulfonyl or $C_1$-$C_6$haloalkylsulfonyl, $R^7$ is hydrogen atom or $C_1$-$C_6$alkyl) and —$C(S)NH_2$.
Y-IV: halogen atom, cyano, $C_1$-$C_6$alkyl and $C_1$-$C_6$alkyl arbitrarily substituted with $R^4$ (wherein $R^4$ is halogen atom, —OH, $C_1$-$C_6$alkoxy, $C_1$-$C_6$haloalkoxy, $C_1$-$C_6$alkylthio, $C_1$-$C_6$haloalkylthio, $C_1$-$C_6$alkylsulfinyl, $C_1$-$C_6$haloalkylsulfinyl, $C_1$-$C_6$alkylsulfonyl or $C_1$-$C_6$haloalkylsulfonyl), $C_2$-$C_6$alkynyl, tri($C_1$-$C_6$alkyl)silylethynyl, —$C(O)NH_2$ and —$C(S)NH_2$.
Y-V: halogen atom, $C_1$-$C_6$alkyl, —$OR^5$, —$OSO_2R^5$ and —$S(O)_rR^5$ (wherein $R^5$ is $C_1$-$C_6$alkyl, $C_1$-$C_6$haloalkyl, $C_2$-$C_6$alkenyl, $C_2$-$C_6$haloalkenyl, $C_3$-$C_6$alkynyl or $C_3$-$C_6$haloalkynyl and r is an integer of 0 to 2).
Y-VI: halogen atom, nitro, $C_1$-$C_6$alkyl, —$NH_2$, —$N(R^7)R^6$ (wherein $R^6$ is $C_1$-$C_6$alkyl, $C_1$-$C_6$haloalkyl, —CHO, —$C(O)R^9$, —$C(O)OR^9$, —$C(O)SR^9$, —$C(S)OR^9$, —$C(S)SR^9$ or —$S(O)_2R^9$, $R^7$ is hydrogen atom, $C_1$-$C_6$alkyl or $C_1$-$C_6$haloalkyl, and $R^9$ is $C_1$-$C_6$alkyl, $C_1$-$C_6$haloalkyl, $C_3$-$C_6$cycloalkyl or $C_3$-$C_6$halocycloalkyl), and —$N=C(R^9)OR^8$ (wherein $R^8$ is $C_1$-$C_6$alkyl, and $R^9$ is $C_1$-$C_6$alkyl or $C_1$-$C_6$haloalkyl).

In the compounds included in the present invention, n indicating the number of substituent Y is an integer of 0 to 4. Among them, n is preferably 0 and 1.

In the compounds included in the present invention, the substituent $R^1$ includes for example the following groups.
That is, $R^1$-I: —$C(O)R^{1a}$ (wherein $R^{1a}$ is $C_1$-$C_4$alkyl, $C_1$-$C_4$haloalkyl, $C_3$-$C_6$cycloalkyl or $C_3$-$C_4$alkynyl).
$R^1$-II: —$C(O)R^{1a}$ and —$C(O)NHR^{1a}$ (wherein $R^{1a}$ is $C_1$-$C_4$alkyl, $C_1$-$C_4$haloalkyl, $C_1$-$C_2$alkyl substituted with $R^{14}$, $C_3$-$C_4$cycloalkyl, $C_3$-$C_4$halocycloalkyl, $C_3$-$C_4$alkynyl, phenyl or phenyl substituted with $(Z)_{p1}$, $R^{14}$ is $C_3$-$C_4$cycloalkyl, $C_1$-$C_4$alkylthio, $C_1$-$C_4$alkylsulfinyl or $C_1$-$C_4$alkylsulfonyl, Z is fluorine atom, p1 is an integer of 1 to 5).
$R^1$-III: —$C(O)R^{1a}$ and —$C(S)R^{1a}$ (wherein $R^{1a}$ is $C_1$-$C_6$alkyl, $C_1$-$C_6$haloalkyl, $C_1$-$C_4$alkyl substituted with $R^{14}$, $C_3$-$C_6$cycloalkyl, $C_3$-$C_6$halocycloalkyl, cyano $C_3$-$C_6$cycloalkyl, E-4, E-5, E-7, $C_2$-$C_6$alkenyl, $C_2$-$C_6$alkynyl, phenyl or phenyl substituted with $(Z)_{p1}$, $R^{14}$ is $C_3$-$C_4$cycloalkyl, $C_1$-$C_4$alkoxy, $C_1$-$C_4$alkylthio, $C_1$-$C_4$alkylsulfinyl or $C_1$-$C_4$alkylsulfonyl, Z is halogen atom, cyano, nitro, $C_1$-$C_6$alkyl, $C_1$-$C_6$haloalkyl, $C_1$-$C_6$alkoxy, $C_1$-$C_6$haloalkoxy, $C_1$-$C_6$alkylsulfonyloxy, $C_1$-$C_6$haloalkylsulfonyloxy, $C_1$-$C_6$alkylsulfonyl, $C_1$-$C_6$haloalkylsulfonyl or —$C(O)NH_2$, when p1 is an integer of 2 or more, each Z may be identical with or different from each other, p1 is an integer of 1 to 5, q3 is 0, and r is an integer of 0 to 2).
$R^1$-IV: —$C(O)OR^{1a}$ and —$C(S)OR^{1a}$ (wherein $R^{1a}$ is $C_1$-$C_6$alkyl, $C_1$-$C_6$haloalkyl, $C_3$-$C_6$cycloalkyl or $C_2$-$C_6$alkynyl).
$R^1$-V: —$C(O)N(R^{1b})R^{1a}$ and —$C(O)N(R^{1b})OR^{1a}$ (wherein $R^{1a}$ is $C_1$-$C_6$alkyl, $C_1$-$C_6$haloalkyl, $C_3$-$C_6$cycloalkyl or $C_2$-$C_6$alkynyl, $R^{1b}$ is hydrogen atom or $C_1$-$C_6$alkyl).
$R^1$-VI: hydrogen atom.

$R^1$-VII: —C(O)$R^{1a}$ and —C(S)$R^{1a}$ (wherein $R^{1a}$ is $C_1$-$C_6$alkyl, $C_1$-$C_6$haloalkyl, $C_1$-$C_4$alkyl substituted with $R^{14}$, $C_3$-$C_8$cycloalkyl, $C_3$-$C_6$halocycloalkyl, cyano $C_3$-$C_6$cycloalkyl, phenyl $C_3$-$C_6$cycloalkyl, E-4 to E-7, $C_2$-$C_6$alkenyl, $C_2$-$C_6$haloalkenyl, $C_2$-$C_6$alkynyl, $C_2$-$C_6$haloalkynyl, phenyl or phenyl substituted with $(Z)_{p1}$, D-1 to D-4, D-15 to D-17, D-21 to D-24, D-52 to D-58 or D-59, $R^{13}$ is $C_1$-$C_6$alkyl or $C_1$-$C_6$haloalkyl, $R^{14}$ is cyano, $C_3$-$C_6$cycloalkyl, $C_1$-$C_6$alkoxy, phenoxy, —NHC(O)$R^{30}$, —NHC(O)O$R^{30}$, $C_1$-$C_6$alkylthio, $C_1$-$C_6$alkylsulfinyl, $C_1$-$C_6$alkylsulfonyl, $C_1$-$C_6$alkoxycarbonyl, $C_5$-$C_6$cycloalkenyl, phenyl or phenyl substituted with $(Z)_{p1}$, D-21, D-22, D-52, D-53 or D-54, $R^{30}$ is $C_1$-$C_6$alkyl, $C_1$-$C_6$cycloalkyl or phenyl, Z is halogen atom, cyano, nitro, $C_1$-$C_6$alkyl, $C_1$-$C_6$haloalkyl, $C_1$-$C_6$alkoxy, $C_1$-$C_6$haloalkoxy, $C_1$-$C_6$alkylsulfonyloxy, $C_1$-$C_6$haloalkylsulfonyloxy, $C_1$-$C_6$alkylthio, $C_1$-$C_6$haloalkylthio, $C_1$-$C_6$alkylsulfinyl, $C_1$-$C_6$haloalkylsulfinyl, $C_1$-$C_6$alkylsulfonyl, $C_1$-$C_6$haloalkylsulfonyl, —C(O)$NH_2$, —C(S)$NH_2$ or —S(O)$_2NH_2$, when p1, p2, p3 or p4 is an integer of 2 or more, each Z may be identical with or different from each other, further, when two Zs are adjacent, the adjacent two Zs may form 5-membered or 6-membered ring together with carbon atoms to which the two Zs are bonded by forming —OCH$_2$O— or —OCH$_2$CH$_2$O—, in this case, hydrogen atoms bonded to each carbon atom forming the ring may be arbitrarily substituted with halogen atom, p1 is an integer of 1 to 5, p2 is an integer of 0 to 4, p3 is an integer of 0 to 3, p4 is an integer of 0 to 2, q3 is 0, r is an integer of 0 to 2, and t is an integer of 0 or 1).

$R^1$-VIII: —C(O)O$R^{1a}$, C(O)S$R^{1a}$, —C(S)O$R^{1a}$ and —C(S)S$R^{1a}$ (wherein $R^{1a}$ is $C_1$-$C_4$alkyl, $C_1$-$C_4$haloalkyl, $C_1$-$C_2$alkyl substituted with $R^{14}$, $C_3$-$C_4$cycloalkyl, $C_3$-$C_4$halocycloalkyl, $C_3$-$C_4$alkynyl, phenyl or phenyl substituted with $(Z)_{p1}$, $R^{14}$ is $C_3$-$C_4$cycloalkyl, $C_1$-$C_4$alkylthio, $C_1$-$C_4$alkylsulfinyl or $C_1$-$C_4$alkylsulfonyl, Z is fluorine atom, p1 is an integer of 1 to 5).

$R^1$-IX: —C(O)N($R^{1b}$)$R^{1a}$, —C(O)N($R^{1b}$)O$R^{1a}$ and —C(S)N($R^{1b}$)$R^{1a}$ (wherein $R^{1a}$ is $C_1$-$C_4$alkyl, $C_1$-$C_4$haloalkyl, $C_1$-$C_2$alkyl substituted with $R^{14}$, $C_3$-$C_4$cycloalkyl, $C_3$-$C_4$halocycloalkyl, $C_3$-$C_4$alkynyl, phenyl or phenyl substituted with $(Z)_{p1}$, $R^{14}$ is $C_3$-$C_4$cycloalkyl, $C_1$-$C_4$alkylthio, $C_1$-$C_4$alkylsulfinyl or $C_1$-$C_4$alkylsulfonyl, Z is fluorine atom, p1 is an integer of 1 to 5, $R^{1b}$ is hydrogen atom or $C_1$-$C_6$alkyl, or $R^{1b}$ together with $R^{1a}$ may form 3- to 7-membered ring together with the nitrogen atom bonding them by forming $C_2$-$C_6$alkylene chain, in this case, the alkylene chain may contain one oxygen atom or sulfur atom).

$R^1$-X: —S(O)$_2R^{1a}$ (wherein $R^{1a}$ is $C_1$-$C_6$alkyl, $C_1$-$C_6$haloalkyl, $C_3$-$C_6$cycloalkyl or $C_2$-$C_6$alkynyl).

In the compounds included in the present invention, the substituent $R^2$ includes for example the following groups. That is, $R^2$-I: hydrogen atom and $C_1$-$C_4$alkyl.

$R^2$-II: hydrogen atom, $C_1$-$C_4$alkyl, $C_1$-$C_2$alkyl substituted with $R^{14a}$ (wherein $R^{14a}$ is cyano or —O$R^{23}$, $R^{23}$ is $C_1$-$C_4$alkyl, $C_1$-$C_4$haloalkyl, $C_1$-$C_4$alkylcarbonyl or $C_1$-$C_4$alkoxycarbonyl), $C_3$-$C_4$alkynyl, $C_1$-$C_4$alkylcarbonyl and $C_1$-$C_4$alkoxycarbonyl.

$R^2$-III: hydrogen atom, $C_1$-$C_6$alkyl, $C_1$-$C_4$alkyl substituted with $R^{14a}$ (wherein $R^{14a}$ is cyano, $C_3$-$C_4$cycloalkyl or —O$R^{23}$, $R^{23}$ is $C_1$-$C_6$alkyl, $C_1$-$C_6$haloalkyl, $C_1$-$C_6$alkylcarbonyl, $C_3$-$C_6$cycloalkylcarbonyl, $C_1$-$C_6$alkoxycarbonyl or phenylcarbonyl), $C_3$-$C_6$alkynyl, $C_1$-$C_6$alkoxy and $C_1$-$C_6$haloalkylthio.

$R^2$-IV: hydrogen, —C(O)$R^{15}$ and —C(O)O$R^{15}$ (wherein $R^{15}$ is $C_1$-$C_6$alkyl, $C_1$-$C_6$haloalkyl, $C_1$-$C_4$alkoxy $C_1$-$C_4$alkyl, $C_1$-$C_4$alkylthio $C_1$-$C_4$alkyl, $C_3$-$C_6$cycloalkyl or $C_3$-$C_6$alkenyl).

$R^2$-V: hydrogen atom, $C_1$-$C_6$alkyl, $C_1$-$C_6$haloalkyl, $C_1$-$C_4$alkyl substituted with $R^{14}$ (wherein $R'^{14}$ is cyano, $C_3$-$C_6$cycloalkyl, —O$R^{23}$, $C_1$-$C_6$alkylthio, $C_1$-$C_6$alkylsulfonyl or phenyl, $R^{23}$ is $C_1$-$C_6$alkyl, $C_1$-$C_6$haloalkyl, —C(O)$R^{30}$ or —C(O)O$R^{30}$, $R^{30}$ is $C_1$-$C_6$alkyl, $C_3$-$C_6$cycloalkyl or phenyl), $C_3$-$C_6$cycloalkyl, $C_3$-$C_6$alkenyl, $C_3$-$C_6$alkynyl, $C_1$-$C_6$alkoxy, $C_1$-$C_6$haloalkylthio and —SN($R^{18}$)$R^{17}$ (wherein $R^{17}$ is $C_1$-$C_6$alkyl, $C_1$-$C_6$alkoxycarbonyl $C_1$-$C_4$alkyl or $C_1$-$C_6$alkoxycarbonyl, $R^{18}$ is $C_1$-$C_6$alkyl or benzyl).

$R^2$-VI: hydrogen atom, —C(O)$R^{15}$, —C(O)O$R^{15}$, —C(O)S$R^5$, —C(O)C(O)O$R^{15}$, —C(S)O$R^{15}$ and —C(S)S$R^{15}$ (wherein $R^{15}$ is $C_1$-$C_6$alkyl, $C_1$-$C_6$haloalkyl, $C_1$-$C_4$alkoxy $C_1$-$C_4$alkyl, $C_1$-$C_4$alkylthio $C_1$-$C_4$alkyl, $C_1$-$C_4$alkylsulfinyl $C_1$-$C_4$alkyl, $C_1$-$C_4$alkylsulfonyl $C_1$-$C_4$alkyl, $C_3$-$C_6$cycloalkyl, $C_2$-$C_6$alkenyl, $C_2$-$C_6$alkynyl or phenyl).

$R^2$-VII: $R^2$ together with $R^1$ forms aziridine ring, azetidine ring, pyrrolidine ring, oxazolidine ring, thiazoridine ring, piperidine ring, morpholine ring, thiomorpholine ring or homopiperidine ring (wherein these rings may be arbitrarily substituted with $C_1$-$C_6$alkyl, oxo or thioxo).

In the compounds included in the present invention, the substituent $R^3$ includes for example the following groups. That is, $R^3$-I: —$CF_3$ and —$CF_2Cl$.

$R^3$-II: —$CHF_2$, —$CF_3$, —$CF_2Cl$, —$CF_2Br$, —$CF_2CHF_2$ and —$CF_2CF_3$.

$R^3$-III: $C_1$-$C_4$alkyl arbitrarily substituted with 2 or more of arbitrary halogen atoms.

$R^3$-IV: $C_1$-$C_4$haloalkyl.

$R^3$-V: $C_1$-$C_6$haloalkyl and $C_3$-$C_8$halocycloalkyl.

$R^3$-VI: $C_1$-$C_6$alkyl, $C_1$-$C_6$haloalkyl, $C_1$-$C_4$alkoxy $C_1$-$C_4$haloalkyl, $C_1$-$C_4$haloalkoxy $C_1$-$C_4$haloalkyl, $C_1$-$C_4$alkylthio $C_1$-$C_4$haloalkyl, $C_1$-$C_4$haloalkylthio $C_1$-$C_4$haloalkyl, cyano $C_1$-$C_6$haloalkyl, $C_3$-$C_6$cycloalkyl and $C_3$-$C_8$halocycloalkyl.

Each group showing the scope of each substituent in the compounds included in the present invention can be arbitrarily combined one another, and all combination thereof falls within the scope of the present invention. Examples of the combination of the scope of X, Y, $R^1$ and $R^2$ include for example the combination shown in Table 1. In the meantime, the combination of Table 1 is for illustrative purposes, and the present invention is not limited thereto.

TABLE 1

| X | Y | $R^1$ | $R^2$ |
|---|---|---|---|
| X-I | Y-I | $R^1$-I | $R^2$-I |
| X-I | Y-I | $R^1$-I | $R^2$-II |
| X-I | Y-I | $R^1$-I | $R^2$-III |
| X-I | Y-I | $R^1$-I | $R^2$-IV |
| X-I | Y-I | $R^1$-I | $R^2$-V |
| X-I | Y-I | $R^1$-I | $R^2$-VI |
| X-I | Y-I | $R^1$-I | $R^2$-VII |
| X-I | Y-I | $R^1$-II | $R^2$-I |
| X-I | Y-I | $R^1$-II | $R^2$-II |
| X-I | Y-I | $R^1$-II | $R^2$-III |
| X-I | Y-I | $R^1$-II | $R^2$-IV |
| X-I | Y-I | $R^1$-III | $R^2$-I |
| X-I | Y-I | $R^1$-III | $R^2$-II |
| X-I | Y-I | $R^1$-IV | $R^2$-I |
| X-I | Y-I | $R^1$-IV | $R^2$-II |
| X-I | Y-I | $R^1$-V | $R^2$-I |
| X-I | Y-I | $R^1$-V | $R^2$-II |
| X-I | Y-I | $R^1$-VI | $R^2$-I |

TABLE 1-continued

| X | Y | R¹ | R² |
|---|---|---|---|
| X-I | Y-I | R¹-VI | R²-II |
| X-I | Y-I | R¹-VII | R²-I |
| X-I | Y-I | R¹-VIII | R²-I |
| X-I | Y-I | R¹-IX | R²-I |
| X-I | Y-I | R¹-X | R²-I |
| X-I | Y-II | R¹-I | R²-I |
| X-I | Y-II | R¹-I | R²-II |
| X-I | Y-II | R¹-I | R²-III |
| X-I | Y-II | R¹-I | R²-IV |
| X-I | Y-II | R¹-I | R²-V |
| X-I | Y-II | R¹-I | R²-VI |
| X-I | Y-II | R¹-I | R²-VII |
| X-I | Y-II | R¹-II | R²-I |
| X-I | Y-II | R¹-II | R²-II |
| X-I | Y-II | R¹-II | R²-III |
| X-I | Y-II | R¹-II | R²-IV |
| X-I | Y-II | R¹-III | R²-I |
| X-I | Y-II | R¹-III | R²-II |
| X-I | Y-II | R¹-IV | R²-I |
| X-I | Y-II | R¹-IV | R²-II |
| X-I | Y-II | R¹-V | R²-I |
| X-I | Y-II | R¹-V | R²-II |
| X-I | Y-II | R¹-VI | R²-I |
| X-I | Y-II | R¹-VI | R²-II |
| X-I | Y-II | R¹-VII | R²-I |
| X-I | Y-II | R¹-VIII | R²-I |
| X-I | Y-II | R¹-IX | R²-I |
| X-I | Y-II | R¹-X | R²-I |
| X-I | Y-III | R¹-I | R²-I |
| X-I | Y-III | R¹-I | R²-II |
| X-I | Y-III | R¹-I | R²-III |
| X-I | Y-III | R¹-I | R²-IV |
| X-I | Y-III | R¹-II | R²-I |
| X-I | Y-III | R¹-II | R²-II |
| X-I | Y-III | R¹-III | R²-I |
| X-I | Y-III | R¹-IV | R²-I |
| X-I | Y-III | R¹-V | R²-I |
| X-I | Y-IV | R¹-I | R²-I |
| X-I | Y-V | R¹-I | R²-I |
| X-I | Y-VI | R¹-I | R²-I |
| X-II | Y-I | R¹-I | R²-I |
| X-II | Y-I | R¹-I | R²-II |
| X-II | Y-I | R¹-I | R²-III |
| X-II | Y-I | R¹-I | R²-IV |
| X-II | Y-I | R¹-I | R²-V |
| X-II | Y-I | R¹-I | R²-VI |
| X-II | Y-I | R¹-I | R²-VII |
| X-II | Y-I | R¹-II | R²-I |
| X-II | Y-I | R¹-II | R²-II |
| X-II | Y-I | R¹-II | R²-III |
| X-II | Y-I | R¹-II | R²-IV |
| X-II | Y-I | R¹-III | R²-I |
| X-II | Y-I | R¹-III | R²-II |
| X-II | Y-I | R¹-IV | R²-I |
| X-II | Y-I | R¹-IV | R²-II |
| X-II | Y-I | R¹-V | R²-I |
| X-II | Y-I | R¹-V | R²-II |
| X-II | Y-I | R¹-VI | R²-I |
| X-II | Y-I | R¹-VI | R²-II |
| X-II | Y-I | R¹-VII | R²-I |
| X-II | Y-I | R¹-VIII | R²-I |
| X-II | Y-I | R¹-IX | R²-I |
| X-II | Y-I | R¹-X | R²-I |
| X-II | Y-II | R¹-I | R²-I |
| X-II | Y-II | R¹-I | R²-II |
| X-II | Y-II | R¹-I | R²-III |
| X-II | Y-II | R¹-I | R²-IV |
| X-II | Y-II | R¹-II | R²-I |
| X-II | Y-II | R¹-II | R²-II |
| X-II | Y-II | R¹-III | R²-I |
| X-II | Y-II | R¹-IV | R²-I |
| X-II | Y-II | R¹-V | R²-I |
| X-II | Y-III | R¹-I | R²-I |
| X-II | Y-III | R¹-I | R²-II |
| X-II | Y-III | R¹-II | R²-I |
| X-II | Y-IV | R¹-I | R²-I |
| X-II | Y-V | R¹-I | R²-I |
| X-II | Y-VI | R¹-I | R²-I |
| X-III | Y-I | R¹-I | R²-I |
| X-III | Y-I | R¹-I | R²-II |
| X-III | Y-I | R¹-I | R²-III |
| X-III | Y-I | R¹-I | R²-IV |
| X-III | Y-I | R¹-II | R²-I |
| X-III | Y-I | R¹-II | R²-II |
| X-III | Y-I | R¹-III | R²-I |
| X-III | Y-I | R¹-IV | R²-I |
| X-III | Y-I | R¹-V | R²-I |
| X-III | Y-II | R¹-I | R²-I |
| X-III | Y-II | R¹-I | R²-II |
| X-III | Y-II | R¹-II | R²-I |
| X-III | Y-III | R¹-I | R²-I |
| X-III | Y-III | R¹-I | R²-II |
| X-III | Y-III | R¹-II | R²-I |
| X-III | Y-IV | R¹-I | R²-I |
| X-III | Y-V | R¹-I | R²-I |
| X-III | Y-VI | R¹-I | R²-I |
| X-IV | Y-I | R¹-I | R²-I |
| X-IV | Y-II | R¹-I | R²-I |
| X-IV | Y-III | R¹-I | R²-I |
| X-IV | Y-IV | R¹-I | R²-I |
| X-IV | Y-V | R¹-I | R²-I |
| X-IV | Y-VI | R¹-I | R²-I |
| X-V | Y-I | R¹-I | R²-I |
| X-V | Y-II | R¹-I | R²-I |
| X-V | Y-III | R¹-I | R²-I |
| X-V | Y-IV | R¹-I | R²-I |
| X-V | Y-V | R¹-I | R²-I |
| X-V | Y-VI | R¹-I | R²-I |
| X-VI | Y-I | R¹-I | R²-I |
| X-VI | Y-II | R¹-I | R²-I |
| X-VI | Y-III | R¹-I | R²-I |
| X-VI | Y-IV | R¹-I | R²-I |
| X-VI | Y-V | R¹-I | R²-I |
| X-VI | Y-VI | R¹-I | R²-I |
| X-VII | Y-I | R¹-I | R²-I |
| X-VII | Y-II | R¹-I | R²-I |
| X-VII | Y-III | R¹-I | R²-I |
| X-VII | Y-IV | R¹-I | R²-I |
| X-VII | Y-V | R¹-I | R²-I |
| X-VII | Y-VI | R¹-I | R²-I |

The compounds of the present invention can be produced for example according to the methods mentioned below.

Production Method A

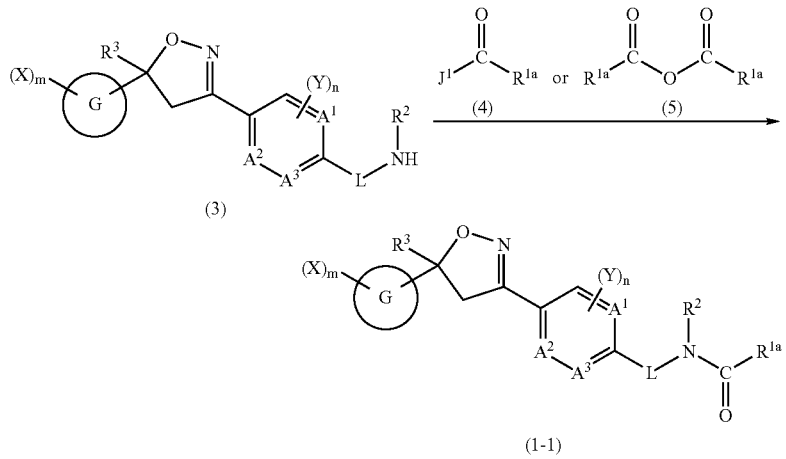

The compound of formula (1-1) (wherein $A^1, A^2, A^3, G, L, X, Y, R^{1a}, R^2, R^3$, m and n are as defined above) that $R^1$ in the formula (1) is —C(O)$R^{1a}$ according to the present invention can be obtained by reacting the compound of formula (3) (wherein $A^1, A^2, A^3, G, L, X, Y, R^2, R^3$, m and n are as defined above) with the compound of formula (4) (wherein $R^{1a}$ is as defined above, $J^1$ is chlorine atom, bromine atom, $C_{1-4}$alkylcarbonyloxy (for example pivaloyloxy), $C_{1-4}$alkoxycarbonyloxy (for example isobutyloxycarbonyloxy) or azolyl (for example imidazol-1-yl)) or the compound of formula (5) (wherein $R^{1a}$ is as defined above), optionally by use of a solvent inactive for the reaction, optionally in the presence of a base.

The reaction substrates can be used in an amount of 1 to 2 equivalents of the compound of formula (4) or (5) based on 1 equivalent of the compound of formula (3).

In case where a solvent is used, the solvent is not specifically limited if it dose not inhibit the progress of the reaction, but it includes for example aromatic hydrocarbons such as benzene, toluene, xylene or the like, aliphatic hydrocarbons such as hexane, heptane or the like, alicyclic hydrocarbons such as cyclohexane or the like, aromatic halogenated hydrocarbons such as chlorobenzene, dichlorobenzene or the like, aliphatic halogenated hydrocarbons such as dichloro methane, chloroform, carbon tetrachloride, 1,2-dichloroethane, 1,1,1-trichloroethane, trichloroethylene, tetrachloroethylene or the like, ethers such as diethyl ether, 1,2-dimethoxyethane, tetrahydrofuran, 1,4-dioxane or the like, esters such as ethyl acetate, ethyl propionate or the like, amides such as N,N-dimethylformamide, N,N-dimethylacetamide, N-methyl-2-pyrrolidone or the like, amines such as triethyl amine, tributyl amine, N,N-dimethyl aniline or the like, pyridines such as pyridine, picoline or the like, acetonitrile and water, and the like. These solvents may be used alone or in a mixture of two or more.

The addition of a base is not necessarily required. However, when the base is used, alkali metal hydroxides such as sodium hydroxide, potassium hydroxide or the like, alkali metal carbonates such as sodium carbonate, potassium carbonate or the like, alkali metal bicarbonates such as sodium hydrogen carbonate, potassium hydrogen carbonate or the like, organic bases such as triethyamine, tributylamine, N,N-dimethylaniline, pyridine, 4-(dimethylamino)pyridine, imidazole, 1,8-diazabicyclo[5.4.0]-7-undecene, and the like can be used in an amount of 1 to 4 equivalents based on the compound of formula (3).

The reaction temperature may be an arbitrary temperature ranging from −60° C. to the reflux temperature of a reaction mixture, and the reaction time may be an arbitrary time ranging from 5 minutes to 100 hours although it varies depending on the concentration of the reaction substrates or the reaction temperature.

Generally, it is preferable to carry out the reaction by using 1 to 1.1 equivalents of the compound of formula (4) or (5) based on 1 equivalent of the compound of formula (3), optionally in the presence of 1 to 2 equivalents of a base such as potassium carbonate, triethylamine, pyridine, 4-(dimethylamino)pyridine or the like, in a solvent such as dichloromethane, chloroform, diethyl ether, tetrahydrofuran, 1,4-dioxane, ethyl acetate, acetonitrile or the like, at a temperature ranging from 0° C. to the reflux temperature of these solvents for 10 minutes to 24 hours.

Production Method B

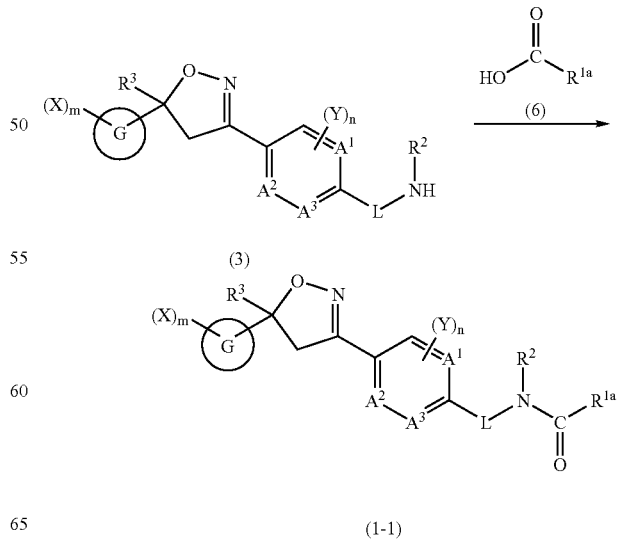

The compound of formula (1-1) (wherein $A^1$, $A^2$, $A^3$, G, L, X, Y, $R^1$, $R^2$, $R^3$, m and n are as defined above) that $R^1$ in the formula (1) is —C(O)$R^{1a}$ according to the present invention can be obtained by reacting the compound of formula (3) (wherein $A^1$, $A^2$, $A^3$, G, L, X, Y, $R^2$, $R^3$, m and n are as defined above) with the compound of formula (6) (wherein $R^{1a}$ is as defined above), optionally by use of a solvent inactive for the reaction, optionally in the presence of a base, by use of a condensation agent.

The reaction substrates can be used in an amount of 1 to 2 equivalents of the compound of formula (6) based on 1 equivalent of the compound of formula (3).

The condensation agent is not specifically limited if it is a compound used for ordinary amide synthesis, but it is for example Mukaiyama agent (2-chloro-N-methylpyridinium iodide), DCC (1,3-dicyclohexyl carbodiimide), WSC (1-ethyl-3-(3-dimethylaminopropyl)-carbodiimide hydrochloride), CDI (carbonyl diimidazole), dimethylpropynyl sulfonium bromide, propargyl triphenyl phosphonium bromide, DEPC (diethyl phosphorocyanidate) or the like, and can be used in an amount of 1 to 4 equivalents based on the compound of formula (3).

In case where a solvent is used, the solvent is not specifically limited if it dose not inhibit the progress of the reaction, but it includes for example aromatic hydrocarbons such as benzene, toluene, xylene or the like, aliphatic hydrocarbons such as hexane, heptane or the like, alicyclic hydrocarbons such as cyclohexane or the like, aromatic halogenated hydrocarbons such as chlorobenzene, dichlorobenzene or the like, aliphatic halogenated hydrocarbons such as dichloro methane, chloroform, carbon tetrachloride, 1,2-dichloroethane, 1,1,1-trichloroethane, trichloroethylene, tetrachloroethylene or the like, ethers such as diethyl ether, t-butyl methyl ether, 1,2-dimethoxyethane, tetrahydrofuran, 1,4-dioxane or the like, esters such as ethyl acetate, ethyl propionate or the like, amides such as N,N-dimethylformamide, N,N-dimethylacetamide, N-methyl-2-pyrrolidone or the like, amines such as triethyl amine, tributyl amine, N,N-dimethyl aniline or the like, pyridines such as pyridine, picoline or the like, acetonitrile and dimethylsulfoxide, and the like. These solvents may be used alone or in a mixture of two or more.

The addition of a base is not necessarily required. However, when the base is used, alkali metal hydroxides such as sodium hydroxide, potassium hydroxide or the like, alkali metal carbonates such as sodium carbonate, potassium carbonate or the like, alkali metal bicarbonates such as sodium hydrogen carbonate, potassium hydrogen carbonate or the like, organic bases such as triethyamine, tributylamine, N,N-dimethylaniline, pyridine, 4-(dimethylamino)pyridine, imidazole, 1,8-diazabicyclo[5.4.0]-7-undecene, and the like can be used in an amount of 1 to 4 equivalents based on the compound of formula (3).

The reaction temperature may be an arbitrary temperature ranging from −60° C. to the reflux temperature of a reaction mixture, and the reaction time may be an arbitrary time ranging from 5 minutes to 100 hours although it varies depending on the concentration of the reaction substrates or the reaction temperature.

Generally, it is preferable to carry out the reaction by using 1 to 1.1 equivalents of the compound of formula (6) and 1 to 4 equivalents of a condensation agent such as WSC (1-ethyl-3-(3-dimethylaminopropyl)-carbodiimide hydrochloride), CDI (carbonyl diimidazole) or the like based on 1 equivalent of the compound of formula (3), optionally in the presence of 1 to 4 equivalents of a base such as potassium carbonate, triethylamine, pyridine, 4-(dimethylamino)pyridine or the like, without solvent or in a solvent such as dichloromethane, chloroform, diethyl ether, tetrahydrofuran, 1,4-dioxane or the like, at a temperature ranging from 0° C. to the reflux temperature of these solvents for 10 minutes to 24 hours.

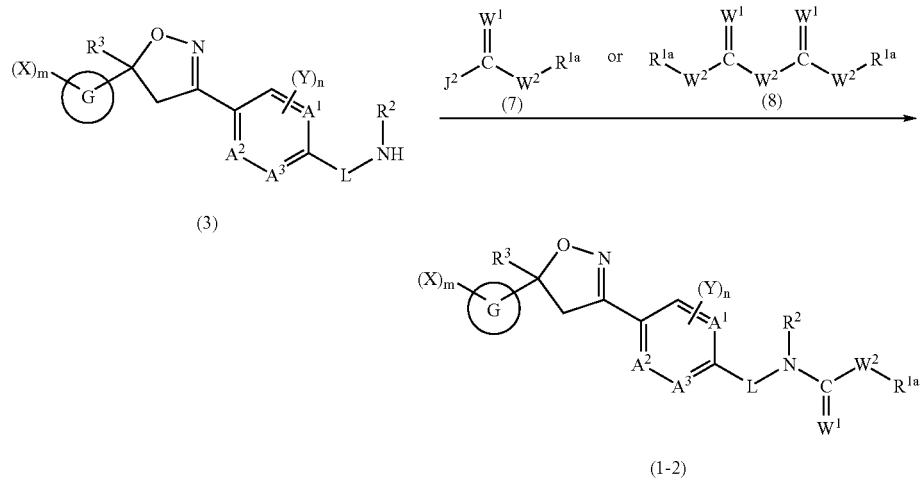

Production Method C

The compound of formula (1-2) (wherein $A^1$, $A^2$, $A^3$, G, L, X, Y, $R^{1a}$, $R^2$, $R^3$, m and n are as defined above, $W^1$ and $W^2$ are independently of each other oxygen atom or sulfur atom) that $R^1$ in the formula (1) is —C($W^1$)—$W^2$—$R^{1a}$ according to the present invention can be obtained by reacting the compound of formula (3) (wherein $A^1$, $A^2$, $A^3$, G, L, X, Y, $R^2$, $R^3$, m and n are as defined above) with the compound of formula (7) (wherein $R^{1a}$ is as defined above, $J^2$ is halogen atom such as chlorine atom, bromine atom or the like, $W^1$ and $W^2$ are independently of each other oxygen atom or sulfur atom) or the compound of formula (8) (wherein $R^{1a}$ is as defined above, $W^1$ and $W^2$ are independently of each other oxygen atom or sulfur atom), by use of a condition similar to that in Production Method A.

Production Method D

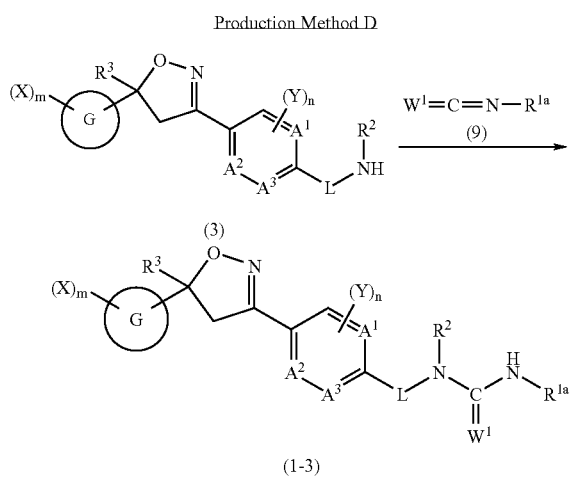

The compound of formula (1-3) (wherein $A^1$, $A^2$, $A^3$, G, L, X, Y, $R^1$, $R^2$, $R^3$, m and n are as defined above, $W^1$ is oxygen atom or sulfur atom) that in the formula (1) $R^1$ is —C($W^1$)NH$R^{1a}$ according to the present invention can be obtained by reacting the compound of formula (3) (wherein $A^1$, $A^2$, $A^3$, G, L, X, Y, $R^2$, $R^3$, m and n are as defined above) with the compound of formula (9) (wherein $R^{1a}$ has the meaning mentioned above, $W^1$ is oxygen atom or sulfur atom), optionally by use of a solvent inactive for the reaction, optionally in the presence of a base.

The reaction substrates can be used in an amount of 1 to 20 equivalents of the compound of formula (9) based on 1 equivalent of the compound of formula (3).

In case where a solvent is used, the solvent is not specifically limited if it dose not inhibit the progress of the reaction, but it includes for example aromatic hydrocarbons such as benzene, toluene, xylene or the like, aliphatic hydrocarbons such as hexane, heptane or the like, alicyclic hydrocarbons such as cyclohexane or the like, aromatic halogenated hydrocarbons such as chlorobenzene, dichlorobenzene or the like, aliphatic halogenated hydrocarbons such as dichloro methane, chloroform, carbon tetrachloride, 1,2-dichloroethane, 1,1,1-trichloroethane, trichloroethylene, tetrachloroethylene or the like, ethers such as diethyl ether, t-butyl methyl ether, 1,2-dimethoxyethane, tetrahydrofuran, 1,4-dioxane or the like, ketones such as acetone, methyl ethyl ketone or the like, alcohols such as methanol, ethanol, ethylene glycol or the like, and acetonitrile, and the like. These solvents may be used alone or in a mixture of two or more.

The addition of a base is not necessarily required. However, when the base is used, for example alkali metal hydrides such as sodium hydride, potassium hydride or the like, alkali metal carbonates such as sodium carbonate, potassium carbonate, sodium hydrogen carbonate or the like, organic bases such as triethyamine, tributylamine, N,N-dimethylaniline, pyridine, 4-(dimethylamino)pyridine, imidazole, 1,8-diazabicyclo[5.4.0]-7-undecene, and the like can be used in an amount of 1 to 4 equivalents based on the compound of formula (3).

The reaction temperature may be an arbitrary temperature ranging from −60° C. to the reflux temperature of a reaction mixture, and the reaction time may be an arbitrary time ranging from 5 minutes to 100 hours although it varies depending on the concentration of the reaction substrates or the reaction temperature.

Generally, it is preferable to carry out the reaction by using 1 to 1.2 equivalents of the compound of formula (9) based on 1 equivalent of the compound of formula (3), optionally by use of a base such as potassium carbonate, triethyl amine, pyridine, 4-(dimethylamino) pyridine or the like in an amount of 1 to 4 equivalents, in a solvent such as dichloromethane, methanol, tetrahydrofuran, 1,4-dioxane, N,N-dimethylformamide, water or the like, at a temperature ranging from 0° C. to the reflux temperature of a reaction mixture for 2 minutes to 24 hours.

Production Method E

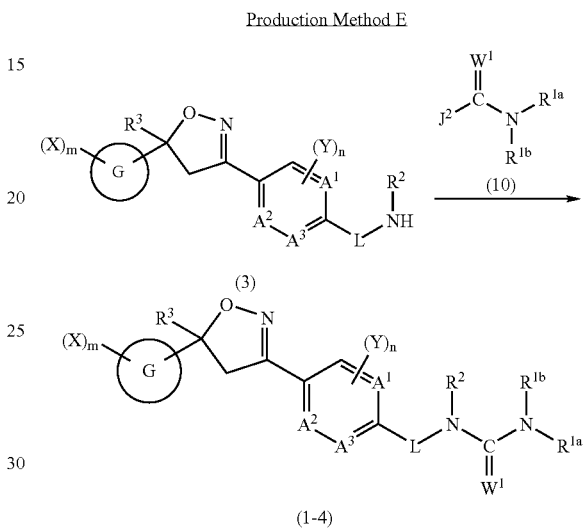

The compound of formula (14) (wherein $A^1$, $A^2$, $A^3$, G, L, X, Y, $R^1$, $R^2$, $R^3$, m and n are as defined above, $W^1$ is oxygen atom or sulfur atom) that in the formula (1) $R^1$ is —C($W^1$)N($R^{1b}$)$R^{1a}$ according to the present invention can be obtained by reacting the compound of formula (3) (wherein $A^1$, $A^2$, $A^3$, G, L, X, Y, $R^2$, $R^3$, m and n are as defined above) with the compound of formula (10) (wherein $R^{1a}$ and $R^{1b}$ have the meaning mentioned above, $J^2$ is halogen atom such as chlorine atom, bromine atom or the like, $W^1$ is oxygen atom or sulfur atom), by use of a condition similar to that in Production Method A.

Production Method F

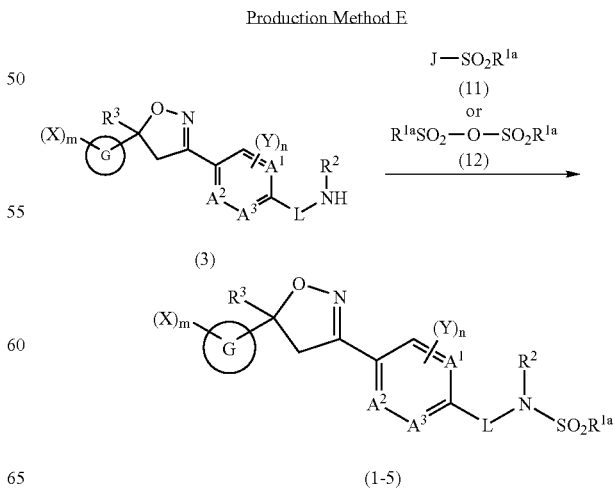

The compound of formula (1-5) (wherein $A^1, A^2, A^3, G, L, X, Y, R^{1a}, R^2, R^3$, m and n are as defined above) that in the formula (1) $R^1$ is —$SO_2R^{1a}$ according to the present invention can be obtained by reacting the compound of formula (3) (wherein $A^1, A^2, A^3, G, L, X, Y, R^2, R^3$, m and n are as defined above) with the compound of formula (11) (wherein $R^{1a}$ has the meaning mentioned above, $J^2$ is halogen atom such as chlorine atom, bromine atom or the like) or the compound of formula (12) (wherein $R^{1a}$ has the meaning mentioned above), by use of a condition similar to that in Production Method A.

Production Method G

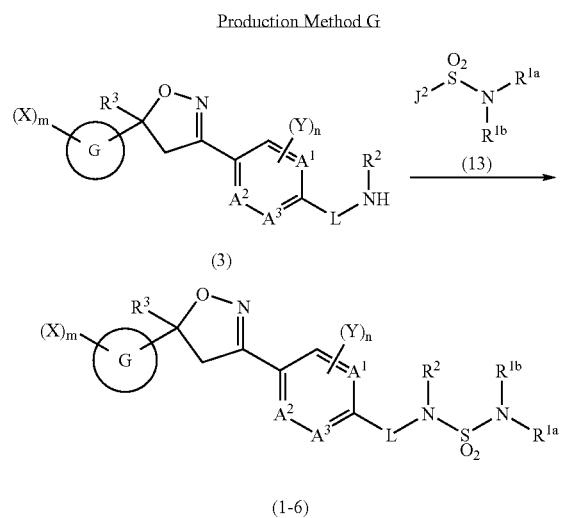

The compound of formula (I-6) (wherein $A^1, A^2, A^3, G, L, X, Y, R^{1a}, R^{1b}, R^2, R^3$, m and n are as defined above) that in the formula (1) $R^1$ is $SO_2N(R^{1b})$ $R^{1a}$ according to the present invention can be obtained by reacting the compound of formula (3) (wherein $A^1, A^2, A^3, G, L, X, Y, R^2, R^3$, m and n are as defined above) with the compound of formula (13) (wherein $R^{1a}$ and $R^{1a}$ have the meaning mentioned above, $J^2$ is halogen atom such as chlorine atom, bromine atom or the like), by use of a condition similar to that in Production Method A.

Production Method H

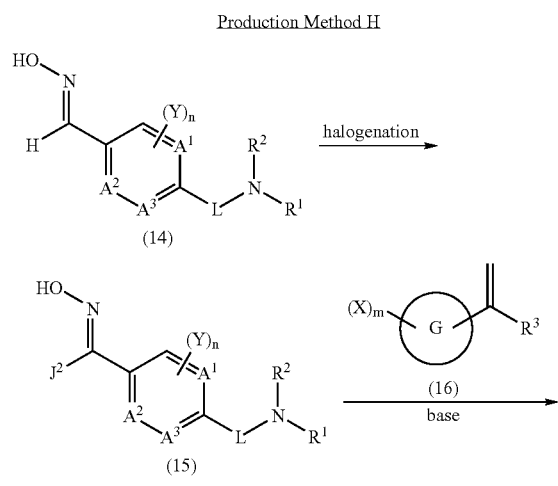

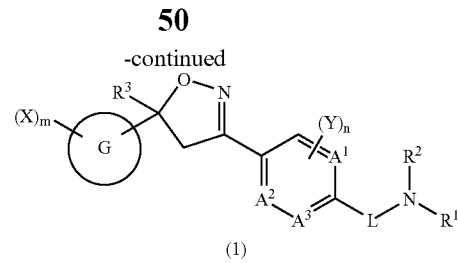

Hydroxamic chloride of formula (15) (wherein $A^1, A^2, A^3, L, Y, R^1, R^2$ and n are as defined above, $J^2$ is halogen atom such as chlorine atom and bromine atom or the like) can be obtained by halogenating the compound of formula (14) (wherein $A^1, A^2, A^3, L, Y, R^1, R^2$ and n are as defined above) using a halogenating reagent optionally by using a solvent inactive for the reaction, optionally in the presence of a base.

Halogenating agents include for example N-halosuccinimides such as N-chlorosuccinimide, N-bromosuccinimide or the like, hypohalogenous acid alkali metal salts such as sodium hypochlorite or the like, hypohalogenous acid esters such as hypochlorous acid-t-butyl ester or the like, simple substance halogens such as chlorine gas or the like, and it can be used in an amount of 1 to 10 equivalents based on the compound of formula (14).

In case where a solvent is used, the solvent is not specifically limited if it dose not inhibit the progress of the reaction, but it includes for example aromatic hydrocarbons such as benzene, toluene, xylene or the like, aliphatic hydrocarbons such as hexane, heptane or the like, alicyclic hydrocarbons such as cyclohexane or the like, aromatic halogenated hydrocarbons such as chlorobenzene, dichlorobenzene or the like, aliphatic halogenated hydrocarbons such as dichloro methane, chloroform, carbon tetrachloride, 1,2-dichloroethane, 1,1,1-trichloroethane, trichloroethylene, tetrachloroethylene or the like, ethers such as diethyl ether, t-butyl methyl ether, 1,2-dimethoxyethane, tetrahydrofuran, 1,4-dioxane or the like, esters such as ethyl acetate, ethyl propionate or the like, amides such as N,N-dimethylformamide, N,N-dimethylacetamide, N-methyl-2-pyrrolidone or the like, alcohols such as methanol, ethanol, ethylene glycol or the like, carboxylic acids such as acetic acid, propionic acid or the like, acetonitrile and water, and the like. These solvents may be used alone or in a mixture of two or more.

The reaction temperature may be an arbitrary temperature ranging from −60° C. to the reflux temperature of a reaction mixture, and the reaction time may be an arbitrary time ranging from 5 minutes to 24 hours although it varies depending on the concentration of the reaction substrates or the reaction temperature.

The compounds of formula (1) (wherein $A^1, A^2, A^3, G, L, X, Y, R^1, R^2, R^3$, m and n are as defined above) according to the present invention can be obtained by reacting the compound of formula (15) obtained as above with the compound of formula (16) (wherein $G, X, R^3$ and m are as defined above) in the presence of a base optionally by use of a solvent inactive for the reaction.

The reaction substrates can be used in an amount of 1 to 5 equivalents of the compound of formula (16) based on 1 equivalent of the compound of formula (15).

The used base includes for example alkali metal hydroxides such as sodium hydroxide, potassium hydroxide or the like, alkali metal carbonates such as sodium carbonate, potassium carbonate or the like, alkali metal bicarbonates such as sodium hydrogen carbonate, potassium hydrogen carbonate or the like, organic bases such as triethyamine, tributylamine, N,N-dimethylaniline, pyridine, 4-(dimethylamino)pyridine, imidazole, 1,8-diazabicyclo[5.4.0]-7-undecene, and the like can be used in an amount of 1 to 5 equivalents based on the compound of formula (15).

In case where a solvent is used, the solvent is not specifically limited if it dose not inhibit the progress of the reaction, but it includes for example aromatic hydrocarbons such as benzene, toluene, xylene or the like, aliphatic hydrocarbons such as hexane, heptane or the like, alicyclic hydrocarbons such as cyclohexane or the like, aromatic halogenated hydrocarbons such as chlorobenzene, dichlorobenzene or the like, aliphatic halogenated hydrocarbons such as dichloro methane, chloroform, carbon tetrachloride, 1,2-dichloroethane, 1,1,1-trichloroethane, trichloroethylene, tetrachloroethylene or the like, ethers such as diethyl ether, 1,2-dimethoxyethane, tetrahydrofuran, 1,4-dioxane or the like, esters such as ethyl acetate, ethyl propionate or the like, amides such as N,N-dimethylformamide, N,N-dimethylacetamide, N-methyl-2-pyrrolidone or the like, and acetonitrile, and the like. These solvents may be used alone or in a mixture of two or more.

The reaction temperature may be an arbitrary temperature ranging from −60° C. to the reflux temperature of a reaction mixture, and the reaction time may be an arbitrary time ranging from 5 minutes to 100 hours although it varies depending on the concentration of the reaction substrates or the reaction temperature.

Generally, the compound of formula (15) can be obtained for example by carrying out the reaction by using 1 to 2 equivalents of a halogenating agent such as N-chlorosuccinimide, sodium hypochlorite aqueous solution, hypochlorous acid-t-butyl ester, chlorine gas or the like based on 1 equivalent of the compound of formula (14) in a solvent such as dichloromethane, chloroform, 1,2-dimethoxyethane, tetrahydrofuran, 1,4-dioxane, N,N-dimethylformamide or the like, at a temperature ranging from 0° C. to the reflux temperature of these solvents for 10 minutes to 2 hours. Then, preferably without the isolation of the compound of formula (15), 1 to 2 equivalents of the compound of formula (16) and 1 to 2 equivalents of a base such as sodium carbonate, sodium hydrogen carbonate, triethyl amine or the like are added, and the reaction is carried out at a temperature ranging from 0° C. to the reflux temperature of these solvents for 10 minutes to 24 hours.

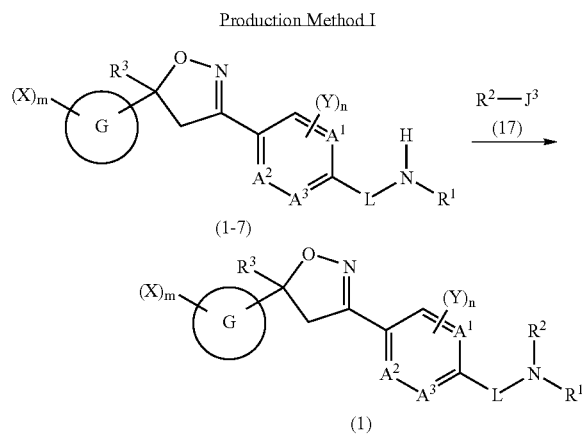

Production Method I

The compound of formula (1) (wherein $A^1, A^2, A^3, G, L, X, Y, R^1, R^3$, m and n are as defined above, $R^2$ has the meaning mentioned above other than hydrogen atom) according to the present invention can be obtained by reacting the compound of formula (1-7) (wherein $A^1, A^2, A^3, G, L, X, Y, R^1, R^3$, m and n are as defined above) that is the compound of formula (1) wherein $R^2$ is hydrogen atom with the compound of formula (17) (wherein $R^2$ has the meaning mentioned above other than hydrogen atom, $J^3$ is a good leaving group such as chlorine atom, bromine atom, iodine atom, $C_1$-$C_4$alkylcarbonyloxy (for example pivaloyloxy), $C_1$-$C_4$alkylsulfonate (for example methane sulfonyloxy), $C_1$-$C_4$haloalkylsulfonate (for example trifluoromethane sulfonyloxy), arylsulfonate (for example benzene sulfonyloxy or p-toluenesulfonyloxy) or azolyl (for example imidazole-1-yl)), optionally in the presence of a base, optionally by use of a solvent inactive for the reaction.

The reaction substrates can be used in an amount of 1 to 50 equivalents of the compound of formula (17) based on 1 equivalent of the compound of formula (1-7).

In case where a solvent is used, the solvent is not specifically limited if it dose not inhibit the progress of the reaction, but it includes for example aromatic hydrocarbons such as benzene, toluene, xylene or the like, aliphatic hydrocarbons such as hexane, heptane or the like, alicyclic hydrocarbons such as cyclohexane or the like, aromatic halogenated hydrocarbons such as chlorobenzene, dichlorobenzene or the like, aliphatic halogenated hydrocarbons such as dichloro methane, chloroform, carbon tetrachloride, 1,2-dichloroethane, 1,1,1-trichloroethane, trichloroethylene, tetrachloroethylene or the like, ethers such as diethyl ether, t-butyl methyl ether, 1,2-dimethoxyethane, tetrahydrofuran, 1,4-dioxane or the like, esters such as ethyl acetate, ethyl propionate or the like, amides such as dimethylformamide, dimethylacetamide, N-methyl-2-pyrrolidone or the like, amines such as triethyl amine, tributyl amine, N,N-dimethyl aniline or the like, pyridines such as pyridine, picoline or the like, alcohols such as methanol, ethanol, ethylene glycol or the like, acetonitrile, dimethylsulfoxide, sulfolane, 1,3-dimethyl-2-imidazolidinone and water, and the like. These solvents may be used alone or in a mixture of two or more.

In case where a base is used, for example alkali metal hydrides such as sodium hydride, potassium hydride or the like, alkali metal hydroxides such as sodium hydroxide, potassium hydroxide or the like, alkali metal alkoxides such as sodium ethoxide, potassium t-butoxide or the like, alkali metal amides such as lithium diisopropylamide, lithium hexamethyldisilazane, sodium amide or the like, organic metal compounds such as t-butyl lithium or the like, alkali metal carbonates such as sodium carbonate, potassium carbonate, sodium hydrogen carbonate or the like, organic bases such as triethyamine, tributylamine, N,N-dimethylaniline, pyridine, 4-(dimethylamino)pyridine, imidazole, 1,8-diazabicyclo [5.4.0]-7-undecene, and the like can be used in an amount of 1 to 4 equivalents based on the compound of formula (1-7).

The reaction temperature may be an arbitrary temperature ranging from −60° C. to the reflux temperature of a reaction mixture, and the reaction time may be an arbitrary time ranging from 5 minutes to 100 hours although it varies depending on the concentration of the reaction substrates or the reaction temperature.

Generally, it is preferable to carry out the reaction by using 1 to 10 equivalents of the compound of formula (17) based on 1 equivalent of the compound of formula (1-7), in a polar solvent such as tetrahydrofuran, 1,4-dioxane, acetonitrile, N,N-dimethylformamide or the like, optionally by use of a base such as sodium hydride, potassium t-butoxide, potassium hydroxide, potassium carbonate, triethylamine, pyridine or the like in an amount of 1 to 3 equivalents based on 1 equivalent of the compound of formula (1-7), at a temperature ranging from 0° C. to 90° C. for 10 minutes to 24 hours.

Production Method J

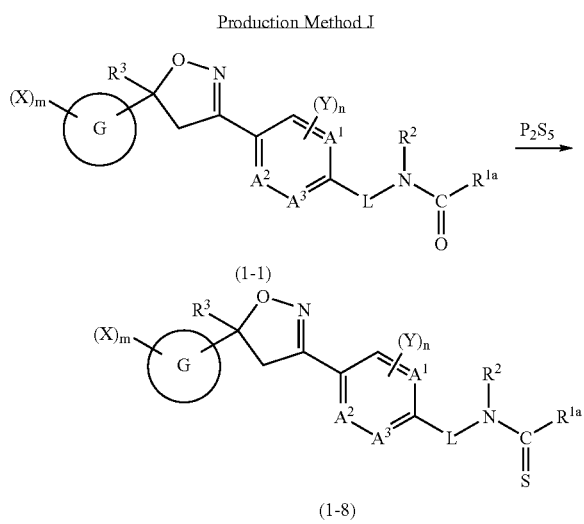

The compound of formula (1-8) (wherein $A^1, A^2, A^3, G, L, X, Y, R^1, R^2, R^3$, m and n are as defined above) according to the present invention that is the compound of formula (1) wherein $R^1$ is —$C(S)R^{1a}$ can be obtained by reacting the compound of formula (1-1) (wherein $A^1, A^2, A^3, G, L, X, Y, R^1, R^2, R^3$, m and n are as defined above) according to the present invention that is the compound of formula (1) wherein $R^1$ is —$C(O)R^{1a}$ with a sulfurizing agent such as diphosphorus pentasulfide, diphosphorus pentasulfide-HMDO (hexamethyldisiloxane), Lawesson's Reagent (2,4-bis(4-methoxyphenyl)-1,3,2,4-dithiadiphosphetane-2,4-disulfide), optionally by using a solvent inactive for the reaction, optionally in the presence of a base.

The reaction substrates can be used in an amount of 1 to 50 equivalents of the sulfurizing agent based on 1 equivalent of the compound of formula (1-1).

In case where a solvent is used, the solvent is not specifically limited if it dose not inhibit the progress of the reaction, but it includes for example aromatic hydrocarbons such as benzene, toluene, xylene or the like, aliphatic hydrocarbons such as hexane, heptane or the like, alicyclic hydrocarbons such as cyclohexane or the like, aromatic halogenated hydrocarbons such as chlorobenzene, dichlorobenzene or the like, aliphatic halogenated hydrocarbons such as dichloro methane, chloroform, carbon tetrachloride, 1,2-dichloroethane, 1,1,1-trichloroethane, trichloroethylene, tetrachloroethylene or the like, ethers such as diethyl ether, t-butyl methyl ether, 1,2-dimethoxyethane, tetrahydrofuran, 1,4-dioxane or the like, amines such as triethyl amine, tributyl amine, N,N-dimethyl aniline or the like, pyridines such as pyridine, picoline or the like, and HMPA (hexamethylphosphoric triamide), and the like. These solvents may be used alone or in a mixture of two or more.

The addition of a base is not necessarily required. However, when the base is used, alkali metal carbonates such as sodium carbonate, potassium carbonate, sodium hydrogen carbonate or the like, organic bases such as triethyamine, tributylamine, N,N-dimethylaniline, pyridine, 4-(dimethylamino)pyridine, imidazole, 1,8-diazabicyclo[5.4.0]-7-undecene, and the like can be used in an amount of 1 to 10 equivalents based on the compound of formula (1-1).

The reaction temperature may be an arbitrary temperature ranging from 0° C. to the reflux temperature of a reaction mixture, and the reaction time may be an arbitrary time ranging from 5 minutes to 100 hours although it varies depending on the concentration of the reaction substrates or the reaction temperature.

Generally, it is preferable to carry out the reaction by using 1 to 10 equivalents of a sulfurizing agent such as diphosphorus pentasulfide, diphosphorus pentasulfide-HMDO, Lawesson's Reagent or the like, based on 1 equivalent of the compound of formula (1-1), optionally in the presence of 1 to 4 equivalents of a base such as sodium hydrogen carbonate, triethyamine, pyridine or the like, in a solvent such as benzene, toluene, chlorobenzene, dichloromethane, chloroform, 1,2-dimethoxyethane, tetrahydrofuran, 1,4-dioxane, HMPA or the like, at a temperature ranging from room temperature to the reflux temperature of the reaction mixture for 10 minutes to 50 hours, or in a solvent amount of pyridine at a temperature of 80° C. to the reflux temperature of the reaction mixture for 1 to 3 hours.

In Production Methods A to J, the aimed compound of the present invention can be obtained by subjecting the reaction mixture after the completion of the reaction to ordinary post-treatment such as a direct concentration, or a concentration after dissolving in an organic solvent and washing with water or a concentration after placing in ice water and extracting with an organic solvent. In addition, when a purification is required, it can be separated and purified by an arbitrary purification process such as recrystallization, column chromatograph, thin layer chromatograph, liquid chromatograph collection or the like.

The compound of formula (3) used in Production Methods A to G can be synthesized according to Reaction Schemes 1 to 3, for example.

Reaction Scheme 1

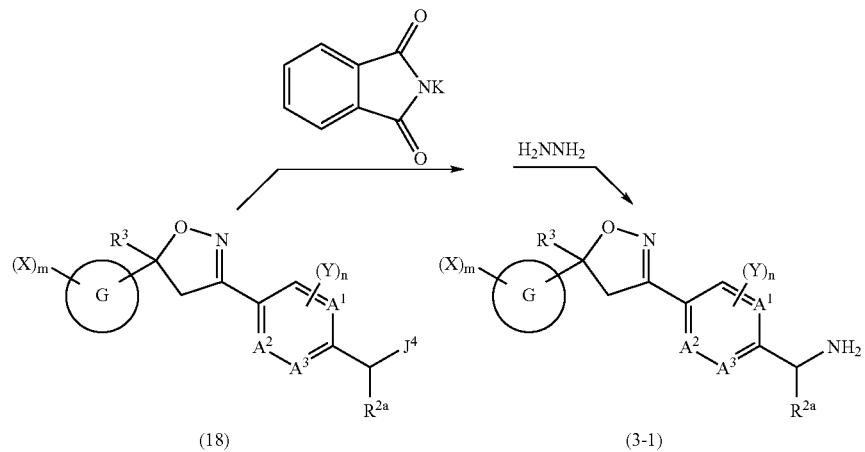

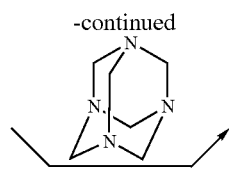

The compound of formula (3-1) (wherein $A^1$, $A^2$, $A^3$, G, X, Y, $R^2$, $R^3$, m and n are as defined above) that in formula (3) L is —CH($R^{2a}$)—, $R^2$ is hydrogen atom can be obtained by reacting the compound of formula (18) (wherein $A^1$, $A^2$, $A^3$, G, X, Y, $R^2$, $R^3$, m and n are as defined above, $J^4$ is chlorine atom, bromine atom, iodine atom or halosulfonyloxy (for example fluorosulfonyloxy) or the like) with potassium phthalimide stated in J. Med. Chem., 2005, vol. 48, p. 1745, Bioorganic & Med. Chem., 2003, vol. 11, p. 4171 or the like, and then subjecting to dephthaloylation with hydrazine, or by reacting the compound of formula (18) mentioned above with hexamethyltetramine stated in J. Am. Chem. Soc., 2005, vol. 127, p. 56 or the like, and then subjecting to hydrolysis.

Reaction Scheme 2

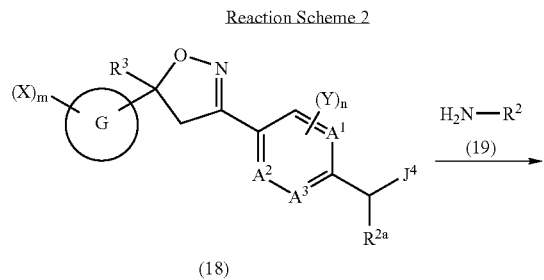

The compound of formula (3-2) (wherein $A^1$, $A^2$, $A^3$, G, X, Y, $R^2$, $R^3$, m and n are as defined above) that in formula (3) L is —CH($R^{2a}$)—, $R^2$ is alkyl, substituted alkyl, alkenyl, alkynyl or the like can be obtained by reacting the compound of formula (18) (wherein $A^1$, $A^2$, $A^3$, G, X, Y, $R^{2a}$, $R^3$, m and n are as defined above, $J^4$ is chlorine atom, bromine atom, iodine atom or halosulfonyloxy (for example fluorosulfonyloxy) or the like) with the compound of formula (19) (wherein $R^2$ is alkyl, substituted alkyl, alkenyl, alkynyl or the like) according to a known method disclosed in documents, for example the reaction condition stated in J. Med. Chem., 1986, vol. 29, p. 40, Organic Letters, 2000, vol. 2, p. 3555 or the like.

Reaction Scheme 3

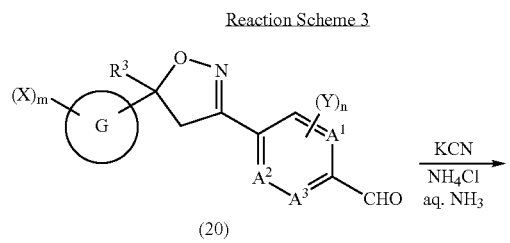

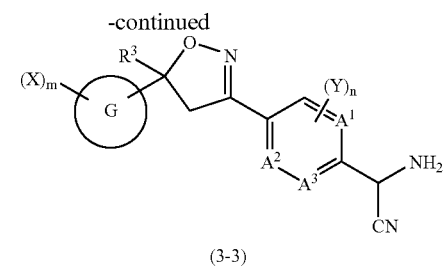

The compound of formula (3-3) (wherein $A^1$, $A^3$, G, X, Y, $R^3$, m and n are as defined above) that in formula (3) L is —CH(CN)—, $R^2$ is hydrogen atom can be obtained by reacting the compound of formula (20) (wherein $A^1$, $A^2$, $A^3$, G, X, Y, $R^{2a}$, $R^3$, m and n are as defined above) according to known Strecker reaction disclosed in documents, for example the reaction condition stated in J. Med. Chem., 1985, vol. 28, p. 1280 or the like.

The compounds of formulae (4) to (13) used in Production Methods A to G are known compounds, and a part thereof is commercially available.

The compounds of formula (14) used in Production Method H can be synthesized as follows, for example.

Reaction Scheme 4

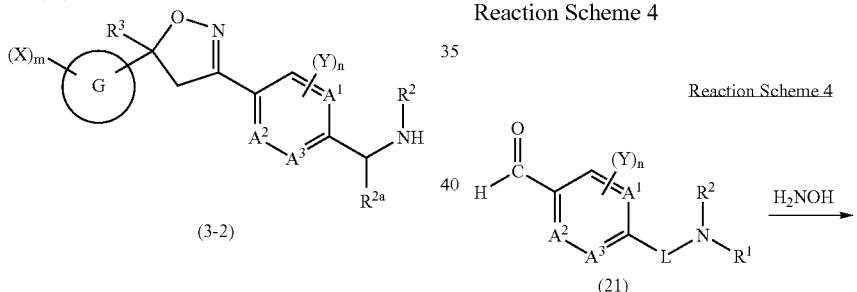

That is, the compound of formula (8) (wherein $A^1$, $A^2$, $A^3$, G, L, Y, $R^1$, $R^2$ and n are as defined above) can be easily obtained by reacting the compound of formula (21) (wherein $A^1$, $A^2$, $A^3$, L, Y, $R^1$, $R^2$ and n are as defined above) with hydroxylamine or a salt thereof according to a known method disclosed in documents, for example the reaction condition stated in J. Med. Chem., 2001, vol. 44, p. 2308 or the like.

The compounds of formula (16) used in Production Method H are known compounds disclosed in WO 2005/085216.

Some of the compounds of formula (17) used in Production Method I are known compounds, and a part thereof is commercially available. Also, the compounds other than the above-mentioned compounds can be synthesized according to methods disclosed in documents, for example a method stated in Chem. Lett., 1976, p. 373, J. Am. Chem. Soc., 1964, vol. 86, p. 4383, J. Org. Chem., 1976, vol. 41, p. 4028 and 1978, vol. 43. p. 3244, Org. Synth., 1988, Collective Volume 6, p. 101, Tetrahedron Lett., 1972, p. 4339, GB 2, 161, 802, EP 0,051, 273 or the like.

Some of the compounds of formula (18) are known compounds disclosed in WO 2005/085216, and the compounds other than the above-mentioned compounds can be synthesized similarly to the known compounds, according to the method disclosed in this document.

Some of the primary amines of formula (19) are known compounds, and a part thereof is commercially available.

The compounds of formula (20) can be synthesized as follows, for example.

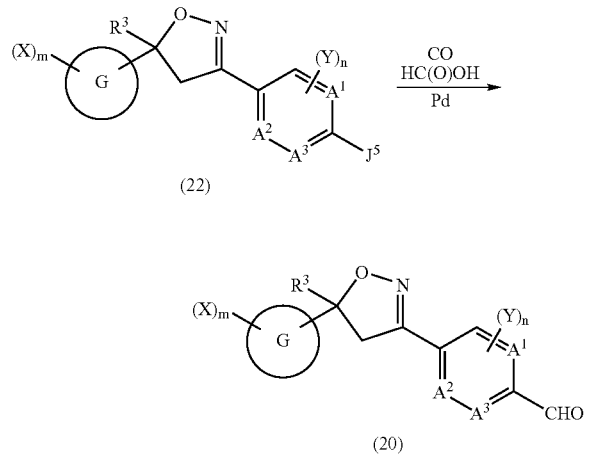

That is, the compound of formula (20) (wherein $A^1, A^2, A^3, G, X, Y, R^3$, m and n are as defined above) can be obtained by subjecting the compound of formula (22) (wherein $A^1, A^2, A^3, G, X, Y, R^3$, m and n are as defined above, $J^5$ is bromine atom, iodine atom, halosulfonyloxy (for example fluorosulfonyloxy), $C_{1-4}$haloalkylsulfonyloxy (for example trifluoromethanesulfonyloxy) or arylsulfonyloxy (for example benzene sulfonyloxy) or the like) to CO insertion reaction by use of a transition metal catalyst such as palladium or the like in the presence of hydride of formic acid or the like, according to methods disclosed in documents, for example a method stated in Bull. Chem. Soc. Jpn., 1994, vol. 67, p. 2329, J. Am. Chem. Soc., 1986, vol. 108, p. 452 or the like.

The compounds of formula (21) can be synthesized as follows, for example.

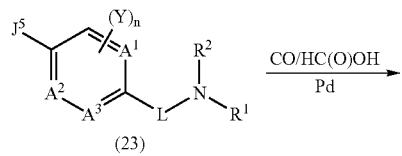

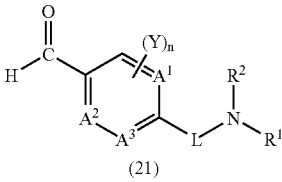

That is, the compound of formula (21) (wherein $A^1, A^2, A^3, L, Y, R^1, R^2$ and n are as defined above) can be obtained by reacting the compound of formula (23) (wherein $A^1, A^2, A^3, L, Y, R^1, R^2$, n and $J^5$ are as defined above) under a condition similar to Reaction Scheme 5.

Some of the compounds of formula (22) are known compounds disclosed in WO 2005/085216, and the compounds other than the above-mentioned compounds can be synthesized similarly to the known compounds, according to the method disclosed in this document.

The compound of formula (23) can be synthesized by reacting the compound of formula (24) shown in Reaction Scheme 7 similarly to Production Methods A to J.

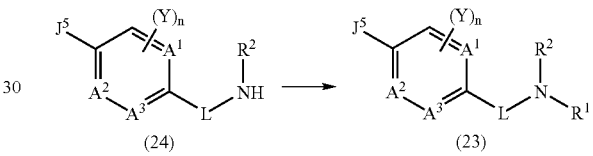

The compounds of formula (24) used in this reaction can be synthesized similarly to Reaction Scheme 8 or Reaction Scheme 9, for example.

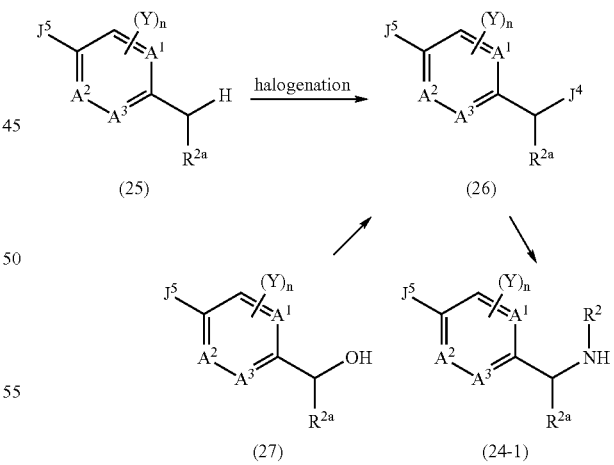

The compound of formula (26) (wherein $A^1, A^2, A^3, Y, R^{2a}$, n and $J^5$ are as defined above, $J^4$ is a halogen atom) can be obtained by halogenating the compound of formula (25) (wherein $A^1, A^2, A^3, Y, R^{2a}$, n and $J^5$ are as defined above) with a halogenating agent such as N-bromosuccinimide or the like, according to methods disclosed in documents, for example a method stated in Tetrahedron, 2004, vol. 60, p. 11075 or the like.

In addition, the compound of formula (26) can be obtained by halogenating the compound of formula (27) (wherein $A^1$, $A^2$, $A^3$, Y, $R^{2a}$, n and $J^5$ are as defined above) according to methods disclosed in documents, for example a method stated in J. Org. Chem., 2005, vol. 70, p. 6066 (thionyl chloride), J. Am. Chem. Soc., 2005, vol. 127, p. 373 (N-bromosuccinimide), Tetrahedron, 2005, vol. 61, p. 5849 (phosphorus pentachloride) or the like.

Further, the compound of formula (26) wherein $J^4$ is halosulfonyloxy can be obtained by reacting the compound of formula (27) according to methods disclosed in documents, for example a method stated in J. Org. Chem., 2004, vol. 69, p. 1227, Tetrahedron, 1988, vol. 44, p. 5583 or the like.

The compounds of formula (24-1) (wherein $A^1$, $A^2$, $A^3$, Y, $R^{2a}$, n and $J^5$ are as defined above) that are the compounds of formula (24) wherein L is —CH($R^{2a}$)—, $R^2$ is alkyl, substituted alkyl, alkenyl, alkynyl or the like can be obtained by reacting the compound of formula (26) obtained as above, similarly to Reaction Scheme 1 or Reaction Scheme 2.

Reaction Scheme 9

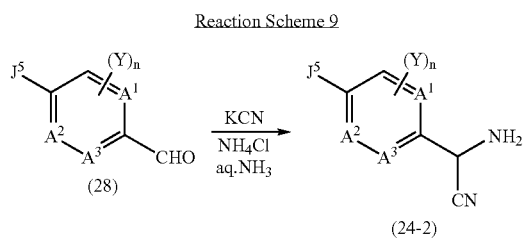

The compounds of formula (24-2) (wherein $A^1$, $A^2$, $A^3$, Y, n and $J^5$ are as defined above) that are the compounds of formula (24) wherein L is —CH(CN)—, $R^2$ is hydrogen atom or the like can be obtained by reacting the compound of formula (28) under a condition similar to Reaction Scheme 3.

Some of the compounds of formula (27) and the compounds of formula (28) are known compounds, and a part thereof is commercially available. In addition, the compounds other than the above-mentioned compounds can be easily synthesized according to known methods disclosed in documents.

In each reaction, after the completion of the reaction, each production intermediate that is a starting compound in Production Methods A to J can be obtained by carrying out normal post-treatments.

In addition, each production intermediate produced by the above-mentioned methods can be used for the following reaction step as such without isolation or purification.

The active compounds included in the present invention concretely include for example the compounds shown in Tables 2 and 3. The compounds that can be used as novel production intermediates for producing the active compounds included in the present invention concretely include for example the compounds shown in Table 4. In the interim, the compounds shown in Tables 2 to 4 are for purposes of illustration and the present invention is not limited thereto.

In the meantime, in Tables, the indication "Et" means ethyl, hereinafter similarly thereto, "n-Pr" and "Pr-n" mean normal propyl, "i-Pr" and "Pr-i" mean isopropyl, "c-Pr" and "Pr-c" mean cyclopropyl, "n-Bu" and "Bu-n" mean normal butyl, "s-Bu" and "Bu-s" mean secondary butyl, "i-Bu" and "Bu-i" mean isobutyl, "t-Bu" and "Bu-t" mean tertiary butyl, "c-Bu" and "Bu-c" mean cyclobutyl, "n-Pen" and "Pen-n" mean normal pentyl, "c-Pen" and "Pen-c" mean cyclopentyl, "n-Hex" and "Hex-n" mean normal hexyl, "c-Hex" and "Hex-c" mean cyclohexyl, "Hept" means heptyl, "Oct" means octyl, "Ph" means phenyl, "1-Naph" means 1-naphthyl, "2-Naph" means 2-naphthyl, and in Tables, aromatic heterocyclic rings of D-1a to D-63a are the following structures, respectively D-1a:
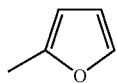

D-2a:
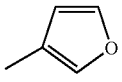

D-3a:
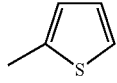

D-4a:
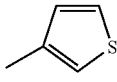

D-5a:
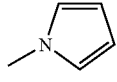

D-8a:
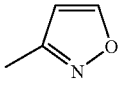

D-9a:
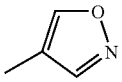

D-10a:
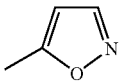

D-10b:
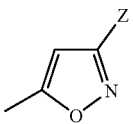

D-11b:
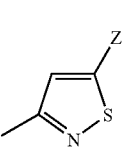

D-12a:
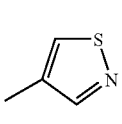

D-13a:
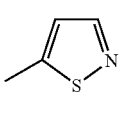

D-13b: 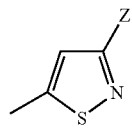
D-14a: 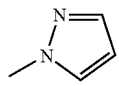
D-15a: 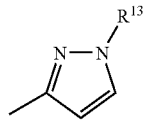
D-16a: 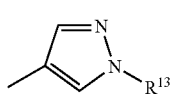
D-17a: 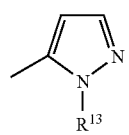
D-17b: 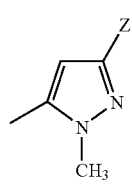
D-18a: 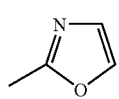
D-21a: 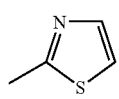
D-21c: 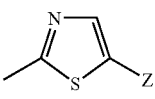
D-22a: 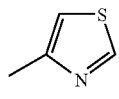
D-23a: 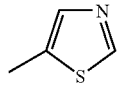
D-24a: 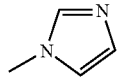
D-28a: 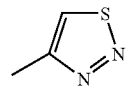
D-29a: 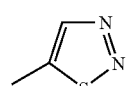
D-29b: 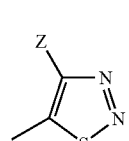
D-30b: 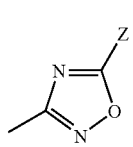
D-31b: 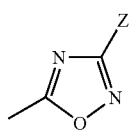
D-32a: 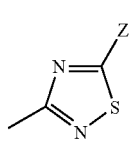
D-33a: 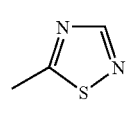
D-34a: 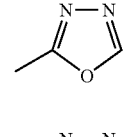
D-35a: 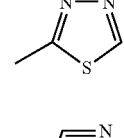
D-36a: 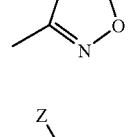
D-36b: 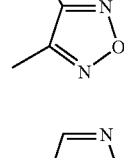
D-37a: 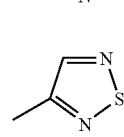

-continued
D-38a: 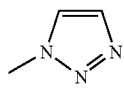
D-41a: 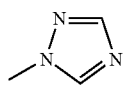
D-44a: 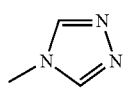
D-48a: 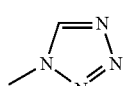
D-48b: 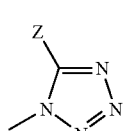
D-49a: 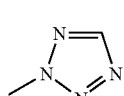
D-50a: 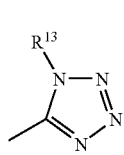
D-51a: 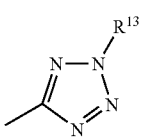
D-52a: 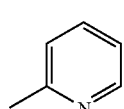
D-52b: 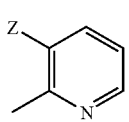
D-52c: 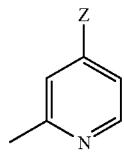
-continued
D-52d: 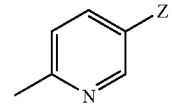
D-52e: 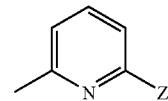
D-52f: 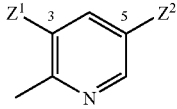
D-53a: 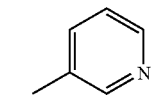
D-53b: 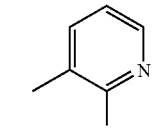
D-53c: 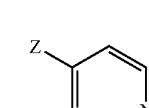
D-53d: 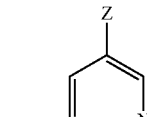
D-53e: 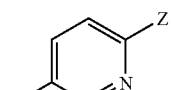
D-54a: 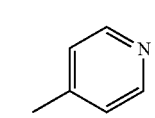
D-54b: 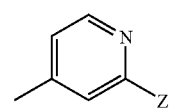
D-54c: 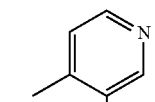

-continued
D-54e: 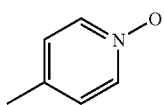
D-55a: 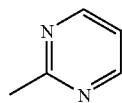
D-55c: 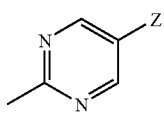
D-56a: 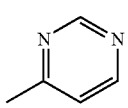
D-57a: 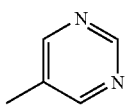
D-58a: 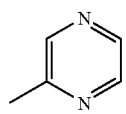
D-59a: 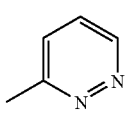
D-60a: 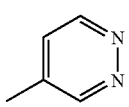
D-61a: 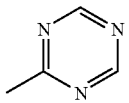
D-62a: 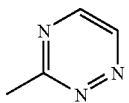
D-63a: 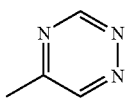
For example, the indication "[C(O)(D-53b)Cl]" means 2-chloronicotinoyl, the indication "[C(O)CH$_2$(D-52a)]" means 2-pyridylacetyl.
In addition, in Tables, aliphatic heterocyclic rings of E-4a to E-43a are the following structures, respectively
E-4a: 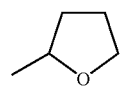
E-5a: 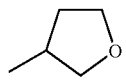
E-6a: 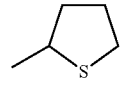
E-7a: 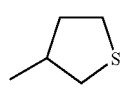
E-7b: 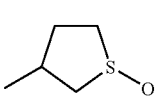
E-7c: 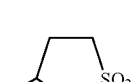
E-8a: 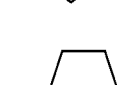
E-9a: 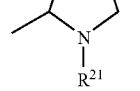
E-10a: 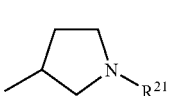
E-10b: 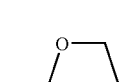
E-11a: 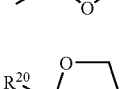
E-11b: 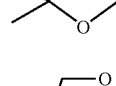
E-11c: 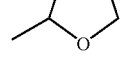
E-18a: 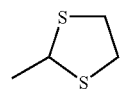

-continued
E-18b: 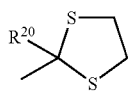
E-23a: 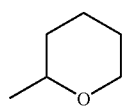
E-24a: 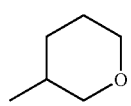
E-25a: 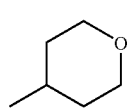
E-26a: 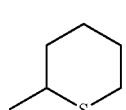
E-27a: 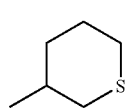
E-28a: 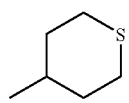
E-30a: 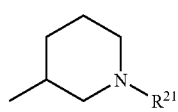
E-31a: 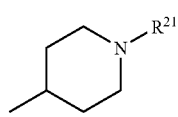
E-34a: 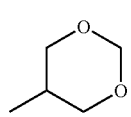
E-43a: 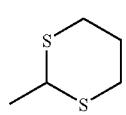
For example, the indication "[C(O)(E-5a)]" means 3-tetrahydrofurylcarbonyl, the indication "[C(O)(E-8a)C(O)OCH₃]" means N-methoxycarbonyl-2-pyrrolidinecarbonyl. Further, in Tables, partially saturated heterocyclic rings of M-11a to M-36a are the following structures, respectively
M-11a: 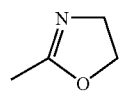
M-11b: 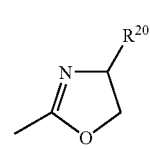
M-11c: 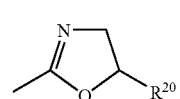
M-14a: 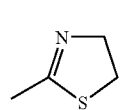
M-14b: 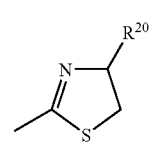
M-14c: 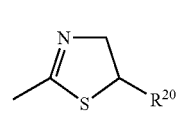
M-17a: 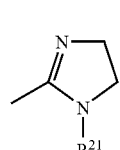
M-28a: 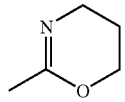
M-32a: 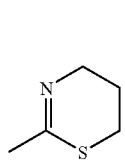
M-36a: 
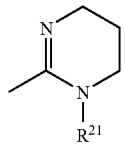

Further, in Tables, T-1 to T-27 are the following structures, respectively
T-1: 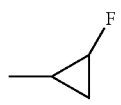
T-2: 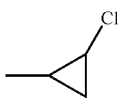
T-3: 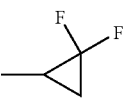
T-4: 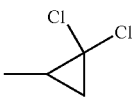
T-5: 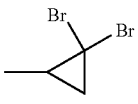
T-6: 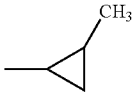
T-7: 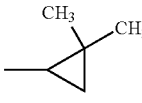
T-8: 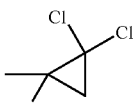
T-9: 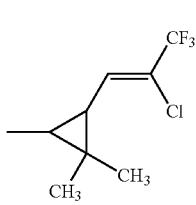
T-10: 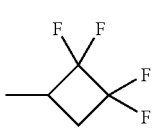
T-11: 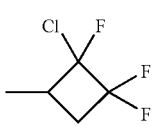
T-12: 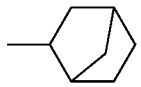
T-13: 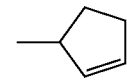
T-14: 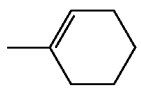
T-15: 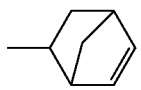
T-16: 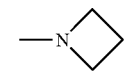
T-17: 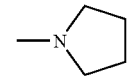
T-18: 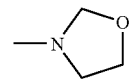
T-19: 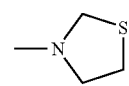
T-19: 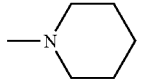
T-20: 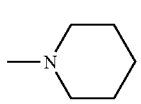
T-21: 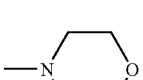
T-22: 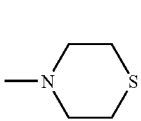
T-23: 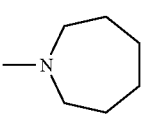

-continued

T-24:
—N⌒N—CH₃

T-25:
—N⌒N—CHO

T-26:
—N⌒N—C(=O)CH₃

T-27:
—N⌒N—C(=O)OCH₃

TABLE 2

In the table, the number showing the substitution position of substituent (X)$_m$ corresponds to the position number indicated in the following structural formulae.

[1] - 1

[1] - 2 (F)

[1] - 3 (Cl)

[1] - 4 (Br)

[1] - 5 (I)

[1] - 6 (CH₃)

[1] - 7 (Et)

[1] - 8 (CF₃)

[1] - 9 (CH₃O)

[1] - 10 (CHF₂O)

TABLE 2-continued
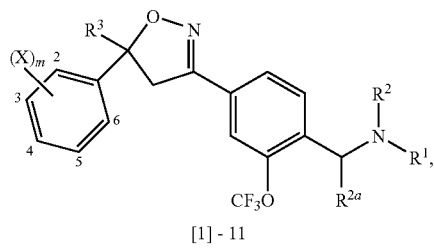
[1] - 11
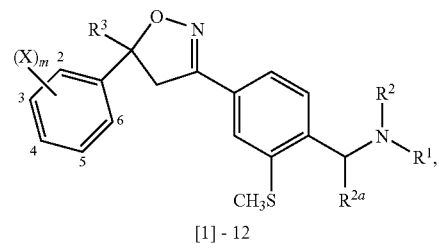
[1] - 12
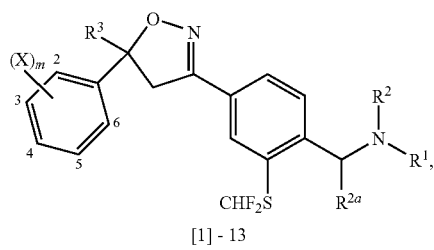
[1] - 13
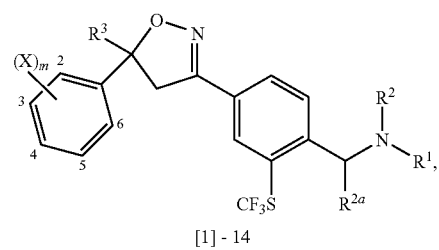
[1] - 14
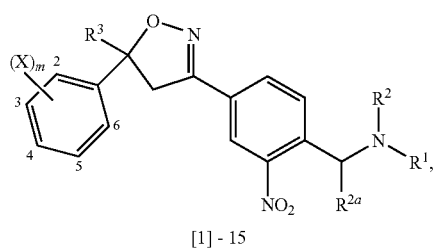
[1] - 15
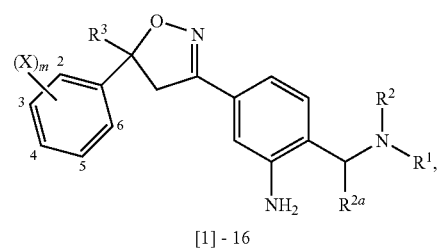
[1] - 16
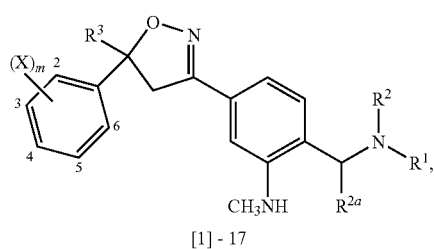
[1] - 17
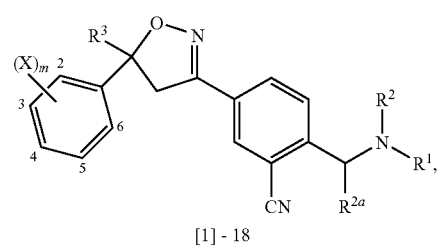
[1] - 18
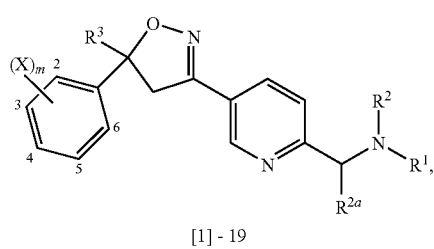
[1] - 19
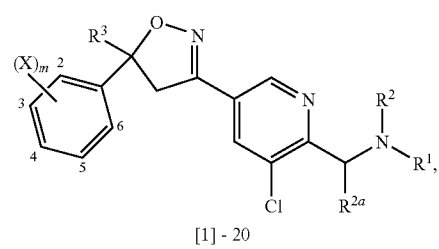
[1] - 20
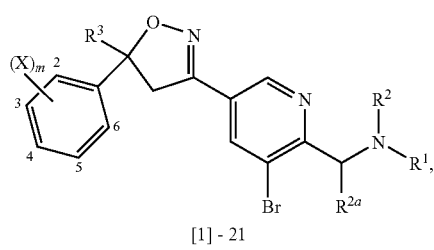
[1] - 21
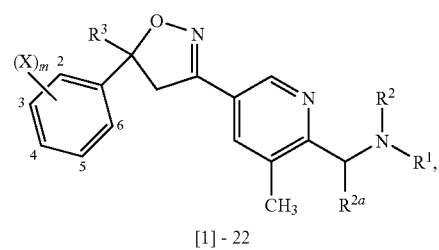
[1] - 22

TABLE 2-continued

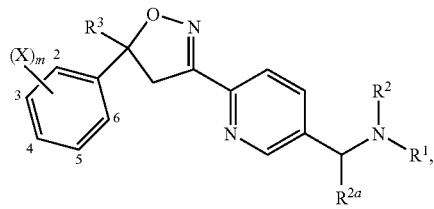

[1] - 23

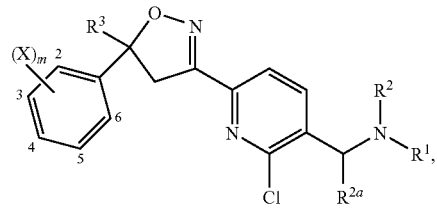

[1] - 24

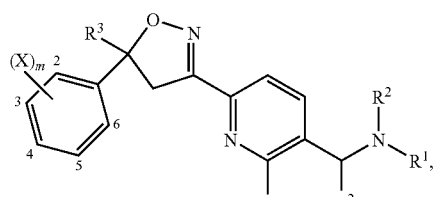

[1] - 25

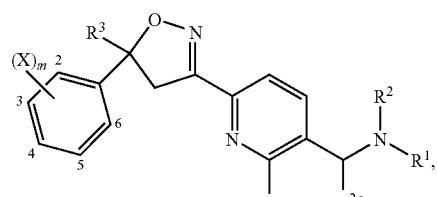

[1] - 26

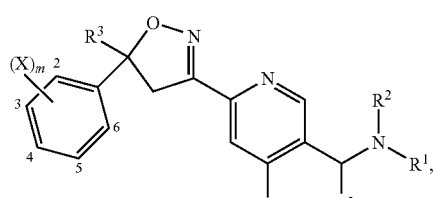

[1] - 27

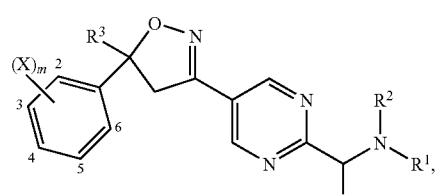

[1] - 28

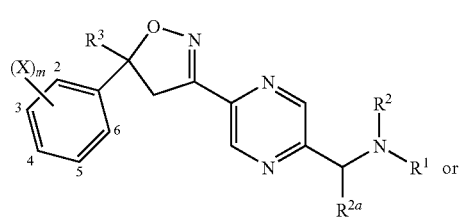

[1] - 29 or

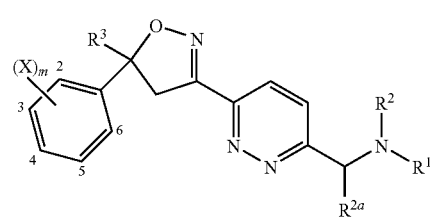

[1] - 30

| (X)$_m$ | R$^3$ | R$^{2a}$ | R$^2$ | R$^1$ |
|---|---|---|---|---|
| 3-F | CF$_3$ | H | H | C(O)Pr-i |
| 3-F | CF$_3$ | H | H | C(O)Pr-c |
| 3-F | CF$_3$ | H | H | C(O)CH$_2$CF$_3$ |
| 3-F | CF$_3$ | CH$_3$ | H | C(O)Pr-c |
| 3-F | CF$_3$ | CH$_3$ | H | C(O)CH$_2$CF$_3$ |
| 4-F | CF$_3$ | H | H | C(O)Pr-i |
| 3-Cl | CF$_3$ | H | H | C(O)Et |
| 3-Cl | CF$_3$ | H | H | C(O)Pr-n |
| 3-Cl | CF$_3$ | H | H | C(O)Pr-i |
| 3-Cl | CF$_3$ | H | H | C(O)Pr-c |
| 3-Cl | CF$_3$ | H | H | C(O)CH$_2$Pr-c |
| 3-Cl | CF$_3$ | H | H | C(O)CH$_2$CH$_2$Cl |
| 3-Cl | CF$_3$ | H | H | C(O)CH$_2$CF$_3$ |
| 3-Cl | CF$_3$ | CH$_3$ | H | C(O)Pr-i |
| 3-Cl | CF$_3$ | CH$_3$ | H | C(O)Pr-c |
| 3-Cl | CF$_3$ | CH$_3$ | H | C(O)CH$_2$CF$_3$ |
| 3-Cl | CF$_2$Cl | H | H | C(O)Et |
| 4-Cl | CF$_3$ | H | H | C(O)Pr-c |
| 3-Br | CHF$_2$ | H | H | C(O)CH$_2$CF$_3$ |
| 3-Br | CF$_3$ | H | H | H |
| 3-Br | CF$_3$ | H | H | C(O)Et |
| 3-Br | CF$_3$ | H | H | C(O)Pr-n |
| 3-Br | CF$_3$ | H | H | C(O)Pr-i |
| 3-Br | CF$_3$ | H | H | C(O)Pr-c |
| 3-Br | CF$_3$ | H | H | C(O)CH$_2$Pr-c |
| 3-Br | CF$_3$ | H | H | C(O)CF$_3$ |
| 3-Br | CF$_3$ | H | H | C(O)CH$_2$CH$_2$Cl |
| 3-Br | CF$_3$ | H | H | C(O)CH$_2$CF$_3$ |
| 3-Br | CF$_3$ | H | H | C(O)CF$_2$CHF$_2$ |

TABLE 2-continued

| | | | | |
|---|---|---|---|---|
| 3-Br | CF$_3$ | H | H | C(O)CF$_2$CF$_3$ |
| 3-Br | CF$_3$ | H | H | C(O)CH$_2$CH$_2$SCH$_3$ |
| 3-Br | CF$_3$ | H | H | C(O)(Ph-2,4-F$_2$) |
| 3-Br | CF$_3$ | H | H | C(O)NHEt |
| 3-Br | CF$_3$ | H | H | C(O)NHPr-i |
| 3-Br | CF$_3$ | H | H | C(O)NHCH$_2$CF$_3$ |
| 3-Br | CF$_3$ | CH$_3$ | H | H |
| 3-Br | CF$_3$ | CH$_3$ | H | C(O)Et |
| 3-Br | CF$_3$ | CH$_3$ | H | C(O)Pr-n |
| 3-Br | CF$_3$ | CH$_3$ | H | C(O)Pr-i |
| 3-Br | CF$_3$ | CH$_3$ | H | C(O)Pr-c |
| 3-Br | CF$_3$ | CH$_3$ | H | C(O)CH$_2$CF$_3$ |
| 3-Br | CF$_3$ | CN | H | H |
| 3-Br | CF$_3$ | CN | H | C(O)Pr-c |
| 3-Br | CF$_3$ | CN | H | C(O)CH$_2$CF$_3$ |
| 3-Br | CF$_2$Cl | H | H | C(O)Et |
| 3-Br | CF$_2$Cl | H | H | C(O)Pr-n |
| 3-Br | CF$_2$Cl | H | H | C(O)Pr-i |
| 3-Br | CF$_2$Cl | H | H | C(O)Pr-c |
| 3-Br | CF$_2$Cl | H | H | C(O)CH$_2$Pr-c |
| 3-Br | CF$_2$Cl | H | H | C(O)CH$_2$CH$_2$Cl |
| 3-Br | CF$_2$Cl | H | H | C(O)CH$_2$CF$_3$ |
| 3-Br | CF$_2$Cl | CH$_3$ | H | C(O)Pr-i |
| 3-Br | CF$_2$Cl | CH$_3$ | H | C(O)Pr-c |
| 3-Br | CF$_2$Cl | CH$_3$ | H | C(O)CH$_2$CF$_3$ |
| 3-Br | CF$_2$Br | CH$_3$ | H | C(O)Pr-c |
| 3-Br | CF$_2$CHF$_2$ | CH$_3$ | H | C(O)CH$_2$CF$_3$ |
| 4-Br | CF$_3$ | H | H | C(O)Pr-i |
| 3-I | CHF$_2$ | H | H | C(O)Pr-c |
| 3-I | CF$_3$ | H | H | H |
| 3-I | CF$_3$ | H | H | C(O)Et |
| 3-I | CF$_3$ | H | H | C(O)Pr-n |
| 3-I | CF$_3$ | H | H | C(O)Pr-i |
| 3-I | CF$_3$ | H | H | C(O)Pr-c |
| 3-I | CF$_3$ | H | H | C(O)CH$_2$Pr-c |
| 3-I | CF$_3$ | H | H | C(O)CF$_3$ |
| 3-I | CF$_3$ | H | H | C(O)CH$_2$CH$_2$Cl |
| 3-I | CF$_3$ | H | H | C(O)CH$_2$CF$_3$ |
| 3-I | CF$_3$ | H | H | C(O)CH$_2$CHF$_2$ |
| 3-I | CF$_3$ | H | H | C(O)CF$_2$CF$_3$ |
| 3-I | CF$_3$ | H | H | C(O)CH$_2$CH$_2$SCH$_3$ |
| 3-I | CF$_3$ | H | H | C(O)(Ph-2,4-F$_2$) |
| 3-I | CF$_3$ | H | H | C(O)NHEt |
| 3-I | CF$_3$ | H | H | C(O)NHPr-i |
| 3-I | CF$_3$ | H | H | C(O)NHCH$_2$CF$_3$ |
| 3-I | CF$_3$ | CH$_3$ | H | H |
| 3-I | CF$_3$ | CH$_3$ | H | C(O)Et |
| 3-I | CF$_3$ | CH$_3$ | H | C(O)Pr-n |
| 3-I | CF$_3$ | CH$_3$ | H | C(O)Pr-i |
| 3-I | CF$_3$ | CH$_3$ | H | C(O)Pr-c |
| 3-I | CF$_3$ | CH$_3$ | H | C(O)CH$_2$CF$_3$ |
| 3-I | CF$_3$ | CN | H | H |
| 3-I | CF$_3$ | CN | H | C(O)Pr-c |
| 3-I | CF$_3$ | CN | H | C(O)CH$_2$CF$_3$ |
| 3-I | CF$_2$Cl | H | H | C(O)Et |
| 3-I | CF$_2$Cl | H | H | C(O)Pr-n |
| 3-I | CF$_2$Cl | H | H | C(O)Pr-i |
| 3-I | CF$_2$Cl | H | H | C(O)Pr-c |
| 3-I | CF$_2$Cl | H | H | C(O)CH$_2$Pr-c |
| 3-I | CF$_2$Cl | H | H | C(O)CH$_2$CH$_2$Cl |
| 3-I | CF$_2$Cl | H | H | C(O)CH$_2$CF$_3$ |
| 3-I | CF$_2$Cl | CH$_3$ | H | C(O)Pr-i |
| 3-I | CF$_2$Cl | CH$_3$ | H | C(O)Pr-c |
| 3-I | CF$_2$Cl | CH$_3$ | H | C(O)CH$_2$CF$_3$ |
| 3-I | CF$_2$Br | H | H | C(O)CH$_2$CF$_3$ |
| 3-I | CF$_2$CHF$_2$ | CH$_3$ | H | C(O)Pr-c |
| 4-I | CF$_3$ | CH$_3$ | H | C(O)CH$_2$CF$_3$ |
| 3-CH$_3$ | CF$_3$ | H | H | C(O)Pr-i |
| 3-Et | CF$_3$ | H | H | C(O)Pr-c |
| 3-i-Pr | CF$_3$ | H | H | C(O)CH$_2$CF$_3$ |
| 3-t-Bu | CF$_3$ | CH$_3$ | H | C(O)Pr-c |
| 3-CF$_3$ | CHF$_2$ | CH$_3$ | H | C(O)CH$_2$CF$_3$ |
| 3-CF$_3$ | CF$_3$ | H | H | H |
| 3-CF$_3$ | CF$_3$ | H | H | C(O)Et |
| 3-CF$_3$ | CF$_3$ | H | H | C(O)Pr-n |
| 3-CF$_3$ | CF$_3$ | H | H | C(O)Pr-i |
| 3-CF$_3$ | CF$_3$ | H | H | C(O)Pr-c |
| 3-CF$_3$ | CF$_3$ | H | H | C(O)CH$_2$Pr-c |
| 3-CF$_3$ | CF$_3$ | H | H | C(O)CF$_3$ |
| 3-CF$_3$ | CF$_3$ | H | H | C(O)CH$_2$CH$_2$Cl |

TABLE 2-continued

| | | | | |
|---|---|---|---|---|
| 3-CF$_3$ | CF$_3$ | H | H | C(O)CH$_2$CF$_3$ |
| 3-CF$_3$ | CF$_3$ | H | H | C(O)CF$_2$CHF$_2$ |
| 3-CF$_3$ | CF$_3$ | H | H | C(O)CF$_2$CF$_3$ |
| 3-CF$_3$ | CF$_3$ | H | H | C(O)CH$_2$CH$_2$SCH$_3$ |
| 3-CF$_3$ | CF$_3$ | H | H | C(O)(Ph-2,4-F$_2$) |
| 3-CF$_3$ | CF$_3$ | H | H | C(O)NHEt |
| 3-CF$_3$ | CF$_3$ | H | H | C(O)NHPr-i |
| 3-CF$_3$ | CF$_3$ | H | H | C(O)NHCH$_2$CF$_3$ |
| 3-CF$_3$ | CF$_3$ | CH$_3$ | H | H |
| 3-CF$_3$ | CF$_3$ | CH$_3$ | H | C(O)Et |
| 3-CF$_3$ | CF$_3$ | CH$_3$ | H | C(O)Pr-n |
| 3-CF$_3$ | CF$_3$ | CH$_3$ | H | C(O)Pr-i |
| 3-CF$_3$ | CF$_3$ | CH$_3$ | H | C(O)Pr-c |
| 3-CF$_3$ | CF$_3$ | CH$_3$ | H | C(O)CH$_2$CF$_3$ |
| 3-CF$_3$ | CF$_3$ | CN | H | H |
| 3-CF$_3$ | CF$_3$ | CN | H | C(O)Pr-c |
| 3-CF$_3$ | CF$_3$ | CN | H | C(O)CH$_2$CF$_3$ |
| 3-CF$_3$ | CF$_2$Cl | H | H | C(O)Et |
| 3-CF$_3$ | CF$_2$Cl | H | H | C(O)Pr-n |
| 3-CF$_3$ | CF$_2$Cl | H | H | C(O)Pr-i |
| 3-CF$_3$ | CF$_2$Cl | H | H | C(O)Pr-c |
| 3-CF$_3$ | CF$_2$Cl | H | H | C(O)CH$_2$Pr-c |
| 3-CF$_3$ | CF$_2$Cl | H | H | C(O)CH$_2$CH$_2$Cl |
| 3-CF$_3$ | CF$_2$Cl | H | H | C(O)CH$_2$CF$_3$ |
| 3-CF$_3$ | CF$_2$Cl | CH$_3$ | H | C(O)Pr-i |
| 3-CF$_3$ | CF$_2$Cl | CH$_3$ | H | C(O)Pr-c |
| 3-CF$_3$ | CF$_2$Cl | CH$_3$ | H | C(O)CH$_2$CF$_3$ |
| 3-CF$_3$ | CF$_2$Br | H | H | C(O)Pr-i |
| 3-CF$_3$ | CF$_2$CHF$_2$ | H | H | C(O)Pr-c |
| 4-CF$_3$ | CF$_3$ | H | H | C(O)CH$_2$CF$_3$ |
| 3-CF$_2$CF$_3$ | CHF$_2$ | CH$_3$ | H | C(O)Pr-c |
| 3-CF$_2$CF$_3$ | CF$_3$ | H | H | H |
| 3-CF$_2$CF$_3$ | CF$_3$ | H | H | C(O)Et |
| 3-CF$_2$CF$_3$ | CF$_3$ | H | H | C(O)Pr-n |
| 3-CF$_2$CF$_3$ | CF$_3$ | H | H | C(O)Pr-i |
| 3-CF$_2$CF$_3$ | CF$_3$ | H | H | C(O)Pr-c |
| 3-CF$_2$CF$_3$ | CF$_3$ | H | H | C(O)CH$_2$Pr-c |
| 3-CF$_2$CF$_3$ | CF$_3$ | H | H | C(O)CF$_3$ |
| 3-CF$_2$CF$_3$ | CF$_3$ | H | H | C(O)CH$_2$CH$_2$Cl |
| 3-CF$_2$CF$_3$ | CF$_3$ | H | H | C(O)CH$_2$CF$_3$ |
| 3-CF$_2$CF$_3$ | CF$_3$ | H | H | C(O)CF$_2$CHF$_2$ |
| 3-CF$_2$CF$_3$ | CF$_3$ | H | H | C(O)CF$_2$CF$_3$ |
| 3-CF$_2$CF$_3$ | CF$_3$ | H | H | C(O)CH$_2$CH$_2$SCH$_3$ |
| 3-CF$_2$CF$_3$ | CF$_3$ | H | H | C(O)(Ph-2,4-F$_2$) |
| 3-CF$_2$CF$_3$ | CF$_3$ | H | H | C(O)NHEt |
| 3-CF$_2$CF$_3$ | CF$_3$ | H | H | C(O)NHPr-i |
| 3-CF$_2$CF$_3$ | CF$_3$ | H | H | C(O)NHCH$_2$CF$_3$ |
| 3-CF$_2$CF$_3$ | CF$_3$ | CH$_3$ | H | H |
| 3-CF$_2$CF$_3$ | CF$_3$ | CH$_3$ | H | C(O)Et |
| 3-CF$_2$CF$_3$ | CF$_3$ | CH$_3$ | H | C(O)Pr-n |
| 3-CF$_2$CF$_3$ | CF$_3$ | CH$_3$ | H | C(O)Pr-i |
| 3-CF$_2$CF$_3$ | CF$_3$ | CH$_3$ | H | C(O)Pr-c |
| 3-CF$_2$CF$_3$ | CF$_3$ | CH$_3$ | H | C(O)CH$_2$CF$_3$ |
| 3-CF$_2$CF$_3$ | CF$_3$ | CN | H | H |
| 3-CF$_2$CF$_3$ | CF$_3$ | CN | H | C(O)Pr-c |
| 3-CF$_2$CF$_3$ | CF$_3$ | CN | H | C(O)CH$_2$CF$_3$ |
| 3-CF$_2$CF$_3$ | CF$_2$Cl | H | H | C(O)Et |
| 3-CF$_2$CF$_3$ | CF$_2$Cl | H | H | C(O)Pr-n |
| 3-CF$_2$CF$_3$ | CF$_2$Cl | H | H | C(O)Pr-i |
| 3-CF$_2$CF$_3$ | CF$_2$Cl | H | H | C(O)Pr-c |
| 3-CF$_2$CF$_3$ | CF$_2$Cl | H | H | C(O)CH$_2$Pr-c |
| 3-CF$_2$CF$_3$ | CF$_2$Cl | H | H | C(O)CH$_2$CH$_2$Cl |
| 3-CF$_2$CF$_3$ | CF$_2$Cl | H | H | C(O)CH$_2$CF$_3$ |
| 3-CF$_2$CF$_3$ | CF$_2$Cl | CH$_3$ | H | C(O)Pr-i |
| 3-CF$_2$CF$_3$ | CF$_2$Cl | CH$_3$ | H | C(O)Pr-c |
| 3-CF$_2$CF$_3$ | CF$_2$Cl | CH$_3$ | H | C(O)CH$_2$CF$_3$ |
| 3-CF$_2$CF$_3$ | CF$_2$Br | CH$_3$ | H | C(O)CH$_2$CF$_3$ |
| 3-CF$_2$CF$_3$ | CF$_2$CHF$_2$ | H | H | C(O)Pr-i |
| 3-CF$_2$CF$_2$CF$_3$ | CHF$_2$ | H | H | C(O)Pr-c |
| 3-CF$_2$CF$_2$CF$_3$ | CF$_3$ | H | H | H |
| 3-CF$_2$CF$_2$CF$_3$ | CF$_3$ | H | H | C(O)Et |
| 3-CF$_2$CF$_2$CF$_3$ | CF$_3$ | H | H | C(O)Pr-n |
| 3-CF$_2$CF$_2$CF$_3$ | CF$_3$ | H | H | C(O)Pr-i |
| 3-CF$_2$CF$_2$CF$_3$ | CF$_3$ | H | H | C(O)Pr-c |
| 3-CF$_2$CF$_2$CF$_3$ | CF$_3$ | H | H | C(O)CH$_2$Pr-c |
| 3-CF$_2$CF$_2$CF$_3$ | CF$_3$ | H | H | C(O)CF$_3$ |
| 3-CF$_2$CF$_2$CF$_3$ | CF$_3$ | H | H | C(O)CH$_2$CH$_2$Cl |
| 3-CF$_2$CF$_2$CF$_3$ | CF$_3$ | H | H | C(O)CH$_2$CF$_3$ |
| 3-CF$_2$CF$_2$CF$_3$ | CF$_3$ | H | H | C(O)CF$_2$CHF$_2$ |
| 3-CF$_2$CF$_2$CF$_3$ | CF$_3$ | H | H | C(O)CF$_2$CF$_3$ |

TABLE 2-continued

| | | | | |
|---|---|---|---|---|
| 3-CF₂CF₂CF₃ | CF₃ | H | H | C(O)CH₂CH₂SCH₃ |
| 3-CF₂CF₂CF₃ | CF₃ | H | H | C(O)(Ph-2,4-F₂) |
| 3-CF₂CF₂CF₃ | CF₃ | H | H | C(O)NHEt |
| 3-CF₂CF₂CF₃ | CF₃ | H | H | C(O)NHPr-i |
| 3-CF₂CF₂CF₃ | CF₃ | H | H | C(O)NHCH₂CF₃ |
| 3-CF₂CF₂CF₃ | CF₃ | CH₃ | H | H |
| 3-CF₂CF₂CF₃ | CF₃ | CH₃ | H | C(O)Et |
| 3-CF₂CF₂CF₃ | CF₃ | CH₃ | H | C(O)Pr-n |
| 3-CF₂CF₂CF₃ | CF₃ | CH₃ | H | C(O)Pr-i |
| 3-CF₂CF₂CF₃ | CF₃ | CH₃ | H | C(O)Pr-c |
| 3-CF₂CF₂CF₃ | CF₃ | CH₃ | H | C(O)CH₂CF₃ |
| 3-CF₂CF₂CF₃ | CF₃ | CN | H | H |
| 3-CF₂CF₂CF₃ | CF₃ | CN | H | C(O)Pr-c |
| 3-CF₂CF₂CF₃ | CF₃ | CN | H | C(O)CH₂CF₃ |
| 3-CF₂CF₂CF₃ | CF₂Cl | H | H | C(O)Et |
| 3-CF₂CF₂CF₃ | CF₂Cl | H | H | C(O)Pr-n |
| 3-CF₂CF₂CF₃ | CF₂Cl | H | H | C(O)Pr-i |
| 3-CF₂CF₂CF₃ | CF₂Cl | H | H | C(O)Pr-c |
| 3-CF₂CF₂CF₃ | CF₂Cl | H | H | C(O)CH₂Pr-c |
| 3-CF₂CF₂CF₃ | CF₂Cl | H | H | C(O)CH₂CH₂Cl |
| 3-CF₂CF₂CF₃ | CF₂Cl | H | H | C(O)CH₂CF₃ |
| 3-CF₂CF₂CF₃ | CF₂Cl | CH₃ | H | C(O)Pr-i |
| 3-CF₂CF₂CF₃ | CF₂Cl | CH₃ | H | C(O)Pr-c |
| 3-CF₂CF₂CF₃ | CF₂Cl | CH₃ | H | C(O)CH₂CF₃ |
| 3-CF₂CF₂CF₃ | CF₂Br | H | H | C(O)CH₂CF₃ |
| 3-CF₂CF₂CF₃ | CF₂CHF₂ | CH₃ | H | C(O)Pr-c |
| 3-CF(CF₃)₂ | CHF₂ | CH₃ | H | C(O)CH₂CF₃ |
| 3-CF(CF₃)₂ | CF₃ | H | H | H |
| 3-CF(CF₃)₂ | CF₃ | H | H | C(O)Et |
| 3-CF(CF₃)₂ | CF₃ | H | H | C(O)Pr-n |
| 3-CF(CF₃)₂ | CF₃ | H | H | C(O)Pr-i |
| 3-CF(CF₃)₂ | CF₃ | H | H | C(O)Pr-c |
| 3-CF(CF₃)₂ | CF₃ | H | H | C(O)CH₂Pr-c |
| 3-CF(CF₃)₂ | CF₃ | H | H | C(O)CF₃ |
| 3-CF(CF₃)₂ | CF₃ | H | H | C(O)CH₂CH₂Cl |
| 3-CF(CF₃)₂ | CF₃ | H | H | C(O)CH₂CF₃ |
| 3-CF(CF₃)₂ | CF₃ | H | H | C(O)CF₂CHF₂ |
| 3-CF(CF₃)₂ | CF₃ | H | H | C(O)CF₂CF₃ |
| 3-CF(CF₃)₂ | CF₃ | H | H | C(O)CH₂CH₂SCH₃ |
| 3-CF(CF₃)₂ | CF₃ | H | H | C(O)(Ph-2,4-F₂) |
| 3-CF(CF₃)₂ | CF₃ | H | H | C(O)NHEt |
| 3-CF(CF₃)₂ | CF₃ | H | H | C(O)NHPr-i |
| 3-CF(CF₃)₂ | CF₃ | H | H | C(O)NHCH₂CF₃ |
| 3-CF(CF₃)₂ | CF₃ | CH₃ | H | H |
| 3-CF(CF₃)₂ | CF₃ | CH₃ | H | C(O)Et |
| 3-CF(CF₃)₂ | CF₃ | CH₃ | H | C(O)Pr-n |
| 3-CF(CF₃)₂ | CF₃ | CH₃ | H | C(O)Pr-i |
| 3-CF(CF₃)₂ | CF₃ | CH₃ | H | C(O)Pr-c |
| 3-CF(CF₃)₂ | CF₃ | CH₃ | H | C(O)CH₂CF₃ |
| 3-CF(CF₃)₂ | CF₃ | CN | H | H |
| 3-CF(CF₃)₂ | CF₃ | CN | H | C(O)Pr-c |
| 3-CF(CF₃)₂ | CF₃ | CN | H | C(O)CH₂CF₃ |
| 3-CF(CF₃)₂ | CF₂Cl | H | H | C(O)Et |
| 3-CF(CF₃)₂ | CF₂Cl | H | H | C(O)Pr-n |
| 3-CF(CF₃)₂ | CF₂Cl | H | H | C(O)Pr-i |
| 3-CF(CF₃)₂ | CF₂Cl | H | H | C(O)Pr-c |
| 3-CF(CF₃)₂ | CF₂Cl | H | H | C(O)CH₂Pr-c |
| 3-CF(CF₃)₂ | CF₂Cl | H | H | C(O)CH₂CH₂Cl |
| 3-CF(CF₃)₂ | CF₂Cl | H | H | C(O)CH₂CF₃ |
| 3-CF(CF₃)₂ | CF₂Cl | CH₃ | H | C(O)Pr-i |
| 3-CF(CF₃)₂ | CF₂Cl | CH₃ | H | C(O)Pr-c |
| 3-CF(CF₃)₂ | CF₂Cl | CH₃ | H | C(O)CH₂CF₃ |
| 3-CF(CF₃)₂ | CF₂Br | H | H | C(O)Pr-i |
| 3-CF(CF₃)₂ | CF₂CHF₂ | H | H | C(O)Pr-c |
| 3-CF₂CF₂CF₂CF₃ | CF₃ | H | H | C(O)Et |
| 3-CF₂CF₂CF₂CF₃ | CF₃ | H | H | C(O)Pr-n |
| 3-CF₂CF₂CF₂CF₃ | CF₃ | H | H | C(O)Pr-i |
| 3-CF₂CF₂CF₂CF₃ | CF₃ | H | H | C(O)Pr-c |
| 3-CF₂CF₂CF₂CF₃ | CF₃ | H | H | C(O)CH₂Pr-c |
| 3-CF₂CF₂CF₂CF₃ | CF₃ | H | H | C(O)CH₂CH₂Cl |
| 3-CF₂CF₂CF₂CF₃ | CF₃ | H | H | C(O)CH₂CF₃ |
| 3-CF₂CF₂CF₂CF₃ | CF₃ | CH₃ | H | C(O)Pr-i |
| 3-CF₂CF₂CF₂CF₃ | CF₃ | CH₃ | H | C(O)Pr-c |
| 3-CF₂CF₂CF₂CF₃ | CF₃ | CH₃ | H | C(O)CH₂CF₃ |
| 3-CF₂CF₂CF₂CF₃ | CF₂Cl | H | H | C(O)CH₂CF₃ |
| 3-CH₂OCH₂CF₃ | CF₃ | CH₃ | H | C(O)Pr-c |
| 3-C(CF₃)₂OH | CF₃ | H | H | C(O)Et |
| 3-C(CF₃)₂OH | CF₃ | H | H | C(O)Pr-n |
| 3-C(CF₃)₂OH | CF₃ | H | H | C(O)Pr-i |
| 3-C(CF₃)₂OH | CF₃ | H | H | C(O)Pr-c |

TABLE 2-continued

| | | | | |
|---|---|---|---|---|
| 3-C(CF$_3$)$_2$OH | CF$_3$ | H | H | C(O)CH$_2$Pr-c |
| 3-C(CF$_3$)$_2$OH | CF$_3$ | H | H | C(O)CH$_2$CH$_2$Cl |
| 3-C(CF$_3$)$_2$OH | CF$_3$ | H | H | C(O)CH$_2$CF$_3$ |
| 3-C(CF$_3$)$_2$OH | CF$_3$ | CH$_3$ | H | C(O)Pr-i |
| 3-C(CF$_3$)$_2$OH | CF$_3$ | CH$_3$ | H | C(O)Pr-c |
| 3-C(CF$_3$)$_2$OH | CF$_3$ | CH$_3$ | H | C(O)CH$_2$CF$_3$ |
| 3-C(CF$_3$)$_2$OH | CF$_2$Cl | CH$_3$ | H | C(O)CH$_2$CF$_3$ |
| 3-C(CF$_3$)$_2$OCH$_3$ | CF$_3$ | H | H | C(O)Et |
| 3-C(CF$_3$)$_2$OCH$_3$ | CF$_3$ | H | H | C(O)Pr-n |
| 3-C(CF$_3$)$_2$OCH$_3$ | CF$_3$ | H | H | C(O)Pr-i |
| 3-C(CF$_3$)$_2$OCH$_3$ | CF$_3$ | H | H | C(O)Pr-c |
| 3-C(CF$_3$)$_2$OCH$_3$ | CF$_3$ | H | H | C(O)CH$_2$Pr-c |
| 3-C(CF$_3$)$_2$OCH$_3$ | CF$_3$ | H | H | C(O)CH$_2$CH$_2$Cl |
| 3-C(CF$_3$)$_2$OCH$_3$ | CF$_3$ | H | H | C(O)CH$_2$CF$_3$ |
| 3-C(CF$_3$)$_2$OCH$_3$ | CF$_3$ | CH$_3$ | H | C(O)Pr-i |
| 3-C(CF$_3$)$_2$OCH$_3$ | CF$_3$ | CH$_3$ | H | C(O)Pr-c |
| 3-C(CF$_3$)$_2$OCH$_3$ | CF$_3$ | CH$_3$ | H | C(O)CH$_2$CF$_3$ |
| 3-C(CF$_3$)$_2$OCH$_3$ | CF$_2$Cl | H | H | C(O)Pr-i |
| 3-CH$_2$SCH$_3$ | CF$_3$ | H | H | C(O)Pr-c |
| 3-CH$_2$SEt | CF$_3$ | H | H | C(O)CH$_2$CF$_3$ |
| 3-CH$_2$SPr-i | CF$_3$ | CH$_3$ | H | C(O)Pr-c |
| 3-CH$_2$SPr-c | CF$_3$ | CH$_3$ | H | C(O)CH$_2$CF$_3$ |
| 3-CH$_2$SCF$_3$ | CF$_3$ | H | H | C(O)Pr-i |
| 3-CH$_2$S(O)CF$_3$ | CF$_3$ | H | H | C(O)Pr-c |
| 3-CH$_2$SO$_2$CF$_3$ | CF$_3$ | H | H | C(O)CH$_2$CF$_3$ |
| 3-CH$_2$SCH$_2$CF$_3$ | CF$_3$ | CH$_3$ | H | C(O)Pr-c |
| 3-(T-3) | CF$_3$ | CH$_3$ | H | C(O)CH$_2$CF$_3$ |
| 3-(T-4) | CF$_3$ | H | H | C(O)Pr-i |
| 3-(T-5) | CF$_3$ | H | H | C(O)Pr-c |
| 3-OCHF$_2$ | CF$_3$ | H | H | C(O)CH$_2$CF$_3$ |
| 4-OCHF$_2$ | CF$_3$ | CH$_3$ | H | C(O)Pr-c |
| 3-OCF$_3$ | CF$_3$ | H | H | C(O)Et |
| 3-OCF$_3$ | CF$_3$ | H | H | C(O)Pr-n |
| 3-OCF$_3$ | CF$_3$ | H | H | C(O)Pr-i |
| 3-OCF$_3$ | CF$_3$ | H | H | C(O)Pr-c |
| 3-OCF$_3$ | CF$_3$ | H | H | C(O)CH$_2$Pr-c |
| 3-OCF$_3$ | CF$_3$ | H | H | C(O)CH$_2$CH$_2$Cl |
| 3-OCF$_3$ | CF$_3$ | H | H | C(O)CH$_2$CF$_3$ |
| 3-OCF$_3$ | CF$_3$ | CH$_3$ | H | C(O)Pr-i |
| 3-OCF$_3$ | CF$_3$ | CH$_3$ | H | C(O)Pr-c |
| 3-OCF$_3$ | CF$_3$ | CH$_3$ | H | C(O)CH$_2$CF$_3$ |
| 3-OCF$_3$ | CF$_2$Cl | CH$_3$ | H | C(O)CH$_2$CF$_3$ |
| 3-OCF$_2$Br | CF$_3$ | H | H | C(O)Et |
| 3-OCF$_2$Br | CF$_3$ | H | H | C(O)Pr-n |
| 3-OCF$_2$Br | CF$_3$ | H | H | C(O)Pr-i |
| 3-OCF$_2$Br | CF$_3$ | H | H | C(O)Pr-c |
| 3-OCF$_2$Br | CF$_3$ | H | H | C(O)CH$_2$Pr-c |
| 3-OCF$_2$Br | CF$_3$ | H | H | C(O)CH$_2$CH$_2$Cl |
| 3-OCF$_2$Br | CF$_3$ | H | H | C(O)CH$_2$CF$_3$ |
| 3-OCF$_2$Br | CF$_3$ | CH$_3$ | H | C(O)Pr-i |
| 3-OCF$_2$Br | CF$_3$ | CH$_3$ | H | C(O)Pr-c |
| 3-OCF$_2$Br | CF$_3$ | CH$_3$ | H | C(O)CH$_2$CF$_3$ |
| 3-OCF$_2$Br | CF$_2$Cl | H | H | C(O)Pr-i |
| 3-OCH$_2$CH$_2$Cl | CF$_3$ | H | H | C(O)Pr-c |
| 3-OCH$_2$CF$_3$ | CF$_3$ | H | H | C(O)CH$_2$CF$_3$ |
| 3-OCF$_2$CHF$_2$ | CF$_3$ | H | H | C(O)Et |
| 3-OCF$_2$CHF$_2$ | CF$_3$ | H | H | C(O)Pr-n |
| 3-OCF$_2$CHF$_2$ | CF$_3$ | H | H | C(O)Pr-i |
| 3-OCF$_2$CHF$_2$ | CF$_3$ | H | H | C(O)Pr-c |
| 3-OCF$_2$CHF$_2$ | CF$_3$ | H | H | C(O)CH$_2$Pr-c |
| 3-OCF$_2$CHF$_2$ | CF$_3$ | H | H | C(O)CH$_2$CH$_2$Cl |
| 3-OCF$_2$CHF$_2$ | CF$_3$ | H | H | C(O)CH$_2$CF$_3$ |
| 3-OCF$_2$CHF$_2$ | CF$_3$ | CH$_3$ | H | C(O)Pr-i |
| 3-OCF$_2$CHF$_2$ | CF$_3$ | CH$_3$ | H | C(O)Pr-c |
| 3-OCF$_2$CHF$_2$ | CF$_3$ | CH$_3$ | H | C(O)CH$_2$CF$_3$ |
| 3-OCF$_2$CHF$_2$ | CF$_2$Cl | CH$_3$ | H | C(O)Pr-c |
| 3-OCF$_2$CHFCl | CF$_3$ | H | H | C(O)Et |
| 3-OCF$_2$CHFCl | CF$_3$ | H | H | C(O)Pr-n |
| 3-OCF$_2$CHFCl | CF$_3$ | H | H | C(O)Pr-i |
| 3-OCF$_2$CHFCl | CF$_3$ | H | H | C(O)Pr-c |
| 3-OCF$_2$CHFCl | CF$_3$ | H | H | C(O)CH$_2$Pr-c |
| 3-OCF$_2$CHFCl | CF$_3$ | H | H | C(O)CH$_2$CH$_2$Cl |
| 3-OCF$_2$CHFCl | CF$_3$ | H | H | C(O)CH$_2$CF$_3$ |
| 3-OCF$_2$CHFCl | CF$_3$ | CH$_3$ | H | C(O)Pr-i |
| 3-OCF$_2$CHFCl | CF$_3$ | CH$_3$ | H | C(O)Pr-c |
| 3-OCF$_2$CHFCl | CF$_3$ | CH$_3$ | H | C(O)CH$_2$CF$_3$ |
| 3-OCF$_2$CHFCl | CF$_2$Cl | CH$_3$ | H | C(O)CH$_2$CF$_3$ |
| 3-OCF$_2$CHFBr | CF$_3$ | H | H | C(O)Pr-i |
| 3-OCF$_2$CF$_2$Br | CF$_3$ | H | H | C(O)Pr-c |
| 3-OCF$_2$CFCl$_2$ | CF$_3$ | H | H | C(O)CH$_2$CF$_3$ |

TABLE 2-continued

| | | | | |
|---|---|---|---|---|
| 3-OCF$_2$CCl$_3$ | CF$_3$ | CH$_3$ | H | C(O)Pr-c |
| 3-OCH$_2$CF$_2$CHF$_2$ | CF$_3$ | CH$_3$ | H | C(O)CH$_2$CF$_3$ |
| 3-OCF$_2$CHFCF$_3$ | CF$_3$ | H | H | C(O)Et |
| 3-OCF$_2$CHFCF$_3$ | CF$_3$ | H | H | C(O)Pr-n |
| 3-OCF$_2$CHFCF$_3$ | CF$_3$ | H | H | C(O)Pr-i |
| 3-OCF$_2$CHFCF$_3$ | CF$_3$ | H | H | C(O)Pr-c |
| 3-OCF$_2$CHFCF$_3$ | CF$_3$ | H | H | C(O)CH$_2$Pr-c |
| 3-OCF$_2$CHFCF$_3$ | CF$_3$ | H | H | C(O)CH$_2$CH$_2$Cl |
| 3-OCF$_2$CHFCF$_3$ | CF$_3$ | H | H | C(O)CH$_2$CF$_3$ |
| 3-OCF$_2$CHFCF$_3$ | CF$_3$ | CH$_3$ | H | C(O)Pr-i |
| 3-OCF$_2$CHFCF$_3$ | CF$_3$ | CH$_3$ | H | C(O)Pr-c |
| 3-OCF$_2$CHFCF$_3$ | CF$_3$ | CH$_3$ | H | C(O)CH$_2$CF$_3$ |
| 3-OCF$_2$CHFCF$_3$ | CF$_2$Cl | H | H | C(O)Pr-i |
| 3-OCH(CF$_3$)$_2$ | CF$_3$ | H | H | C(O)Pr-c |
| 3-OCF$_2$CFBrCF$_3$ | CF$_3$ | H | H | C(O)CH$_2$CF$_3$ |
| 3-OCF$_2$CHFOCF$_3$ | CF$_3$ | H | H | C(O)Et |
| 3-OCF$_2$CHFOCF$_3$ | CF$_3$ | H | H | C(O)Pr-n |
| 3-OCF$_2$CHFOCF$_3$ | CF$_3$ | H | H | C(O)Pr-i |
| 3-OCF$_2$CHFOCF$_3$ | CF$_3$ | H | H | C(O)Pr-c |
| 3-OCF$_2$CHFOCF$_3$ | CF$_3$ | H | H | C(O)CH$_2$Pr-c |
| 3-OCF$_2$CHFOCF$_3$ | CF$_3$ | H | H | C(O)CH$_2$CH$_2$Cl |
| 3-OCF$_2$CHFOCF$_3$ | CF$_3$ | H | H | C(O)CH$_2$CF$_3$ |
| 3-OCF$_2$CHFOCF$_3$ | CF$_3$ | CH$_3$ | H | C(O)Pr-i |
| 3-OCF$_2$CHFOCF$_3$ | CF$_3$ | CH$_3$ | H | C(O)Pr-c |
| 3-OCF$_2$CHFOCF$_3$ | CF$_3$ | CH$_3$ | H | C(O)CH$_2$CF$_3$ |
| 3-OCF$_2$CHFOCF$_3$ | CF$_2$Cl | CH$_3$ | H | C(O)Pr-c |
| 3-OCF$_2$CHFOCF$_2$CF$_3$ | CF$_3$ | CH$_3$ | H | C(O)CH$_2$CF$_3$ |
| 3-OCH$_2$CH=CF$_2$ | CF$_3$ | H | H | C(O)Pr-i |
| 3-OCH$_2$CF=CF$_2$ | CF$_3$ | H | H | C(O)Pr-c |
| 3-OCH$_2$CH=CCl$_2$ | CF$_3$ | H | H | C(O)CH$_2$CF$_3$ |
| 3-OCH$_2$CCl=CCl$_2$ | CF$_3$ | CH$_3$ | H | C(O)Pr-c |
| 3-OSO$_2$CHCl$_2$ | CF$_3$ | CH$_3$ | H | C(O)CH$_2$CF$_3$ |
| 3-OSO$_2$CF$_3$ | CF$_3$ | H | H | C(O)Pr-i |
| 3-OSO$_2$CH$_2$CF$_3$ | CF$_3$ | H | H | C(O)Pr-c |
| 3-OPh | CF$_3$ | H | H | C(O)CH$_2$CF$_3$ |
| 3-O(Ph-2-Cl) | CF$_3$ | CH$_3$ | H | C(O)Pr-c |
| 3-O(Ph-3-Cl) | CF$_3$ | CH$_3$ | H | C(O)CH$_2$CF$_3$ |
| 3-O(Ph-4-Cl) | CF$_3$ | H | H | C(O)Pr-i |
| 3-O(Ph-4-Br) | CF$_3$ | H | H | C(O)Pr-c |
| 3-O(Ph-2-CF$_3$) | CF$_3$ | H | H | C(O)CH$_2$CF$_3$ |
| 3-O(Ph-3-CF$_3$) | CF$_3$ | CH$_3$ | H | C(O)Pr-c |
| 3-O(Ph-4-CF$_3$) | CF$_3$ | CH$_3$ | H | C(O)CH$_2$CF$_3$ |
| 3-O(Ph-2-Cl-4-CF$_3$) | CF$_3$ | H | H | C(O)Pr-i |
| 3-O(D-21c)Br | CF$_3$ | H | H | C(O)Pr-c |
| 3-O(D-21c)CF$_3$ | CF$_3$ | H | H | C(O)CH$_2$CF$_3$ |
| 3-O(D-52d)Br | CF$_3$ | CH$_3$ | H | C(O)Pr-c |
| 3-O(D-52d)CF$_3$ | CF$_3$ | CH$_3$ | H | C(O)CH$_2$CF$_3$ |
| 3-O[(D-52f)-3-Cl-5-CF$_3$] | CF$_3$ | H | H | C(O)Pr-i |
| 3-O(D-55c)Br | CF$_3$ | H | H | C(O)Pr-c |
| 3-SCH$_3$ | CF$_3$ | H | H | C(O)CH$_2$CF$_3$ |
| 3-S(O)CH$_3$ | CF$_3$ | CH$_3$ | H | C(O)Pr-c |
| 3-SO$_2$CH$_3$ | CF$_3$ | CH$_3$ | H | C(O)CH$_2$CF$_3$ |
| 3-SEt | CF$_3$ | H | H | C(O)Pr-i |
| 3-S(O)Et | CF$_3$ | H | H | C(O)Pr-c |
| 3-SO$_2$Et | CF$_3$ | H | H | C(O)CH$_2$CF$_3$ |
| 3-SPr-n | CF$_3$ | CH$_3$ | H | C(O)Pr-c |
| 3-S(O)Pr-n | CF$_3$ | CH$_3$ | H | C(O)CH$_2$CF$_3$ |
| 3-SO$_2$Pr-n | CF$_3$ | H | H | C(O)Pr-i |
| 3-SPr-i | CF$_3$ | H | H | C(O)Pr-c |
| 3-S(O)Pr-i | CF$_3$ | H | H | C(O)CH$_2$CF$_3$ |
| 3-SO$_2$Pr-i | CF$_3$ | CH$_3$ | H | C(O)Pr-c |
| 3-SBu-n | CF$_3$ | CH$_3$ | H | C(O)CH$_2$CF$_3$ |
| 3-S(O)Bu-n | CF$_3$ | H | H | C(O)Pr-i |
| 3-SO$_2$Bu-n | CF$_3$ | H | H | C(O)Pr-c |
| 3-SBu-t | CF$_3$ | H | H | C(O)CH$_2$CF$_3$ |
| 3-S(O)Bu-t | CF$_3$ | CH$_3$ | H | C(O)Pr-c |
| 3-SO$_2$Bu-t | CF$_3$ | CH$_3$ | H | C(O)CH$_2$CF$_3$ |
| 3-SCH$_2$F | CF$_3$ | H | H | C(O)Pr-i |
| 3-S(O)CH$_2$F | CF$_3$ | H | H | C(O)Pr-c |
| 3-SO$_2$CH$_2$F | CF$_3$ | H | H | C(O)CH$_2$CF$_3$ |
| 3-SCHF$_2$ | CF$_3$ | CH$_3$ | H | C(O)Pr-c |
| 3-S(O)CHF$_2$ | CF$_3$ | CH$_3$ | H | C(O)CH$_2$CF$_3$ |
| 3-SO$_2$CHF$_2$ | CF$_3$ | H | H | C(O)Pr-i |
| 3-SCF$_3$ | CHF$_2$ | H | H | C(O)Pr-c |
| 3-SCF$_3$ | CF$_3$ | H | H | H |
| 3-SCF$_3$ | CF$_3$ | H | H | C(O)Et |
| 3-SCF$_3$ | CF$_3$ | H | H | C(O)Pr-n |
| 3-SCF$_3$ | CF$_3$ | H | H | C(O)Pr-i |
| 3-SCF$_3$ | CF$_3$ | H | H | C(O)Pr-c |
| 3-SCF$_3$ | CF$_3$ | H | H | C(O)CH$_2$Pr-c |

TABLE 2-continued

| | | | | |
|---|---|---|---|---|
| 3-SCF₃ | CF₃ | H | H | C(O)CF₃ |
| 3-SCF₃ | CF₃ | H | H | C(O)CH₂CH₂Cl |
| 3-SCF₃ | CF₃ | H | H | C(O)CH₂CF₃ |
| 3-SCF₃ | CF₃ | H | H | C(O)CF₂CHF₂ |
| 3-SCF₃ | CF₃ | H | H | C(O)CF₂CF₃ |
| 3-SCF₃ | CF₃ | H | H | C(O)CH₂CH₂SCH₃ |
| 3-SCF₃ | CF₃ | H | H | C(O)(Ph-2,4-F₂) |
| 3-SCF₃ | CF₃ | H | H | C(O)NHEt |
| 3-SCF₃ | CF₃ | H | H | C(O)NHPr-i |
| 3-SCF₃ | CF₃ | H | H | C(O)NHCH₂CF₃ |
| 3-SCF₃ | CF₃ | CH₃ | H | H |
| 3-SCF₃ | CF₃ | CH₃ | H | C(O)Et |
| 3-SCF₃ | CF₃ | CH₃ | H | C(O)Pr-n |
| 3-SCF₃ | CF₃ | CH₃ | H | C(O)Pr-i |
| 3-SCF₃ | CF₃ | CH₃ | H | C(O)Pr-c |
| 3-SCF₃ | CF₃ | CH₃ | H | C(O)CH₂CF₃ |
| 3-SCF₃ | CF₃ | CN | H | H |
| 3-SCF₃ | CF₃ | CN | H | C(O)Pr-c |
| 3-SCF₃ | CF₃ | CN | H | C(O)CH₂CF₃ |
| 3-SCF₃ | CF₂Cl | H | H | C(O)Et |
| 3-SCF₃ | CF₂Cl | H | H | C(O)Pr-n |
| 3-SCF₃ | CF₂Cl | H | H | C(O)Pr-i |
| 3-SCF₃ | CF₂Cl | H | H | C(O)Pr-c |
| 3-SCF₃ | CF₂Cl | H | H | C(O)CH₂Pr-c |
| 3-SCF₃ | CF₂Cl | H | H | C(O)CH₂CH₂Cl |
| 3-SCF₃ | CF₂Cl | H | H | C(O)CH₂CF₃ |
| 3-SCF₃ | CF₂Cl | CH₃ | H | C(O)Pr-i |
| 3-SCF₃ | CF₂Cl | CH₃ | H | C(O)Pr-c |
| 3-SCF₃ | CF₂Cl | CH₃ | H | C(O)CH₂CF₃ |
| 3-SCF₃ | CF₂Br | H | H | C(O)CH₂CF₃ |
| 3-SCF₃ | CF₂CHF₂ | CH₃ | H | C(O)Pr-c |
| 3-S(O)CF₃ | CF₃ | CH₃ | H | C(O)CH₂CF₃ |
| 3-SO₂CF₃ | CF₃ | H | H | C(O)Pr-i |
| 3-SCF₂Cl | CHF₂ | H | H | C(O)Pr-c |
| 3-SCF₂Cl | CF₃ | H | H | H |
| 3-SCF₂Cl | CF₃ | H | H | C(O)Et |
| 3-SCF₂Cl | CF₃ | H | H | C(O)Pr-n |
| 3-SCF₂Cl | CF₃ | H | H | C(O)Pr-i |
| 3-SCF₂Cl | CF₃ | H | H | C(O)Pr-c |
| 3-SCF₂Cl | CF₃ | H | H | C(O)CH₂Pr-c |
| 3-SCF₂Cl | CF₃ | H | H | C(O)CF₃ |
| 3-SCF₂Cl | CF₃ | H | H | C(O)CH₂CH₂Cl |
| 3-SCF₂Cl | CF₃ | H | H | C(O)CH₂CF₃ |
| 3-SCF₂Cl | CF₃ | H | H | C(O)CF₂CHF₂ |
| 3-SCF₂Cl | CF₃ | H | H | C(O)CF₂CF₃ |
| 3-SCF₂Cl | CF₃ | H | H | C(O)CH₂CH₂SCH₃ |
| 3-SCF₂Cl | CF₃ | H | H | C(O)(Ph-2,4-F₂) |
| 3-SCF₂Cl | CF₃ | H | H | C(O)NHEt |
| 3-SCF₂Cl | CF₃ | H | H | C(O)NHPr-i |
| 3-SCF₂Cl | CF₃ | H | H | C(O)NHCH₂CF₃ |
| 3-SCF₂Cl | CF₃ | CH₃ | H | H |
| 3-SCF₂Cl | CF₃ | CH₃ | H | C(O)Et |
| 3-SCF₂Cl | CF₃ | CH₃ | H | C(O)Pr-n |
| 3-SCF₂Cl | CF₃ | CH₃ | H | C(O)Pr-i |
| 3-SCF₂Cl | CF₃ | CH₃ | H | C(O)Pr-c |
| 3-SCF₂Cl | CF₃ | CH₃ | H | C(O)CH₂CF₃ |
| 3-SCF₂Cl | CF₃ | CN | H | H |
| 3-SCF₂Cl | CF₃ | CN | H | C(O)Pr-c |
| 3-SCF₂Cl | CF₃ | CN | H | C(O)CH₂CF₃ |
| 3-SCF₂Cl | CF₂Cl | H | H | C(O)Et |
| 3-SCF₂Cl | CF₂Cl | H | H | C(O)Pr-n |
| 3-SCF₂Cl | CF₂Cl | H | H | C(O)Pr-i |
| 3-SCF₂Cl | CF₂Cl | H | H | C(O)Pr-c |
| 3-SCF₂Cl | CF₂Cl | H | H | C(O)CH₂Pr-c |
| 3-SCF₂Cl | CF₂Cl | H | H | C(O)CH₂CH₂Cl |
| 3-SCF₂Cl | CF₂Cl | H | H | C(O)CH₂CF₃ |
| 3-SCF₂Cl | CF₂Cl | CH₃ | H | C(O)Pr-i |
| 3-SCF₂Cl | CF₂Cl | CH₃ | H | C(O)Pr-c |
| 3-SCF₂Cl | CF₂Cl | CH₃ | H | C(O)CH₂CF₃ |
| 3-SCF₂Cl | CF₂Br | H | H | C(O)CH₂CF₃ |
| 3-SCF₂Cl | CF₂CHF₂ | CH₃ | H | C(O)Pr-c |
| 3-S(O)CF₂Cl | CF₃ | CH₃ | H | C(O)CH₂CF₃ |
| 3-SO₂CF₂Cl | CF₃ | H | H | C(O)Pr-i |
| 3-SCF₂Br | CHF₂ | H | H | C(O)Pr-c |
| 3-SCF₂Br | CF₃ | H | H | H |
| 3-SCF₂Br | CF₃ | H | H | C(O)Et |
| 3-SCF₂Br | CF₃ | H | H | C(O)Pr-n |
| 3-SCF₂Br | CF₃ | H | H | C(O)Pr-i |
| 3-SCF₂Br | CF₃ | H | H | C(O)Pr-c |
| 3-SCF₂Br | CF₃ | H | H | C(O)CH₂Pr-c |

TABLE 2-continued

| | | | | |
|---|---|---|---|---|
| 3-SCF₂Br | CF₃ | H | H | C(O)CF₃ |
| 3-SCF₂Br | CF₃ | H | H | C(O)CH₂CH₂Cl |
| 3-SCF₂Br | CF₃ | H | H | C(O)CH₂CF₃ |
| 3-SCF₂Br | CF₃ | H | H | C(O)CF₂CHF₂ |
| 3-SCF₂Br | CF₃ | H | H | C(O)CF₂CF₃ |
| 3-SCF₂Br | CF₃ | H | H | C(O)CH₂CH₂SCH₃ |
| 3-SCF₂Br | CF₃ | H | H | C(O)(Ph-2,4-F₂) |
| 3-SCF₂Br | CF₃ | H | H | C(O)NHEt |
| 3-SCF₂Br | CF₃ | H | H | C(O)NHPr-i |
| 3-SCF₂Br | CF₃ | H | H | C(O)NHCH₂CF₃ |
| 3-SCF₂Br | CF₃ | CH₃ | H | H |
| 3-SCF₂Br | CF₃ | CH₃ | H | C(O)Et |
| 3-SCF₂Br | CF₃ | CH₃ | H | C(O)Pr-n |
| 3-SCF₂Br | CF₃ | CH₃ | H | C(O)Pr-i |
| 3-SCF₂Br | CF₃ | CH₃ | H | C(O)Pr-c |
| 3-SCF₂Br | CF₃ | CH₃ | H | C(O)CH₂CF₃ |
| 3-SCF₂Br | CF₃ | CN | H | H |
| 3-SCF₂Br | CF₃ | CN | H | C(O)Pr-c |
| 3-SCF₂Br | CF₃ | CN | H | C(O)CH₂CF₃ |
| 3-SCF₂Br | CF₂Cl | H | H | C(O)Et |
| 3-SCF₂Br | CF₂Cl | H | H | C(O)Pr-n |
| 3-SCF₂Br | CF₂Cl | H | H | C(O)Pr-i |
| 3-SCF₂Br | CF₂Cl | H | H | C(O)Pr-c |
| 3-SCF₂Br | CF₂Cl | H | H | C(O)CH₂Pr-c |
| 3-SCF₂Br | CF₂Cl | H | H | C(O)CH₂CH₂Cl |
| 3-SCF₂Br | CF₂Cl | H | H | C(O)CH₂CF₃ |
| 3-SCF₂Br | CF₂Cl | CH₃ | H | C(O)Pr-i |
| 3-SCF₂Br | CF₂Cl | CH₃ | H | C(O)Pr-c |
| 3-SCF₂Br | CF₂Cl | CH₃ | H | C(O)CH₂CF₃ |
| 3-SCF₂Br | CF₂Br | H | H | C(O)CH₂CF₃ |
| 3-SCF₂Br | CH₂CHF₂ | CH₃ | H | C(O)Pr-c |
| 3-S(O)CF₂Br | CF₃ | CH₃ | H | C(O)CH₂CF₃ |
| 3-SO₂CF₂Br | CF₃ | H | H | C(O)Pr-i |
| 3-SCH₂CF₃ | CF₃ | H | H | C(O)Pr-c |
| 3-SCF₂CHF₂ | CF₃ | H | H | C(O)CH₂CF₃ |
| 3-SCF₂CHFCl | CF₃ | CH₃ | H | C(O)Pr-c |
| 3-SCF₂CF₃ | CF₃ | CH₃ | H | C(O)CH₂CF₃ |
| 3-SCF₂CF₂Br | CF₃ | H | H | C(O)Pr-i |
| 3-SCF₂CHFCF₃ | CF₃ | H | H | C(O)Pr-c |
| 3-SCF₂CF₂CF₃ | CF₃ | H | H | C(O)CH₂CF₃ |
| 3-S(Ph-4-Cl) | CF₃ | CH₃ | H | C(O)Pr-c |
| 3-S(Ph-4-Br) | CF₃ | CH₃ | H | C(O)CH₂CF₃ |
| 3-S(Ph-4-CF₃) | CF₃ | H | H | C(O)Pr-i |
| 3-S(D-21c)Br | CF₃ | H | H | C(O)Pr-c |
| 3-S(D-21c)CF₃ | CF₃ | H | H | C(O)CH₂CF₃ |
| 3-S(D-52d)Br | CF₃ | CH₃ | H | C(O)Pr-c |
| 3-S(D-52d)CF₃ | CF₃ | CH₃ | H | C(O)CH₂CF₃ |
| 3-S[(D-52f)-3-Cl-5-CF₃] | CF₃ | H | H | C(O)Pr-i |
| 3-S(D-55c)Br | CF₃ | H | H | C(O)Pr-c |
| 3-SF₅ | CHF₂ | H | H | C(O)CH₂CF₃ |
| 3-SF₅ | CF₃ | H | H | H |
| 3-SF₅ | CF₃ | H | H | C(O)Et |
| 3-SF₅ | CF₃ | H | H | C(O)Pr-n |
| 3-SF₅ | CF₃ | H | H | C(O)Pr-i |
| 3-SF₅ | CF₃ | H | H | C(O)Pr-c |
| 3-SF₅ | CF₃ | H | H | C(O)CH₂Pr-c |
| 3-SF₅ | CF₃ | H | H | C(O)CF₃ |
| 3-SF₅ | CF₃ | H | H | C(O)CH₂CH₂Cl |
| 3-SF₅ | CF₃ | H | H | C(O)CH₂CF₃ |
| 3-SF₅ | CF₃ | H | H | C(O)CF₂CHF₂ |
| 3-SF₅ | CF₃ | H | H | C(O)CF₂CF₃ |
| 3-SF₅ | CF₃ | H | H | C(O)CH₂CH₂SCH₃ |
| 3-SF₅ | CF₃ | H | H | C(O)(Ph-2,4-F₂) |
| 3-SF₅ | CF₃ | H | H | C(O)NHEt |
| 3-SF₅ | CF₃ | H | H | C(O)NHPr-i |
| 3-SF₅ | CF₃ | H | H | C(O)NHCH₂CF₃ |
| 3-SF₅ | CF₃ | CH₃ | H | H |
| 3-SF₅ | CF₃ | CH₃ | H | C(O)Et |
| 3-SF₅ | CF₃ | CH₃ | H | C(O)Pr-n |
| 3-SF₅ | CF₃ | CH₃ | H | C(O)Pr-i |
| 3-SF₅ | CF₃ | CH₃ | H | C(O)Pr-c |
| 3-SF₅ | CF₃ | CH₃ | H | C(O)CH₂CF₃ |
| 3-SF₅ | CF₃ | CN | H | H |
| 3-SF₅ | CF₃ | CN | H | C(O)Pr-c |
| 3-SF₅ | CF₃ | CN | H | C(O)CH₂CF₃ |
| 3-SF₅ | CF₂Cl | H | H | C(O)Et |
| 3-SF₅ | CF₂Cl | H | H | C(O)Pr-n |
| 3-SF₅ | CF₂Cl | H | H | C(O)Pr-i |
| 3-SF₅ | CF₂Cl | H | H | C(O)Pr-c |
| 3-SF₅ | CF₂Cl | H | H | C(O)CH₂Pr-c |

TABLE 2-continued

| | | | | |
|---|---|---|---|---|
| 3-SF$_5$ | CF$_2$Cl | H | H | C(O)CH$_2$CH$_2$Cl |
| 3-SF$_5$ | CF$_2$Cl | H | H | C(O)CH$_2$CF$_3$ |
| 3-SF$_5$ | CF$_2$Cl | CH$_3$ | H | C(O)Pr-i |
| 3-SF$_5$ | CF$_2$Cl | CH$_3$ | H | C(O)Pr-c |
| 3-SF$_5$ | CF$_2$Cl | CH$_3$ | H | C(O)CH$_2$CF$_3$ |
| 3-SF$_5$ | CF$_2$Br | CH$_3$ | H | C(O)Pr-c |
| 3-SF$_5$ | CF$_2$CHF$_2$ | CH$_3$ | H | C(O)CH$_2$CF$_3$ |
| 3-NO$_2$ | CF$_3$ | H | H | C(O)Pr-i |
| 3-CN | CF$_3$ | H | H | C(O)Pr-c |
| 3-C(O)NH$_2$ | CF$_3$ | H | H | C(O)CH$_2$CF$_3$ |
| 3-C(S)NH$_2$ | CF$_3$ | CH$_3$ | H | C(O)Pr-c |
| 3-SO$_2$NHCH$_3$ | CF$_3$ | CH$_3$ | H | C(O)CH$_2$CF$_3$ |
| 3-SO$_2$N(CH$_3$)$_2$ | CF$_3$ | H | H | C(O)Pr-i |
| 3-Si(CH$_3$)$_3$ | CF$_3$ | H | H | C(O)Pr-c |
| 2,3-F$_2$ | CF$_3$ | H | H | C(O)CH$_2$CF$_3$ |
| 2,4-F$_2$ | CF$_3$ | CH$_3$ | H | C(O)Pr-c |
| 2,5-F$_2$ | CF$_3$ | CH$_3$ | H | C(O)CH$_2$CF$_3$ |
| 3,4-F$_2$ | CF$_3$ | H | H | C(O)Pr-i |
| 3,4-F$_2$ | CF$_3$ | H | H | C(O)Pr-c |
| 3,4-F$_2$ | CF$_3$ | H | H | C(O)CH$_2$CF$_3$ |
| 3,4-F$_2$ | CF$_3$ | CH$_3$ | H | C(O)Pr-c |
| 3,4-F$_2$ | CF$_3$ | CH$_3$ | H | C(O)CH$_2$CF$_3$ |
| 3,5-F$_2$ | CF$_3$ | H | H | C(O)Pr-i |
| 3,5-F$_2$ | CF$_3$ | H | H | C(O)Pr-c |
| 3,5-F$_2$ | CF$_3$ | H | H | C(O)CH$_2$CF$_3$ |
| 3,5-F$_2$ | CF$_3$ | CH$_3$ | H | C(O)Pr-c |
| 3,5-F$_2$ | CF$_3$ | CH$_3$ | H | C(O)CH$_2$CF$_3$ |
| 2-Cl-4-F | CF$_3$ | H | H | C(O)Pr-i |
| 2-F-3-Cl | CF$_3$ | H | H | C(O)Pr-c |
| 3-Cl-4-F | CHF$_2$ | H | H | C(O)CH$_2$CF$_3$ |
| 3-Cl-4-F | CF$_3$ | H | H | H |
| 3-Cl-4-F | CF$_3$ | H | H | C(O)Et |
| 3-Cl-4-F | CF$_3$ | H | H | C(O)Pr-n |
| 3-Cl-4-F | CF$_3$ | H | H | C(O)Pr-i |
| 3-Cl-4-F | CF$_3$ | H | H | C(O)Pr-c |
| 3-Cl-4-F | CF$_3$ | H | H | C(O)CH$_2$Pr-c |
| 3-Cl-4-F | CF$_3$ | H | H | C(O)CF$_3$ |
| 3-Cl-4-F | CF$_3$ | H | H | C(O)CH$_2$CH$_2$Cl |
| 3-Cl-4-F | CF$_3$ | H | H | C(O)CH$_2$CF$_3$ |
| 3-Cl-4-F | CF$_3$ | H | H | C(O)CF$_2$CHF$_2$ |
| 3-Cl-4-F | CF$_3$ | H | H | C(O)CF$_2$CF$_3$ |
| 3-Cl-4-F | CF$_3$ | H | H | C(O)CH$_2$CH$_2$SCH$_3$ |
| 3-Cl-4-F | CF$_3$ | H | H | C(O)(Ph-2,4-F$_2$) |
| 3-Cl-4-F | CF$_3$ | H | H | C(O)NHEt |
| 3-Cl-4-F | CF$_3$ | H | H | C(O)NHPr-i |
| 3-Cl-4-F | CF$_3$ | H | H | C(O)NHCH$_2$CF$_3$ |
| 3-Cl-4-F | CF$_3$ | CH$_3$ | H | H |
| 3-Cl-4-F | CF$_3$ | CH$_3$ | H | C(O)Et |
| 3-Cl-4-F | CF$_3$ | CH$_3$ | H | C(O)Pr-n |
| 3-Cl-4-F | CF$_3$ | CH$_3$ | H | C(O)Pr-i |
| 3-Cl-4-F | CF$_3$ | CH$_3$ | H | C(O)Pr-c |
| 3-Cl-4-F | CF$_3$ | CH$_3$ | H | C(O)CH$_2$CF$_3$ |
| 3-Cl-4-F | CF$_3$ | CN | H | H |
| 3-Cl-4-F | CF$_3$ | CN | H | C(O)Pr-c |
| 3-Cl-4-F | CF$_3$ | CN | H | C(O)CH$_2$CF$_3$ |
| 3-Cl-4-F | CF$_2$Cl | H | H | C(O)Et |
| 3-Cl-4-F | CF$_2$Cl | H | H | C(O)Pr-n |
| 3-Cl-4-F | CF$_2$Cl | H | H | C(O)Pr-i |
| 3-Cl-4-F | CF$_2$Cl | H | H | C(O)Pr-c |
| 3-Cl-4-F | CF$_2$Cl | H | H | C(O)CH$_2$Pr-c |
| 3-Cl-4-F | CF$_2$Cl | H | H | C(O)CH$_2$CH$_2$Cl |
| 3-Cl-4-F | CF$_2$Cl | H | H | C(O)CH$_2$CF$_3$ |
| 3-Cl-4-F | CF$_2$Cl | CH$_3$ | H | C(O)Pr-i |
| 3-Cl-4-F | CF$_2$Cl | CH$_3$ | H | C(O)Pr-c |
| 3-Cl-4-F | CF$_2$Cl | CH$_3$ | H | C(O)CH$_2$CF$_3$ |
| 3-Cl-4-F | CF$_2$Br | CH$_3$ | H | C(O)Pr-c |
| 3-Cl-4-F | CF$_2$CHF$_2$ | CH$_3$ | H | C(O)CH$_2$CF$_3$ |
| 2-F-4-Cl | CF$_3$ | H | H | C(O)Pr-i |
| 3-F-4-Cl | CF$_3$ | H | H | C(O)Pr-c |
| 3-F-5-Cl | CHF$_2$ | H | H | C(O)CH$_2$CF$_3$ |
| 3-F-5-Cl | CF$_3$ | H | H | H |
| 3-F-5-Cl | CF$_3$ | H | H | C(O)Et |
| 3-F-5-Cl | CF$_3$ | H | H | C(O)Pr-n |
| 3-F-5-Cl | CF$_3$ | H | H | C(O)Pr-i |
| 3-F-5-Cl | CF$_3$ | H | H | C(O)Pr-c |
| 3-F-5-Cl | CF$_3$ | H | H | C(O)CH$_2$Pr-c |
| 3-F-5-Cl | CF$_3$ | H | H | C(O)CF$_3$ |
| 3-F-5-Cl | CF$_3$ | H | H | C(O)CH$_2$CH$_2$Cl |
| 3-F-5-Cl | CF$_3$ | H | H | C(O)CH$_2$CF$_3$ |
| 3-F-5-Cl | CF$_3$ | H | H | C(O)CF$_2$CHF$_2$ |

TABLE 2-continued

| | | | | |
|---|---|---|---|---|
| 3-F-5-Cl | CF$_3$ | H | H | C(O)CF$_2$CF$_3$ |
| 3-F-5-Cl | CF$_3$ | H | H | C(O)CH$_2$CH$_2$SCH$_3$ |
| 3-F-5-Cl | CF$_3$ | H | H | C(O)(Ph-2,4-F$_2$) |
| 3-F-5-Cl | CF$_3$ | H | H | C(O)NHEt |
| 3-F-5-Cl | CF$_3$ | H | H | C(O)NHPr-i |
| 3-F-5-Cl | CF$_3$ | H | H | C(O)NHCH$_2$CF$_3$ |
| 3-F-5-Cl | CF$_3$ | CH$_3$ | H | H |
| 3-F-5-Cl | CF$_3$ | CH$_3$ | H | C(O)Et |
| 3-F-5-Cl | CF$_3$ | CH$_3$ | H | C(O)Pr-n |
| 3-F-5-Cl | CF$_3$ | CH$_3$ | H | C(O)Pr-i |
| 3-F-5-Cl | CF$_3$ | CH$_3$ | H | C(O)Pr-c |
| 3-F-5-Cl | CF$_3$ | CH$_3$ | H | C(O)CH$_2$CF$_3$ |
| 3-F-5-Cl | CF$_3$ | CN | H | H |
| 3-F-5-Cl | CF$_3$ | CN | H | C(O)Pr-c |
| 3-F-5-Cl | CF$_3$ | CN | H | C(O)CH$_2$CF$_3$ |
| 3-F-5-Cl | CF$_2$Cl | H | H | C(O)Et |
| 3-F-5-Cl | CF$_2$Cl | H | H | C(O)Pr-n |
| 3-F-5-Cl | CF$_2$Cl | H | H | C(O)Pr-i |
| 3-F-5-Cl | CF$_2$Cl | H | H | C(O)Pr-c |
| 3-F-5-Cl | CF$_2$Cl | H | H | C(O)CH$_2$Pr-c |
| 3-F-5-Cl | CF$_2$Cl | H | H | C(O)CH$_2$CH$_2$Cl |
| 3-F-5-Cl | CF$_2$Cl | H | H | C(O)CH$_2$CF$_3$ |
| 3-F-5-Cl | CF$_2$Cl | CH$_3$ | H | C(O)Pr-i |
| 3-F-5-Cl | CF$_2$Cl | CH$_3$ | H | C(O)Pr-c |
| 3-F-5-Cl | CF$_2$Cl | CH$_3$ | H | C(O)CH$_2$CF$_3$ |
| 3-F-5-Cl | CF$_2$Br | CH$_3$ | H | C(O)Pr-c |
| 3-F-5-Cl | CF$_2$CHF$_2$ | CH$_3$ | H | C(O)CH$_2$CF$_3$ |
| 2,3-Cl$_2$ | CF$_3$ | H | H | C(O)Pr-i |
| 2,4-Cl$_2$ | CF$_3$ | H | H | C(O)Pr-c |
| 2,5-Cl$_2$ | CF$_3$ | H | H | C(O)CH$_2$CF$_3$ |
| 3,4-Cl$_2$ | CHF$_2$ | CH$_3$ | H | C(O)Pr-c |
| 3,4-Cl$_2$ | CF$_3$ | H | H | H |
| 3,4-Cl$_2$ | CF$_3$ | H | H | C(O)Et |
| 3,4-Cl$_2$ | CF$_3$ | H | H | C(O)Pr-n |
| 3,4-Cl$_2$ | CF$_3$ | H | H | C(O)Pr-i |
| 3,4-Cl$_2$ | CF$_3$ | H | H | C(O)Pr-c |
| 3,4-Cl$_2$ | CF$_3$ | H | H | C(O)CH$_2$Pr-c |
| 3,4-Cl$_2$ | CF$_3$ | H | H | C(O)CF$_3$ |
| 3,4-Cl$_2$ | CF$_3$ | H | H | C(O)CH$_2$CH$_2$Cl |
| 3,4-Cl$_2$ | CF$_3$ | H | H | C(O)CH$_2$CF$_3$ |
| 3,4-Cl$_2$ | CF$_3$ | H | H | C(O)CF$_2$CHF$_2$ |
| 3,4-Cl$_2$ | CF$_3$ | H | H | C(O)CF$_2$CF$_3$ |
| 3,4-Cl$_2$ | CF$_3$ | H | H | C(O)CH$_2$CH$_2$SCH$_3$ |
| 3,4-Cl$_2$ | CF$_3$ | H | H | C(O)(Ph-2,4-F$_2$) |
| 3,4-Cl$_2$ | CF$_3$ | H | H | C(O)NHEt |
| 3,4-Cl$_2$ | CF$_3$ | H | H | C(O)NHPr-i |
| 3,4-Cl$_2$ | CF$_3$ | H | H | C(O)NHCH$_2$CF$_3$ |
| 3,4-Cl$_2$ | CF$_3$ | CH$_3$ | H | H |
| 3,4-Cl$_2$ | CF$_3$ | CH$_3$ | H | C(O)Et |
| 3,4-Cl$_2$ | CF$_3$ | CH$_3$ | H | C(O)Pr-n |
| 3,4-Cl$_2$ | CF$_3$ | CH$_3$ | H | C(O)Pr-i |
| 3,4-Cl$_2$ | CF$_3$ | CH$_3$ | H | C(O)Pr-c |
| 3,4-Cl$_2$ | CF$_3$ | CH$_3$ | H | C(O)CH$_2$CF$_3$ |
| 3,4-Cl$_2$ | CF$_3$ | CN | H | H |
| 3,4-Cl$_2$ | CF$_3$ | CN | H | C(O)Pr-c |
| 3,4-Cl$_2$ | CF$_3$ | CN | H | C(O)CH$_2$CF$_3$ |
| 3,4-Cl$_2$ | CF$_2$Cl | H | H | C(O)Et |
| 3,4-Cl$_2$ | CF$_2$Cl | H | H | C(O)Pr-n |
| 3,4-Cl$_2$ | CF$_2$Cl | H | H | C(O)Pr-i |
| 3,4-Cl$_2$ | CF$_2$Cl | H | H | C(O)Pr-c |
| 3,4-Cl$_2$ | CF$_2$Cl | H | H | C(O)CH$_2$Pr-c |
| 3,4-Cl$_2$ | CF$_2$Cl | H | H | C(O)CH$_2$CH$_2$Cl |
| 3,4-Cl$_2$ | CF$_2$Cl | H | H | C(O)CH$_2$CF$_3$ |
| 3,4-Cl$_2$ | CF$_2$Cl | CH$_3$ | H | C(O)Pr-i |
| 3,4-Cl$_2$ | CF$_2$Cl | CH$_3$ | H | C(O)Pr-c |
| 3,4-Cl$_2$ | CF$_2$Cl | CH$_3$ | H | C(O)CH$_2$CF$_3$ |
| 3,4-Cl$_2$ | CF$_2$Br | CH$_3$ | H | C(O)CH$_2$CF$_3$ |
| 3,4-Cl$_2$ | CH$_2$CHF$_2$ | H | H | C(O)Pr-i |
| 3,5-Cl$_2$ | CH$_3$ | H | H | C(O)Pr-c |
| 3,5-Cl$_2$ | Et | H | H | C(O)CH$_2$CF$_3$ |
| 3,5-Cl$_2$ | n-Pr | CH$_3$ | H | C(O)Pr-c |
| 3,5-Cl$_2$ | i-Pr | CH$_3$ | H | C(O)CH$_2$CF$_3$ |
| 3,5-Cl$_2$ | c-Pr | H | H | C(O)Pr-i |
| 3,5-Cl$_2$ | CH$_2$F | H | H | C(O)Pr-c |
| 3,5-Cl$_2$ | CH$_2$Cl | H | H | C(O)CH$_2$CF$_3$ |
| 3,5-Cl$_2$ | CH$_2$Br | CH$_3$ | H | C(O)Pr-c |
| 3,5-Cl$_2$ | CH$_2$I | CH$_3$ | H | C(O)CH$_2$CF$_3$ |
| 3,5-Cl$_2$ | CHF$_2$ | H | H | C(O)Et |
| 3,5-Cl$_2$ | CHF$_2$ | H | H | C(O)Pr-n |
| 3,5-Cl$_2$ | CHF$_2$ | H | H | C(O)Pr-i |

TABLE 2-continued

| | | | | |
|---|---|---|---|---|
| 3,5-Cl$_2$ | CHF$_2$ | H | H | C(O)Pr-c |
| 3,5-Cl$_2$ | CHF$_2$ | H | H | C(O)CH$_2$Pr-c |
| 3,5-Cl$_2$ | CHF$_2$ | H | H | C(O)CH$_2$CH$_2$Cl |
| 3,5-Cl$_2$ | CHF$_2$ | H | H | C(O)CH$_2$CF$_3$ |
| 3,5-Cl$_2$ | CHF$_2$ | CH$_3$ | H | C(O)Pr-i |
| 3,5-Cl$_2$ | CHF$_2$ | CH$_3$ | H | C(O)Pr-c |
| 3,5-Cl$_2$ | CHF$_2$ | CH$_3$ | H | C(O)CH$_2$CF$_3$ |
| 3,5-Cl$_2$ | CHFCl | H | H | C(O)Pr-i |
| 3,5-Cl$_2$ | CHFCl | H | H | C(O)Pr-c |
| 3,5-Cl$_2$ | CHFCl | H | H | C(O)CH$_2$CF$_3$ |
| 3,5-Cl$_2$ | CHFCl | CH$_3$ | H | C(O)Pr-c |
| 3,5-Cl$_2$ | CHFCl | CH$_3$ | H | C(O)CH$_2$CF$_3$ |
| 3,5-Cl$_2$ | CHCl$_2$ | H | H | C(O)Pr-i |
| 3,5-Cl$_2$ | CHCl$_2$ | H | H | C(O)Pr-c |
| 3,5-Cl$_2$ | CHCl$_2$ | H | H | C(O)CH$_2$CF$_3$ |
| 3,5-Cl$_2$ | CHCl$_2$ | CH$_3$ | H | C(O)Pr-c |
| 3,5-Cl$_2$ | CHCl$_2$ | CH$_3$ | H | C(O)CH$_2$CF$_3$ |
| 3,5-Cl$_2$ | CHFBr | H | H | C(O)Pr-i |
| 3,5-Cl$_2$ | CHFBr | H | H | C(O)Pr-c |
| 3,5-Cl$_2$ | CHFBr | H | H | C(O)CH$_2$CF$_3$ |
| 3,5-Cl$_2$ | CHFBr | CH$_3$ | H | C(O)Pr-c |
| 3,5-Cl$_2$ | CHFBr | CH$_3$ | H | C(O)CH$_2$CF$_3$ |
| 3,5-Cl$_2$ | CF$_3$ | H | H | H |
| 3,5-Cl$_2$ | CF$_3$ | H | CH$_3$ | H |
| 3,5-Cl$_2$ | CF$_3$ | H | Et | H |
| 3,5-Cl$_2$ | CF$_3$ | H | c-Pr | H |
| 3,5-Cl$_2$ | CF$_3$ | H | H | CHO |
| 3,5-Cl$_2$ | CF$_3$ | H | H | C(O)CH$_3$ |
| 3,5-Cl$_2$ | CF$_3$ | H | H | C(O)Et |
| 3,5-Cl$_2$ | CF$_3$ | H | CH$_3$ | C(O)Et |
| 3,5-Cl$_2$ | CF$_3$ | H | Et | C(O)Et |
| 3,5-Cl$_2$ | CF$_3$ | H | CH$_2$OCH$_3$ | C(O)Et |
| 3,5-Cl$_2$ | CF$_3$ | H | CH$_2$OEt | C(O)Et |
| 3,5-Cl$_2$ | CF$_3$ | H | CH$_2$OCH$_2$CF$_3$ | C(O)Et |
| 3,5-Cl$_2$ | CF$_3$ | H | CH$_2$OC(O)CH$_3$ | C(O)Et |
| 3,5-Cl$_2$ | CF$_3$ | H | CH$_2$OC(O)OCH$_3$ | C(O)Et |
| 3,5-Cl$_2$ | CF$_3$ | H | CH$_2$CN | C(O)Et |
| 3,5-Cl$_2$ | CF$_3$ | H | CH$_2$C≡CH | C(O)Et |
| 3,5-Cl$_2$ | CF$_3$ | H | C(O)CH$_3$ | C(O)Et |
| 3,5-Cl$_2$ | CF$_3$ | H | C(O)OCH$_3$ | C(O)Et |
| 3,5-Cl$_2$ | CF$_3$ | H | SCCl$_3$ | C(O)Et |
| 3,5-Cl$_2$ | CF$_3$ | H | H | C(O)Pr-n |
| 3,5-Cl$_2$ | CF$_3$ | H | CH$_3$ | C(O)Pr-n |
| 3,5-Cl$_2$ | CF$_3$ | H | Et | C(O)Pr-n |
| 3,5-Cl$_2$ | CF$_3$ | H | CH$_2$OCH$_3$ | C(O)Pr-n |
| 3,5-Cl$_2$ | CF$_3$ | H | CH$_2$OEt | C(O)Pr-n |
| 3,5-Cl$_2$ | CF$_3$ | H | CH$_2$OCH$_2$CF$_3$ | C(O)Pr-n |
| 3,5-Cl$_2$ | CF$_3$ | H | CH$_2$OC(O)CH$_3$ | C(O)Pr-n |
| 3,5-Cl$_2$ | CF$_3$ | H | CH$_2$OC(O)OCH$_3$ | C(O)Pr-n |
| 3,5-Cl$_2$ | CF$_3$ | H | CH$_2$CN | C(O)Pr-n |
| 3,5-Cl$_2$ | CF$_3$ | H | CH$_2$C≡CH | C(O)Pr-n |
| 3,5-Cl$_2$ | CF$_3$ | H | C(O)CH$_3$ | C(O)Pr-n |
| 3,5-Cl$_2$ | CF$_3$ | H | C(O)OCH$_3$ | C(O)Pr-n |
| 3,5-Cl$_2$ | CF$_3$ | H | SCCl$_3$ | C(O)Pr-n |
| 3,5-Cl$_2$ | CF$_3$ | H | H | C(O)Pr-i |
| 3,5-Cl$_2$ | CF$_3$ | H | CH$_3$ | C(O)Pr-i |
| 3,5-Cl$_2$ | CF$_3$ | H | Et | C(O)Pr-i |
| 3,5-Cl$_2$ | CF$_3$ | H | CH$_2$OCH$_3$ | C(O)Pr-i |
| 3,5-Cl$_2$ | CF$_3$ | H | CH$_2$OEt | C(O)Pr-i |
| 3,5-Cl$_2$ | CF$_3$ | H | CH$_2$OCH$_2$CF$_3$ | C(O)Pr-i |
| 3,5-Cl$_2$ | CF$_3$ | H | CH$_2$OC(O)CH$_3$ | C(O)Pr-i |
| 3,5-Cl$_2$ | CF$_3$ | H | CH$_2$OC(O)Et | C(O)Pr-i |
| 3,5-Cl$_2$ | CF$_3$ | H | CH$_2$OC(O)Pr-i | C(O)Pr-i |
| 3,5-Cl$_2$ | CF$_3$ | H | CH$_2$OC(O)Pr-c | C(O)Pr-i |
| 3,5-Cl$_2$ | CF$_3$ | H | CH$_2$OC(O)Bu-t | C(O)Pr-i |
| 3,5-Cl$_2$ | CF$_3$ | H | CH$_2$OC(O)Ph | C(O)Pr-i |
| 3,5-Cl$_2$ | CF$_3$ | H | CH$_2$OC(O)OCH$_3$ | C(O)Pr-i |
| 3,5-Cl$_2$ | CF$_3$ | H | CH$_2$CN | C(O)Pr-i |
| 3,5-Cl$_2$ | CF$_3$ | H | CH$_2$C≡CH | C(O)Pr-i |
| 3,5-Cl$_2$ | CF$_3$ | H | C(O)CH$_3$ | C(O)Pr-i |
| 3,5-Cl$_2$ | CF$_3$ | H | C(O)Et | C(O)Pr-i |
| 3,5-Cl$_2$ | CF$_3$ | H | C(O)Pr-i | C(O)Pr-i |
| 3,5-Cl$_2$ | CF$_3$ | H | C(O)Pr-c | C(O)Pr-i |
| 3,5-Cl$_2$ | CF$_3$ | H | C(O)Bu-t | C(O)Pr-i |
| 3,5-Cl$_2$ | CF$_3$ | H | C(O)CH$_2$OCH$_3$ | C(O)Pr-i |
| 3,5-Cl$_2$ | CF$_3$ | H | C(O)CH$_2$SCH$_3$ | C(O)Pr-i |
| 3,5-Cl$_2$ | CF$_3$ | H | C(O)OCH$_3$ | C(O)Pr-i |
| 3,5-Cl$_2$ | CF$_3$ | H | C(O)OEt | C(O)Pr-i |
| 3,5-Cl$_2$ | CF$_3$ | H | C(O)OPr-i | C(O)Pr-i |
| 3,5-Cl$_2$ | CF$_3$ | H | C(O)OPr-c | C(O)Pr-i |

TABLE 2-continued

| | | | | |
|---|---|---|---|---|
| 3,5-Cl$_2$ | CF$_3$ | H | C(O)OCH$_2$Cl | C(O)Pr-i |
| 3,5-Cl$_2$ | CF$_3$ | H | C(O)OCH$_2$CH$_2$Cl | C(O)Pr-i |
| 3,5-Cl$_2$ | CF$_3$ | H | C(O)OCH$_2$CH$_2$OCH$_3$ | C(O)Pr-i |
| 3,5-Cl$_2$ | CF$_3$ | H | C(O)OCH$_2$CH=CH$_2$ | C(O)Pr-i |
| 3,5-Cl$_2$ | CF$_3$ | H | C(O)OCH$_2$C≡CH | C(O)Pr-i |
| 3,5-Cl$_2$ | CF$_3$ | H | SCCl$_3$ | C(O)Pr-i |
| 3,5-Cl$_2$ | CF$_3$ | H | SN(Bu-n)$_2$ | C(O)Pr-i |
| 3,5-Cl$_2$ | CF$_3$ | H | SN(Pr-i)CH$_2$CH$_2$C(O)OEt | C(O)Pr-i |
| 3,5-Cl$_2$ | CF$_3$ | H | SN(CH$_2$Ph)CH$_2$CH$_2$C(O)OEt | C(O)Pr-i |
| 3,5-Cl$_2$ | CF$_3$ | H | SN(CH$_3$)C(O)OBu-n | C(O)Pr-i |
| 3,5-Cl$_2$ | CF$_3$ | H | H | C(O)Pr-c |
| 3,5-Cl$_2$ | CF$_3$ | H | CH$_3$ | C(O)Pr-c |
| 3,5-Cl$_2$ | CF$_3$ | H | Et | C(O)Pr-c |
| 3,5-Cl$_2$ | CF$_3$ | H | CH$_2$OCH$_3$ | C(O)Pr-c |
| 3,5-Cl$_2$ | CF$_3$ | H | CH$_2$OEt | C(O)Pr-c |
| 3,5-Cl$_2$ | CF$_3$ | H | CH$_2$OCH$_2$CF$_3$ | C(O)Pr-c |
| 3,5-Cl$_2$ | CF$_3$ | H | CH$_2$OC(O)CH$_3$ | C(O)Pr-c |
| 3,5-Cl$_2$ | CF$_3$ | H | CH$_2$OC(O)Et | C(O)Pr-c |
| 3,5-Cl$_2$ | CF$_3$ | H | CH$_2$OC(O)Pr-i | C(O)Pr-c |
| 3,5-Cl$_2$ | CF$_3$ | H | CH$_2$OC(O)Pr-c | C(O)Pr-c |
| 3,5-Cl$_2$ | CF$_3$ | H | CH$_2$OC(O)Bu-t | C(O)Pr-c |
| 3,5-Cl$_2$ | CF$_3$ | H | CH$_2$OC(O)Ph | C(O)Pr-c |
| 3,5-Cl$_2$ | CF$_3$ | H | CH$_2$OC(O)OCH$_3$ | C(O)Pr-c |
| 3,5-Cl$_2$ | CF$_3$ | H | CH$_2$CN | C(O)Pr-c |
| 3,5-Cl$_2$ | CF$_3$ | H | CH$_2$C≡CH | C(O)Pr-c |
| 3,5-Cl$_2$ | CF$_3$ | H | C(O)CH$_3$ | C(O)Pr-c |
| 3,5-Cl$_2$ | CF$_3$ | H | C(O)Et | C(O)Pr-c |
| 3,5-Cl$_2$ | CF$_3$ | H | C(O)Pr-i | C(O)Pr-c |
| 3,5-Cl$_2$ | CF$_3$ | H | C(O)Pr-c | C(O)Pr-c |
| 3,5-Cl$_2$ | CF$_3$ | H | C(O)Bu-t | C(O)Pr-c |
| 3,5-Cl$_2$ | CF$_3$ | H | C(O)CH$_2$OCH$_3$ | C(O)Pr-c |
| 3,5-Cl$_2$ | CF$_3$ | H | C(O)CH$_2$SCH$_3$ | C(O)Pr-c |
| 3,5-Cl$_2$ | CF$_3$ | H | C(O)OCH$_3$ | C(O)Pr-c |
| 3,5-Cl$_2$ | CF$_3$ | H | C(O)OEt | C(O)Pr-c |
| 3,5-Cl$_2$ | CF$_3$ | H | C(O)OPr-i | C(O)Pr-c |
| 3,5-Cl$_2$ | CF$_3$ | H | C(O)OPr-c | C(O)Pr-c |
| 3,5-Cl$_2$ | CF$_3$ | H | C(O)OCH$_2$Cl | C(O)Pr-c |
| 3,5-Cl$_2$ | CF$_3$ | H | C(O)OCH$_2$CH$_2$Cl | C(O)Pr-c |
| 3,5-Cl$_2$ | CF$_3$ | H | C(O)OCH$_2$CH$_2$OCH$_3$ | C(O)Pr-c |
| 3,5-Cl$_2$ | CF$_3$ | H | C(O)OCH$_2$CHCH$_2$ | C(O)Pr-c |
| 3,5-Cl$_2$ | CF$_3$ | H | C(O)OCH$_2$C≡CH | C(O)Pr-c |
| 3,5-Cl$_2$ | CF$_3$ | H | SCCl$_3$ | C(O)Pr-c |
| 3,5-Cl$_2$ | CF$_3$ | H | SN(Bu-n)$_2$ | C(O)Pr-c |
| 3,5-Cl$_2$ | CF$_3$ | H | SN(Pr-i)CH$_2$CH$_2$C(O)OEt | C(O)Pr-c |
| 3,5-Cl$_2$ | CF$_3$ | H | SN(CH$_2$Ph)CH$_2$CH$_2$C(O)OEt | C(O)Pr-c |
| 3,5-Cl$_2$ | CF$_3$ | H | SN(CH$_3$)C(O)OBu-n | C(O)Pr-c |
| 3,5-Cl$_2$ | CF$_3$ | H | H | C(O)Bu-n |
| 3,5-Cl$_2$ | CF$_3$ | H | H | C(O)Bu-i |
| 3,5-Cl$_2$ | CF$_3$ | H | H | C(O)CH$_2$Pr-c |
| 3,5-Cl$_2$ | CF$_3$ | H | CH$_3$ | C(O)CH$_2$Pr-c |
| 3,5-Cl$_2$ | CF$_3$ | H | Et | C(O)CH$_2$Pr-c |
| 3,5-Cl$_2$ | CF$_3$ | H | CH$_2$OCH$_3$ | C(O)CH$_2$Pr-c |
| 3,5-Cl$_2$ | CF$_3$ | H | CH$_2$OEt | C(O)CH$_2$Pr-c |
| 3,5-Cl$_2$ | CF$_3$ | H | CH$_2$OCH$_2$CF$_3$ | C(O)CH$_2$Pr-c |
| 3,5-Cl$_2$ | CF$_3$ | H | CH$_2$OC(O)CH$_3$ | C(O)CH$_2$Pr-c |
| 3,5-Cl$_2$ | CF$_3$ | H | CH$_2$OC(O)OCH$_3$ | C(O)CH$_2$Pr-c |
| 3,5-Cl$_2$ | CF$_3$ | H | CH$_2$CN | C(O)CH$_2$Pr-c |
| 3,5-Cl$_2$ | CF$_3$ | H | CH$_2$C≡OH | C(O)CH$_2$Pr-c |
| 3,5-Cl$_2$ | CF$_3$ | H | C(O)CH$_3$ | C(O)CH$_2$Pr-c |
| 3,5-Cl$_2$ | CF$_3$ | H | C(O)OCH$_3$ | C(O)CH$_2$Pr-c |
| 3,5-Cl$_2$ | CF$_3$ | H | SCCl$_3$ | C(O)CH$_2$Pr-c |
| 3,5-Cl$_2$ | CF$_3$ | H | H | C(O)Bu-s |
| 3,5-Cl$_2$ | CF$_3$ | H | H | C(O)(T-6) |
| 3,5-Cl$_2$ | CF$_3$ | H | H | C(O)Bu-c |
| 3,5-Cl$_2$ | CF$_3$ | H | H | C(O)Bu-t |
| 3,5-Cl$_2$ | CF$_3$ | H | H | C(O)Pen-n |
| 3,5-Cl$_2$ | CF$_3$ | H | H | C(O)Pen-c |
| 3,5-Cl$_2$ | CF$_3$ | H | H | C(O)CH$_2$Bu-i |
| 3,5-Cl$_2$ | CF$_3$ | H | H | C(O)CH$_2$Bu-s |
| 3,5-Cl$_2$ | CF$_3$ | H | H | C(O)CH$_2$Bu-c |
| 3,5-Cl$_2$ | CF$_3$ | H | H | C(O)CH$_2$Bu-t |
| 3,5-Cl$_2$ | CF$_3$ | H | H | C(O)CH$_2$(T-6) |
| 3,5-Cl$_2$ | CF$_3$ | H | H | C(O)CH(CH$_3$)Pr-n |
| 3,5-Cl$_2$ | CF$_3$ | H | H | C(O)CH(Et)$_2$ |
| 3,5-Cl$_2$ | CF$_3$ | H | H | C(O)C(CH$_3$)$_2$Et |
| 3,5-Cl$_2$ | CF$_3$ | H | H | C(O)(T-7) |
| 3,5-Cl$_2$ | CF$_3$ | H | H | C(O)Pen-c |
| 3,5-Cl$_2$ | CF$_3$ | H | H | C(O)Hex-n |
| 3,5-Cl$_2$ | CF$_3$ | H | H | C(O)CH$_2$(T-7) |
| 3,5-Cl$_2$ | CF$_3$ | H | H | C(O)CH$_2$Pen-c |

TABLE 2-continued

| | | | | |
|---|---|---|---|---|
| 3,5-Cl$_2$ | CF$_3$ | H | H | C(O)CH(CH$_3$)Bu-i |
| 3,5-Cl$_2$ | CF$_3$ | H | H | C(O)C(CH$_3$)$_2$Pr-n |
| 3,5-Cl$_2$ | CF$_3$ | H | H | C(O)Hex-c |
| 3,5-Cl$_2$ | CF$_3$ | H | H | C(O)Hept |
| 3,5-Cl$_2$ | CF$_3$ | H | H | C(O)CH$_2$Hex-c |
| 3,5-Cl$_2$ | CF$_3$ | H | H | C(O)Oct |
| 3,5-Cl$_2$ | CF$_3$ | H | H | C(O)CH$_2$(T-12) |
| 3,5-Cl$_2$ | CF$_3$ | H | H | C(O)CH$_2$F |
| 3,5-Cl$_2$ | CF$_3$ | H | H | C(O)CH$_2$Cl |
| 3,5-Cl$_2$ | CF$_3$ | H | H | C(O)CH$_2$Br |
| 3,5-Cl$_2$ | CF$_3$ | H | H | C(O)CHF$_2$ |
| 3,5-Cl$_2$ | CF$_3$ | H | H | C(O)CHFCl |
| 3,5-Cl$_2$ | CF$_3$ | H | H | C(O)CHCl$_2$ |
| 3,5-Cl$_2$ | CF$_3$ | H | H | C(O)OHFBr |
| 3,5-Cl$_2$ | CF$_3$ | H | H | C(O)CF$_3$ |
| 3,5-Cl$_2$ | CF$_3$ | H | H | C(O)CF$_2$Cl |
| 3,5-Cl$_2$ | CF$_3$ | H | H | C(O)CFCl$_2$ |
| 3,5-Cl$_2$ | CF$_3$ | H | H | C(O)CCl$_3$ |
| 3,5-Cl$_2$ | CF$_3$ | H | H | C(O)CF$_2$Br |
| 3,5-Cl$_2$ | CF$_3$ | H | H | C(O)CFClBr |
| 3,5-Cl$_2$ | CF$_3$ | H | H | C(O)CCl$_2$Br |
| 3,5-Cl$_2$ | CF$_3$ | H | H | C(O)CH$_2$CH$_2$F |
| 3,5-Cl$_2$ | CF$_3$ | H | H | C(O)CHFCH$_3$ |
| 3,5-Cl$_2$ | CF$_3$ | H | H | C(O)CH$_2$CH$_2$Cl |
| 3,5-Cl$_2$ | CF$_3$ | H | CH$_3$ | C(O)CH$_2$CH$_2$Cl |
| 3,5-Cl$_2$ | CF$_3$ | H | Et | C(O)CH$_2$CH$_2$Cl |
| 3,5-Cl$_2$ | CF$_3$ | H | CH$_2$OCH$_3$ | C(O)CH$_2$CH$_2$Cl |
| 3,5-Cl$_2$ | CF$_3$ | H | CH$_2$OEt | C(O)CH$_2$CH$_2$Cl |
| 3,5-Cl$_2$ | CF$_3$ | H | CH$_2$OCH$_2$CF$_3$ | C(O)CH$_2$CH$_2$Cl |
| 3,5-Cl$_2$ | CF$_3$ | H | CH$_2$OC(O)CH$_3$ | C(O)CH$_2$CH$_2$Cl |
| 3,5-Cl$_2$ | CF$_3$ | H | CH$_2$OC(O)OCH$_3$ | C(O)CH$_2$CH$_2$Cl |
| 3,5-Cl$_2$ | CF$_3$ | H | CH$_2$CN | C(O)CH$_2$CH$_2$Cl |
| 3,5-Cl$_2$ | CF$_3$ | H | CH$_2$C≡CH | C(O)CH$_2$CH$_2$Cl |
| 3,5-Cl$_2$ | CF$_3$ | H | C(O)CH$_3$ | C(O)CH$_2$CH$_2$Cl |
| 3,5-Cl$_2$ | CF$_3$ | H | C(O)OCH$_3$ | C(O)CH$_2$CH$_2$Cl |
| 3,5-Cl$_2$ | CF$_3$ | H | SCCl$_3$ | C(O)CH$_2$CH$_2$Cl |
| 3,5-Cl$_2$ | CF$_3$ | H | H | C(O)CHClCH$_3$ |
| 3,5-Cl$_2$ | CF$_3$ | H | H | C(O)CHClCH$_3$(R) |
| 3,5-Cl$_2$ | CF$_3$ | H | H | C(O)CHClCH$_3$(S) |
| 3,5-Cl$_2$ | CF$_3$ | H | H | C(O)CH$_2$CH$_2$Br |
| 3,5-Cl$_2$ | CF$_3$ | H | H | C(O)CHBrCH$_3$ |
| 3,5-Cl$_2$ | CF$_3$ | H | H | C(O)CH$_2$CHF$_2$ |
| 3,5-Cl$_2$ | CF$_3$ | H | H | C(O)CH$_2$CHFCl |
| 3,5-Cl$_2$ | CF$_3$ | H | H | C(O)CFClCH$_3$ |
| 3,5-Cl$_2$ | CF$_3$ | H | H | C(O)CH$_2$CHCl$_2$ |
| 3,5-Cl$_2$ | CF$_3$ | H | H | C(O)CHClCH$_2$Cl |
| 3,5-Cl$_2$ | CF$_3$ | H | H | C(O)CH$_2$CHFBr |
| 3,5-Cl$_2$ | CF$_3$ | H | H | C(O)CHBrCH$_2$F |
| 3,5-Cl$_2$ | CF$_3$ | H | H | C(O)CHClCH$_2$Br |
| 3,5-Cl$_2$ | CF$_3$ | H | H | C(O)CHBrCH$_2$Cl |
| 3,5-Cl$_2$ | CF$_3$ | H | H | C(O)CClBrCH$_3$ |
| 3,5-Cl$_2$ | CF$_3$ | H | H | C(O)CHBrCH$_2$Br |
| 3,5-Cl$_2$ | CF$_3$ | H | H | C(O)CH$_2$CF$_3$ |
| 3,5-Cl$_2$ | CF$_3$ | H | CH$_3$ | C(O)CH$_2$CF$_3$ |
| 3,5-Cl$_2$ | CF$_3$ | H | Et | C(O)CH$_2$CF$_3$ |
| 3,5-Cl$_2$ | CF$_3$ | H | c-Pr | C(O)CH$_2$CF$_3$ |
| 3,5-Cl$_2$ | CF$_3$ | H | CH$_2$OCH$_3$ | C(O)CH$_2$CF$_3$ |
| 3,5-Cl$_2$ | CF$_3$ | H | CH$_2$OEt | C(O)CH$_2$CF$_3$ |
| 3,5-Cl$_2$ | CF$_3$ | H | CH$_2$OCH$_2$CH$_2$Cl | C(O)CH$_2$CF$_3$ |
| 3,5-Cl$_2$ | CF$_3$ | H | CH$_2$OCH$_2$CHF$_2$ | C(O)CH$_2$CF$_3$ |
| 3,5-Cl$_2$ | CF$_3$ | H | CH$_2$OCH$_2$CF$_3$ | C(O)CH$_2$CF$_3$ |
| 3,5-Cl$_2$ | CF$_3$ | H | CH$_2$OCH$_2$CH$_2$OCH$_3$ | C(O)CH$_2$CF$_3$ |
| 3,5-Cl$_2$ | CF$_3$ | H | CH$_2$OCH$_2$Ph | C(O)CH$_2$CF$_3$ |
| 3,5-Cl$_2$ | CF$_3$ | H | CH$_2$OC(O)CH$_3$ | C(O)CH$_2$CF$_3$ |
| 3,5-Cl$_2$ | CF$_3$ | H | CH$_2$OC(O)Et | C(O)CH$_2$CF$_3$ |
| 3,5-Cl$_2$ | CF$_3$ | H | CH$_2$OC(O)Pr-n | C(O)CH$_2$CF$_3$ |
| 3,5-Cl$_2$ | CF$_3$ | H | CH$_2$OC(O)Pr-i | C(O)CH$_2$CF$_3$ |
| 3,5-Cl$_2$ | CF$_3$ | H | CH$_2$OC(O)Pr-c | C(O)CH$_2$CF$_3$ |
| 3,5-Cl$_2$ | CF$_3$ | H | CH$_2$OC(O)Bu-n | C(O)CH$_2$CF$_3$ |
| 3,5-Cl$_2$ | CF$_3$ | H | CH$_2$OC(O)Bu-i | C(O)CH$_2$CF$_3$ |
| 3,5-Cl$_2$ | CF$_3$ | H | CH$_2$OC(O)Bu-s | C(O)CH$_2$CF$_3$ |
| 3,5-Cl$_2$ | CF$_3$ | H | CH$_2$OC(O)Bu-t | C(O)CH$_2$CF$_3$ |
| 3,5-Cl$_2$ | CF$_3$ | H | CH$_2$OC(O)CH$_2$Ph | C(O)CH$_2$CF$_3$ |
| 3,5-Cl$_2$ | CF$_3$ | H | CH$_2$OC(O)Ph | C(O)CH$_2$CF$_3$ |
| 3,5-Cl$_2$ | CF$_3$ | H | CH$_2$OC(O)OCH$_3$ | C(O)CH$_2$CF$_3$ |
| 3,5-Cl$_2$ | CF$_3$ | H | CH$_2$OC(O)OEt | C(O)CH$_2$CF$_3$ |
| 3,5-Cl$_2$ | CF$_3$ | H | CH$_2$OC(O)OBu-n | C(O)CH$_2$CF$_3$ |
| 3,5-Cl$_2$ | CF$_3$ | H | CH$_2$OC(O)OBu-i | C(O)CH$_2$CF$_3$ |
| 3,5-Cl$_2$ | CF$_3$ | H | CH$_2$OC(O)OCH$_2$Ph | C(O)CH$_2$CF$_3$ |
| 3,5-Cl$_2$ | CF$_3$ | H | CH$_2$OC(O)OPh | C(O)CH$_2$CF$_3$ |

TABLE 2-continued

| | | | | |
|---|---|---|---|---|
| 3,5-Cl$_2$ | CF$_3$ | H | CH$_2$OC(O)NHPh | C(O)CH$_2$CF$_3$ |
| 3,5-Cl$_2$ | CF$_3$ | H | CH$_2$OPh | C(O)CH$_2$CF$_3$ |
| 3,5-Cl$_2$ | CF$_3$ | H | CH$_2$SCH$_3$ | C(O)CH$_2$CF$_3$ |
| 3,5-Cl$_2$ | CF$_3$ | H | CH$_2$SO$_2$CH$_3$ | C(O)CH$_2$CF$_3$ |
| 3,5-Cl$_2$ | CF$_3$ | H | CH$_2$SC(O)CH$_3$ | C(O)CH$_2$CF$_3$ |
| 3,5-Cl$_2$ | CF$_3$ | H | CH$_2$SC(O)Et | C(O)CH$_2$CF$_3$ |
| 3,5-Cl$_2$ | CF$_3$ | H | CH$_2$SC(O)Ph | C(O)CH$_2$CF$_3$ |
| 3,5-Cl$_2$ | CF$_3$ | H | CH$_2$SC(S)OCH$_3$ | C(O)CH$_2$CF$_3$ |
| 3,5-Cl$_2$ | CF$_3$ | H | CH$_2$SC(S)OEt | C(O)CH$_2$CF$_3$ |
| 3,5-Cl$_2$ | CF$_3$ | H | CH$_2$SC(S)OPr-n | C(O)CH$_2$CF$_3$ |
| 3,5-Cl$_2$ | CF$_3$ | H | CH$_2$SC(S)OPr-i | C(O)CH$_2$CF$_3$ |
| 3,5-Cl$_2$ | CF$_3$ | H | CH$_2$SC(S)N(CH$_3$)$_2$ | C(O)CH$_2$CF$_3$ |
| 3,5-Cl$_2$ | CF$_3$ | H | CH$_2$SC(S)(T-17) | C(O)CH$_2$CF$_3$ |
| 3,5-Cl$_2$ | CF$_3$ | H | CH$_2$N(CH$_3$)$_2$ | C(O)CH$_2$CF$_3$ |
| 3,5-Cl$_2$ | CF$_3$ | H | CH$_2$N(CH$_3$)C(O)CH$_3$ | C(O)CH$_2$CF$_3$ |
| 3,5-Cl$_2$ | CF$_3$ | H | CH$_2$NHC(O)OCH$_3$ | C(O)CH$_2$CF$_3$ |
| 3,5-Cl$_2$ | CF$_3$ | H | CH$_2$N(CH$_3$)C(O)OCH$_3$ | C(O)CH$_2$CF$_3$ |
| 3,5-Cl$_2$ | CF$_3$ | H | CH$_2$N(CH$_3$)SO$_2$CH$_3$ | C(O)CH$_2$CF$_3$ |
| 3,5-Cl$_2$ | CF$_3$ | H | CH$_2$CN | C(O)CH$_2$CF$_3$ |
| 3,5-Cl$_2$ | CF$_3$ | H | CH$_2$C(O)OCH$_3$ | C(O)CH$_2$CF$_3$ |
| 3,5-Cl$_2$ | CF$_3$ | H | CH$_2$CH=CH$_2$ | C(O)CH$_2$CF$_3$ |
| 3,5-Cl$_2$ | CF$_3$ | H | CH$_2$C≡CH | C(O)CH$_2$CF$_3$ |
| 3,5-Cl$_2$ | CF$_3$ | H | C(O)CH$_3$ | C(O)CH$_2$CF$_3$ |
| 3,5-Cl$_2$ | CF$_3$ | H | C(O)Et | C(O)CH$_2$CF$_3$ |
| 3,5-Cl$_2$ | CF$_3$ | H | C(O)Pr-n | C(O)CH$_2$CF$_3$ |
| 3,5-Cl$_2$ | CF$_3$ | H | C(O)Pr-i | C(O)CH$_2$CF$_3$ |
| 3,5-Cl$_2$ | CF$_3$ | H | C(O)Pr-c | C(O)CH$_2$CF$_3$ |
| 3,5-Cl$_2$ | CF$_3$ | H | C(O)Bu-n | C(O)CH$_2$CF$_3$ |
| 3,5-Cl$_2$ | CF$_3$ | H | C(O)Bu-i | C(O)CH$_2$CF$_3$ |
| 3,5-Cl$_2$ | CF$_3$ | H | C(O)Bu-s | C(O)CH$_2$CF$_3$ |
| 3,5-Cl$_2$ | CF$_3$ | H | C(O)Bu-t | C(O)CH$_2$CF$_3$ |
| 3,5-Cl$_2$ | CF$_3$ | H | C(O)CH$_2$OCH$_3$ | C(O)CH$_2$CF$_3$ |
| 3,5-Cl$_2$ | CF$_3$ | H | C(O)CH$_2$SCH$_3$ | C(O)CH$_2$CF$_3$ |
| 3,5-Cl$_2$ | CF$_3$ | H | C(O)CH$_2$SO$_2$CH$_3$ | C(O)CH$_2$CF$_3$ |
| 3,5-Cl$_2$ | CF$_3$ | H | C(O)CH=CH$_2$ | C(O)CH$_2$CF$_3$ |
| 3,5-Cl$_2$ | CF$_3$ | H | C(O)Ph | C(O)CH$_2$CF$_3$ |
| 3,5-Cl$_2$ | CF$_3$ | H | C(O)OCH$_3$ | C(O)CH$_2$CF$_3$ |
| 3,5-Cl$_2$ | CF$_3$ | H | C(O)OEt | C(O)CH$_2$CF$_3$ |
| 3,5-Cl$_2$ | CF$_3$ | H | C(O)OPr-n | C(O)CH$_2$CF$_3$ |
| 3,5-Cl$_2$ | CF$_3$ | H | C(O)OPr-i | C(O)CH$_2$CF$_3$ |
| 3,5-Cl$_2$ | CF$_3$ | H | C(O)OPr-c | C(O)CH$_2$CF$_3$ |
| 3,5-Cl$_2$ | CF$_3$ | H | C(O)OBu-i | C(O)CH$_2$CF$_3$ |
| 3,5-Cl$_2$ | CF$_3$ | H | C(O)OCH$_2$Cl | C(O)CH$_2$CF$_3$ |
| 3,5-Cl$_2$ | CF$_3$ | H | C(O)OCH$_2$CH$_2$Cl | C(O)CH$_2$CF$_3$ |
| 3,5-Cl$_2$ | CF$_3$ | H | C(O)OCH$_2$CH$_2$OCH$_3$ | C(O)CH$_2$CF$_3$ |
| 3,5-Cl$_2$ | CF$_3$ | H | C(O)OCH$_2$CH$_2$SO$_2$CH$_3$ | C(O)CH$_2$CF$_3$ |
| 3,5-Cl$_2$ | CF$_3$ | H | C(O)OCH=CH$_2$ | C(O)CH$_2$CF$_3$ |
| 3,5-Cl$_2$ | CF$_3$ | H | C(O)OCH$_2$CH=CH$_2$ | C(O)CH$_2$CF$_3$ |
| 3,5-Cl$_2$ | CF$_3$ | H | C(O)OCH$_2$C≡CH | C(O)CH$_2$CF$_3$ |
| 3,5-Cl$_2$ | CF$_3$ | H | C(O)SCH$_3$ | C(O)CH$_2$CF$_3$ |
| 3,5-Cl$_2$ | CF$_3$ | H | C(S)OCH$_3$ | C(O)CH$_2$CF$_3$ |
| 3,5-Cl$_2$ | CF$_3$ | H | C(S)SCH$_3$ | C(O)CH$_2$CF$_3$ |
| 3,5-Cl$_2$ | CF$_3$ | H | SCCl$_3$ | C(O)CH$_2$CF$_3$ |
| 3,5-Cl$_2$ | CF$_3$ | H | SN(Bu-n)$_2$ | C(O)CH$_2$CF$_3$ |
| 3,5-Cl$_2$ | CF$_3$ | H | S(T-21) | C(O)CH$_2$CF$_3$ |
| 3,5-Cl$_2$ | CF$_3$ | H | SN(Pr-i)CH$_2$CH$_2$C(O)OEt | C(O)CH$_2$CF$_3$ |
| 3,5-Cl$_2$ | CF$_3$ | H | SN(CH$_2$Ph)CH$_2$CH$_2$C(O)OEt | C(O)CH$_2$CF$_3$ |
| 3,5-Cl$_2$ | CF$_3$ | H | SN(CH$_3$)C(O)OBu-n | C(O)CH$_2$CF$_3$ |
| 3,5-Cl$_2$ | CF$_3$ | H | H | C(O)CH$_2$CF$_2$Cl |
| 3,5-Cl$_2$ | CF$_3$ | H | H | C(O)CH$_2$CFCl$_2$ |
| 3,5-Cl$_2$ | CF$_3$ | H | H | C(O)CH$_2$CCl$_3$ |
| 3,5-Cl$_2$ | CF$_3$ | H | H | C(O)CH$_2$CF$_2$Br |
| 3,5-Cl$_2$ | CF$_3$ | H | H | C(O)CH$_2$CFClBr |
| 3,5-Cl$_2$ | CF$_3$ | H | H | C(O)CH$_2$CCl$_2$Br |
| 3,5-Cl$_2$ | CF$_3$ | H | H | C(O)CClBrCH$_2$Cl |
| 3,5-Cl$_2$ | CF$_3$ | H | H | C(O)CF$_2$CHF$_2$ |
| 3,5-Cl$_2$ | CF$_3$ | H | H | C(O)CHClCF$_3$ |
| 3,5-Cl$_2$ | CF$_3$ | H | H | C(O)CF$_2$CF$_3$ |
| 3,5-Cl$_2$ | CF$_3$ | H | H | C(O)CH$_2$CHFCH$_3$ |
| 3,5-Cl$_2$ | CF$_3$ | H | H | C(O)CHFCH$_2$CH$_3$ |
| 3,5-Cl$_2$ | CF$_3$ | H | H | C(O)CH$_2$CHClCH$_3$ |
| 3,5-Cl$_2$ | CF$_3$ | H | H | C(O)CH$_2$CHClCH$_3$(R) |
| 3,5-Cl$_2$ | CF$_3$ | H | H | C(O)CH$_2$CHClCH$_3$(S) |
| 3,5-Cl$_2$ | CF$_3$ | H | H | C(O)CHClCH$_2$CH$_3$ |
| 3,5-Cl$_2$ | CF$_3$ | H | H | C(O)CH$_2$CHBrCH$_3$ |
| 3,5-Cl$_2$ | CF$_3$ | H | H | C(O)CH(CH$_3$)CH$_2$F |
| 3,5-Cl$_2$ | CF$_3$ | H | H | C(O)CH(CH$_3$)CH$_2$F(R) |
| 3,5-Cl$_2$ | CF$_3$ | H | H | C(O)CH(CH$_3$)CH$_2$F(S) |
| 3,5-Cl$_2$ | CF$_3$ | H | H | C(O)CF(CH$_3$)$_2$ |
| 3,5-Cl$_2$ | CF$_3$ | H | H | C(O)CH(CH$_3$)CH$_2$Cl |

TABLE 2-continued

| | | | | |
|---|---|---|---|---|
| 3,5-Cl$_2$ | CF$_3$ | H | H | C(O)CH(CH$_3$)CH$_2$Br |
| 3,5-Cl$_2$ | CF$_3$ | H | H | C(O)CH(CH$_3$)CH$_2$Br(R) |
| 3,5-Cl$_2$ | CF$_3$ | H | H | C(O)CH(CH$_3$)CH$_2$Br(S) |
| 3,5-Cl$_2$ | CF$_3$ | H | H | C(O)CH$_2$CFClCH$_3$ |
| 3,5-Cl$_2$ | CF$_3$ | H | H | C(O)CH$_2$CHClCH$_2$Cl |
| 3,5-Cl$_2$ | CF$_3$ | H | H | C(O)CH$_2$CHBrCH$_2$F |
| 3,5-Cl$_2$ | CF$_3$ | H | H | C(O)CH$_2$CHClCH$_2$Br |
| 3,5-Cl$_2$ | CF$_3$ | H | H | C(O)CH$_2$CHBrCH$_2$Cl |
| 3,5-Cl$_2$ | CF$_3$ | H | H | C(O)CH$_2$CClBrCH$_3$ |
| 3,5-Cl$_2$ | CF$_3$ | H | H | C(O)CH$_2$CHBrCH$_2$Br |
| 3,5-Cl$_2$ | CF$_3$ | H | H | C(O)CH$_2$CH$_2$CF$_3$ |
| 3,5-Cl$_2$ | CF$_3$ | H | H | C(O)CH$_2$CH$_2$CF$_2$Br |
| 3,5-Cl$_2$ | CF$_3$ | H | H | C(O)CH$_2$CClBrCH$_2$Cl |
| 3,5-Cl$_2$ | CF$_3$ | H | H | C(O)CH$_2$CF$_2$CHF$_2$ |
| 3,5-Cl$_2$ | CF$_3$ | H | H | C(O)CH$_2$CHClCF$_3$ |
| 3,5-Cl$_2$ | CF$_3$ | H | H | C(O)CH$_2$CF$_2$CF$_3$ |
| 3,5-Cl$_2$ | CF$_3$ | H | H | C(O)CF$_2$CHFCF$_3$ |
| 3,5-Cl$_2$ | CF$_3$ | H | H | C(O)CF$_2$CF$_2$CHF$_2$ |
| 3,5-Cl$_2$ | CF$_3$ | H | H | C(O)CF$_2$CF$_2$CF$_3$ |
| 3,5-Cl$_2$ | CF$_3$ | H | H | C(O)(T-1) |
| 3,5-Cl$_2$ | CF$_3$ | H | H | C(O)(T-2) |
| 3,5-Cl$_2$ | CF$_3$ | H | H | C(O)(T-3) |
| 3,5-Cl$_2$ | CF$_3$ | H | H | C(O)(T-4) |
| 3,5-Cl$_2$ | CF$_3$ | H | H | C(O)(T-5) |
| 3,5-Cl$_2$ | CF$_3$ | H | H | C(O)CH$_2$CHFCH$_2$CH$_3$ |
| 3,5-Cl$_2$ | CF$_3$ | H | H | C(O)CH$_2$CHClCH$_2$CH$_3$ |
| 3,5-Cl$_2$ | CF$_3$ | H | H | C(O)CH$_2$CF(CH$_3$)$_2$ |
| 3,5-Cl$_2$ | CF$_3$ | H | H | C(O)C(CH$_3$)$_2$CH$_2$Cl |
| 3,5-Cl$_2$ | CF$_3$ | H | H | C(O)C(CH$_3$)$_2$CH$_2$Br |
| 3,5-Cl$_2$ | CF$_3$ | H | H | C(O)CH$_2$CF$_2$CHFCF$_3$ |
| 3,5-Cl$_2$ | CF$_3$ | H | H | C(O)CH$_2$CF$_2$CF$_2$CHF$_2$ |
| 3,5-Cl$_2$ | CF$_3$ | H | H | C(O)CH$_2$CF$_2$CF$_2$CF$_3$ |
| 3,5-Cl$_2$ | CF$_3$ | H | H | C(O)CH$_2$(T-1) |
| 3,5-Cl$_2$ | CF$_3$ | H | H | C(O)CH$_2$(T-2) |
| 3,5-Cl$_2$ | CF$_3$ | H | H | C(O)CH$_2$(T-3) |
| 3,5-Cl$_2$ | CF$_3$ | H | H | C(O)CH$_2$(T-4) |
| 3,5-Cl$_2$ | CF$_3$ | H | H | C(O)CH$_2$(T-5) |
| 3,5-Cl$_2$ | CF$_3$ | H | H | C(O)(T-8) |
| 3,5-Cl$_2$ | CF$_3$ | H | H | C(O)C(CH$_3$)$_2$CHBrCH$_2$Br |
| 3,5-Cl$_2$ | CF$_3$ | H | H | C(O)CH$_2$(T-10) |
| 3,5-Cl$_2$ | CF$_3$ | H | H | C(O)CH$_2$(T-11) |
| 3,5-Cl$_2$ | CF$_3$ | H | H | C(O)CH$_2$OCH$_3$ |
| 3,5-Cl$_2$ | CF$_3$ | H | H | C(O)CH$_2$OEt |
| 3,5-Cl$_2$ | CF$_3$ | H | H | C(O)CH$_2$OPr-n |
| 3,5-Cl$_2$ | CF$_3$ | H | H | C(O)CH$_2$OPr-i |
| 3,5-Cl$_2$ | CF$_3$ | H | H | C(O)CH$_2$OBu-i |
| 3,5-Cl$_2$ | CF$_3$ | H | H | C(O)CH$_2$OCH$_2$CH$_2$Cl |
| 3,5-Cl$_2$ | CF$_3$ | H | H | C(O)CH$_2$OCH$_2$CF$_3$ |
| 3,5-Cl$_2$ | CF$_3$ | H | H | C(O)CH$_2$OCH$_2$CH$_2$OCH$_3$ |
| 3,5-Cl$_2$ | CF$_3$ | H | H | C(O)CH$_2$OCH$_2$CH$_2$OCH$_2$CF$_3$ |
| 3,5-Cl$_2$ | CF$_3$ | H | H | C(O)CH$_2$OCH$_2$CH$_2$OCH$_2$CH$_2$OCH$_3$ |
| 3,5-Cl$_2$ | CF$_3$ | H | H | C(O)CH$_2$OCH$_2$CH$_2$SCH$_3$ |
| 3,5-Cl$_2$ | CF$_3$ | H | H | C(O)CH$_2$OCH$_2$CH$_2$SEt |
| 3,5-Cl$_2$ | CF$_3$ | H | H | C(O)CH$_2$OCH$_2$CH$_2$SCH$_2$CF$_3$ |
| 3,5-Cl$_2$ | CF$_3$ | H | H | C(O)CH$_2$OCH$_2$Ph |
| 3,5-Cl$_2$ | CF$_3$ | H | H | C(O)CH$_2$OC(O)CH$_3$ |
| 3,5-Cl$_2$ | CF$_3$ | H | H | C(O)CH$_2$OC(O)CF$_3$ |
| 3,5-Cl$_2$ | CF$_3$ | H | H | C(O)CH$_2$OC(O)NHCH$_3$ |
| 3,5-Cl$_2$ | CF$_3$ | H | H | C(O)CH$_2$OC(O)N(CH$_3$)$_2$ |
| 3,5-Cl$_2$ | CF$_3$ | H | H | C(O)CH$_2$OC(O)NHEt |
| 3,5-Cl$_2$ | CF$_3$ | H | H | C(O)CH$_2$OC(O)N(Et)$_2$ |
| 3,5-Cl$_2$ | CF$_3$ | H | H | C(O)CH$_2$OC(O)NHPr-n |
| 3,5-Cl$_2$ | CF$_3$ | H | H | C(O)CH$_2$OC(O)NHPr-i |
| 3,5-Cl$_2$ | CF$_3$ | H | H | C(O)CH$_2$OC(O)NHPr-c |
| 3,5-Cl$_2$ | CF$_3$ | H | H | C(O)CH$_2$OC(O)NHBu-t |
| 3,5-Cl$_2$ | CF$_3$ | H | H | C(O)CH$_2$OC(O)NHCH$_2$CF$_3$ |
| 3,5-Cl$_2$ | CF$_3$ | H | H | C(O)CH$_2$OC(O)NHCH$_2$CH$_2$OCH$_3$ |
| 3,5-Cl$_2$ | CF$_3$ | H | H | C(O)CH$_2$OC(O)NHCH$_2$CH$_2$SCH$_3$ |
| 3,5-Cl$_2$ | CF$_3$ | H | H | C(O)CH$_2$OC(O)NHCH$_2$CH=CH$_2$ |
| 3,5-Cl$_2$ | CF$_3$ | H | H | C(O)CH$_2$OC(O)NHCH$_2$Ph |
| 3,5-Cl$_2$ | CF$_3$ | H | H | C(O)CH$_2$OC(O)NHCH$_2$(D-52a) |
| 3,5-Cl$_2$ | CF$_3$ | H | H | C(O)CH$_2$OC(O)NHCH$_2$(D-53a) |
| 3,5-Cl$_2$ | CF$_3$ | H | H | C(O)CH$_2$OC(O)NHCH$_2$(D-54a) |
| 3,5-Cl$_2$ | CF$_3$ | H | H | C(O)CH$_2$OC(O)NHPh |
| 3,5-Cl$_2$ | CF$_3$ | H | H | C(O)CH$_2$OC(O)(T-17) |
| 3,5-Cl$_2$ | CF$_3$ | H | H | C(O)CH$_2$OC(O)(T-20) |
| 3,5-Cl$_2$ | CF$_3$ | H | H | C(O)CH$_2$OC(O)(T-21) |
| 3,5-Cl$_2$ | CF$_3$ | H | H | C(O)CH$_2$OC(O)(T-22) |
| 3,5-Cl$_2$ | CF$_3$ | H | H | C(O)CH$_2$OC(S)NHCH$_3$ |
| 3,5-Cl$_2$ | CF$_3$ | H | H | C(O)CH$_2$OC(S)N(CH$_3$)$_2$ |

TABLE 2-continued

| | | | | |
|---|---|---|---|---|
| 3,5-Cl$_2$ | CF$_3$ | H | H | C(O)CH$_2$OC(S)NHEt |
| 3,5-Cl$_2$ | CF$_3$ | H | H | C(O)CH$_2$OC(S)NHCH$_2$CF$_3$ |
| 3,5-Cl$_2$ | CF$_3$ | H | H | C(O)CH$_2$OP(O)(OEt)$_2$ |
| 3,5-Cl$_2$ | CF$_3$ | H | H | C(O)CH$_2$OP(S)(OCH$_3$)$_2$ |
| 3,5-Cl$_2$ | CF$_3$ | H | H | C(O)CH$_2$OP(S)(OEt)$_2$ |
| 3,5-Cl$_2$ | CF$_3$ | H | H | C(O)CH$_2$OPh |
| 3,5-Cl$_2$ | CF$_3$ | H | H | C(O)CH$_2$O(Ph-2-F) |
| 3,5-Cl$_2$ | CF$_3$ | H | H | C(O)CH$_2$O(Ph-3-F) |
| 3,5-Cl$_2$ | CF$_3$ | H | H | C(O)CH$_2$O(Ph-4-F) |
| 3,5-Cl$_2$ | CF$_3$ | H | H | C(O)CH(CH$_3$)OCH$_3$ |
| 3,5-Cl$_2$ | CF$_3$ | H | H | C(O)CH(CH$_3$)OCH$_3$(R) |
| 3,5-Cl$_2$ | CF$_3$ | H | H | C(O)CH(CH$_3$)OCH$_3$(S) |
| 3,5-Cl$_2$ | CF$_3$ | H | H | C(O)CH(CH$_3$)OC(O)NHCH$_3$ |
| 3,5-Cl$_2$ | CF$_3$ | H | H | C(O)CH(CH$_3$)OC(O)N(CH$_3$)$_2$ |
| 3,5-Cl$_2$ | CF$_3$ | H | H | C(O)CH(CH$_3$)OC(O)NHEt |
| 3,5-Cl$_2$ | CF$_3$ | H | H | C(O)CH(CH$_3$)OC(O)NHCH$_2$CF$_3$ |
| 3,5-Cl$_2$ | CF$_3$ | H | H | C(O)C(CH$_3$)$_2$OCH$_3$ |
| 3,5-Cl$_2$ | CF$_3$ | H | H | C(O)CH$_2$CH$_2$OCH$_3$ |
| 3,5-Cl$_2$ | CF$_3$ | H | H | C(O)CH$_2$CH$_2$OEt |
| 3,5-Cl$_2$ | CF$_3$ | H | H | C(O)CH(Et)OCH$_3$ |
| 3,5-Cl$_2$ | CF$_3$ | H | H | C(O)CH(CH$_3$)CH$_2$OCH$_3$ |
| 3,5-Cl$_2$ | CF$_3$ | H | H | C(O)CH(CH$_3$)CH$_2$OCH$_3$(R) |
| 3,5-Cl$_2$ | CF$_3$ | H | H | C(O)CH(CH$_3$)CH$_2$OCH$_3$(S) |
| 3,5-Cl$_2$ | CF$_3$ | H | H | C(O)CH(Et)CH$_2$OCH$_3$ |
| 3,5-Cl$_2$ | CF$_3$ | H | H | C(O)C(CH$_3$)$_2$CH$_2$OCH$_3$ |
| 3,5-Cl$_2$ | CF$_3$ | H | H | C(O)CH$_2$CH$_2$CH$_2$OCH$_3$ |
| 3,5-Cl$_2$ | CF$_3$ | H | H | C(O)CH(CF$_3$)OCH$_3$ |
| 3,5-Cl$_2$ | CF$_3$ | H | H | C(O)CH$_2$CH(OCH$_3$)$_2$ |
| 3,5-Cl$_2$ | CF$_3$ | H | H | C(O)CH$_2$CH(OEt)$_2$ |
| 3,5-Cl$_2$ | CF$_3$ | H | H | C(O)CH$_2$(E-4a) |
| 3,5-Cl$_2$ | CF$_3$ | H | H | C(O)CH$_2$(E-5a) |
| 3,5-Cl$_2$ | CF$_3$ | H | H | C(O)CH$_2$(E-10a) |
| 3,5-Cl$_2$ | CF$_3$ | H | H | C(O)CH$_2$(E-10b)CH$_3$ |
| 3,5-Cl$_2$ | CF$_3$ | H | H | C(O)CH$_2$(E-11a) |
| 3,5-Cl$_2$ | CF$_3$ | H | H | C(O)CH$_2$(E-11b)CH$_3$ |
| 3,5-Cl$_2$ | CF$_3$ | H | H | C(O)CH$_2$(E-11c) |
| 3,5-Cl$_2$ | CF$_3$ | H | H | C(O)CH$_2$(E-23a) |
| 3,5-Cl$_2$ | CF$_3$ | H | H | C(O)CH$_2$(E-24a) |
| 3,5-Cl$_2$ | CF$_3$ | H | H | C(O)CH$_2$(E-25a) |
| 3,5-Cl$_2$ | CF$_3$ | H | H | C(O)CH$_2$CH$_2$(E-10a) |
| 3,5-Cl$_2$ | CF$_3$ | H | H | C(O)(E-4a) |
| 3,5-Cl$_2$ | CF$_3$ | H | H | C(O)(E-5a) |
| 3,5-Cl$_2$ | CF$_3$ | H | H | C(O)(E-24a) |
| 3,5-Cl$_2$ | CF$_3$ | H | H | C(O)(E-25a) |
| 3,5-Cl$_2$ | CF$_3$ | H | H | C(O)(E-34a) |
| 3,5-Cl$_2$ | CF$_3$ | H | H | C(O)CH$_2$SCH$_3$ |
| 3,5-Cl$_2$ | CF$_3$ | H | H | C(O)CH$_2$S(O)CH$_3$ |
| 3,5-Cl$_2$ | CF$_3$ | H | H | C(O)CH$_2$SO$_2$CH$_3$ |
| 3,5-Cl$_2$ | CF$_3$ | H | H | C(O)CH$_2$SEt |
| 3,5-Cl$_2$ | CF$_3$ | H | H | C(O)CH$_2$S(O)Et |
| 3,5-Cl$_2$ | CF$_3$ | H | H | C(O)CH$_2$SO$_2$Et |
| 3,5-Cl$_2$ | CF$_3$ | H | H | C(O)CH$_2$SPr-n |
| 3,5-Cl$_2$ | CF$_3$ | H | H | C(O)CH$_2$S(O)Pr-n |
| 3,5-Cl$_2$ | CF$_3$ | H | H | C(O)CH$_2$SO$_2$Pr-n |
| 3,5-Cl$_2$ | CF$_3$ | H | H | C(O)CH$_2$SPr-i |
| 3,5-Cl$_2$ | CF$_3$ | H | H | C(O)CH$_2$S(O)Pr-i |
| 3,5-Cl$_2$ | CF$_3$ | H | H | C(O)CH$_2$SO$_2$Pr-i |
| 3,5-Cl$_2$ | CF$_3$ | H | H | C(O)CH$_2$SBu-n |
| 3,5-Cl$_2$ | CF$_3$ | H | H | C(O)CH$_2$SBu-i |
| 3,5-Cl$_2$ | CF$_3$ | H | H | C(O)CH$_2$SBu-s |
| 3,5-Cl$_2$ | CF$_3$ | H | H | C(O)CH$_2$SBu-t |
| 3,5-Cl$_2$ | CF$_3$ | H | H | C(O)CH$_2$S(O)Bu-t |
| 3,5-Cl$_2$ | CF$_3$ | H | H | C(O)CH$_2$SO$_2$Bu-t |
| 3,5-Cl$_2$ | CF$_3$ | H | H | C(O)CH$_2$SHex-n |
| 3,5-Cl$_2$ | CF$_3$ | H | H | C(O)CH$_2$SHex-c |
| 3,5-Cl$_2$ | CF$_3$ | H | H | C(O)CH$_2$SCH$_2$CF$_3$ |
| 3,5-Cl$_2$ | CF$_3$ | H | H | C(O)CH$_2$S(O)CH$_2$CF$_3$ |
| 3,5-Cl$_2$ | CF$_3$ | H | H | C(O)CH$_2$SO$_2$CH$_2$CF$_3$ |
| 3,5-Cl$_2$ | CF$_3$ | H | H | C(O)CH$_2$SCH$_2$CH$_2$OH |
| 3,5-Cl$_2$ | CF$_3$ | H | H | C(O)CH$_2$SCH$_2$CH$_2$OCH$_3$ |
| 3,5-Cl$_2$ | CF$_3$ | H | H | C(O)CH$_2$S(O)CH$_2$CH$_2$OCH$_3$ |
| 3,5-Cl$_2$ | CF$_3$ | H | H | C(O)CH$_2$SO$_2$CH$_2$CH$_2$OCH$_3$ |
| 3,5-Cl$_2$ | CF$_3$ | H | H | C(O)CH$_2$SCH$_2$CH$_2$OEt |
| 3,5-Cl$_2$ | CF$_3$ | H | H | C(O)CH$_2$S(O)CH$_2$CH$_2$OEt |
| 3,5-Cl$_2$ | CF$_3$ | H | H | C(O)CH$_2$SO$_2$CH$_2$CH$_2$OEt |
| 3,5-Cl$_2$ | CF$_3$ | H | H | C(O)CH$_2$SCH$_2$CH$_2$OCH$_2$CF$_3$ |
| 3,5-Cl$_2$ | CF$_3$ | H | H | C(O)CH$_2$S(O)CH$_2$CH$_2$OCH$_2$CF$_3$ |
| 3,5-Cl$_2$ | CF$_3$ | H | H | C(O)CH$_2$SO$_2$CH$_2$CH$_2$OCH$_2$CF$_3$ |
| 3,5-Cl$_2$ | CF$_3$ | H | H | C(O)CH$_2$SCH$_2$CH$_2$OC(O)CF$_3$ |
| 3,5-Cl$_2$ | CF$_3$ | H | H | C(O)CH$_2$SCH$_2$CH$_2$SCH$_3$ |

TABLE 2-continued

| | | | | |
|---|---|---|---|---|
| 3,5-Cl$_2$ | CF$_3$ | H | H | C(O)CH$_2$SCH$_2$CH$_2$SCH$_2$CF$_3$ |
| 3,5-Cl$_2$ | CF$_3$ | H | H | C(O)CH$_2$SCH$_2$Si(CH$_3$)$_3$ |
| 3,5-Cl$_2$ | CF$_3$ | H | H | C(O)CH$_2$SCH$_2$C(O)CH$_3$ |
| 3,5-Cl$_2$ | CF$_3$ | H | H | C(O)CH$_2$SCH$_2$CH$_2$C(O)OCH$_3$ |
| 3,5-Cl$_2$ | CF$_3$ | H | H | C(O)CH$_2$S(O)CH$_2$CH$_2$C(O)OCH$_3$ |
| 3,5-Cl$_2$ | CF$_3$ | H | H | C(O)CH$_2$SO$_2$CH$_2$CH$_2$C(O)OCH$_3$ |
| 3,5-Cl$_2$ | CF$_3$ | H | H | C(O)CH$_2$SCH$_2$C(O)N(Et)$_2$ |
| 3,5-Cl$_2$ | CF$_3$ | H | H | C(O)CH$_2$S(O)CH$_2$C(O)N(Et)$_2$ |
| 3,5-Cl$_2$ | CF$_3$ | H | H | C(O)CH$_2$SO$_2$CH$_2$C(O)N(Et)$_2$ |
| 3,5-Cl$_2$ | CF$_3$ | H | H | C(O)CH$_2$SCH$_2$C(O)NHCH$_2$CF$_3$ |
| 3,5-Cl$_2$ | CF$_3$ | H | H | C(O)CH$_2$S(O)CH$_2$C(O)NHCH$_2$CF$_3$ |
| 3,5-Cl$_2$ | CF$_3$ | H | H | C(O)CH$_2$SO$_2$CH$_2$C(O)NHCH$_2$CF$_3$ |
| 3,5-Cl$_2$ | CF$_3$ | H | H | C(O)CH$_2$SCH$_2$CH=CH$_2$ |
| 3,5-Cl$_2$ | CF$_3$ | H | H | C(O)CH$_2$SCH$_2$C≡CH |
| 3,5-Cl$_2$ | CF$_3$ | H | H | C(O)CH$_2$SCH$_2$Ph |
| 3,5-Cl$_2$ | CF$_3$ | H | H | C(O)CH$_2$S(O)CH$_2$Ph |
| 3,5-Cl$_2$ | CF$_3$ | H | H | C(O)CH$_2$SO$_2$CH$_2$Ph |
| 3,5-Cl$_2$ | CF$_3$ | H | H | C(O)CH$_2$SCH$_2$(Ph-2-F) |
| 3,5-Cl$_2$ | CF$_3$ | H | H | C(O)CH$_2$SCH$_2$(Ph-3-F) |
| 3,5-Cl$_2$ | CF$_3$ | H | H | C(O)CH$_2$SCH$_2$(Ph-4-F) |
| 3,5-Cl$_2$ | CF$_3$ | H | H | C(O)CH$_2$SC(O)CH$_3$ |
| 3,5-Cl$_2$ | CF$_3$ | H | H | C(O)CH$_2$SC(O)Ph |
| 3,5-Cl$_2$ | CF$_3$ | H | H | C(O)CH$_2$SC(O)N(CH$_3$)$_2$ |
| 3,5-Cl$_2$ | CF$_3$ | H | H | C(O)CH$_2$SC(O)NHEt |
| 3,5-Cl$_2$ | CF$_3$ | H | H | C(O)CH$_2$SC(O)N(Et)$_2$ |
| 3,5-Cl$_2$ | CF$_3$ | H | H | C(O)CH$_2$SC(O)NHCH$_2$CF$_3$ |
| 3,5-Cl$_2$ | CF$_3$ | H | H | C(O)CH$_2$SC(S)OCH$_3$ |
| 3,5-Cl$_2$ | CF$_3$ | H | H | C(O)CH$_2$SC(S)OEt |
| 3,5-Cl$_2$ | CF$_3$ | H | H | C(O)CH$_2$SC(S)(T-17) |
| 3,5-Cl$_2$ | CF$_3$ | H | H | C(O)CH$_2$SC(S)NHCH$_3$ |
| 3,5-Cl$_2$ | CF$_3$ | H | H | C(O)CH$_2$SC(S)N(CH$_3$)$_2$ |
| 3,5-Cl$_2$ | CF$_3$ | H | H | C(O)CH$_2$SC(S)NHEt |
| 3,5-Cl$_2$ | CF$_3$ | H | H | C(O)CH$_2$SC(S)NHCH$_2$CF$_3$ |
| 3,5-Cl$_2$ | CF$_3$ | H | H | C(O)CH$_2$SPh |
| 3,5-Cl$_2$ | CF$_3$ | H | H | C(O)CH$_2$S(O)Ph |
| 3,5-Cl$_2$ | CF$_3$ | H | H | C(O)CH$_2$SO$_2$Ph |
| 3,5-Cl$_2$ | CF$_3$ | H | H | C(O)CH$_2$S(D-21a) |
| 3,5-Cl$_2$ | CF$_3$ | H | H | C(O)CH$_2$SO$_2$(D-21a) |
| 3,5-Cl$_2$ | CF$_3$ | H | H | C(O)CH$_2$S(D-52a) |
| 3,5-Cl$_2$ | CF$_3$ | H | H | C(O)CH$_2$S(O)(D-52a) |
| 3,5-Cl$_2$ | CF$_3$ | H | H | C(O)CH$_2$SO$_2$(D-52a) |
| 3,5-Cl$_2$ | CF$_3$ | H | H | C(O)CH$_2$S(D-55a) |
| 3,5-Cl$_2$ | CF$_3$ | H | H | C(O)CH$_2$S(O)(D-55a) |
| 3,5-Cl$_2$ | CF$_3$ | H | H | C(O)CH$_2$SO$_2$(D-55a) |
| 3,5-Cl$_2$ | CF$_3$ | H | H | C(O)CH$_2$SSCH$_3$ |
| 3,5-Cl$_2$ | CF$_3$ | H | H | C(O)CH$_2$SS(Ph-2-NO$_2$) |
| 3,5-Cl$_2$ | CF$_3$ | H | H | C(O)CH$_2$SO$_2$NH$_2$ |
| 3,5-Cl$_2$ | CF$_3$ | H | H | C(O)CH$_2$SO$_2$NHCH$_3$ |
| 3,5-Cl$_2$ | CF$_3$ | H | H | C(O)CH$_2$SO$_2$N(CH$_3$)$_2$ |
| 3,5-Cl$_2$ | CF$_3$ | H | H | C(O)CH$_2$SO$_2$NHEt |
| 3,5-Cl$_2$ | CF$_3$ | H | H | C(O)CH$_2$SO$_2$N(Et)$_2$ |
| 3,5-Cl$_2$ | CF$_3$ | H | H | C(O)CH$_2$SO$_2$NHPr-n |
| 3,5-Cl$_2$ | CF$_3$ | H | H | C(O)CH$_2$SO$_2$NHPr-i |
| 3,5-Cl$_2$ | CF$_3$ | H | H | C(O)CH$_2$SO$_2$NHPr-c |
| 3,5-Cl$_2$ | CF$_3$ | H | H | C(O)CH$_2$SO$_2$NHBu-t |
| 3,5-Cl$_2$ | CF$_3$ | H | H | C(O)CH$_2$SO$_2$NHCH$_2$CF$_3$ |
| 3,5-Cl$_2$ | CF$_3$ | H | H | C(O)CH$_2$SO$_2$NHCH$_2$CH$_2$OCH$_3$ |
| 3,5-Cl$_2$ | CF$_3$ | H | H | C(O)CH$_2$SO$_2$NHCH$_2$CH$_2$SCH$_3$ |
| 3,5-Cl$_2$ | CF$_3$ | H | H | C(O)CH$_2$SO$_2$NHCH$_2$CH$_2$CH$_2$SCH$_3$ |
| 3,5-Cl$_2$ | CF$_3$ | H | H | C(O)CH$_2$SO$_2$NHCH$_2$CH=CH$_2$ |
| 3,5-Cl$_2$ | CF$_3$ | H | H | C(O)CH$_2$SO$_2$NHCH$_2$Ph |
| 3,5-Cl$_2$ | CF$_3$ | H | H | C(O)CH$_2$SO$_2$NHCH$_2$(D-52a) |
| 3,5-Cl$_2$ | CF$_3$ | H | H | C(O)CH$_2$SO$_2$NHCH$_2$(D-53a) |
| 3,5-Cl$_2$ | CF$_3$ | H | H | C(O)CH$_2$SO$_2$NHCH$_2$(D-54a) |
| 3,5-Cl$_2$ | CF$_3$ | H | H | C(O)CH$_2$SO$_2$NHPh |
| 3,5-Cl$_2$ | CF$_3$ | H | H | C(O)CH$_2$SO$_2$(T-17) |
| 3,5-Cl$_2$ | CF$_3$ | H | H | C(O)CH$_2$SO$_2$(T-20) |
| 3,5-Cl$_2$ | CF$_3$ | H | H | C(O)CH$_2$SO$_2$(T-21) |
| 3,5-Cl$_2$ | CF$_3$ | H | H | C(O)CH$_2$SO$_2$(T-22) |
| 3,5-Cl$_2$ | CF$_3$ | H | H | C(O)CH(CH$_3$)SCH$_3$ |
| 3,5-Cl$_2$ | CF$_3$ | H | H | C(O)OH(CH$_3$)SCH$_3$(R) |
| 3,5-Cl$_2$ | CF$_3$ | H | H | C(O)CH(CH$_3$)SCH$_3$(S) |
| 3,5-Cl$_2$ | CF$_3$ | H | H | C(O)CH(CH$_3$)S(O)CH$_3$ |
| 3,5-Cl$_2$ | CF$_3$ | H | H | C(O)CH(CH$_3$)SO$_2$CH$_3$ |
| 3,5-Cl$_2$ | CF$_3$ | H | H | C(O)C(CH$_3$)$_2$SCH$_3$ |
| 3,5-Cl$_2$ | CF$_3$ | H | H | C(O)C(CH$_3$)$_2$S(O)CH$_3$ |
| 3,5-Cl$_2$ | CF$_3$ | H | H | C(O)C(CH$_3$)$_2$SO$_2$CH$_3$ |
| 3,5-Cl$_2$ | CF$_3$ | H | H | C(O)CH$_2$CH$_2$SCH$_3$ |
| 3,5-Cl$_2$ | CF$_3$ | H | H | C(O)CH$_2$CH$_2$S(O)CH$_3$ |
| 3,5-Cl$_2$ | CF$_3$ | H | H | C(O)CH$_2$CH$_2$SO$_2$CH$_3$ |

TABLE 2-continued

| | | | | |
|---|---|---|---|---|
| 3,5-Cl$_2$ | CF$_3$ | H | H | C(O)CH$_2$CH$_2$SEt |
| 3,5-Cl$_2$ | CF$_3$ | H | H | C(O)CH$_2$CH$_2$SPr-n |
| 3,5-Cl$_2$ | CF$_3$ | H | H | C(O)CH$_2$CH$_2$SPr-i |
| 3,5-Cl$_2$ | CF$_3$ | H | H | C(O)CH$_2$CH$_2$SBu-t |
| 3,5-Cl$_2$ | CF$_3$ | H | H | C(O)CH$_2$CH$_2$SCH$_2$CF$_3$ |
| 3,5-Cl$_2$ | CF$_3$ | H | H | C(O)CH$_2$CH$_2$SPh |
| 3,5-Cl$_2$ | CF$_3$ | H | H | C(O)CH(CH$_3$)CH$_2$SCH$_3$ |
| 3,5-Cl$_2$ | CF$_3$ | H | H | C(O)CH(CH$_3$)CH$_2$S(O)CH$_3$ |
| 3,5-Cl$_2$ | CF$_3$ | H | H | C(O)CH(CH$_3$)CH$_2$SO$_2$CH$_3$ |
| 3,5-Cl$_2$ | CF$_3$ | H | H | C(O)C(CH$_3$)$_2$CH$_2$SCH$_3$ |
| 3,5-Cl$_2$ | CF$_3$ | H | H | C(O)C(CH$_3$)$_2$CH$_2$S(O)CH$_3$ |
| 3,5-Cl$_2$ | CF$_3$ | H | H | C(O)C(CH$_3$)$_2$CH$_2$SO$_2$CH$_3$ |
| 3,5-Cl$_2$ | CF$_3$ | H | H | C(O)CH$_2$CH$_2$CH$_2$SCH$_3$ |
| 3,5-Cl$_2$ | CF$_3$ | H | H | C(O)CH$_2$(E-6a) |
| 3,5-Cl$_2$ | CF$_3$ | H | H | C(O)CH$_2$(E-7a) |
| 3,5-Cl$_2$ | CF$_3$ | H | H | C(O)CH$_2$(E-7b) |
| 3,5-Cl$_2$ | CF$_3$ | H | H | C(O)CH$_2$(E-7c) |
| 3,5-Cl$_2$ | CF$_3$ | H | H | C(O)CH$_2$(E-18a) |
| 3,5-Cl$_2$ | CF$_3$ | H | H | C(O)CH$_2$(E-18b)CH$_3$ |
| 3,5-Cl$_2$ | CF$_3$ | H | H | C(O)CH$_2$(E-26a) |
| 3,5-Cl$_2$ | CF$_3$ | H | H | C(O)CH$_2$(E-27a) |
| 3,5-Cl$_2$ | CF$_3$ | H | H | C(O)CH$_2$(E-28a) |
| 3,5-Cl$_2$ | CF$_3$ | H | H | C(O)CH$_2$(E-43a) |
| 3,5-Cl$_2$ | CF$_3$ | H | H | C(O)(E-6a) |
| 3,5-Cl$_2$ | CF$_3$ | H | H | C(O)(E-7a) |
| 3,5-Cl$_2$ | CF$_3$ | H | H | C(O)(E-7b) |
| 3,5-Cl$_2$ | CF$_3$ | H | H | C(O)(E-7c) |
| 3,5-Cl$_2$ | CF$_3$ | H | H | C(O)(E-27a) |
| 3,5-Cl$_2$ | CF$_3$ | H | H | C(O)(E-28a) |
| 3,5-Cl$_2$ | CF$_3$ | H | H | C(O)CH$_2$N(CH$_3$)$_2$ |
| 3,5-Cl$_2$ | CF$_3$ | H | H | C(O)CH$_2$NHC(O)CH$_3$ |
| 3,5-Cl$_2$ | CF$_3$ | H | H | C(O)CH$_2$NHC(O)Et |
| 3,5-Cl$_2$ | CF$_3$ | H | H | C(O)CH$_2$NHC(O)Pr-n |
| 3,5-Cl$_2$ | CF$_3$ | H | H | C(O)CH$_2$NHC(O)Pr-i |
| 3,5-Cl$_2$ | CF$_3$ | H | H | C(O)CH$_2$NHC(O)Pr-c |
| 3,5-Cl$_2$ | CF$_3$ | H | H | C(O)CH$_2$NHC(O)Bu-n |
| 3,5-Cl$_2$ | CF$_3$ | H | H | C(O)CH$_2$NHC(O)Bu-i |
| 3,5-Cl$_2$ | CF$_3$ | H | H | C(O)CH$_2$NHC(O)Bu-s |
| 3,5-Cl$_2$ | CF$_3$ | H | H | C(O)CH$_2$NHC(O)Bu-t |
| 3,5-Cl$_2$ | CF$_3$ | H | H | C(O)CH$_2$NHC(O)CF$_3$ |
| 3,5-Cl$_2$ | CF$_3$ | H | H | C(O)CH$_2$N(CH$_3$)C(O)CF$_3$ |
| 3,5-Cl$_2$ | CF$_3$ | H | H | C(O)CH$_2$NHC(O)CF$_2$Cl |
| 3,5-Cl$_2$ | CF$_3$ | H | H | C(O)CH$_2$NHC(O)CH$_2$CHFBr |
| 3,5-Cl$_2$ | CF$_3$ | H | H | C(O)CH$_2$NHC(O)CH$_2$CF$_3$ |
| 3,5-Cl$_2$ | CF$_3$ | H | H | C(O)CH$_2$N(CH$_3$)C(O)CH$_2$CF$_3$ |
| 3,5-Cl$_2$ | CF$_3$ | H | H | C(O)CH$_2$NHC(O)CH$_2$CF$_2$CH$_3$ |
| 3,5-Cl$_2$ | CF$_3$ | H | H | C(O)CH$_2$NHC(O)CH$_2$CF$_2$CF$_2$Cl |
| 3,5-Cl$_2$ | CF$_3$ | H | H | C(O)CH$_2$NHC(O)CH$_2$CFClCF$_2$Cl |
| 3,5-Cl$_2$ | CF$_3$ | H | H | C(O)CH$_2$NHC(O)Ph |
| 3,5-Cl$_2$ | CF$_3$ | H | H | C(O)CH$_2$NHC(O)(D-17a)CH$_3$ |
| 3,5-Cl$_2$ | CF$_3$ | H | H | C(O)CH$_2$NHC(O)(D-17b)Cl |
| 3,5-Cl$_2$ | CF$_3$ | H | H | C(O)CH$_2$NHC(O)(D-21a) |
| 3,5-Cl$_2$ | CF$_3$ | H | H | C(O)CH$_2$NHC(O)(D-22a) |
| 3,5-Cl$_2$ | CF$_3$ | H | H | C(O)CH$_2$NHC(O)(D-23a) |
| 3,5-Cl$_2$ | CF$_3$ | H | H | C(O)CH$_2$NHC(O)(D-52a) |
| 3,5-Cl$_2$ | CF$_3$ | H | H | C(O)CH$_2$NHC(O)(D-53a) |
| 3,5-Cl$_2$ | CF$_3$ | H | H | C(O)CH$_2$NHC(O)(D-54a) |
| 3,5-Cl$_2$ | CF$_3$ | H | H | C(O)CH$_2$NHC(O)OCH$_3$ |
| 3,5-Cl$_2$ | CF$_3$ | H | H | C(O)CH$_2$NHC(O)OEt |
| 3,5-Cl$_2$ | CF$_3$ | H | H | C(O)CH$_2$NHC(O)OPr-n |
| 3,5-Cl$_2$ | CF$_3$ | H | H | C(O)CH$_2$NHC(O)OPr-i |
| 3,5-Cl$_2$ | CF$_3$ | H | H | C(O)CH$_2$NHC(O)OBu-t |
| 3,5-Cl$_2$ | CF$_3$ | H | H | C(O)CH$_2$NHC(O)OCH$_2$CF$_3$ |
| 3,5-Cl$_2$ | CF$_3$ | H | H | C(O)CH$_2$NHC(O)SCH$_3$ |
| 3,5-Cl$_2$ | CF$_3$ | H | H | C(O)CH$_2$NHC(O)N(CH$_3$)$_2$ |
| 3,5-Cl$_2$ | CF$_3$ | H | H | C(O)CH$_2$NHC(O)NHCH$_2$CF$_3$ |
| 3,5-Cl$_2$ | CF$_3$ | H | H | C(O)CH$_2$NHC(S)OCH$_3$ |
| 3,5-Cl$_2$ | CF$_3$ | H | H | C(O)CH$_2$NHC(S)SCH$_3$ |
| 3,5-Cl$_2$ | CF$_3$ | H | H | C(O)CH$_2$NHC(S)NHEt |
| 3,5-Cl$_2$ | CF$_3$ | H | H | C(O)CH$_2$NHC(S)NHCH$_2$CF$_3$ |
| 3,5-Cl$_2$ | CF$_3$ | H | H | C(O)CH$_2$NHSO$_2$CH$_3$ |
| 3,5-Cl$_2$ | CF$_3$ | H | H | C(O)CH$_2$N(CH$_3$)SO$_2$CH$_3$ |
| 3,5-Cl$_2$ | CF$_3$ | H | H | C(O)CH$_2$NHSO$_2$Et |
| 3,5-Cl$_2$ | CF$_3$ | H | H | C(O)CH$_2$NHSO$_2$CF$_3$ |
| 3,5-Cl$_2$ | CF$_3$ | H | H | C(O)CH$_2$N(CH$_3$)SO$_2$CF$_3$ |
| 3,5-Cl$_2$ | CF$_3$ | H | H | C(O)CH$_2$NHSO$_2$Ph |
| 3,5-Cl$_2$ | CF$_3$ | H | H | C(O)CH$_2$NHSO$_2$N(CH$_3$)$_2$ |
| 3,5-Cl$_2$ | CF$_3$ | H | H | C(O)CH$_2$NHP(S)(OCH$_3$)$_2$ |
| 3,5-Cl$_2$ | CF$_3$ | H | H | C(O)CH$_2$NHP(S)(OEt)$_2$ |
| 3,5-Cl$_2$ | CF$_3$ | H | H | C(O)CH$_2$(T-26) |

TABLE 2-continued

| | | | | |
|---|---|---|---|---|
| 3,5-Cl$_2$ | CF$_3$ | H | H | C(O)CH(CH$_3$)NHC(O)CH$_3$ |
| 3,5-Cl$_2$ | CF$_3$ | H | H | C(O)CH(CH$_3$)NHC(O)CF$_3$ |
| 3,5-Cl$_2$ | CF$_3$ | H | H | C(O)CH(CH$_3$)NHC(O)OCH$_3$ |
| 3,5-Cl$_2$ | CF$_3$ | H | H | C(O)CH(CH$_3$)NHC(O)OBu-t |
| 3,5-Cl$_2$ | CF$_3$ | H | H | C(O)CH(CH$_3$)NHC(O)OCH$_2$CF$_3$ |
| 3,5-Cl$_2$ | CF$_3$ | H | H | C(O)CH(CH$_3$)NHC(O)N(CH$_3$)$_2$ |
| 3,5-Cl$_2$ | CF$_3$ | H | H | C(O)CH(CH$_3$)NHC(O)NHCH$_2$CF$_3$ |
| 3,5-Cl$_2$ | CF$_3$ | H | H | C(O)CH(CH$_3$)NHC(O)Ph |
| 3,5-Cl$_2$ | CF$_3$ | H | H | C(O)CH(Et)NHC(O)CH$_3$ |
| 3,5-Cl$_2$ | CF$_3$ | H | H | C(O)CH(Et)NHC(O)OCH$_3$ |
| 3,5-Cl$_2$ | CF$_3$ | H | H | C(O)C(CH$_3$)$_2$NHC(O)CH$_3$ |
| 3,5-Cl$_2$ | CF$_3$ | H | H | C(O)C(CH$_3$)$_2$NHC(O)OCH$_3$ |
| 3,5-Cl$_2$ | CF$_3$ | H | H | C(O)CH$_2$CH$_2$NHC(O)CH$_3$ |
| 3,5-Cl$_2$ | CF$_3$ | H | H | C(O)CH$_2$CH$_2$N(CH$_3$)C(O)CH$_3$ |
| 3,5-Cl$_2$ | CF$_3$ | H | H | C(O)CH(CH$_3$)CH$_2$NHC(O)CH$_3$ |
| 3,5-Cl$_2$ | CF$_3$ | H | H | C(O)CH(CH$_3$)CH$_2$NHC(O)OCH$_3$ |
| 3,5-Cl$_2$ | CF$_3$ | H | H | C(O)C(CH$_3$)$_2$CH$_2$NHC(O)CH$_3$ |
| 3,5-Cl$_2$ | CF$_3$ | H | H | C(O)C(CH$_3$)$_2$CH$_2$NHC(O)OCH$_3$ |
| 3,5-Cl$_2$ | CF$_3$ | H | H | C(O)CH$_2$CH$_2$CH$_2$N(CH$_3$)$_2$ |
| 3,5-Cl$_2$ | CF$_3$ | H | H | C(O)CH$_2$CH$_2$CH$_2$NHC(O)CH$_3$ |
| 3,5-Cl$_2$ | CF$_3$ | H | H | C(O)CH$_2$CH$_2$CH$_2$NHC(O)OCH$_3$ |
| 3,5-Cl$_2$ | CF$_3$ | H | H | C(O)(E-8a)C(O)CH$_3$ |
| 3,5-Cl$_2$ | CF$_3$ | H | H | C(O)(E-8a)C(O)OCH$_3$ |
| 3,5-Cl$_2$ | CF$_3$ | H | H | C(O)(E-9a)C(O)CH$_3$ |
| 3,5-Cl$_2$ | CF$_3$ | H | H | C(O)(E-9a)C(O)OCH$_3$ |
| 3,5-Cl$_2$ | CF$_3$ | H | H | C(O)(E-30a)C(O)CH$_3$ |
| 3,5-Cl$_2$ | CF$_3$ | H | H | C(O)(E-30a)C(O)OCH$_3$ |
| 3,5-Cl$_2$ | CF$_3$ | H | H | C(O)(E-31a)C(O)CH$_3$ |
| 3,5-Cl$_2$ | CF$_3$ | H | H | C(O)(E-31a)C(O)OCH$_3$ |
| 3,5-Cl$_2$ | CF$_3$ | H | H | C(O)CH$_2$Si(CH$_3$)$_3$ |
| 3,5-Cl$_2$ | CF$_3$ | H | H | C(O)C(CH$_3$)$_2$CHO |
| 3,5-Cl$_2$ | CF$_3$ | H | H | C(O)CH$_2$C(O)CH$_3$ |
| 3,5-Cl$_2$ | CF$_3$ | H | H | C(O)CH=NOCH$_3$ |
| 3,5-Cl$_2$ | CF$_3$ | H | H | C(O)CH=NOCH$_2$CF$_3$ |
| 3,5-Cl$_2$ | CF$_3$ | H | H | C(O)C(CH$_3$)=NOCH$_3$ |
| 3,5-Cl$_2$ | CF$_3$ | H | H | C(O)C(CH$_3$)=NOCH$_2$CF$_3$ |
| 3,5-Cl$_2$ | CF$_3$ | H | H | C(O)CH$_2$CH=NOH |
| 3,5-Cl$_2$ | CF$_3$ | H | H | C(O)CH$_2$CH=NOCH$_3$ |
| 3,5-Cl$_2$ | CF$_3$ | H | H | C(O)CH$_2$CH=NOEt |
| 3,5-Cl$_2$ | CF$_3$ | H | H | C(O)CH$_2$CH=NOCH$_2$Pr-c |
| 3,5-Cl$_2$ | CF$_3$ | H | H | C(O)CH$_2$CH=NOCH$_2$CF$_3$ |
| 3,5-Cl$_2$ | CF$_3$ | H | H | C(O)CH$_2$CH=NOCH$_2$CN |
| 3,5-Cl$_2$ | CF$_3$ | H | H | C(O)CH$_2$CH=NOCH$_2$CH=CH$_2$ |
| 3,5-Cl$_2$ | CF$_3$ | H | H | C(O)CH$_2$CH=NOCH$_2$C≡CH |
| 3,5-Cl$_2$ | CF$_3$ | H | H | C(O)CH$_2$CH=NOCH$_2$Ph |
| 3,5-Cl$_2$ | CF$_3$ | H | H | C(O)CH$_2$C(CH$_3$)=NOH |
| 3,5-Cl$_2$ | CF$_3$ | H | H | C(O)CH$_2$C(CH$_3$)=NOCH$_3$ |
| 3,5-Cl$_2$ | CF$_3$ | H | H | C(O)CH$_2$CH$_2$CH=NOCH$_3$ |
| 3,5-Cl$_2$ | CF$_3$ | H | H | C(O)CH$_2$CN |
| 3,5-Cl$_2$ | CF$_3$ | H | H | C(O)CH(CH$_3$)CN |
| 3,5-Cl$_2$ | CF$_3$ | H | H | C(O)C(CH$_3$)$_2$CN |
| 3,5-Cl$_2$ | CF$_3$ | H | H | C(O)CH$_2$C(O)OCH$_3$ |
| 3,5-Cl$_2$ | CF$_3$ | H | H | C(O)CH$_2$C(O)OEt |
| 3,5-Cl$_2$ | CF$_3$ | H | H | C(O)CH$_2$C(O)OPr-i |
| 3,5-Cl$_2$ | CF$_3$ | H | H | C(O)CH$_2$C(O)OBu-t |
| 3,5-Cl$_2$ | CF$_3$ | H | H | C(O)CH$_2$C(O)OCH$_2$CF$_3$ |
| 3,5-Cl$_2$ | CF$_3$ | H | H | C(O)CH(CH$_3$)C(O)OCH$_3$ |
| 3,5-Cl$_2$ | CF$_3$ | H | H | C(O)CH(CH$_3$)C(O)OEt |
| 3,5-Cl$_2$ | CF$_3$ | H | H | C(O)CH$_2$CH$_2$C(O)OCH$_3$ |
| 3,5-Cl$_2$ | CF$_3$ | H | H | C(O)CH$_2$CH$_2$C(O)OEt |
| 3,5-Cl$_2$ | CF$_3$ | H | H | C(O)CH$_2$C(O)SCH$_3$ |
| 3,5-Cl$_2$ | CF$_3$ | H | H | C(O)CH$_2$C(O)NH$_2$ |
| 3,5-Cl$_2$ | CF$_3$ | H | H | C(O)CH$_2$C(O)NHCH$_3$ |
| 3,5-Cl$_2$ | CF$_3$ | H | H | C(O)CH$_2$C(O)N(CH$_3$)$_2$ |
| 3,5-Cl$_2$ | CF$_3$ | H | H | C(O)CH$_2$C(O)NHEt |
| 3,5-Cl$_2$ | CF$_3$ | H | H | C(O)CH(CH$_3$)C(O)NH$_2$ |
| 3,5-Cl$_2$ | CF$_3$ | H | H | C(O)CH(CH$_3$)C(O)NHCH$_3$ |
| 3,5-Cl$_2$ | CF$_3$ | H | H | C(O)CH(CH$_3$)C(O)NHEt |
| 3,5-Cl$_2$ | CF$_3$ | H | H | C(O)CH$_2$C(OCH$_3$)=NH |
| 3,5-Cl$_2$ | CF$_3$ | H | H | C(O)CH$_2$C(OEt)=NH |
| 3,5-Cl$_2$ | CF$_3$ | H | H | C(O)CH$_2$(M-11a) |
| 3,5-Cl$_2$ | CF$_3$ | H | H | C(O)CH$_2$[(M-11b)CF$_3$] |
| 3,5-Cl$_2$ | CF$_3$ | H | H | C(O)CH$_2$[(M-11c)CF$_3$] |
| 3,5-Cl$_2$ | CF$_3$ | H | H | C(O)CH$_2$(M-28a) |
| 3,5-Cl$_2$ | CF$_3$ | H | H | C(O)CH$_2$C(S)SCH$_3$ |
| 3,5-Cl$_2$ | CF$_3$ | H | H | C(O)CH$_2$C(S)NH$_2$ |
| 3,5-Cl$_2$ | CF$_3$ | H | H | C(O)CH(CH$_3$)C(S)NH$_2$ |
| 3,5-Cl$_2$ | CF$_3$ | H | H | C(O)CH$_2$C(SCH$_3$)=NH |
| 3,5-Cl$_2$ | CF$_3$ | H | H | C(O)CH$_2$(M-14a) |
| 3,5-Cl$_2$ | CF$_3$ | H | H | C(O)CH$_2$[(M-14b)CF$_3$] |

TABLE 2-continued

| | | | | |
|---|---|---|---|---|
| 3,5-Cl$_2$ | CF$_3$ | H | H | C(O)CH$_2$[(M-14c)CF$_3$] |
| 3,5-Cl$_2$ | CF$_3$ | H | H | C(O)CH$_2$(M-32a) |
| 3,5-Cl$_2$ | CF$_3$ | H | H | C(O)CH$_2$C(NH$_2$)=NH |
| 3,5-Cl$_2$ | CF$_3$ | H | H | C(O)CH$_2$[(M-17a)H] |
| 3,5-Cl$_2$ | CF$_3$ | H | H | C(O)CH$_2$[(M-36a)H] |
| 3,5-Cl$_2$ | CF$_3$ | H | H | C(O)CH$_2$C(NH$_2$)NOH |
| 3,5-Cl$_2$ | CF$_3$ | H | H | C(O)CH=CH$_2$ |
| 3,5-Cl$_2$ | CF$_3$ | H | H | C(O)CH=CHCH$_3$ |
| 3,5-Cl$_2$ | CF$_3$ | H | H | C(O)C(CH$_3$)=CH$_2$ |
| 3,5-Cl$_2$ | CF$_3$ | H | H | C(O)CH$_2$CH$_2$CH=CH$_2$ |
| 3,5-Cl$_2$ | CF$_3$ | H | H | C(O)CH$_2$CH=CHCH$_3$ |
| 3,5-Cl$_2$ | CF$_3$ | H | H | C(O)CH=CHEt |
| 3,5-Cl$_2$ | CF$_3$ | H | H | C(O)CH=C(CH$_3$)$_2$ |
| 3,5-Cl$_2$ | CF$_3$ | H | H | C(O)C(CH$_3$)=CHCH$_3$ |
| 3,5-Cl$_2$ | CF$_3$ | H | H | C(O)C(Et)=CH$_2$ |
| 3,5-Cl$_2$ | CF$_3$ | H | H | C(O)CH=CHPr-n |
| 3,5-Cl$_2$ | CF$_3$ | H | H | C(O)C(CH$_3$)=CHEt |
| 3,5-Cl$_2$ | CF$_3$ | H | H | C(O)C(Et)=CHCH$_3$ |
| 3,5-Cl$_2$ | CF$_3$ | H | H | C(O)CH=CHBu-n |
| 3,5-Cl$_2$ | CF$_3$ | H | H | C(O)CH$_2$(T-13) |
| 3,5-Cl$_2$ | CF$_3$ | H | H | C(O)(T-14) |
| 3,5-Cl$_2$ | CF$_3$ | H | H | C(O)(T-15) |
| 3,5-Cl$_2$ | CF$_3$ | H | H | C(O)C(CH$_3$)=CHCH(CH$_3$)CH$_2$CH=CH$_2$ |
| 3,5-Cl$_2$ | CF$_3$ | H | H | C(O)CH=C(CH$_3$)CH$_2$CH$_2$CH=C(CH$_3$)$_2$ |
| 3,5-Cl$_2$ | CF$_3$ | H | H | C(O)CF=CH$_2$ |
| 3,5-Cl$_2$ | CF$_3$ | H | H | C(O)CH=CHCl |
| 3,5-Cl$_2$ | CF$_3$ | H | H | C(O)CCl=CH$_2$ |
| 3,5-Cl$_2$ | CF$_3$ | H | H | C(O)CH=CHBr |
| 3,5-Cl$_2$ | CF$_3$ | H | H | C(O)CBr=CH$_2$ |
| 3,5-Cl$_2$ | CF$_3$ | H | H | C(O)CH=CCl$_2$ |
| 3,5-Cl$_2$ | CF$_3$ | H | H | C(O)CCl=CHCl |
| 3,5-Cl$_2$ | CF$_3$ | H | H | C(O)CBr=CHBr |
| 3,5-Cl$_2$ | CF$_3$ | H | H | C(O)CCl=CCl$_2$ |
| 3,5-Cl$_2$ | CF$_3$ | H | H | C(O)C(CH$_3$)=CHBr |
| 3,5-Cl$_2$ | CF$_3$ | H | H | C(O)CH=CClCH$_3$ |
| 3,5-Cl$_2$ | CF$_3$ | H | H | C(O)CH=CBrCH$_3$ |
| 3,5-Cl$_2$ | CF$_3$ | H | H | C(O)CH=CClCF$_3$ |
| 3,5-Cl$_2$ | CF$_3$ | H | H | C(O)(T-9) |
| 3,5-Cl$_2$ | CF$_3$ | H | H | C(O)C(OCH$_3$)=CH$_2$ |
| 3,5-Cl$_2$ | CF$_3$ | H | H | C(O)C(OCH$_2$OCH$_3$)=CH$_2$ |
| 3,5-Cl$_2$ | CF$_3$ | H | H | C(O)CBr=CHOCH$_3$ |
| 3,5-Cl$_2$ | CF$_3$ | H | H | C(O)C(CH$_3$)=CHOEt |
| 3,5-Cl$_2$ | CF$_3$ | H | H | C(O)C(CH$_3$)=CHPh |
| 3,5-Cl$_2$ | CF$_3$ | H | H | C(O)C≡CH |
| 3,5-Cl$_2$ | CF$_3$ | H | H | C(O)CH$_2$CH$_2$C≡CH |
| 3,5-Cl$_2$ | CF$_3$ | H | H | C(O)C≡CCl |
| 3,5-Cl$_2$ | CF$_3$ | H | H | C(O)C≡CBr |
| 3,5-Cl$_2$ | CF$_3$ | H | H | C(O)C≡Cl |
| 3,5-Cl$_2$ | CF$_3$ | H | H | C(O)C≡CPh |
| 3,5-Cl$_2$ | CF$_3$ | H | H | C(O)C≡C(1-Naph) |
| 3,5-Cl$_2$ | CF$_3$ | H | H | C(O)C≡C(D-3a) |
| 3,5-Cl$_2$ | CF$_3$ | H | H | C(O)C≡C(D-4a) |
| 3,5-Cl$_2$ | CF$_3$ | H | H | C(O)C≡C(D-52a) |
| 3,5-Cl$_2$ | CF$_3$ | H | H | C(O)C≡C(D-53a) |
| 3,5-Cl$_2$ | CF$_3$ | H | H | C(O)CH$_2$Ph |
| 3,5-Cl$_2$ | CF$_3$ | H | H | C(O)CH$_2$(Ph-2-F) |
| 3,5-Cl$_2$ | CF$_3$ | H | H | C(O)CH$_2$(Ph-3-F) |
| 3,5-Cl$_2$ | CF$_3$ | H | H | C(O)CH$_2$(Ph-4-F) |
| 3,5-Cl$_2$ | CF$_3$ | H | H | C(O)CH$_2$(Ph-2-OCH$_3$) |
| 3,5-Cl$_2$ | CF$_3$ | H | H | C(O)CH$_2$(Ph-3-OCH$_3$) |
| 3,5-Cl$_2$ | CF$_3$ | H | H | C(O)CH$_2$(Ph-4-OCH$_3$) |
| 3,5-Cl$_2$ | CF$_3$ | H | H | C(O)CH$_2$(Ph-2-SCH$_3$) |
| 3,5-Cl$_2$ | CF$_3$ | H | H | C(O)CH$_2$(Ph-2-SO$_2$CH$_3$) |
| 3,5-Cl$_2$ | CF$_3$ | H | H | C(O)CH$_2$(Ph-4-SCH$_3$) |
| 3,5-Cl$_2$ | CF$_3$ | H | H | C(O)CH$_2$(Ph-4-SO$_2$CH$_3$) |
| 3,5-Cl$_2$ | CF$_3$ | H | H | C(O)CH$_2$(Ph-2-NO$_2$) |
| 3,5-Cl$_2$ | CF$_3$ | H | H | C(O)CH$_2$(Ph-3-NO$_2$) |
| 3,5-Cl$_2$ | CF$_3$ | H | H | C(O)CH$_2$(Ph-4-NO$_2$) |
| 3,5-Cl$_2$ | CF$_3$ | H | H | C(O)CH$_2$(Ph-2-CN) |
| 3,5-Cl$_2$ | CF$_3$ | H | H | C(O)CH$_2$(Ph-3-CN) |
| 3,5-Cl$_2$ | CF$_3$ | H | H | C(O)CH$_2$(Ph-4-CN) |
| 3,5-Cl$_2$ | CF$_3$ | H | H | C(O)CH(CH$_3$)Ph |
| 3,5-Cl$_2$ | CF$_3$ | H | H | C(O)CH(CH$_3$)Ph(R) |
| 3,5-Cl$_2$ | CF$_3$ | H | H | C(O)CH(CH$_3$)Ph(S) |
| 3,5-Cl$_2$ | CF$_3$ | H | H | C(O)CH(Et)Ph |
| 3,5-Cl$_2$ | CF$_3$ | H | H | C(O)CH(CF$_3$)Ph |
| 3,5-Cl$_2$ | CF$_3$ | H | H | C(O)CH(OCH$_3$)Ph |
| 3,5-Cl$_2$ | CF$_3$ | H | H | C(O)C(CH$_3$)$_2$Ph |
| 3,5-Cl$_2$ | CF$_3$ | H | H | C(O)CH$_2$(1-Naph) |
| 3,5-Cl$_2$ | CF$_3$ | H | H | C(O)CH$_2$(1-Naph) |

TABLE 2-continued

| | | | | |
|---|---|---|---|---|
| 3,5-Cl$_2$ | CF$_3$ | H | H | C(O)CH$_2$(D-1a) |
| 3,5-Cl$_2$ | CF$_3$ | H | H | C(O)CH$_2$(D-2a) |
| 3,5-Cl$_2$ | CF$_3$ | H | H | C(O)CH$_2$(D-3a) |
| 3,5-Cl$_2$ | CF$_3$ | H | H | C(O)CH$_2$(D-4a) |
| 3,5-Cl$_2$ | CF$_3$ | H | H | C(O)CH$_2$(D-14a) |
| 3,5-Cl$_2$ | CF$_3$ | H | H | C(O)CH$_2$(D-21a) |
| 3,5-Cl$_2$ | CF$_3$ | H | H | C(O)CH$_2$(D-22a) |
| 3,5-Cl$_2$ | CF$_3$ | H | H | C(O)CH$_2$(D-23a) |
| 3,5-Cl$_2$ | CF$_3$ | H | H | C(O)CH$_2$(D-24a) |
| 3,5-Cl$_2$ | CF$_3$ | H | H | C(O)CH$_2$(D-41a) |
| 3,5-Cl$_2$ | CF$_3$ | H | H | C(O)CH$_2$(D-52a) |
| 3,5-Cl$_2$ | CF$_3$ | H | H | C(O)CH$_2$(D-53a) |
| 3,5-Cl$_2$ | CF$_3$ | H | H | C(O)CH$_2$(D-54a) |
| 3,5-Cl$_2$ | CF$_3$ | H | H | C(O)C(O)CH$_3$ |
| 3,5-Cl$_2$ | CF$_3$ | H | H | C(O)C(O)OCH$_3$ |
| 3,5-Cl$_2$ | CF$_3$ | H | H | C(O)Ph |
| 3,5-Cl$_2$ | CF$_3$ | H | H | C(O)(Ph-2-F) |
| 3,5-Cl$_2$ | CF$_3$ | H | H | C(O)(Ph-3-F) |
| 3,5-Cl$_2$ | CF$_3$ | H | H | C(O)(Ph-4-F) |
| 3,5-Cl$_2$ | CF$_3$ | H | H | C(O)(Ph-2-Cl) |
| 3,5-Cl$_2$ | CF$_3$ | H | H | C(O)(Ph-3-Cl) |
| 3,5-Cl$_2$ | CF$_3$ | H | H | C(O)(Ph-4-Cl) |
| 3,5-Cl$_2$ | CF$_3$ | H | H | C(O)(Ph-2-Br) |
| 3,5-Cl$_2$ | CF$_3$ | H | H | C(O)(Ph-2-I) |
| 3,5-Cl$_2$ | CF$_3$ | H | H | C(O)(Ph-2-CH$_3$) |
| 3,5-Cl$_2$ | CF$_3$ | H | H | C(O)(Ph-2-CF$_3$) |
| 3,5-Cl$_2$ | CF$_3$ | H | H | C(O)(Ph-2-OCH$_3$) |
| 3,5-Cl$_2$ | CF$_3$ | H | H | C(O)(Ph-2-OCHF$_2$) |
| 3,5-Cl$_2$ | CF$_3$ | H | H | C(O)(Ph-2-SCH$_3$) |
| 3,5-Cl$_2$ | CF$_3$ | H | H | C(O)[Ph-2-S(O)CH$_3$] |
| 3,5-Cl$_2$ | CF$_3$ | H | H | C(O)(Ph-2-SO$_2$CH$_3$) |
| 3,5-Cl$_2$ | CF$_3$ | H | H | C(O)(Ph-2-NO$_2$) |
| 3,5-Cl$_2$ | CF$_3$ | H | H | C(O)(Ph-2-CN) |
| 3,5-Cl$_2$ | CF$_3$ | H | H | C(O)[Ph-2-C(O)NH$_2$] |
| 3,5-Cl$_2$ | CF$_3$ | H | H | C(O)[Ph-2-C(S)NH$_2$] |
| 3,5-Cl$_2$ | CF$_3$ | H | H | C(O)(Ph-2,3-F$_2$) |
| 3,5-Cl$_2$ | CF$_3$ | H | H | C(O)(Ph-2,4-F$_2$) |
| 3,5-Cl$_2$ | CF$_3$ | H | H | C(O)(Ph-2,5-F$_2$) |
| 3,5-Cl$_2$ | CF$_3$ | H | H | C(O)(Ph-2,6-F$_2$) |
| 3,5-Cl$_2$ | CF$_3$ | H | H | C(O)(Ph-3,4-F$_2$) |
| 3,5-Cl$_2$ | CF$_3$ | H | H | C(O)(Ph-3,5-F$_2$) |
| 3,5-Cl$_2$ | CF$_3$ | H | H | C(O)(Ph-2,4-Cl$_2$) |
| 3,5-Cl$_2$ | CF$_3$ | H | H | C(O)(Ph-2,6-Cl$_2$) |
| 3,5-Cl$_2$ | CF$_3$ | H | H | C(O)(1-Naph) |
| 3,5-Cl$_2$ | CF$_3$ | H | H | C(O)(2-Naph) |
| 3,5-Cl$_2$ | CF$_3$ | H | H | C(O)(D-1a) |
| 3,5-Cl$_2$ | CF$_3$ | H | H | C(O)(D-2a) |
| 3,5-Cl$_2$ | CF$_3$ | H | H | C(O)(D-3a) |
| 3,5-Cl$_2$ | CF$_3$ | H | H | C(O)(D-4a) |
| 3,5-Cl$_2$ | CF$_3$ | H | H | C(O)(D-8a) |
| 3,5-Cl$_2$ | CF$_3$ | H | H | C(O)(D-9a) |
| 3,5-Cl$_2$ | CF$_3$ | H | H | C(O)(D-10a) |
| 3,5-Cl$_2$ | CF$_3$ | H | H | C(O)(D-10b)CH$_3$ |
| 3,5-Cl$_2$ | CF$_3$ | H | H | C(O)(D-11b)CH$_3$ |
| 3,5-Cl$_2$ | CF$_3$ | H | H | C(O)(D-12a) |
| 3,5-Cl$_2$ | CF$_3$ | H | H | C(O)(D-13a) |
| 3,5-Cl$_2$ | CF$_3$ | H | H | C(O)(D-13b)CH$_3$ |
| 3,5-Cl$_2$ | CF$_3$ | H | H | C(O)(D-14a) |
| 3,5-Cl$_2$ | CF$_3$ | H | H | C(O)(D-15a)CH$_3$ |
| 3,5-Cl$_2$ | CF$_3$ | H | H | C(O)(D-16a)CH$_3$ |
| 3,5-Cl$_2$ | CF$_3$ | H | H | C(O)(D-17a)CH$_3$ |
| 3,5-Cl$_2$ | CF$_3$ | H | H | C(O)(D-17b)Cl |
| 3,5-Cl$_2$ | CF$_3$ | H | H | C(O)(D-18a) |
| 3,5-Cl$_2$ | CF$_3$ | H | H | C(O)(D-21a) |
| 3,5-Cl$_2$ | CF$_3$ | H | H | C(O)(D-22a) |
| 3,5-Cl$_2$ | CF$_3$ | H | H | C(O)(D-23a) |
| 3,5-Cl$_2$ | CF$_3$ | H | H | C(O)(D-24a) |
| 3,5-Cl$_2$ | CF$_3$ | H | H | C(O)(D-28a) |
| 3,5-Cl$_2$ | CF$_3$ | H | H | C(O)(D-29a) |
| 3,5-Cl$_2$ | CF$_3$ | H | H | C(O)(D-29b)CH$_3$ |
| 3,5-Cl$_2$ | CF$_3$ | H | H | C(O)(D-30b)CH$_3$ |
| 3,5-Cl$_2$ | CF$_3$ | H | H | C(O)(D-31b)CH$_3$ |
| 3,5-Cl$_2$ | CF$_3$ | H | H | C(O)(D-32a)CH$_3$ |
| 3,5-Cl$_2$ | CF$_3$ | H | H | C(O)(D-33a) |
| 3,5-Cl$_2$ | CF$_3$ | H | H | C(O)(D-34a) |
| 3,5-Cl$_2$ | CF$_3$ | H | H | C(O)(D-35a) |
| 3,5-Cl$_2$ | CF$_3$ | H | H | C(O)(D-36a) |
| 3,5-Cl$_2$ | CF$_3$ | H | H | C(O)(D-36b)CH$_3$ |
| 3,5-Cl$_2$ | CF$_3$ | H | H | C(O)(D-37a) |
| 3,5-Cl$_2$ | CF$_3$ | H | H | C(O)(D-38a) |

TABLE 2-continued

| | | | | |
|---|---|---|---|---|
| 3,5-Cl$_2$ | CF$_3$ | H | H | C(O)(D-41a) |
| 3,5-Cl$_2$ | CF$_3$ | H | H | C(O)(D-44a) |
| 3,5-Cl$_2$ | CF$_3$ | H | H | C(O)(D-52a) |
| 3,5-Cl$_2$ | CF$_3$ | H | H | C(O)(D-52b)F |
| 3,5-Cl$_2$ | CF$_3$ | H | H | C(O)(D-52b)Cl |
| 3,5-Cl$_2$ | CF$_3$ | H | H | C(O)(D-52b)Br |
| 3,5-Cl$_2$ | CF$_3$ | H | H | C(O)(D-52b)CH$_3$ |
| 3,5-Cl$_2$ | CF$_3$ | H | H | C(O)(D-52b)OCH$_3$ |
| 3,5-Cl$_2$ | CF$_3$ | H | H | C(O)(D-52b)SCH$_3$ |
| 3,5-Cl$_2$ | CF$_3$ | H | H | C(O)(D-52c)Cl |
| 3,5-Cl$_2$ | CF$_3$ | H | H | C(O)(D-52d)F |
| 3,5-Cl$_2$ | CF$_3$ | H | H | C(O)(D-52d)Cl |
| 3,5-Cl$_2$ | CF$_3$ | H | H | C(O)(D-52e)F |
| 3,5-Cl$_2$ | CF$_3$ | H | H | C(O)(D-52e)Cl |
| 3,5-Cl$_2$ | CF$_3$ | H | H | C(O)(D-53a) |
| 3,5-Cl$_2$ | CF$_3$ | H | H | C(O)(D-53b)F |
| 3,5-Cl$_2$ | CF$_3$ | H | H | C(O)(D-53b)Cl |
| 3,5-Cl$_2$ | CF$_3$ | H | H | C(O)(D-53b)Br |
| 3,5-Cl$_2$ | CF$_3$ | H | H | C(O)(D-53b)CH$_3$ |
| 3,5-Cl$_2$ | CF$_3$ | H | H | C(O)(D-53b)OCH$_3$ |
| 3,5-Cl$_2$ | CF$_3$ | H | H | C(O)(D-53b)SCH$_3$ |
| 3,5-Cl$_2$ | CF$_3$ | H | H | C(O)(D-53b)CN |
| 3,5-Cl$_2$ | CF$_3$ | H | H | C(O)(D-53c)Cl |
| 3,5-Cl$_2$ | CF$_3$ | H | H | C(O)(D-53c)CH$_3$ |
| 3,5-Cl$_2$ | CF$_3$ | H | H | C(O)(D-53c)CF$_3$ |
| 3,5-Cl$_2$ | CF$_3$ | H | H | C(O)(D-53c)CH$_2$OCH$_3$ |
| 3,5-Cl$_2$ | CF$_3$ | H | H | C(O)(D-53d)Cl |
| 3,5-Cl$_2$ | CF$_3$ | H | H | C(O)(D-53e)F |
| 3,5-Cl$_2$ | CF$_3$ | H | H | C(O)(D-53e)Cl |
| 3,5-Cl$_2$ | CF$_3$ | H | H | C(O)(D-54a) |
| 3,5-Cl$_2$ | CF$_3$ | H | H | C(O)(D-54b)Cl |
| 3,5-Cl$_2$ | CF$_3$ | H | H | C(O)(D-54c)Cl |
| 3,5-Cl$_2$ | CF$_3$ | H | H | C(O)(D-54c)OCH$_3$ |
| 3,5-Cl$_2$ | CF$_3$ | H | H | C(O)(D-54c)NO$_2$ |
| 3,5-Cl$_2$ | CF$_3$ | H | H | C(O)(D-54c)CN |
| 3,5-Cl$_2$ | CF$_3$ | H | H | C(O)(D-54e) |
| 3,5-Cl$_2$ | CF$_3$ | H | H | C(O)(D-55a) |
| 3,5-Cl$_2$ | CF$_3$ | H | H | C(O)(D-56a) |
| 3,5-Cl$_2$ | CF$_3$ | H | H | C(O)(D-57a) |
| 3,5-Cl$_2$ | CF$_3$ | H | H | C(O)(D-58a) |
| 3,5-Cl$_2$ | CF$_3$ | H | H | C(O)(D-59a) |
| 3,5-Cl$_2$ | CF$_3$ | H | H | C(O)(D-60a) |
| 3,5-Cl$_2$ | CF$_3$ | H | H | C(O)(D-61a) |
| 3,5-Cl$_2$ | CF$_3$ | H | H | C(O)(D-62a) |
| 3,5-Cl$_2$ | CF$_3$ | H | H | C(O)(D-63a) |
| 3,5-Cl$_2$ | CF$_3$ | H | H | C(O)OCH$_3$ |
| 3,5-Cl$_2$ | CF$_3$ | H | H | C(O)OEt |
| 3,5-Cl$_2$ | CF$_3$ | H | H | C(O)OPr-i |
| 3,5-Cl$_2$ | CF$_3$ | H | H | C(O)OBu-i |
| 3,5-Cl$_2$ | CF$_3$ | H | H | C(O)OCH$_2$CH$_2$Cl |
| 3,5-Cl$_2$ | CF$_3$ | H | H | C(O)OCH$_2$CH=CHCl |
| 3,5-Cl$_2$ | CF$_3$ | H | H | C(O)OCH$_2$Ph |
| 3,5-Cl$_2$ | CF$_3$ | H | H | C(O)OPh |
| 3,5-Cl$_2$ | CF$_3$ | H | H | C(O)NHCH$_3$ |
| 3,5-Cl$_2$ | CF$_3$ | H | H | C(O)N(CH$_3$)$_2$ |
| 3,5-Cl$_2$ | CF$_3$ | H | H | C(O)NHEt |
| 3,5-Cl$_2$ | CF$_3$ | H | H | C(O)N(Et)$_2$ |
| 3,5-Cl$_2$ | CF$_3$ | H | H | C(O)NHPr-n |
| 3,5-Cl$_2$ | CF$_3$ | H | H | C(O)NHPr-i |
| 3,5-Cl$_2$ | CF$_3$ | H | H | C(O)NHPr-c |
| 3,5-Cl$_2$ | CF$_3$ | H | H | C(O)NHBu-n |
| 3,5-Cl$_2$ | CF$_3$ | H | H | C(O)NHBu-i |
| 3,5-Cl$_2$ | CF$_3$ | H | H | C(O)NHBu-s |
| 3,5-Cl$_2$ | CF$_3$ | H | H | C(O)NHBu-c |
| 3,5-Cl$_2$ | CF$_3$ | H | H | C(O)NHBu-t |
| 3,5-Cl$_2$ | CF$_3$ | H | H | C(O)(T-16) |
| 3,5-Cl$_2$ | CF$_3$ | H | H | C(O)(T-17) |
| 3,5-Cl$_2$ | CF$_3$ | H | H | C(O)(T-20) |
| 3,5-Cl$_2$ | CF$_3$ | H | H | C(O)(T-23) |
| 3,5-Cl$_2$ | CF$_3$ | H | H | C(O)NHCH$_2$CH$_2$Cl |
| 3,5-Cl$_2$ | CF$_3$ | H | H | C(O)NHCH$_2$CF$_3$ |
| 3,5-Cl$_2$ | CF$_3$ | H | H | C(O)N(CH$_3$)CH$_2$CF$_3$ |
| 3,5-Cl$_2$ | CF$_3$ | H | H | C(O)(T-18) |
| 3,5-Cl$_2$ | CF$_3$ | H | H | C(O)(T-21) |
| 3,5-Cl$_2$ | CF$_3$ | H | H | C(O)(T-19) |
| 3,5-Cl$_2$ | CF$_3$ | H | H | C(O)(T-22) |
| 3,5-Cl$_2$ | CF$_3$ | H | H | C(O)(T-24) |
| 3,5-Cl$_2$ | CF$_3$ | H | H | C(O)(T-25) |
| 3,5-Cl$_2$ | CF$_3$ | H | H | C(O)(T-26) |
| 3,5-Cl$_2$ | CF$_3$ | H | H | C(O)(T-27) |

TABLE 2-continued

| | | | | |
|---|---|---|---|---|
| 3,5-Cl$_2$ | CF$_3$ | H | H | C(O)NHC(O)CH$_3$ |
| 3,5-Cl$_2$ | CF$_3$ | H | H | C(O)NHC(O)Ph |
| 3,5-Cl$_2$ | CF$_3$ | H | H | C(O)NHC(O)OCH$_3$ |
| 3,5-Cl$_2$ | CF$_3$ | H | H | C(O)NHC(O)OCH$_2$CF$_3$ |
| 3,5-Cl$_2$ | CF$_3$ | H | H | C(O)NHPh |
| 3,5-Cl$_2$ | CF$_3$ | H | H | C(O)N(CH$_3$)Ph |
| 3,5-Cl$_2$ | CF$_3$ | H | H | C(O)NH(Ph-2-F) |
| 3,5-Cl$_2$ | CF$_3$ | H | H | C(O)NH(Ph-4-F) |
| 3,5-Cl$_2$ | CF$_3$ | H | H | C(O)NH(Ph-2-Cl) |
| 3,5-Cl$_2$ | CF$_3$ | H | H | C(O)NH(Ph-3-Cl) |
| 3,5-Cl$_2$ | CF$_3$ | H | H | C(O)NH(Ph-4-Cl) |
| 3,5-Cl$_2$ | CF$_3$ | H | H | C(O)NH(Ph-2-OCH$_3$) |
| 3,5-Cl$_2$ | CF$_3$ | H | H | C(O)NH(Ph-2-OEt) |
| 3,5-Cl$_2$ | CF$_3$ | H | H | C(O)NH(Ph-4-CN) |
| 3,5-Cl$_2$ | CF$_3$ | H | H | C(O)NH(D-3a) |
| 3,5-Cl$_2$ | CF$_3$ | H | H | C(O)NH(D-4a) |
| 3,5-Cl$_2$ | CF$_3$ | H | H | C(O)NH(D-52a) |
| 3,5-Cl$_2$ | CF$_3$ | H | H | C(O)NH(D-54a) |
| 3,5-Cl$_2$ | CF$_3$ | H | H | C(O)NH(D-55a) |
| 3,5-Cl$_2$ | CF$_3$ | H | H | C(O)NH(D-56a) |
| 3,5-Cl$_2$ | CF$_3$ | H | H | C(O)NH(D-58a) |
| 3,5-Cl$_2$ | CF$_3$ | H | H | C(O)NH(D-59a) |
| 3,5-Cl$_2$ | CF$_3$ | H | H | C(S)Et |
| 3,5-Cl$_2$ | CF$_3$ | H | H | C(S)Pr-n |
| 3,5-Cl$_2$ | CF$_3$ | H | H | C(S)Pr-i |
| 3,5-Cl$_2$ | CF$_3$ | H | H | C(S)Pr-c |
| 3,5-Cl$_2$ | CF$_3$ | H | H | C(S)CH$_2$Pr-c |
| 3,5-Cl$_2$ | CF$_3$ | H | H | C(S)CH$_2$CF$_3$ |
| 3,5-Cl$_2$ | CF$_3$ | H | H | C(S)NHEt |
| 3,5-Cl$_2$ | CF$_3$ | H | H | C(S)NHPr-i |
| 3,5-Cl$_2$ | CF$_3$ | H | H | C(S)NHPr-c |
| 3,5-Cl$_2$ | CF$_3$ | H | H | C(S)NHCH$_2$CF$_3$ |
| 3,5-Cl$_2$ | CF$_3$ | H | H | SO$_2$CH$_3$ |
| 3,5-Cl$_2$ | CF$_3$ | H | H | SO$_2$Et |
| 3,5-Cl$_2$ | CF$_3$ | H | H | SO$_2$Pr-i |
| 3,5-Cl$_2$ | CF$_3$ | H | H | SO$_2$Ph |
| 3,5-Cl$_2$ | CF$_3$ | CH$_3$ | H | H |
| 3,5-Cl$_2$ | CF$_3$ | CH$_3$(R) | H | H |
| 3,5-Cl$_2$ | CF$_3$ | CH$_3$(S) | H | H |
| 3,5-Cl$_2$ | CF$_3$ | CH$_3$ | H | C(O)Et |
| 3,5-Cl$_2$ | CF$_3$ | CH$_3$ | H | C(O)Pr-n |
| 3,5-Cl$_2$ | CF$_3$ | CH$_3$(R) | H | C(O)Pr-i |
| 3,5-Cl$_2$ | CF$_3$ | CH$_3$(S) | H | C(O)Pr-i |
| 3,5-Cl$_2$ | CF$_3$ | CH$_3$ | H | C(O)Pr-i |
| 3,5-Cl$_2$ | CF$_3$ | CH$_3$ | H | C(O)Pr-c |
| 3,5-Cl$_2$ | CF$_3$ | CH$_3$(R) | H | C(O)Pr-c |
| 3,5-Cl$_2$ | CF$_3$ | CH$_3$(S) | H | C(O)Pr-c |
| 3,5-Cl$_2$ | CF$_3$ | CH$_3$ | H | C(O)Bu-i |
| 3,5-Cl$_2$ | CF$_3$ | CH$_3$ | H | C(O)CH$_2$Pr-c |
| 3,5-Cl$_2$ | CF$_3$ | CH$_3$ | H | C(O)Bu-s |
| 3,5-Cl$_2$ | CF$_3$ | CH$_3$ | H | C(O)CF$_3$ |
| 3,5-Cl$_2$ | CF$_3$ | CH$_3$ | H | C(O)CH$_2$CH$_2$Cl |
| 3,5-Cl$_2$ | CF$_3$ | CH$_3$ | H | C(O)CH$_2$CF$_3$ |
| 3,5-Cl$_2$ | CF$_3$ | CH$_3$(R) | H | C(O)CH$_2$CF$_3$ |
| 3,5-Cl$_2$ | CF$_3$ | CH$_3$(S) | H | C(O)CH$_2$CF$_3$ |
| 3,5-Cl$_2$ | CF$_3$ | CH$_3$ | H | C(O)CF$_2$CHF$_2$ |
| 3,5-Cl$_2$ | CF$_3$ | CH$_3$ | H | C(O)CF$_2$CF$_3$ |
| 3,5-Cl$_2$ | CF$_3$ | CH$_3$ | H | C(O)CH$_2$CH$_2$OCH$_3$ |
| 3,5-Cl$_2$ | CF$_3$ | CH$_3$ | H | C(O)(E-5a) |
| 3,5-Cl$_2$ | CF$_3$ | CH$_3$ | H | C(O)CH$_2$CH$_2$SCH$_3$ |
| 3,5-Cl$_2$ | CF$_3$ | CH$_3$ | H | C(O)CH=C(CH$_3$)$_2$ |
| 3,5-Cl$_2$ | CF$_3$ | CH$_3$ | H | C(O)CH$_2$CH$_2$C≡CH |
| 3,5-Cl$_2$ | CF$_3$ | CH$_3$ | H | C(O)(Ph-2,4-F$_2$) |
| 3,5-Cl$_2$ | CF$_3$ | CH$_3$ | H | C(O)(Ph-3,5-F$_2$) |
| 3,5-Cl$_2$ | CF$_3$ | CH$_3$ | H | C(O)NHEt |
| 3,5-Cl$_2$ | CF$_3$ | CH$_3$ | H | C(O)NHPr-i |
| 3,5-Cl$_2$ | CF$_3$ | CH$_3$ | H | C(O)NHPr-c |
| 3,5-Cl$_2$ | CF$_3$ | CH$_3$ | H | C(O)NHCH$_2$CH$_2$Cl |
| 3,5-Cl$_2$ | CF$_3$ | CH$_3$ | H | C(O)NHCH$_2$CF$_3$ |
| 3,5-Cl$_2$ | CF$_3$ | CH$_3$ | H | C(O)NHOCH$_3$ |
| 3,5-Cl$_2$ | CF$_3$ | CH$_3$ | H | C(S)CH$_2$CF$_3$ |
| 3,5-Cl$_2$ | CF$_3$ | Et | H | C(O)Et |
| 3,5-Cl$_2$ | CF$_3$ | Et | H | C(O)Pr-n |
| 3,5-Cl$_2$ | CF$_3$ | Et | H | C(O)Pr-i |
| 3,5-Cl$_2$ | CF$_3$ | Et | H | C(O)Pr-c |
| 3,5-Cl$_2$ | CF$_3$ | Et | H | C(O)CH$_2$Pr-c |
| 3,5-Cl$_2$ | CF$_3$ | Et | H | C(O)CH$_2$CH$_2$Cl |
| 3,5-Cl$_2$ | CF$_3$ | Et | H | C(O)CH$_2$CF$_3$ |
| 3,5-Cl$_2$ | CF$_3$ | n-Pr | H | C(O)Et |
| 3,5-Cl$_2$ | CF$_3$ | n-Pr | H | C(O)Pr-n |

TABLE 2-continued

| | | | | |
|---|---|---|---|---|
| 3,5-Cl₂ | CF₃ | n-Pr | H | C(O)Pr-i |
| 3,5-Cl₂ | CF₃ | n-Pr | H | C(O)Pr-c |
| 3,5-Cl₂ | CF₃ | n-Pr | H | C(O)CH₂Pr-c |
| 3,5-Cl₂ | CF₃ | n-Pr | H | C(O)CH₂CH₂Cl |
| 3,5-Cl₂ | CF₃ | n-Pr | H | C(O)CH₂CF₃ |
| 3,5-Cl₂ | CF₃ | i-Pr | H | C(O)Et |
| 3,5-Cl₂ | CF₃ | i-Pr | H | C(O)Pr-n |
| 3,5-Cl₂ | CF₃ | i-Pr | H | C(O)Pr-i |
| 3,5-Cl₂ | CF₃ | i-Pr | H | C(O)Pr-c |
| 3,5-Cl₂ | CF₃ | i-Pr | H | C(O)CH₂Pr-c |
| 3,5-Cl₂ | CF₃ | i-Pr | H | C(O)CH₂CH₂Cl |
| 3,5-Cl₂ | CF₃ | i-Pr | H | C(O)CH₂CF₃ |
| 3,5-Cl₂ | CF₃ | c-Pr | H | C(O)Et |
| 3,5-Cl₂ | CF₃ | c-Pr | H | C(O)Pr-n |
| 3,5-Cl₂ | CF₃ | c-Pr | H | C(O)Pr-i |
| 3,5-Cl₂ | CF₃ | c-Pr | H | C(O)Pr-c |
| 3,5-Cl₂ | CF₃ | c-Pr | H | C(O)CH₂Pr-c |
| 3,5-Cl₂ | CF₃ | c-Pr | H | C(O)CH₂CH₂Cl |
| 3,5-Cl₂ | CF₃ | c-Pr | H | C(O)CH₂CF₃ |
| 3,5-Cl₂ | CF₃ | CF₃ | H | C(O)Et |
| 3,5-Cl₂ | CF₃ | CF₃ | H | C(O)Pr-n |
| 3,5-Cl₂ | CF₃ | CF₃ | H | C(O)Pr-i |
| 3,5-Cl₂ | CF₃ | CF₃ | H | C(O)Pr-c |
| 3,5-Cl₂ | CF₃ | CF₃ | H | C(O)Bu-i |
| 3,5-Cl₂ | CF₃ | CF₃ | H | C(O)CH₂Pr-c |
| 3,5-Cl₂ | CF₃ | CF₃ | H | C(O)Bu-s |
| 3,5-Cl₂ | CF₃ | CF₃ | H | C(O)CF₃ |
| 3,5-Cl₂ | CF₃ | CF₃ | H | C(O)CH₂CH₂Cl |
| 3,5-Cl₂ | CF₃ | CF₃ | H | C(O)CH₂CF₃ |
| 3,5-Cl₂ | CF₃ | CF₃ | H | C(O)CF₂CHF₂ |
| 3,5-Cl₂ | CF₃ | CF₃ | H | C(O)CF₂CF₃ |
| 3,5-Cl₂ | CF₃ | CF₃ | H | C(O)CH₂CH₂OCH₃ |
| 3,5-Cl₂ | CF₃ | CF₃ | H | C(O)(E-5a) |
| 3,5-Cl₂ | CF₃ | CF₃ | H | C(O)CH₂CH₂SCH₃ |
| 3,5-Cl₂ | CF₃ | CF₃ | H | C(O)CH=C(CH₃)₂ |
| 3,5-Cl₂ | CF₃ | CF₃ | H | C(O)CH₂CH₂C≡CH |
| 3,5-Cl₂ | CF₃ | CF₃ | H | C(O)(Ph-2,4-F₂) |
| 3,5-Cl₂ | CF₃ | CF₃ | H | C(O)(Ph-3,5-F₂) |
| 3,5-Cl₂ | CF₃ | CF₃ | H | C(O)NHEt |
| 3,5-Cl₂ | CF₃ | CF₃ | H | C(O)NHPr-i |
| 3,5-Cl₂ | CF₃ | CF₃ | H | C(O)NHPr-c |
| 3,5-Cl₂ | CF₃ | CF₃ | H | C(O)NHCH₂CH₂Cl |
| 3,5-Cl₂ | CF₃ | CF₃ | H | C(O)NHCH₂CF₃ |
| 3,5-Cl₂ | CF₃ | CF₃ | H | C(O)NHOCH₃ |
| 3,5-Cl₂ | CF₃ | CF₃ | H | C(S)CH₂CF₃ |
| 3,5-Cl₂ | CF₃ | CN | H | H |
| 3,5-Cl₂ | CF₃ | CN(R) | H | H |
| 3,5-Cl₂ | CF₃ | CN(S) | H | H |
| 3,5-Cl₂ | CF₃ | CN | H | C(O)Et |
| 3,5-Cl₂ | CF₃ | CN | H | C(O)Pr-n |
| 3,5-Cl₂ | CF₃ | CN | H | C(O)Pr-i |
| 3,5-Cl₂ | CF₃ | CN(R) | H | C(O)Pr-i |
| 3,5-Cl₂ | CF₃ | CN(S) | H | C(O)Pr-i |
| 3,5-Cl₂ | CF₃ | CN | H | C(O)Pr-c |
| 3,5-Cl₂ | CF₃ | CN(R) | H | C(O)Pr-c |
| 3,5-Cl₂ | CF₃ | CN(S) | H | C(O)Pr-c |
| 3,5-Cl₂ | CF₃ | CN | H | C(O)Bu-i |
| 3,5-Cl₂ | CF₃ | CN | H | C(O)CH₂Pr-c |
| 3,5-Cl₂ | CF₃ | CN | H | C(O)Bu-s |
| 3,5-Cl₂ | CF₃ | CN | H | C(O)CF₃ |
| 3,5-Cl₂ | CF₃ | CN | H | C(O)CH₂CH₂Cl |
| 3,5-Cl₂ | CF₃ | CN | H | C(O)CH₂CF₃ |
| 3,5-Cl₂ | CF₃ | CN(R) | H | C(O)CH₂CF₃ |
| 3,5-Cl₂ | CF₃ | CN(S) | H | C(O)CH₂CF₃ |
| 3,5-Cl₂ | CF₃ | CN | H | C(O)CF₂CHF₂ |
| 3,5-Cl₂ | CF₃ | CN | H | C(O)CF₂CF₃ |
| 3,5-Cl₂ | CF₃ | CN | H | C(O)CH₂CH₂OCH₃ |
| 3,5-Cl₂ | CF₃ | CN | H | C(O)(E-5a) |
| 3,5-Cl₂ | CF₃ | CN | H | C(O)CH₂CH₂SCH₃ |
| 3,5-Cl₂ | CF₃ | CN | H | C(O)CH=C(CH₃)₂ |
| 3,5-Cl₂ | CF₃ | CN | H | C(O)CH₂CH₂C≡CH |
| 3,5-Cl₂ | CF₃ | CN | H | C(O)(Ph-2,4-F₂) |
| 3,5-Cl₂ | CF₃ | CN | H | C(O)(Ph-3,5-F₂) |
| 3,5-Cl₂ | CF₃ | CN | H | C(O)NHEt |
| 3,5-Cl₂ | CF₃ | CN | H | C(O)NHPr-i |
| 3,5-Cl₂ | CF₃ | CN | H | C(O)NHPr-c |
| 3,5-Cl₂ | CF₃ | CN | H | C(O)NHCH₂CH₂Cl |
| 3,5-Cl₂ | CF₃ | CN | H | C(O)NHCH₂CF₃ |
| 3,5-Cl₂ | CF₃ | CN | H | C(O)NHOCH₃ |
| 3,5-Cl₂ | CF₃ | CN | H | C(S)CH₂CF₃ |

TABLE 2-continued

| | | | | |
|---|---|---|---|---|
| 3,5-Cl$_2$ | CF$_3$ | C(O)OCH$_3$ | H | C(O)Et |
| 3,5-Cl$_2$ | CF$_3$ | C(O)OCH$_3$ | H | C(O)Pr-n |
| 3,5-Cl$_2$ | CF$_3$ | C(O)OCH$_3$ | H | C(O)Pr-i |
| 3,5-Cl$_2$ | CF$_3$ | C(O)OCH$_3$ | H | C(O)Pr-c |
| 3,5-Cl$_2$ | CF$_3$ | C(O)OCH$_3$ | H | C(O)CH$_2$Pr-c |
| 3,5-Cl$_2$ | CF$_3$ | C(O)OCH$_3$ | H | C(O)CF$_3$ |
| 3,5-Cl$_2$ | CF$_3$ | C(O)OCH$_3$ | H | C(O)CH$_2$CH$_2$Cl |
| 3,5-Cl$_2$ | CF$_3$ | C(O)OCH$_3$ | H | C(O)CH$_2$CF$_3$ |
| 3,5-Cl$_2$ | CF$_3$ | C(O)OCH$_3$ | H | C(O)CF$_2$CHF$_2$ |
| 3,5-Cl$_2$ | CF$_3$ | C(O)OCH$_3$ | H | C(O)CF$_2$CF$_3$ |
| 3,5-Cl$_2$ | CF$_3$ | C(O)OCH$_3$ | H | C(O)CH$_2$CH$_2$SCH$_3$ |
| 3,5-Cl$_2$ | CF$_3$ | C(O)OCH$_3$ | H | C(O)(Ph-2,4-F$_2$) |
| 3,5-Cl$_2$ | CF$_3$ | C(O)OCH$_3$ | H | C(O)NHEt |
| 3,5-Cl$_2$ | CF$_3$ | C(O)OCH$_3$ | H | C(O)NHPr-i |
| 3,5-Cl$_2$ | CF$_3$ | C(O)OCH$_3$ | H | C(O)NHCH$_2$CF$_3$ |
| 3,5-Cl$_2$ | CF$_3$ | C(O)NH$_2$ | H | C(O)Et |
| 3,5-Cl$_2$ | CF$_3$ | C(O)NH$_2$ | H | C(O)Pr-n |
| 3,5-Cl$_2$ | CF$_3$ | C(O)NH$_2$ | H | C(O)Pr-i |
| 3,5-Cl$_2$ | CF$_3$ | C(O)NH$_2$ | H | C(O)Pr-c |
| 3,5-Cl$_2$ | CF$_3$ | C(O)NH$_2$ | H | C(O)CH$_2$Pr-c |
| 3,5-Cl$_2$ | CF$_3$ | C(O)NH$_2$ | H | C(O)CF$_3$ |
| 3,5-Cl$_2$ | CF$_3$ | C(O)NH$_2$ | H | C(O)CH$_2$CH$_2$Cl |
| 3,5-Cl$_2$ | CF$_3$ | C(O)NH$_2$ | H | C(O)CH$_2$CF$_3$ |
| 3,5-Cl$_2$ | CF$_3$ | C(O)NH$_2$ | H | C(O)CF$_2$CHF$_2$ |
| 3,5-Cl$_2$ | CF$_3$ | C(O)NH$_2$ | H | C(O)CF$_2$CF$_3$ |
| 3,5-Cl$_2$ | CF$_3$ | C(O)NH$_2$ | H | C(O)CH$_2$CH$_2$SCH$_3$ |
| 3,5-Cl$_2$ | CF$_3$ | C(O)NH$_2$ | H | C(O)(Ph-2,4-F$_2$) |
| 3,5-Cl$_2$ | CF$_3$ | C(O)NH$_2$ | H | C(O)NHEt |
| 3,5-Cl$_2$ | CF$_3$ | C(O)NH$_2$ | H | C(O)NHPr-i |
| 3,5-Cl$_2$ | CF$_3$ | C(O)NH$_2$ | H | C(O)NHCH$_2$CF$_3$ |
| 3,5-Cl$_2$ | CF$_3$ | C(S)NH$_2$ | H | C(O)Et |
| 3,5-Cl$_2$ | CF$_3$ | C(S)NH$_2$ | H | C(O)Pr-n |
| 3,5-Cl$_2$ | CF$_3$ | C(S)NH$_2$ | H | C(O)Pr-i |
| 3,5-Cl$_2$ | CF$_3$ | C(S)NH$_2$ | H | C(O)Pr-c |
| 3,5-Cl$_2$ | CF$_3$ | C(S)NH$_2$ | H | C(O)CH$_2$Pr-c |
| 3,5-Cl$_2$ | CF$_3$ | C(S)NH$_2$ | H | C(O)CF$_3$ |
| 3,5-Cl$_2$ | CF$_3$ | C(S)NH$_2$ | H | C(O)CH$_2$CH$_2$Cl |
| 3,5-Cl$_2$ | CF$_3$ | C(S)NH$_2$ | H | C(O)CH$_2$CF$_3$ |
| 3,5-Cl$_2$ | CF$_3$ | C(S)NH$_2$ | H | C(O)CF$_2$CHF$_2$ |
| 3,5-Cl$_2$ | CF$_3$ | C(S)NH$_2$ | H | C(O)CF$_2$CF$_3$ |
| 3,5-Cl$_2$ | CF$_3$ | C(S)NH$_2$ | H | C(O)CH$_2$CH$_2$SCH$_3$ |
| 3,5-Cl$_2$ | CF$_3$ | C(S)NH$_2$ | H | C(O)(Ph-2,4-F$_2$) |
| 3,5-Cl$_2$ | CF$_3$ | C(S)NH$_2$ | H | C(O)NHEt |
| 3,5-Cl$_2$ | CF$_3$ | C(S)NH$_2$ | H | C(O)NHPr-i |
| 3,5-Cl$_2$ | CF$_3$ | C(S)NH$_2$ | H | C(O)NHCH$_2$CF$_3$ |
| 3,5-Cl$_2$ | CF$_2$Cl | H | H | H |
| 3,5-Cl$_2$ | CF$_2$Cl | H | H | C(O)Et |
| 3,5-Cl$_2$ | CF$_2$Cl | H | H | C(O)Pr-n |
| 3,5-Cl$_2$ | CF$_2$Cl | H | H | C(O)Pr-i |
| 3,5-Cl$_2$ | CF$_2$Cl | H | Et | C(O)Pr-i |
| 3,5-Cl$_2$ | CF$_2$Cl | H | CH$_2$OCH$_3$ | C(O)Pr-i |
| 3,5-Cl$_2$ | CF$_2$Cl | H | CH$_2$OC(O)CH$_3$ | C(O)Pr-i |
| 3,5-Cl$_2$ | CF$_2$Cl | H | CH$_2$OC(O)OCH$_3$ | C(O)Pr-i |
| 3,5-Cl$_2$ | CF$_2$Cl | H | CH$_2$CN | C(O)Pr-i |
| 3,5-Cl$_2$ | CF$_2$Cl | H | CH$_2$C≡CH | C(O)Pr-i |
| 3,5-Cl$_2$ | CF$_2$Cl | H | C(O)CH$_3$ | C(O)Pr-i |
| 3,5-Cl$_2$ | CF$_2$Cl | H | C(O)OCH$_3$ | C(O)Pr-i |
| 3,5-Cl$_2$ | CF$_2$Cl | H | H | C(O)Pr-c |
| 3,5-Cl$_2$ | CF$_2$Cl | H | Et | C(O)Pr-c |
| 3,5-Cl$_2$ | CF$_2$Cl | H | CH$_2$OCH$_3$ | C(O)Pr-c |
| 3,5-Cl$_2$ | CF$_2$Cl | H | CH$_2$OC(O)CH$_3$ | C(O)Pr-c |
| 3,5-Cl$_2$ | CF$_2$Cl | H | CH$_2$OC(O)OCH$_3$ | C(O)Pr-c |
| 3,5-Cl$_2$ | CF$_2$Cl | H | CH$_2$CN | C(O)Pr-c |
| 3,5-Cl$_2$ | CF$_2$Cl | H | CH$_2$C≡CH | C(O)Pr-c |
| 3,5-Cl$_2$ | CF$_2$Cl | H | C(O)CH$_3$ | C(O)Pr-c |
| 3,5-Cl$_2$ | CF$_2$Cl | H | C(O)OCH$_3$ | C(O)Pr-c |
| 3,5-Cl$_2$ | CF$_2$Cl | H | H | C(O)Bu-i |
| 3,5-Cl$_2$ | CF$_2$Cl | H | H | C(O)CH$_2$Pr-c |
| 3,5-Cl$_2$ | CF$_2$Cl | H | H | C(O)Bu-s |
| 3,5-Cl$_2$ | CF$_2$Cl | H | H | C(O)CF$_3$ |
| 3,5-Cl$_2$ | CF$_2$Cl | H | H | C(O)CH$_2$CH$_2$Cl |
| 3,5-Cl$_2$ | CF$_2$Cl | H | H | C(O)CH$_2$CF$_3$ |
| 3,5-Cl$_2$ | CF$_2$Cl | H | Et | C(O)CH$_2$CF$_3$ |
| 3,5-Cl$_2$ | CF$_2$Cl | H | CH$_2$OCH$_3$ | C(O)CH$_2$CF$_3$ |
| 3,5-Cl$_2$ | CF$_2$Cl | H | CH$_2$OC(O)CH$_3$ | C(O)CH$_2$CF$_3$ |
| 3,5-Cl$_2$ | CF$_2$Cl | H | CH$_2$OC(O)OCH$_3$ | C(O)CH$_2$CF$_3$ |
| 3,5-Cl$_2$ | CF$_2$Cl | H | CH$_2$CN | C(O)CH$_2$CF$_3$ |
| 3,5-Cl$_2$ | CF$_2$Cl | H | CH$_2$C≡CH | C(O)CH$_2$CF$_3$ |
| 3,5-Cl$_2$ | CF$_2$Cl | H | C(O)CH$_3$ | C(O)CH$_2$CF$_3$ |
| 3,5-Cl$_2$ | CF$_2$Cl | H | C(O)OCH$_3$ | C(O)CH$_2$CF$_3$ |

TABLE 2-continued

| | | | | |
|---|---|---|---|---|
| 3,5-Cl$_2$ | CF$_2$Cl | H | H | C(O)CF$_2$CHF$_2$ |
| 3,5-Cl$_2$ | CF$_2$Cl | H | H | C(O)CF$_2$CF$_3$ |
| 3,5-Cl$_2$ | CF$_2$Cl | H | H | C(O)CH$_2$CH$_2$OCH$_3$ |
| 3,5-Cl$_2$ | CF$_2$Cl | H | H | C(O)(E-5a) |
| 3,5-Cl$_2$ | CF$_2$Cl | H | H | C(O)CH$_2$CH$_2$SCH$_3$ |
| 3,5-Cl$_2$ | CF$_2$Cl | H | H | C(O)CH=C(CH$_3$)$_2$ |
| 3,5-Cl$_2$ | CF$_2$Cl | H | H | C(O)CH$_2$CH$_2$C≡CH |
| 3,5-Cl$_2$ | CF$_2$Cl | H | H | C(O)(Ph-3-F) |
| 3,5-Cl$_2$ | CF$_2$Cl | H | H | C(O)(Ph-2,4-F$_2$) |
| 3,5-Cl$_2$ | CF$_2$Cl | H | H | C(O)(Ph-3,5-F$_2$) |
| 3,5-Cl$_2$ | CF$_2$Cl | H | H | C(O)NHEt |
| 3,5-Cl$_2$ | CF$_2$Cl | H | H | C(O)NHPr-i |
| 3,5-Cl$_2$ | CF$_2$Cl | H | H | C(O)NHPr-c |
| 3,5-Cl$_2$ | CF$_2$Cl | H | H | C(O)NHCH$_2$CF$_3$ |
| 3,5-Cl$_2$ | CF$_2$Cl | H | H | C(O)NHOCH$_3$ |
| 3,5-Cl$_2$ | CF$_2$Cl | H | H | C(S)CH$_2$CF$_3$ |
| 3,5-Cl$_2$ | CF$_2$Cl | CH$_3$ | H | H |
| 3,5-Cl$_2$ | CF$_2$Cl | CH$_3$ | H | C(O)Et |
| 3,5-Cl$_2$ | CF$_2$Cl | CH$_3$ | H | C(O)Pr-n |
| 3,5-Cl$_2$ | CF$_2$Cl | CH$_3$ | H | C(O)Pr-i |
| 3,5-Cl$_2$ | CF$_2$Cl | CH$_3$ | H | C(O)Pr-c |
| 3,5-Cl$_2$ | CF$_2$Cl | CH$_3$ | H | C(O)CH$_2$CF$_3$ |
| 3,5-Cl$_2$ | CF$_2$Cl | CH$_3$ | H | C(O)NHEt |
| 3,5-Cl$_2$ | CF$_2$Cl | CH$_3$ | H | C(O)NHPr-i |
| 3,5-Cl$_2$ | CF$_2$Cl | CH$_3$ | H | C(O)NHPr-c |
| 3,5-Cl$_2$ | CF$_2$Cl | CH$_3$ | H | C(O)NHCH$_2$CH$_2$Cl |
| 3,5-Cl$_2$ | CF$_2$Cl | CH$_3$ | H | C(O)NHCH$_2$CF$_3$ |
| 3,5-Cl$_2$ | CF$_2$Cl | CF$_3$ | H | C(O)Pr-i |
| 3,5-Cl$_2$ | CF$_2$Cl | CN | H | H |
| 3,5-Cl$_2$ | CF$_2$Cl | CN | H | C(O)Pr-i |
| 3,5-Cl$_2$ | CF$_2$Cl | CN | H | C(O)Pr-c |
| 3,5-Cl$_2$ | CF$_2$Cl | CN | H | C(O)CH$_2$CF$_3$ |
| 3,5-Cl$_2$ | CF$_2$Cl | CN | H | C(O)NHEt |
| 3,5-Cl$_2$ | CFCl$_2$ | H | H | C(O)Pr-i |
| 3,5-Cl$_2$ | CCl$_3$ | H | H | C(O)Pr-c |
| 3,5-Cl$_2$ | CF$_2$Br | H | H | C(O)Et |
| 3,5-Cl$_2$ | CF$_2$Br | H | H | C(O)Pr-n |
| 3,5-Cl$_2$ | CF$_2$Br | H | H | C(O)Pr-i |
| 3,5-Cl$_2$ | CF$_2$Br | H | H | C(O)Pr-c |
| 3,5-Cl$_2$ | CF$_2$Br | H | H | C(O)CH$_2$Pr-c |
| 3,5-Cl$_2$ | CF$_2$Br | H | H | C(O)CH$_2$CH$_2$Cl |
| 3,5-Cl$_2$ | CF$_2$Br | H | H | C(O)CH$_2$CF$_3$ |
| 3,5-Cl$_2$ | CF$_2$Br | CH$_3$ | H | C(O)Pr-i |
| 3,5-Cl$_2$ | CF$_2$Br | CH$_3$ | H | C(O)Pr-c |
| 3,5-Cl$_2$ | CF$_2$Br | CH$_3$ | H | C(O)CH$_2$CF$_3$ |
| 3,5-Cl$_2$ | CFClBr | H | H | C(O)CH$_2$CF$_3$ |
| 3,5-Cl$_2$ | CFBr$_2$ | CH$_3$ | H | C(O)Pr-c |
| 3,5-Cl$_2$ | CF$_2$I | CH$_3$ | H | C(O)CH$_2$CF$_3$ |
| 3,5-Cl$_2$ | CF$_2$CHF$_2$ | H | H | C(O)Et |
| 3,5-Cl$_2$ | CF$_2$CHF$_2$ | H | H | C(O)Pr-n |
| 3,5-Cl$_2$ | CF$_2$CHF$_2$ | H | H | C(O)Pr-i |
| 3,5-Cl$_2$ | CF$_2$CHF$_2$ | H | H | C(O)Pr-c |
| 3,5-Cl$_2$ | CF$_2$CHF$_2$ | H | H | C(O)CH$_2$Pr-c |
| 3,5-Cl$_2$ | CF$_2$CHF$_2$ | H | H | C(O)CH$_2$CH$_2$Cl |
| 3,5-Cl$_2$ | CF$_2$CHF$_2$ | H | H | C(O)CH$_2$CF$_3$ |
| 3,5-Cl$_2$ | CF$_2$CHF$_2$ | CH$_3$ | H | C(O)Pr-i |
| 3,5-Cl$_2$ | CF$_2$CHF$_2$ | CH$_3$ | H | C(O)Pr-c |
| 3,5-Cl$_2$ | CF$_2$CHF$_2$ | CH$_3$ | H | C(O)CH$_2$CF$_3$ |
| 3,5-Cl$_2$ | CF$_2$CF$_3$ | H | H | C(O)Pr-i |
| 3,5-Cl$_2$ | CF$_2$CF$_3$ | H | H | C(O)Pr-c |
| 3,5-Cl$_2$ | CF$_2$CF$_3$ | H | H | C(O)CH$_2$CF$_3$ |
| 3,5-Cl$_2$ | CF$_2$CF$_3$ | CH$_3$ | H | C(O)Pr-c |
| 3,5-Cl$_2$ | CF$_2$CF$_3$ | CH$_3$ | H | C(O)CH$_2$CF$_3$ |
| 3,5-Cl$_2$ | CF$_2$CF$_2$Cl | H | H | C(O)Pr-i |
| 3,5-Cl$_2$ | CFClCF$_3$ | H | H | C(O)Pr-c |
| 3,5-Cl$_2$ | CFClCF$_2$Cl | H | H | C(O)CH$_2$CF$_3$ |
| 3,5-Cl$_2$ | CF$_2$CF$_2$Br | CH$_3$ | H | C(O)Pr-c |
| 3,5-Cl$_2$ | CFBrCF$_3$ | CH$_3$ | H | C(O)CH$_2$CF$_3$ |
| 3,5-Cl$_2$ | CF$_2$CHFCF$_3$ | H | H | C(O)Pr-i |
| 3,5-Cl$_2$ | CF$_2$CF$_2$CF$_3$ | H | H | C(O)Pr-c |
| 3,5-Cl$_2$ | CF(CF$_3$)$_2$ | H | H | C(O)CH$_2$CF$_3$ |
| 3,5-Cl$_2$ | CF$_2$CFClCF$_2$Cl | CH$_3$ | H | C(O)Pr-c |
| 3,5-Cl$_2$ | CF$_2$CFBrCF$_2$Cl | CH$_3$ | H | C(O)CH$_2$CF$_3$ |
| 3,5-Cl$_2$ | CH$_2$OCH$_2$CF$_3$ | H | H | C(O)Pr-i |
| 3,5-Cl$_2$ | CH$_2$OCH(CF$_3$)$_2$ | H | H | C(O)Pr-c |
| 3,5-Cl$_2$ | CF$_2$OCH$_3$ | H | H | C(O)Pr-i |
| 3,5-Cl$_2$ | CF$_2$OCH$_3$ | H | H | C(O)Pr-c |
| 3,5-Cl$_2$ | CF$_2$OCH$_3$ | H | H | C(O)CH$_2$CF$_3$ |
| 3,5-Cl$_2$ | CF$_2$OCH$_3$ | CH$_3$ | H | C(O)Pr-c |
| 3,5-Cl$_2$ | CF$_2$OCH$_3$ | CH$_3$ | H | C(O)CH$_2$CF$_3$ |

TABLE 2-continued

| | | | | |
|---|---|---|---|---|
| 3,5-Cl$_2$ | CH$_2$SCF$_3$ | H | H | C(O)CH$_2$CF$_3$ |
| 3,5-Cl$_2$ | CH$_2$SCH$_2$CF$_3$ | CH$_3$ | H | C(O)Pr-c |
| 3,5-Cl$_2$ | CF$_2$SCH$_3$ | CH$_3$ | H | C(O)CH$_2$CF$_3$ |
| 3,5-Cl$_2$ | CF$_2$SEt | H | H | C(O)Pr-i |
| 3,5-Cl$_2$ | CF$_2$SPr-n | H | H | C(O)Pr-c |
| 3,5-Cl$_2$ | CF$_2$SPr-i | H | H | C(O)CH$_2$CF$_3$ |
| 3,5-Cl$_2$ | CF$_2$SCH$_2$Ph | CH$_3$ | H | C(O)Pr-c |
| 3,5-Cl$_2$ | CF$_2$SPh | CH$_3$ | H | C(O)CH$_2$CF$_3$ |
| 3,5-Cl$_2$ | CF$_2$CN | H | H | C(O)Pr-i |
| 3,5-Cl$_2$ | CF$_2$C(O)OCH$_3$ | H | H | C(O)Pr-c |
| 3,5-Cl$_2$ | CF$_2$C(O)OEt | H | H | C(O)CH$_2$CF$_3$ |
| 3,5-Cl$_2$ | CF$_2$C(O)NH$_2$ | CH$_3$ | H | C(O)Pr-c |
| 3,5-Cl$_2$ | CF$_2$SO$_2$N(CH$_3$)$_2$ | CH$_3$ | H | C(O)CH$_2$CF$_3$ |
| 3,5-Cl$_2$ | T-3 | H | H | C(O)Pr-i |
| 3,5-Cl$_2$ | T-3 | H | H | C(O)Pr-c |
| 3,5-Cl$_2$ | T-3 | H | H | C(O)CH$_2$CF$_3$ |
| 3,5-Cl$_2$ | T-3 | CH$_3$ | H | C(O)Pr-c |
| 3,5-Cl$_2$ | T-3 | CH$_3$ | H | C(O)CH$_2$CF$_3$ |
| 3,5-Cl$_2$ | T-4 | H | H | C(O)Pr-i |
| 3,5-Cl$_2$ | T-5 | H | H | C(O)Pr-c |
| 3,5-Cl$_2$ | CN | H | H | C(O)CH$_2$CF$_3$ |
| 3,5-Cl$_2$ | Ph | CH$_3$ | H | C(O)Pr-c |
| 3,5-Cl$_2$ | Ph-2-F | CH$_3$ | H | C(O)CH$_2$CF$_3$ |
| 3,5-Cl$_2$ | Ph-3-F | H | H | C(O)Pr-i |
| 3,5-Cl$_2$ | Ph-4-F | H | H | C(O)Pr-c |
| 3,5-Cl$_2$ | Ph-2-Cl | H | H | C(O)CH$_2$CF$_3$ |
| 3,5-Cl$_2$ | Ph-3-Cl | CH$_3$ | H | C(O)Pr-c |
| 3,5-Cl$_2$ | Ph-4-Cl | CH$_3$ | H | C(O)CH$_2$CF$_3$ |
| 3-Br-4-F | CHF$_2$ | H | H | C(O)Pr-i |
| 3-Br-4-F | CF$_3$ | H | H | H |
| 3-Br-4-F | CF$_3$ | H | H | C(O)Et |
| 3-Br-4-F | CF$_3$ | H | H | C(O)Pr-n |
| 3-Br-4-F | CF$_3$ | H | H | C(O)Pr-i |
| 3-Br-4-F | CF$_3$ | H | H | C(O)Pr-c |
| 3-Br-4-F | CF$_3$ | H | H | C(O)CH$_2$Pr-c |
| 3-Br-4-F | CF$_3$ | H | H | C(O)CF$_3$ |
| 3-Br-4-F | CF$_3$ | H | H | C(O)CH$_2$CH$_2$Cl |
| 3-Br-4-F | CF$_3$ | H | H | C(O)CH$_2$CF$_3$ |
| 3-Br-4-F | CF$_3$ | H | H | C(O)CF$_2$CHF$_2$ |
| 3-Br-4-F | CF$_3$ | H | H | C(O)CF$_2$CF$_3$ |
| 3-Br-4-F | CF$_3$ | H | H | C(O)CH$_2$CH$_2$SCH$_3$ |
| 3-Br-4-F | CF$_3$ | H | H | C(O)(Ph-2,4-F$_2$) |
| 3-Br-4-F | CF$_3$ | H | H | C(O)NHEt |
| 3-Br-4-F | CF$_3$ | H | H | C(O)NHPr-i |
| 3-Br-4-F | CF$_3$ | H | H | C(O)NHCH$_2$CF$_3$ |
| 3-Br-4-F | CF$_3$ | CH$_3$ | H | H |
| 3-Br-4-F | CF$_3$ | CH$_3$ | H | C(O)Et |
| 3-Br-4-F | CF$_3$ | CH$_3$ | H | C(O)Pr-n |
| 3-Br-4-F | CF$_3$ | CH$_3$ | H | C(O)Pr-i |
| 3-Br-4-F | CF$_3$ | CH$_3$ | H | C(O)Pr-c |
| 3-Br-4-F | CF$_3$ | CH$_3$ | H | C(O)CH$_2$CF$_3$ |
| 3-Br-4-F | CF$_3$ | CN | H | H |
| 3-Br-4-F | CF$_3$ | CN | H | C(O)Pr-c |
| 3-Br-4-F | CF$_3$ | CN | H | C(O)CH$_2$CF$_3$ |
| 3-Br-4-F | CF$_2$Cl | H | H | C(O)Et |
| 3-Br-4-F | CF$_2$Cl | H | H | C(O)Pr-n |
| 3-Br-4-F | CF$_2$Cl | H | H | C(O)Pr-i |
| 3-Br-4-F | CF$_2$Cl | H | H | C(O)Pr-c |
| 3-Br-4-F | CF$_2$Cl | H | H | C(O)CH$_2$Pr-c |
| 3-Br-4-F | CF$_2$Cl | H | H | C(O)CH$_2$CH$_2$Cl |
| 3-Br-4-F | CF$_2$Cl | H | H | C(O)CH$_2$CF$_3$ |
| 3-Br-4-F | CF$_2$Cl | CH$_3$ | H | C(O)Pr-i |
| 3-Br-4-F | CF$_2$Cl | CH$_3$ | H | C(O)Pr-c |
| 3-Br-4-F | CF$_2$Cl | CH$_3$ | H | C(O)CH$_2$CF$_3$ |
| 3-Br-4-F | CF$_2$Br | H | H | C(O)Pr-c |
| 3-Br-4-F | CH$_2$CHF$_2$ | H | H | C(O)CH$_2$CF$_3$ |
| 2-F-4-Br | CF$_3$ | CH$_3$ | H | C(O)Pr-c |
| 3-F-4-Br | CF$_3$ | CH$_3$ | H | C(O)CH$_2$CF$_3$ |
| 2-F-5-Br | CF$_3$ | H | H | C(O)Pr-i |
| 3-F-5-Br | CHF$_2$ | H | H | C(O)Pr-c |
| 3-F-5-Br | CF$_3$ | H | H | H |
| 3-F-5-Br | CF$_3$ | H | H | C(O)Et |
| 3-F-5-Br | CF$_3$ | H | H | C(O)Pr-n |
| 3-F-5-Br | CF$_3$ | H | H | C(O)Pr-i |
| 3-F-5-Br | CF$_3$ | H | H | C(O)Pr-c |
| 3-F-5-Br | CF$_3$ | H | H | C(O)CH$_2$Pr-c |
| 3-F-5-Br | CF$_3$ | H | H | C(O)CF$_3$ |
| 3-F-5-Br | CF$_3$ | H | H | C(O)CH$_2$CH$_2$Cl |
| 3-F-5-Br | CF$_3$ | H | H | C(O)CH$_2$CF$_3$ |
| 3-F-5-Br | CF$_3$ | H | H | C(O)CF$_2$CHF$_2$ |

TABLE 2-continued

| | | | | |
|---|---|---|---|---|
| 3-F-5-Br | $CF_3$ | H | H | $C(O)CF_2CF_3$ |
| 3-F-5-Br | $CF_3$ | H | H | $C(O)CH_2CH_2SCH_3$ |
| 3-F-5-Br | $CF_3$ | H | H | $C(O)(Ph-2,4-F_2)$ |
| 3-F-5-Br | $CF_3$ | H | H | $C(O)NHEt$ |
| 3-F-5-Br | $CF_3$ | H | H | $C(O)NHPr-i$ |
| 3-F-5-Br | $CF_3$ | H | H | $C(O)NHCH_2CF_3$ |
| 3-F-5-Br | $CF_3$ | $CH_3$ | H | H |
| 3-F-5-Br | $CF_3$ | $CH_3$ | H | $C(O)Et$ |
| 3-F-5-Br | $CF_3$ | $CH_3$ | H | $C(O)Pr-n$ |
| 3-F-5-Br | $CF_3$ | $CH_3$ | H | $C(O)Pr-i$ |
| 3-F-5-Br | $CF_3$ | $CH_3$ | H | $C(O)Pr-c$ |
| 3-F-5-Br | $CF_3$ | $CH_3$ | H | $C(O)CH_2CF_3$ |
| 3-F-5-Br | $CF_3$ | CN | H | H |
| 3-F-5-Br | $CF_3$ | CN | H | $C(O)Pr-c$ |
| 3-F-5-Br | $CF_3$ | CN | H | $C(O)CH_2CF_3$ |
| 3-F-5-Br | $CF_2Cl$ | H | H | $C(O)Et$ |
| 3-F-5-Br | $CF_2Cl$ | H | H | $C(O)Pr-n$ |
| 3-F-5-Br | $CF_2Cl$ | H | H | $C(O)Pr-i$ |
| 3-F-5-Br | $CF_2Cl$ | H | H | $C(O)Pr-c$ |
| 3-F-5-Br | $CF_2Cl$ | H | H | $C(O)CH_2Pr-c$ |
| 3-F-5-Br | $CF_2Cl$ | H | H | $C(O)CH_2CH_2Cl$ |
| 3-F-5-Br | $CF_2Cl$ | H | H | $C(O)CH_2CF_3$ |
| 3-F-5-Br | $CF_2Cl$ | $CH_3$ | H | $C(O)Pr-i$ |
| 3-F-5-Br | $CF_2Cl$ | $CH_3$ | H | $C(O)Pr-c$ |
| 3-F-5-Br | $CF_2Cl$ | $CH_3$ | H | $C(O)CH_2CF_3$ |
| 3-F-5-Br | $CF_2Br$ | H | H | $C(O)CH_2CF_3$ |
| 3-F-5-Br | $CF_2CHF_2$ | $CH_3$ | H | $C(O)Pr-c$ |
| 3-Cl-5-Br | $CHF_2$ | H | H | $C(O)Pr-i$ |
| 3-Cl-5-Br | $CHF_2$ | H | H | $C(O)Pr-c$ |
| 3-Cl-5-Br | $CHF_2$ | H | H | $C(O)CH_2CF_3$ |
| 3-Cl-5-Br | $CHF_2$ | $CH_3$ | H | $C(O)Pr-c$ |
| 3-Cl-5-Br | $CHF_2$ | $CH_3$ | H | $C(O)CH_2CF_3$ |
| 3-Cl-5-Br | $CHFCl$ | $CH_3$ | H | $C(O)CH_2CF_3$ |
| 3-Cl-5-Br | $CHCl_2$ | H | H | $C(O)Pr-i$ |
| 3-Cl-5-Br | $CHFBr$ | H | H | $C(O)Pr-c$ |
| 3-Cl-5-Br | $CF_3$ | H | H | H |
| 3-Cl-5-Br | $CF_3$ | H | H | $C(O)Et$ |
| 3-Cl-5-Br | $CF_3$ | H | H | $C(O)Pr-n$ |
| 3-Cl-5-Br | $CF_3$ | H | H | $C(O)Pr-i$ |
| 3-Cl-5-Br | $CF_3$ | H | Et | $C(O)Pr-i$ |
| 3-Cl-5-Br | $CF_3$ | H | $CH_2OCH_3$ | $C(O)Pr-i$ |
| 3-Cl-5-Br | $CF_3$ | H | $CH_2OC(O)CH_3$ | $C(O)Pr-i$ |
| 3-Cl-5-Br | $CF_3$ | H | $CH_2OC(O)OCH_3$ | $C(O)Pr-i$ |
| 3-Cl-5-Br | $CF_3$ | H | $CH_2CN$ | $C(O)Pr-i$ |
| 3-Cl-5-Br | $CF_3$ | H | $CH_2C\equiv CH$ | $C(O)Pr-i$ |
| 3-Cl-5-Br | $CF_3$ | H | $C(O)CH_3$ | $C(O)Pr-i$ |
| 3-Cl-5-Br | $CF_3$ | H | $C(O)OCH_3$ | $C(O)Pr-i$ |
| 3-Cl-5-Br | $CF_3$ | H | H | $C(O)Pr-c$ |
| 3-Cl-5-Br | $CF_3$ | H | Et | $C(O)Pr-c$ |
| 3-Cl-5-Br | $CF_3$ | H | $CH_2OCH_3$ | $C(O)Pr-c$ |
| 3-Cl-5-Br | $CF_3$ | H | $CH_2OC(O)CH_3$ | $C(O)Pr-c$ |
| 3-Cl-5-Br | $CF_3$ | H | $CH_2OC(O)OCH_3$ | $C(O)Pr-c$ |
| 3-Cl-5-Br | $CF_3$ | H | $CH_2CN$ | $C(O)Pr-c$ |
| 3-Cl-5-Br | $CF_3$ | H | $CH_2C\equiv CH$ | $C(O)Pr-c$ |
| 3-Cl-5-Br | $CF_3$ | H | $C(O)CH_3$ | $C(O)Pr-c$ |
| 3-Cl-5-Br | $CF_3$ | H | $C(O)OCH_3$ | $C(O)Pr-c$ |
| 3-Cl-5-Br | $CF_3$ | H | H | $C(O)Bu-i$ |
| 3-Cl-5-Br | $CF_3$ | H | H | $C(O)CH_2Pr-c$ |
| 3-Cl-5-Br | $CF_3$ | H | H | $C(O)Bu-s$ |
| 3-Cl-5-Br | $CF_3$ | H | H | $C(O)CF_3$ |
| 3-Cl-5-Br | $CF_3$ | H | H | $C(O)CH_2CH_2Cl$ |
| 3-Cl-5-Br | $CF_3$ | H | H | $C(O)CH_2CF_3$ |
| 3-Cl-5-Br | $CF_3$ | H | Et | $C(O)CH_2CF_3$ |
| 3-Cl-5-Br | $CF_3$ | H | $CH_2OCH_3$ | $C(O)CH_2CF_3$ |
| 3-Cl-5-Br | $CF_3$ | H | $CH_2OC(O)CH_3$ | $C(O)CH_2CF_3$ |
| 3-Cl-5-Br | $CF_3$ | H | $CH_2OC(O)OCH_3$ | $C(O)CH_2CF_3$ |
| 3-Cl-5-Br | $CF_3$ | H | $CH_2CN$ | $C(O)CH_2CF_3$ |
| 3-Cl-5-Br | $CF_3$ | H | $CH_2C\equiv CH$ | $C(O)CH_2CF_3$ |
| 3-Cl-5-Br | $CF_3$ | H | $C(O)CH_3$ | $C(O)CH_2CF_3$ |
| 3-Cl-5-Br | $CF_3$ | H | $C(O)OCH_3$ | $C(O)CH_2CF_3$ |
| 3-Cl-5-Br | $CF_3$ | H | H | $C(O)CF_2CHF_2$ |
| 3-Cl-5-Br | $CF_3$ | H | H | $C(O)CF_2CF_3$ |
| 3-Cl-5-Br | $CF_3$ | H | H | $C(O)CH_2CH_2OCH_3$ |
| 3-Cl-5-Br | $CF_3$ | H | H | $C(O)(E-5a)$ |
| 3-Cl-5-Br | $CF_3$ | H | H | $C(O)CH_2CH_2SCH_3$ |
| 3-Cl-5-Br | $CF_3$ | H | H | $C(O)CH=C(CH_3)_2$ |
| 3-Cl-5-Br | $CF_3$ | H | H | $C(O)CH_2CH_2C\equiv OH$ |
| 3-Cl-5-Br | $CF_3$ | H | H | $C(O)(Ph-3-F)$ |
| 3-Cl-5-Br | $CF_3$ | H | H | $C(O)(Ph-2,4-F_2)$ |
| 3-Cl-5-Br | $CF_3$ | H | H | $C(O)(Ph-3,5-F_2)$ |

TABLE 2-continued

| | | | | |
|---|---|---|---|---|
| 3-Cl-5-Br | CF$_3$ | H | H | C(O)NHEt |
| 3-Cl-5-Br | CF$_3$ | H | H | C(O)NHPr-i |
| 3-Cl-5-Br | CF$_3$ | H | H | C(O)NHPr-c |
| 3-Cl-5-Br | CF$_3$ | H | H | C(O)NHCH$_2$CF$_3$ |
| 3-Cl-5-Br | CF$_3$ | H | H | C(O)NHOCH$_3$ |
| 3-Cl-5-Br | CF$_3$ | H | H | C(S)CH$_2$CF$_3$ |
| 3-Cl-5-Br | CF$_3$ | CH$_3$ | H | H |
| 3-Cl-5-Br | CF$_3$ | CH$_3$ | H | C(O)Et |
| 3-Cl-5-Br | CF$_3$ | CH$_3$ | H | C(O)Pr-n |
| 3-Cl-5-Br | CF$_3$ | CH$_3$ | H | C(O)Pr-i |
| 3-Cl-5-Br | CF$_3$ | CH$_3$ | H | C(O)Pr-c |
| 3-Cl-5-Br | CF$_3$ | CH$_3$ | H | C(O)CH$_2$CF$_3$ |
| 3-Cl-5-Br | CF$_3$ | CH$_3$ | H | C(O)NHEt |
| 3-Cl-5-Br | CF$_3$ | CH$_3$ | H | C(O)NHPr-i |
| 3-Cl-5-Br | CF$_3$ | CH$_3$ | H | C(O)NHPr-c |
| 3-Cl-5-Br | CF$_3$ | CH$_3$ | H | C(O)NHCH$_2$CH$_2$Cl |
| 3-Cl-5-Br | CF$_3$ | CH$_3$ | H | C(O)NHCH$_2$CF$_3$ |
| 3-Cl-5-Br | CF$_3$ | CF$_3$ | H | C(O)Pr-i |
| 3-Cl-5-Br | CF$_3$ | CN | H | H |
| 3-Cl-5-Br | CF$_3$ | CN | H | C(O)Pr-i |
| 3-Cl-5-Br | CF$_3$ | CN | H | C(O)Pr-c |
| 3-Cl-5-Br | CF$_3$ | CN | H | C(O)CH$_2$CF$_3$ |
| 3-Cl-5-Br | CF$_3$ | CN | H | C(O)NHEt |
| 3-Cl-5-Br | CF$_2$Cl | H | H | H |
| 3-Cl-5-Br | CF$_2$Cl | H | H | C(O)Et |
| 3-Cl-5-Br | CF$_2$Cl | H | H | C(O)Pr-n |
| 3-Cl-5-Br | CF$_2$Cl | H | H | C(O)Pr-i |
| 3-Cl-5-Br | CF$_2$Cl | H | H | C(O)Pr-c |
| 3-Cl-5-Br | CF$_2$Cl | H | H | C(O)CH$_2$Pr-c |
| 3-Cl-5-Br | CF$_2$Cl | H | H | C(O)CF$_3$ |
| 3-Cl-5-Br | CF$_2$Cl | H | H | C(O)CH$_2$CH$_2$Cl |
| 3-Cl-5-Br | CF$_2$Cl | H | H | C(O)CH$_2$CF$_3$ |
| 3-Cl-5-Br | CF$_2$Cl | H | H | C(O)CF$_2$CHF$_2$ |
| 3-Cl-5-Br | CF$_2$Cl | H | H | C(O)CF$_2$CF$_3$ |
| 3-Cl-5-Br | CF$_2$Cl | H | H | C(O)CH$_2$CH$_2$SCH$_3$ |
| 3-Cl-5-Br | CF$_2$Cl | H | H | C(O)(Ph-2,4-F$_2$) |
| 3-Cl-5-Br | CF$_2$Cl | H | H | C(O)NHEt |
| 3-Cl-5-Br | CF$_2$Cl | H | H | C(O)NHPr-i |
| 3-Cl-5-Br | CF$_2$Cl | H | H | C(O)NHCH$_2$CF$_3$ |
| 3-Cl-5-Br | CF$_2$Cl | CH$_3$ | H | H |
| 3-Cl-5-Br | CF$_2$Cl | CH$_3$ | H | C(O)Et |
| 3-Cl-5-Br | CF$_2$Cl | CH$_3$ | H | C(O)Pr-n |
| 3-Cl-5-Br | CF$_2$Cl | CH$_3$ | H | C(O)Pr-i |
| 3-Cl-5-Br | CF$_2$Cl | CH$_3$ | H | C(O)Pr-c |
| 3-Cl-5-Br | CF$_2$Cl | CH$_3$ | H | C(O)CH$_2$CF$_3$ |
| 3-Cl-5-Br | CF$_2$Cl | CN | H | H |
| 3-Cl-5-Br | CF$_2$Cl | CN | H | C(O)Pr-c |
| 3-Cl-5-Br | CF$_2$Cl | CN | H | C(O)CH$_2$CF$_3$ |
| 3-Cl-5-Br | CF$_2$Br | H | H | C(O)Pr-i |
| 3-Cl-5-Br | CF$_2$Br | H | H | C(O)Pr-c |
| 3-Cl-5-Br | CF$_2$Br | H | H | C(O)CH$_2$CF$_3$ |
| 3-Cl-5-Br | CF$_2$Br | CH$_3$ | H | C(O)Pr-c |
| 3-Cl-5-Br | CF$_2$Br | CH$_3$ | H | C(O)CH$_2$CF$_3$ |
| 3-Cl-5-Br | CF$_2$CHF$_2$ | H | H | C(O)Pr-i |
| 3-Cl-5-Br | CF$_2$CHF$_2$ | H | H | C(O)Pr-c |
| 3-Cl-5-Br | CH$_2$CHF$_2$ | H | H | C(O)CH$_2$CF$_3$ |
| 3-Cl-5-Br | CF$_2$CHF$_2$ | CH$_3$ | H | C(O)Pr-c |
| 3-Cl-5-Br | CF$_2$CHF$_2$ | CH$_3$ | H | C(O)CH$_2$CF$_3$ |
| 3-Cl-5-Br | CF$_2$CF$_3$ | H | H | C(O)CH$_2$CF$_3$ |
| 3-Cl-5-Br | CF$_2$OCH$_3$ | CH$_3$ | H | C(O)Pr-c |
| 3-Cl-5-Br | CF$_2$SCH$_3$ | CH$_3$ | H | C(O)CH$_2$CF$_3$ |
| 3-Cl-5-Br | T-3 | H | H | C(O)Pr-i |
| 3,4-Br$_2$ | CHF$_2$ | H | H | C(O)Pr-c |
| 3,4-Br$_2$ | CF$_3$ | H | H | H |
| 3,4-Br$_2$ | CF$_3$ | H | H | C(O)Et |
| 3,4-Br$_2$ | CF$_3$ | H | H | C(O)Pr-n |
| 3,4-Br$_2$ | CF$_3$ | H | H | C(O)Pr-i |
| 3,4-Br$_2$ | CF$_3$ | H | H | C(O)Pr-c |
| 3,4-Br$_2$ | CF$_3$ | H | H | C(O)CH$_2$Pr-c |
| 3,4-Br$_2$ | CF$_3$ | H | H | C(O)CF$_3$ |
| 3,4-Br$_2$ | CF$_3$ | H | H | C(O)CH$_2$CH$_2$Cl |
| 3,4-Br$_2$ | CF$_3$ | H | H | C(O)CH$_2$CF$_3$ |
| 3,4-Br$_2$ | CF$_3$ | H | H | C(O)CF$_2$CHF$_2$ |
| 3,4-Br$_2$ | CF$_3$ | H | H | C(O)CF$_2$CF$_3$ |
| 3,4-Br$_2$ | CF$_3$ | H | H | C(O)CH$_2$CH$_2$SCH$_3$ |
| 3,4-Br$_2$ | CF$_3$ | H | H | C(O)(Ph-2,4-F$_2$) |
| 3,4-Br$_2$ | CF$_3$ | H | H | C(O)NHEt |
| 3,4-Br$_2$ | CF$_3$ | H | H | C(O)NHPr-i |
| 3,4-Br$_2$ | CF$_3$ | H | H | C(O)NHCH$_2$CF$_3$ |
| 3,4-Br$_2$ | CF$_3$ | CH$_3$ | H | H |

TABLE 2-continued

| | | | | |
|---|---|---|---|---|
| 3,4-Br₂ | CF₃ | CH₃ | H | C(O)Et |
| 3,4-Br₂ | CF₃ | CH₃ | H | C(O)Pr-n |
| 3,4-Br₂ | CF₃ | CH₃ | H | C(O)Pr-i |
| 3,4-Br₂ | CF₃ | CH₃ | H | C(O)Pr-c |
| 3,4-Br₂ | CF₃ | CH₃ | H | C(O)CH₂CF₃ |
| 3,4-Br₂ | CF₃ | CN | H | H |
| 3,4-Br₂ | CF₃ | CN | H | C(O)Pr-c |
| 3,4-Br₂ | CF₃ | CN | H | C(O)CH₂CF₃ |
| 3,4-Br₂ | CF₂Cl | H | H | C(O)Et |
| 3,4-Br₂ | CF₂Cl | H | H | C(O)Pr-n |
| 3,4-Br₂ | CF₂Cl | H | H | C(O)Pr-i |
| 3,4-Br₂ | CF₂Cl | H | H | C(O)Pr-c |
| 3,4-Br₂ | CF₂Cl | H | H | C(O)CH₂Pr-c |
| 3,4-Br₂ | CF₂Cl | H | H | C(O)CH₂CH₂Cl |
| 3,4-Br₂ | CF₂Cl | H | H | C(O)CH₂CF₃ |
| 3,4-Br₂ | CF₂Cl | CH₃ | H | C(O)Pr-i |
| 3,4-Br₂ | CF₂Cl | CH₃ | H | C(O)Pr-c |
| 3,4-Br₂ | CF₂Cl | CH₃ | H | C(O)CH₂CF₃ |
| 3,4-Br₂ | CF₂Br | H | H | C(O)CH₂CF₃ |
| 3,4-Br₂ | CF₂CHF₂ | CH₃ | H | C(O)Pr-c |
| 3,5-Br₂ | CHF₂ | H | H | C(O)Pr-i |
| 3,5-Br₂ | CHF₂ | H | H | C(O)Pr-c |
| 3,5-Br₂ | CHF₂ | H | H | C(O)CH₂CF₃ |
| 3,5-Br₂ | CHF₂ | CH₃ | H | C(O)Pr-c |
| 3,5-Br₂ | CHF₂ | CH₃ | H | C(O)CH₂CF₃ |
| 3,5-Br₂ | CHFCl | CH₃ | H | C(O)CH₂CF₃ |
| 3,5-Br₂ | CHCl₂ | H | H | C(O)Pr-i |
| 3,5-Br₂ | CHFBr | H | H | C(O)Pr-c |
| 3,5-Br₂ | CF₃ | H | H | H |
| 3,5-Br₂ | CF₃ | H | H | C(O)Et |
| 3,5-Br₂ | CF₃ | H | H | C(O)Pr-n |
| 3,5-Br₂ | CF₃ | H | H | C(O)Pr-i |
| 3,5-Br₂ | CF₃ | H | Et | C(O)Pr-i |
| 3,5-Br₂ | CF₃ | H | CH₂OCH₃ | C(O)Pr-i |
| 3,5-Br₂ | CF₃ | H | CH₂OC(O)CH₃ | C(O)Pr-i |
| 3,5-Br₂ | CF₃ | H | CH₂OC(O)OCH₃ | C(O)Pr-i |
| 3,5-Br₂ | CF₃ | H | CH₂CN | C(O)Pr-i |
| 3,5-Br₂ | CF₃ | H | CH₂C≡CH | C(O)Pr-i |
| 3,5-Br₂ | CF₃ | H | C(O)CH₃ | C(O)Pr-i |
| 3,5-Br₂ | CF₃ | H | C(O)OCH₃ | C(O)Pr-i |
| 3,5-Br₂ | CF₃ | H | H | C(O)Pr-c |
| 3,5-Br₂ | CF₃ | H | Et | C(O)Pr-c |
| 3,5-Br₂ | CF₃ | H | CH₂OCH₃ | C(O)Pr-c |
| 3,5-Br₂ | CF₃ | H | CH₂OC(O)CH₃ | C(O)Pr-c |
| 3,5-Br₂ | CF₃ | H | CH₂OC(O)OCH₃ | C(O)Pr-c |
| 3,5-Br₂ | CF₃ | H | CH₂CN | C(O)Pr-c |
| 3,5-Br₂ | CF₃ | H | CH₂C≡CH | C(O)Pr-c |
| 3,5-Br₂ | CF₃ | H | C(O)CH₃ | C(O)Pr-c |
| 3,5-Br₂ | CF₃ | H | C(O)OCH₃ | C(O)Pr-c |
| 3,5-Br₂ | CF₃ | H | H | C(O)Bu-i |
| 3,5-Br₂ | CF₃ | H | H | C(O)CH₂Pr-c |
| 3,5-Br₂ | CF₃ | H | H | C(O)Bu-s |
| 3,5-Br₂ | CF₃ | H | H | C(O)CF₃ |
| 3,5-Br₂ | CF₃ | H | H | C(O)CH₂CH₂Cl |
| 3,5-Br₂ | CF₃ | H | H | C(O)CH₂CF₃ |
| 3,5-Br₂ | CF₃ | H | Et | C(O)CH₂CF₃ |
| 3,5-Br₂ | CF₃ | H | CH₂OCH₃ | C(O)CH₂CF₃ |
| 3,5-Br₂ | CF₃ | H | CH₂OC(O)CH₃ | C(O)CH₂CF₃ |
| 3,5-Br₂ | CF₃ | H | CH₂OC(O)OCH₃ | C(O)CH₂CF₃ |
| 3,5-Br₂ | CF₃ | H | CH₂CN | C(O)CH₂CF₃ |
| 3,5-Br₂ | CF₃ | H | CH₂C≡CH | C(O)CH₂CF₃ |
| 3,5-Br₂ | CF₃ | H | C(O)CH₃ | C(O)CH₂CF₃ |
| 3,5-Br₂ | CF₃ | H | C(O)OCH₃ | C(O)CH₂CF₃ |
| 3,5-Br₂ | CF₃ | H | H | C(O)CF₂CHF₂ |
| 3,5-Br₂ | CF₃ | H | H | C(O)CF₂CF₃ |
| 3,5-Br₂ | CF₃ | H | H | C(O)CH₂CH₂OCH₃ |
| 3,5-Br₂ | CF₃ | H | H | C(O)(E-5a) |
| 3,5-Br₂ | CF₃ | H | H | C(O)CH₂CH₂SCH₃ |
| 3,5-Br₂ | CF₃ | H | H | C(O)CH═C(CH₃)₂ |
| 3,5-Br₂ | CF₃ | H | H | C(O)CH₂CH₂C≡CH |
| 3,5-Br₂ | CF₃ | H | H | C(O)(Ph-3-F) |
| 3,5-Br₂ | CF₃ | H | H | C(O)(Ph-2,4-F₂) |
| 3,5-Br₂ | CF₃ | H | H | C(O)(Ph-3,5-F₂) |
| 3,5-Br₂ | CF₃ | H | H | C(O)NHEt |
| 3,5-Br₂ | CF₃ | H | H | C(O)NHPr-i |
| 3,5-Br₂ | CF₃ | H | H | C(O)NHPr-c |
| 3,5-Br₂ | CF₃ | H | H | C(O)NHCH₂CF₃ |
| 3,5-Br₂ | CF₃ | H | H | C(O)NHOCH₃ |
| 3,5-Br₂ | CF₃ | H | H | C(S)CH₂CF₃ |
| 3,5-Br₂ | CF₃ | CH₃ | H | H |

TABLE 2-continued

| | | | | |
|---|---|---|---|---|
| 3,5-Br₂ | CF₃ | CH₃ | H | C(O)Et |
| 3,5-Br₂ | CF₃ | CH₃ | H | C(O)Pr-n |
| 3,5-Br₂ | CF₃ | CH₃ | H | C(O)Pr-i |
| 3,5-Br₂ | CF₃ | CH₃ | H | C(O)Pr-c |
| 3,5-Br₂ | CF₃ | CH₃ | H | C(O)CH₂CF₃ |
| 3,5-Br₂ | CF₃ | CH₃ | H | C(O)NHEt |
| 3,5-Br₂ | CF₃ | CH₃ | H | C(O)NHPr-i |
| 3,5-Br₂ | CF₃ | CH₃ | H | C(O)NHPr-c |
| 3,5-Br₂ | CF₃ | CH₃ | H | C(O)NHCH₂CH₂Cl |
| 3,5-Br₂ | CF₃ | CH₃ | H | C(O)NHCH₂CF₃ |
| 3,5-Br₂ | CF₃ | CF₃ | H | C(O)Pr-i |
| 3,5-Br₂ | CF₃ | CN | H | H |
| 3,5-Br₂ | CF₃ | CN | H | C(O)Pr-i |
| 3,5-Br₂ | CF₃ | CN | H | C(O)Pr-c |
| 3,5-Br₂ | CF₃ | CN | H | C(O)CH₂CF₃ |
| 3,5-Br₂ | CF₃ | CN | H | C(O)NHEt |
| 3,5-Br₂ | CF₂Cl | H | H | H |
| 3,5-Br₂ | CF₂Cl | H | H | C(O)Et |
| 3,5-Br₂ | CF₂Cl | H | H | C(O)Pr-n |
| 3,5-Br₂ | CF₂Cl | H | H | C(O)Pr-i |
| 3,5-Br₂ | CF₂Cl | H | H | C(O)Pr-c |
| 3,5-Br₂ | CF₂Cl | H | H | C(O)CH₂Pr-c |
| 3,5-Br₂ | CF₂Cl | H | H | C(O)CF₃ |
| 3,5-Br₂ | CF₂Cl | H | H | C(O)CH₂CH₂Cl |
| 3,5-Br₂ | CF₂Cl | H | H | C(O)CH₂CF₃ |
| 3,5-Br₂ | CF₂Cl | H | H | C(O)CF₂CHF₂ |
| 3,5-Br₂ | CF₂Cl | H | H | C(O)CF₂CF₃ |
| 3,5-Br₂ | CF₂Cl | H | H | C(O)CH₂CH₂SCH₃ |
| 3,5-Br₂ | CF₂Cl | H | H | C(O)(Ph-2,4-F₂) |
| 3,5-Br₂ | CF₂Cl | H | H | C(O)NHEt |
| 3,5-Br₂ | CF₂Cl | H | H | C(O)NHPr-i |
| 3,5-Br₂ | CF₂Cl | H | H | C(O)NHCH₂CF₃ |
| 3,5-Br₂ | CF₂Cl | CH₃ | H | H |
| 3,5-Br₂ | CF₂Cl | CH₃ | H | C(O)Et |
| 3,5-Br₂ | CF₂Cl | CH₃ | H | C(O)Pr-n |
| 3,5-Br₂ | CF₂Cl | CH₃ | H | C(O)Pr-i |
| 3,5-Br₂ | CF₂Cl | CH₃ | H | C(O)Pr-c |
| 3,5-Br₂ | CF₂Cl | CH₃ | H | C(O)CH₂CF₃ |
| 3,5-Br₂ | CF₂Cl | CN | H | H |
| 3,5-Br₂ | CF₂Cl | CN | H | C(O)Pr-c |
| 3,5-Br₂ | CF₂Cl | CN | H | C(O)CH₂CF₃ |
| 3,5-Br₂ | CF₂Br | H | H | C(O)Pr-i |
| 3,5-Br₂ | CF₂Br | H | H | C(O)Pr-c |
| 3,5-Br₂ | CF₂Br | H | H | C(O)CH₂CF₃ |
| 3,5-Br₂ | CF₂Br | CH₃ | H | C(O)Pr-c |
| 3,5-Br₂ | CF₂Br | CH₃ | H | C(O)CH₂CF₃ |
| 3,5-Br₂ | CF₂CHF₂ | H | H | C(O)Pr-i |
| 3,5-Br₂ | CF₂CHF₂ | H | H | C(O)Pr-c |
| 3,5-Br₂ | CF₂CHF₂ | H | H | C(O)CH₂CF₃ |
| 3,5-Br₂ | CF₂CHF₂ | CH₃ | H | C(O)Pr-c |
| 3,5-Br₂ | CF₂CHF₂ | CH₃ | H | C(O)CH₂CF₃ |
| 3,5-Br₂ | CF₂CF₃ | H | H | C(O)CH₂CF₃ |
| 3,5-Br₂ | CF₂OCH₃ | CH₃ | H | C(O)Pr-c |
| 3,5-Br₂ | CF₂SCH₃ | CH₃ | H | C(O)CH₂CF₃ |
| 3,5-Br₂ | T-3 | H | H | C(O)Pr-i |
| 3-F-5-I | CHF₂ | H | H | C(O)Pr-c |
| 3-F-5-I | CF₃ | H | H | H |
| 3-F-5-I | CF₃ | H | H | C(O)Et |
| 3-F-5-I | CF₃ | H | H | C(O)Pr-n |
| 3-F-5-I | CF₃ | H | H | C(O)Pr-i |
| 3-F-5-I | CF₃ | H | H | C(O)Pr-c |
| 3-F-5-I | CF₃ | H | H | C(O)CH₂Pr-c |
| 3-F-5-I | CF₃ | H | H | C(O)CF₃ |
| 3-F-5-I | CF₃ | H | H | C(O)CH₂CH₂Cl |
| 3-F-5-I | CF₃ | H | H | C(O)CH₂CF₃ |
| 3-F-5-I | CF₃ | H | H | C(O)CF₂CHF₂ |
| 3-F-5-I | CF₃ | H | H | C(O)CF₂CF₃ |
| 3-F-5-I | CF₃ | H | H | C(O)CH₂CH₂SCH₃ |
| 3-F-5-I | CF₃ | H | H | C(O)(Ph-2,4-F₂) |
| 3-F-5-I | CF₃ | H | H | C(O)NHEt |
| 3-F-5-I | CF₃ | H | H | C(O)NHPr-i |
| 3-F-5-I | CF₃ | H | H | C(O)NHCH₂CF₃ |
| 3-F-5-I | CF₃ | CH₃ | H | H |
| 3-F-5-I | CF₃ | CH₃ | H | C(O)Et |
| 3-F-5-I | CF₃ | CH₃ | H | C(O)Pr-n |
| 3-F-5-I | CF₃ | CH₃ | H | C(O)Pr-i |
| 3-F-5-I | CF₃ | CH₃ | H | C(O)Pr-c |
| 3-F-5-I | CF₃ | CH₃ | H | C(O)CH₂CF₃ |
| 3-F-5-I | CF₃ | CN | H | H |
| 3-F-5-I | CF₃ | CN | H | C(O)Pr-c |

TABLE 2-continued

| | | | | |
|---|---|---|---|---|
| 3-F-5-I | CF₃ | CN | H | C(O)CH₂CF₃ |
| 3-F-5-I | CF₂Cl | H | H | C(O)Et |
| 3-F-5-I | CF₂Cl | H | H | C(O)Pr-n |
| 3-F-5-I | CF₂Cl | H | H | C(O)Pr-i |
| 3-F-5-I | CF₂Cl | H | H | C(O)Pr-c |
| 3-F-5-I | CF₂Cl | H | H | C(O)CH₂Pr-c |
| 3-F-5-I | CF₂Cl | H | H | C(O)CH₂CH₂Cl |
| 3-F-5-I | CF₂Cl | H | H | C(O)CH₂CF₃ |
| 3-F-5-I | CF₂Cl | CH₃ | H | C(O)Pr-i |
| 3-F-5-I | CF₂Cl | CH₃ | H | C(O)Pr-c |
| 3-F-5-I | CF₂Cl | CH₃ | H | C(O)CH₂CF₃ |
| 3-F-5-I | CF₂Br | H | H | C(O)CH₂CF₃ |
| 3-F-5-I | CF₂CHF₂ | CH₃ | H | C(O)Pr-c |
| 3-Cl-5-I | CHF₂ | CH₃ | H | C(O)CH₂CF₃ |
| 3-Cl-5-I | CF₃ | H | H | H |
| 3-Cl-5-I | CF₃ | H | H | C(O)Et |
| 3-Cl-5-I | CF₃ | H | H | C(O)Pr-n |
| 3-Cl-5-I | CF₃ | H | H | C(O)Pr-i |
| 3-Cl-5-I | CF₃ | H | H | C(O)Pr-c |
| 3-Cl-5-I | CF₃ | H | H | C(O)CH₂Pr-c |
| 3-Cl-5-I | CF₃ | H | H | C(O)CF₃ |
| 3-Cl-5-I | CF₃ | H | H | C(O)CH₂CH₂Cl |
| 3-Cl-5-I | CF₃ | H | H | C(O)CH₂CF₃ |
| 3-Cl-5-I | CF₃ | H | H | C(O)CF₂CHF₂ |
| 3-Cl-5-I | CF₃ | H | H | C(O)CF₂CF₃ |
| 3-Cl-5-I | CF₃ | H | H | C(O)CH₂CH₂SCH₃ |
| 3-Cl-5-I | CF₃ | H | H | C(O)(Ph-2,4-F₂) |
| 3-Cl-5-I | CF₃ | H | H | C(O)NHEt |
| 3-Cl-5-I | CF₃ | H | H | C(O)NHPr-i |
| 3-Cl-5-I | CF₃ | H | H | C(O)NHCH₂CF₃ |
| 3-Cl-5-I | CF₃ | CH₃ | H | H |
| 3-Cl-5-I | CF₃ | CH₃ | H | C(O)Et |
| 3-Cl-5-I | CF₃ | CH₃ | H | C(O)Pr-n |
| 3-Cl-5-I | CF₃ | CH₃ | H | C(O)Pr-i |
| 3-Cl-5-I | CF₃ | CH₃ | H | C(O)Pr-c |
| 3-Cl-5-I | CF₃ | CH₃ | H | C(O)CH₂CF₃ |
| 3-Cl-5-I | CF₃ | CN | H | H |
| 3-Cl-5-I | CF₃ | CN | H | C(O)Pr-c |
| 3-Cl-5-I | CF₃ | CN | H | C(O)CH₂CF₃ |
| 3-Cl-5-I | CF₂Cl | H | H | C(O)Et |
| 3-Cl-5-I | CF₂Cl | H | H | C(O)Pr-n |
| 3-Cl-5-I | CF₂Cl | H | H | C(O)Pr-i |
| 3-Cl-5-I | CF₂Cl | H | H | C(O)Pr-c |
| 3-Cl-5-I | CF₂Cl | H | H | C(O)CH₂Pr-c |
| 3-Cl-5-I | CF₂Cl | H | H | C(O)CH₂CH₂Cl |
| 3-Cl-5-I | CF₂Cl | H | H | C(O)CH₂CF₃ |
| 3-Cl-5-I | CF₂Cl | CH₃ | H | C(O)Pr-i |
| 3-Cl-5-I | CF₂Cl | CH₃ | H | C(O)Pr-c |
| 3-Cl-5-I | CF₂Cl | CH₃ | H | C(O)CH₂CF₃ |
| 3-Cl-5-I | CF₂Br | H | H | C(O)Pr-i |
| 3-Cl-5-I | CH₂CHF₂ | H | H | C(O)Pr-c |
| 3,5-I₂ | CF₃ | H | H | C(O)Pr-i |
| 3,5-I₂ | CF₃ | H | H | C(O)Pr-c |
| 3,5-I₂ | CF₃ | H | H | C(O)CH₂CF₃ |
| 3,5-I₂ | CF₃ | CH₃ | H | C(O)Pr-c |
| 3,5-I₂ | CF₃ | CH₃ | H | C(O)CH₂CF₃ |
| 3-F-4-CH₃ | CF₃ | H | H | C(O)CH₂CF₃ |
| 3-F-5-CH₃ | CF₃ | CH₃ | H | C(O)Pr-c |
| 3-Cl-4-CH₃ | CF₃ | CH₃ | H | C(O)CH₂CF₃ |
| 3-Cl-5-CH₃ | CF₃ | H | H | C(O)Et |
| 3-Cl-5-CH₃ | CF₃ | H | H | C(O)Pr-n |
| 3-Cl-5-CH₃ | CF₃ | H | H | C(O)Pr-i |
| 3-Cl-5-CH₃ | CF₃ | H | H | C(O)Pr-c |
| 3-Cl-5-CH₃ | CF₃ | H | H | C(O)CH₂Pr-c |
| 3-Cl-5-CH₃ | CF₃ | H | H | C(O)CH₂CH₂Cl |
| 3-Cl-5-CH₃ | CF₃ | H | H | C(O)CH₂CF₃ |
| 3-Cl-5-CH₃ | CF₃ | CH₃ | H | C(O)Pr-i |
| 3-Cl-5-CH₃ | CF₃ | CH₃ | H | C(O)Pr-c |
| 3-Cl-5-CH₃ | CF₃ | CH₃ | H | C(O)CH₂CF₃ |
| 3-Cl-5-CH₃ | CF₂Cl | H | H | C(O)Pr-i |
| 3-Br-5-CH₃ | CF₃ | H | H | C(O)Et |
| 3-Br-5-CH₃ | CF₃ | H | H | C(O)Pr-n |
| 3-Br-5-CH₃ | CF₃ | H | H | C(O)Pr-i |
| 3-Br-5-CH₃ | CF₃ | H | H | C(O)Pr-c |
| 3-Br-5-CH₃ | CF₃ | H | H | C(O)CH₂Pr-c |
| 3-Br-5-CH₃ | CF₃ | H | H | C(O)CH₂CH₂Cl |
| 3-Br-5-CH₃ | CF₃ | H | H | C(O)CH₂CF₃ |
| 3-Br-5-CH₃ | CF₃ | CH₃ | H | C(O)Pr-i |
| 3-Br-5-CH₃ | CF₃ | CH₃ | H | C(O)Pr-c |
| 3-Br-5-CH₃ | CF₃ | CH₃ | H | C(O)CH₂CF₃ |

TABLE 2-continued

| | | | | |
|---|---|---|---|---|
| 3-Br-5-CH$_3$ | CF$_2$Cl | H | H | C(O)Pr-c |
| 3,5-(CH$_3$)$_2$ | CF$_3$ | H | H | C(O)Pr-i |
| 3,5-(CH$_3$)$_2$ | CF$_3$ | H | H | C(O)Pr-c |
| 3,5-(CH$_3$)$_2$ | CF$_3$ | H | H | C(O)CH$_2$CF$_3$ |
| 3,5-(CH$_3$)$_2$ | CF$_3$ | CH$_3$ | H | C(O)Pr-c |
| 3,5-(CH$_3$)$_2$ | CF$_3$ | CH$_3$ | H | C(O)CH$_2$CF$_3$ |
| 3-Br-5-Et | CF$_3$ | H | H | C(O)CH$_2$CF$_3$ |
| 3-Cl-5-Pr-i | CF$_3$ | CH$_3$ | H | C(O)Pr-c |
| 3-Br-5-Pr-i | CF$_3$ | CH$_3$ | H | C(O)CH$_2$CF$_3$ |
| 3-Cl-5-Bu-t | CF$_3$ | H | H | C(O)Pr-i |
| 3-Br-5-Bu-t | CF$_3$ | H | H | C(O)Pr-c |
| 2-F-3-CF$_3$ | CF$_3$ | H | H | C(O)CH$_2$CF$_3$ |
| 3-CF$_3$-4-F | CHF$_2$ | CH$_3$ | H | C(O)Pr-c |
| 3-CF$_3$-4-F | CF$_3$ | H | H | H |
| 3-CF$_3$-4-F | CF$_3$ | H | H | C(O)Et |
| 3-CF$_3$-4-F | CF$_3$ | H | H | C(O)Pr-n |
| 3-CF$_3$-4-F | CF$_3$ | H | H | C(O)Pr-i |
| 3-CF$_3$-4-F | CF$_3$ | H | H | C(O)Pr-c |
| 3-CF$_3$-4-F | CF$_3$ | H | H | C(O)CH$_2$Pr-c |
| 3-CF$_3$-4-F | CF$_3$ | H | H | C(O)CF$_3$ |
| 3-CF$_3$-4-F | CF$_3$ | H | H | C(O)CH$_2$CH$_2$Cl |
| 3-CF$_3$-4-F | CF$_3$ | H | H | C(O)CH$_2$CF$_3$ |
| 3-CF$_3$-4-F | CF$_3$ | H | H | C(O)CF$_2$CHF$_2$ |
| 3-CF$_3$-4-F | CF$_3$ | H | H | C(O)CF$_2$CF$_3$ |
| 3-CF$_3$-4-F | CF$_3$ | H | H | C(O)CH$_2$CH$_2$SCH$_3$ |
| 3-CF$_3$-4-F | CF$_3$ | H | H | C(O)(Ph-2,4-F$_2$) |
| 3-CF$_3$-4-F | CF$_3$ | H | H | C(O)NHEt |
| 3-CF$_3$-4-F | CF$_3$ | H | H | C(O)NHPr-i |
| 3-CF$_3$-4-F | CF$_3$ | H | H | C(O)NHCH$_2$CF$_3$ |
| 3-CF$_3$-4-F | CF$_3$ | CH$_3$ | H | H |
| 3-CF$_3$-4-F | CF$_3$ | CH$_3$ | H | C(O)Et |
| 3-CF$_3$-4-F | CF$_3$ | CH$_3$ | H | C(O)Pr-n |
| 3-CF$_3$-4-F | CF$_3$ | CH$_3$ | H | C(O)Pr-i |
| 3-CF$_3$-4-F | CF$_3$ | CH$_3$ | H | C(O)Pr-c |
| 3-CF$_3$-4-F | CF$_3$ | CH$_3$ | H | C(O)CH$_2$CF$_3$ |
| 3-CF$_3$-4-F | CF$_3$ | CN | H | H |
| 3-CF$_3$-4-F | CF$_3$ | CN | H | C(O)Pr-c |
| 3-CF$_3$-4-F | CF$_3$ | CN | H | C(O)CH$_2$CF$_3$ |
| 3-CF$_3$-4-F | CF$_2$Cl | H | H | C(O)Et |
| 3-CF$_3$-4-F | CF$_2$Cl | H | H | C(O)Pr-n |
| 3-CF$_3$-4-F | CF$_2$Cl | H | H | C(O)Pr-i |
| 3-CF$_3$-4-F | CF$_2$Cl | H | H | C(O)Pr-c |
| 3-CF$_3$-4-F | CF$_2$Cl | H | H | C(O)CH$_2$Pr-c |
| 3-CF$_3$-4-F | CF$_2$Cl | H | H | C(O)CH$_2$CH$_2$Cl |
| 3-CF$_3$-4-F | CF$_2$Cl | H | H | C(O)CH$_2$CF$_3$ |
| 3-CF$_3$-4-F | CF$_2$Cl | CH$_3$ | H | C(O)Pr-i |
| 3-CF$_3$-4-F | CF$_2$Cl | CH$_3$ | H | C(O)Pr-c |
| 3-CF$_3$-4-F | CF$_2$Cl | CH$_3$ | H | C(O)CH$_2$CF$_3$ |
| 3-CF$_3$-4-F | CF$_2$Br | CH$_3$ | H | C(O)CH$_2$CF$_3$ |
| 3-CF$_3$-4-F | CH$_2$CHF$_2$ | H | H | C(O)Pr-i |
| 2-F-5-CF$_3$ | CF$_3$ | H | H | C(O)Pr-c |
| 3-F-5-CF$_3$ | CHF$_2$ | H | H | C(O)CH$_2$CF$_3$ |
| 3-F-5-CF$_3$ | CF$_3$ | H | H | H |
| 3-F-5-CF$_3$ | CF$_3$ | H | H | C(O)Et |
| 3-F-5-CF$_3$ | CF$_3$ | H | H | C(O)Pr-n |
| 3-F-5-CF$_3$ | CF$_3$ | H | H | C(O)Pr-i |
| 3-F-5-CF$_3$ | CF$_3$ | H | H | C(O)Pr-c |
| 3-F-5-CF$_3$ | CF$_3$ | H | H | C(O)CH$_2$Pr-c |
| 3-F-5-CF$_3$ | CF$_3$ | H | H | C(O)CF$_3$ |
| 3-F-5-CF$_3$ | CF$_3$ | H | H | C(O)CH$_2$CH$_2$Cl |
| 3-F-5-CF$_3$ | CF$_3$ | H | H | C(O)CH$_2$CF$_3$ |
| 3-F-5-CF$_3$ | CF$_3$ | H | H | C(O)CF$_2$CHF$_2$ |
| 3-F-5-CF$_3$ | CF$_3$ | H | H | C(O)CF$_2$CF$_3$ |
| 3-F-5-CF$_3$ | CF$_3$ | H | H | C(O)CH$_2$CH$_2$SCH$_3$ |
| 3-F-5-CF$_3$ | CF$_3$ | H | H | C(O)(Ph-2,4-F$_2$) |
| 3-F-5-CF$_3$ | CF$_3$ | H | H | C(O)NHEt |
| 3-F-5-CF$_3$ | CF$_3$ | H | H | C(O)NHPr-i |
| 3-F-5-CF$_3$ | CF$_3$ | H | H | C(O)NHCH$_2$CF$_3$ |
| 3-F-5-CF$_3$ | CF$_3$ | CH$_3$ | H | H |
| 3-F-5-CF$_3$ | CF$_3$ | CH$_3$ | H | C(O)Et |
| 3-F-5-CF$_3$ | CF$_3$ | CH$_3$ | H | C(O)Pr-n |
| 3-F-5-CF$_3$ | CF$_3$ | CH$_3$ | H | C(O)Pr-i |
| 3-F-5-CF$_3$ | CF$_3$ | CH$_3$ | H | C(O)Pr-c |
| 3-F-5-CF$_3$ | CF$_3$ | CH$_3$ | H | C(O)CH$_2$CF$_3$ |
| 3-F-5-CF$_3$ | CF$_3$ | CN | H | H |
| 3-F-5-CF$_3$ | CF$_3$ | CN | H | C(O)Pr-c |
| 3-F-5-CF$_3$ | CF$_3$ | CN | H | C(O)CH$_2$CF$_3$ |
| 3-F-5-CF$_3$ | CF$_2$Cl | H | H | C(O)Et |
| 3-F-5-CF$_3$ | CF$_2$Cl | H | H | C(O)Pr-n |
| 3-F-5-CF$_3$ | CF$_2$Cl | H | H | C(O)Pr-i |

TABLE 2-continued

| | | | | |
|---|---|---|---|---|
| 3-F-5-CF$_3$ | CF$_2$Cl | H | H | C(O)Pr-c |
| 3-F-5-CF$_3$ | CF$_2$Cl | H | H | C(O)CH$_2$Pr-c |
| 3-F-5-CF$_3$ | CF$_2$Cl | H | H | C(O)CH$_2$CH$_2$Cl |
| 3-F-5-CF$_3$ | CF$_2$Cl | H | H | C(O)CH$_2$CF$_3$ |
| 3-F-5-CF$_3$ | CF$_2$Cl | CH$_3$ | H | C(O)Pr-i |
| 3-F-5-CF$_3$ | CF$_2$Cl | CH$_3$ | H | C(O)Pr-c |
| 3-F-5-CF$_3$ | CF$_2$Cl | CH$_3$ | H | C(O)CH$_2$CF$_3$ |
| 3-F-5-CF$_3$ | CF$_2$Br | CH$_3$ | H | C(O)Pr-c |
| 3-F-5-CF$_3$ | CF$_2$CHF$_2$ | CH$_3$ | H | C(O)CH$_2$CF$_3$ |
| 3-CF$_3$-4-Cl | CHF$_2$ | H | H | C(O)Pr-i |
| 3-CF$_3$-4-Cl | CF$_3$ | H | H | H |
| 3-CF$_3$-4-Cl | CF$_3$ | H | H | C(O)Et |
| 3-CF$_3$-4-Cl | CF$_3$ | H | H | C(O)Pr-n |
| 3-CF$_3$-4-Cl | CF$_3$ | H | H | C(O)Pr-i |
| 3-CF$_3$-4-Cl | CF$_3$ | H | H | C(O)Pr-c |
| 3-CF$_3$-4-Cl | CF$_3$ | H | H | C(O)CH$_2$Pr-c |
| 3-CF$_3$-4-Cl | CF$_3$ | H | H | C(O)CF$_3$ |
| 3-CF$_3$-4-Cl | CF$_3$ | H | H | C(O)CH$_2$CH$_2$Cl |
| 3-CF$_3$-4-Cl | CF$_3$ | H | H | C(O)CH$_2$CF$_3$ |
| 3-CF$_3$-4-Cl | CF$_3$ | H | H | C(O)CF$_2$CHF$_2$ |
| 3-CF$_3$-4-Cl | CF$_3$ | H | H | C(O)CF$_2$CF$_3$ |
| 3-CF$_3$-4-Cl | CF$_3$ | H | H | C(O)CH$_2$CH$_2$SCH$_3$ |
| 3-CF$_3$-4-Cl | CF$_3$ | H | H | C(O)(Ph-2,4-F$_2$) |
| 3-CF$_3$-4-Cl | CF$_3$ | H | H | C(O)NHEt |
| 3-CF$_3$-4-Cl | CF$_3$ | H | H | C(O)NHPr-i |
| 3-CF$_3$-4-Cl | CF$_3$ | H | H | C(O)NHCH$_2$CF$_3$ |
| 3-CF$_3$-4-Cl | CF$_3$ | CH$_3$ | H | H |
| 3-CF$_3$-4-Cl | CF$_3$ | CH$_3$ | H | C(O)Et |
| 3-CF$_3$-4-Cl | CF$_3$ | CH$_3$ | H | C(O)Pr-n |
| 3-CF$_3$-4-Cl | CF$_3$ | CH$_3$ | H | C(O)Pr-i |
| 3-CF$_3$-4-Cl | CF$_3$ | CH$_3$ | H | C(O)Pr-c |
| 3-CF$_3$-4-Cl | CF$_3$ | CH$_3$ | H | C(O)CH$_2$CF$_3$ |
| 3-CF$_3$-4-Cl | CF$_3$ | CN | H | H |
| 3-CF$_3$-4-Cl | CF$_3$ | CN | H | C(O)Pr-c |
| 3-CF$_3$-4-Cl | CF$_3$ | CN | H | C(O)CH$_2$CF$_3$ |
| 3-CF$_3$-4-Cl | CF$_2$Cl | H | H | C(O)Et |
| 3-CF$_3$-4-Cl | CF$_2$Cl | H | H | C(O)Pr-n |
| 3-CF$_3$-4-Cl | CF$_2$Cl | H | H | C(O)Pr-i |
| 3-CF$_3$-4-Cl | CF$_2$Cl | H | H | C(O)Pr-c |
| 3-CF$_3$-4-Cl | CF$_2$Cl | H | H | C(O)CH$_2$Pr-c |
| 3-CF$_3$-4-Cl | CF$_2$Cl | H | H | C(O)CH$_2$CH$_2$Cl |
| 3-CF$_3$-4-Cl | CF$_2$Cl | H | H | C(O)CH$_2$CF$_3$ |
| 3-CF$_3$-4-Cl | CF$_2$Cl | CH$_3$ | H | C(O)Pr-i |
| 3-CF$_3$-4-Cl | CF$_2$Cl | CH$_3$ | H | C(O)Pr-c |
| 3-CF$_3$-4-Cl | CF$_2$Cl | CH$_3$ | H | C(O)CH$_2$CF$_3$ |
| 3-CF$_3$-4-Cl | CF$_2$Br | H | H | C(O)Pr-c |
| 3-CF$_3$-4-Cl | CF$_2$CHF$_2$ | H | H | C(O)CH$_2$CF$_3$ |
| 3-Cl-5-CF$_3$ | CHF$_2$ | H | H | C(O)Pr-i |
| 3-Cl-5-CF$_3$ | CHF$_2$ | H | H | C(O)Pr-c |
| 3-Cl-5-CF$_3$ | CHF$_2$ | H | H | C(O)CH$_2$CF$_3$ |
| 3-Cl-5-CF$_3$ | CHF$_2$ | CH$_3$ | H | C(O)Pr-c |
| 3-Cl-5-CF$_3$ | CHF$_2$ | CH$_3$ | H | C(O)CH$_2$CF$_3$ |
| 3-Cl-5-CF$_3$ | CHFCl | CH$_3$ | H | C(O)Pr-c |
| 3-Cl-5-CF$_3$ | CHCl$_2$ | CH$_3$ | H | C(O)CH$_2$CF$_3$ |
| 3-Cl-5-CF$_3$ | CHFBr | H | H | C(O)Pr-i |
| 3-Cl-5-CF$_3$ | CF$_3$ | H | H | H |
| 3-Cl-5-CF$_3$ | CF$_3$ | H | H | C(O)Et |
| 3-Cl-5-CF$_3$ | CF$_3$ | H | H | C(O)Pr-n |
| 3-Cl-5-CF$_3$ | CF$_3$ | H | H | C(O)Pr-i |
| 3-Cl-5-CF$_3$ | CF$_3$ | H | H | C(O)Pr-c |
| 3-Cl-5-CF$_3$ | CF$_3$ | H | H | C(O)Bu-i |
| 3-Cl-5-CF$_3$ | CF$_3$ | H | H | C(O)CH$_2$Pr-c |
| 3-Cl-5-CF$_3$ | CF$_3$ | H | H | C(O)Bu-s |
| 3-Cl-5-CF$_3$ | CF$_3$ | H | H | C(O)CF$_3$ |
| 3-Cl-5-CF$_3$ | CF$_3$ | H | H | C(O)CH$_2$CH$_2$Cl |
| 3-Cl-5-CF$_3$ | CF$_3$ | H | H | C(O)CH$_2$CF$_3$ |
| 3-Cl-5-CF$_3$ | CF$_3$ | H | H | C(O)CF$_2$CHF$_2$ |
| 3-Cl-5-CF$_3$ | CF$_3$ | H | H | C(O)CF$_2$CF$_3$ |
| 3-Cl-5-CF$_3$ | CF$_3$ | H | H | C(O)CH$_2$CH$_2$OCH$_3$ |
| 3-Cl-5-CF$_3$ | CF$_3$ | H | H | C(O)(E-5a) |
| 3-Cl-5-CF$_3$ | CF$_3$ | H | H | C(O)CH$_2$CH$_2$SCH$_3$ |
| 3-Cl-5-CF$_3$ | CF$_3$ | H | H | C(O)CH=C(CH$_3$)$_2$ |
| 3-Cl-5-CF$_3$ | CF$_3$ | H | H | C(O)CH$_2$CH$_2$C≡CH |
| 3-Cl-5-CF$_3$ | CF$_3$ | H | H | C(O)(Ph-3-F) |
| 3-Cl-5-CF$_3$ | CF$_3$ | H | H | C(O)(Ph-2,4-F$_2$) |
| 3-Cl-5-CF$_3$ | CF$_3$ | H | H | C(O)(Ph-3,5-F$_2$) |
| 3-Cl-5-CF$_3$ | CF$_3$ | H | H | C(O)NHEt |
| 3-Cl-5-CF$_3$ | CF$_3$ | H | H | C(O)NHPr-i |
| 3-Cl-5-CF$_3$ | CF$_3$ | H | H | C(O)NHPr-c |
| 3-Cl-5-CF$_3$ | CF$_3$ | H | H | C(O)NHCH$_2$CF$_3$ |

TABLE 2-continued

| | | | | |
|---|---|---|---|---|
| 3-Cl-5-$CF_3$ | $CF_3$ | H | H | C(O)NHOCH$_3$ |
| 3-Cl-5-$CF_3$ | $CF_3$ | H | H | C(S)CH$_2$CF$_3$ |
| 3-Cl-5-$CF_3$ | $CF_3$ | CH$_3$ | H | H |
| 3-Cl-5-$CF_3$ | $CF_3$ | CH$_3$ | H | C(O)Et |
| 3-Cl-5-$CF_3$ | $CF_3$ | CH$_3$ | H | C(O)Pr-n |
| 3-Cl-5-$CF_3$ | $CF_3$ | CH$_3$ | H | C(O)Pr-i |
| 3-Cl-5-$CF_3$ | $CF_3$ | CH$_3$ | H | C(O)Pr-c |
| 3-Cl-5-$CF_3$ | $CF_3$ | CH$_3$ | H | C(O)CH$_2$CF$_3$ |
| 3-Cl-5-$CF_3$ | $CF_3$ | CH$_3$ | H | C(O)NHEt |
| 3-Cl-5-$CF_3$ | $CF_3$ | CH$_3$ | H | C(O)NHPr-i |
| 3-Cl-5-$CF_3$ | $CF_3$ | CH$_3$ | H | C(O)NHPr-c |
| 3-Cl-5-$CF_3$ | $CF_3$ | CH$_3$ | H | C(O)NHCH$_2$CH$_2$Cl |
| 3-Cl-5-$CF_3$ | $CF_3$ | CH$_3$ | H | C(O)NHCH$_2$CF$_3$ |
| 3-Cl-5-$CF_3$ | $CF_3$ | CF$_3$ | H | C(O)Pr-i |
| 3-Cl-5-$CF_3$ | $CF_3$ | CN | H | H |
| 3-Cl-5-$CF_3$ | $CF_3$ | CN | H | C(O)Pr-i |
| 3-Cl-5-$CF_3$ | $CF_3$ | CN | H | C(O)Pr-c |
| 3-Cl-5-$CF_3$ | $CF_3$ | CN | H | C(O)CH$_2$CF$_3$ |
| 3-Cl-5-$CF_3$ | $CF_3$ | CN | H | C(O)NHEt |
| 3-Cl-5-$CF_3$ | CF$_2$Cl | H | H | C(O)Et |
| 3-Cl-5-$CF_3$ | CF$_2$Cl | H | H | C(O)Pr-n |
| 3-Cl-5-$CF_3$ | CF$_2$Cl | H | H | C(O)Pr-i |
| 3-Cl-5-$CF_3$ | CF$_2$Cl | H | H | C(O)Pr-c |
| 3-Cl-5-$CF_3$ | CF$_2$Cl | H | H | C(O)CH$_2$Pr-c |
| 3-Cl-5-$CF_3$ | CF$_2$Cl | H | H | C(O)CF$_3$ |
| 3-Cl-5-$CF_3$ | CF$_2$Cl | H | H | C(O)CH$_2$CH$_2$Cl |
| 3-Cl-5-$CF_3$ | CF$_2$Cl | H | H | C(O)CH$_2$CF$_3$ |
| 3-Cl-5-$CF_3$ | CF$_2$Cl | H | H | C(O)CF$_2$CHF$_2$ |
| 3-Cl-5-$CF_3$ | CF$_2$Cl | H | H | C(O)CF$_2$CF$_3$ |
| 3-Cl-5-$CF_3$ | CF$_2$Cl | H | H | C(O)CH$_2$CH$_2$SCH$_3$ |
| 3-Cl-5-$CF_3$ | CF$_2$Cl | H | H | C(O)(Ph-2,4-F$_2$) |
| 3-Cl-5-$CF_3$ | CF$_2$Cl | H | H | C(O)NHEt |
| 3-Cl-5-$CF_3$ | CF$_2$Cl | H | H | C(O)NHPr-i |
| 3-Cl-5-$CF_3$ | CF$_2$Cl | H | H | C(O)NHCH$_2$CF$_3$ |
| 3-Cl-5-$CF_3$ | CF$_2$Cl | CH$_3$ | H | C(O)Et |
| 3-Cl-5-$CF_3$ | CF$_2$Cl | CH$_3$ | H | C(O)Pr-n |
| 3-Cl-5-$CF_3$ | CF$_2$Cl | CH$_3$ | H | C(O)Pr-i |
| 3-Cl-5-$CF_3$ | CF$_2$Cl | CH$_3$ | H | C(O)Pr-c |
| 3-Cl-5-$CF_3$ | CF$_2$Cl | CH$_3$ | H | C(O)CH$_2$CF$_3$ |
| 3-Cl-5-$CF_3$ | CF$_2$Cl | CN | H | C(O)Pr-c |
| 3-Cl-5-$CF_3$ | CF$_2$Cl | CN | H | C(O)CH$_2$CF$_3$ |
| 3-Cl-5-$CF_3$ | CF$_2$Br | H | H | C(O)Pr-i |
| 3-Cl-5-$CF_3$ | CF$_2$Br | H | H | C(O)Pr-c |
| 3-Cl-5-$CF_3$ | CF$_2$Br | H | H | C(O)CH$_2$CF$_3$ |
| 3-Cl-5-$CF_3$ | CF$_2$Br | CH$_3$ | H | C(O)Pr-c |
| 3-Cl-5-$CF_3$ | CF$_2$Br | CH$_3$ | H | C(O)CH$_2$CF$_3$ |
| 3-Cl-5-$CF_3$ | CF$_2$CHF$_2$ | H | H | C(O)Pr-i |
| 3-Cl-5-$CF_3$ | CF$_2$CHF$_2$ | H | H | C(O)Pr-c |
| 3-Cl-5-$CF_3$ | CF$_2$CHF$_2$ | H | H | C(O)CH$_2$CF$_3$ |
| 3-Cl-5-$CF_3$ | CF$_2$CHF$_2$ | CH$_3$ | H | C(O)Pr-c |
| 3-Cl-5-$CF_3$ | CF$_2$CHF$_2$ | CH$_3$ | H | C(O)CH$_2$CF$_3$ |
| 3-Cl-5-$CF_3$ | CF$_2$CF$_3$ | H | H | C(O)Pr-c |
| 3-Cl-5-$CF_3$ | CF$_2$OCH$_3$ | H | H | C(O)CH$_2$CF$_3$ |
| 3-Cl-5-$CF_3$ | CF$_2$SCH$_3$ | CH$_3$ | H | C(O)Pr-c |
| 3-Cl-5-$CF_3$ | T-3 | CH$_3$ | H | C(O)CH$_2$CF$_3$ |
| 3-Br-5-$CF_3$ | CHF$_2$ | H | H | C(O)Pr-i |
| 3-Br-5-$CF_3$ | CHF$_2$ | H | H | C(O)Pr-c |
| 3-Br-5-$CF_3$ | CHF$_2$ | H | H | C(O)CH$_2$CF$_3$ |
| 3-Br-5-$CF_3$ | CHF$_2$ | CH$_3$ | H | C(O)Pr-c |
| 3-Br-5-$CF_3$ | CHF$_2$ | CH$_3$ | H | C(O)CH$_2$CF$_3$ |
| 3-Br-5-$CF_3$ | CHFCl | H | H | C(O)Pr-i |
| 3-Br-5-$CF_3$ | CHCl$_2$ | H | H | C(O)Pr-c |
| 3-Br-5-$CF_3$ | CHFBr | H | H | C(O)CH$_2$CF$_3$ |
| 3-Br-5-$CF_3$ | $CF_3$ | H | H | H |
| 3-Br-5-$CF_3$ | $CF_3$ | H | H | C(O)Et |
| 3-Br-5-$CF_3$ | $CF_3$ | H | H | C(O)Pr-n |
| 3-Br-5-$CF_3$ | $CF_3$ | H | H | C(O)Pr-i |
| 3-Br-5-$CF_3$ | $CF_3$ | H | H | C(O)Pr-c |
| 3-Br-5-$CF_3$ | $CF_3$ | H | H | C(O)Bu-i |
| 3-Br-5-$CF_3$ | $CF_3$ | H | H | C(O)CH$_2$Pr-c |
| 3-Br-5-$CF_3$ | $CF_3$ | H | H | C(O)Bu-s |
| 3-Br-5-$CF_3$ | $CF_3$ | H | H | C(O)CF$_3$ |
| 3-Br-5-$CF_3$ | $CF_3$ | H | H | C(O)CH$_2$CH$_2$Cl |
| 3-Br-5-$CF_3$ | $CF_3$ | H | H | C(O)CH$_2$CF$_3$ |
| 3-Br-5-$CF_3$ | $CF_3$ | H | H | C(O)CF$_2$CHF$_2$ |
| 3-Br-5-$CF_3$ | $CF_3$ | H | H | C(O)CF$_2$CF$_3$ |
| 3-Br-5-$CF_3$ | $CF_3$ | H | H | C(O)CH$_2$CH$_2$OCH$_3$ |
| 3-Br-5-$CF_3$ | $CF_3$ | H | H | C(O)(E-5a) |
| 3-Br-5-$CF_3$ | $CF_3$ | H | H | C(O)CH$_2$CH$_2$SCH$_3$ |
| 3-Br-5-$CF_3$ | $CF_3$ | H | H | C(O)CH=C(CH$_3$)$_2$ |

TABLE 2-continued

| | | | | |
|---|---|---|---|---|
| 3-Br-5-CF$_3$ | CF$_3$ | H | H | C(O)CH$_2$CH$_2$C≡CH |
| 3-Br-5-CF$_3$ | CF$_3$ | H | H | C(O)(Ph-3-F) |
| 3-Br-5-CF$_3$ | CF$_3$ | H | H | C(O)(Ph-2,4-F$_2$) |
| 3-Br-5-CF$_3$ | CF$_3$ | H | H | C(O)(Ph-3,5-F$_2$) |
| 3-Br-5-CF$_3$ | CF$_3$ | H | H | C(O)NHEt |
| 3-Br-5-CF$_3$ | CF$_3$ | H | H | C(O)NHPr-i |
| 3-Br-5-CF$_3$ | CF$_3$ | H | H | C(O)NHPr-c |
| 3-Br-5-CF$_3$ | CF$_3$ | H | H | C(O)NHCH$_2$CF$_3$ |
| 3-Br-5-CF$_3$ | CF$_3$ | H | H | C(O)NHOCH$_3$ |
| 3-Br-5-CF$_3$ | CF$_3$ | H | H | C(S)CH$_2$CF$_3$ |
| 3-Br-5-CF$_3$ | CF$_3$ | CH$_3$ | H | H |
| 3-Br-5-CF$_3$ | CF$_3$ | CH$_3$ | H | C(O)Et |
| 3-Br-5-CF$_3$ | CF$_3$ | CH$_3$ | H | C(O)Pr-n |
| 3-Br-5-CF$_3$ | CF$_3$ | CH$_3$ | H | C(O)Pr-i |
| 3-Br-5-CF$_3$ | CF$_3$ | CH$_3$ | H | C(O)Pr-c |
| 3-Br-5-CF$_3$ | CF$_3$ | CH$_3$ | H | C(O)CH$_2$CF$_3$ |
| 3-Br-5-CF$_3$ | CF$_3$ | CH$_3$ | H | C(O)NHEt |
| 3-Br-5-CF$_3$ | CF$_3$ | CH$_3$ | H | C(O)NHPr-i |
| 3-Br-5-CF$_3$ | CF$_3$ | CH$_3$ | H | C(O)NHPr-c |
| 3-Br-5-CF$_3$ | CF$_3$ | CH$_3$ | H | C(O)NHCH$_2$CH$_2$Cl |
| 3-Br-5-CF$_3$ | CF$_3$ | CH$_3$ | H | C(O)NHCH$_2$CF$_3$ |
| 3-Br-5-CF$_3$ | CF$_3$ | CF$_3$ | H | C(O)Pr-i |
| 3-Br-5-CF$_3$ | CF$_3$ | CN | H | H |
| 3-Br-5-CF$_3$ | CF$_3$ | CN | H | C(O)Pr-i |
| 3-Br-5-CF$_3$ | CF$_3$ | CN | H | C(O)Pr-c |
| 3-Br-5-CF$_3$ | CF$_3$ | CN | H | C(O)CH$_2$CF$_3$ |
| 3-Br-5-CF$_3$ | CF$_3$ | CN | H | C(O)NHEt |
| 3-Br-5-CF$_3$ | CF$_2$Cl | H | H | C(O)Et |
| 3-Br-5-CF$_3$ | CF$_2$Cl | H | H | C(O)Pr-n |
| 3-Br-5-CF$_3$ | CF$_2$Cl | H | H | C(O)Pr-i |
| 3-Br-5-CF$_3$ | CF$_2$Cl | H | H | C(O)Pr-c |
| 3-Br-5-CF$_3$ | CF$_2$Cl | H | H | C(O)CH$_2$Pr-c |
| 3-Br-5-CF$_3$ | CF$_2$Cl | H | H | C(O)CF$_3$ |
| 3-Br-5-CF$_3$ | CF$_2$Cl | H | H | C(O)CH$_2$CH$_2$Cl |
| 3-Br-5-CF$_3$ | CF$_2$Cl | H | H | C(O)CH$_2$CF$_3$ |
| 3-Br-5-CF$_3$ | CF$_2$Cl | H | H | C(O)CF$_2$CHF$_2$ |
| 3-Br-5-CF$_3$ | CF$_2$Cl | H | H | C(O)CF$_2$CF$_3$ |
| 3-Br-5-CF$_3$ | CF$_2$Cl | H | H | C(O)CH$_2$CH$_2$SCH$_3$ |
| 3-Br-5-CF$_3$ | CF$_2$Cl | H | H | C(O)(Ph-2,4-F$_2$) |
| 3-Br-5-CF$_3$ | CF$_2$Cl | H | H | C(O)NHEt |
| 3-Br-5-CF$_3$ | CF$_2$Cl | H | H | C(O)NHPr-i |
| 3-Br-5-CF$_3$ | CF$_2$Cl | H | H | C(O)NHCH$_2$CF$_3$ |
| 3-Br-5-CF$_3$ | CF$_2$Cl | CH$_3$ | H | C(O)Et |
| 3-Br-5-CF$_3$ | CF$_2$Cl | CH$_3$ | H | C(O)Pr-n |
| 3-Br-5-CF$_3$ | CF$_2$Cl | CH$_3$ | H | C(O)Pr-i |
| 3-Br-5-CF$_3$ | CF$_2$Cl | CH$_3$ | H | C(O)Pr-c |
| 3-Br-5-CF$_3$ | CF$_2$Cl | CH$_3$ | H | C(O)CH$_2$CF$_3$ |
| 3-Br-5-CF$_3$ | CF$_2$Cl | CN | H | C(O)Pr-c |
| 3-Br-5-CF$_3$ | CF$_2$Cl | CN | H | C(O)CH$_2$CF$_3$ |
| 3-Br-5-CF$_3$ | CF$_2$Br | H | H | C(O)Pr-i |
| 3-Br-5-CF$_3$ | CF$_2$Br | H | H | C(O)Pr-c |
| 3-Br-5-CF$_3$ | CF$_2$Br | H | H | C(O)CH$_2$CF$_3$ |
| 3-Br-5-CF$_3$ | CF$_2$Br | CH$_3$ | H | C(O)Pr-c |
| 3-Br-5-CF$_3$ | CF$_2$Br | CH$_3$ | H | C(O)CH$_2$CF$_3$ |
| 3-Br-5-CF$_3$ | CF$_2$CHF$_2$ | H | H | C(O)Pr-i |
| 3-Br-5-CF$_3$ | CF$_2$CHF$_2$ | H | H | C(O)Pr-c |
| 3-Br-5-CF$_3$ | CF$_2$CHF$_2$ | H | H | C(O)CH$_2$CF$_3$ |
| 3-Br-5-CF$_3$ | CF$_2$CHF$_2$ | CH$_3$ | H | C(O)Pr-c |
| 3-Br-5-CF$_3$ | CF$_2$CHF$_2$ | CH$_3$ | H | C(O)CH$_2$CF$_3$ |
| 3-Br-5-CF$_3$ | CF$_2$CF$_3$ | CH$_3$ | H | C(O)Pr-c |
| 3-Br-5-CF$_3$ | CF$_2$OCH$_3$ | CH$_3$ | H | C(O)CH$_2$CF$_3$ |
| 3-Br-5-CF$_3$ | CF$_2$SCH$_3$ | H | H | C(O)Pr-i |
| 3-Br-5-CF$_3$ | T-3 | H | H | C(O)Pr-c |
| 3-CH$_3$-5-CF$_3$ | CF$_3$ | H | H | C(O)Et |
| 3-CH$_3$-5-CF$_3$ | CF$_3$ | H | H | C(O)Pr-n |
| 3-CH$_3$-5-CF$_3$ | CF$_3$ | H | H | C(O)Pr-i |
| 3-CH$_3$-5-CF$_3$ | CF$_3$ | H | H | C(O)Pr-c |
| 3-CH$_3$-5-CF$_3$ | CF$_3$ | H | H | C(O)CH$_2$Pr-c |
| 3-CH$_3$-5-CF$_3$ | CF$_3$ | H | H | C(O)CH$_2$CH$_2$Cl |
| 3-CH$_3$-5-CF$_3$ | CF$_3$ | H | H | C(O)CH$_2$CF$_3$ |
| 3-CH$_3$-5-CF$_3$ | CF$_3$ | CH$_3$ | H | C(O)Pr-i |
| 3-CH$_3$-5-CF$_3$ | CF$_3$ | CH$_3$ | H | C(O)Pr-c |
| 3-CH$_3$-5-CF$_3$ | CF$_3$ | CH$_3$ | H | C(O)CH$_2$CF$_3$ |
| 3-CH$_3$-5-CF$_3$ | CF$_2$Cl | H | H | C(O)CH$_2$CF$_3$ |
| 3-Et-5-CF$_3$ | CF$_3$ | CH$_3$ | H | C(O)Pr-c |
| 3-i-Pr-5-CF$_3$ | CF$_3$ | CH$_3$ | H | C(O)CH$_2$CF$_3$ |
| 3-t-Bu-5-CF$_3$ | CF$_3$ | H | H | C(O)Pr-i |
| 3,5-(CF$_3$)$_2$ | CHF$_2$ | H | H | C(O)Pr-i |
| 3,5-(CF$_3$)$_2$ | CHF$_2$ | H | H | C(O)Pr-c |
| 3,5-(CF$_3$)$_2$ | CHF$_2$ | H | H | C(O)CH$_2$CF$_3$ |

TABLE 2-continued

| | | | | |
|---|---|---|---|---|
| 3,5-(CF$_3$)$_2$ | CHF$_2$ | CH$_3$ | H | C(O)Pr-c |
| 3,5-(CF$_3$)$_2$ | CHF$_2$ | CH$_3$ | H | C(O)CH$_2$CF$_3$ |
| 3,5-(CF$_3$)$_2$ | CHFCl | H | H | C(O)Pr-c |
| 3,5-(CF$_3$)$_2$ | CHCl$_2$ | H | H | C(O)CH$_2$CF$_3$ |
| 3,5-(CF$_3$)$_2$ | CHFBr | CH$_3$ | H | C(O)Pr-c |
| 3,5-(CF$_3$)$_2$ | CF$_3$ | H | H | H |
| 3,5-(CF$_3$)$_2$ | CF$_3$ | H | H | C(O)Et |
| 3,5-(CF$_3$)$_2$ | CF$_3$ | H | H | C(O)Pr-n |
| 3,5-(CF$_3$)$_2$ | CF$_3$ | H | H | C(O)Pr-i |
| 3,5-(CF$_3$)$_2$ | CF$_3$ | H | Et | C(O)Pr-i |
| 3,5-(CF$_3$)$_2$ | CF$_3$ | H | CH$_2$OCH$_3$ | C(O)Pr-i |
| 3,5-(CF$_3$)$_2$ | CF$_3$ | H | CH$_2$OC(O)CH$_3$ | C(O)Pr-i |
| 3,5-(CF$_3$)$_2$ | CF$_3$ | H | CH$_2$OC(O)OCH$_3$ | C(O)Pr-i |
| 3,5-(CF$_3$)$_2$ | CF$_3$ | H | CH$_2$CN | C(O)Pr-i |
| 3,5-(CF$_3$)$_2$ | CF$_3$ | H | CH$_2$C≡CH | C(O)Pr-i |
| 3,5-(CF$_3$)$_2$ | CF$_3$ | H | C(O)CH$_3$ | C(O)Pr-i |
| 3,5-(CF$_3$)$_2$ | CF$_3$ | H | C(O)OCH$_3$ | C(O)Pr-i |
| 3,5-(CF$_3$)$_2$ | CF$_3$ | H | H | C(O)Pr-c |
| 3,5-(CF$_3$)$_2$ | CF$_3$ | H | Et | C(O)Pr-c |
| 3,5-(CF$_3$)$_2$ | CF$_3$ | H | CH$_2$OCH$_3$ | C(O)Pr-c |
| 3,5-(CF$_3$)$_2$ | CF$_3$ | H | CH$_2$OC(O)CH$_3$ | C(O)Pr-c |
| 3,5-(CF$_3$)$_2$ | CF$_3$ | H | CH$_2$OC(O)OCH$_3$ | C(O)Pr-c |
| 3,5-(CF$_3$)$_2$ | CF$_3$ | H | CH$_2$CN | C(O)Pr-c |
| 3,5-(CF$_3$)$_2$ | CF$_3$ | H | CH$_2$C≡CH | C(O)Pr-c |
| 3,5-(CF$_3$)$_2$ | CF$_3$ | H | C(O)CH$_3$ | C(O)Pr-c |
| 3,5-(CF$_3$)$_2$ | CF$_3$ | H | C(O)OCH$_3$ | C(O)Pr-c |
| 3,5-(CF$_3$)$_2$ | CF$_3$ | H | H | C(O)Bu-i |
| 3,5-(CF$_3$)$_2$ | CF$_3$ | H | H | C(O)CH$_2$Pr-c |
| 3,5-(CF$_3$)$_2$ | CF$_3$ | H | H | C(O)Bu-s |
| 3,5-(CF$_3$)$_2$ | CF$_3$ | H | H | C(O)CF$_3$ |
| 3,5-(CF$_3$)$_2$ | CF$_3$ | H | H | C(O)CH$_2$CH$_2$Cl |
| 3,5-(CF$_3$)$_2$ | CF$_3$ | H | H | C(O)CH$_2$CF$_3$ |
| 3,5-(CF$_3$)$_2$ | CF$_3$ | H | Et | C(O)CH$_2$CF$_3$ |
| 3,5-(CF$_3$)$_2$ | CF$_3$ | H | CH$_2$OCH$_3$ | C(O)CH$_2$CF$_3$ |
| 3,5-(CF$_3$)$_2$ | CF$_3$ | H | CH$_2$OC(O)CH$_3$ | C(O)CH$_2$CF$_3$ |
| 3,5-(CF$_3$)$_2$ | CF$_3$ | H | CH$_2$OC(O)OCH$_3$ | C(O)CH$_2$CF$_3$ |
| 3,5-(CF$_3$)$_2$ | CF$_3$ | H | CH$_2$CN | C(O)CH$_2$CF$_3$ |
| 3,5-(CF$_3$)$_2$ | CF$_3$ | H | CH$_2$C≡CH | C(O)CH$_2$CF$_3$ |
| 3,5-(CF$_3$)$_2$ | CF$_3$ | H | C(O)CH$_3$ | C(O)CH$_2$CF$_3$ |
| 3,5-(CF$_3$)$_2$ | CF$_3$ | H | C(O)OCH$_3$ | C(O)CH$_2$CF$_3$ |
| 3,5-(CF$_3$)$_2$ | CF$_3$ | H | H | C(O)CF$_2$CHF$_2$ |
| 3,5-(CF$_3$)$_2$ | CF$_3$ | H | H | C(O)CF$_2$CF$_3$ |
| 3,5-(CF$_3$)$_2$ | CF$_3$ | H | H | C(O)CH$_2$CH$_2$OCH$_3$ |
| 3,5-(CF$_3$)$_2$ | CF$_3$ | H | H | C(O)(E-5a) |
| 3,5-(CF$_3$)$_2$ | CF$_3$ | H | H | C(O)CH$_2$CH$_2$SCH$_3$ |
| 3,5-(CF$_3$)$_2$ | CF$_3$ | H | H | C(O)CH=C(CH$_3$)$_2$ |
| 3,5-(CF$_3$)$_2$ | CF$_3$ | H | H | C(O)CH$_2$CH$_2$C≡CH |
| 3,5-(CF$_3$)$_2$ | CF$_3$ | H | H | C(O)(Ph-3-F) |
| 3,5-(CF$_3$)$_2$ | CF$_3$ | H | H | C(O)(Ph-2,4-F$_2$) |
| 3,5-(CF$_3$)$_2$ | CF$_3$ | H | H | C(O)(Ph-3,5-F$_2$) |
| 3,5-(CF$_3$)$_2$ | CF$_3$ | H | H | C(O)NHEt |
| 3,5-(CF$_3$)$_2$ | CF$_3$ | H | H | C(O)NHPr-i |
| 3,5-(CF$_3$)$_2$ | CF$_3$ | H | H | C(O)NHPr-c |
| 3,5-(CF$_3$)$_2$ | CF$_3$ | H | H | C(O)NHCH$_2$CF$_3$ |
| 3,5-(CF$_3$)$_2$ | CF$_3$ | H | H | C(O)NHOCH$_3$ |
| 3,5-(CF$_3$)$_2$ | CF$_3$ | H | H | C(S)CH$_2$CF$_3$ |
| 3,5-(CF$_3$)$_2$ | CF$_3$ | CH$_3$ | H | H |
| 3,5-(CF$_3$)$_2$ | CF$_3$ | CH$_3$ | H | C(O)Et |
| 3,5-(CF$_3$)$_2$ | CF$_3$ | CH$_3$ | H | C(O)Pr-n |
| 3,5-(CF$_3$)$_2$ | CF$_3$ | CH$_3$ | H | C(O)Pr-i |
| 3,5-(CF$_3$)$_2$ | CF$_3$ | CH$_3$ | H | C(O)Pr-c |
| 3,5-(CF$_3$)$_2$ | CF$_3$ | CH$_3$ | H | C(O)CH$_2$CF$_3$ |
| 3,5-(CF$_3$)$_2$ | CF$_3$ | CH$_3$ | H | C(O)NHEt |
| 3,5-(CF$_3$)$_2$ | CF$_3$ | CH$_3$ | H | C(O)NHPr-i |
| 3,5-(CF$_3$)$_2$ | CF$_3$ | CH$_3$ | H | C(O)NHPr-c |
| 3,5-(CF$_3$)$_2$ | CF$_3$ | CH$_3$ | H | C(O)NHCH$_2$CH$_2$Cl |
| 3,5-(CF$_3$)$_2$ | CF$_3$ | CH$_3$ | H | C(O)NHCH$_2$CF$_3$ |
| 3,5-(CF$_3$)$_2$ | CF$_3$ | CF$_3$ | H | C(O)Pr-i |
| 3,5-(CF$_3$)$_2$ | CF$_3$ | CN | H | H |
| 3,5-(CF$_3$)$_2$ | CF$_3$ | CN | H | C(O)Pr-i |
| 3,5-(CF$_3$)$_2$ | CF$_3$ | CN | H | C(O)Pr-c |
| 3,5-(CF$_3$)$_2$ | CF$_3$ | CN | H | C(O)CH$_2$CF$_3$ |
| 3,5-(CF$_3$)$_2$ | CF$_3$ | CN | H | C(O)NHEt |
| 3,5-(CF$_3$)$_2$ | CF$_2$Cl | H | H | H |
| 3,5-(CF$_3$)$_2$ | CF$_2$Cl | H | H | C(O)Et |
| 3,5-(CF$_3$)$_2$ | CF$_2$Cl | H | H | C(O)Pr-n |
| 3,5-(CF$_3$)$_2$ | CF$_2$Cl | H | H | C(O)Pr-i |
| 3,5-(CF$_3$)$_2$ | CF$_2$Cl | H | H | C(O)Pr-c |
| 3,5-(CF$_3$)$_2$ | CF$_2$Cl | H | H | C(O)CH$_2$Pr-c |
| 3,5-(CF$_3$)$_2$ | CF$_2$Cl | H | H | C(O)CF$_3$ |

TABLE 2-continued

| | | | | |
|---|---|---|---|---|
| 3,5-(CF₃)₂ | CF₂Cl | H | H | C(O)CH₂CH₂Cl |
| 3,5-(CF₃)₂ | CF₂Cl | H | H | C(O)CH₂CF₃ |
| 3,5-(CF₃)₂ | CF₂Cl | H | H | C(O)CF₂CHF₂ |
| 3,5-(CF₃)₂ | CF₂Cl | H | H | C(O)CF₂CF₃ |
| 3,5-(CF₃)₂ | CF₂Cl | H | H | C(O)CH₂CH₂SCH₃ |
| 3,5-(CF₃)₂ | CF₂Cl | H | H | C(O)(Ph-2,4-F₂) |
| 3,5-(CF₃)₂ | CF₂Cl | H | H | C(O)NHEt |
| 3,5-(CF₃)₂ | CF₂Cl | H | H | C(O)NHPr-i |
| 3,5-(CF₃)₂ | CF₂Cl | H | H | C(O)NHCH₂CF₃ |
| 3,5-(CF₃)₂ | CF₂Cl | CH₃ | H | H |
| 3,5-(CF₃)₂ | CF₂Cl | CH₃ | H | C(O)Et |
| 3,5-(CF₃)₂ | CF₂Cl | CH₃ | H | C(O)Pr-n |
| 3,5-(CF₃)₂ | CF₂Cl | CH₃ | H | C(O)Pr-i |
| 3,5-(CF₃)₂ | CF₂Cl | CH₃ | H | C(O)Pr-c |
| 3,5-(CF₃)₂ | CF₂Cl | CH₃ | H | C(O)CH₂CF₃ |
| 3,5-(CF₃)₂ | CF₂Cl | CN | H | H |
| 3,5-(CF₃)₂ | CF₂Cl | CN | H | C(O)Pr-c |
| 3,5-(CF₃)₂ | CF₂Cl | CN | H | C(O)CH₂CF₃ |
| 3,5-(CF₃)₂ | CF₂Br | H | H | C(O)Pr-i |
| 3,5-(CF₃)₂ | CF₂Br | H | H | C(O)Pr-c |
| 3,5-(CF₃)₂ | CF₂Br | H | H | C(O)CH₂CF₃ |
| 3,5-(CF₃)₂ | CF₂Br | CH₃ | H | C(O)Pr-c |
| 3,5-(CF₃)₂ | CF₂Br | CH₃ | H | C(O)CH₂CF₃ |
| 3,5-(CF₃)₂ | CH₂CHF₂ | H | H | C(O)Pr-i |
| 3,5-(CF₃)₂ | CH₂CHF₂ | H | H | C(O)Pr-c |
| 3,5-(CF₃)₂ | CH₂CHF₂ | H | H | C(O)CH₂CF₃ |
| 3,5-(CF₃)₂ | CH₂CHF₂ | CH₃ | H | C(O)Pr-c |
| 3,5-(CF₃)₂ | CH₂CHF₂ | CH₃ | H | C(O)CH₂CF₃ |
| 3,5-(CF₃)₂ | CH₂CF₃ | CH₃ | H | C(O)CH₂CF₃ |
| 3,5-(CF₃)₂ | CF₂OCH₃ | H | H | C(O)Pr-i |
| 3,5-(CF₃)₂ | CF₂SCH₃ | H | H | C(O)Pr-c |
| 3,5-(CF₃)₂ | T-3 | H | H | C(O)CH₂CF₃ |
| 3-Cl-5-CF₂CF₃ | CF₃ | H | H | C(O)Pr-i |
| 3-Cl-5-CF₂CF₃ | CF₃ | H | H | C(O)Pr-c |
| 3-Cl-5-CF₂CF₃ | CF₃ | H | H | C(O)CH₂CF₃ |
| 3-Cl-5-CF₂CF₃ | CF₃ | CH₃ | H | C(O)Pr-c |
| 3-Cl-5-CF₂CF₃ | CF₃ | CH₃ | H | C(O)CH₂CF₃ |
| 3-Br-5-CF₂CF₃ | CF₃ | H | H | C(O)Pr-i |
| 3-Br-5-CF₂CF₃ | CF₃ | H | H | C(O)Pr-c |
| 3-Br-5-CF₂CF₃ | CF₃ | H | H | C(O)CH₂CF₃ |
| 3-Br-5-CF₂CF₃ | CF₃ | CH₃ | H | C(O)Pr-c |
| 3-Br-5-CF₂CF₃ | CF₃ | CH₃ | H | C(O)CH₂CF₃ |
| 3-CH₃-5-CF₂CF₃ | CF₃ | CH₃ | H | C(O)Pr-c |
| 3-Cl-5-CF₂CF₂CF₃ | CF₃ | CH₃ | H | C(O)CH₂CF₃ |
| 3-Br-5-CF₂CF₂CF₃ | CF₃ | H | H | C(O)Pr-i |
| 3-CH₃-5-CF₂CF₂CF₃ | CF₃ | H | H | C(O)Pr-c |
| 3-Cl-5-CF(CF₃)₂ | CF₃ | H | H | C(O)CH₂CF₃ |
| 3-Br-5-CF(CF₃)₂ | CF₃ | CH₃ | H | C(O)Pr-c |
| 3-CH₃-5-CF(CF₃)₂ | CF₃ | CH₃ | H | C(O)CH₂CF₃ |
| 3-Cl-5-CH₂OCH₃ | CF₃ | H | H | C(O)Pr-i |
| 3-Cl-5-CH₂OCH₂CF₃ | CF₃ | H | H | C(O)Pr-c |
| 3-Cl-5-C(CF₃)₂OH | CF₃ | H | H | C(O)CH₂CF₃ |
| 3-Br-5-C(CF₃)₂OH | CF₃ | CH₃ | H | C(O)Pr-c |
| 3-CH₃-5-C(CF₃)₂OH | CF₃ | CH₃ | H | C(O)CH₂CF₃ |
| 3,5-[C(CF₃)₂OH]₂ | CF₃ | H | H | C(O)Pr-i |
| 3-Cl-5-C(CF₃)₂OCH₃ | CF₃ | H | H | C(O)Pr-c |
| 3-Br-5-C(CF₃)₂OCH₃ | CF₃ | H | H | C(O)CH₂CF₃ |
| 3-CH₃-5-C(CF₃)₂OCH₃ | CF₃ | CH₃ | H | C(O)Pr-c |
| 3,5-[C(CF₃)₂OCH₃]₂ | CF₃ | CH₃ | H | C(O)CH₂CF₃ |
| 3-CF₃-5-CH₂SCH₃ | CF₃ | H | H | C(O)Pr-i |
| 3-CF₃-5-CH₂S(O)CH₃ | CF₃ | H | H | C(O)Pr-c |
| 3-CF₃-5-CH₂SO₂CH₃ | CF₃ | H | H | C(O)CH₂CF₃ |
| 3-Cl-4-OCH₃ | CF₃ | CH₃ | H | C(O)Pr-c |
| 3-Cl-5-OCH₃ | CF₃ | CH₃ | H | C(O)CH₂CF₃ |
| 3-Br-5-OCH₃ | CF₃ | H | H | C(O)Pr-i |
| 3-CF₃-5-OCH₃ | CF₃ | H | H | C(O)Et |
| 3-CF₃-5-OCH₃ | CF₃ | H | H | C(O)Pr-n |
| 3-CF₃-5-OCH₃ | CF₃ | H | H | C(O)Pr-i |
| 3-CF₃-5-OCH₃ | CF₃ | H | H | C(O)Pr-c |
| 3-CF₃-5-OCH₃ | CF₃ | H | H | C(O)CH₂Pr-c |
| 3-CF₃-5-OCH₃ | CF₃ | H | H | C(O)CH₂CH₂Cl |
| 3-CF₃-5-OCH₃ | CF₃ | H | H | C(O)CH₂CF₃ |
| 3-CF₃-5-OCH₃ | CF₃ | CH₃ | H | C(O)Pr-i |
| 3-CF₃-5-OCH₃ | CF₃ | CH₃ | H | C(O)Pr-c |
| 3-CF₃-5-OCH₃ | CF₃ | CH₃ | H | C(O)CH₂CF₃ |
| 3-CF₃-5-OCH₃ | CF₂Cl | H | H | C(O)Pr-c |
| 3-F-4-OCHF₂ | CF₃ | H | H | C(O)CH₂CF₃ |
| 3-Cl-4-OCHF₂ | CF₃ | CH₃ | H | C(O)Pr-c |
| 3-Cl-5-OCHF₂ | CHF₂ | CH₃ | H | C(O)CH₂CF₃ |
| 3-Cl-5-OCHF₂ | CF₃ | H | H | H |

TABLE 2-continued

| | | | | |
|---|---|---|---|---|
| 3-Cl-5-OCHF$_2$ | CF$_3$ | H | H | C(O)Et |
| 3-Cl-5-OCHF$_2$ | CF$_3$ | H | H | C(O)Pr-n |
| 3-Cl-5-OCHF$_2$ | CF$_3$ | H | H | C(O)Pr-i |
| 3-Cl-5-OCHF$_2$ | CF$_3$ | H | H | C(O)Pr-c |
| 3-Cl-5-OCHF$_2$ | CF$_3$ | H | H | C(O)CH$_2$Pr-c |
| 3-Cl-5-OCHF$_2$ | CF$_3$ | H | H | C(O)CF$_3$ |
| 3-Cl-5-OCHF$_2$ | CF$_3$ | H | H | C(O)CH$_2$CH$_2$Cl |
| 3-Cl-5-OCHF$_2$ | CF$_3$ | H | H | C(O)CH$_2$CF$_3$ |
| 3-Cl-5-OCHF$_2$ | CF$_3$ | H | H | C(O)CF$_2$CHF$_2$ |
| 3-Cl-5-OCHF$_2$ | CF$_3$ | H | H | C(O)CF$_2$CF$_3$ |
| 3-Cl-5-OCHF$_2$ | CF$_3$ | H | H | C(O)CH$_2$CH$_2$SCH$_3$ |
| 3-Cl-5-OCHF$_2$ | CF$_3$ | H | H | C(O)(Ph-2,4-F$_2$) |
| 3-Cl-5-OCHF$_2$ | CF$_3$ | H | H | C(O)NHEt |
| 3-Cl-5-OCHF$_2$ | CF$_3$ | H | H | C(O)NHPr-i |
| 3-Cl-5-OCHF$_2$ | CF$_3$ | H | H | C(O)NHCH$_2$CF$_3$ |
| 3-Cl-5-OCHF$_2$ | CF$_3$ | CH$_3$ | H | H |
| 3-Cl-5-OCHF$_2$ | CF$_3$ | CH$_3$ | H | C(O)Et |
| 3-Cl-5-OCHF$_2$ | CF$_3$ | CH$_3$ | H | C(O)Pr-n |
| 3-Cl-5-OCHF$_2$ | CF$_3$ | CH$_3$ | H | C(O)Pr-i |
| 3-Cl-5-OCHF$_2$ | CF$_3$ | CH$_3$ | H | C(O)Pr-c |
| 3-Cl-5-OCHF$_2$ | CF$_3$ | CH$_3$ | H | C(O)CH$_2$CF$_3$ |
| 3-Cl-5-OCHF$_2$ | CF$_3$ | CN | H | H |
| 3-Cl-5-OCHF$_2$ | CF$_3$ | CN | H | C(O)Pr-c |
| 3-Cl-5-OCHF$_2$ | CF$_3$ | CN | H | C(O)CH$_2$CF$_3$ |
| 3-Cl-5-OCHF$_2$ | CF$_2$Cl | H | H | C(O)Et |
| 3-Cl-5-OCHF$_2$ | CF$_2$Cl | H | H | C(O)Pr-n |
| 3-Cl-5-OCHF$_2$ | CF$_2$Cl | H | H | C(O)Pr-i |
| 3-Cl-5-OCHF$_2$ | CF$_2$Cl | H | H | C(O)Pr-c |
| 3-Cl-5-OCHF$_2$ | CF$_2$Cl | H | H | C(O)CH$_2$Pr-c |
| 3-Cl-5-OCHF$_2$ | CF$_2$Cl | H | H | C(O)CH$_2$CH$_2$Cl |
| 3-Cl-5-OCHF$_2$ | CF$_2$Cl | H | H | C(O)CH$_2$CF$_3$ |
| 3-Cl-5-OCHF$_2$ | CF$_2$Cl | CH$_3$ | H | C(O)Pr-i |
| 3-Cl-5-OCHF$_2$ | CF$_2$Cl | CH$_3$ | H | C(O)Pr-c |
| 3-Cl-5-OCHF$_2$ | CF$_2$Cl | CH$_3$ | H | C(O)CH$_2$CF$_3$ |
| 3-Cl-5-OCHF$_2$ | CF$_2$Br | H | H | C(O)Pr-i |
| 3-Cl-5-OCHF$_2$ | CF$_2$CHF$_2$ | H | H | C(O)Pr-c |
| 3-Br-4-OCHF$_2$ | CF$_3$ | H | H | C(O)CH$_2$CF$_3$ |
| 3-Br-5-OCHF$_2$ | CHF$_2$ | CH$_3$ | H | C(O)Pr-c |
| 3-Br-5-OCHF$_2$ | CF$_3$ | H | H | H |
| 3-Br-5-OCHF$_2$ | CF$_3$ | H | H | C(O)Et |
| 3-Br-5-OCHF$_2$ | CF$_3$ | H | H | C(O)Pr-n |
| 3-Br-5-OCHF$_2$ | CF$_3$ | H | H | C(O)Pr-i |
| 3-Br-5-OCHF$_2$ | CF$_3$ | H | H | C(O)Pr-c |
| 3-Br-5-OCHF$_2$ | CF$_3$ | H | H | C(O)CH$_2$Pr-c |
| 3-Br-5-OCHF$_2$ | CF$_3$ | H | H | C(O)CF$_3$ |
| 3-Br-5-OCHF$_2$ | CF$_3$ | H | H | C(O)CH$_2$CH$_2$Cl |
| 3-Br-5-OCHF$_2$ | CF$_3$ | H | H | C(O)CH$_2$CF$_3$ |
| 3-Br-5-OCHF$_2$ | CF$_3$ | H | H | C(O)CF$_2$CHF$_2$ |
| 3-Br-5-OCHF$_2$ | CF$_3$ | H | H | C(O)CF$_2$CF$_3$ |
| 3-Br-5-OCHF$_2$ | CF$_3$ | H | H | C(O)CH$_2$CH$_2$SCH$_3$ |
| 3-Br-5-OCHF$_2$ | CF$_3$ | H | H | C(O)(Ph-2,4-F$_2$) |
| 3-Br-5-OCHF$_2$ | CF$_3$ | H | H | C(O)NHEt |
| 3-Br-5-OCHF$_2$ | CF$_3$ | H | H | C(O)NHPr-i |
| 3-Br-5-OCHF$_2$ | CF$_3$ | H | H | C(O)NHCH$_2$CF$_3$ |
| 3-Br-5-OCHF$_2$ | CF$_3$ | CH$_3$ | H | H |
| 3-Br-5-OCHF$_2$ | CF$_3$ | CH$_3$ | H | C(O)Et |
| 3-Br-5-OCHF$_2$ | CF$_3$ | CH$_3$ | H | C(O)Pr-n |
| 3-Br-5-OCHF$_2$ | CF$_3$ | CH$_3$ | H | C(O)Pr-i |
| 3-Br-5-OCHF$_2$ | CF$_3$ | CH$_3$ | H | C(O)Pr-c |
| 3-Br-5-OCHF$_2$ | CF$_3$ | CH$_3$ | H | C(O)CH$_2$CF$_3$ |
| 3-Br-5-OCHF$_2$ | CF$_3$ | CN | H | H |
| 3-Br-5-OCHF$_2$ | CF$_3$ | CN | H | C(O)Pr-c |
| 3-Br-5-OCHF$_2$ | CF$_3$ | CN | H | C(O)CH$_2$CF$_3$ |
| 3-Br-5-OCHF$_2$ | CF$_2$Cl | H | H | C(O)Et |
| 3-Br-5-OCHF$_2$ | CF$_2$Cl | H | H | C(O)Pr-n |
| 3-Br-5-OCHF$_2$ | CF$_2$Cl | H | H | C(O)Pr-i |
| 3-Br-5-OCHF$_2$ | CF$_2$Cl | H | H | C(O)Pr-c |
| 3-Br-5-OCHF$_2$ | CF$_2$Cl | H | H | C(O)CH$_2$Pr-c |
| 3-Br-5-OCHF$_2$ | CF$_2$Cl | H | H | C(O)CH$_2$CH$_2$Cl |
| 3-Br-5-OCHF$_2$ | CF$_2$Cl | H | H | C(O)CH$_2$CF$_3$ |
| 3-Br-5-OCHF$_2$ | CF$_2$Cl | CH$_3$ | H | C(O)Pr-i |
| 3-Br-5-OCHF$_2$ | CF$_2$Cl | CH$_3$ | H | C(O)Pr-c |
| 3-Br-5-OCHF$_2$ | CF$_2$Cl | CH$_3$ | H | C(O)CH$_2$CF$_3$ |
| 3-Br-5-OCHF$_2$ | CF$_2$Br | CH$_3$ | H | C(O)CH$_2$CF$_3$ |
| 3-Br-5-OCHF$_2$ | CF$_2$CHF$_2$ | H | H | C(O)Pr-i |
| 3-CH$_3$-5-OCHF$_2$ | CF$_3$ | H | H | C(O)Pr-c |
| 3-CF$_3$-5-OCHF$_2$ | CHF$_2$ | H | H | C(O)CH$_2$CF$_3$ |
| 3-CF$_3$-5-OCHF$_2$ | CF$_3$ | H | H | H |
| 3-CF$_3$-5-OCHF$_2$ | CF$_3$ | H | H | C(O)Et |
| 3-CF$_3$-5-OCHF$_2$ | CF$_3$ | H | H | C(O)Pr-n |

TABLE 2-continued

| | | | | |
|---|---|---|---|---|
| 3-CF₃-5-OCHF₂ | CF₃ | H | H | C(O)Pr-i |
| 3-CF₃-5-OCHF₂ | CF₃ | H | H | C(O)Pr-c |
| 3-CF₃-5-OCHF₂ | CF₃ | H | H | C(O)CH₂Pr-c |
| 3-CF₃-5-OCHF₂ | CF₃ | H | H | C(O)CF₃ |
| 3-CF₃-5-OCHF₂ | CF₃ | H | H | C(O)CH₂CH₂Cl |
| 3-CF₃-5-OCHF₂ | CF₃ | H | H | C(O)CH₂CF₃ |
| 3-CF₃-5-OCHF₂ | CF₃ | H | H | C(O)CF₂CHF₂ |
| 3-CF₃-5-OCHF₂ | CF₃ | H | H | C(O)CF₂CF₃ |
| 3-CF₃-5-OCHF₂ | CF₃ | H | H | C(O)CH₂CH₂SCH₃ |
| 3-CF₃-5-OCHF₂ | CF₃ | H | H | C(O)(Ph-2,4-F₂) |
| 3-CF₃-5-OCHF₂ | CF₃ | H | H | C(O)NHEt |
| 3-CF₃-5-OCHF₂ | CF₃ | H | H | C(O)NHPr-i |
| 3-CF₃-5-OCHF₂ | CF₃ | H | H | C(O)NHCH₂CF₃ |
| 3-CF₃-5-OCHF₂ | CF₃ | CH₃ | H | H |
| 3-CF₃-5-OCHF₂ | CF₃ | CH₃ | H | C(O)Et |
| 3-CF₃-5-OCHF₂ | CF₃ | CH₃ | H | C(O)Pr-n |
| 3-CF₃-5-OCHF₂ | CF₃ | CH₃ | H | C(O)Pr-i |
| 3-CF₃-5-OCHF₂ | CF₃ | CH₃ | H | C(O)Pr-c |
| 3-CF₃-5-OCHF₂ | CF₃ | CH₃ | H | C(O)CH₂CF₃ |
| 3-CF₃-5-OCHF₂ | CF₃ | CN | H | H |
| 3-CF₃-5-OCHF₂ | CF₃ | CN | H | C(O)Pr-c |
| 3-CF₃-5-OCHF₂ | CF₃ | CN | H | C(O)CH₂CF₃ |
| 3-CF₃-5-OCHF₂ | CF₂Cl | H | H | C(O)Et |
| 3-CF₃-5-OCHF₂ | CF₂Cl | H | H | C(O)Pr-n |
| 3-CF₃-5-OCHF₂ | CF₂Cl | H | H | C(O)Pr-i |
| 3-CF₃-5-OCHF₂ | CF₂Cl | H | H | C(O)Pr-c |
| 3-CF₃-5-OCHF₂ | CF₂Cl | H | H | C(O)CH₂Pr-c |
| 3-CF₃-5-OCHF₂ | CF₂Cl | H | H | C(O)CH₂CH₂Cl |
| 3-CF₃-5-OCHF₂ | CF₂Cl | H | H | C(O)CH₂CF₃ |
| 3-CF₃-5-OCHF₂ | CF₂Cl | CH₃ | H | C(O)Pr-i |
| 3-CF₃-5-OCHF₂ | CF₂Cl | CH₃ | H | C(O)Pr-c |
| 3-CF₃-5-OCHF₂ | CF₂Cl | CH₃ | H | C(O)CH₂CF₃ |
| 3-CF₃-5-OCHF₂ | CF₂Br | CH₃ | H | C(O)Pr-c |
| 3-CF₃-5-OCHF₂ | CH₂CHF₂ | CH₃ | H | C(O)CH₂CF₃ |
| 3,5-(OCHF₂)₂ | CF₃ | H | H | C(O)Pr-i |
| 3-F-4-OCF₃ | CF₃ | H | H | C(O)Pr-c |
| 3-Cl-4-OCF₃ | CF₃ | H | H | C(O)CH₂CF₃ |
| 3-Cl-5-OCF₃ | CHF₂ | CH₃ | H | C(O)Pr-c |
| 3-Cl-5-OCF₃ | CF₃ | H | H | H |
| 3-Cl-5-OCF₃ | CF₃ | H | H | C(O)Et |
| 3-Cl-5-OCF₃ | CF₃ | H | H | C(O)Pr-n |
| 3-Cl-5-OCF₃ | CF₃ | H | H | C(O)Pr-i |
| 3-Cl-5-OCF₃ | CF₃ | H | H | C(O)Pr-c |
| 3-Cl-5-OCF₃ | CF₃ | H | H | C(O)CH₂Pr-c |
| 3-Cl-5-OCF₃ | CF₃ | H | H | C(O)CF₃ |
| 3-Cl-5-OCF₃ | CF₃ | H | H | C(O)CH₂CH₂Cl |
| 3-Cl-5-OCF₃ | CF₃ | H | H | C(O)CH₂CF₃ |
| 3-Cl-5-OCF₃ | CF₃ | H | H | C(O)CH₂CHF₂ |
| 3-Cl-5-OCF₃ | CF₃ | H | H | C(O)CF₂CF₃ |
| 3-Cl-5-OCF₃ | CF₃ | H | H | C(O)CH₂CH₂SCH₃ |
| 3-Cl-5-OCF₃ | CF₃ | H | H | C(O)(Ph-2,4-F₂) |
| 3-Cl-5-OCF₃ | CF₃ | H | H | C(O)NHEt |
| 3-Cl-5-OCF₃ | CF₃ | H | H | C(O)NHPr-i |
| 3-Cl-5-OCF₃ | CF₃ | H | H | C(O)NHCH₂CF₃ |
| 3-Cl-5-OCF₃ | CF₃ | CH₃ | H | H |
| 3-Cl-5-OCF₃ | CF₃ | CH₃ | H | C(O)Et |
| 3-Cl-5-OCF₃ | CF₃ | CH₃ | H | C(O)Pr-n |
| 3-Cl-5-OCF₃ | CF₃ | CH₃ | H | C(O)Pr-i |
| 3-Cl-5-OCF₃ | CF₃ | CH₃ | H | C(O)Pr-c |
| 3-Cl-5-OCF₃ | CF₃ | CH₃ | H | C(O)CH₂CF₃ |
| 3-Cl-5-OCF₃ | CF₃ | CN | H | H |
| 3-Cl-5-OCF₃ | CF₃ | CN | H | C(O)Pr-c |
| 3-Cl-5-OCF₃ | CF₃ | CN | H | C(O)CH₂CF₃ |
| 3-Cl-5-OCF₃ | CF₂Cl | H | H | C(O)Et |
| 3-Cl-5-OCF₃ | CF₂Cl | H | H | C(O)Pr-n |
| 3-Cl-5-OCF₃ | CF₂Cl | H | H | C(O)Pr-i |
| 3-Cl-5-OCF₃ | CF₂Cl | H | H | C(O)Pr-c |
| 3-Cl-5-OCF₃ | CF₂Cl | H | H | C(O)CH₂Pr-c |
| 3-Cl-5-OCF₃ | CF₂Cl | H | H | C(O)CH₂CH₂Cl |
| 3-Cl-5-OCF₃ | CF₂Cl | H | H | C(O)CH₂CF₃ |
| 3-Cl-5-OCF₃ | CF₂Cl | CH₃ | H | C(O)Pr-i |
| 3-Cl-5-OCF₃ | CF₂Cl | CH₃ | H | C(O)Pr-c |
| 3-Cl-5-OCF₃ | CF₂Cl | CH₃ | H | C(O)CH₂CF₃ |
| 3-Cl-5-OCF₃ | CF₂Br | CH₃ | H | C(O)CH₂CF₃ |
| 3-Cl-5-OCF₃ | CF₂CHF₂ | H | H | C(O)Pr-i |
| 3-Br-4-OCF₃ | CF₃ | H | H | C(O)Pr-c |
| 3-Br-5-OCF₃ | CHF₂ | H | H | C(O)CH₂CF₃ |
| 3-Br-5-OCF₃ | CF₃ | H | H | H |
| 3-Br-5-OCF₃ | CF₃ | H | H | C(O)Et |
| 3-Br-5-OCF₃ | CF₃ | H | H | C(O)Pr-n |

TABLE 2-continued

| | | | | |
|---|---|---|---|---|
| 3-Br-5-OCF$_3$ | CF$_3$ | H | H | C(O)Pr-i |
| 3-Br-5-OCF$_3$ | CF$_3$ | H | H | C(O)Pr-c |
| 3-Br-5-OCF$_3$ | CF$_3$ | H | H | C(O)CH$_2$Pr-c |
| 3-Br-5-OCF$_3$ | CF$_3$ | H | H | C(O)CF$_3$ |
| 3-Br-5-OCF$_3$ | CF$_3$ | H | H | C(O)CH$_2$CH$_2$Cl |
| 3-Br-5-OCF$_3$ | CF$_3$ | H | H | C(O)CH$_2$CF$_3$ |
| 3-Br-5-OCF$_3$ | CF$_3$ | H | H | C(O)CF$_2$CHF$_2$ |
| 3-Br-5-OCF$_3$ | CF$_3$ | H | H | C(O)CF$_2$CF$_3$ |
| 3-Br-5-OCF$_3$ | CF$_3$ | H | H | C(O)CH$_2$CH$_2$SCH$_3$ |
| 3-Br-5-OCF$_3$ | CF$_3$ | H | H | C(O)(Ph-2,4-F$_2$) |
| 3-Br-5-OCF$_3$ | CF$_3$ | H | H | C(O)NHEt |
| 3-Br-5-OCF$_3$ | CF$_3$ | H | H | C(O)NHPr-i |
| 3-Br-5-OCF$_3$ | CF$_3$ | H | H | C(O)NHCH$_2$CF$_3$ |
| 3-Br-5-OCF$_3$ | CF$_3$ | CH$_3$ | H | H |
| 3-Br-5-OCF$_3$ | CF$_3$ | CH$_3$ | H | C(O)Et |
| 3-Br-5-OCF$_3$ | CF$_3$ | CH$_3$ | H | C(O)Pr-n |
| 3-Br-5-OCF$_3$ | CF$_3$ | CH$_3$ | H | C(O)Pr-i |
| 3-Br-5-OCF$_3$ | CF$_3$ | CH$_3$ | H | C(O)Pr-c |
| 3-Br-5-OCF$_3$ | CF$_3$ | CH$_3$ | H | C(O)CH$_2$CF$_3$ |
| 3-Br-5-OCF$_3$ | CF$_3$ | CN | H | H |
| 3-Br-5-OCF$_3$ | CF$_3$ | CN | H | C(O)Pr-c |
| 3-Br-5-OCF$_3$ | CF$_3$ | CN | H | C(O)CH$_2$CF$_3$ |
| 3-Br-5-OCF$_3$ | CF$_2$Cl | H | H | C(O)Et |
| 3-Br-5-OCF$_3$ | CF$_2$Cl | H | H | C(O)Pr-n |
| 3-Br-5-OCF$_3$ | CF$_2$Cl | H | H | C(O)Pr-i |
| 3-Br-5-OCF$_3$ | CF$_2$Cl | H | H | C(O)Pr-c |
| 3-Br-5-OCF$_3$ | CF$_2$Cl | H | H | C(O)CH$_2$Pr-c |
| 3-Br-5-OCF$_3$ | CF$_2$Cl | H | H | C(O)CH$_2$CH$_2$Cl |
| 3-Br-5-OCF$_3$ | CF$_2$Cl | H | H | C(O)CH$_2$CF$_3$ |
| 3-Br-5-OCF$_3$ | CF$_2$Cl | CH$_3$ | H | C(O)Pr-i |
| 3-Br-5-OCF$_3$ | CF$_2$Cl | CH$_3$ | H | C(O)Pr-c |
| 3-Br-5-OCF$_3$ | CF$_2$Cl | CH$_3$ | H | C(O)CH$_2$CF$_3$ |
| 3-Br-5-OCF$_3$ | CF$_2$Br | CH$_3$ | H | C(O)Pr-c |
| 3-Br-5-OCF$_3$ | CF$_2$CHF$_2$ | CH$_3$ | H | C(O)CH$_2$CF$_3$ |
| 3-CH$_3$-5-OCF$_3$ | CF$_3$ | H | H | C(O)Pr-i |
| 3-CF$_3$-5-OCF$_3$ | CHF$_2$ | H | H | C(O)Pr-c |
| 3-CF$_3$-5-OCF$_3$ | CF$_3$ | H | H | H |
| 3-CF$_3$-5-OCF$_3$ | CF$_3$ | H | H | C(O)Et |
| 3-CF$_3$-5-OCF$_3$ | CF$_3$ | H | H | C(O)Pr-n |
| 3-CF$_3$-5-OCF$_3$ | CF$_3$ | H | H | C(O)Pr-i |
| 3-CF$_3$-5-OCF$_3$ | CF$_3$ | H | H | C(O)Pr-c |
| 3-CF$_3$-5-OCF$_3$ | CF$_3$ | H | H | C(O)CH$_2$Pr-c |
| 3-CF$_3$-5-OCF$_3$ | CF$_3$ | H | H | C(O)CF$_3$ |
| 3-CF$_3$-5-OCF$_3$ | CF$_3$ | H | H | C(O)CH$_2$CH$_2$Cl |
| 3-CF$_3$-5-OCF$_3$ | CF$_3$ | H | H | C(O)CH$_2$CF$_3$ |
| 3-CF$_3$-5-OCF$_3$ | CF$_3$ | H | H | C(O)CF$_2$CHF$_2$ |
| 3-CF$_3$-5-OCF$_3$ | CF$_3$ | H | H | C(O)CF$_2$CF$_3$ |
| 3-CF$_3$-5-OCF$_3$ | CF$_3$ | H | H | C(O)CH$_2$CH$_2$SCH$_3$ |
| 3-CF$_3$-5-OCF$_3$ | CF$_3$ | H | H | C(O)(Ph-2,4-F$_2$) |
| 3-CF$_3$-5-OCF$_3$ | CF$_3$ | H | H | C(O)NHEt |
| 3-CF$_3$-5-OCF$_3$ | CF$_3$ | H | H | C(O)NHPr-i |
| 3-CF$_3$-5-OCF$_3$ | CF$_3$ | H | H | C(O)NHCH$_2$CF$_3$ |
| 3-CF$_3$-5-OCF$_3$ | CF$_3$ | CH$_3$ | H | H |
| 3-CF$_3$-5-OCF$_3$ | CF$_3$ | CH$_3$ | H | C(O)Et |
| 3-CF$_3$-5-OCF$_3$ | CF$_3$ | CH$_3$ | H | C(O)Pr-n |
| 3-CF$_3$-5-OCF$_3$ | CF$_3$ | CH$_3$ | H | C(O)Pr-i |
| 3-CF$_3$-5-OCF$_3$ | CF$_3$ | CH$_3$ | H | C(O)Pr-c |
| 3-CF$_3$-5-OCF$_3$ | CF$_3$ | CH$_3$ | H | C(O)CH$_2$CF$_3$ |
| 3-CF$_3$-5-OCF$_3$ | CF$_3$ | CN | H | H |
| 3-CF$_3$-5-OCF$_3$ | CF$_3$ | CN | H | C(O)Pr-c |
| 3-CF$_3$-5-OCF$_3$ | CF$_3$ | CN | H | C(O)CH$_2$CF$_3$ |
| 3-CF$_3$-5-OCF$_3$ | CF$_2$Cl | H | H | C(O)Et |
| 3-CF$_3$-5-OCF$_3$ | CF$_2$Cl | H | H | C(O)Pr-n |
| 3-CF$_3$-5-OCF$_3$ | CF$_2$Cl | H | H | C(O)Pr-i |
| 3-CF$_3$-5-OCF$_3$ | CF$_2$Cl | H | H | C(O)Pr-c |
| 3-CF$_3$-5-OCF$_3$ | CF$_2$Cl | H | H | C(O)CH$_2$Pr-c |
| 3-CF$_3$-5-OCF$_3$ | CF$_2$Cl | H | H | C(O)CH$_2$CH$_2$Cl |
| 3-CF$_3$-5-OCF$_3$ | CF$_2$Cl | H | H | C(O)CH$_2$CF$_3$ |
| 3-CF$_3$-5-OCF$_3$ | CF$_2$Cl | CH$_3$ | H | C(O)Pr-i |
| 3-CF$_3$-5-OCF$_3$ | CF$_2$Cl | CH$_3$ | H | C(O)Pr-c |
| 3-CF$_3$-5-OCF$_3$ | CF$_2$Cl | CH$_3$ | H | C(O)CH$_2$CF$_3$ |
| 3-CF$_3$-5-OCF$_3$ | CF$_2$Br | H | H | C(O)CH$_2$CF$_3$ |
| 3-CF$_3$-5-OCF$_3$ | CF$_2$CHF$_2$ | CH$_3$ | H | C(O)Pr-c |
| 3-F-5-OCF$_2$Br | CF$_3$ | CH$_3$ | H | C(O)CH$_2$CF$_3$ |
| 3-Cl-5-OCF$_2$Br | CF$_3$ | H | H | C(O)Pr-i |
| 3-CH$_3$-5-OCF$_2$Br | CF$_3$ | H | H | C(O)Pr-c |
| 3-F-5-OCF$_2$CHF$_2$ | CF$_3$ | H | H | C(O)CH$_2$CF$_3$ |
| 3-Cl-5-OCF$_2$CHF$_2$ | CF$_3$ | CH$_3$ | H | C(O)Pr-c |
| 3-CH$_3$-5-OCF$_2$CHF$_2$ | CF$_3$ | CH$_3$ | H | C(O)CH$_2$CF$_3$ |
| 3-F-5-OCF$_2$CHFCl | CF$_3$ | H | H | C(O)Pr-i |

TABLE 2-continued

| | | | | |
|---|---|---|---|---|
| 3-Cl-5-OCF$_2$CHFCl | CF$_3$ | H | H | C(O)Pr-c |
| 3-Br-5-OCF$_2$CHFCl | CF$_3$ | H | H | C(O)CH$_2$CF$_3$ |
| 3-F-5-OCF$_2$CHFCF$_3$ | CF$_3$ | CH$_3$ | H | C(O)Pr-c |
| 3-Cl-5-OCF$_2$CHFCF$_3$ | CF$_3$ | CH$_3$ | H | C(O)CH$_2$CF$_3$ |
| 3-CH$_3$-5-OCF$_2$CHFCF$_3$ | CF$_3$ | H | H | C(O)Pr-i |
| 3-F-5-OCF$_2$CHFOCF$_3$ | CF$_3$ | H | H | C(O)Pr-c |
| 3-Cl-5-OCF$_2$CHFOCF$_3$ | CF$_3$ | H | H | C(O)CH$_2$CF$_3$ |
| 3-CH$_3$-5-OCF$_2$CHFOCF$_3$ | CF$_3$ | CH$_3$ | H | C(O)Pr-c |
| 3-CF$_2$OCF$_2$O-4 | CF$_3$ | CH$_3$ | H | C(O)CH$_2$CF$_3$ |
| 3-OCF$_2$O-4 | CF$_3$ | H | H | C(O)Pr-i |
| 3-OCF$_2$CF$_2$O-4 | CF$_3$ | H | H | C(O)Pr-c |
| 3-Cl-5-SCH$_3$ | CF$_3$ | H | H | C(O)CH$_2$CF$_3$ |
| 3-Cl-5-S(O)CH$_3$ | CF$_3$ | CH$_3$ | H | C(O)Pr-c |
| 3-Cl-5-SO$_2$CH$_3$ | CF$_3$ | CH$_3$ | H | C(O)CH$_2$CF$_3$ |
| 3-Br-5-SCH$_3$ | CF$_3$ | H | H | C(O)Pr-i |
| 3-Br-5-S(O)CH$_3$ | CF$_3$ | H | H | C(O)Pr-c |
| 3-Br-5-SO$_2$CH$_3$ | CF$_3$ | H | H | C(O)CH$_2$CF$_3$ |
| 3-Cl-5-SCF$_3$ | CHF$_2$ | CH$_3$ | H | C(O)Pr-c |
| 3-Cl-5-SCF$_3$ | CF$_3$ | H | H | H |
| 3-Cl-5-SCF$_3$ | CF$_3$ | H | H | C(O)Et |
| 3-Cl-5-SCF$_3$ | CF$_3$ | H | H | C(O)Pr-n |
| 3-Cl-5-SCF$_3$ | CF$_3$ | H | H | C(O)Pr-i |
| 3-Cl-5-SCF$_3$ | CF$_3$ | H | H | C(O)Pr-c |
| 3-Cl-5-SCF$_3$ | CF$_3$ | H | H | C(O)CH$_2$Pr-c |
| 3-Cl-5-SCF$_3$ | CF$_3$ | H | H | C(O)CF$_3$ |
| 3-Cl-5-SCF$_3$ | CF$_3$ | H | H | C(O)CH$_2$CH$_2$Cl |
| 3-Cl-5-SCF$_3$ | CF$_3$ | H | H | C(O)CH$_2$CF$_3$ |
| 3-Cl-5-SCF$_3$ | CF$_3$ | H | H | C(O)CF$_2$CHF$_2$ |
| 3-Cl-5-SCF$_3$ | CF$_3$ | H | H | C(O)CF$_2$CF$_3$ |
| 3-Cl-5-SCF$_3$ | CF$_3$ | H | H | C(O)CH$_2$CH$_2$SCH$_3$ |
| 3-Cl-5-SCF$_3$ | CF$_3$ | H | H | C(O)(Ph-2,4-F$_2$) |
| 3-Cl-5-SCF$_3$ | CF$_3$ | H | H | C(O)NHEt |
| 3-Cl-5-SCF$_3$ | CF$_3$ | H | H | C(O)NHPr-i |
| 3-Cl-5-SCF$_3$ | CF$_3$ | H | H | C(O)NHCH$_2$CF$_3$ |
| 3-Cl-5-SCF$_3$ | CF$_3$ | CH$_3$ | H | H |
| 3-Cl-5-SCF$_3$ | CF$_3$ | CH$_3$ | H | C(O)Et |
| 3-Cl-5-SCF$_3$ | CF$_3$ | CH$_3$ | H | C(O)Pr-n |
| 3-Cl-5-SCF$_3$ | CF$_3$ | CH$_3$ | H | C(O)Pr-i |
| 3-Cl-5-SCF$_3$ | CF$_3$ | CH$_3$ | H | C(O)Pr-c |
| 3-Cl-5-SCF$_3$ | CF$_3$ | CH$_3$ | H | C(O)CH$_2$CF$_3$ |
| 3-Cl-5-SCF$_3$ | CF$_3$ | CN | H | H |
| 3-Cl-5-SCF$_3$ | CF$_3$ | CN | H | C(O)Pr-c |
| 3-Cl-5-SCF$_3$ | CF$_3$ | CN | H | C(O)CH$_2$CF$_3$ |
| 3-Cl-5-SCF$_3$ | CF$_2$Cl | H | H | C(O)Et |
| 3-Cl-5-SCF$_3$ | CF$_2$Cl | H | H | C(O)Pr-n |
| 3-Cl-5-SCF$_3$ | CF$_2$Cl | H | H | C(O)Pr-i |
| 3-Cl-5-SCF$_3$ | CF$_2$Cl | H | H | C(O)Pr-c |
| 3-Cl-5-SCF$_3$ | CF$_2$Cl | H | H | C(O)CH$_2$Pr-c |
| 3-Cl-5-SCF$_3$ | CF$_2$Cl | H | H | C(O)CH$_2$CH$_2$Cl |
| 3-Cl-5-SCF$_3$ | CF$_2$Cl | H | H | C(O)CH$_2$CF$_3$ |
| 3-Cl-5-SCF$_3$ | CF$_2$Cl | CH$_3$ | H | C(O)Pr-i |
| 3-Cl-5-SCF$_3$ | CF$_2$Cl | CH$_3$ | H | C(O)Pr-c |
| 3-Cl-5-SCF$_3$ | CF$_2$Cl | CH$_3$ | H | C(O)CH$_2$CF$_3$ |
| 3-Cl-5-SCF$_3$ | CF$_2$Br | CH$_3$ | H | C(O)CH$_2$CF$_3$ |
| 3-Cl-5-SCF$_3$ | CF$_2$CHF$_2$ | H | H | C(O)Pr-i |
| 3-Cl-5-S(O)CF$_3$ | CF$_3$ | H | H | C(O)Pr-i |
| 3-Cl-5-S(O)CF$_3$ | CF$_3$ | H | H | C(O)Pr-c |
| 3-Cl-5-S(O)CF$_3$ | CF$_3$ | H | H | C(O)CH$_2$CF$_3$ |
| 3-Cl-5-S(O)CF$_3$ | CF$_3$ | CH$_3$ | H | C(O)Pr-c |
| 3-Cl-5-S(O)CF$_3$ | CF$_3$ | CH$_3$ | H | C(O)CH$_2$CF$_3$ |
| 3-Cl-5-SO$_2$CF$_3$ | CF$_3$ | H | H | C(O)Pr-i |
| 3-Cl-5-SO$_2$CF$_3$ | CF$_3$ | H | H | C(O)Pr-c |
| 3-Cl-5-SO$_2$CF$_3$ | CF$_3$ | H | H | C(O)CH$_2$CF$_3$ |
| 3-Cl-5-SO$_2$CF$_3$ | CF$_3$ | CH$_3$ | H | C(O)Pr-c |
| 3-Cl-5-SO$_2$CF$_3$ | CF$_3$ | CH$_3$ | H | C(O)CH$_2$CF$_3$ |
| 3-Br-5-SCF$_3$ | CHF$_2$ | H | H | C(O)Pr-c |
| 3-Br-5-SCF$_3$ | CF$_3$ | H | H | H |
| 3-Br-5-SCF$_3$ | CF$_3$ | H | H | C(O)Et |
| 3-Br-5-SCF$_3$ | CF$_3$ | H | H | C(O)Pr-n |
| 3-Br-5-SCF$_3$ | CF$_3$ | H | H | C(O)Pr-i |
| 3-Br-5-SCF$_3$ | CF$_3$ | H | H | C(O)Pr-c |
| 3-Br-5-SCF$_3$ | CF$_3$ | H | H | C(O)CH$_2$Pr-c |
| 3-Br-5-SCF$_3$ | CF$_3$ | H | H | C(O)CF$_3$ |
| 3-Br-5-SCF$_3$ | CF$_3$ | H | H | C(O)CH$_2$CH$_2$Cl |
| 3-Br-5-SCF$_3$ | CF$_3$ | H | H | C(O)CH$_2$CF$_3$ |
| 3-Br-5-SCF$_3$ | CF$_3$ | H | H | C(O)CF$_2$CHF$_2$ |
| 3-Br-5-SCF$_3$ | CF$_3$ | H | H | C(O)CF$_2$CF$_3$ |
| 3-Br-5-SCF$_3$ | CF$_3$ | H | H | C(O)CH$_2$CH$_2$SCH$_3$ |
| 3-Br-5-SCF$_3$ | CF$_3$ | H | H | C(O)(Ph-2,4-F$_2$) |
| 3-Br-5-SCF$_3$ | CF$_3$ | H | H | C(O)NHEt |

TABLE 2-continued

| | | | | |
|---|---|---|---|---|
| 3-Br-5-SCF$_3$ | CF$_3$ | H | H | C(O)NHPr-i |
| 3-Br-5-SCF$_3$ | CF$_3$ | H | H | C(O)NHCH$_2$CF$_3$ |
| 3-Br-5-SCF$_3$ | CF$_3$ | CH$_3$ | H | H |
| 3-Br-5-SCF$_3$ | CF$_3$ | CH$_3$ | H | C(O)Et |
| 3-Br-5-SCF$_3$ | CF$_3$ | CH$_3$ | H | C(O)Pr-n |
| 3-Br-5-SCF$_3$ | CF$_3$ | CH$_3$ | H | C(O)Pr-i |
| 3-Br-5-SCF$_3$ | CF$_3$ | CH$_3$ | H | C(O)Pr-c |
| 3-Br-5-SCF$_3$ | CF$_3$ | CH$_3$ | H | C(O)CH$_2$CF$_3$ |
| 3-Br-5-SCF$_3$ | CF$_3$ | CN | H | H |
| 3-Br-5-SCF$_3$ | CF$_3$ | CN | H | C(O)Pr-c |
| 3-Br-5-SCF$_3$ | CF$_3$ | CN | H | C(O)CH$_2$CF$_3$ |
| 3-Br-5-SCF$_3$ | CF$_2$Cl | H | H | C(O)Et |
| 3-Br-5-SCF$_3$ | CF$_2$Cl | H | H | C(O)Pr-n |
| 3-Br-5-SCF$_3$ | CF$_2$Cl | H | H | C(O)Pr-i |
| 3-Br-5-SCF$_3$ | CF$_2$Cl | H | H | C(O)Pr-c |
| 3-Br-5-SCF$_3$ | CF$_2$Cl | H | H | C(O)CH$_2$Pr-c |
| 3-Br-5-SCF$_3$ | CF$_2$Cl | H | H | C(O)CH$_2$CH$_2$Cl |
| 3-Br-5-SCF$_3$ | CF$_2$Cl | H | H | C(O)CH$_2$CF$_3$ |
| 3-Br-5-SCF$_3$ | CF$_2$Cl | CH$_3$ | H | C(O)Pr-i |
| 3-Br-5-SCF$_3$ | CF$_2$Cl | CH$_3$ | H | C(O)Pr-c |
| 3-Br-5-SCF$_3$ | CF$_2$Cl | CH$_3$ | H | C(O)CH$_2$CF$_3$ |
| 3-Br-5-SCF$_3$ | CF$_2$Br | H | H | C(O)CH$_2$CF$_3$ |
| 3-Br-5-SCF$_3$ | CH$_2$CHF$_2$ | CH$_3$ | H | C(O)Pr-c |
| 3-Br-5-S(O)CF$_3$ | CF$_3$ | H | H | C(O)Pr-i |
| 3-Br-5-S(O)CF$_3$ | CF$_3$ | H | H | C(O)Pr-c |
| 3-Br-5-S(O)CF$_3$ | CF$_3$ | H | H | C(O)CH$_2$CF$_3$ |
| 3-Br-5-S(O)CF$_3$ | CF$_3$ | CH$_3$ | H | C(O)Pr-c |
| 3-Br-5-S(O)CF$_3$ | CF$_3$ | CH$_3$ | H | C(O)CH$_2$CF$_3$ |
| 3-Br-5-SO$_2$CF$_3$ | CF$_3$ | H | H | C(O)Pr-i |
| 3-Br-5-SO$_2$CF$_3$ | CF$_3$ | H | H | C(O)Pr-c |
| 3-Br-5-SO$_2$CF$_3$ | CF$_3$ | H | H | C(O)CH$_2$CF$_3$ |
| 3-Br-5-SO$_2$CF$_3$ | CF$_3$ | CH$_3$ | H | C(O)Pr-c |
| 3-Br-5-SO$_2$CF$_3$ | CF$_3$ | CH$_3$ | H | C(O)CH$_2$CF$_3$ |
| 3-Cl-5-SCF$_2$CHFCl | CF$_3$ | H | H | C(O)Pr-i |
| 3-Cl-5-SCF$_2$CHFCl | CF$_3$ | H | H | C(O)Pr-c |
| 3-Cl-5-SCF$_2$CHFCl | CF$_3$ | H | H | C(O)CH$_2$CF$_3$ |
| 3-Cl-5-SCF$_2$CHFCl | CF$_3$ | CH$_3$ | H | C(O)Pr-c |
| 3-Cl-5-SCF$_2$CHFCl | CF$_3$ | CH$_3$ | H | C(O)CH$_2$CF$_3$ |
| 3-Cl-5-S(O)CF$_2$CHFCl | CF$_3$ | CH$_3$ | H | C(O)CH$_2$CF$_3$ |
| 3-Cl-5-SO$_2$CF$_2$CHFCl | CF$_3$ | H | H | C(O)Pr-i |
| 3-Br-5-SCF$_2$CHFCl | CF$_3$ | H | H | C(O)Pr-i |
| 3-Br-5-SCF$_2$CHFCl | CF$_3$ | H | H | C(O)Pr-c |
| 3-Br-5-SCF$_2$CHFCl | CF$_3$ | H | H | C(O)CH$_2$CF$_3$ |
| 3-Br-5-SCH$_2$CHFCl | CF$_3$ | CH$_3$ | H | C(O)Pr-c |
| 3-Br-5-SCF$_2$CHFCl | CF$_3$ | CH$_3$ | H | C(O)CH$_2$CF$_3$ |
| 3-Br-5-S(O)CF$_2$CHFCl | CF$_3$ | H | H | C(O)Pr-c |
| 3-Br-5-SO$_2$CF$_2$CHFCl | CF$_3$ | H | H | C(O)CH$_2$CF$_3$ |
| 3-Cl-5-SPh | CF$_3$ | CH$_3$ | H | C(O)Pr-c |
| 3-Cl-5-S(O)Ph | CF$_3$ | CH$_3$ | H | C(O)CH$_2$CF$_3$ |
| 3-Cl-5-SO$_2$Ph | CF$_3$ | H | H | C(O)Pr-i |
| 3-NO$_2$-4-F | CF$_3$ | H | H | C(O)Pr-c |
| 2-F-5-NO$_2$ | CF$_3$ | H | H | C(O)CH$_2$CF$_3$ |
| 3-F-5-NO$_2$ | CF$_3$ | CH$_3$ | H | C(O)Pr-c |
| 3-NO$_2$-4-Cl | CF$_3$ | CH$_3$ | H | C(O)CH$_2$CF$_3$ |
| 3-Cl-5-NO$_2$ | CF$_3$ | H | H | C(O)Pr-i |
| 3-Cl-5-NO$_2$ | CF$_3$ | H | H | C(O)Pr-c |
| 3-Cl-5-NO$_2$ | CF$_3$ | H | H | C(O)CH$_2$CF$_3$ |
| 3-Cl-5-NO$_2$ | CF$_3$ | CH$_3$ | H | C(O)Pr-c |
| 3-Cl-5-NO$_2$ | CF$_3$ | CH$_3$ | H | C(O)CH$_2$CF$_3$ |
| 3-Br-5-NO$_2$ | CF$_3$ | H | H | C(O)Pr-i |
| 3-Br-5-NO$_2$ | CF$_3$ | H | H | C(O)Pr-c |
| 3-Br-5-NO$_2$ | CF$_3$ | H | H | C(O)CH$_2$CF$_3$ |
| 3-Br-5-NO$_2$ | CF$_3$ | CH$_3$ | H | C(O)Pr-c |
| 3-Br-5-NO$_2$ | CF$_3$ | CH$_3$ | H | C(O)CH$_2$CF$_3$ |
| 3-CH$_3$-5-NO$_2$ | CF$_3$ | H | H | C(O)Pr-i |
| 3-CF$_3$-4-NO$_2$ | CF$_3$ | H | H | C(O)Pr-c |
| 3-CF$_3$-5-NO$_2$ | CF$_3$ | H | H | C(O)Et |
| 3-CF$_3$-5-NO$_2$ | CF$_3$ | H | H | C(O)Pr-n |
| 3-CF$_3$-5-NO$_2$ | CF$_3$ | H | H | C(O)Pr-i |
| 3-CF$_3$-5-NO$_2$ | CF$_3$ | H | H | C(O)Pr-c |
| 3-CF$_3$-5-NO$_2$ | CF$_3$ | H | H | C(O)CH$_2$Pr-c |
| 3-CF$_3$-5-NO$_2$ | CF$_3$ | H | H | C(O)CH$_2$CH$_2$Cl |
| 3-CF$_3$-5-NO$_2$ | CF$_3$ | H | H | C(O)CH$_2$CF$_3$ |
| 3-CF$_3$-5-NO$_2$ | CF$_3$ | CH$_3$ | H | C(O)Pr-i |
| 3-CF$_3$-5-NO$_2$ | CF$_3$ | CH$_3$ | H | C(O)Pr-c |
| 3-CF$_3$-5-NO$_2$ | CF$_3$ | CH$_3$ | H | C(O)CH$_2$CF$_3$ |
| 3-CF$_3$-5-NO$_2$ | CF$_2$Cl | H | H | C(O)CH$_2$CF$_3$ |
| 3,5-(NO$_2$)$_2$ | CF$_3$ | CH$_3$ | H | C(O)Pr-c |
| 3-Cl-5-NHC(O)CF$_3$ | CF$_3$ | CH$_3$ | H | C(O)CH$_2$CF$_3$ |
| 3-Cl-5-N(CH$_3$)C(O)CF$_3$ | CF$_3$ | H | H | C(O)Pr-i |

TABLE 2-continued

| | | | | |
|---|---|---|---|---|
| 3-Cl-5-N(Et)C(O)CF$_3$ | CF$_3$ | H | H | C(O)Pr-c |
| 3-Cl-5-N(CH$_3$)C(O)CF$_2$Cl | CF$_3$ | H | H | C(O)CH$_2$CF$_3$ |
| 3-Cl-5-N(Et)C(O)CF$_2$Cl | CF$_3$ | CH$_3$ | H | C(O)Pr-c |
| 3-Cl-5-N(CH$_3$)C(O)CF$_2$Br | CF$_3$ | CH$_3$ | H | C(O)CH$_2$CF$_3$ |
| 3-Cl-5-N(Et)C(O)CF$_2$Br | CF$_3$ | H | H | C(O)Pr-i |
| 3-Cl-5-N(CH$_3$)SO$_2$CF$_3$ | CF$_3$ | H | H | C(O)Pr-c |
| 3-Cl-5-N(Et)SO$_2$CF$_3$ | CF$_3$ | H | H | C(O)CH$_2$CF$_3$ |
| 3-CF$_3$-5-NHC(O)CH$_3$ | CF$_3$ | CH$_3$ | H | C(O)Pr-c |
| 3-CF$_3$-5-N(CH$_3$)C(O)CH$_3$ | CF$_3$ | CH$_3$ | H | C(O)CH$_2$CF$_3$ |
| 3-CF$_3$-5-N(Et)C(O)CH$_3$ | CF$_3$ | H | H | C(O)Pr-i |
| 3-CF$_3$-5-NHC(O)CF$_3$ | CF$_3$ | H | H | C(O)Pr-c |
| 3-CF$_3$-5-N(CH$_3$)C(O)CF$_3$ | CF$_3$ | H | H | C(O)CH$_2$CF$_3$ |
| 3-CF$_3$-5-N(Et)C(O)CF$_3$ | CF$_3$ | CH$_3$ | H | C(O)Pr-c |
| 3-CF$_3$-5-N(CH$_3$)C(O)CF$_2$Cl | CF$_3$ | CH$_3$ | H | C(O)CH$_2$CF$_3$ |
| 3-CF$_3$-5-N(Et)C(O)CF$_2$Cl | CF$_3$ | H | H | C(O)Pr-i |
| 3-CF$_3$-5-N(CH$_3$)C(O)CF$_2$Br | CF$_3$ | H | H | C(O)Pr-c |
| 3-CF$_3$-5-N(Et)C(O)CF$_2$Br | CF$_3$ | H | H | C(O)CH$_2$CF$_3$ |
| 3-CF$_3$-5-N(CH$_3$)SO$_2$CF$_3$ | CF$_3$ | CH$_3$ | H | C(O)Pr-c |
| 3-CF$_3$-5-N(Et)SO$_2$CF$_3$ | CF$_3$ | CH$_3$ | H | C(O)CH$_2$CF$_3$ |
| 3-NO$_2$-5-NHC(O)CH$_3$ | CF$_3$ | H | H | C(O)Pr-i |
| 3-CN-4-F | CF$_3$ | H | H | C(O)Pr-c |
| 3-F-4-CN | CF$_3$ | H | H | C(O)CH$_2$CF$_3$ |
| 3-F-5-CN | CF$_3$ | CH$_3$ | H | C(O)Pr-c |
| 3-Cl-4-CN | CF$_3$ | CH$_3$ | H | C(O)CH$_2$CF$_3$ |
| 3-Cl-5-CN | CF$_3$ | H | H | C(O)Et |
| 3-Cl-5-CN | CF$_3$ | H | H | C(O)Pr-n |
| 3-Cl-5-CN | CF$_3$ | H | H | C(O)Pr-i |
| 3-Cl-5-CN | CF$_3$ | H | H | C(O)Pr-c |
| 3-Cl-5-CN | CF$_3$ | H | H | C(O)CH$_2$Pr-c |
| 3-Cl-5-CN | CF$_3$ | H | H | C(O)CH$_2$CH$_2$Cl |
| 3-Cl-5-CN | CF$_3$ | H | H | C(O)CH$_2$CF$_3$ |
| 3-Cl-5-CN | CF$_3$ | CH$_3$ | H | C(O)Pr-i |
| 3-Cl-5-CN | CF$_3$ | CH$_3$ | H | C(O)Pr-c |
| 3-Cl-5-CN | CF$_3$ | CH$_3$ | H | C(O)CH$_2$CF$_3$ |
| 3-Cl-5-CN | CF$_2$Cl | H | H | C(O)Pr-i |
| 3-Br-5-CN | CF$_3$ | H | H | C(O)Et |
| 3-Br-5-CN | CF$_3$ | H | H | C(O)Pr-n |
| 3-Br-5-CN | CF$_3$ | H | H | C(O)Pr-i |
| 3-Br-5-CN | CF$_3$ | H | H | C(O)Pr-c |
| 3-Br-5-CN | CF$_3$ | H | H | C(O)CH$_2$Pr-c |
| 3-Br-5-CN | CF$_3$ | H | H | C(O)CH$_2$CH$_2$Cl |
| 3-Br-5-CN | CF$_3$ | H | H | C(O)CH$_2$CF$_3$ |
| 3-Br-5-CN | CF$_3$ | CH$_3$ | H | C(O)Pr-i |
| 3-Br-5-CN | CF$_3$ | CH$_3$ | H | C(O)Pr-c |
| 3-Br-5-CN | CF$_3$ | CH$_3$ | H | C(O)CH$_2$CF$_3$ |
| 3-Br-5-CN | CF$_2$Cl | H | H | C(O)Pr-c |
| 3-CH$_3$-5-CN | CF$_3$ | H | H | C(O)CH$_2$CF$_3$ |
| 3-CF$_3$-5-CN | CHF$_2$ | CH$_3$ | H | C(O)Pr-c |
| 3-CF$_3$-5-CN | CF$_3$ | H | H | H |
| 3-CF$_3$-5-CN | CF$_3$ | H | H | C(O)Et |
| 3-CF$_3$-5-CN | CF$_3$ | H | H | C(O)Pr-n |
| 3-CF$_3$-5-CN | CF$_3$ | H | H | C(O)Pr-i |
| 3-CF$_3$-5-CN | CF$_3$ | H | H | C(O)Pr-c |
| 3-CF$_3$-5-CN | CF$_3$ | H | H | C(O)CH$_2$Pr-c |
| 3-CF$_3$-5-CN | CF$_3$ | H | H | C(O)CF$_3$ |
| 3-CF$_3$-5-CN | CF$_3$ | H | H | C(O)CH$_2$CH$_2$Cl |
| 3-CF$_3$-5-CN | CF$_3$ | H | H | C(O)CH$_2$CF$_3$ |
| 3-CF$_3$-5-CN | CF$_3$ | H | H | C(O)CF$_2$CHF$_2$ |
| 3-CF$_3$-5-CN | CF$_3$ | H | H | C(O)CF$_2$CF$_3$ |
| 3-CF$_3$-5-CN | CF$_3$ | H | H | C(O)CH$_2$CH$_2$SCH$_3$ |
| 3-CF$_3$-5-CN | CF$_3$ | H | H | C(O)(Ph-2,4-F$_2$) |
| 3-CF$_3$-5-CN | CF$_3$ | H | H | C(O)NHEt |
| 3-CF$_3$-5-CN | CF$_3$ | H | H | C(O)NHPr-i |
| 3-CF$_3$-5-CN | CF$_3$ | H | H | C(O)NHCH$_2$CF$_3$ |
| 3-CF$_3$-5-CN | CF$_3$ | CH$_3$ | H | H |
| 3-CF$_3$-5-CN | CF$_3$ | CH$_3$ | H | C(O)Et |
| 3-CF$_3$-5-CN | CF$_3$ | CH$_3$ | H | C(O)Pr-n |
| 3-CF$_3$-5-CN | CF$_3$ | CH$_3$ | H | C(O)Pr-i |
| 3-CF$_3$-5-CN | CF$_3$ | CH$_3$ | H | C(O)Pr-c |
| 3-CF$_3$-5-CN | CF$_3$ | CH$_3$ | H | C(O)CH$_2$CF$_3$ |
| 3-CF$_3$-5-CN | CF$_3$ | CN | H | H |
| 3-CF$_3$-5-CN | CF$_3$ | CN | H | C(O)Pr-c |
| 3-CF$_3$-5-CN | CF$_3$ | CN | H | C(O)CH$_2$CF$_3$ |
| 3-CF$_3$-5-CN | CF$_2$Cl | H | H | C(O)Et |
| 3-CF$_3$-5-CN | CF$_2$Cl | H | H | C(O)Pr-n |
| 3-CF$_3$-5-CN | CF$_2$Cl | H | H | C(O)Pr-i |
| 3-CF$_3$-5-CN | CF$_2$Cl | H | H | C(O)Pr-c |
| 3-CF$_3$-5-CN | CF$_2$Cl | H | H | C(O)CH$_2$Pr-c |
| 3-CF$_3$-5-CN | CF$_2$Cl | H | H | C(O)CH$_2$CH$_2$Cl |
| 3-CF$_3$-5-CN | CF$_2$Cl | H | H | C(O)CH$_2$CF$_3$ |

TABLE 2-continued

| | | | | |
|---|---|---|---|---|
| 3-CF$_3$-5-CN | CF$_2$Cl | CH$_3$ | H | C(O)Pr-i |
| 3-CF$_3$-5-CN | CF$_2$Cl | CH$_3$ | H | C(O)Pr-c |
| 3-CF$_3$-5-CN | CF$_2$Cl | CH$_3$ | H | C(O)CH$_2$CF$_3$ |
| 3-CF$_3$-5-CN | CF$_2$Br | CH$_3$ | H | C(O)CH$_2$CF$_3$ |
| 3-CF$_3$-5-CN | CF$_2$CHF$_2$ | H | H | C(O)Pr-i |
| 3-NO$_2$-5-CN | CF$_3$ | H | H | C(O)Pr-c |
| 3,5-(CN)$_2$ | CF$_3$ | H | H | C(O)CH$_2$CF$_3$ |
| 3-F-5-C(O)OCH$_3$ | CF$_3$ | CH$_3$ | H | C(O)Pr-c |
| 3-Cl-5-C(O)OCH$_3$ | CF$_3$ | CH$_3$ | H | C(O)CH$_2$CF$_3$ |
| 3-Br-5-C(O)OCH$_3$ | CF$_3$ | H | H | C(O)Pr-i |
| 3-CF$_3$-5-C(O)OCH$_3$ | CF$_3$ | H | H | C(O)Pr-c |
| 3-NO$_2$-5-C(O)OCH$_3$ | CF$_3$ | H | H | C(O)CH$_2$CF$_3$ |
| 3-F-5-C(O)NH$_2$ | CF$_3$ | CH$_3$ | H | C(O)Pr-c |
| 3-F-5-C(O)NHCH$_3$ | CF$_3$ | CH$_3$ | H | C(O)CH$_2$CF$_3$ |
| 3-F-5-C(O)N(CH$_3$)$_2$ | CF$_3$ | H | H | C(O)Pr-i |
| 3-Cl-5-C(O)NH$_2$ | CF$_3$ | H | H | C(O)Pr-c |
| 3-Cl-5-C(O)NHCH$_3$ | CF$_3$ | H | H | C(O)CH$_2$CF$_3$ |
| 3-Cl-5-C(O)N(CH$_3$)$_2$ | CF$_3$ | CH$_3$ | H | C(O)Pr-c |
| 3-Br-5-C(O)NH$_2$ | CF$_3$ | CH$_3$ | H | C(O)CH$_2$CF$_3$ |
| 3-Br-5-C(O)NHCH$_3$ | CF$_3$ | H | H | C(O)Pr-i |
| 3-Br-5-C(O)N(CH$_3$)$_2$ | CF$_3$ | H | H | C(O)Pr-c |
| 3-CF$_3$-5-C(O)NH$_2$ | CF$_3$ | H | H | C(O)CH$_2$CF$_3$ |
| 3-CF$_3$-5-C(O)NHCH$_3$ | CF$_3$ | CH$_3$ | H | C(O)Pr-c |
| 3-CF$_3$-5-C(O)N(CH$_3$)$_2$ | CF$_3$ | CH$_3$ | H | C(O)CH$_2$CF$_3$ |
| 3-NO$_2$-5-C(O)NH$_2$ | CF$_3$ | H | H | C(O)Pr-i |
| 3-NO$_2$-5-C(O)NHCH$_3$ | CF$_3$ | H | H | C(O)Pr-c |
| 3-NO$_2$-5-C(O)N(CH$_3$)$_2$ | CF$_3$ | H | H | C(O)CH$_2$CF$_3$ |
| 3-Cl-5-SO$_2$OCH$_3$ | CF$_3$ | CH$_3$ | H | C(O)Pr-c |
| 3-CH$_3$-5-SO$_2$OCH$_3$ | CF$_3$ | CH$_3$ | H | C(O)CH$_2$CF$_3$ |
| 3-Cl-5-SO$_2$NH$_2$ | CF$_3$ | H | H | C(O)Pr-i |
| 3-CH$_3$-5-SO$_2$NH$_2$ | CF$_3$ | H | H | C(O)Pr-c |
| 3-Cl-5-SO$_2$NHCH$_3$ | CF$_3$ | H | H | C(O)CH$_2$CF$_3$ |
| 3-Cl-5-SO$_2$N(CH$_3$)$_2$ | CF$_3$ | CH$_3$ | H | C(O)Pr-c |
| 3-CH$_3$-5-Ph | CF$_3$ | CH$_3$ | H | C(O)CH$_2$CF$_3$ |
| 2-CH=CHCH=CH-3 | CF$_3$ | H | H | C(O)Pr-i |
| 3-CH=CHCH=CH-4 | CF$_3$ | H | H | C(O)Pr-c |
| 2,3,4-F$_3$ | CF$_3$ | H | H | C(O)CH$_2$CF$_3$ |
| 2,3,5-F$_3$ | CF$_3$ | CH$_3$ | H | C(O)Pr-c |
| 2,3,6-F$_3$ | CF$_3$ | CH$_3$ | H | C(O)CH$_2$CF$_3$ |
| 2,4,5-F$_3$ | CF$_3$ | H | H | C(O)Pr-i |
| 3,4,5-F$_3$ | CHF$_2$ | H | H | C(O)Pr-c |
| 3,4,5-F$_3$ | CF$_3$ | H | H | H |
| 3,4,5-F$_3$ | CF$_3$ | H | H | C(O)Et |
| 3,4,5-F$_3$ | CF$_3$ | H | H | C(O)Pr-n |
| 3,4,5-F$_3$ | CF$_3$ | H | H | C(O)Pr-i |
| 3,4,5-F$_3$ | CF$_3$ | H | H | C(O)Pr-c |
| 3,4,5-F$_3$ | CF$_3$ | H | H | C(O)CH$_2$Pr-c |
| 3,4,5-F$_3$ | CF$_3$ | H | H | C(O)CF$_3$ |
| 3,4,5-F$_3$ | CF$_3$ | H | H | C(O)CH$_2$CH$_2$Cl |
| 3,4,5-F$_3$ | CF$_3$ | H | H | C(O)CH$_2$CF$_3$ |
| 3,4,5-F$_3$ | CF$_3$ | H | H | C(O)CF$_2$CHF$_2$ |
| 3,4,5-F$_3$ | CF$_3$ | H | H | C(O)CF$_2$CF$_3$ |
| 3,4,5-F$_3$ | CF$_3$ | H | H | C(O)CH$_2$CH$_2$SCH$_3$ |
| 3,4,5-F$_3$ | CF$_3$ | H | H | C(O)(Ph-2,4-F$_2$) |
| 3,4,5-F$_3$ | CF$_3$ | H | H | C(O)NHEt |
| 3,4,5-F$_3$ | CF$_3$ | H | H | C(O)NHPr-i |
| 3,4,5-F$_3$ | CF$_3$ | H | H | C(O)NHCH$_2$CF$_3$ |
| 3,4,5-F$_3$ | CF$_3$ | CH$_3$ | H | H |
| 3,4,5-F$_3$ | CF$_3$ | CH$_3$ | H | C(O)Et |
| 3,4,5-F$_3$ | CF$_3$ | CH$_3$ | H | C(O)Pr-n |
| 3,4,5-F$_3$ | CF$_3$ | CH$_3$ | H | C(O)Pr-i |
| 3,4,5-F$_3$ | CF$_3$ | CH$_3$ | H | C(O)Pr-c |
| 3,4,5-F$_3$ | CF$_3$ | CH$_3$ | H | C(O)CH$_2$CF$_3$ |
| 3,4,5-F$_3$ | CF$_3$ | CN | H | H |
| 3,4,5-F$_3$ | CF$_3$ | CN | H | C(O)Pr-c |
| 3,4,5-F$_3$ | CF$_3$ | CN | H | C(O)CH$_2$CF$_3$ |
| 3,4,5-F$_3$ | CF$_2$Cl | H | H | C(O)Et |
| 3,4,5-F$_3$ | CF$_2$Cl | H | H | C(O)Pr-n |
| 3,4,5-F$_3$ | CF$_2$Cl | H | H | C(O)Pr-i |
| 3,4,5-F$_3$ | CF$_2$Cl | H | H | C(O)Pr-c |
| 3,4,5-F$_3$ | CF$_2$Cl | H | H | C(O)CH$_2$Pr-c |
| 3,4,5-F$_3$ | CF$_2$Cl | H | H | C(O)CH$_2$CH$_2$Cl |
| 3,4,5-F$_3$ | CF$_2$Cl | H | H | C(O)CH$_2$CF$_3$ |
| 3,4,5-F$_3$ | CF$_2$Cl | CH$_3$ | H | C(O)Pr-i |
| 3,4,5-F$_3$ | CF$_2$Cl | CH$_3$ | H | C(O)Pr-c |
| 3,4,5-F$_3$ | CF$_2$Cl | CH$_3$ | H | C(O)CH$_2$CF$_3$ |
| 3,4,5-F$_3$ | CF$_2$Br | H | H | C(O)CH$_2$CF$_3$ |
| 3,4,5-F$_3$ | CF$_2$CHF$_2$ | CH$_3$ | H | C(O)Pr-c |
| 2,6-F$_2$-3-Cl | CF$_3$ | CH$_3$ | H | C(O)CH$_2$CF$_3$ |
| 3,5-Cl$_2$-4-F | CHF$_2$ | H | H | C(O)Pr-i |

TABLE 2-continued

| | | | | |
|---|---|---|---|---|
| 3,5-Cl$_2$-4-F | CHF$_2$ | H | H | C(O)Pr-c |
| 3,5-Cl$_2$-4-F | CHF$_2$ | H | H | C(O)CH$_2$CF$_3$ |
| 3,5-Cl$_2$-4-F | CHF$_2$ | CH$_3$ | H | C(O)Pr-c |
| 3,5-Cl$_2$-4-F | CHF$_2$ | CH$_3$ | H | C(O)CH$_2$CF$_3$ |
| 3,5-Cl$_2$-4-F | CHFCl | H | H | C(O)Pr-i |
| 3,5-Cl$_2$-4-F | CHCl$_2$ | H | H | C(O)Pr-c |
| 3,5-Cl$_2$-4-F | CHFBr | H | H | C(O)CH$_2$CF$_3$ |
| 3,5-Cl$_2$-4-F | CF$_3$ | H | H | H |
| 3,5-Cl$_2$-4-F | CF$_3$ | H | H | C(O)Et |
| 3,5-Cl$_2$-4-F | CF$_3$ | H | H | C(O)Pr-n |
| 3,5-Cl$_2$-4-F | CF$_3$ | H | H | C(O)Pr-i |
| 3,5-Cl$_2$-4-F | CF$_3$ | H | H | C(O)Pr-c |
| 3,5-Cl$_2$-4-F | CF$_3$ | H | H | C(O)Bu-i |
| 3,5-Cl$_2$-4-F | CF$_3$ | H | H | C(O)CH$_2$Pr-c |
| 3,5-Cl$_2$-4-F | CF$_3$ | H | H | C(O)Bu-s |
| 3,5-Cl$_2$-4-F | CF$_3$ | H | H | C(O)CF$_3$ |
| 3,5-Cl$_2$-4-F | CF$_3$ | H | H | C(O)CH$_2$CH$_2$Cl |
| 3,5-Cl$_2$-4-F | CF$_3$ | H | H | C(O)CH$_2$CF$_3$ |
| 3,5-Cl$_2$-4-F | CF$_3$ | H | H | C(O)CF$_2$CHF$_2$ |
| 3,5-Cl$_2$-4-F | CF$_3$ | H | H | C(O)CF$_2$CF$_3$ |
| 3,5-Cl$_2$-4-F | CF$_3$ | H | H | C(O)CH$_2$CH$_2$OCH$_3$ |
| 3,5-Cl$_2$-4-F | CF$_3$ | H | H | C(O)(E-5a) |
| 3,5-Cl$_2$-4-F | CF$_3$ | H | H | C(O)CH$_2$CH$_2$SCH$_3$ |
| 3,5-Cl$_2$-4-F | CF$_3$ | H | H | C(O)CH=C(CH$_3$)$_2$ |
| 3,5-Cl$_2$-4-F | CF$_3$ | H | H | C(O)CH$_2$CH$_2$C≡CH |
| 3,5-Cl$_2$-4-F | CF$_3$ | H | H | C(O)(Ph-3-F) |
| 3,5-Cl$_2$-4-F | CF$_3$ | H | H | C(O)(Ph-2,4-F$_2$) |
| 3,5-Cl$_2$-4-F | CF$_3$ | H | H | C(O)(Ph-3,5-F$_2$) |
| 3,5-Cl$_2$-4-F | CF$_3$ | H | H | C(O)NHEt |
| 3,5-Cl$_2$-4-F | CF$_3$ | H | H | C(O)NHPr-i |
| 3,5-Cl$_2$-4-F | CF$_3$ | H | H | C(O)NHPr-c |
| 3,5-Cl$_2$-4-F | CF$_3$ | H | H | C(O)NHCH$_2$CF$_3$ |
| 3,5-Cl$_2$-4-F | CF$_3$ | H | H | C(O)NHOCH$_3$ |
| 3,5-Cl$_2$-4-F | CF$_3$ | H | H | C(S)CH$_2$CF$_3$ |
| 3,5-Cl$_2$-4-F | CF$_3$ | CH$_3$ | H | H |
| 3,5-Cl$_2$-4-F | CF$_3$ | CH$_3$ | H | C(O)Et |
| 3,5-Cl$_2$-4-F | CF$_3$ | CH$_3$ | H | C(O)Pr-n |
| 3,5-Cl$_2$-4-F | CF$_3$ | CH$_3$ | H | C(O)Pr-i |
| 3,5-Cl$_2$-4-F | CF$_3$ | CH$_3$ | H | C(O)Pr-c |
| 3,5-Cl$_2$-4-F | CF$_3$ | CH$_3$ | H | C(O)CH$_2$CF$_3$ |
| 3,5-Cl$_2$-4-F | CF$_3$ | CH$_3$ | H | C(O)NHEt |
| 3,5-Cl$_2$-4-F | CF$_3$ | CH$_3$ | H | C(O)NHPr-i |
| 3,5-Cl$_2$-4-F | CF$_3$ | CH$_3$ | H | C(O)NHPr-c |
| 3,5-Cl$_2$-4-F | CF$_3$ | CH$_3$ | H | C(O)NHCH$_2$CH$_2$Cl |
| 3,5-Cl$_2$-4-F | CF$_3$ | CH$_3$ | H | C(O)NHCH$_2$CF$_3$ |
| 3,5-Cl$_2$-4-F | CF$_3$ | CF$_3$ | H | C(O)Pr-i |
| 3,5-Cl$_2$-4-F | CF$_3$ | CN | H | H |
| 3,5-Cl$_2$-4-F | CF$_3$ | CN | H | C(O)Pr-i |
| 3,5-Cl$_2$-4-F | CF$_3$ | CN | H | C(O)Pr-c |
| 3,5-Cl$_2$-4-F | CF$_3$ | CN | H | C(O)CH$_2$CF$_3$ |
| 3,5-Cl$_2$-4-F | CF$_3$ | CN | H | C(O)NHEt |
| 3,5-Cl$_2$-4-F | CF$_2$Cl | H | H | C(O)Et |
| 3,5-Cl$_2$-4-F | CF$_2$Cl | H | H | C(O)Pr-n |
| 3,5-Cl$_2$-4-F | CF$_2$Cl | H | H | C(O)Pr-i |
| 3,5-Cl$_2$-4-F | CF$_2$Cl | H | H | C(O)Pr-c |
| 3,5-Cl$_2$-4-F | CF$_2$Cl | H | H | C(O)CH$_2$Pr-c |
| 3,5-Cl$_2$-4-F | CF$_2$Cl | H | H | C(O)CF$_3$ |
| 3,5-Cl$_2$-4-F | CF$_2$Cl | H | H | C(O)CH$_2$CH$_2$Cl |
| 3,5-Cl$_2$-4-F | CF$_2$Cl | H | H | C(O)CH$_2$CF$_3$ |
| 3,5-Cl$_2$-4-F | CF$_2$Cl | H | H | C(O)CF$_2$CHF$_2$ |
| 3,5-Cl$_2$-4-F | CF$_2$Cl | H | H | C(O)CF$_2$CF$_3$ |
| 3,5-Cl$_2$-4-F | CF$_2$Cl | H | H | C(O)CH$_2$CH$_2$SCH$_3$ |
| 3,5-Cl$_2$-4-F | CF$_2$Cl | H | H | C(O)(Ph-2,4-F$_2$) |
| 3,5-Cl$_2$-4-F | CF$_2$Cl | H | H | C(O)NHEt |
| 3,5-Cl$_2$-4-F | CF$_2$Cl | H | H | C(O)NHPr-i |
| 3,5-Cl$_2$-4-F | CF$_2$Cl | H | H | C(O)NHCH$_2$CF$_3$ |
| 3,5-Cl$_2$-4-F | CF$_2$Cl | CH$_3$ | H | C(O)Et |
| 3,5-Cl$_2$-4-F | CF$_2$Cl | CH$_3$ | H | C(O)Pr-n |
| 3,5-Cl$_2$-4-F | CF$_2$Cl | CH$_3$ | H | C(O)Pr-i |
| 3,5-Cl$_2$-4-F | CF$_2$Cl | CH$_3$ | H | C(O)Pr-c |
| 3,5-Cl$_2$-4-F | CF$_2$Cl | CH$_3$ | H | C(O)CH$_2$CF$_3$ |
| 3,5-Cl$_2$-4-F | CF$_2$Cl | CN | H | C(O)Pr-c |
| 3,5-Cl$_2$-4-F | CF$_2$Cl | CN | H | C(O)CH$_2$CF$_3$ |
| 3,5-Cl$_2$-4-F | CF$_2$Br | H | H | C(O)Pr-i |
| 3,5-Cl$_2$-4-F | CF$_2$Br | H | H | C(O)Pr-c |
| 3,5-Cl$_2$-4-F | CF$_2$Br | H | H | C(O)CH$_2$CF$_3$ |
| 3,5-Cl$_2$-4-F | CF$_2$Br | CH$_3$ | H | C(O)Pr-c |
| 3,5-Cl$_2$-4-F | CF$_2$Br | CH$_3$ | H | C(O)CH$_2$CF$_3$ |
| 3,5-Cl$_2$-4-F | CF$_2$CHF$_2$ | H | H | C(O)Pr-i |
| 3,5-Cl$_2$-4-F | CF$_2$CHF$_2$ | H | H | C(O)Pr-c |

TABLE 2-continued

| | | | | |
|---|---|---|---|---|
| 3,5-Cl$_2$-4-F | CF$_2$CHF$_2$ | H | H | C(O)CH$_2$CF$_3$ |
| 3,5-Cl$_2$-4-F | CF$_2$CHF$_2$ | CH$_3$ | H | C(O)Pr-c |
| 3,5-Cl$_2$-4-F | CF$_2$CHF$_2$ | CH$_3$ | H | C(O)CH$_2$CF$_3$ |
| 3,5-Cl$_2$-4-F | CF$_2$CF$_3$ | CH$_3$ | H | C(O)Pr-c |
| 3,5-Cl$_2$-4-F | CF$_2$OCH$_3$ | CH$_3$ | H | C(O)CH$_2$CF$_3$ |
| 3,5-Cl$_2$-4-F | CF$_2$SCH$_3$ | H | H | C(O)Pr-i |
| 3,5-Cl$_2$-4-F | T-3 | H | H | C(O)Pr-c |
| 3,4,5-Cl$_3$ | CHF$_2$ | H | H | C(O)Pr-i |
| 3,4,5-Cl$_3$ | CHF$_2$ | H | H | C(O)Pr-c |
| 3,4,5-Cl$_3$ | CHF$_2$ | H | H | C(O)CH$_2$CF$_3$ |
| 3,4,5-Cl$_3$ | CHF$_2$ | CH$_3$ | H | C(O)Pr-c |
| 3,4,5-Cl$_3$ | CHF$_2$ | CH$_3$ | H | C(O)CH$_2$CF$_3$ |
| 3,4,5-Cl$_3$ | CHFCl | H | H | C(O)CH$_2$CF$_3$ |
| 3,4,5-Cl$_3$ | CHCl$_2$ | CH$_3$ | H | C(O)Pr-c |
| 3,4,5-Cl$_3$ | CHFBr | CH$_3$ | H | C(O)CH$_2$CF$_3$ |
| 3,4,5-Cl$_3$ | CF$_3$ | H | H | H |
| 3,4,5-Cl$_3$ | CF$_3$ | H | H | C(O)Et |
| 3,4,5-Cl$_3$ | CF$_3$ | H | H | C(O)Pr-n |
| 3,4,5-Cl$_3$ | CF$_3$ | H | H | C(O)Pr-i |
| 3,4,5-Cl$_3$ | CF$_3$ | H | Et | C(O)Pr-i |
| 3,4,5-Cl$_3$ | CF$_3$ | H | CH$_2$OCH$_3$ | C(O)Pr-i |
| 3,4,5-Cl$_3$ | CF$_3$ | H | CH$_2$OC(O)CH$_3$ | C(O)Pr-i |
| 3,4,5-Cl$_3$ | CF$_3$ | H | CH$_2$OC(O)OCH$_3$ | C(O)Pr-i |
| 3,4,5-Cl$_3$ | CF$_3$ | H | CH$_2$CN | C(O)Pr-i |
| 3,4,5-Cl$_3$ | CF$_3$ | H | CH$_2$C≡CH | C(O)Pr-i |
| 3,4,5-Cl$_3$ | CF$_3$ | H | C(O)CH$_3$ | C(O)Pr-i |
| 3,4,5-Cl$_3$ | CF$_3$ | H | C(O)OCH$_3$ | C(O)Pr-i |
| 3,4,5-Cl$_3$ | CF$_3$ | H | H | C(O)Pr-c |
| 3,4,5-Cl$_3$ | CF$_3$ | H | Et | C(O)Pr-c |
| 3,4,5-Cl$_3$ | CF$_3$ | H | CH$_2$OCH$_3$ | C(O)Pr-c |
| 3,4,5-Cl$_3$ | CF$_3$ | H | CH$_2$OC(O)CH$_3$ | C(O)Pr-c |
| 3,4,5-Cl$_3$ | CF$_3$ | H | CH$_2$OC(O)OCH$_3$ | C(O)Pr-c |
| 3,4,5-Cl$_3$ | CF$_3$ | H | CH$_2$CN | C(O)Pr-c |
| 3,4,5-Cl$_3$ | CF$_3$ | H | CH$_2$C≡CH | C(O)Pr-c |
| 3,4,5-Cl$_3$ | CF$_3$ | H | C(O)CH$_3$ | C(O)Pr-c |
| 3,4,5-Cl$_3$ | CF$_3$ | H | C(O)OCH$_3$ | C(O)Pr-c |
| 3,4,5-Cl$_3$ | CF$_3$ | H | H | C(O)Bu-i |
| 3,4,5-Cl$_3$ | CF$_3$ | H | H | C(O)CH$_2$Pr-c |
| 3,4,5-Cl$_3$ | CF$_3$ | H | H | C(O)Bu-s |
| 3,4,5-Cl$_3$ | CF$_3$ | H | H | C(O)CF$_3$ |
| 3,4,5-Cl$_3$ | CF$_3$ | H | H | C(O)CH$_2$CH$_2$Cl |
| 3,4,5-Cl$_3$ | CF$_3$ | H | H | C(O)CH$_2$CF$_3$ |
| 3,4,5-Cl$_3$ | CF$_3$ | H | Et | C(O)CH$_2$CF$_3$ |
| 3,4,5-Cl$_3$ | CF$_3$ | H | CH$_2$OCH$_3$ | C(O)CH$_2$CF$_3$ |
| 3,4,5-Cl$_3$ | CF$_3$ | H | CH$_2$OC(O)CH$_3$ | C(O)CH$_2$CF$_3$ |
| 3,4,5-Cl$_3$ | CF$_3$ | H | CH$_2$OC(O)OCH$_3$ | C(O)CH$_2$CF$_3$ |
| 3,4,5-Cl$_3$ | CF$_3$ | H | CH$_2$CN | C(O)CH$_2$CF$_3$ |
| 3,4,5-Cl$_3$ | CF$_3$ | H | CH$_2$C≡CH | C(O)CH$_2$CF$_3$ |
| 3,4,5-Cl$_3$ | CF$_3$ | H | C(O)CH$_3$ | C(O)CH$_2$CF$_3$ |
| 3,4,5-Cl$_3$ | CF$_3$ | H | C(O)OCH$_3$ | C(O)CH$_2$CF$_3$ |
| 3,4,5-Cl$_3$ | CF$_3$ | H | H | C(O)CF$_2$CHF$_2$ |
| 3,4,5-Cl$_3$ | CF$_3$ | H | H | C(O)CF$_2$CF$_3$ |
| 3,4,5-Cl$_3$ | CF$_3$ | H | H | C(O)CH$_2$CH$_2$OCH$_3$ |
| 3,4,5-Cl$_3$ | CF$_3$ | H | H | C(O)(E-5a) |
| 3,4,5-Cl$_3$ | CF$_3$ | H | H | C(O)CH$_2$CH$_2$SCH$_3$ |
| 3,4,5-Cl$_3$ | CF$_3$ | H | H | C(O)CH═C(CH$_3$)$_2$ |
| 3,4,5-Cl$_3$ | CF$_3$ | H | H | C(O)CH$_2$CH$_2$C≡CH |
| 3,4,5-Cl$_3$ | CF$_3$ | H | H | C(O)(Ph-3-F) |
| 3,4,5-Cl$_3$ | CF$_3$ | H | H | C(O)(Ph-2,4-F$_2$) |
| 3,4,5-Cl$_3$ | CF$_3$ | H | H | C(O)(Ph-3,5-F$_2$) |
| 3,4,5-Cl$_3$ | CF$_3$ | H | H | C(O)NHEt |
| 3,4,5-Cl$_3$ | CF$_3$ | H | H | C(O)NHPr-i |
| 3,4,5-Cl$_3$ | CF$_3$ | H | H | C(O)NHPr-c |
| 3,4,5-Cl$_3$ | CF$_3$ | H | H | C(O)NHCH$_2$CF$_3$ |
| 3,4,5-Cl$_3$ | CF$_3$ | H | H | C(O)NHOCH$_3$ |
| 3,4,5-Cl$_3$ | CF$_3$ | H | H | C(S)CH$_2$CF$_3$ |
| 3,4,5-Cl$_3$ | CF$_3$ | CH$_3$ | H | H |
| 3,4,5-Cl$_3$ | CF$_3$ | CH$_3$ | H | C(O)Et |
| 3,4,5-Cl$_3$ | CF$_3$ | CH$_3$ | H | C(O)Pr-n |
| 3,4,5-Cl$_3$ | CF$_3$ | CH$_3$ | H | C(O)Pr-i |
| 3,4,5-Cl$_3$ | CF$_3$ | CH$_3$ | H | C(O)Pr-c |
| 3,4,5-Cl$_3$ | CF$_3$ | CH$_3$ | H | C(O)CH$_2$CF$_3$ |
| 3,4,5-Cl$_3$ | CF$_3$ | CH$_3$ | H | C(O)NHEt |
| 3,4,5-Cl$_3$ | CF$_3$ | CH$_3$ | H | C(O)NHPr-i |
| 3,4,5-Cl$_3$ | CF$_3$ | CH$_3$ | H | C(O)NHPr-c |
| 3,4,5-Cl$_3$ | CF$_3$ | CH$_3$ | H | C(O)NHCH$_2$CH$_2$Cl |
| 3,4,5-Cl$_3$ | CF$_3$ | CH$_3$ | H | C(O)NHCH$_2$CF$_3$ |
| 3,4,5-Cl$_3$ | CF$_3$ | CF$_3$ | H | C(O)Pr-i |
| 3,4,5-Cl$_3$ | CF$_3$ | CN | H | H |
| 3,4,5-Cl$_3$ | CF$_3$ | CN | H | C(O)Pr-i |

TABLE 2-continued

| | | | | |
|---|---|---|---|---|
| 3,4,5-Cl$_3$ | CF$_3$ | CN | H | C(O)Pr-c |
| 3,4,5-Cl$_3$ | CF$_3$ | CN | H | C(O)CH$_2$CF$_3$ |
| 3,4,5-Cl$_3$ | CF$_3$ | CN | H | C(O)NHEt |
| 3,4,5-Cl$_3$ | CF$_2$Cl | H | H | H |
| 3,4,5-Cl$_3$ | CF$_2$Cl | H | H | C(O)Et |
| 3,4,5-Cl$_3$ | CF$_2$Cl | H | H | C(O)Pr-n |
| 3,4,5-Cl$_3$ | CF$_2$Cl | H | H | C(O)Pr-i |
| 3,4,5-Cl$_3$ | CF$_2$Cl | H | H | C(O)Pr-c |
| 3,4,5-Cl$_3$ | CF$_2$Cl | H | H | C(O)CH$_2$Pr-c |
| 3,4,5-Cl$_3$ | CF$_2$Cl | H | H | C(O)CF$_3$ |
| 3,4,5-Cl$_3$ | CF$_2$Cl | H | H | C(O)CH$_2$CH$_2$Cl |
| 3,4,5-Cl$_3$ | CF$_2$Cl | H | H | C(O)CH$_2$CF$_3$ |
| 3,4,5-Cl$_3$ | CF$_2$Cl | H | H | C(O)CH$_2$CHF$_2$ |
| 3,4,5-Cl$_3$ | CF$_2$Cl | H | H | C(O)CF$_2$CF$_3$ |
| 3,4,5-Cl$_3$ | CF$_2$Cl | H | H | C(O)CH$_2$CH$_2$SCH$_3$ |
| 3,4,5-Cl$_3$ | CF$_2$Cl | H | H | C(O)(Ph-2,4-F$_2$) |
| 3,4,5-Cl$_3$ | CF$_2$Cl | H | H | C(O)NHEt |
| 3,4,5-Cl$_3$ | CF$_2$Cl | H | H | C(O)NHPr-i |
| 3,4,5-Cl$_3$ | CF$_2$Cl | H | H | C(O)NHCH$_2$CF$_3$ |
| 3,4,5-Cl$_3$ | CF$_2$Cl | CH$_3$ | H | H |
| 3,4,5-Cl$_3$ | CF$_2$Cl | CH$_3$ | H | C(O)Et |
| 3,4,5-Cl$_3$ | CF$_2$Cl | CH$_3$ | H | C(O)Pr-n |
| 3,4,5-Cl$_3$ | CF$_2$Cl | CH$_3$ | H | C(O)Pr-i |
| 3,4,5-Cl$_3$ | CF$_2$Cl | CH$_3$ | H | C(O)Pr-c |
| 3,4,5-Cl$_3$ | CF$_2$Cl | CH$_3$ | H | C(O)CH$_2$CF$_3$ |
| 3,4,5-Cl$_3$ | CF$_2$Cl | CN | H | H |
| 3,4,5-Cl$_3$ | CF$_2$Cl | CN | H | C(O)Pr-c |
| 3,4,5-Cl$_3$ | CF$_2$Cl | CN | H | C(O)CH$_2$CF$_3$ |
| 3,4,5-Cl$_3$ | CF$_2$Br | H | H | C(O)Pr-i |
| 3,4,5-Cl$_3$ | CF$_2$Br | H | H | C(O)Pr-c |
| 3,4,5-Cl$_3$ | CF$_2$Br | H | H | C(O)CH$_2$CF$_3$ |
| 3,4,5-Cl$_3$ | CF$_2$Br | CH$_3$ | H | C(O)Pr-c |
| 3,4,5-Cl$_3$ | CF$_2$Br | CH$_3$ | H | C(O)CH$_2$CF$_3$ |
| 3,4,5-Cl$_3$ | CF$_2$CHF$_2$ | H | H | C(O)Pr-i |
| 3,4,5-Cl$_3$ | CF$_2$CHF$_2$ | H | H | C(O)Pr-c |
| 3,4,5-Cl$_3$ | CF$_2$CHF$_2$ | H | H | C(O)CH$_2$CF$_3$ |
| 3,4,5-Cl$_3$ | CF$_2$CHF$_2$ | CH$_3$ | H | C(O)Pr-c |
| 3,4,5-Cl$_3$ | CF$_2$CHF$_2$ | CH$_3$ | H | C(O)CH$_2$CF$_3$ |
| 3,4,5-Cl$_3$ | CF$_2$CF$_3$ | H | H | C(O)Pr-i |
| 3,4,5-Cl$_3$ | CF$_2$OCH$_3$ | H | H | C(O)Pr-c |
| 3,4,5-Cl$_3$ | CF$_2$SCH$_3$ | H | H | C(O)CH$_2$CF$_3$ |
| 3,4,5-Cl$_3$ | T-3 | CH$_3$ | H | C(O)Pr-c |
| 3,5-Br$_2$-4-F | CHF$_2$ | H | H | C(O)Pr-i |
| 3,5-Br$_2$-4-F | CHF$_2$ | H | H | C(O)Pr-c |
| 3,5-Br$_2$-4-F | CHF$_2$ | H | H | C(O)CH$_2$CF$_3$ |
| 3,5-Br$_2$-4-F | CHF$_2$ | CH$_3$ | H | C(O)Pr-c |
| 3,5-Br$_2$-4-F | CHF$_2$ | CH$_3$ | H | C(O)CH$_2$CF$_3$ |
| 3,5-Br$_2$-4-F | CHFCl | CH$_3$ | H | C(O)CH$_2$CF$_3$ |
| 3,5-Br$_2$-4-F | CHCl$_2$ | H | H | C(O)Pr-i |
| 3,5-Br$_2$-4-F | CHFBr | H | H | C(O)Pr-c |
| 3,5-Br$_2$-4-F | CF$_3$ | H | H | H |
| 3,5-Br$_2$-4-F | CF$_3$ | H | H | C(O)Et |
| 3,5-Br$_2$-4-F | CF$_3$ | H | H | C(O)Pr-n |
| 3,5-Br$_2$-4-F | CF$_3$ | H | H | C(O)Pr-i |
| 3,5-Br$_2$-4-F | CF$_3$ | H | H | C(O)Pr-c |
| 3,5-Br$_2$-4-F | CF$_3$ | H | H | C(O)Bu-i |
| 3,5-Br$_2$-4-F | CF$_3$ | H | H | C(O)CH$_2$Pr-c |
| 3,5-Br$_2$-4-F | CF$_3$ | H | H | C(O)Bu-s |
| 3,5-Br$_2$-4-F | CF$_3$ | H | H | C(O)CF$_3$ |
| 3,5-Br$_2$-4-F | CF$_3$ | H | H | C(O)CH$_2$CH$_2$Cl |
| 3,5-Br$_2$-4-F | CF$_3$ | H | H | C(O)CH$_2$CF$_3$ |
| 3,5-Br$_2$-4-F | CF$_3$ | H | H | C(O)CF$_2$CHF$_2$ |
| 3,5-Br$_2$-4-F | CF$_3$ | H | H | C(O)CF$_2$CF$_3$ |
| 3,5-Br$_2$-4-F | CF$_3$ | H | H | C(O)CH$_2$CH$_2$OCH$_3$ |
| 3,5-Br$_2$-4-F | CF$_3$ | H | H | C(O)(E-5a) |
| 3,5-Br$_2$-4-F | CF$_3$ | H | H | C(O)CH$_2$CH$_2$SCH$_3$ |
| 3,5-Br$_2$-4-F | CF$_3$ | H | H | C(O)CH=C(CH$_3$)$_2$ |
| 3,5-Br$_2$-4-F | CF$_3$ | H | H | C(O)CH$_2$CH$_2$C≡CH |
| 3,5-Br$_2$-4-F | CF$_3$ | H | H | C(O)(Ph-3-F) |
| 3,5-Br$_2$-4-F | CF$_3$ | H | H | C(O)(Ph-2,4-F$_2$) |
| 3,5-Br$_2$-4-F | CF$_3$ | H | H | C(O)(Ph-3,5-F$_2$) |
| 3,5-Br$_2$-4-F | CF$_3$ | H | H | C(O)NHEt |
| 3,5-Br$_2$-4-F | CF$_3$ | H | H | C(O)NHPr-i |
| 3,5-Br$_2$-4-F | CF$_3$ | H | H | C(O)NHPr-c |
| 3,5-Br$_2$-4-F | CF$_3$ | H | H | C(O)NHCH$_2$CF$_3$ |
| 3,5-Br$_2$-4-F | CF$_3$ | H | H | C(O)NHOCH$_3$ |
| 3,5-Br$_2$-4-F | CF$_3$ | H | H | C(S)CH$_2$CF$_3$ |
| 3,5-Br$_2$-4-F | CF$_3$ | CH$_3$ | H | H |
| 3,5-Br$_2$-4-F | CF$_3$ | CH$_3$ | H | C(O)Et |
| 3,5-Br$_2$-4-F | CF$_3$ | CH$_3$ | H | C(O)Pr-n |

TABLE 2-continued

| | | | | |
|---|---|---|---|---|
| 3,5-Br$_2$-4-F | CF$_3$ | CH$_3$ | H | C(O)Pr-i |
| 3,5-Br$_2$-4-F | CF$_3$ | CH$_3$ | H | C(O)Pr-c |
| 3,5-Br$_2$-4-F | CF$_3$ | CH$_3$ | H | C(O)CH$_2$CF$_3$ |
| 3,5-Br$_2$-4-F | CF$_3$ | CH$_3$ | H | C(O)NHEt |
| 3,5-Br$_2$-4-F | CF$_3$ | CH$_3$ | H | C(O)NHPr-i |
| 3,5-Br$_2$-4-F | CF$_3$ | CH$_3$ | H | C(O)NHPr-c |
| 3,5-Br$_2$-4-F | CF$_3$ | CH$_3$ | H | C(O)NHCH$_2$CH$_2$Cl |
| 3,5-Br$_2$-4-F | CF$_3$ | CH$_3$ | H | C(O)NHCH$_2$CF$_3$ |
| 3,5-Br$_2$-4-F | CF$_3$ | CF$_3$ | H | C(O)Pr-i |
| 3,5-Br$_2$-4-F | CF$_3$ | CN | H | H |
| 3,5-Br$_2$-4-F | CF$_3$ | CN | H | C(O)Pr-i |
| 3,5-Br$_2$-4-F | CF$_3$ | CN | H | C(O)Pr-c |
| 3,5-Br$_2$-4-F | CF$_3$ | CN | H | C(O)CH$_2$CF$_3$ |
| 3,5-Br$_2$-4-F | CF$_3$ | CN | H | C(O)NHEt |
| 3,5-Br$_2$-4-F | CF$_2$Cl | H | H | C(O)Et |
| 3,5-Br$_2$-4-F | CF$_2$Cl | H | H | C(O)Pr-n |
| 3,5-Br$_2$-4-F | CF$_2$Cl | H | H | C(O)Pr-i |
| 3,5-Br$_2$-4-F | CF$_2$Cl | H | H | C(O)Pr-c |
| 3,5-Br$_2$-4-F | CF$_2$Cl | H | H | C(O)CH$_2$Pr-c |
| 3,5-Br$_2$-4-F | CF$_2$Cl | H | H | C(O)CF$_3$ |
| 3,5-Br$_2$-4-F | CF$_2$Cl | H | H | C(O)CH$_2$CH$_2$Cl |
| 3,5-Br$_2$-4-F | CF$_2$Cl | H | H | C(O)CH$_2$CF$_3$ |
| 3,5-Br$_2$-4-F | CF$_2$Cl | H | H | C(O)CF$_2$CHF$_2$ |
| 3,5-Br$_2$-4-F | CF$_2$Cl | H | H | C(O)CF$_2$CF$_3$ |
| 3,5-Br$_2$-4-F | CF$_2$Cl | H | H | C(O)CH$_2$CH$_2$SCH$_3$ |
| 3,5-Br$_2$-4-F | CF$_2$Cl | H | H | C(O)(Ph-2,4-F$_2$) |
| 3,5-Br$_2$-4-F | CF$_2$Cl | H | H | C(O)NHEt |
| 3,5-Br$_2$-4-F | CF$_2$Cl | H | H | C(O)NHPr-i |
| 3,5-Br$_2$-4-F | CF$_2$Cl | H | H | C(O)NHCH$_2$CF$_3$ |
| 3,5-Br$_2$-4-F | CF$_2$Cl | CH$_3$ | H | C(O)Et |
| 3,5-Br$_2$-4-F | CF$_2$Cl | CH$_3$ | H | C(O)Pr-n |
| 3,5-Br$_2$-4-F | CF$_2$Cl | CH$_3$ | H | C(O)Pr-i |
| 3,5-Br$_2$-4-F | CF$_2$Cl | CH$_3$ | H | C(O)Pr-c |
| 3,5-Br$_2$-4-F | CF$_2$Cl | CH$_3$ | H | C(O)CH$_2$CF$_3$ |
| 3,5-Br$_2$-4-F | CF$_2$Cl | CN | H | C(O)Pr-c |
| 3,5-Br$_2$-4-F | CF$_2$Cl | CN | H | C(O)CH$_2$CF$_3$ |
| 3,5-Br$_2$-4-F | CF$_2$Br | H | H | C(O)Pr-i |
| 3,5-Br$_2$-4-F | CF$_2$Br | H | H | C(O)Pr-c |
| 3,5-Br$_2$-4-F | CF$_2$Br | H | H | C(O)CH$_2$CF$_3$ |
| 3,5-Br$_2$-4-F | CF$_2$Br | CH$_3$ | H | C(O)Pr-c |
| 3,5-Br$_2$-4-F | CF$_2$Br | CH$_3$ | H | C(O)CH$_2$CF$_3$ |
| 3,5-Br$_2$-4-F | CF$_2$CHF$_2$ | H | H | C(O)Pr-i |
| 3,5-Br$_2$-4-F | CF$_2$CHF$_2$ | H | H | C(O)Pr-c |
| 3,5-Br$_2$-4-F | CF$_2$CHF$_2$ | H | H | C(O)CH$_2$CF$_3$ |
| 3,5-Br$_2$-4-F | CF$_2$CHF$_2$ | CH$_3$ | H | C(O)Pr-c |
| 3,5-Br$_2$-4-F | CF$_2$CHF$_2$ | CH$_3$ | H | C(O)CH$_2$CF$_3$ |
| 3,5-Br$_2$-4-F | CF$_2$CF$_3$ | H | H | C(O)CH$_2$CF$_3$ |
| 3,5-Br$_2$-4-F | CF$_2$OCH$_3$ | CH$_3$ | H | C(O)Pr-c |
| 3,5-Br$_2$-4-F | CF$_2$SCH$_3$ | CH$_3$ | H | C(O)CH$_2$CF$_3$ |
| 3,5-Br$_2$-4-F | T-3 | H | H | C(O)Pr-i |
| 3,4,5-Br$_3$ | CHF$_2$ | H | H | C(O)Pr-c |
| 3,4,5-Br$_3$ | CF$_3$ | H | H | H |
| 3,4,5-Br$_3$ | CF$_3$ | H | H | C(O)Et |
| 3,4,5-Br$_3$ | CF$_3$ | H | H | C(O)Pr-n |
| 3,4,5-Br$_3$ | CF$_3$ | H | H | C(O)Pr-i |
| 3,4,5-Br$_3$ | CF$_3$ | H | H | C(O)Pr-c |
| 3,4,5-Br$_3$ | CF$_3$ | H | H | C(O)CH$_2$Pr-c |
| 3,4,5-Br$_3$ | CF$_3$ | H | H | C(O)CF$_3$ |
| 3,4,5-Br$_3$ | CF$_3$ | H | H | C(O)CH$_2$CH$_2$Cl |
| 3,4,5-Br$_3$ | CF$_3$ | H | H | C(O)CH$_2$CF$_3$ |
| 3,4,5-Br$_3$ | CF$_3$ | H | H | C(O)CF$_2$CHF$_2$ |
| 3,4,5-Br$_3$ | CF$_3$ | H | H | C(O)CF$_2$CF$_3$ |
| 3,4,5-Br$_3$ | CF$_3$ | H | H | C(O)CH$_2$CH$_2$SCH$_3$ |
| 3,4,5-Br$_3$ | CF$_3$ | H | H | C(O)(Ph-2,4-F$_2$) |
| 3,4,5-Br$_3$ | CF$_3$ | H | H | C(O)NHEt |
| 3,4,5-Br$_3$ | CF$_3$ | H | H | C(O)NHPr-i |
| 3,4,5-Br$_3$ | CF$_3$ | H | H | C(O)NHCH$_2$CF$_3$ |
| 3,4,5-Br$_3$ | CF$_3$ | CH$_3$ | H | H |
| 3,4,5-Br$_3$ | CF$_3$ | CH$_3$ | H | C(O)Et |
| 3,4,5-Br$_3$ | CF$_3$ | CH$_3$ | H | C(O)Pr-n |
| 3,4,5-Br$_3$ | CF$_3$ | CH$_3$ | H | C(O)Pr-i |
| 3,4,5-Br$_3$ | CF$_3$ | CH$_3$ | H | C(O)Pr-c |
| 3,4,5-Br$_3$ | CF$_3$ | CH$_3$ | H | C(O)CH$_2$CF$_3$ |
| 3,4,5-Br$_3$ | CF$_3$ | CN | H | H |
| 3,4,5-Br$_3$ | CF$_3$ | CN | H | C(O)Pr-c |
| 3,4,5-Br$_3$ | CF$_3$ | CN | H | C(O)CH$_2$CF$_3$ |
| 3,4,5-Br$_3$ | CF$_2$Cl | H | H | C(O)Et |
| 3,4,5-Br$_3$ | CF$_2$Cl | H | H | C(O)Pr-n |
| 3,4,5-Br$_3$ | CF$_2$Cl | H | H | C(O)Pr-i |
| 3,4,5-Br$_3$ | CF$_2$Cl | H | H | C(O)Pr-c |

TABLE 2-continued

| | | | | |
|---|---|---|---|---|
| 3,4,5-Br$_3$ | CF$_2$Cl | H | H | C(O)CH$_2$Pr-c |
| 3,4,5-Br$_3$ | CF$_2$Cl | H | H | C(O)CH$_2$CH$_2$Cl |
| 3,4,5-Br$_3$ | CF$_2$Cl | H | H | C(O)CH$_2$CF$_3$ |
| 3,4,5-Br$_3$ | CF$_2$Cl | CH$_3$ | H | C(O)Pr-i |
| 3,4,5-Br$_3$ | CF$_2$Cl | CH$_3$ | H | C(O)Pr-c |
| 3,4,5-Br$_3$ | CF$_2$Cl | CH$_3$ | H | C(O)CH$_2$CF$_3$ |
| 3,4,5-Br$_3$ | CF$_2$Br | H | H | C(O)CH$_2$CF$_3$ |
| 3,4,5-Br$_3$ | CF$_2$CHF$_2$ | CH$_3$ | H | C(O)Pr-c |
| 2,3-F$_2$-4-CH$_3$ | CF$_3$ | CH$_3$ | H | C(O)CH$_2$CF$_3$ |
| 3,5-F$_2$-4-CH$_3$ | CF$_3$ | H | H | C(O)Pr-i |
| 2-F-3-CH$_3$-5-Cl | CF$_3$ | H | H | C(O)Pr-c |
| 3,5-Cl$_2$-4-CH$_3$ | CF$_3$ | H | H | C(O)CH$_2$CF$_3$ |
| 3,5-Br$_2$-4-CH$_3$ | CF$_3$ | CH$_3$ | H | C(O)Pr-c |
| 2,3-F$_2$-4-CF$_3$ | CF$_3$ | CH$_3$ | H | C(O)CH$_2$CF$_3$ |
| 3,4-F$_2$-5-CF$_3$ | CHF$_2$ | H | H | C(O)Pr-i |
| 3,4-F$_2$-5-CF$_3$ | CHF$_2$ | H | H | C(O)Pr-c |
| 3,4-F$_2$-5-CF$_3$ | CHF$_2$ | H | H | C(O)CH$_2$CF$_3$ |
| 3,4-F$_2$-5-CF$_3$ | CHF$_2$ | CH$_3$ | H | C(O)Pr-c |
| 3,4-F$_2$-5-CF$_3$ | CHF$_2$ | CH$_3$ | H | C(O)CH$_2$CF$_3$ |
| 3,4-F$_2$-5-CF$_3$ | CHFCl | H | H | C(O)Pr-i |
| 3,4-F$_2$-5-CF$_3$ | CHCl$_2$ | H | H | C(O)Pr-c |
| 3,4-F$_2$-5-CF$_3$ | CHFBr | H | H | C(O)CH$_2$CF$_3$ |
| 3,4-F$_2$-5-CF$_3$ | CF$_3$ | H | H | H |
| 3,4-F$_2$-5-CF$_3$ | CF$_3$ | H | H | C(O)Et |
| 3,4-F$_2$-5-CF$_3$ | CF$_3$ | H | H | C(O)Pr-n |
| 3,4-F$_2$-5-CF$_3$ | CF$_3$ | H | H | C(O)Pr-i |
| 3,4-F$_2$-5-CF$_3$ | CF$_3$ | H | H | C(O)Pr-c |
| 3,4-F$_2$-5-CF$_3$ | CF$_3$ | H | H | C(O)Bu-i |
| 3,4-F$_2$-5-CF$_3$ | CF$_3$ | H | H | C(O)CH$_2$Pr-c |
| 3,4-F$_2$-5-CF$_3$ | CF$_3$ | H | H | C(O)Bu-s |
| 3,4-F$_2$-5-CF$_3$ | CF$_3$ | H | H | C(O)CF$_3$ |
| 3,4-F$_2$-5-CF$_3$ | CF$_3$ | H | H | C(O)CH$_2$CH$_2$Cl |
| 3,4-F$_2$-5-CF$_3$ | CF$_3$ | H | H | C(O)CH$_2$CF$_3$ |
| 3,4-F$_2$-5-CF$_3$ | CF$_3$ | H | H | C(O)CF$_2$CHF$_2$ |
| 3,4-F$_2$-5-CF$_3$ | CF$_3$ | H | H | C(O)CF$_2$CF$_3$ |
| 3,4-F$_2$-5-CF$_3$ | CF$_3$ | H | H | C(O)CH$_2$CH$_2$OCH$_3$ |
| 3,4-F$_2$-5-CF$_3$ | CF$_3$ | H | H | C(O)(E-5a) |
| 3,4-F$_2$-5-CF$_3$ | CF$_3$ | H | H | C(O)CH$_2$CH$_2$SCH$_3$ |
| 3,4-F$_2$-5-CF$_3$ | CF$_3$ | H | H | C(O)CH=C(CH$_3$)$_2$ |
| 3,4-F$_2$-5-CF$_3$ | CF$_3$ | H | H | C(O)CH$_2$CH$_2$C≡CH |
| 3,4-F$_2$-5-CF$_3$ | CF$_3$ | H | H | C(O)(Ph-3-F) |
| 3,4-F$_2$-5-CF$_3$ | CF$_3$ | H | H | C(O)(Ph-2,4-F$_2$) |
| 3,4-F$_2$-5-CF$_3$ | CF$_3$ | H | H | C(O)(Ph-3,5-F$_2$) |
| 3,4-F$_2$-5-CF$_3$ | CF$_3$ | H | H | C(O)NHEt |
| 3,4-F$_2$-5-CF$_3$ | CF$_3$ | H | H | C(O)NHPr-i |
| 3,4-F$_2$-5-CF$_3$ | CF$_3$ | H | H | C(O)NHPr-c |
| 3,4-F$_2$-5-CF$_3$ | CF$_3$ | H | H | C(O)NHCH$_2$CF$_3$ |
| 3,4-F$_2$-5-CF$_3$ | CF$_3$ | H | H | C(O)NHOCH$_3$ |
| 3,4-F$_2$-5-CF$_3$ | CF$_3$ | H | H | C(S)CH$_2$CF$_3$ |
| 3,4-F$_2$-5-CF$_3$ | CF$_3$ | CH$_3$ | H | H |
| 3,4-F$_2$-5-CF$_3$ | CF$_3$ | CH$_3$ | H | C(O)Et |
| 3,4-F$_2$-5-CF$_3$ | CF$_3$ | CH$_3$ | H | C(O)Pr-n |
| 3,4-F$_2$-5-CF$_3$ | CF$_3$ | CH$_3$ | H | C(O)Pr-i |
| 3,4-F$_2$-5-CF$_3$ | CF$_3$ | CH$_3$ | H | C(O)Pr-c |
| 3,4-F$_2$-5-CF$_3$ | CF$_3$ | CH$_3$ | H | C(O)CH$_2$CF$_3$ |
| 3,4-F$_2$-5-CF$_3$ | CF$_3$ | CH$_3$ | H | C(O)NHEt |
| 3,4-F$_2$-5-CF$_3$ | CF$_3$ | CH$_3$ | H | C(O)NHPr-i |
| 3,4-F$_2$-5-CF$_3$ | CF$_3$ | CH$_3$ | H | C(O)NHPr-c |
| 3,4-F$_2$-5-CF$_3$ | CF$_3$ | CH$_3$ | H | C(O)NHCH$_2$CH$_2$Cl |
| 3,4-F$_2$-5-CF$_3$ | CF$_3$ | CH$_3$ | H | C(O)NHCH$_2$CF$_3$ |
| 3,4-F$_2$-5-CF$_3$ | CF$_3$ | CF$_3$ | H | C(O)Pr-i |
| 3,4-F$_2$-5-CF$_3$ | CF$_3$ | CN | H | H |
| 3,4-F$_2$-5-CF$_3$ | CF$_3$ | CN | H | C(O)Pr-i |
| 3,4-F$_2$-5-CF$_3$ | CF$_3$ | CN | H | C(O)Pr-c |
| 3,4-F$_2$-5-CF$_3$ | CF$_3$ | CN | H | C(O)CH$_2$CF$_3$ |
| 3,4-F$_2$-5-CF$_3$ | CF$_3$ | CN | H | C(O)NHEt |
| 3,4-F$_2$-5-CF$_3$ | CF$_2$Cl | H | H | C(O)Et |
| 3,4-F$_2$-5-CF$_3$ | CF$_2$Cl | H | H | C(O)Pr-n |
| 3,4-F$_2$-5-CF$_3$ | CF$_2$Cl | H | H | C(O)Pr-i |
| 3,4-F$_2$-5-CF$_3$ | CF$_2$Cl | H | H | C(O)Pr-c |
| 3,4-F$_2$-5-CF$_3$ | CF$_2$Cl | H | H | C(O)CH$_2$Pr-c |
| 3,4-F$_2$-5-CF$_3$ | CF$_2$Cl | H | H | C(O)CF$_3$ |
| 3,4-F$_2$-5-CF$_3$ | CF$_2$Cl | H | H | C(O)CH$_2$CH$_2$Cl |
| 3,4-F$_2$-5-CF$_3$ | CF$_2$Cl | H | H | C(O)CH$_2$CF$_3$ |
| 3,4-F$_2$-5-CF$_3$ | CF$_2$Cl | H | H | C(O)CF$_2$CHF$_2$ |
| 3,4-F$_2$-5-CF$_3$ | CF$_2$Cl | H | H | C(O)CF$_2$CF$_3$ |
| 3,4-F$_2$-5-CF$_3$ | CF$_2$Cl | H | H | C(O)CH$_2$CH$_2$SCH$_3$ |
| 3,4-F$_2$-5-CF$_3$ | CF$_2$Cl | H | H | C(O)(Ph-2,4-F$_2$) |
| 3,4-F$_2$-5-CF$_3$ | CF$_2$Cl | H | H | C(O)NHEt |
| 3,4-F$_2$-5-CF$_3$ | CF$_2$Cl | H | H | C(O)NHPr-i |

TABLE 2-continued

| | | | | |
|---|---|---|---|---|
| 3,4-F$_2$-5-CF$_3$ | CF$_2$Cl | H | H | C(O)NHCH$_2$CF$_3$ |
| 3,4-F$_2$-5-CF$_3$ | CF$_2$Cl | CH$_3$ | H | C(O)Et |
| 3,4-F$_2$-5-CF$_3$ | CF$_2$Cl | CH$_3$ | H | C(O)Pr-n |
| 3,4-F$_2$-5-CF$_3$ | CF$_2$Cl | CH$_3$ | H | C(O)Pr-i |
| 3,4-F$_2$-5-CF$_3$ | CF$_2$Cl | CH$_3$ | H | C(O)Pr-c |
| 3,4-F$_2$-5-CF$_3$ | CF$_2$Cl | CH$_3$ | H | C(O)CH$_2$CF$_3$ |
| 3,4-F$_2$-5-CF$_3$ | CF$_2$Cl | CN | H | C(O)Pr-c |
| 3,4-F$_2$-5-CF$_3$ | CF$_2$Cl | CN | H | C(O)CH$_2$CF$_3$ |
| 3,4-F$_2$-5-CF$_3$ | CF$_2$Br | H | H | C(O)Pr-i |
| 3,4-F$_2$-5-CF$_3$ | CF$_2$Br | H | H | C(O)Pr-c |
| 3,4-F$_2$-5-CF$_3$ | CF$_2$Br | H | H | C(O)CH$_2$CF$_3$ |
| 3,4-F$_2$-5-CF$_3$ | CF$_2$Br | CH$_3$ | H | C(O)Pr-c |
| 3,4-F$_2$-5-CF$_3$ | CF$_2$Br | CH$_3$ | H | C(O)CH$_2$CF$_3$ |
| 3,4-F$_2$-5-CF$_3$ | CF$_2$CHF$_2$ | H | H | C(O)Pr-i |
| 3,4-F$_2$-5-CF$_3$ | CF$_2$CHF$_2$ | H | H | C(O)Pr-c |
| 3,4-F$_2$-5-CF$_3$ | CF$_2$CHF$_2$ | H | H | C(O)CH$_2$CF$_3$ |
| 3,4-F$_2$-5-CF$_3$ | CF$_2$CHF$_2$ | CH$_3$ | H | C(O)Pr-c |
| 3,4-F$_2$-5-CF$_3$ | CF$_2$CHF$_2$ | CH$_3$ | H | C(O)CH$_2$CF$_3$ |
| 3,4-F$_2$-5-CF$_3$ | CF$_2$CF$_3$ | CH$_3$ | H | C(O)Pr-c |
| 3,4-F$_2$-5-CF$_3$ | CF$_2$OCH$_3$ | CH$_3$ | H | C(O)CH$_2$CF$_3$ |
| 3,4-F$_2$-5-CF$_3$ | CF$_2$SCH$_3$ | H | H | C(O)Pr-i |
| 3,4-F$_2$-5-CF$_3$ | T-3 | H | H | C(O)Pr-c |
| 2-F-3-Cl-5-CF$_3$ | CF$_3$ | H | H | C(O)CH$_2$CF$_3$ |
| 3-Cl-4-F-5-CF$_3$ | CHF$_2$ | H | H | C(O)Pr-i |
| 3-Cl-4-F-5-CF$_3$ | CHF$_2$ | H | H | C(O)Pr-c |
| 3-Cl-4-F-5-CF$_3$ | CHF$_2$ | H | H | C(O)CH$_2$CF$_3$ |
| 3-Cl-4-F-5-CF$_3$ | CHF$_2$ | CH$_3$ | H | C(O)Pr-c |
| 3-Cl-4-F-5-CF$_3$ | CHF$_2$ | CH$_3$ | H | C(O)CH$_2$CF$_3$ |
| 3-Cl-4-F-5-CF$_3$ | CHFCl | CH$_3$ | H | C(O)Pr-c |
| 3-Cl-4-F-5-CF$_3$ | CHCl$_2$ | CH$_3$ | H | C(O)CH$_2$CF$_3$ |
| 3-Cl-4-F-5-CF$_3$ | CHFBr | H | H | C(O)Pr-i |
| 3-Cl-4-F-5-CF$_3$ | CF$_3$ | H | H | H |
| 3-Cl-4-F-5-CF$_3$ | CF$_3$ | H | H | C(O)Et |
| 3-Cl-4-F-5-CF$_3$ | CF$_3$ | H | H | C(O)Pr-n |
| 3-Cl-4-F-5-CF$_3$ | CF$_3$ | H | H | C(O)Pr-i |
| 3-Cl-4-F-5-CF$_3$ | CF$_3$ | H | H | C(O)Pr-c |
| 3-Cl-4-F-5-CF$_3$ | CF$_3$ | H | H | C(O)Bu-i |
| 3-Cl-4-F-5-CF$_3$ | CF$_3$ | H | H | C(O)CH$_2$Pr-c |
| 3-Cl-4-F-5-CF$_3$ | CF$_3$ | H | H | C(O)Bu-s |
| 3-Cl-4-F-5-CF$_3$ | CF$_3$ | H | H | C(O)CF$_3$ |
| 3-Cl-4-F-5-CF$_3$ | CF$_3$ | H | H | C(O)CH$_2$CH$_2$Cl |
| 3-Cl-4-F-5-CF$_3$ | CF$_3$ | H | H | C(O)CH$_2$CF$_3$ |
| 3-Cl-4-F-5-CF$_3$ | CF$_3$ | H | H | C(O)CF$_2$CHF$_2$ |
| 3-Cl-4-F-5-CF$_3$ | CF$_3$ | H | H | C(O)CF$_2$CF$_3$ |
| 3-Cl-4-F-5-CF$_3$ | CF$_3$ | H | H | C(O)CH$_2$CH$_2$OCH$_3$ |
| 3-Cl-4-F-5-CF$_3$ | CF$_3$ | H | H | C(O)(E-5a) |
| 3-Cl-4-F-5-CF$_3$ | CF$_3$ | H | H | C(O)CH$_2$CH$_2$SCH$_3$ |
| 3-Cl-4-F-5-CF$_3$ | CF$_3$ | H | H | C(O)CH=C(CH$_3$)$_2$ |
| 3-Cl-4-F-5-CF$_3$ | CF$_3$ | H | H | C(O)CH$_2$CH$_2$C≡CH |
| 3-Cl-4-F-5-CF$_3$ | CF$_3$ | H | H | C(O)(Ph-3-F) |
| 3-Cl-4-F-5-CF$_3$ | CF$_3$ | H | H | C(O)(Ph-2,4-F$_2$) |
| 3-Cl-4-F-5-CF$_3$ | CF$_3$ | H | H | C(O)(Ph-3,5-F$_2$) |
| 3-Cl-4-F-5-CF$_3$ | CF$_3$ | H | H | C(O)NHEt |
| 3-Cl-4-F-5-CF$_3$ | CF$_3$ | H | H | C(O)NHPr-i |
| 3-Cl-4-F-5-CF$_3$ | CF$_3$ | H | H | C(O)NHPr-c |
| 3-Cl-4-F-5-CF$_3$ | CF$_3$ | H | H | C(O)NHCH$_2$CF$_3$ |
| 3-Cl-4-F-5-CF$_3$ | CF$_3$ | H | H | C(O)NHOCH$_3$ |
| 3-Cl-4-F-5-CF$_3$ | CF$_3$ | H | H | C(S)CH$_2$CF$_3$ |
| 3-Cl-4-F-5-CF$_3$ | CF$_3$ | CH$_3$ | H | H |
| 3-Cl-4-F-5-CF$_3$ | CF$_3$ | CH$_3$ | H | C(O)Et |
| 3-Cl-4-F-5-CF$_3$ | CF$_3$ | CH$_3$ | H | C(O)Pr-n |
| 3-Cl-4-F-5-CF$_3$ | CF$_3$ | CH$_3$ | H | C(O)Pr-i |
| 3-Cl-4-F-5-CF$_3$ | CF$_3$ | CH$_3$ | H | C(O)Pr-c |
| 3-Cl-4-F-5-CF$_3$ | CF$_3$ | CH$_3$ | H | C(O)CH$_2$CF$_3$ |
| 3-Cl-4-F-5-CF$_3$ | CF$_3$ | CH$_3$ | H | C(O)NHEt |
| 3-Cl-4-F-5-CF$_3$ | CF$_3$ | CH$_3$ | H | C(O)NHPr-i |
| 3-Cl-4-F-5-CF$_3$ | CF$_3$ | CH$_3$ | H | C(O)NHPr-c |
| 3-Cl-4-F-5-CF$_3$ | CF$_3$ | CH$_3$ | H | C(O)NHCH$_2$CH$_2$Cl |
| 3-Cl-4-F-5-CF$_3$ | CF$_3$ | CH$_3$ | H | C(O)NHCH$_2$CF$_3$ |
| 3-Cl-4-F-5-CF$_3$ | CF$_3$ | CF$_3$ | H | C(O)Pr-i |
| 3-Cl-4-F-5-CF$_3$ | CF$_3$ | CN | H | H |
| 3-Cl-4-F-5-CF$_3$ | CF$_3$ | CN | H | C(O)Pr-i |
| 3-Cl-4-F-5-CF$_3$ | CF$_3$ | CN | H | C(O)Pr-c |
| 3-Cl-4-F-5-CF$_3$ | CF$_3$ | CN | H | C(O)CH$_2$CF$_3$ |
| 3-Cl-4-F-5-CF$_3$ | CF$_3$ | CN | H | C(O)NHEt |
| 3-Cl-4-F-5-CF$_3$ | CF$_2$Cl | H | H | C(O)Et |
| 3-Cl-4-F-5-CF$_3$ | CF$_2$Cl | H | H | C(O)Pr-n |
| 3-Cl-4-F-5-CF$_3$ | CF$_2$Cl | H | H | C(O)Pr-i |
| 3-Cl-4-F-5-CF$_3$ | CF$_2$Cl | H | H | C(O)Pr-c |
| 3-Cl-4-F-5-CF$_3$ | CF$_2$Cl | H | H | C(O)CH$_2$Pr-c |

TABLE 2-continued

| | | | | |
|---|---|---|---|---|
| 3-Cl-4-F-5-CF$_3$ | CF$_2$Cl | H | H | C(O)CF$_3$ |
| 3-Cl-4-F-5-CF$_3$ | CF$_2$Cl | H | H | C(O)CH$_2$CH$_2$Cl |
| 3-Cl-4-F-5-CF$_3$ | CF$_2$Cl | H | H | C(O)CH$_2$CF$_3$ |
| 3-Cl-4-F-5-CF$_3$ | CF$_2$Cl | H | H | C(O)CF$_2$CHF$_2$ |
| 3-Cl-4-F-5-CF$_3$ | CF$_2$Cl | H | H | C(O)CF$_2$CF$_3$ |
| 3-Cl-4-F-5-CF$_3$ | CF$_2$Cl | H | H | C(O)CH$_2$CH$_2$SCH$_3$ |
| 3-Cl-4-F-5-CF$_3$ | CF$_2$Cl | H | H | C(O)(Ph-2,4-F$_2$) |
| 3-Cl-4-F-5-CF$_3$ | CF$_2$Cl | H | H | C(O)NHEt |
| 3-Cl-4-F-5-CF$_3$ | CF$_2$Cl | H | H | C(O)NHPr-i |
| 3-Cl-4-F-5-CF$_3$ | CF$_2$Cl | H | H | C(O)NHCH$_2$CF$_3$ |
| 3-Cl-4-F-5-CF$_3$ | CF$_2$Cl | CH$_3$ | H | C(O)Et |
| 3-Cl-4-F-5-CF$_3$ | CF$_2$Cl | CH$_3$ | H | C(O)Pr-n |
| 3-Cl-4-F-5-CF$_3$ | CF$_2$Cl | CH$_3$ | H | C(O)Pr-i |
| 3-Cl-4-F-5-CF$_3$ | CF$_2$Cl | CH$_3$ | H | C(O)Pr-c |
| 3-Cl-4-F-5-CF$_3$ | CF$_2$Cl | CH$_3$ | H | C(O)CH$_2$CF$_3$ |
| 3-Cl-4-F-5-CF$_3$ | CF$_2$Cl | CN | H | C(O)Pr-c |
| 3-Cl-4-F-5-CF$_3$ | CF$_2$Cl | CN | H | C(O)CH$_2$CF$_3$ |
| 3-Cl-4-F-5-CF$_3$ | CF$_2$Br | H | H | C(O)Pr-i |
| 3-Cl-4-F-5-CF$_3$ | CF$_2$Br | H | H | C(O)Pr-c |
| 3-Cl-4-F-5-CF$_3$ | CF$_2$Br | H | H | C(O)CH$_2$CF$_3$ |
| 3-Cl-4-F-5-CF$_3$ | CF$_2$Br | CH$_3$ | H | C(O)Pr-c |
| 3-Cl-4-F-5-CF$_3$ | CF$_2$Br | CH$_3$ | H | C(O)CH$_2$CF$_3$ |
| 3-Cl-4-F-5-CF$_3$ | CF$_2$CHF$_2$ | H | H | C(O)Pr-i |
| 3-Cl-4-F-5-CF$_3$ | CF$_2$CHF$_2$ | H | H | C(O)Pr-c |
| 3-Cl-4-F-5-CF$_3$ | CF$_2$CHF$_2$ | H | H | C(O)CH$_2$CF$_3$ |
| 3-Cl-4-F-5-CF$_3$ | CF$_2$CHF$_2$ | CH$_3$ | H | C(O)Pr-c |
| 3-Cl-4-F-5-CF$_3$ | CF$_2$CHF$_2$ | CH$_3$ | H | C(O)CH$_2$CF$_3$ |
| 3-Cl-4-F-5-CF$_3$ | CF$_2$CF$_3$ | H | H | C(O)Pr-c |
| 3-Cl-4-F-5-CF$_3$ | CF$_2$OCH$_3$ | H | H | C(O)CH$_2$CF$_3$ |
| 3-Cl-4-F-5-CF$_3$ | CF$_2$SCH$_3$ | CH$_3$ | H | C(O)Pr-c |
| 3-Cl-4-F-5-CF$_3$ | T-3 | CH$_3$ | H | C(O)CH$_2$CF$_3$ |
| 3,4-Cl$_2$-5-CF$_3$ | CHF$_2$ | H | H | C(O)Pr-i |
| 3,4-Cl$_2$-5-CF$_3$ | CHF$_2$ | H | H | C(O)Pr-c |
| 3,4-Cl$_2$-5-CF$_3$ | CHF$_2$ | H | H | C(O)CH$_2$CF$_3$ |
| 3,4-Cl$_2$-5-CF$_3$ | CHF$_2$ | CH$_3$ | H | C(O)Pr-c |
| 3,4-Cl$_2$-5-CF$_3$ | CHF$_2$ | CH$_3$ | H | C(O)CH$_2$CF$_3$ |
| 3,4-Cl$_2$-5-CF$_3$ | CHFCl | H | H | C(O)Pr-i |
| 3,4-Cl$_2$-5-CF$_3$ | CHCl$_2$ | H | H | C(O)Pr-c |
| 3,4-Cl$_2$-5-CF$_3$ | CHFBr | H | H | C(O)CH$_2$CF$_3$ |
| 3,4-Cl$_2$-5-CF$_3$ | CF$_3$ | H | H | H |
| 3,4-Cl$_2$-5-CF$_3$ | CF$_3$ | H | H | C(O)Et |
| 3,4-Cl$_2$-5-CF$_3$ | CF$_3$ | H | H | C(O)Pr-n |
| 3,4-Cl$_2$-5-CF$_3$ | CF$_3$ | H | H | C(O)Pr-i |
| 3,4-Cl$_2$-5-CF$_3$ | CF$_3$ | H | H | C(O)Pr-c |
| 3,4-Cl$_2$-5-CF$_3$ | CF$_3$ | H | H | C(O)Bu-i |
| 3,4-Cl$_2$-5-CF$_3$ | CF$_3$ | H | H | C(O)CH$_2$Pr-c |
| 3,4-Cl$_2$-5-CF$_3$ | CF$_3$ | H | H | C(O)Bu-s |
| 3,4-Cl$_2$-5-CF$_3$ | CF$_3$ | H | H | C(O)CF$_3$ |
| 3,4-Cl$_2$-5-CF$_3$ | CF$_3$ | H | H | C(O)CH$_2$CH$_2$Cl |
| 3,4-Cl$_2$-5-CF$_3$ | CF$_3$ | H | H | C(O)CH$_2$CF$_3$ |
| 3,4-Cl$_2$-5-CF$_3$ | CF$_3$ | H | H | C(O)CF$_2$CHF$_2$ |
| 3,4-Cl$_2$-5-CF$_3$ | CF$_3$ | H | H | C(O)CF$_2$CF$_3$ |
| 3,4-Cl$_2$-5-CF$_3$ | CF$_3$ | H | H | C(O)CH$_2$CH$_2$OCH$_3$ |
| 3,4-Cl$_2$-5-CF$_3$ | CF$_3$ | H | H | C(O)(E-5a) |
| 3,4-Cl$_2$-5-CF$_3$ | CF$_3$ | H | H | C(O)CH$_2$CH$_2$SCH$_3$ |
| 3,4-Cl$_2$-5-CF$_3$ | CF$_3$ | H | H | C(O)CH=C(CH$_3$)$_2$ |
| 3,4-Cl$_2$-5-CF$_3$ | CF$_3$ | H | H | C(O)CH$_2$CH$_2$C≡CH |
| 3,4-Cl$_2$-5-CF$_3$ | CF$_3$ | H | H | C(O)(Ph-3-F) |
| 3,4-Cl$_2$-5-CF$_3$ | CF$_3$ | H | H | C(O)(Ph-2,4-F$_2$) |
| 3,4-Cl$_2$-5-CF$_3$ | CF$_3$ | H | H | C(O)(Ph-3,5-F$_2$) |
| 3,4-Cl$_2$-5-CF$_3$ | CF$_3$ | H | H | C(O)NHEt |
| 3,4-Cl$_2$-5-CF$_3$ | CF$_3$ | H | H | C(O)NHPr-i |
| 3,4-Cl$_2$-5-CF$_3$ | CF$_3$ | H | H | C(O)NHPr-c |
| 3,4-Cl$_2$-5-CF$_3$ | CF$_3$ | H | H | C(O)NHCH$_2$CF$_3$ |
| 3,4-Cl$_2$-5-CF$_3$ | CF$_3$ | H | H | C(O)NHOCH$_3$ |
| 3,4-Cl$_2$-5-CF$_3$ | CF$_3$ | H | H | C(S)CH$_2$CF$_3$ |
| 3,4-Cl$_2$-5-CF$_3$ | CF$_3$ | CH$_3$ | H | H |
| 3,4-Cl$_2$-5-CF$_3$ | CF$_3$ | CH$_3$ | H | C(O)Et |
| 3,4-Cl$_2$-5-CF$_3$ | CF$_3$ | CH$_3$ | H | C(O)Pr-n |
| 3,4-Cl$_2$-5-CF$_3$ | CF$_3$ | CH$_3$ | H | C(O)Pr-i |
| 3,4-Cl$_2$-5-CF$_3$ | CF$_3$ | CH$_3$ | H | C(O)Pr-c |
| 3,4-Cl$_2$-5-CF$_3$ | CF$_3$ | CH$_3$ | H | C(O)CH$_2$CF$_3$ |
| 3,4-Cl$_2$-5-CF$_3$ | CF$_3$ | CH$_3$ | H | C(O)NHEt |
| 3,4-Cl$_2$-5-CF$_3$ | CF$_3$ | CH$_3$ | H | C(O)NHPr-i |
| 3,4-Cl$_2$-5-CF$_3$ | CF$_3$ | CH$_3$ | H | C(O)NHPr-c |
| 3,4-Cl$_2$-5-CF$_3$ | CF$_3$ | CH$_3$ | H | C(O)NHCH$_2$CH$_2$Cl |
| 3,4-Cl$_2$-5-CF$_3$ | CF$_3$ | CH$_3$ | H | C(O)NHCH$_2$CF$_3$ |
| 3,4-Cl$_2$-5-CF$_3$ | CF$_3$ | CF$_3$ | H | C(O)Pr-i |
| 3,4-Cl$_2$-5-CF$_3$ | CF$_3$ | CN | H | H |
| 3,4-Cl$_2$-5-CF$_3$ | CF$_3$ | CN | H | C(O)Pr-i |

TABLE 2-continued

| | | | | |
|---|---|---|---|---|
| 3,4-Cl$_2$-5-CF$_3$ | CF$_3$ | CN | H | C(O)Pr-c |
| 3,4-Cl$_2$-5-CF$_3$ | CF$_3$ | CN | H | C(O)CH$_2$CF$_3$ |
| 3,4-Cl$_2$-5-CF$_3$ | CF$_3$ | CN | H | C(O)NHEt |
| 3,4-Cl$_2$-5-CF$_3$ | CF$_2$Cl | H | H | C(O)Et |
| 3,4-Cl$_2$-5-CF$_3$ | CF$_2$Cl | H | H | C(O)Pr-n |
| 3,4-Cl$_2$-5-CF$_3$ | CF$_2$Cl | H | H | C(O)Pr-i |
| 3,4-Cl$_2$-5-CF$_3$ | CF$_2$Cl | H | H | C(O)Pr-c |
| 3,4-Cl$_2$-5-CF$_3$ | CF$_2$Cl | H | H | C(O)CH$_2$Pr-c |
| 3,4-Cl$_2$-5-CF$_3$ | CF$_2$Cl | H | H | C(O)CF$_3$ |
| 3,4-Cl$_2$-5-CF$_3$ | CF$_2$Cl | H | H | C(O)CH$_2$CH$_2$Cl |
| 3,4-Cl$_2$-5-CF$_3$ | CF$_2$Cl | H | H | C(O)CH$_2$CF$_3$ |
| 3,4-Cl$_2$-5-CF$_3$ | CF$_2$Cl | H | H | C(O)CF$_2$CHF$_2$ |
| 3,4-Cl$_2$-5-CF$_3$ | CF$_2$Cl | H | H | C(O)CF$_2$CF$_3$ |
| 3,4-Cl$_2$-5-CF$_3$ | CF$_2$Cl | H | H | C(O)CH$_2$CH$_2$SCH$_3$ |
| 3,4-Cl$_2$-5-CF$_3$ | CF$_2$Cl | H | H | C(O)(Ph-2,4-F$_2$) |
| 3,4-Cl$_2$-5-CF$_3$ | CF$_2$Cl | H | H | C(O)NHEt |
| 3,4-Cl$_2$-5-CF$_3$ | CF$_2$Cl | H | H | C(O)NHPr-i |
| 3,4-Cl$_2$-5-CF$_3$ | CF$_2$Cl | H | H | C(O)NHCH$_2$CF$_3$ |
| 3,4-Cl$_2$-5-CF$_3$ | CF$_2$Cl | CH$_3$ | H | C(O)Et |
| 3,4-Cl$_2$-5-CF$_3$ | CF$_2$Cl | CH$_3$ | H | C(O)Pr-n |
| 3,4-Cl$_2$-5-CF$_3$ | CF$_2$Cl | CH$_3$ | H | C(O)Pr-i |
| 3,4-Cl$_2$-5-CF$_3$ | CF$_2$Cl | CH$_3$ | H | C(O)Pr-c |
| 3,4-Cl$_2$-5-CF$_3$ | CF$_2$Cl | CH$_3$ | H | C(O)CH$_2$CF$_3$ |
| 3,4-Cl$_2$-5-CF$_3$ | CF$_2$Cl | CN | H | C(O)Pr-c |
| 3,4-Cl$_2$-5-CF$_3$ | CF$_2$Cl | CN | H | C(O)CH$_2$CF$_3$ |
| 3,4-Cl$_2$-5-CF$_3$ | CF$_2$Br | H | H | C(O)Pr-i |
| 3,4-Cl$_2$-5-CF$_3$ | CF$_2$Br | H | H | C(O)Pr-c |
| 3,4-Cl$_2$-5-CF$_3$ | CF$_2$Br | H | H | C(O)CH$_2$CF$_3$ |
| 3,4-Cl$_2$-5-CF$_3$ | CF$_2$Br | CH$_3$ | H | C(O)Pr-c |
| 3,4-Cl$_2$-5-CF$_3$ | CF$_2$Br | CH$_3$ | H | C(O)CH$_2$CF$_3$ |
| 3,4-Cl$_2$-5-CF$_3$ | CF$_2$CHF$_2$ | H | H | C(O)Pr-i |
| 3,4-Cl$_2$-5-CF$_3$ | CF$_2$CHF$_2$ | H | H | C(O)Pr-c |
| 3,4-Cl$_2$-5-CF$_3$ | CF$_2$CHF$_2$ | H | H | C(O)CH$_2$CF$_3$ |
| 3,4-Cl$_2$-5-CF$_3$ | CF$_2$CHF$_2$ | CH$_3$ | H | C(O)Pr-c |
| 3,4-Cl$_2$-5-CF$_3$ | CF$_2$CHF$_2$ | CH$_3$ | H | C(O)CH$_2$CF$_3$ |
| 3,4-Cl$_2$-5-CF$_3$ | CF$_2$CF$_3$ | CH$_3$ | H | C(O)Pr-c |
| 3,4-Cl$_2$-5-CF$_3$ | CF$_2$OCH$_3$ | CH$_3$ | H | C(O)CH$_2$CF$_3$ |
| 3,4-Cl$_2$-5-CF$_3$ | CF$_2$SCH$_3$ | H | H | C(O)Pr-i |
| 3,4-Cl$_2$-5-CF$_3$ | T-3 | H | H | C(O)Pr-c |
| 3,5-(CF$_3$)$_2$-4-Cl | CHF$_2$ | H | H | C(O)Pr-i |
| 3,5-(CF$_3$)$_2$-4-Cl | CHF$_2$ | H | H | C(O)Pr-c |
| 3,5-(CF$_3$)$_2$-4-Cl | CHF$_2$ | H | H | C(O)CH$_2$CF$_3$ |
| 3,5-(CF$_3$)$_2$-4-Cl | CHF$_2$ | CH$_3$ | H | C(O)Pr-c |
| 3,5-(CF$_3$)$_2$-4-Cl | CHF$_2$ | CH$_3$ | H | C(O)CH$_2$CF$_3$ |
| 3,5-(CF$_3$)$_2$-4-Cl | CHFCl | H | H | C(O)CH$_2$CF$_3$ |
| 3,5-(CF$_3$)$_2$-4-Cl | CHCl$_2$ | CH$_3$ | H | C(O)Pr-c |
| 3,5-(CF$_3$)$_2$-4-Cl | CHFBr | CH$_3$ | H | C(O)CH$_2$CF$_3$ |
| 3,5-(CF$_3$)$_2$-4-Cl | CF$_3$ | H | H | H |
| 3,5-(CF$_3$)$_2$-4-Cl | CF$_3$ | H | H | C(O)Et |
| 3,5-(CF$_3$)$_2$-4-Cl | CF$_3$ | H | H | C(O)Pr-n |
| 3,5-(CF$_3$)$_2$-4-Cl | CF$_3$ | H | H | C(O)Pr-i |
| 3,5-(CF$_3$)$_2$-4-Cl | CF$_3$ | H | H | C(O)Pr-c |
| 3,5-(CF$_3$)$_2$-4-Cl | CF$_3$ | H | H | C(O)Bu-i |
| 3,5-(CF$_3$)$_2$-4-Cl | CF$_3$ | H | H | C(O)CH$_2$Pr-c |
| 3,5-(CF$_3$)$_2$-4-Cl | CF$_3$ | H | H | C(O)Bu-s |
| 3,5-(CF$_3$)$_2$-4-Cl | CF$_3$ | H | H | C(O)CF$_3$ |
| 3,5-(CF$_3$)$_2$-4-Cl | CF$_3$ | H | H | C(O)CH$_2$CH$_2$Cl |
| 3,5-(CF$_3$)$_2$-4-Cl | CF$_3$ | H | H | C(O)CH$_2$CF$_3$ |
| 3,5-(CF$_3$)$_2$-4-Cl | CF$_3$ | H | H | C(O)CF$_2$CHF$_2$ |
| 3,5-(CF$_3$)$_2$-4-Cl | CF$_3$ | H | H | C(O)CF$_2$CF$_3$ |
| 3,5-(CF$_3$)$_2$-4-Cl | CF$_3$ | H | H | C(O)CH$_2$CH$_2$OCH$_3$ |
| 3,5-(CF$_3$)$_2$-4-Cl | CF$_3$ | H | H | C(O)(E-5a) |
| 3,5-(CF$_3$)$_2$-4-Cl | CF$_3$ | H | H | C(O)CH$_2$CH$_2$SCH$_3$ |
| 3,5-(CF$_3$)$_2$-4-Cl | CF$_3$ | H | H | C(O)CH=C(CH$_3$)$_2$ |
| 3,5-(CF$_3$)$_2$-4-Cl | CF$_3$ | H | H | C(O)CH$_2$CH$_2$C≡CH |
| 3,5-(CF$_3$)$_2$-4-Cl | CF$_3$ | H | H | C(O)(Ph-3-F) |
| 3,5-(CF$_3$)$_2$-4-Cl | CF$_3$ | H | H | C(O)(Ph-2,4-F$_2$) |
| 3,5-(CF$_3$)$_2$-4-Cl | CF$_3$ | H | H | C(O)(Ph-3,5-F$_2$) |
| 3,5-(CF$_3$)$_2$-4-Cl | CF$_3$ | H | H | C(O)NHEt |
| 3,5-(CF$_3$)$_2$-4-Cl | CF$_3$ | H | H | C(O)NHPr-i |
| 3,5-(CF$_3$)$_2$-4-Cl | CF$_3$ | H | H | C(O)NHPr-c |
| 3,5-(CF$_3$)$_2$-4-Cl | CF$_3$ | H | H | C(O)NHCH$_2$CF$_3$ |
| 3,5-(CF$_3$)$_2$-4-Cl | CF$_3$ | H | H | C(O)NHOCH$_3$ |
| 3,5-(CF$_3$)$_2$-4-Cl | CF$_3$ | H | H | C(S)CH$_2$CF$_3$ |
| 3,5-(CF$_3$)$_2$-4-Cl | CF$_3$ | CH$_3$ | H | H |
| 3,5-(CF$_3$)$_2$-4-Cl | CF$_3$ | CH$_3$ | H | C(O)Et |
| 3,5-(CF$_3$)$_2$-4-Cl | CF$_3$ | CH$_3$ | H | C(O)Pr-n |
| 3,5-(CF$_3$)$_2$-4-Cl | CF$_3$ | CH$_3$ | H | C(O)Pr-i |
| 3,5-(CF$_3$)$_2$-4-Cl | CF$_3$ | CH$_3$ | H | C(O)Pr-c |
| 3,5-(CF$_3$)$_2$-4-Cl | CF$_3$ | CH$_3$ | H | C(O)CH$_2$CF$_3$ |

TABLE 2-continued

| | | | | |
|---|---|---|---|---|
| 3,5-(CF₃)₂-4-Cl | CF₃ | CH₃ | H | C(O)NHEt |
| 3,5-(CF₃)₂-4-Cl | CF₃ | CH₃ | H | C(O)NHPr-i |
| 3,5-(CF₃)₂-4-Cl | CF₃ | CH₃ | H | C(O)NHPr-c |
| 3,5-(CF₃)₂-4-Cl | CF₃ | CH₃ | H | C(O)NHCH₂CH₂Cl |
| 3,5-(CF₃)₂-4-Cl | CF₃ | CH₃ | H | C(O)NHCH₂CF₃ |
| 3,5-(CF₃)₂-4-Cl | CF₃ | CF₃ | H | C(O)Pr-i |
| 3,5-(CF₃)₂-4-Cl | CF₃ | CN | H | H |
| 3,5-(CF₃)₂-4-Cl | CF₃ | CN | H | C(O)Pr-i |
| 3,5-(CF₃)₂-4-Cl | CF₃ | CN | H | C(O)Pr-c |
| 3,5-(CF₃)₂-4-Cl | CF₃ | CN | H | C(O)CH₂CF₃ |
| 3,5-(CF₃)₂-4-Cl | CF₃ | CN | H | C(O)NHEt |
| 3,5-(CF₃)₂-4-Cl | CF₂Cl | H | H | C(O)Et |
| 3,5-(CF₃)₂-4-Cl | CF₂Cl | H | H | C(O)Pr-n |
| 3,5-(CF₃)₂-4-Cl | CF₂Cl | H | H | C(O)Pr-i |
| 3,5-(CF₃)₂-4-Cl | CF₂Cl | H | H | C(O)Pr-c |
| 3,5-(CF₃)₂-4-Cl | CF₂Cl | H | H | C(O)CH₂Pr-c |
| 3,5-(CF₃)₂-4-Cl | CF₂Cl | H | H | C(O)CF₃ |
| 3,5-(CF₃)₂-4-Cl | CF₂Cl | H | H | C(O)CH₂CH₂Cl |
| 3,5-(CF₃)₂-4-Cl | CF₂Cl | H | H | C(O)CH₂CF₃ |
| 3,5-(CF₃)₂-4-Cl | CF₂Cl | H | H | C(O)CF₂CHF₂ |
| 3,5-(CF₃)₂-4-Cl | CF₂Cl | H | H | C(O)CF₂CF₃ |
| 3,5-(CF₃)₂-4-Cl | CF₂Cl | H | H | C(O)CH₂CH₂SCH₃ |
| 3,5-(CF₃)₂-4-Cl | CF₂Cl | H | H | C(O)(Ph-2,4-F₂) |
| 3,5-(CF₃)₂-4-Cl | CF₂Cl | H | H | C(O)NHEt |
| 3,5-(CF₃)₂-4-Cl | CF₂Cl | H | H | C(O)NHPr-i |
| 3,5-(CF₃)₂-4-Cl | CF₂Cl | H | H | C(O)NHCH₂CF₃ |
| 3,5-(CF₃)₂-4-Cl | CF₂Cl | CH₃ | H | C(O)Et |
| 3,5-(CF₃)₂-4-Cl | CF₂Cl | CH₃ | H | C(O)Pr-n |
| 3,5-(CF₃)₂-4-Cl | CF₂Cl | CH₃ | H | C(O)Pr-i |
| 3,5-(CF₃)₂-4-Cl | CF₂Cl | CH₃ | H | C(O)Pr-c |
| 3,5-(CF₃)₂-4-Cl | CF₂Cl | CH₃ | H | C(O)CH₂CF₃ |
| 3,5-(CF₃)₂-4-Cl | CF₂Cl | CN | H | C(O)Pr-c |
| 3,5-(CF₃)₂-4-Cl | CF₂Cl | CN | H | C(O)CH₂CF₃ |
| 3,5-(CF₃)₂-4-Cl | CF₂Br | H | H | C(O)Pr-i |
| 3,5-(CF₃)₂-4-Cl | CF₂Br | H | H | C(O)Pr-c |
| 3,5-(CF₃)₂-4-Cl | CF₂Br | H | H | C(O)CH₂CF₃ |
| 3,5-(CF₃)₂-4-Cl | CF₂Br | CH₃ | H | C(O)Pr-c |
| 3,5-(CF₃)₂-4-Cl | CF₂Br | CH₃ | H | C(O)CH₂CF₃ |
| 3,5-(CF₃)₂-4-Cl | CF₂CHF₂ | H | H | C(O)Pr-i |
| 3,5-(CF₃)₂-4-Cl | CF₂CHF₂ | H | H | C(O)Pr-c |
| 3,5-(CF₃)₂-4-Cl | CF₂CHF₂ | H | H | C(O)CH₂CF₃ |
| 3,5-(CF₃)₂-4-Cl | CF₂CHF₂ | CH₃ | H | C(O)Pr-c |
| 3,5-(CF₃)₂-4-Cl | CF₂CHF₂ | CH₃ | H | C(O)CH₂CF₃ |
| 3,5-(CF₃)₂-4-Cl | CF₂CF₃ | H | H | C(O)Pr-i |
| 3,5-(CF₃)₂-4-Cl | CF₂OCH₃ | H | H | C(O)Pr-c |
| 3,5-(CF₃)₂-4-Cl | CF₂SCH₃ | H | H | C(O)CH₂CF₃ |
| 3,5-(CF₃)₂-4-Cl | T-3 | CH₃ | H | C(O)Pr-c |
| 3,5-Cl₂-4-OH | CF₃ | CH₃ | H | C(O)CH₂CF₃ |
| 3,5-Br₂-4-OH | CF₃ | H | H | C(O)Pr-i |
| 3,5-I₂-4-OH | CF₃ | H | H | C(O)Pr-c |
| 3,5-F₂-4-OCH₃ | CF₃ | H | H | C(O)CH₂CF₃ |
| 3,5-Cl₂-4-OCH₃ | CF₃ | CH₃ | H | C(O)Pr-c |
| 3-F-5-Br-4-OCH₃ | CF₃ | CH₃ | H | C(O)CH₂CF₃ |
| 3-Cl-5-Br-4-OCH₃ | CF₃ | H | H | C(O)Pr-i |
| 3,5-Br₂-4-OCH₃ | CF₃ | H | H | C(O)Pr-c |
| 3,5-Cl₂-4-OEt | CF₃ | H | H | C(O)CH₂CF₃ |
| 3,5-Br₂-4-OEt | CF₃ | CH₃ | H | C(O)Pr-c |
| 3,5-Cl₂-4-OPr-n | CF₃ | CH₃ | H | C(O)CH₂CF₃ |
| 3,5-Cl₂-4-OCHF₂ | CF₃ | H | H | C(O)Pr-i |
| 3,5-Br₂-4-OCHF₂ | CF₃ | H | H | C(O)Pr-c |
| 3,5-F₂-4-OCF₃ | CF₃ | H | H | C(O)CH₂CF₃ |
| 3,5-Cl₂-4-OCH₂CH=CH₂ | CF₃ | CH₃ | H | C(O)Pr-c |
| 3,5-Cl₂-4-OCH₂C≡CH | CF₃ | CH₃ | H | C(O)CH₂CF₃ |
| 3,5-Cl₂-4-OSi(CH₃)₃ | CF₃ | H | H | C(O)Pr-i |
| 3,5-Cl₂-4-OSi(CH₃)₂Bu-t | CF₃ | H | H | C(O)Pr-c |
| 3,5-F₂-4-NO₂ | CF₃ | H | H | C(O)CH₂CF₃ |
| 3,5-Cl₂-4-NO₂ | CF₃ | CH₃ | H | C(O)Pr-c |
| 3,5-Cl₂-4-NH₂ | CF₃ | H | H | C(O)Pr-i |
| 3,5-Cl₂-4-NH₂ | CF₃ | H | H | C(O)Pr-c |
| 3,5-Cl₂-4-NH₂ | CF₃ | H | H | C(O)CH₂CF₃ |
| 3,5-Cl₂-4-NH₂ | CF₃ | CH₃ | H | C(O)Pr-c |
| 3,5-Cl₂-4-NH₂ | CF₃ | CH₃ | H | C(O)CH₂CF₃ |
| 3,5-Br₂-4-NH₂ | CF₃ | H | H | C(O)Pr-i |
| 3,5-Br₂-4-NH₂ | CF₃ | H | H | C(O)Pr-c |
| 3,5-Br₂-4-NH₂ | CF₃ | H | H | C(O)CH₂CF₃ |
| 3,5-Br₂-4-NH₂ | CF₃ | CH₃ | H | C(O)Pr-c |
| 3,5-Br₂-4-NH₂ | CF₃ | CH₃ | H | C(O)CH₂CF₃ |
| 3,5-I₂-4-NH₂ | CF₃ | CH₃ | H | C(O)CH₂CF₃ |
| 3,5-F₂-4-CN | CF₃ | H | H | C(O)Pr-i |
| 3,5-Cl₂-4-CN | CF₃ | H | H | C(O)Pr-c |

TABLE 2-continued

| | | | | |
|---|---|---|---|---|
| 3,5-Br$_2$-4-CN | CF$_3$ | H | H | C(O)CH$_2$CF$_3$ |
| 2,3,5,6-F$_4$ | CF$_3$ | CH$_3$ | H | C(O)Pr-c |
| 2,3,4,5,6-F$_5$ | CF$_3$ | CH$_3$ | H | C(O)CH$_2$CF$_3$ |
| 3-Cl-5-CF$_3$ | CF$_3$ | H | H | C(O)CH$_3$ |
| 3-Cl-5-CF$_3$ | CF$_3$ | H | Et | C(O)Et |
| 3-Cl-5-CF$_3$ | CF$_3$ | H | CH$_2$Pr-c | C(O)Et |
| 3-Cl-5-CF$_3$ | CF$_3$ | H | CH$_2$OCH$_3$ | C(O)Et |
| 3-Cl-5-CF$_3$ | CF$_3$ | H | CH$_2$CN | C(O)Et |
| 3-Cl-5-CF$_3$ | CF$_3$ | H | CH$_2$CH=CH$_2$ | C(O)Et |
| 3-Cl-5-CF$_3$ | CF$_3$ | H | CH$_2$C≡CH | C(O)Et |
| 3-Cl-5-CF$_3$ | CF$_3$ | CH$_3$ | Et | C(O)Et |
| 3-Cl-5-CF$_3$ | CF$_3$ | CH$_3$ | CH$_2$Pr-c | C(O)Et |
| 3-Cl-5-CF$_3$ | CF$_3$ | CH$_3$ | CH$_2$OCH$_3$ | C(O)Et |
| 3-Cl-5-CF$_3$ | CF$_3$ | CH$_3$ | CH$_2$CN | C(O)Et |
| 3-Cl-5-CF$_3$ | CF$_3$ | CH$_3$ | CH$_2$C≡CH | C(O)Et |
| 3-Cl-5-CF$_3$ | CF$_3$ | H | Et | C(O)Pr-n |
| 3-Cl-5-CF$_3$ | CF$_3$ | H | CH$_2$Pr-c | C(O)Pr-n |
| 3-Cl-5-CF$_3$ | CF$_3$ | H | CH$_2$OCH$_3$ | C(O)Pr-n |
| 3-Cl-5-CF$_3$ | CF$_3$ | H | CH$_2$CN | C(O)Pr-n |
| 3-Cl-5-CF$_3$ | CF$_3$ | H | CH$_2$C≡CH | C(O)Pr-n |
| 3-Cl-5-CF$_3$ | CF$_3$ | CN | H | C(O)Pr-n |
| 3-Cl-5-CF$_3$ | CF$_3$ | C≡CH | H | C(O)Pr-n |
| 3-Cl-5-CF$_3$ | CF$_3$ | H | CH$_3$ | C(O)Pr-c |
| 3-Cl-5-CF$_3$ | CF$_3$ | H | Et | C(O)Pr-c |
| 3-Cl-5-CF$_3$ | CF$_3$ | H | n-Pr | C(O)Pr-c |
| 3-Cl-5-CF$_3$ | CF$_3$ | H | CH$_2$Pr-c | C(O)Pr-c |
| 3-Cl-5-CF$_3$ | CF$_3$ | H | CH$_2$OCH$_3$ | C(O)Pr-c |
| 3-Cl-5-CF$_3$ | CF$_3$ | H | CH$_2$CN | C(O)Pr-c |
| 3-Cl-5-CF$_3$ | CF$_3$ | H | CH$_2$CH=CH$_2$ | C(O)Pr-c |
| 3-Cl-5-CF$_3$ | CF$_3$ | H | CH$_2$C≡CH | C(O)Pr-c |
| 3-Cl-5-CF$_3$ | CF$_3$ | CH$_3$ | Et | C(O)Pr-c |
| 3-Cl-5-CF$_3$ | CF$_3$ | CH$_3$ | CH$_2$Pr-c | C(O)Pr-c |
| 3-Cl-5-CF$_3$ | CF$_3$ | CH$_3$ | CH$_2$OCH$_3$ | C(O)Pr-c |
| 3-Cl-5-CF$_3$ | CF$_3$ | CH$_3$ | CH$_2$CN | C(O)Pr-c |
| 3-Cl-5-CF$_3$ | CF$_3$ | CH$_3$ | CH$_2$C≡CH | C(O)Pr-c |
| 3-Cl-5-CF$_3$ | CF$_3$ | C≡CH | H | C(O)Pr-c |
| 3-Cl-5-CF$_3$ | CF$_3$ | H | Et | C(O)CH$_2$Pr-c |
| 3-Cl-5-CF$_3$ | CF$_3$ | H | CH$_2$Pr-c | C(O)CH$_2$Pr-c |
| 3-Cl-5-CF$_3$ | CF$_3$ | H | CH$_2$OCH$_3$ | C(O)CH$_2$Pr-c |
| 3-Cl-5-CF$_3$ | CF$_3$ | H | CH$_2$CN | C(O)CH$_2$Pr-c |
| 3-Cl-5-CF$_3$ | CF$_3$ | H | CH$_2$CH=CH$_2$ | C(O)CH$_2$Pr-c |
| 3-Cl-5-CF$_3$ | CF$_3$ | H | CH$_2$C≡CH | C(O)CH$_2$Pr-c |
| 3-Cl-5-CF$_3$ | CF$_3$ | CH$_3$ | H | C(O)CH$_2$Pr-c |
| 3-Cl-5-CF$_3$ | CF$_3$ | CN | H | C(O)CH$_2$Pr-c |
| 3-Cl-5-CF$_3$ | CF$_3$ | C≡CH | H | C(O)CH$_2$Pr-c |
| 3-Cl-5-CF$_3$ | CF$_3$ | H | H | C(O)(T-6) |
| 3-Cl-5-CF$_3$ | CF$_3$ | CH$_3$ | H | C(O)(T-6) |
| 3-Cl-5-CF$_3$ | CF$_3$ | H | H | C(O)Bu-c |
| 3-Cl-5-CF$_3$ | CF$_3$ | H | Et | C(O)CH$_2$CF$_3$ |
| 3-Cl-5-CF$_3$ | CF$_3$ | H | CH$_2$Pr-c | C(O)CH$_2$CF$_3$ |
| 3-Cl-5-CF$_3$ | CF$_3$ | H | CH$_2$OCH$_3$ | C(O)CH$_2$CF$_3$ |
| 3-Cl-5-CF$_3$ | CF$_3$ | H | CH$_2$CN | C(O)CH$_2$CF$_3$ |
| 3-Cl-5-CF$_3$ | CF$_3$ | H | CH$_2$C≡CH | C(O)CH$_2$CF$_3$ |
| 3-Cl-5-CF$_3$ | CF$_3$ | C≡CH | H | C(O)CH$_2$CF$_3$ |
| 3-Cl-5-CF$_3$ | CF$_3$ | H | H | C(O)CH$_2$CH$_2$CF$_3$ |
| 3-Cl-5-CF$_3$ | CF$_3$ | H | Et | C(O)(E-5a) |
| 3-Cl-5-CF$_3$ | CF$_3$ | H | CH$_2$Pr-c | C(O)(E-5a) |
| 3-Cl-5-CF$_3$ | CF$_3$ | H | CH$_2$OCH$_3$ | C(O)(E-5a) |
| 3-Cl-5-CF$_3$ | CF$_3$ | H | CH$_2$CN | C(O)(E-5a) |
| 3-Cl-5-CF$_3$ | CF$_3$ | H | CH$_2$C≡CH | C(O)(E-5a) |
| 3-Cl-5-CF$_3$ | CF$_3$ | CH$_3$ | H | C(O)(E-5a) |
| 3-Cl-5-CF$_3$ | CF$_3$ | CN | H | C(O)(E-5a) |
| 3-Cl-5-CF$_3$ | CF$_3$ | C≡CH | H | C(O)(E-5a) |
| 3-Cl-5-CF$_3$ | CF$_3$ | H | CH$_2$CH=CH$_2$ | C(O)NHEt |
| 3-Cl-5-CF$_3$ | CF$_3$ | H | CH$_2$C≡CH | C(O)NHEt |
| 3-Cl-5-CF$_3$ | CF$_3$ | CH$_3$ | H | C(O)NHCH$_2$C≡CH |
| 3-Cl-5-CF$_3$ | CF$_3$ | H | H | C(O)(T-17) |
| 3-Cl-5-CF$_3$ | CF$_3$ | H | H | C(O)(T-22) |
| 3-Cl-5-CF$_3$ | CF$_3$ | H | H | C(S)CH$_2$Pr-c |
| 3-Cl-5-CF$_3$ | CF$_3$ | CH$_3$ | H | C(S)CH$_2$Pr-c |
| 3-Br-5-CF$_3$ | CF$_3$ | H | H | C(O)CH$_3$ |
| 3-Br-5-CF$_3$ | CF$_3$ | H | Et | C(O)Et |
| 3-Br-5-CF$_3$ | CF$_3$ | H | CH$_2$Pr-c | C(O)Et |
| 3-Br-5-CF$_3$ | CF$_3$ | H | CH$_2$OCH$_3$ | C(O)Et |
| 3-Br-5-CF$_3$ | CF$_3$ | H | CH$_2$CN | C(O)Et |
| 3-Br-5-CF$_3$ | CF$_3$ | H | CH$_2$CH=CH$_2$ | C(O)Et |
| 3-Br-5-CF$_3$ | CF$_3$ | H | CH$_2$C≡CH | C(O)Et |
| 3-Br-5-CF$_3$ | CF$_3$ | CH$_3$ | Et | C(O)Et |
| 3-Br-5-CF$_3$ | CF$_3$ | CH$_3$ | CH$_2$Pr-c | C(O)Et |
| 3-Br-5-CF$_3$ | CF$_3$ | CH$_3$ | CH$_2$OCH$_3$ | C(O)Et |

TABLE 2-continued

| | | | | |
|---|---|---|---|---|
| 3-Br-5-CF$_3$ | CF$_3$ | CH$_3$ | CH$_2$CN | C(O)Et |
| 3-Br-5-CF$_3$ | CF$_3$ | CH$_3$ | CH$_2$C≡CH | C(O)Et |
| 3-Br-5-CF$_3$ | CF$_3$ | H | Et | C(O)Pr-n |
| 3-Br-5-CF$_3$ | CF$_3$ | H | CH$_2$Pr-c | C(O)Pr-n |
| 3-Br-5-CF$_3$ | CF$_3$ | H | CH$_2$OCH$_3$ | C(O)Pr-n |
| 3-Br-5-CF$_3$ | CF$_3$ | H | CH$_2$CN | C(O)Pr-n |
| 3-Br-5-CF$_3$ | CF$_3$ | H | CH$_2$C≡CH | C(O)Pr-n |
| 3-Br-5-CF$_3$ | CF$_3$ | CN | H | C(O)Pr-n |
| 3-Br-5-CF$_3$ | CF$_3$ | C≡CH | H | C(O)Pr-n |
| 3-Br-5-CF$_3$ | CF$_3$ | H | CH$_3$ | C(O)Pr-c |
| 3-Br-5-CF$_3$ | CF$_3$ | H | Et | C(O)Pr-c |
| 3-Br-5-CF$_3$ | CF$_3$ | H | n-Pr | C(O)Pr-c |
| 3-Br-5-CF$_3$ | CF$_3$ | H | CH$_2$Pr-c | C(O)Pr-c |
| 3-Br-5-CF$_3$ | CF$_3$ | H | CH$_2$OCH$_3$ | C(O)Pr-c |
| 3-Br-5-CF$_3$ | CF$_3$ | H | CH$_2$CN | C(O)Pr-c |
| 3-Br-5-CF$_3$ | CF$_3$ | H | CH$_2$CH=CH$_2$ | C(O)Pr-c |
| 3-Br-5-CF$_3$ | CF$_3$ | H | CH$_2$C≡OH | C(O)Pr-c |
| 3-Br-5-CF$_3$ | CF$_3$ | CH$_3$ | Et | C(O)Pr-c |
| 3-Br-5-CF$_3$ | CF$_3$ | CH$_3$ | CH$_2$Pr-c | C(O)Pr-c |
| 3-Br-5-CF$_3$ | CF$_3$ | CH$_3$ | CH$_2$OCH$_3$ | C(O)Pr-c |
| 3-Br-5-CF$_3$ | CF$_3$ | CH$_3$ | CH$_2$CN | C(O)Pr-c |
| 3-Br-5-CF$_3$ | CF$_3$ | CH$_3$ | CH$_2$C≡CH | C(O)Pr-c |
| 3-Br-5-CF$_3$ | CF$_3$ | C≡CH | H | C(O)Pr-c |
| 3-Br-5-CF$_3$ | CF$_3$ | H | Et | C(O)CH$_2$Pr-c |
| 3-Br-5-CF$_3$ | CF$_3$ | H | CH$_2$Pr-c | C(O)CH$_2$Pr-c |
| 3-Br-5-CF$_3$ | CF$_3$ | H | CH$_2$OCH$_3$ | C(O)CH$_2$Pr-c |
| 3-Br-5-CF$_3$ | CF$_3$ | H | CH$_2$CN | C(O)CH$_2$Pr-c |
| 3-Br-5-CF$_3$ | CF$_3$ | H | CH$_2$CH=CH$_2$ | C(O)CH$_2$Pr-c |
| 3-Br-5-CF$_3$ | CF$_3$ | H | CH$_2$C≡CH | C(O)CH$_2$Pr-c |
| 3-Br-5-CF$_3$ | CF$_3$ | CH$_3$ | H | C(O)CH$_2$Pr-c |
| 3-Br-5-CF$_3$ | CF$_3$ | CN | H | C(O)CH$_2$Pr-c |
| 3-Br-5-CF$_3$ | CF$_3$ | C≡CH | H | C(O)CH$_2$Pr-c |
| 3-Br-5-CF$_3$ | CF$_3$ | H | H | C(O)(T-6) |
| 3-Br-5-CF$_3$ | CF$_3$ | CH$_3$ | H | C(O)(T-6) |
| 3-Br-5-CF$_3$ | CF$_3$ | H | H | C(O)Bu-C |
| 3-Br-5-CF$_3$ | CF$_3$ | H | Et | C(O)CH$_2$CF$_3$ |
| 3-Br-5-CF$_3$ | CF$_3$ | H | CH$_2$Pr-c | C(O)CH$_2$CF$_3$ |
| 3-Br-5-CF$_3$ | CF$_3$ | H | CH$_2$OCH$_3$ | C(O)CH$_2$CF$_3$ |
| 3-Br-5-CF$_3$ | CF$_3$ | H | CH$_2$CN | C(O)CH$_2$CF$_3$ |
| 3-Br-5-CF$_3$ | CF$_3$ | H | CH$_2$C≡CH | C(O)CH$_2$CF$_3$ |
| 3-Br-5-CF$_3$ | CF$_3$ | C≡CH | H | C(O)CH$_2$CF$_3$ |
| 3-Br-5-CF$_3$ | CF$_3$ | H | H | C(O)CH$_2$CH$_2$CF$_3$ |
| 3-Br-5-CF$_3$ | CF$_3$ | H | Et | C(O)(E-5a) |
| 3-Br-5-CF$_3$ | CF$_3$ | H | CH$_2$Pr-c | C(O)(E-5a) |
| 3-Br-5-CF$_3$ | CF$_3$ | H | CH$_2$OCH$_3$ | C(O)(E-5a) |
| 3-Br-5-CF$_3$ | CF$_3$ | H | CH$_2$CN | C(O)(E-5a) |
| 3-Br-5-CF$_3$ | CF$_3$ | H | CH$_2$C≡CH | C(O)(E-5a) |
| 3-Br-5-CF$_3$ | CF$_3$ | CH$_3$ | H | C(O)(E-5a) |
| 3-Br-5-CF$_3$ | CF$_3$ | CN | H | C(O)(E-5a) |
| 3-Br-5-CF$_3$ | CF$_3$ | C≡CH | H | C(O)(E-5a) |
| 3-Br-5-CF$_3$ | CF$_3$ | H | CH$_2$CH=CH$_2$ | C(O)NHEt |
| 3-Br-5-CF$_3$ | CF$_3$ | H | CH$_2$C≡CH | C(O)NHEt |
| 3-Br-5-CF$_3$ | CF$_3$ | CH$_3$ | H | C(O)NHCH$_2$C≡CH |
| 3-Br-5-CF$_3$ | CF$_3$ | H | H | C(O)(T-17) |
| 3-Br-5-CF$_3$ | CF$_3$ | H | H | C(O)(T-22) |
| 3-Br-5-CF$_3$ | CF$_3$ | H | H | C(S)CH$_2$Pr-c |
| 3-Br-5-CF$_3$ | CF$_3$ | CH$_3$ | H | C(S)CH$_2$Pr-c |
| 3-I-5-CF$_3$ | CF$_3$ | H | H | C(O)Et |
| 3-I-5-CF$_3$ | CF$_3$ | H | Et | C(O)Et |
| 3-I-5-CF$_3$ | CF$_3$ | H | CH$_2$C≡CH | C(O)Et |
| 3-I-5-CF$_3$ | CF$_3$ | CH$_3$ | H | C(O)Et |
| 3-I-5-CF$_3$ | CF$_3$ | H | H | C(O)Pr-n |
| 3-I-5-CF$_3$ | CF$_3$ | H | Et | C(O)Pr-n |
| 3-I-5-CF$_3$ | CF$_3$ | CH$_3$ | H | C(O)Pr-n |
| 3-I-5-CF$_3$ | CF$_3$ | H | H | C(O)Pr-i |
| 3-I-5-CF$_3$ | CF$_3$ | CH$_3$ | H | C(O)Pr-i |
| 3-I-5-CF$_3$ | CF$_3$ | H | H | C(O)Pr-c |
| 3-I-5-CF$_3$ | CF$_3$ | H | Et | C(O)Pr-c |
| 3-I-5-CF$_3$ | CF$_3$ | H | CH$_2$Pr-c | C(O)Pr-c |

TABLE 2-continued

| | | | | |
|---|---|---|---|---|
| 3-I-5-CF$_3$ | CF$_3$ | H | CH$_2$OCH$_3$ | C(O)Pr-c |
| 3-I-5-CF$_3$ | CF$_3$ | H | CH$_2$C≡CH | C(O)Pr-c |
| 3-I-5-CF$_3$ | CF$_3$ | CH$_3$ | H | C(O)Pr-c |
| 3-I-5-CF$_3$ | CF$_3$ | CH$_3$ | Et | C(O)Pr-c |
| 3-I-5-CF$_3$ | CF$_3$ | CH$_3$ | CH$_2$CN | C(O)Pr-c |
| 3-I-5-CF$_3$ | CF$_3$ | CH$_3$ | CH$_2$C≡CH | C(O)Pr-c |
| 3-I-5-CF$_3$ | CF$_3$ | H | H | C(O)Bu-i |
| 3-I-5-CF$_3$ | CF$_3$ | H | H | C(O)CH$_2$Pr-c |
| 3-I-5-CF$_3$ | CF$_3$ | H | Et | C(O)CH$_2$Pr-c |
| 3-I-5-CF$_3$ | CF$_3$ | CH$_3$ | H | C(O)CH$_2$Pr-c |
| 3-I-5-CF$_3$ | CF$_3$ | H | H | C(O)CH$_2$CF$_3$ |
| 3-I-5-CF$_3$ | CF$_3$ | CH$_3$ | H | C(O)CH$_2$CF$_3$ |
| 3-I-5-CF$_3$ | CF$_3$ | H | H | C(O)(E-5a) |
| 3-I-5-CF$_3$ | CF$_3$ | CH$_3$ | H | C(O)(E-5a) |
| 3-I-5-CF$_3$ | CF$_3$ | H | H | C(O)NHEt |
| 3-I-5-CF$_3$ | CF$_3$ | H | H | C(O)NHPr-c |
| 3-I-5-CF$_3$ | CF$_3$ | CH$_3$ | H | C(O)NHPr-c |
| 3-I-5-CF$_3$ | CF$_3$ | CH$_3$ | H | C(O)NHCH$_2$C≡CH |
| 3,5-(CF$_3$)$_2$ | CF$_3$ | H | H | C(O)CH$_3$ |
| 3,5-(CF$_3$)$_2$ | CF$_3$ | H | Et | C(O)Et |
| 3,5-(CF$_3$)$_2$ | CF$_3$ | H | CH$_2$Pr-c | C(O)Et |
| 3,5-(CF$_3$)$_2$ | CF$_3$ | H | CH$_2$OCH$_3$ | C(O)Et |
| 3,5-(CF$_3$)$_2$ | CF$_3$ | H | CH$_2$CN | C(O)Et |
| 3,5-(CF$_3$)$_2$ | CF$_3$ | H | CH$_2$CH=CH$_2$ | C(O)Et |
| 3,5-(CF$_3$)$_2$ | CF$_3$ | H | CH$_2$C≡CH | C(O)Et |
| 3,5-(CF$_3$)$_2$ | CF$_3$ | CH$_3$ | Et | C(O)Et |
| 3,5-(CF$_3$)$_2$ | CF$_3$ | CH$_3$ | CH$_2$Pr-c | C(O)Et |
| 3,5-(CF$_3$)$_2$ | CF$_3$ | CH$_3$ | CH$_2$OCH$_3$ | C(O)Et |
| 3,5-(CF$_3$)$_2$ | CF$_3$ | CH$_3$ | CH$_2$CN | C(O)Et |
| 3,5-(CF$_3$)$_2$ | CF$_3$ | CH$_3$ | CH$_2$C≡CH | C(O)Et |
| 3,5-(CF$_3$)$_2$ | CF$_3$ | H | Et | C(O)Pr-n |
| 3,5-(CF$_3$)$_2$ | CF$_3$ | H | CH$_2$Pr-c | C(O)Pr-n |
| 3,5-(CF$_3$)$_2$ | CF$_3$ | H | CH$_2$OCH$_3$ | C(O)Pr-n |
| 3,5-(CF$_3$)$_2$ | CF$_3$ | H | CH$_2$CN | C(O)Pr-n |
| 3,5-(CF$_3$)$_2$ | CF$_3$ | H | CH$_2$C≡CH | C(O)Pr-n |
| 3,5-(CF$_3$)$_2$ | CF$_3$ | CN | H | C(O)Pr-n |
| 3,5-(CF$_3$)$_2$ | CF$_3$ | C≡CH | H | C(O)Pr-n |
| 3,5-(CF$_3$)$_2$ | CF$_3$ | H | CH$_3$ | C(O)Pr-c |
| 3,5-(CF$_3$)$_2$ | CF$_3$ | H | n-Pr | C(O)Pr-c |
| 3,5-(CF$_3$)$_2$ | CF$_3$ | H | CH$_2$Pr-c | C(O)Pr-c |
| 3,5-(CF$_3$)$_2$ | CF$_3$ | H | CH$_2$CH=CH$_2$ | C(O)Pr-c |
| 3,5-(CF$_3$)$_2$ | CF$_3$ | CH$_3$ | Et | C(O)Pr-c |
| 3,5-(CF$_3$)$_2$ | CF$_3$ | CH$_3$ | CH$_2$Pr-c | C(O)Pr-c |
| 3,5-(CF$_3$)$_2$ | CF$_3$ | CH$_3$ | CH$_2$OCH$_3$ | C(O)Pr-c |
| 3,5-(CF$_3$)$_2$ | CF$_3$ | CH$_3$ | CH$_2$CN | C(O)Pr-c |
| 3,5-(CF$_3$)$_2$ | CF$_3$ | CH$_3$ | CH$_2$C≡CH | C(O)Pr-c |
| 3,5-(CF$_3$)$_2$ | CF$_3$ | C≡CH | H | C(O)Pr-c |
| 3,5-(CF$_3$)$_2$ | CF$_3$ | H | Et | C(O)CH$_2$Pr-c |
| 3,5-(CF$_3$)$_2$ | CF$_3$ | H | CH$_2$Pr-c | C(O)CH$_2$Pr-c |
| 3,5-(CF$_3$)$_2$ | CF$_3$ | H | CH$_2$OCH$_3$ | C(O)CH$_2$Pr-c |
| 3,5-(CF$_3$)$_2$ | CF$_3$ | H | CH$_2$CN | C(O)CH$_2$Pr-c |
| 3,5-(CF$_3$)$_2$ | CF$_3$ | H | CH$_2$CH=CH$_2$ | C(O)CH$_2$Pr-c |
| 3,5-(CF$_3$)$_2$ | CF$_3$ | H | CH$_2$C≡CH | C(O)CH$_2$Pr-c |
| 3,5-(CF$_3$)$_2$ | CF$_3$ | CH$_3$ | H | C(O)CH$_2$Pr-c |
| 3,5-(CF$_3$)$_2$ | CF$_3$ | CN | H | C(O)CH$_2$Pr-c |
| 3,5-(CF$_3$)$_2$ | CF$_3$ | C≡CH | H | C(O)CH$_2$Pr-c |
| 3,5-(CF$_3$)$_2$ | CF$_3$ | H | H | C(O)(T-6) |
| 3,5-(CF$_3$)$_2$ | CF$_3$ | CH$_3$ | H | C(O)(T-6) |
| 3,5-(CF$_3$)$_2$ | CF$_3$ | H | H | C(O)Bu-c |
| 3,5-(CF$_3$)$_2$ | CF$_3$ | H | CH$_2$Pr-c | C(O)CH$_2$CF$_3$ |
| 3,5-(CF$_3$)$_2$ | CF$_3$ | C≡CH | H | C(O)CH$_2$CF$_3$ |
| 3,5-(CF$_3$)$_2$ | CF$_3$ | H | H | C(O)CH$_2$CH$_2$CF$_3$ |
| 3,5-(CF$_3$)$_2$ | CF$_3$ | H | Et | C(O)(E-5a) |
| 3,5-(CF$_3$)$_2$ | CF$_3$ | H | CH$_2$Pr-c | C(O)(E-5a) |
| 3,5-(CF$_3$)$_2$ | CF$_3$ | H | CH$_2$OCH$_3$ | C(O)(E-5a) |
| 3,5-(CF$_3$)$_2$ | CF$_3$ | H | CH$_2$CN | C(O)(E-5a) |
| 3,5-(CF$_3$)$_2$ | CF$_3$ | H | CH$_2$C≡CH | C(O)(E-5a) |
| 3,5-(CF$_3$)$_2$ | CF$_3$ | CH$_3$ | H | C(O)(E-5a) |
| 3,5-(CF$_3$)$_2$ | CF$_3$ | CN | H | C(O)(E-5a) |
| 3,5-(CF$_3$)$_2$ | CF$_3$ | C≡CH | H | C(O)(E-5a) |
| 3,5-(CF$_3$)$_2$ | CF$_3$ | H | CH$_2$CH=CH$_2$ | C(O)NHEt |
| 3,5-(CF$_3$)$_2$ | CF$_3$ | H | CH$_2$C≡CH | C(O)NHEt |
| 3,5-(CF$_3$)$_2$ | CF$_3$ | CH$_3$ | H | C(O)NHCH$_2$C≡CH |
| 3,5-(CF$_3$)$_2$ | CF$_3$ | H | H | C(O)(T-17) |
| 3,5-(CF$_3$)$_2$ | CF$_3$ | H | H | C(O)(T-22) |
| 3,5-(CF$_3$)$_2$ | CF$_3$ | H | H | C(S)CH$_2$Pr-c |
| 3,5-(CF$_3$)$_2$ | CF$_3$ | CH$_3$ | H | C(S)CH$_2$Pr-c |
| 3,5-Cl$_2$-4-F | CF$_3$ | H | H | C(O)CH$_3$ |
| 3,5-Cl$_2$-4-F | CF$_3$ | H | Et | C(O)Et |
| 3,5-Cl$_2$-4-F | CF$_3$ | H | CH$_2$Pr-c | C(O)Et |

TABLE 2-continued

| | | | | |
|---|---|---|---|---|
| 3,5-Cl₂-4-F | CF₃ | H | CH₂OCH₃ | C(O)Et |
| 3,5-Cl₂-4-F | CF₃ | H | CH₂CN | C(O)Et |
| 3,5-Cl₂-4-F | CF₃ | H | CH₂CH=CH₂ | C(O)Et |
| 3,5-Cl₂-4-F | CF₃ | H | CH₂C≡CH | C(O)Et |
| 315-Cl₂-4-F | CF₃ | CH₃ | Et | C(O)Et |
| 3,5-Cl₂-4-F | CF₃ | CH₃ | CH₂Pr-c | C(O)Et |
| 3,5-Cl₂-4-F | CF₃ | CH₃ | CH₂OCH₃ | C(O)Et |
| 3,5-Cl₂-4-F | CF₃ | CH₃ | CH₂CN | C(O)Et |
| 3,5-Cl₂-4-F | CF₃ | CH₃ | CH₂C≡CH | C(O)Et |
| 3,5-Cl₂-4-F | CF₃ | H | Et | C(O)Pr-n |
| 3,5-Cl₂-4-F | CF₃ | H | CH₂Pr-c | C(O)Pr-n |
| 3,5-Cl₂-4-F | CF₃ | H | CH₂OCH₃ | C(O)Pr-n |
| 3,5-Cl₂-4-F | CF₃ | H | CH₂CN | C(O)Pr-n |
| 3,5-Cl₂-4-F | CF₃ | H | CH₂C≡CH | C(O)Pr-n |
| 3,5-Cl₂-4-F | CF₃ | CN | H | C(O)Pr-n |
| 3,5-Cl₂-4-F | CF₃ | C≡CH | H | C(O)Pr-n |
| 3,5-Cl₂-4-F | CF₃ | H | CH₃ | C(O)Pr-c |
| 3,5-Cl₂-4-F | CF₃ | H | Et | C(O)Pr-c |
| 3,5-Cl₂-4-F | CF₃ | H | n-Pr | C(O)Pr-c |
| 3,5-Cl₂-4-F | CF₃ | H | CH₂Pr-c | C(O)Pr-c |
| 3,5-Cl₂-4-F | CF₃ | H | CH₂OCH₃ | C(O)Pr-c |
| 3,5-Cl₂-4-F | CF₃ | H | CH₂CN | C(O)Pr-c |
| 3,5-Cl₂-4-F | CF₃ | H | CH₂CH=CH₂ | C(O)Pr-c |
| 3,5-Cl₂-4-F | CF₃ | H | CH₂C≡CH | C(O)Pr-c |
| 3,5-Cl₂-4-F | CF₃ | CH₃ | Et | C(O)Pr-c |
| 3,5-Cl₂-4-F | CF₃ | CH₃ | CH₂Pr-c | C(O)Pr-c |
| 3,5-Cl₂-4-F | CF₃ | CH₃ | CH₂OCH₃ | C(O)Pr-c |
| 3,5-Cl₂-4-F | CF₃ | CH₃ | CH₂CN | C(O)Pr-c |
| 3,5-Cl₂-4-F | CF₃ | CH₃ | CH₂C≡CH | C(O)Pr-c |
| 3,5-Cl₂-4-F | CF₃ | C≡CH | H | C(O)Pr-c |
| 3,5-Cl₂-4-F | CF₃ | H | Et | C(O)CH₂Pr-c |
| 3,5-Cl₂-4-F | CF₃ | H | CH₂Pr-c | C(O)CH₂Pr-c |
| 3,5-Cl₂-4-F | CF₃ | H | CH₂OCH₃ | C(O)CH₂Pr-c |
| 3,5-Cl₂-4-F | CF₃ | H | CH₂CN | C(O)CH₂Pr-c |
| 3,5-Cl₂-4-F | CF₃ | H | CH₂CH=CH₂ | C(O)CH₂Pr-c |
| 3,5-Cl₂-4-F | CF₃ | H | CH₂C≡CH | C(O)CH₂Pr-c |
| 3,5-Cl₂-4-F | CF₃ | CH₃ | H | C(O)CH₂Pr-c |
| 3,5-Cl₂-4-F | CF₃ | CN | H | C(O)CH₂Pr-c |
| 3,5-Cl₂-4-F | CF₃ | C≡CH | H | C(O)CH₂Pr-c |
| 3,5-Cl₂-4-F | CF₃ | H | H | C(O)(T-6) |
| 3,5-Cl₂-4-F | CF₃ | CH₃ | H | C(O)(T-6) |
| 3,5-Cl₂-4-F | CF₃ | H | H | C(O)Bu-c |
| 3,5-Cl₂-4-F | CF₃ | H | Et | C(O)CH₂CF₃ |
| 3,5-Cl₂-4-F | CF₃ | H | CH₂Pr-c | C(O)CH₂CF₃ |
| 3,5-Cl₂-4-F | CF₃ | H | CH₂OCH₃ | C(O)CH₂CF₃ |
| 3,5-Cl₂-4-F | CF₃ | H | CH₂CN | C(O)CH₂CF₃ |
| 3,5-Cl₂-4-F | CF₃ | H | CH₂C≡CH | C(O)CH₂CF₃ |
| 3,5-Cl₂-4-F | CF₃ | C≡CH | H | C(O)CH₂CF₃ |
| 3,5-Cl₂-4-F | CF₃ | H | H | C(O)CH₂CH₂CF₃ |
| 3,5-Cl₂-4-F | CF₃ | H | Et | C(O)(E-5a) |
| 3,5-Cl₂-4-F | CF₃ | H | CH₂Pr-c | C(O)(E-5a) |
| 3,5-Cl₂-4-F | CF₃ | H | CH₂OCH₃ | C(O)(E-5a) |
| 3,5-Cl₂-4-F | CF₃ | H | CH₂CN | C(O)(E-5a) |
| 3,5-Cl₂-4-F | CF₃ | H | CH₂C≡CH | C(O)(E-5a) |
| 3,5-Cl₂-4-F | CF₃ | CH₃ | H | C(O)(E-5a) |
| 3,5-Cl₂-4-F | CF₃ | CN | H | C(O)(E-5a) |
| 3,5-Cl₂-4-F | CF₃ | C≡CH | H | C(O)(E-5a) |
| 3,5-Cl₂-4-F | CF₃ | H | CH₂CH=CH₂ | C(O)NHEt |
| 3,5-Cl₂-4-F | CF₃ | H | CH₂C≡CH | C(O)NHEt |
| 3,5-Cl₂-4-F | CF₃ | CH₃ | H | C(O)NHCH₂C≡CH |
| 3,5-Cl₂-4-F | CF₃ | H | H | C(O)(T-17) |
| 3,5-Cl₂-4-F | CF₃ | H | H | C(O)(T-22) |
| 3,5-Cl₂-4-F | CF₃ | H | H | C(S)CH₂Pr-c |
| 3,5-Cl₂-4-F | CF₃ | CH₃ | H | C(S)CH₂Pr-c |
| 3,5-Br₂-4-F | CF₃ | H | H | C(O)CH₃ |
| 3,5-Br₂-4-F | CF₃ | H | Et | C(O)Et |
| 3,5-Br₂-4-F | CF₃ | H | CH₂Pr-c | C(O)Et |
| 3,5-Br₂-4-F | CF₃ | H | CH₂OCH₃ | C(O)Et |
| 3,5-Br₂-4-F | CF₃ | H | CH₂CN | C(O)Et |
| 3,5-Br₂-4-F | CF₃ | H | CH₂CH=CH₂ | C(O)Et |
| 3,5-Br₂-4-F | CF₃ | H | CH₂C≡CH | C(O)Et |
| 3,5-Br₂-4-F | CF₃ | CH₃ | Et | C(O)Et |
| 3,5-Br₂-4-F | CF₃ | CH₃ | CH₂Pr-c | C(O)Et |
| 3,5-Br₂-4-F | CF₃ | CH₃ | CH₂OCH₃ | C(O)Et |
| 3,5-Br₂-4-F | CF₃ | CH₃ | CH₂CN | C(O)Et |
| 3,5-Br₂-4-F | CF₃ | CH₃ | CH₂C≡CH | C(O)Et |
| 3,5-Br₂-4-F | CF₃ | H | Et | C(O)Pr-n |
| 3,5-Br₂-4-F | CF₃ | H | CH₂Pr-c | C(O)Pr-n |
| 3,5-Br₂-4-F | CF₃ | H | CH₂OCH₃ | C(O)Pr-n |
| 3,5-Br₂-4-F | CF₃ | H | CH₂CN | C(O)Pr-n |

TABLE 2-continued

| | | | | |
|---|---|---|---|---|
| 3,5-$Br_2$-4-F | $CF_3$ | H | $CH_2C\equiv CH$ | C(O)Pr-n |
| 3,5-$Br_2$-4-F | $CF_3$ | CN | H | C(O)Pr-n |
| 3,5-$Br_2$-4-F | $CF_3$ | $C\equiv CH$ | H | C(O)Pr-n |
| 3,5-$Br_2$-4-F | $CF_3$ | H | $CH_3$ | C(O)Pr-c |
| 3,5-$Br_2$-4-F | $CF_3$ | H | Et | C(O)Pr-c |
| 3,5-$Br_2$-4-F | $CF_3$ | H | n-Pr | C(O)Pr-c |
| 3,5-$Br_2$-4-F | $CF_3$ | H | $CH_2$Pr-c | C(O)Pr-c |
| 3,5-$Br_2$-4-F | $CF_3$ | H | $CH_2OCH_3$ | C(O)Pr-c |
| 3,5-$Br_2$-4-F | $CF_3$ | H | $CH_2CN$ | C(O)Pr-c |
| 3,5-$Br_2$-4-F | $CF_3$ | H | $CH_2CH=CH_2$ | C(O)Pr-c |
| 3,5-$Br_2$-4-F | $CF_3$ | H | $CH_2C\equiv CH$ | C(O)Pr-c |
| 3,5-$Br_2$-4-F | $CF_3$ | $CH_3$ | Et | C(O)Pr-c |
| 3,5-$Br_2$-4-F | $CF_3$ | $CH_3$ | $CH_2$Pr-c | C(O)Pr-c |
| 3,5-$Br_2$-4-F | $CF_3$ | $CH_3$ | $CH_2OCH_3$ | C(O)Pr-c |
| 3,5-$Br_2$-4-F | $CF_3$ | $CH_3$ | $CH_2CN$ | C(O)Pr-c |
| 3,5-$Br_2$-4-F | $CF_3$ | $CH_3$ | $CH_2C\equiv CH$ | C(O)Pr-c |
| 3,5-$Br_2$-4-F | $CF_3$ | $C\equiv CH$ | H | C(O)Pr-c |
| 3,5-$Br_2$-4-F | $CF_3$ | H | Et | C(O)$CH_2$Pr-c |
| 3,5-$Br_2$-4-F | $CF_3$ | H | $CH_2$Pr-c | C(O)$CH_2$Pr-c |
| 3,5-$Br_2$-4-F | $CF_3$ | H | $CH_2OCH_3$ | C(O)$CH_2$Pr-c |
| 3,5-$Br_2$-4-F | $CF_3$ | H | $CH_2CN$ | C(O)$CH_2$Pr-c |
| 3,5-$Br_2$-4-F | $CF_3$ | H | $CH_2CH=CH_2$ | C(O)$CH_2$Pr-c |
| 3,5-$Br_2$-4-F | $CF_3$ | H | $CH_2C\equiv CH$ | C(O)$CH_2$Pr-c |
| 3,5-$Br_2$-4-F | $CF_3$ | $CH_3$ | H | C(O)$CH_2$Pr-c |
| 3,5-$Br_2$-4-F | $CF_3$ | CN | H | C(O)$CH_2$Pr-c |
| 3,5-$Br_2$-4-F | $CF_3$ | $C\equiv CH$ | H | C(O)$CH_2$Pr-c |
| 3,5-$Br_2$-4-F | $CF_3$ | H | H | C(O)(T-6) |
| 3,5-$Br_2$-4-F | $CF_3$ | $CH_3$ | H | C(O)(T-6) |
| 3,5-$Br_2$-4-F | $CF_3$ | H | H | C(O)Bu-c |
| 3,5-$Br_2$-4-F | $CF_3$ | H | Et | C(O)$CH_2CF_3$ |
| 3,5-$Br_2$-4-F | $CF_3$ | H | $CH_2$Pr-c | C(O)$CH_2CF_3$ |
| 3,5-$Br_2$-4-F | $CF_3$ | H | $CH_2OCH_3$ | C(O)$CH_2CF_3$ |
| 3,5-$Br_2$-4-F | $CF_3$ | H | $CH_2CN$ | C(O)$CH_2CF_3$ |
| 3,5-$Br_2$-4-F | $CF_3$ | H | $CH_2C\equiv CH$ | C(O)$CH_2CF_3$ |
| 3,5-$Br_2$-4-F | $CF_3$ | $C\equiv CH$ | H | C(O)$CH_2CF_3$ |
| 3,5-$Br_2$-4-F | $CF_3$ | H | H | C(O)$CH_2CH_2CF_3$ |
| 3,5-$Br_2$-4-F | $CF_3$ | H | Et | C(O)(E-5a) |
| 3,5-$Br_2$-4-F | $CF_3$ | H | $CH_2$Pr-c | C(O)(E-5a) |
| 3,5-$Br_2$-4-F | $CF_3$ | H | $CH_2OCH_3$ | C(O)(E-5a) |
| 3,5-$Br_2$-4-F | $CF_3$ | H | $CH_2CN$ | C(O)(E-5a) |
| 3,5-$Br_2$-4-F | $CF_3$ | H | $CH_2C\equiv CH$ | C(O)(E-5a) |
| 3,5-$Br_2$-4-F | $CF_3$ | $CH_3$ | H | C(O)(E-5a) |
| 3,5-$Br_2$-4-F | $CF_3$ | CN | H | C(O)(E-5a) |
| 3,5-$Br_2$-4-F | $CF_3$ | $C\equiv CH$ | H | C(O)(E-5a) |
| 3,5-$Br_2$-4-F | $CF_3$ | H | $CH_2CH=CH_2$ | C(O)NHEt |
| 3,5-$Br_2$-4-F | $CF_3$ | H | $CH_2C\equiv CH$ | C(O)NHEt |
| 3,5-$Br_2$-4-F | $CF_3$ | $CH_3$ | H | C(O)NH$CH_2C\equiv CH$ |
| 3,5-$Br_2$-4-F | $CF_3$ | H | H | C(O)(T-17) |
| 3,5-$Br_2$-4-F | $CF_3$ | H | H | C(O)(T-22) |
| 3,5-$Br_2$-4-F | $CF_3$ | H | H | C(S)$CH_2$Pr-c |
| 3,5-$Br_2$-4-F | $CF_3$ | $CH_3$ | H | C(S)$CH_2$Pr-c |

The indication "-" means no-substitution.

TABLE 3

In the table, the numbers showing the substitution positions of substituents $(X)_m$ and $(Y)_n$ correspond to the position numbers indicated in the following structural formulae. The indication "—" means no-substitution.

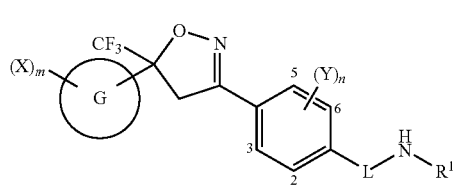

[2]-1 or

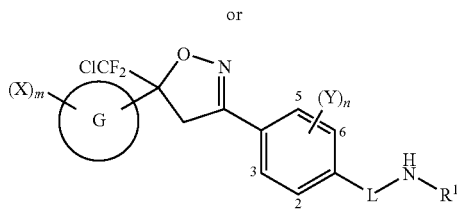

[2]-2

In addition, substituent G in the above-mentioned formulae [2]-1 to [2]-6 indicates aromatic 6-membered ring shown by any one of G-1, G-3 or G-4 mentioned below, or aromatic 5-membered ring shown by any one of G-13, G-14, G-17, G-20, G-21 or G-22 mentioned below.

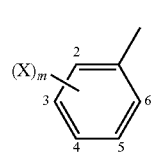

G-1

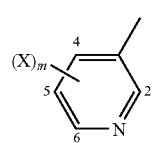

G-3

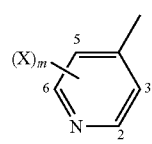

G-4

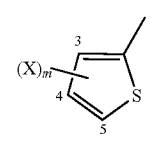

G-13

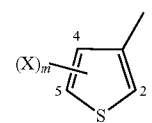

G-14

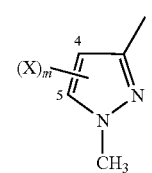

G-17a

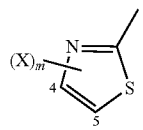
G-20

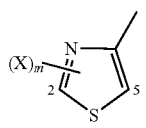
G-21

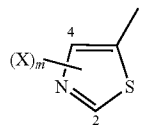
G-22

| G | (X)$_m$ | (Y)$_n$ | L | R$^1$ |
|---|---|---|---|---|
| G-1 | 3-CF$_3$ | 2-Pr-i | CH$_2$ | C(O)Et |
| G-1 | 3-CF$_3$ | 2-OEt | CH$_2$ | C(O)Pr-n |
| G-1 | 3-CF$_3$ | 2-OPr-i | CH$_2$ | C(O)Pr-i |
| G-1 | 3-CF$_3$ | 2-OSO$_2$CH$_3$ | CH$_2$ | C(O)Pr-c |
| G-1 | 3-CF$_3$ | 2-SEt | CH$_2$ | C(O)CH$_2$Pr-c |
| G-1 | 3-CF$_3$ | 2-SPr-i | CH$_2$ | C(O)CH$_2$CH$_2$Cl |
| G-1 | 3-CF$_3$ | 2-NHEt | CH$_2$ | C(O)CH$_2$CF$_3$ |
| G-1 | 3-CF$_3$ | 2-NHPr-i | CH$_2$ | C(O)Et |
| G-1 | 3-CF$_3$ | 2-N(CH$_3$)$_2$ | CH$_2$ | C(O)Pr-n |
| G-1 | 3-CF$_3$ | 2-NHC(O)CH$_3$ | CH$_2$ | C(O)Pr-i |
| G-1 | 3-CF$_2$CF$_3$ | 2-Pr-i | CH$_2$ | C(O)Pr-c |
| G-1 | 3-CF$_2$CF$_3$ | 2-OEt | CH$_2$ | C(O)CH$_2$Pr-c |
| G-1 | 3-CF$_2$CF$_3$ | 2-OPr-i | CH$_2$ | C(O)CH$_2$CH$_2$Cl |
| G-1 | 3-CF$_2$CF$_3$ | 2-OSO$_2$CH$_3$ | CH$_2$ | C(O)CH$_2$CF$_3$ |
| G-1 | 3-CF$_2$CF$_3$ | 2-SEt | CH$_2$ | C(O)Et |
| G-1 | 3-CF$_2$CF$_3$ | 2-SPr-i | CH$_2$ | C(O)Pr-n |
| G-1 | 3-CF$_2$CF$_3$ | 2-NHEt | CH$_2$ | C(O)Pr-i |
| G-1 | 3-CF$_2$CF$_3$ | 2-NHPr-i | CH$_2$ | C(O)Pr-c |
| G-1 | 3-CF$_2$CF$_3$ | 2-N(CH$_3$)$_2$ | CH$_2$ | C(O)CH$_2$Pr-c |
| G-1 | 3-CF$_2$CF$_3$ | 2-NHC(O)CH$_2$ | CH$_2$ | C(O)CH$_2$CH$_2$Cl |
| G-1 | 3-SF$_5$ | 2-Pr-i | CH$_2$ | C(O)CH$_2$CF$_3$ |
| G-1 | 3-SF$_5$ | 2-OEt | CH$_2$ | C(O)Et |
| G-1 | 3-SF$_5$ | 2-OPr-i | CH$_2$ | C(O)Pr-n |
| G-1 | 3-SF$_5$ | 2-OSO$_2$CH$_3$ | CH$_2$ | C(O)Pr-i |
| G-1 | 3-SF$_5$ | 2-SEt | CH$_2$ | C(O)Pr-c |
| G-1 | 3-SF$_5$ | 2-SPr-i | CH$_2$ | C(O)CH$_2$Pr-c |
| G-1 | 3-SF$_5$ | 2-NHEt | CH$_2$ | C(O)CH$_2$CH$_2$Cl |
| G-1 | 3-SF$_5$ | 2-NHPr-i | CH$_2$ | C(O)CH$_2$CF$_3$ |
| G-1 | 3-SF$_5$ | 2-N(CH$_3$)$_2$ | CH$_2$ | C(O)Et |
| G-1 | 3-SF$_5$ | 2-NHC(O)CH$_3$ | CH$_2$ | C(O)Pr-n |
| G-1 | 3,5-Cl$_2$ | — | C(CH$_3$)$_2$ | C(O)Et |
| G-1 | 3,5-Cl$_2$ | — | C(CH$_3$)$_2$ | C(O)Pr-n |
| G-1 | 3,5-Cl$_2$ | — | C(CH$_3$)$_2$ | C(O)Pr-i |
| G-1 | 3,5-Cl$_2$ | — | C(CH$_3$)$_2$ | C(O)Pr-c |
| G-1 | 3,5-Cl$_2$ | — | C(CH$_3$)$_2$ | C(O)CH$_2$Pr-c |
| G-1 | 3,5-Cl$_2$ | — | C(CH$_3$)$_2$ | C(O)CH$_2$CH$_2$Cl |
| G-1 | 3,5-Cl$_2$ | — | C(CH$_3$)$_2$ | C(O)CH$_2$CF$_3$ |
| G-1 | 3,5-Cl$_2$ | — | CH$_2$CH$_2$ | C(O)Pr-i |
| G-1 | 3,5-Cl$_2$ | — | CH$_2$CH$_2$ | C(O)Pr-c |
| G-1 | 3,5-Cl$_2$ | — | CH$_2$CH$_2$ | C(O)CH$_2$CF$_3$ |
| G-1 | 3,5-Cl$_2$ | — | CH(CH$_3$)CH$_2$ | C(O)Et |
| G-1 | 3,5-Cl$_2$ | — | CH(CH$_3$)CH$_2$ | C(O)Pr-n |
| G-1 | 3,5-Cl$_2$ | — | CH(CH$_3$)CH$_2$ | C(O)Pr-i |
| G-1 | 3,5-Cl$_2$ | — | CH(CH$_3$)CH$_2$ | C(O)Pr-c |
| G-1 | 3,5-Cl$_2$ | — | CH(CH$_3$)CH$_2$ | C(O)CH$_2$Pr-c |
| G-1 | 3,5-Cl$_2$ | — | CH(CH$_3$)CH$_2$ | C(O)CH$_2$CH$_2$Cl |
| G-1 | 3,5-Cl$_2$ | — | CH(CH$_3$)CH$_2$ | C(O)CH$_2$CF$_3$ |
| G-1 | 3,5-Cl$_2$ | — | CH$_2$CH(CH$_3$) | C(O)Pr-i |
| G-1 | 3,5-Cl$_2$ | — | CH$_2$CH(CH$_3$) | C(O)Pr-c |
| G-1 | 3,5-Cl$_2$ | — | CH$_2$CH(CH$_3$) | C(O)CH$_2$CF$_3$ |
| G-1 | 3,5-Cl$_2$ | — | N(CH$_3$) | C(O)Pr-i |
| G-1 | 3,5-Cl$_2$ | — | N(CH$_3$) | C(O)Pr-c |
| G-1 | 3,5-Cl$_2$ | — | N(CH$_3$) | C(O)CH$_2$CF$_3$ |
| G-1 | 3,5-Cl$_2$ | — | N[C(O)CH$_3$] | C(O)Pr-i |
| G-1 | 3,5-Cl$_2$ | — | N[C(O)CH$_3$] | C(O)Pr-c |

| | | | | |
|---|---|---|---|---|
| G-1 | 3,5-Cl₂ | — | N[C(O)CH₃] | C(O)CH₂CF₃ |
| G-1 | 3,5-Cl₂ | — | N[C(O)CF₃] | C(O)Pr-i |
| G-1 | 3,5-Cl₂ | — | N[C(O)CF₃] | C(O)CH₂CF₃ |
| G-1 | 3,5-Cl₂ | — | N[C(O)OCH₃] | C(O)Pr-i |
| G-1 | 3,5-Cl₂ | — | N[C(O)OCH₃] | C(O)Pr-c |
| G-1 | 3,5-Cl₂ | — | N[C(O)OCH₃] | C(O)CH₂CF₃ |
| G-1 | 3,5-Cl₂ | 2-F | C(CH₃)₂ | C(O)Pr-i |
| G-1 | 3,5-Cl₂ | 2-F | C(CH₃)₂ | C(O)Pr-c |
| G-1 | 3,5-Cl₂ | 2-F | C(CH₃)₂ | C(O)CH₂CF₃ |
| G-1 | 3,5-Cl₂ | 2-F | CH₂CH₂ | C(O)Pr-i |
| G-1 | 3,5-Cl₂ | 2-F | CH₂CH₂ | C(O)Pr-c |
| G-1 | 3,5-Cl₂ | 2-F | CH₂CH₂ | C(O)CH₂CF₃ |
| G-1 | 3,5-Cl₂ | 3-F | CH₂ | C(O)Pr-i |
| G-1 | 3,5-Cl₂ | 2-Cl | C(CH₃)₂ | C(O)Pr-i |
| G-1 | 3,5-Cl₂ | 2-Cl | C(CH₃)₂ | C(O)Pr-c |
| G-1 | 3,5-Cl₂ | 2-Cl | C(CH₃)₂ | C(O)CH₂CF₃ |
| G-1 | 3,5-Cl₂ | 2-Cl | CH₂CH₂ | C(O)Et |
| G-1 | 3,5-Cl₂ | 2-Cl | CH₂CH₂ | C(O)Pr-n |
| G-1 | 3,5-Cl₂ | 2-Cl | CH₂CH₂ | C(O)Pr-i |
| G-1 | 3,5-Cl₂ | 2-Cl | CH₂CH₂ | C(O)Pr-c |
| G-1 | 3,5-Cl₂ | 2-Cl | CH₂CH₂ | C(O)CH₂Pr-c |
| G-1 | 3,5-Cl₂ | 2-Cl | CH₂CH₂ | C(O)CH₂CH₂Cl |
| G-1 | 3,5-Cl₂ | 2-Cl | CH₂CH₂ | C(O)CH₂CF₃ |
| G-1 | 3,5-Cl₂ | 2-Cl | CH(CH₃)CH₂ | C(O)Pr-i |
| G-1 | 3,5-Cl₂ | 2-Cl | CH(CH₃)CH₂ | C(O)Pr-c |
| G-1 | 3,5-Cl₂ | 2-Cl | CH(CH₃)CH₂ | C(O)CH₂CF₃ |
| G-1 | 3,5-Cl₂ | 2-Cl | CH₂CH(CH₃) | C(O)Et |
| G-1 | 3,5-Cl₂ | 2-Cl | CH₂CH(CH₃) | C(O)Pr-n |
| G-1 | 3,5-Cl₂ | 2-Cl | CH₂CH(CH₃) | C(O)Pr-i |
| G-1 | 3,5-Cl₂ | 2-Cl | CH₂CH(CH₃) | C(O)Pr-c |
| G-1 | 3,5-Cl₂ | 2-Cl | CH₂CH(CH₃) | C(O)CH₂Pr-c |
| G-1 | 3,5-Cl₂ | 2-Cl | CH₂CH(CH₃) | C(O)CH₂CH₂Cl |
| G-1 | 3,5-Cl₂ | 2-Cl | CH₂CH(CH₃) | C(O)CH₂CF₃ |
| G-1 | 3,5-Cl₂ | 2-Cl | CH₂NH | C(O)Pr-i |
| G-1 | 3,5-Cl₂ | 2-Cl | CH₂NH | C(O)Pr-c |
| G-1 | 3,5-Cl₂ | 2-Cl | CH₂NH | C(O)CH₂CF₃ |
| G-1 | 3,5-Cl₂ | 2-Cl | NH | C(O)Pr-i |
| G-1 | 3,5-Cl₂ | 2-Cl | NH | C(O)Pr-c |
| G-1 | 3,5-Cl₂ | 2-Cl | NH | C(O)CH₂CF₃ |
| G-1 | 3,5-Cl₂ | 2-Cl | N(CH₃) | C(O)Pr-i |
| G-1 | 3,5-Cl₂ | 2-Cl | N(CH₃) | C(O)Pr-c |
| G-1 | 3,5-Cl₂ | 2-Cl | N(CH₃) | C(O)CH₂CF₃ |
| G-1 | 3,5-Cl₂ | 2-Cl | N[C(O)CH₃] | C(O)Pr-i |
| G-1 | 3,5-Cl₂ | 2-Cl | N[C(O)CH₃] | C(O)Pr-c |
| G-1 | 3,5-Cl₂ | 2-Cl | N[C(O)CH₃] | C(O)CH₂CF₃ |
| G-1 | 3,5-Cl₂ | 2-Cl | N[C(O)CF₃] | C(O)Pr-i |
| G-1 | 3,5-Cl₂ | 2-Cl | N[C(O)CF₃] | C(O)Pr-c |
| G-1 | 3,5-Cl₂ | 2-Cl | N[C(O)CF₃] | C(O)CH₂CF₃ |
| G-1 | 3,5-Cl₂ | 2-Cl | N[C(O)OCH₃] | C(O)Pr-i |
| G-1 | 3,5-Cl₂ | 2-Cl | N[C(O)OCH₃] | C(O)Pr-c |
| G-1 | 3,5-Cl₂ | 2-Cl | N[C(O)OCH₃] | C(O)CH₂CF₃ |
| G-1 | 3,5-Cl₂ | 3-Cl | CH₂ | C(O)Pr-c |
| G-1 | 3,5-Cl₂ | 2-Br | CH₂CH₂ | C(O)Pr-i |
| G-1 | 3,5-Cl₂ | 2-Br | CH₂CH₂ | C(O)Pr-c |
| G-1 | 3,5-Cl₂ | 2-Br | CH₂CH₂ | C(O)CH₂CF₃ |
| G-1 | 3,5-Cl₂ | 3-Br | CH₂ | C(O)CH₂Pr-c |
| G-1 | 3,5-Cl₂ | 2-I | CH₂CH₂ | C(O)Pr-i |
| G-1 | 3,5-Cl₂ | 2-I | CH₂CH₂ | C(O)Pr-c |
| G-1 | 3,5-Cl₂ | 2-I | CH₂CH₂ | C(O)CH₂CF₃ |
| G-1 | 3,5-Cl₂ | 2-CH₃ | CH₂CH₂ | C(O)Pr-i |
| G-1 | 3,5-Cl₂ | 2-CH₃ | CH₂CH₂ | C(O)Pr-c |
| G-1 | 3,5-Cl₂ | 2-CH₃ | CH₂CH₂ | C(O)CH₂CF₃ |
| G-1 | 3,5-Cl₂ | 3-CH₃ | CH₂ | C(O)CH₂CH₂Cl |
| G-1 | 3,5-Cl₂ | 2-Et | CH₂CH₂ | C(O)Pr-i |
| G-1 | 3,5-Cl₂ | 2-Et | CH₂CH₂ | C(O)Pr-c |
| G-1 | 3,5-Cl₂ | 2-Et | CH₂CH₂ | C(O)CH₂CF₃ |
| G-1 | 3,5-Cl₂ | 2-Pr-n | CH₂ | C(O)CH₂CF₃ |
| G-1 | 3,5-Cl₂ | 2-Pr-i | CH₂ | C(O)Et |
| G-1 | 3,5-Cl₂ | 2-Pr-i | CH₂ | C(O)Pr-n |
| G-1 | 3,5-Cl₂ | 2-Pr-i | CH₂ | C(O)Pr-i |
| G-1 | 3,5-Cl₂ | 2-Pr-i | CH₂ | C(O)Pr-c |
| G-1 | 3,5-Cl₂ | 2-Pr-i | CH₂ | C(O)CH₂Pr-c |
| G-1 | 3,5-Cl₂ | 2-Pr-i | CH₂ | C(O)CH₂CH₂Cl |
| G-1 | 3,5-Cl₂ | 2-Pr-i | CH₂ | C(O)CH₂CF₃ |
| G-1 | 3,5-Cl₂ | 2-Bu-n | CH₂ | C(O)Et |
| G-1 | 3,5-Cl₂ | 2-Bu-s | CH₂ | C(O)Pr-n |
| G-1 | 3,5-Cl₂ | 2-Bu-t | CH₂ | C(O)Pr-i |
| G-1 | 3,5-Cl₂ | 2-CF₃ | CH₂CH₂ | C(O)Pr-i |
| G-1 | 3,5-Cl₂ | 2-CF₃ | CH₂CH₂ | C(O)Pr-c |
| G-1 | 3,5-Cl₂ | 2-CF₃ | CH₂CH₂ | C(O)CH₂CF₃ |
| G-1 | 3,5-Cl₂ | 2-CF₂CF₃ | CH₂ | C(O)Pr-c |

| | | | | |
|---|---|---|---|---|
| G-1 | 3,5-Cl$_2$ | 2-CH$_2$OH | CH$_2$ | C(O)CH$_2$Pr-c |
| G-1 | 3,5-Cl$_2$ | 2-CH$_2$OCH$_3$ | CH$_2$ | C(O)Pr-i |
| G-1 | 3,5-Cl$_2$ | 2-CH$_2$OCH$_3$ | CH$_2$ | C(O)Pr-c |
| G-1 | 3,5-Cl$_2$ | 2-CH$_2$OCH$_3$ | CH$_2$ | C(O)CH$_2$CF$_3$ |
| G-1 | 3,5-Cl$_2$ | 2-CH$_2$OEt | CH$_2$ | C(O)CH$_2$CH$_2$Cl |
| G-1 | 3,5-Cl$_2$ | 2-CH$_2$OPr-n | CH$_2$ | C(O)CH$_2$CF$_3$ |
| G-1 | 3,5-Cl$_2$ | 2-CH$_2$OPr-i | CH$_2$ | C(O)Et |
| G-1 | 3,5-Cl$_2$ | 2-CH$_2$OPr-c | CH$_2$ | C(O)Pr-n |
| G-1 | 3,5-Cl$_2$ | 2-CH$_2$OCH$_2$CF$_3$ | CH$_2$ | C(O)Pr-i |
| G-1 | 3,5-Cl$_2$ | 2-CH$_2$CH$_2$OCH$_3$ | CH$_2$ | C(O)Pr-c |
| G-1 | 3,5-Cl$_2$ | 2-CH$_2$SCH$_3$ | CH$_2$ | C(O)Pr-i |
| G-1 | 3,5-Cl$_2$ | 2-CH$_2$SCH$_3$ | CH$_2$ | C(O)Pr-c |
| G-1 | 3,5-Cl$_2$ | 2-CH$_2$SCH$_3$ | CH$_2$ | C(O)CH$_2$CF$_3$ |
| G-1 | 3,5-Cl$_2$ | 2-CH$_2$S(O)CH$_3$ | CH$_2$ | C(O)CH$_2$Pr-c |
| G-1 | 3,5-Cl$_2$ | 2-CH$_2$SO$_2$CH$_3$ | CH$_2$ | C(O)CH$_2$CH$_2$Cl |
| G-1 | 3,5-Cl$_2$ | 2-CH$_2$SCF$_3$ | CH$_2$ | C(O)Pr-i |
| G-1 | 3,5-Cl$_2$ | 2-CH$_2$SCF$_3$ | CH$_2$ | C(O)Pr-c |
| G-1 | 3,5-Cl$_2$ | 2-CH$_2$SCF$_3$ | CH$_2$ | C(O)CH$_2$CF$_3$ |
| G-1 | 3,5-Cl$_2$ | 2-CH$_2$S(O)CF$_3$ | CH$_2$ | C(O)CH$_2$CF$_3$ |
| G-1 | 3,5-Cl$_2$ | 2-CH$_2$SO$_2$CF$_3$ | CH$_2$ | C(O)Et |
| G-1 | 3,5-Cl$_2$ | 2-CH$_2$Ph | CH$_2$ | C(O)Pr-n |
| G-1 | 3,5-Cl$_2$ | 2-CH$_2$(D-14a) | CH$_2$ | C(O)Pr-i |
| G-1 | 3,5-Cl$_2$ | 2-CH$_2$(D-24a) | CH$_2$ | C(O)Pr-c |
| G-1 | 3,5-Cl$_2$ | 2-CH$_2$(D-41a) | CH$_2$ | C(O)CH$_2$Pr-c |
| G-1 | 3,5-Cl$_2$ | 2-OCH$_3$ | CH$_2$CH$_2$ | C(O)Pr-i |
| G-1 | 3,5-Cl$_2$ | 2-OCH$_3$ | CH$_2$CH$_2$ | C(O)Pr-c |
| G-1 | 3,5-Cl$_2$ | 2-OCH$_3$ | CH$_2$CH$_2$ | C(O)CH$_2$CF$_3$ |
| G-1 | 3,5-Cl$_2$ | 2-OEt | CH$_2$ | C(O)Et |
| G-1 | 3,5-Cl$_2$ | 2-OEt | CH$_2$ | C(O)Pr-n |
| G-1 | 3,5-Cl$_2$ | 2-OEt | CH$_2$ | C(O)Pr-i |
| G-1 | 3,5-Cl$_2$ | 2-OEt | CH$_2$ | C(O)Pr-c |
| G-1 | 3,5-Cl$_2$ | 2-OEt | CH$_2$ | C(O)CH$_2$Pr-c |
| G-1 | 3,5-Cl$_2$ | 2-OEt | CH$_2$ | C(O)CH$_2$CH$_2$Cl |
| G-1 | 3,5-Cl$_2$ | 2-OEt | CH$_2$ | C(O)CH$_2$CF$_3$ |
| G-1 | 3,5-Cl$_2$ | 2-OPr-n | CH$_2$ | C(O)CH$_2$CH$_2$Cl |
| G-1 | 3,5-Cl$_2$ | 2-OPr-i | CH$_2$ | C(O)Et |
| G-1 | 3,5-Cl$_2$ | 2-OPr-i | CH$_2$ | C(O)Pr-n |
| G-1 | 3,5-Cl$_2$ | 2-OPr-i | CH$_2$ | C(O)Pr-i |
| G-1 | 3,5-Cl$_2$ | 2-OPr-i | CH$_2$ | C(O)Pr-c |
| G-1 | 3,5-Cl$_2$ | 2-OPr-i | CH$_2$ | C(O)CH$_2$Pr-c |
| G-1 | 3,5-Cl$_2$ | 2-OPr-i | CH$_2$ | C(O)CH$_2$CH$_2$Cl |
| G-1 | 3,5-Cl$_2$ | 2-OPr-i | CH$_2$ | C(O)CH$_2$CF$_3$ |
| G-1 | 3,5-Cl$_2$ | 2-OBu-n | CH$_2$ | C(O)CH$_2$CF$_3$ |
| G-1 | 3,5-Cl$_2$ | 2-OPen-n | CH$_2$ | C(O)Et |
| G-1 | 3,5-Cl$_2$ | 2-OHex-n | CH$_2$ | C(O)Pr-n |
| G-1 | 3,5-Cl$_2$ | 2-OCHF$_2$ | CH$_2$CH$_2$ | C(O)Pr-i |
| G-1 | 3,5-Cl$_2$ | 2-OCHF$_2$ | CH$_2$CH$_2$ | C(O)Pr-c |
| G-1 | 3,5-Cl$_2$ | 2-OCHF$_2$ | CH$_2$CH$_2$ | C(O)CH$_2$CF$_3$ |
| G-1 | 3,5-Cl$_2$ | 2-OCF$_3$ | CH$_2$CH$_2$ | C(O)Pr-i |
| G-1 | 3,5-Cl$_2$ | 2-OCF$_3$ | CH$_2$CH$_2$ | C(O)Pr-c |
| G-1 | 3,5-Cl$_2$ | 2-OCF$_3$ | CH$_2$CH$_2$ | C(O)CH$_2$CF$_3$ |
| G-1 | 3,5-Cl$_2$ | 2-OCF$_2$Br | CH$_2$ | C(O)Pr-i |
| G-1 | 3,5-Cl$_2$ | 2-OCF$_2$CHF$_2$ | CH$_2$ | C(O)Pr-c |
| G-1 | 3,5-Cl$_2$ | 2-OCF$_2$CHFCl | CH$_2$ | C(O)CH$_2$Pr-c |
| G-1 | 3,5-Cl$_2$ | 2-OCF$_2$CHFCF$_3$ | CH$_2$ | C(O)CH$_2$CH$_2$Cl |
| G-1 | 3,5-Cl$_2$ | 2-OCF$_2$CHFOCF$_3$ | CH$_2$ | C(O)CH$_2$CF$_3$ |
| G-1 | 3,5-Cl$_2$ | 2-OSO$_2$CH$_3$ | CH$_2$ | C(O)Et |
| G-1 | 3,5-Cl$_2$ | 2-OSO$_2$CH$_3$ | CH$_2$ | C(O)Pr-n |
| G-1 | 3,5-Cl$_2$ | 2-OSO$_2$CH$_3$ | CH$_2$ | C(O)Pr-i |
| G-1 | 3,5-Cl$_2$ | 2-OSO$_2$CH$_3$ | CH$_2$ | C(O)Pr-c |
| G-1 | 3,5-Cl$_2$ | 2-OSO$_2$CH$_3$ | CH$_2$ | C(O)CH$_2$Pr-c |
| G-1 | 3,5-Cl$_2$ | 2-OSO$_2$CH$_3$ | CH$_2$ | C(O)CH$_2$CH$_2$Cl |
| G-1 | 3,5-Cl$_2$ | 2-OSO$_2$CH$_3$ | CH$_2$ | C(O)CH$_2$CF$_3$ |
| G-1 | 3,5-Cl$_2$ | 2-OSO$_2$Et | CH$_2$ | C(O)Et |
| G-1 | 3,5-Cl$_2$ | 2-OSO$_2$Pr-i | CH$_2$ | C(O)Pr-n |
| G-1 | 3,5-Cl$_2$ | 2-OSO$_2$CF$_3$ | CH$_2$ | C(O)Pr-i |
| G-1 | 3,5-Cl$_2$ | 2-OPh | CH$_2$ | C(O)Pr-c |
| G-1 | 3,5-Cl$_2$ | 2-SCH$_3$ | CH$_2$CH$_2$ | C(O)Pr-i |
| G-1 | 3,5-Cl$_2$ | 2-SCH$_3$ | CH$_2$CH$_2$ | C(O)Pr-c |
| G-1 | 3,5-Cl$_2$ | 2-SCH$_3$ | CH$_2$CH$_2$ | C(O)CH$_2$CF$_3$ |
| G-1 | 3,5-Cl$_2$ | 2-S(O)CH$_3$ | CH$_2$ | C(O)CH$_2$Pr-c |
| G-1 | 3,5-Cl$_2$ | 2-SO$_2$CH$_3$ | CH$_2$ | C(O)CH$_2$CH$_2$Cl |
| G-1 | 3,5-Cl$_2$ | 2-SEt | CH$_2$ | C(O)Et |
| G-1 | 3,5-Cl$_2$ | 2-SEt | CH$_2$ | C(O)Pr-n |
| G-1 | 3,5-Cl$_2$ | 2-SEt | CH$_2$ | C(O)Pr-i |
| G-1 | 3,5-Cl$_2$ | 2-SEt | CH$_2$ | C(O)Pr-c |
| G-1 | 3,5-Cl$_2$ | 2-SEt | CH$_2$ | C(O)CH$_2$Pr-c |
| G-1 | 3,5-Cl$_2$ | 2-SEt | CH$_2$ | C(O)CH$_2$CH$_2$Cl |
| G-1 | 3,5-Cl$_2$ | 2-SEt | CH$_2$ | C(O)CH$_2$CF$_3$ |
| G-1 | 3,5-Cl$_2$ | 2-S(O)Et | CH$_2$ | C(O)CH$_2$CF$_3$ |
| G-1 | 3,5-Cl$_2$ | 2-SO$_2$Et | CH$_2$ | C(O)Et |
| G-1 | 3,5-Cl$_2$ | 2-SPr-n | CH$_2$ | C(O)Pr-n |

| | | | | |
|---|---|---|---|---|
| G-1 | 3,5-Cl$_2$ | 2-S(O)Pr-n | CH$_2$ | C(O)Pr-i |
| G-1 | 3,5-Cl$_2$ | 2-SO$_2$Pr-n | CH$_2$ | C(O)Pr-c |
| G-1 | 3,5-Cl$_2$ | 2-SPr-i | CH$_2$ | C(O)Et |
| G-1 | 3,5-Cl$_2$ | 2-SPr-i | CH$_2$ | C(O)Pr-n |
| G-1 | 3,5-Cl$_2$ | 2-SPr-i | CH$_2$ | C(O)Pr-i |
| G-1 | 3,5-Cl$_2$ | 2-SPr-i | CH$_2$ | C(O)Pr-c |
| G-1 | 3,5-Cl$_2$ | 2-SPr-i | CH$_2$ | C(O)CH$_2$Pr-c |
| G-1 | 3,5-Cl$_2$ | 2-SPr-i | CH$_2$ | C(O)CH$_2$CH$_2$Cl |
| G-1 | 3,5-Cl$_2$ | 2-SPr-i | CH$_2$ | C(O)CH$_2$CF$_3$ |
| G-1 | 3,5-Cl$_2$ | 2-S(O)Pr-i | CH$_2$ | C(O)CH$_2$Pr-c |
| G-1 | 3,5-Cl$_2$ | 2-SO$_2$Pr-i | CH$_2$ | C(O)CH$_2$CH$_2$Cl |
| G-1 | 3,5-Cl$_2$ | 2-SCHF$_2$ | CH$_2$CH$_2$ | C(O)Pr-i |
| G-1 | 3,5-Cl$_2$ | 2-SCHF$_2$ | CH$_2$CH$_2$ | C(O)Pr-c |
| G-1 | 3,5-Cl$_2$ | 2-SCHF$_2$ | CH$_2$CH$_2$ | C(O)CH$_2$CF$_3$ |
| G-1 | 3,5-Cl$_2$ | 2-S(O)CHF$_2$ | CH$_2$ | C(O)CH$_2$CF$_3$ |
| G-1 | 3,5-Cl$_2$ | 2-SO$_2$CHF$_2$ | CH$_2$ | C(O)Et |
| G-1 | 3,5-Cl$_2$ | 2-SCF$_3$ | CH$_2$CH$_2$ | C(O)Pr-i |
| G-1 | 3,5-Cl$_2$ | 2-SCF$_3$ | CH$_2$CH$_2$ | C(O)Pr-c |
| G-1 | 3,5-Cl$_2$ | 2-SCF$_3$ | CH$_2$CH$_2$ | C(O)CH$_2$CF$_3$ |
| G-1 | 3,5-Cl$_2$ | 2-S(O)CF$_3$ | CH$_2$ | C(O)Pr-n |
| G-1 | 3,5-Cl$_2$ | 2-SO$_2$CF$_3$ | CH$_2$ | C(O)Pr-i |
| G-1 | 3,5-Cl$_2$ | 2-SCF$_2$Br | CH$_2$ | C(O)Pr-c |
| G-1 | 3,5-Cl$_2$ | 2-S(O)CF$_2$Br | CH$_2$ | C(O)CH$_2$Pr-c |
| G-1 | 3,5-Cl$_2$ | 2-SO$_2$CF$_2$Br | CH$_2$ | C(O)CH$_2$CH$_2$Cl |
| G-1 | 3,5-Cl$_2$ | 2-SCF$_2$CHFCl | CH$_2$ | C(O)CH$_2$CF$_3$ |
| G-1 | 3,5-Cl$_2$ | 2-S(O)CF$_2$CHFCl | CH$_2$ | C(O)Et |
| G-1 | 3,5-Cl$_2$ | 2-SO$_2$CF$_2$CHFCl | CH$_2$ | C(O)Pr-n |
| G-1 | 3,5-Cl$_2$ | 2-SPh | CH$_2$ | C(O)Pr-i |
| G-1 | 3,5-Cl$_2$ | 2-S(O)Ph | CH$_2$ | C(O)Pr-c |
| G-1 | 3,5-Cl$_2$ | 2-SO$_2$Ph | CH$_2$ | C(O)CH$_2$Pr-c |
| G-1 | 3,5-Cl$_2$ | 2-NO$_2$ | CH$_2$CH$_2$ | C(O)Pr-i |
| G-1 | 3,5-Cl$_2$ | 2-NO$_2$ | CH$_2$CH$_2$ | C(O)Pr-c |
| G-1 | 3,5-Cl$_2$ | 2-NO$_2$ | CH$_2$CH$_2$ | C(O)CH$_2$CF$_3$ |
| G-1 | 3,5-Cl$_2$ | 2-NHCH$_3$ | CH$_2$CH$_2$ | C(O)Pr-i |
| G-1 | 3,5-Cl$_2$ | 2-NHCH$_3$ | CH$_2$CH$_2$ | C(O)Pr-c |
| G-1 | 3,5-Cl$_2$ | 2-NHCH$_3$ | CH$_2$CH$_2$ | C(O)CH$_2$CF$_3$ |
| G-1 | 3,5-Cl$_2$ | 2-NHEt | CH$_2$ | C(O)Et |
| G-1 | 3,5-Cl$_2$ | 2-NHEt | CH$_2$ | C(O)Pr-n |
| G-1 | 3,5-Cl$_2$ | 2-NHEt | CH$_2$ | C(O)Pr-i |
| G-1 | 3,5-Cl$_2$ | 2-NHEt | CH$_2$ | C(O)Pr-c |
| G-1 | 3,5-Cl$_2$ | 2-NHEt | CH$_2$ | C(O)CH$_2$Pr-c |
| G-1 | 3,5-Cl$_2$ | 2-NHEt | CH$_2$ | C(O)CH$_2$CH$_2$Cl |
| G-1 | 3,5-Cl$_2$ | 2-NHEt | CH$_2$ | C(O)CH$_2$CF$_3$ |
| G-1 | 3,5-Cl$_2$ | 2-NHPr-n | CH$_2$ | C(O)Pr-i |
| G-1 | 3,5-Cl$_2$ | 2-NHPr-n | CH$_2$ | C(O)Pr-c |
| G-1 | 3,5-Cl$_2$ | 2-NHPr-n | CH$_2$ | C(O)CH$_2$CF$_3$ |
| G-1 | 3,5-Cl$_2$ | 2-NHPr-i | CH$_2$ | C(O)Et |
| G-1 | 3,5-Cl$_2$ | 2-NHPr-i | CH$_2$ | C(O)Pr-n |
| G-1 | 3,5-Cl$_2$ | 2-NHPr-i | CH$_2$ | C(O)Pr-i |
| G-1 | 3,5-Cl$_2$ | 2-NHPr-i | CH$_2$ | C(O)Pr-c |
| G-1 | 3,5-Cl$_2$ | 2-NHPr-i | CH$_2$ | C(O)CH$_2$Pr-c |
| G-1 | 3,5-Cl$_2$ | 2-NHPr-i | CH$_2$ | C(O)CH$_2$CH$_2$Cl |
| G-1 | 3,5-Cl$_2$ | 2-NHPr-i | CH$_2$ | C(O)CH$_2$CF$_3$ |
| G-1 | 3,5-Cl$_2$ | 2-N(CH$_3$)$_2$ | CH$_2$ | C(O)Pr-i |
| G-1 | 3,5-Cl$_2$ | 2-N(CH$_3$)$_2$ | CH$_2$ | C(O)Pr-c |
| G-1 | 3,5-Cl$_2$ | 2-N(CH$_3$)$_2$ | CH$_2$ | C(O)CH$_2$CF$_3$ |
| G-1 | 3,5-Cl$_2$ | 2-N(CH$_3$)Et | CH$_2$ | C(O)CH$_2$CH$_2$Cl |
| G-1 | 3,5-Cl$_2$ | 2-N(Et)$_2$ | CH$_2$ | C(O)CH$_2$CF$_3$ |
| G-1 | 3,5-Cl$_2$ | 2-NHCHO | CH$_2$ | C(O)Pr-i |
| G-1 | 3,5-Cl$_2$ | 2-NHCHO | CH$_2$ | C(O)Pr-c |
| G-1 | 3,5-Cl$_2$ | 2-NHCHO | CH$_2$ | C(O)CH$_2$CF$_3$ |
| G-1 | 3,5-Cl$_2$ | 2-NHC(O)CH$_3$ | CH$_2$ | C(O)Et |
| G-1 | 3,5-Cl$_2$ | 2-NHC(O)CH$_3$ | CH$_2$ | C(O)Pr-n |
| G-1 | 3,5-Cl$_2$ | 2-NHC(O)CH$_3$ | CH$_2$ | C(O)Pr-i |
| G-1 | 3,5-Cl$_2$ | 2-NHC(O)CH$_3$ | CH$_2$ | C(O)Pr-c |
| G-1 | 3,5-Cl$_2$ | 2-NHC(O)CH$_3$ | CH$_2$ | C(O)CH$_2$Pr-c |
| G-1 | 3,5-Cl$_2$ | 2-NHC(O)CH$_3$ | CH$_2$ | C(O)CH$_2$CH$_2$Cl |
| G-1 | 3,5-Cl$_2$ | 2-NHC(O)CH$_3$ | CH$_2$ | C(O)CH$_2$CF$_3$ |
| G-1 | 3,5-Cl$_2$ | 2-NHC(O)CH$_3$ | CH$_2$CH$_2$ | C(O)Pr-i |
| G-1 | 3,5-Cl$_2$ | 2-NHC(O)CH$_3$ | CH$_2$CH$_2$ | C(O)Pr-c |
| G-1 | 3,5-Cl$_2$ | 2-NHC(O)CH$_3$ | CH$_2$CH$_2$ | C(O)CH$_2$CF$_3$ |
| G-1 | 3,5-Cl$_2$ | 2-NHC(O)Et | CH$_2$ | C(O)Pr-i |
| G-1 | 3,5-Cl$_2$ | 2-NHC(O)Et | CH$_2$ | C(O)Pr-c |
| G-1 | 3,5-Cl$_2$ | 2-NHC(O)Et | CH$_2$ | C(O)CH$_2$CF$_3$ |
| G-1 | 3,5-Cl$_2$ | 2-NHC(O)Pr-n | CH$_2$ | C(O)Pr-i |
| G-1 | 3,5-Cl$_2$ | 2-NHC(O)Pr-i | CH$_2$ | C(O)Pr-c |
| G-1 | 3,5-Cl$_2$ | 2-NHC(O)Pr-c | CH$_2$ | C(O)CH$_2$CF$_3$ |
| G-1 | 3,5-Cl$_2$ | 2-NHC(O)Bu-t | CH$_2$ | C(O)Et |
| G-1 | 3,5-Cl$_2$ | 2-NHC(O)CF$_3$ | CH$_2$ | C(O)Pr-i |
| G-1 | 3,5-Cl$_2$ | 2-NHC(O)CF$_3$ | CH$_2$ | C(O)Pr-c |
| G-1 | 3,5-Cl$_2$ | 2-NHC(O)CF$_3$ | CH$_2$ | C(O)CH$_2$CF$_3$ |
| G-1 | 3,5-Cl$_2$ | 2-NHC(O)OCH$_3$ | CH$_2$ | C(O)Pr-i |

| | | | | |
|---|---|---|---|---|
| G-1 | 3,5-Cl$_2$ | 2-NHC(O)OCH$_3$ | CH$_2$ | C(O)Pr-c |
| G-1 | 3,5-Cl$_2$ | 2-NHC(O)OCH$_3$ | CH$_2$ | C(O)CH$_2$CF$_3$ |
| G-1 | 3,5-Cl$_2$ | 2-NHC(O)OEt | CH$_2$ | C(O)Pr-n |
| G-1 | 3,5-Cl$_2$ | 2-NHC(O)SCH$_3$ | CH$_2$ | C(O)Pr-i |
| G-1 | 3,5-Cl$_2$ | 2-NHC(O)SCH$_3$ | CH$_2$ | C(O)Pr-c |
| G-1 | 3,5-Cl$_2$ | 2-NHC(O)SCH$_3$ | CH$_2$ | C(O)CH$_2$CF$_3$ |
| G-1 | 3,5-Cl$_2$ | 2-NHC(O)SEt | CH$_2$ | C(O)Pr-i |
| G-1 | 3,5-Cl$_2$ | 2-NHC(S)OCH$_3$ | CH$_2$ | C(O)Pr-i |
| G-1 | 3,5-Cl$_2$ | 2-NHC(S)OCH$_3$ | CH$_2$ | C(O)Pr-c |
| G-1 | 3,5-Cl$_2$ | 2-NHC(S)OCH$_3$ | CH$_2$ | C(O)CH$_2$CF$_3$ |
| G-1 | 3,5-Cl$_2$ | 2-NHC(S)OEt | CH$_2$ | C(O)Pr-c |
| G-1 | 3,5-Cl$_2$ | 2-NHC(S)SCH$_3$ | CH$_2$ | C(O)Pr-i |
| G-1 | 3,5-Cl$_2$ | 2-NHC(S)SCH$_3$ | CH$_2$ | C(O)Pr-c |
| G-1 | 3,5-Cl$_2$ | 2-NHC(S)SCH$_3$ | CH$_2$ | C(O)CH$_2$CF$_3$ |
| G-1 | 3,5-Cl$_2$ | 2-NHC(S)SEt | CH$_2$ | C(O)CH$_2$Pr-c |
| G-1 | 3,5-Cl$_2$ | 2-NHSO$_2$CH$_3$ | CH$_2$ | C(O)Pr-i |
| G-1 | 3,5-Cl$_2$ | 2-NHSO$_2$CH$_3$ | CH$_2$ | C(O)Pr-c |
| G-1 | 3,5-Cl$_2$ | 2-NHSO$_2$CH$_3$ | CH$_2$ | C(O)CH$_2$CF$_3$ |
| G-1 | 3,5-Cl$_2$ | 2-NHSO$_2$CF$_3$ | CH$_2$ | C(O)Pr-i |
| G-1 | 3,5-Cl$_2$ | 2-NHSO$_2$CF$_3$ | CH$_2$ | C(O)Pr-c |
| G-1 | 3,5-Cl$_2$ | 2-NHSO$_2$CF$_3$ | CH$_2$ | C(O)CH$_2$CF$_3$ |
| G-1 | 3,5-Cl$_2$ | 2-N(CH$_3$)CHO | CH$_2$ | C(O)Pr-i |
| G-1 | 3,5-Cl$_2$ | 2-N(CH$_3$)CHO | CH$_2$ | C(O)Pr-c |
| G-1 | 3,5-Cl$_2$ | 2-N(CH$_3$)CHO | CH$_2$ | C(O)CH$_2$CF$_3$ |
| G-1 | 3,5-Cl$_2$ | 2-N(CH$_3$)C(O)CH$_3$ | CH$_2$ | C(O)CH$_2$CH$_2$Cl |
| G-1 | 3,5-Cl$_2$ | 2-N(CH$_3$)C(O)Et | CH$_2$ | C(O)CH$_2$CF$_3$ |
| G-1 | 3,5-Cl$_2$ | 2-N(CH$_3$)C(O)Pr-n | CH$_2$ | C(O)Et |
| G-1 | 3,5-Cl$_2$ | 2-N(CH$_3$)C(O)Pr-i | CH$_2$ | C(O)Pr-n |
| G-1 | 3,5-Cl$_2$ | 2-N(CH$_3$)C(O)Pr-c | CH$_2$ | C(O)Pr-i |
| G-1 | 3,5-Cl$_2$ | 2-N(CH$_3$)C(O)Bu-t | CH$_2$ | C(O)Pr-c |
| G-1 | 3,5-Cl$_2$ | 2-N(CH$_3$)C(O)CF$_3$ | CH$_2$ | C(O)CH$_2$Pr-c |
| G-1 | 3,5-Cl$_2$ | 2-N(CH$_3$)C(O)OCH$_3$ | CH$_2$ | C(O)CH$_2$CH$_2$Cl |
| G-1 | 3,5-Cl$_2$ | 2-N(CH$_3$)C(O)OEt | CH$_2$ | C(O)CH$_2$CF$_3$ |
| G-1 | 3,5-Cl$_2$ | 2-N(CH$_3$)C(O)SCH$_3$ | CH$_2$ | C(O)Et |
| G-1 | 3,5-Cl$_2$ | 2-N(CH$_3$)C(O)SEt | CH$_2$ | C(O)Pr-n |
| G-1 | 3,5-Cl$_2$ | 2-N(CH$_3$)C(S)OCH$_3$ | CH$_2$ | C(O)Pr-i |
| G-1 | 3,5-Cl$_2$ | 2-N(CH$_3$)C(S)OEt | CH$_2$ | C(O)Pr-c |
| G-1 | 3,5-Cl$_2$ | 2-N(CH$_3$)C(S)SCH$_3$ | CH$_2$ | C(O)CH$_2$Pr-c |
| G-1 | 3,5-Cl$_2$ | 2-N(CH$_3$)C(S)SEt | CH$_2$ | C(O)CH$_2$CH$_2$Cl |
| G-1 | 3,5-Cl$_2$ | 2-N(CH$_3$)SO$_2$CH$_3$ | CH$_2$ | C(O)CH$_2$CF$_3$ |
| G-1 | 3,5-Cl$_2$ | 2-N(CH$_3$)SO$_2$CF$_3$ | CH$_2$ | C(O)Et |
| G-1 | 3,5-Cl$_2$ | 2-N(Et)CHO | CH$_2$ | C(O)Pr-n |
| G-1 | 3,5-Cl$_2$ | 2-N(Et)C(O)CH$_3$ | CH$_2$ | C(O)Pr-i |
| G-1 | 3,5-Cl$_2$ | 2-N(Et)C(O)Et | CH$_2$ | C(O)Pr-c |
| G-1 | 3,5-Cl$_2$ | 2-N(Et)C(O)Pr-n | CH$_2$ | C(O)CH$_2$Pr-c |
| G-1 | 3,5-Cl$_2$ | 2-N(Et)C(O)Pr-i | CH$_2$ | C(O)CH$_2$CH$_2$Cl |
| G-1 | 3,5-Cl$_2$ | 2-N(Et)C(O)Pr-c | CH$_2$ | C(O)CH$_2$CF$_3$ |
| G-1 | 3,5-Cl$_2$ | 2-N(Et)C(O)Bu-t | CH$_2$ | C(O)Et |
| G-1 | 3,5-Cl$_2$ | 2-N(Et)C(O)CF$_3$ | CH$_2$ | C(O)Pr-n |
| G-1 | 3,5-Cl$_2$ | 2-N(Et)C(O)OCH$_3$ | CH$_2$ | C(O)Pr-i |
| G-1 | 3,5-Cl$_2$ | 2-N(Et)C(O)OEt | CH$_2$ | C(O)Pr-c |
| G-1 | 3,5-Cl$_2$ | 2-N(Et)C(O)SCH$_3$ | CH$_2$ | C(O)CH$_2$Pr-c |
| G-1 | 3,5-Cl$_2$ | 2-N(Et)C(O)SEt | CH$_2$ | C(O)CH$_2$CH$_2$Cl |
| G-1 | 3,5-Cl$_2$ | 2-N(Et)C(S)OCH$_3$ | CH$_2$ | C(O)CH$_2$CF$_3$ |
| G-1 | 3,5-Cl$_2$ | 2-N(Et)C(S)OEt | CH$_2$ | C(O)Et |
| G-1 | 3,5-Cl$_2$ | 2-N(Et)C(S)SCH$_3$ | CH$_2$ | C(O)Pr-n |
| G-1 | 3,5-Cl$_2$ | 2-N(Et)C(S)SEt | CH$_2$ | C(O)Pr-i |
| G-1 | 3,5-Cl$_2$ | 2-N(Et)SO$_2$CH$_3$ | CH$_2$ | C(O)Pr-c |
| G-1 | 3,5-Cl$_2$ | 2-N(Et)SO$_2$CF$_3$ | CH$_2$ | C(O)CH$_2$Pr-c |
| G-1 | 3,5-Cl$_2$ | 2-N=CHOCH$_3$ | CH$_2$ | C(O)CH$_2$CH$_2$Cl |
| G-1 | 3,5-Cl$_2$ | 2-N=C(CH$_3$)OCH$_3$ | CH$_2$ | C(O)Pr-i |
| G-1 | 3,5-Cl$_2$ | 2-N=C(CH$_3$)OCH$_3$ | CH$_2$ | C(O)Pr-c |
| G-1 | 3,5-Cl$_2$ | 2-N=C(CH$_3$)OCH$_3$ | CH$_2$ | C(O)CH$_2$CF$_3$ |
| G-1 | 3,5-Cl$_2$ | 2-(D-5a) | CH$_2$ | C(O)CH$_2$CF$_3$ |
| G-1 | 3,5-Cl$_2$ | 2-C(O)OCH$_3$ | CH$_2$ | C(O)Et |
| G-1 | 3,5-Cl$_2$ | 2-C(O)NH$_2$ | CH$_2$ | C(O)Pr-n |
| G-1 | 3,5-Cl$_2$ | 2-(M-11a) | CH$_2$ | C(O)Pr-i |
| G-1 | 3,5-Cl$_2$ | 2-C(S)NH$_2$ | CH$_2$ | C(O)Pr-i |
| G-1 | 3,5-Cl$_2$ | 2-C(S)NH$_2$ | CH$_2$ | C(O)Pr-c |
| G-1 | 3,5-Cl$_2$ | 2-C(S)NH$_2$ | CH$_2$ | C(O)CH$_2$CF$_3$ |
| G-1 | 3,5-Cl$_2$ | 2-(M-14a) | CH$_2$ | C(O)Pr-c |
| G-1 | 3,5-Cl$_2$ | 2-Ph | CH$_2$ | C(O)CH$_2$Pr-c |
| G-1 | 3,5-Cl$_2$ | 2-(D-14a) | CH$_2$ | C(O)CH$_2$CH$_2$Cl |
| G-1 | 3,5-Cl$_2$ | 2-(D-24a) | CH$_2$ | C(O)CH$_2$CF$_3$ |
| G-1 | 3,5-Cl$_2$ | 2-(D-41a) | CH$_2$ | C(O)Et |
| G-1 | 3,5-Cl$_2$ | 2-(D-48a) | CH$_2$ | C(O)Pr-n |
| G-1 | 3,5-Cl$_2$ | 2-(D-48b)CH$_3$ | CH$_2$ | C(O)Pr-i |
| G-1 | 3,5-Cl$_2$ | 2-(D-49a) | CH$_2$ | C(O)Pr-c |
| G-1 | 3,5-Cl$_2$ | 2-(D-50a)H | CH$_2$ | C(O)CH$_2$Pr-c |
| G-1 | 3,5-Cl$_2$ | 2-(D-50a)CH$_3$ | CH$_2$ | C(O)CH$_2$CH$_2$Cl |
| G-1 | 3,5-Cl$_2$ | 2-(D-51a)H | CH$_2$ | C(O)CH$_2$CF$_3$ |
| G-1 | 3,5-Cl$_2$ | 2-(D-51a)CH$_3$ | CH$_2$ | C(O)Et |

| | | | | |
|---|---|---|---|---|
| G-1 | 3,5-Cl$_2$ | 2,3-F$_2$ | CH$_2$ | C(O)Pr-n |
| G-1 | 3,5-Cl$_2$ | 2,5-F$_2$ | CH$_2$ | C(O)Pr-i |
| G-1 | 3,5-Cl$_2$ | 2,6-F$_2$ | CH$_2$ | C(O)Pr-c |
| G-1 | 3,5-Cl$_2$ | 2-F-6-Cl | CH$_2$ | C(O)CH$_2$Pr-c |
| G-1 | 3,5-Cl$_2$ | 2-F-6-Br | CH$_2$ | C(O)CH$_2$CH$_2$Cl |
| G-1 | 3,5-Cl$_2$ | 2-F-6-CF$_3$ | CH$_2$ | C(O)CH$_2$CF$_3$ |
| G-1 | 3,5-Cl$_2$ | 2-F-6-NO$_2$ | CH$_2$ | C(O)Et |
| G-1 | 3,5-Cl$_2$ | 2-Cl-3-F | CH$_2$ | C(O)Pr-n |
| G-1 | 3,5-Cl$_2$ | 2,3-Cl$_2$ | CH$_2$ | C(O)Pr-i |
| G-1 | 3,5-Cl$_2$ | 2-Cl-5-F | CH$_2$ | C(O)Pr-c |
| G-1 | 3,5-Cl$_2$ | 2,5-Cl$_2$ | CH$_2$ | C(O)CH$_2$Pr-c |
| G-1 | 3,5-Cl$_2$ | 2,6-Cl$_2$ | CH$_2$ | C(O)CH$_2$CH$_2$Cl |
| G-1 | 3,5-Cl$_2$ | 2-Br-3-F | CH$_2$ | C(O)CH$_2$CF$_3$ |
| G-1 | 3,5-Cl$_2$ | 2-Br-5-F | CH$_2$ | C(O)Et |
| G-1 | 3,5-Cl$_2$ | 2-CH$_3$-3-F | CH$_2$ | C(O)Pr-i |
| G-1 | 3,5-Cl$_2$ | 2-CH$_3$-3-F | CH$_2$ | C(O)Pr-c |
| G-1 | 3,5-Cl$_2$ | 2-CH$_3$-3-F | CH$_2$ | C(O)CH$_2$CF$_3$ |
| G-1 | 3,5-Cl$_2$ | 2-CH$_3$-3-Cl | CH$_2$ | C(O)Pr-n |
| G-1 | 3,5-Cl$_2$ | 2,3-(CH$_3$)$_2$ | CH$_2$ | C(O)Pr-i |
| G-1 | 3,5-Cl$_2$ | 2-CH$_3$-5-F | CH$_2$ | C(O)Pr-c |
| G-1 | 3,5-Cl$_2$ | 2-CH$_3$-5-Cl | CH$_2$ | C(O)CH$_2$Pr-c |
| G-1 | 3,5-Cl$_2$ | 2,5-(CH$_3$)$_2$ | CH$_2$ | C(O)CH$_2$CH$_2$Cl |
| G-1 | 3,5-Cl$_2$ | 2-CH$_3$-6-F | CH$_2$ | C(O)Pr-i |
| G-1 | 3,5-Cl$_2$ | 2-CH$_3$-6-F | CH$_2$ | C(O)Pr-c |
| G-1 | 3,5-Cl$_2$ | 2-CH$_3$-6-F | CH$_2$ | C(O)CH$_2$CF$_3$ |
| G-1 | 3,5-Cl$_2$ | 2-CH$_3$-6-Cl | CH$_2$ | C(O)CH$_2$CF$_3$ |
| G-1 | 3,5-Cl$_2$ | 2,6-(CH$_3$)$_2$ | CH$_2$ | C(O)Et |
| G-1 | 3,5-Cl$_2$ | 2-CH$_3$-6-CF$_3$ | CH$_2$ | C(O)Pr-n |
| G-1 | 3,5-Cl$_2$ | 2-CF$_3$-5-F | CH$_2$ | C(O)Pr-i |
| G-1 | 3,5-Cl$_2$ | 2-CF$_3$-5-Cl | CH$_2$ | C(O)Pr-c |
| G-1 | 3,5-Cl$_2$ | 2-OCH$_3$-3-F | CH$_2$ | C(O)CH$_2$Pr-c |
| G-1 | 3,5-Cl$_2$ | 2-OCH$_3$-5-F | CH$_2$ | C(O)CH$_2$CH$_2$Cl |
| G-1 | 3,5-Cl$_2$ | 2-OCH$_3$-5-Cl | CH$_2$ | C(O)CH$_2$CF$_3$ |
| G-1 | 3,5-Cl$_2$ | 2-CN-3-F | CH$_2$ | C(O)Et |
| G-1 | 3-Cl-5-Br | 2-Pr-i | CH$_2$ | C(O)Pr-n |
| G-1 | 3-Cl-5-Br | 2-OEt | CH$_2$ | C(O)Pr-i |
| G-1 | 3-Cl-5-Br | 2-OPr-i | CH$_2$ | C(O)Pr-c |
| G-1 | 3-Cl-5-Br | 2-OSO$_2$CH$_3$ | CH$_2$ | C(O)CH$_2$Pr-c |
| G-1 | 3-Cl-5-Br | 2-SEt | CH$_2$ | C(O)CH$_2$CH$_2$Cl |
| G-1 | 3-Cl-5-Br | 2-SPr-i | CH$_2$ | C(O)CH$_2$CF$_3$ |
| G-1 | 3-Cl-5-Br | 2-NHEt | CH$_2$ | C(O)Et |
| G-1 | 3-Cl-5-Br | 2-NHPr-i | CH$_2$ | C(O)Pr-n |
| G-1 | 3-Cl-5-Br | 2-N(CH$_3$)$_2$ | CH$_2$ | C(O)Pr-i |
| G-1 | 3-Cl-5-Br | 2-NHC(O)CH$_3$ | CH$_2$ | C(O)Pr-c |
| G-1 | 3,5-Br$_2$ | 2-Pr-i | CH$_2$ | C(O)CH$_2$Pr-c |
| G-1 | 3,5-Br$_2$ | 2-OEt | CH$_2$ | C(O)CH$_2$CH$_2$Cl |
| G-1 | 3,5-Br$_2$ | 2-OPr-i | CH$_2$ | C(O)CH$_2$CF$_3$ |
| G-1 | 3,5-Br$_2$ | 2-OSO$_2$CH$_3$ | CH$_2$ | C(O)Et |
| G-1 | 3,5-Br$_2$ | 2-SEt | CH$_2$ | C(O)Pr-n |
| G-1 | 3,5-Br$_2$ | 2-SPr-i | CH$_2$ | C(O)Pr-i |
| G-1 | 3,5-Br$_2$ | 2-NHEt | CH$_2$ | C(O)Pr-c |
| G-1 | 3,5-Br$_2$ | 2-NHPr-i | CH$_2$ | C(O)CH$_2$Pr-c |
| G-1 | 3,5-Br$_2$ | 2-N(CH$_3$)$_2$ | CH$_2$ | C(O)CH$_2$CH$_2$Cl |
| G-1 | 3,5-Br$_2$ | 2-NHC(O)CH$_3$ | CH$_2$ | C(O)CH$_2$CF$_3$ |
| G-1 | 3-Cl-5-I | 2-Pr-i | CH$_2$ | C(O)Et |
| G-1 | 3-Cl-5-I | 2-OEt | CH$_2$ | C(O)Pr-n |
| G-1 | 3-Cl-5-I | 2-OPr-i | CH$_2$ | C(O)Pr-i |
| G-1 | 3-Cl-5-I | 2-OSO$_2$CH$_3$ | CH$_2$ | C(O)Pr-c |
| G-1 | 3-Cl-5-I | 2-SEt | CH$_2$ | C(O)CH$_2$Pr-c |
| G-1 | 3-Cl-5-I | 2-SPr-i | CH$_2$ | C(O)CH$_2$CH$_2$Cl |
| G-1 | 3-Cl-5-I | 2-NHEt | CH$_2$ | C(O)CH$_2$CF$_3$ |
| G-1 | 3-Cl-5-I | 2-NHPr-i | CH$_2$ | C(O)Et |
| G-1 | 3-Cl-5-I | 2-N(CH$_3$)$_2$ | CH$_2$ | C(O)Pr-n |
| G-1 | 3-Cl-5-I | 2-NHC(O)CH$_3$ | CH$_2$ | C(O)Pr-i |
| G-1 | 3-CF$_3$-4-F | 2-Pr-i | CH$_2$ | C(O)Pr-c |
| G-1 | 3-CF$_3$-4-F | 2-OEt | CH$_2$ | C(O)CH$_2$Pr-c |
| G-1 | 3-CF$_3$-4-F | 2-OPr-i | CH$_2$ | C(O)CH$_2$CH$_2$Cl |
| G-1 | 3-CF$_3$-4-F | 2-OSO$_2$CH$_3$ | CH$_2$ | C(O)CH$_2$CF$_3$ |
| G-1 | 3-CF$_3$-4-F | 2-SEt | CH$_2$ | C(O)Et |
| G-1 | 3-CF$_3$-4-F | 2-SPr-i | CH$_2$ | C(O)Pr-n |
| G-1 | 3-CF$_3$-4-F | 2-NHEt | CH$_2$ | C(O)Pr-i |
| G-1 | 3-CF$_3$-4-F | 2-NHPr-i | CH$_2$ | C(O)Pr-c |
| G-1 | 3-CF$_3$-4-F | 2-N(CH$_3$)$_2$ | CH$_2$ | C(O)CH$_2$Pr-c |
| G-1 | 3-CF$_3$-4-F | 2-NHC(O)CH$_3$ | CH$_2$ | C(O)CH$_2$CH$_2$Cl |
| G-1 | 3-F-5-CF$_3$ | 2-Pr-i | CH$_2$ | C(O)CH$_2$CF$_3$ |
| G-1 | 3-F-5-CF$_3$ | 2-OEt | CH$_2$ | C(O)Et |
| G-1 | 3-F-5-CF$_3$ | 2-OPr-i | CH$_2$ | C(O)Pr-n |
| G-1 | 3-F-5-CF$_3$ | 2-OSO$_2$CH$_3$ | CH$_2$ | C(O)Pr-i |
| G-1 | 3-F-5-CF$_3$ | 2-SEt | CH$_2$ | C(O)Pr-c |
| G-1 | 3-F-5-CF$_3$ | 2-SPr-i | CH$_2$ | C(O)CH$_2$Pr-c |
| G-1 | 3-F-5-CF$_3$ | 2-NHEt | CH$_2$ | C(O)CH$_2$CH$_2$Cl |
| G-1 | 3-F-5-CF$_3$ | 2-NHPr-i | CH$_2$ | C(O)CH$_2$CF$_3$ |

| | | | | |
|---|---|---|---|---|
| G-1 | 3-F-5-CF₃ | 2-N(CH₃)₂ | CH₂ | C(O)Et |
| G-1 | 3-F-5-CF₃ | 2-NHC(O)CH₃ | CH₂ | C(O)Pr-n |
| G-1 | 3-CF₃-4-Cl | 2-Pr-i | CH₂ | C(O)Pr-i |
| G-1 | 3-CF₃-4-Cl | 2-OEt | CH₂ | C(O)Pr-c |
| G-1 | 3-CF₃-4-Cl | 2-OPr-i | CH₂ | C(O)CH₂Pr-c |
| G-1 | 3-CF₃-4-Cl | 2-OSO₂CH₃ | CH₂ | C(O)CH₂CH₂Cl |
| G-1 | 3-CF₃-4-Cl | 2-SEt | CH₂ | C(O)CH₂CF₃ |
| G-1 | 3-CF₃-4-Cl | 2-SPr-i | CH₂ | C(O)Et |
| G-1 | 3-CF₃-4-Cl | 2-NHEt | CH₂ | C(O)Pr-n |
| G-1 | 3-CF₃-4-Cl | 2-NHPr-i | CH₂ | C(O)Pr-i |
| G-1 | 3-CF₃-4-Cl | 2-N(CH₃)₂ | CH₂ | C(O)Pr-c |
| G-1 | 3-CF₃-4-Cl | 2-NHC(O)CH₃ | CH₂ | C(O)CH₂Pr-c |
| G-1 | 3-Cl-5-CF₃ | 2-Pr-i | CH₂ | C(O)CH₂CH₂Cl |
| G-1 | 3-Cl-5-CF₃ | 2-OEt | CH₂ | C(O)CH₂CF₃ |
| G-1 | 3-Cl-5-CF₃ | 2-OPr-i | CH₂ | C(O)Et |
| G-1 | 3-Cl-5-CF₃ | 2-OSO₂CH₃ | CH₂ | C(O)Pr-n |
| G-1 | 3-Cl-5-CF₃ | 2-SEt | CH₂ | C(O)Pr-i |
| G-1 | 3-Cl-5-CF₃ | 2-SPr-i | CH₂ | C(O)Pr-c |
| G-1 | 3-Cl-5-CF₃ | 2-NHEt | CH₂ | C(O)CH₂Pr-c |
| G-1 | 3-Cl-5-CF₃ | 2-NHPr-i | CH₂ | C(O)CH₂CH₂Cl |
| G-1 | 3-Cl-5-CF₃ | 2-N(CH₃)₂ | CH₂ | C(O)CH₂CF₃ |
| G-1 | 3-Cl-5-CF₃ | 2-NHC(O)CH₃ | CH₂ | C(O)Et |
| G-1 | 3-Br-5-CF₃ | 2-Pr-i | CH₂ | C(O)Pr-n |
| G-1 | 3-Br-5-CF₃ | 2-OEt | CH₂ | C(O)Pr-i |
| G-1 | 3-Br-5-CF₃ | 2-OPr-i | CH₂ | C(O)Pr-c |
| G-1 | 3-Br-5-CF₃ | 2-OSO₂CH₃ | CH₂ | C(O)CH₂Pr-c |
| G-1 | 3-Br-5-CF₃ | 2-SEt | CH₂ | C(O)CH₂CH₂Cl |
| G-1 | 3-Br-5-CF₃ | 2-SPr-i | CH₂ | C(O)CH₂CF₃ |
| G-1 | 3-Br-5-CF₃ | 2-NHEt | CH₂ | C(O)Et |
| G-1 | 3-Br-5-CF₃ | 2-NHPr-i | CH₂ | C(O)Pr-n |
| G-1 | 3-Br-5-CF₃ | 2-N(CH₃)₂ | CH₂ | C(O)Pr-i |
| G-1 | 3-Br-5-CF₃ | 2-NHC(O)CH₃ | CH₂ | C(O)Pr-c |
| G-1 | 3,5-(CF₃)₂ | 2-Pr-i | CH₂ | C(O)CH₂Pr-c |
| G-1 | 3,5-(CF₃)₂ | 2-OEt | CH₂ | C(O)CH₂CH₂Cl |
| G-1 | 3,5-(CF₃)₂ | 2-OPr-i | CH₂ | C(O)CH₂CF₃ |
| G-1 | 3,5-(CF₃)₂ | 2-OSO₂CH₃ | CH₂ | C(O)Et |
| G-1 | 3,5-(CF₃)₂ | 2-SEt | CH₂ | C(O)Pr-n |
| G-1 | 3,5-(CF₃)₂ | 2-SPr-i | CH₂ | C(O)Pr-i |
| G-1 | 3,5-(CF₃)₂ | 2-NHEt | CH₂ | C(O)Pr-c |
| G-1 | 3,5-(CF₃)₂ | 2-NHPr-i | CH₂ | C(O)CH₂Pr-c |
| G-1 | 3,5-(CF₃)₂ | 2-N(CH₃)₂ | CH₂ | C(O)CH₂CH₂Cl |
| G-1 | 3,5-(CF₃)₂ | 2-NHC(O)CH₃ | CH₂ | C(O)CH₂CF₃ |
| G-1 | 3,5-Cl₂-4-F | 2-Pr-i | CH₂ | C(O)Et |
| G-1 | 3,5-Cl₂-4-F | 2-OEt | CH₂ | C(O)Pr-n |
| G-1 | 3,5-Cl₂-4-F | 2-OPr-i | CH₂ | C(O)Pr-i |
| G-1 | 3,5-Cl₂-4-F | 2-OSO₂CH₃ | CH₂ | C(O)Pr-c |
| G-1 | 3,5-Cl₂-4-F | 2-SEt | CH₂ | C(O)CH₂Pr-c |
| G-1 | 3,5-Cl₂-4-F | 2-SPr-i | CH₂ | C(O)CH₂CH₂Cl |
| G-1 | 3,5-Cl₂-4-F | 2-NHEt | CH₂ | C(O)CH₂CF₃ |
| G-1 | 3,5-Cl₂-4-F | 2-NHPr-i | CH₂ | C(O)Et |
| G-1 | 3,5-Cl₂-4-F | 2-N(CH₃)₂ | CH₂ | C(O)Pr-n |
| G-1 | 3,5-Cl₂-4-F | 2-NHC(O)CH₃ | CH₂ | C(O)Pr-i |
| G-1 | 3,4,5-Cl₃ | 2-Pr-i | CH₂ | C(O)Pr-c |
| G-1 | 3,4,5-Cl₃ | 2-OEt | CH₂ | C(O)CH₂Pr-c |
| G-1 | 3,4,5-Cl₃ | 2-OPr-i | CH₂ | C(O)CH₂CH₂Cl |
| G-1 | 3,4,5-Cl₃ | 2-OSO₂CH₃ | CH₂ | C(O)CH₂CF₃ |
| G-1 | 3,4,5-Cl₃ | 2-SEt | CH₂ | C(O)Et |
| G-1 | 3,4,5-Cl₃ | 2-SPr-i | CH₂ | C(O)Pr-n |
| G-1 | 3,4,5-Cl₃ | 2-NHEt | CH₂ | C(O)Pr-i |
| G-1 | 3,4,5-Cl₃ | 2-NHPr-i | CH₂ | C(O)Pr-c |
| G-1 | 3,4,5-Cl₃ | 2-N(CH₃)₂ | CH₂ | C(O)CH₂Pr-c |
| G-1 | 3,4,5-Cl₃ | 2-NHC(O)CH₃ | CH₂ | C(O)CH₂CH₂Cl |
| G-1 | 3,5-Br₂-4-F | 2-Pr-i | CH₂ | C(O)CH₂CF₃ |
| G-1 | 3,5-Br₂-4-F | 2-OEt | CH₂ | C(O)Et |
| G-1 | 3,5-Br₂-4-F | 2-OPr-i | CH₂ | C(O)Pr-n |
| G-1 | 3,5-Br₂-4-F | 2-OSO₂CH₃ | CH₂ | C(O)Pr-i |
| G-1 | 3,5-Br₂-4-F | 2-SEt | CH₂ | C(O)Pr-c |
| G-1 | 3,5-Br₂-4-F | 2-SPr-i | CH₂ | C(O)CH₂Pr-c |
| G-1 | 3,5-Br₂-4-F | 2-NHEt | CH₂ | C(O)CH₂CH₂Cl |
| G-1 | 3,5-Br₂-4-F | 2-NHPr-i | CH₂ | C(O)CH₂CF₃ |
| G-1 | 3,5-Br₂-4-F | 2-N(CH₃)₂ | CH₂ | C(O)Et |
| G-1 | 3,5-Br₂-4-F | 2-NHC(O)CH₃ | CH₂ | C(O)Pr-n |
| G-1 | 3,4-F₂-5-CF₃ | 2-Pr-i | CH₂ | C(O)Pr-i |
| G-1 | 3,4-F₂-5-CF₃ | 2-OEt | CH₂ | C(O)Pr-c |
| G-1 | 3,4-F₂-5-CF₃ | 2-OPr-i | CH₂ | C(O)CH₂Pr-c |
| G-1 | 3,4-F₂-5-CF₃ | 2-OSO₂CH₃ | CH₂ | C(O)CH₂CH₂Cl |
| G-1 | 3,4-F₂-5-CF₃ | 2-SEt | CH₂ | C(O)CH₂CF₃ |
| G-1 | 3,4-F₂-5-CF₃ | 2-SPr-i | CH₂ | C(O)Et |
| G-1 | 3,4-F₂-5-CF₃ | 2-NHEt | CH₂ | C(O)Pr-n |
| G-1 | 3,4-F₂-5-CF₃ | 2-NHPr-i | CH₂ | C(O)Pr-i |
| G-1 | 3,4-F₂-5-CF₃ | 2-N(CH₃)₂ | CH₂ | C(O)Pr-c |
| G-1 | 3,4-F₂-5-CF₃ | 2-NHC(O)CH₃ | CH₂ | C(O)CH₂Pr-c |

| | | | | |
|---|---|---|---|---|
| G-1 | 3-Cl-4-F-5-CF$_3$ | 2-Pr-i | CH$_2$ | C(O)CH$_2$CH$_2$Cl |
| G-1 | 3-Cl-4-F-5-CF$_3$ | 2-OEt | CH$_2$ | C(O)CH$_2$CF$_3$ |
| G-1 | 3-Cl-4-F-5-CF$_3$ | 2-OPr-i | CH$_2$ | C(O)Et |
| G-1 | 3-Cl-4-F-5-CF$_3$ | 2-OSO$_2$CH$_3$ | CH$_2$ | C(O)Pr-n |
| G-1 | 3-Cl-4-F-5-CF$_3$ | 2-SEt | CH$_2$ | C(O)Pr-i |
| G-1 | 3-Cl-4-F-5-CF$_3$ | 2-SPr-i | CH$_2$ | C(O)Pr-c |
| G-1 | 3-Cl-4-F-5-CF$_3$ | 2-NHEt | CH$_2$ | C(O)CH$_2$Pr-c |
| G-1 | 3-Cl-4-F-5-CF$_3$ | 2-NHPr-i | CH$_2$ | C(O)CH$_2$CH$_2$Cl |
| G-1 | 3-Cl-4-F-5-CF$_3$ | 2-N(CH$_3$)$_2$ | CH$_2$ | C(O)CH$_2$CF$_3$ |
| G-1 | 3-Cl-4-F-5-CF$_3$ | 2-NHC(O)CH$_3$ | CH$_2$ | C(O)Et |
| G-1 | 3,4-Cl$_2$-5-CF$_3$ | 2-Pr-i | CH$_2$ | C(O)Pr-n |
| G-1 | 3,4-Cl$_2$-5-CF$_3$ | 2-OEt | CH$_2$ | C(O)Pr-i |
| G-1 | 3,4-Cl$_2$-5-CF$_3$ | 2-OPr-i | CH$_2$ | C(O)Pr-c |
| G-1 | 3,4-Cl$_2$-5-CF$_3$ | 2-OSO$_2$CH$_3$ | CH$_2$ | C(O)CH$_2$Pr-c |
| G-1 | 3,4-Cl$_2$-5-CF$_3$ | 2-SEt | CH$_2$ | C(O)CH$_2$CH$_2$Cl |
| G-1 | 3,4-Cl$_2$-5-CF$_3$ | 2-SPr-i | CH$_2$ | C(O)CH$_2$CF$_3$ |
| G-1 | 3,4-Cl$_2$-5-CF$_3$ | 2-NHEt | CH$_2$ | C(O)Et |
| G-1 | 3,4-Cl$_2$-5-CF$_3$ | 2-NHPr-i | CH$_2$ | C(O)Pr-n |
| G-1 | 3,4-Cl$_2$-5-CF$_3$ | 2-N(CH$_3$)$_2$ | CH$_2$ | C(O)Pr-i |
| G-1 | 3,4-Cl$_2$-5-CF$_3$ | 2-NHC(O)CH$_3$ | CH$_2$ | C(O)Pr-c |
| G-1 | 3,5-(CF$_3$)$_2$-4-Cl | 2-Pr-i | CH$_2$ | C(O)CH$_2$Pr-c |
| G-1 | 3,5-(CF$_3$)$_2$-4-Cl | 2-OEt | CH$_2$ | C(O)CH$_2$CH$_2$Cl |
| G-1 | 3,5-(CF$_3$)$_2$-4-Cl | 2-OPr-i | CH$_2$ | C(O)CH$_2$CF$_3$ |
| G-1 | 3,5-(CF$_3$)$_2$-4-Cl | 2-OSO$_2$CH$_3$ | CH$_2$ | C(O)Et |
| G-1 | 3,5-(CF$_3$)$_2$-4-Cl | 2-SEt | CH$_2$ | C(O)Pr-n |
| G-1 | 3,5-(CF$_3$)$_2$-4-Cl | 2-SPr-i | CH$_2$ | C(O)Pr-i |
| G-1 | 3,5-(CF$_3$)$_2$-4-Cl | 2-NHEt | CH$_2$ | C(O)Pr-c |
| G-1 | 3,5-(CF$_3$)$_2$-4-Cl | 2-NHPr-i | CH$_2$ | C(O)CH$_2$Pr-c |
| G-1 | 3,5-(CF$_3$)$_2$-4-Cl | 2-N(CH$_3$)$_2$ | CH$_2$ | C(O)CH$_2$CH$_2$Cl |
| G-1 | 3,5-(CF$_3$)$_2$-4-Cl | 2-NHC(O)CH$_3$ | CH$_2$ | C(O)CH$_2$CF$_3$ |
| G-3 | 5-Cl | 2-Cl | CH$_2$ | C(O)Et |
| G-3 | 5-CF$_3$ | 2-Cl | CH$_2$ | C(O)Pr-i |
| G-3 | 5-CF$_3$ | 2-Cl | CH$_2$ | C(O)Pr-c |
| G-3 | 5-CF$_3$ | 2-Cl | CH$_2$ | C(O)CH$_2$CF$_3$ |
| G-3 | 5-CF$_3$-6-Cl | 2-Cl | CH$_2$ | C(O)Pr-n |
| G-3 | 5-NO$_2$-6-Cl | 2-Cl | CH$_2$ | C(O)Pr-i |
| G-4 | 2-Cl | 2-Cl | CH$_2$ | C(O)Pr-c |
| G-4 | 2-Br | 2-Cl | CH$_2$ | C(O)CH$_2$Pr-c |
| G-4 | 2-CF$_3$ | 2-Cl | CH$_2$ | C(O)Pr-i |
| G-4 | 2-CF$_3$ | 2-Cl | CH$_2$ | C(O)Pr-c |
| G-4 | 2-CF$_3$ | 2-Cl | CH$_2$ | C(O)CH$_2$CF$_3$ |
| G-4 | 2,6-F$_2$ | 2-Cl | CH$_2$ | C(O)CH$_2$CH$_2$Cl |
| G-4 | 2,6-Cl$_2$ | — | CH(CH$_3$) | C(O)Pr-i |
| G-4 | 2,6-Cl$_2$ | — | CH(CH$_3$) | C(O)Pr-c |
| G-4 | 2,6-Cl$_2$ | — | CH(CH$_3$) | C(O)CH$_2$CF$_3$ |
| G-4 | 2,6-Cl$_2$ | 2-F | CH$_2$ | C(O)Pr-i |
| G-4 | 2,6-Cl$_2$ | 2-F | CH$_2$ | C(O)Pr-c |
| G-4 | 2,6-Cl$_2$ | 2-F | CH$_2$ | C(O)CH$_2$CF$_3$ |
| G-4 | 2,6-Cl$_2$ | 2-Cl | CH$_2$ | C(O)Et |
| G-4 | 2,6-Cl$_2$ | 2-Cl | CH$_2$ | C(O)Pr-n |
| G-4 | 2,6-Cl$_2$ | 2-Cl | CH$_2$ | C(O)Pr-i |
| G-4 | 2,6-Cl$_2$ | 2-Cl | CH$_2$ | C(O)Pr-c |
| G-4 | 2,6-Cl$_2$ | 2-Cl | CH$_2$ | C(O)CH$_2$Pr-c |
| G-4 | 2,6-Cl$_2$ | 2-Cl | CH$_2$ | C(O)CH$_2$CH$_2$Cl |
| G-4 | 2,6-Cl$_2$ | 2-Cl | CH$_2$ | C(O)CH$_2$CF$_3$ |
| G-4 | 2,6-Cl$_2$ | 2-Br | CH$_2$ | C(O)Pr-i |
| G-4 | 2,6-Cl$_2$ | 2-Br | CH$_2$ | C(O)Pr-c |
| G-4 | 2,6-Cl$_2$ | 2-Br | CH$_2$ | C(O)CH$_2$CF$_3$ |
| G-4 | 2,6-Cl$_2$ | 2-I | CH$_2$ | C(O)Pr-i |
| G-4 | 2,6-Cl$_2$ | 2-I | CH$_2$ | C(O)Pr-c |
| G-4 | 2,6-Cl$_2$ | 2-I | CH$_2$ | C(O)CH$_2$CF$_3$ |
| G-4 | 2,6-Cl$_2$ | 2-CH$_3$ | CH$_2$ | C(O)Pr-i |
| G-4 | 2,6-Cl$_2$ | 2-CH$_3$ | CH$_2$ | C(O)Pr-c |
| G-4 | 2,6-Cl$_2$ | 2-CH$_3$ | CH$_2$ | C(O)CH$_2$CF$_3$ |
| G-4 | 2,6-Cl$_2$ | 2-Et | CH$_2$ | C(O)Pr-i |
| G-4 | 2,6-Cl$_2$ | 2-Et | CH$_2$ | C(O)Pr-c |
| G-4 | 2,6-Cl$_2$ | 2-Et | CH$_2$ | C(O)CH$_2$CF$_3$ |
| G-4 | 2,6-Cl$_2$ | 2-CF$_3$ | CH$_2$ | C(O)Pr-i |
| G-4 | 2,6-Cl$_2$ | 2-CF$_3$ | CH$_2$ | C(O)Pr-c |
| G-4 | 2,6-Cl$_2$ | 2-CF$_3$ | CH$_2$ | C(O)CH$_2$CF$_3$ |
| G-4 | 2,6-Cl$_2$ | 2-OCH$_3$ | CH$_2$ | C(O)CH$_2$CF$_3$ |
| G-4 | 2,6-Cl$_2$ | 2-OCHF$_2$ | CH$_2$ | C(O)Et |
| G-4 | 2,6-Cl$_2$ | 2-OCF$_3$ | CH$_2$ | C(O)Pr-n |
| G-4 | 2,6-Cl$_2$ | 2-SCH$_3$ | CH$_2$ | C(O)Pr-i |

| | | | | |
|---|---|---|---|---|
| G-4 | 2,6-Cl$_2$ | 2-SCF$_3$ | CH$_2$ | C(O)Pr-c |
| G-4 | 2,6-Cl$_2$ | 2-NO$_2$ | CH$_2$ | C(O)CH$_2$Pr-c |
| G-4 | 2,6-Cl$_2$ | 2-NHCH$_3$ | CH$_2$ | C(O)CH$_2$CH$_2$Cl |
| G-4 | 2,6-Cl$_2$ | 2-NHC(O)CH$_3$ | CH$_2$ | C(O)CH$_2$CF$_3$ |
| G-4 | 2,6-Br$_2$ | 2-Cl | CH$_2$ | C(O)Pr-i |
| G-4 | 2,6-Br$_2$ | 2-Cl | CH$_2$ | C(O)Pr-c |
| G-4 | 2,6-Br$_2$ | 2-Cl | CH$_2$ | C(O)CH$_2$CF$_3$ |
| G-4 | 2-Br-6-CF$_3$ | 2-Cl | CH$_2$ | C(O)Pr-i |
| G-4 | 2-Br-6-CF$_3$ | 2-Cl | CH$_2$ | C(O)Pr-c |
| G-4 | 2-Br-6-CF$_3$ | 2-Cl | CH$_2$ | C(O)CH$_2$CF$_3$ |
| G-4 | 2,6-(CF$_3$)$_2$ | 2-Cl | CH$_2$ | C(O)Pr-i |
| G-4 | 2,6-(CF$_3$)$_2$ | 2-Cl | CH$_2$ | C(O)Pr-c |
| G-4 | 2,6-(CF$_3$)$_2$ | 2-Cl | CH$_2$ | C(O)CH$_2$CF$_3$ |
| G-13 | 4-CF$_3$ | 2-Cl | CH$_2$ | C(O)Pr-i |
| G-13 | 4-CF$_3$ | 2-Cl | CH$_2$ | C(O)Pr-c |
| G-13 | 4-CF$_3$ | 2-Cl | CH$_2$ | C(O)CH$_2$CF$_3$ |
| G-13 | 5-CF$_3$ | 2-Cl | CH$_2$ | C(O)Pr-i |
| G-13 | 5-CF$_3$ | 2-Cl | CH$_2$ | C(O)Pr-c |
| G-13 | 5-CF$_3$ | 2-Cl | CH$_2$ | C(O)CH$_2$CF$_3$ |
| G-13 | 4,5-Cl$_2$ | 2-Cl | CH$_2$ | C(O)Pr-i |
| G-13 | 4,5-Cl$_2$ | 2-Cl | CH$_2$ | C(O)Pr-c |
| G-13 | 4,5-Cl$_2$ | 2-Cl | CH$_2$ | C(O)CH$_2$CF$_3$ |
| G-13 | 4-Cl-5-Br | 2-Cl | CH$_2$ | C(O)Pr-i |
| G-13 | 4-Cl-5-Br | 2-Cl | CH$_2$ | C(O)Pr-c |
| G-13 | 4-Cl-5-Br | 2-Cl | CH$_2$ | C(O)CH$_2$CF$_3$ |
| G-13 | 4-Br-5-Cl | 2-Cl | CH$_2$ | C(O)Pr-i |
| G-13 | 4-Br-5-Cl | 2-Cl | CH$_2$ | C(O)Pr-c |
| G-13 | 4-Br-5-Cl | 2-Cl | CH$_2$ | C(O)CH$_2$CF$_3$ |
| G-13 | 4,5-Br$_2$ | 2-Cl | CH$_2$ | C(O)Pr-i |
| G-13 | 4,5-Br$_2$ | 2-Cl | CH$_2$ | C(O)Pr-c |
| G-13 | 4,5-Br$_2$ | 2-Cl | CH$_2$ | C(O)CH$_2$CF$_3$ |
| G-14 | 5-CF$_3$ | 2-Cl | CH$_2$ | C(O)Pr-i |
| G-14 | 5-CF$_3$ | 2-Cl | CH$_2$ | C(O)Pr-c |
| G-14 | 5-CF$_3$ | 2-Cl | CH$_2$ | C(O)CH$_2$CF$_3$ |
| G-17a | 5-CF$_3$ | 2-Cl | CH$_2$ | C(O)Pr-i |
| G-17a | 5-CF$_3$ | 2-Cl | CH$_2$ | C(O)Pr-c |
| G-17a | 5-CF$_3$ | 2-Cl | CH$_2$ | C(O)CH$_2$CF$_3$ |
| G-20 | 4-CF$_3$ | 2-Cl | CH$_2$ | C(O)Pr-i |
| G-20 | 4-CF$_3$ | 2-Cl | CH$_2$ | C(O)Pr-c |
| G-20 | 4-CF$_3$ | 2-Cl | CH$_2$ | C(O)CH$_2$CF$_3$ |
| G-20 | 5-CF$_3$ | 2-Cl | CH$_2$ | C(O)Pr-i |
| G-20 | 5-CF$_3$ | 2-Cl | CH$_2$ | C(O)Pr-c |
| G-20 | 5-CF$_3$ | 2-Cl | CH$_2$ | C(O)CH$_2$CF$_3$ |
| G-21 | 2-CF$_3$ | 2-Cl | CH$_2$ | C(O)Pr-i |
| G-21 | 2-CF$_3$ | 2-Cl | CH$_2$ | C(O)Pr-c |
| G-21 | 2-CF$_3$ | 2-Cl | CH$_2$ | C(O)CH$_2$CF$_3$ |
| G-22 | 2-Cl | 2-Cl | CH$_2$ | C(O)Pr-i |
| G-22 | 2-Cl | 2-Cl | CH$_2$ | C(O)Pr-c |
| G-22 | 2-Cl | 2-Cl | CH$_2$ | C(O)CH$_2$CF$_3$ |

TABLE 4

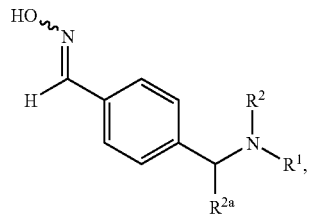

[3]-1

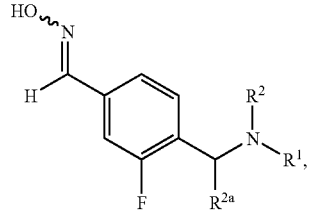

[3]-2

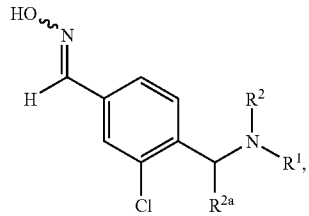

[3]-3

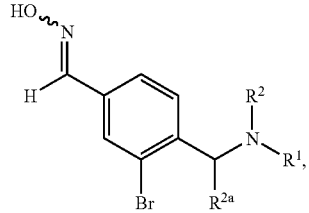

[3]-4

TABLE 4-continued
[3]-5 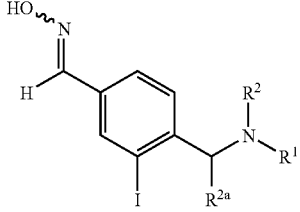
[3]-6 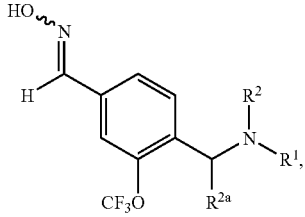
[3]-7 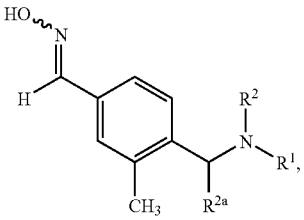
[3]-8 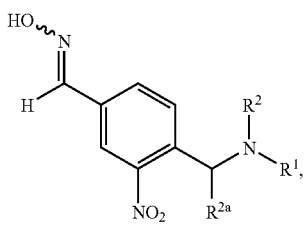
[3]-9 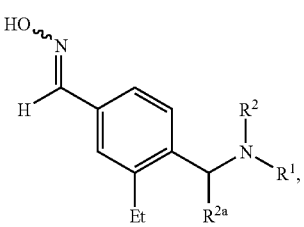
[3]-10 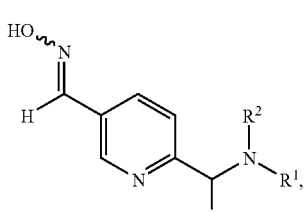
[3]-11 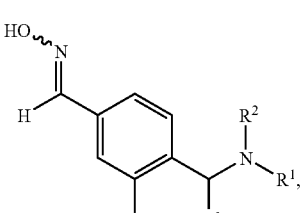
[3]-12 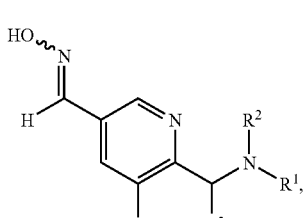
[3]-13 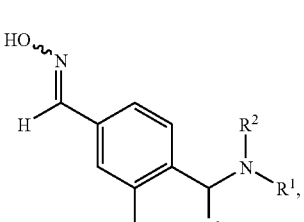
[3]-14 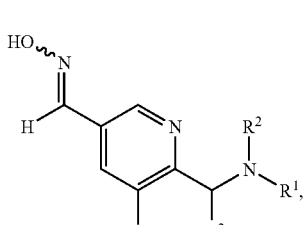
[3]-15 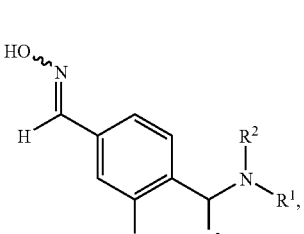
[3]-16 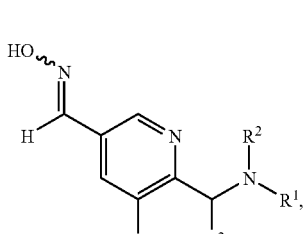

TABLE 4-continued
[3]-17
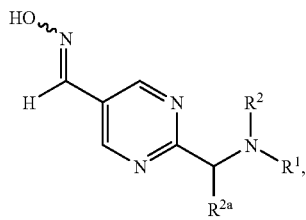
[3]-18
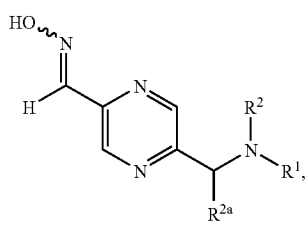
[3]-19
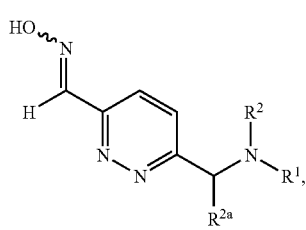
[3]-20
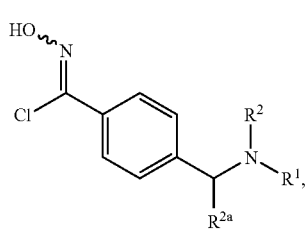
[3]-21
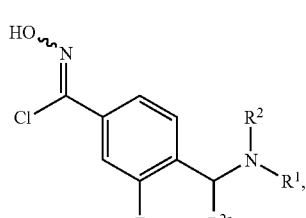
[3]-22
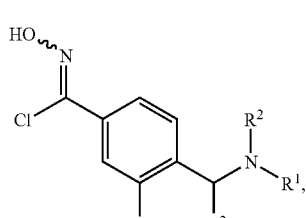
TABLE 4-continued
[3]-23
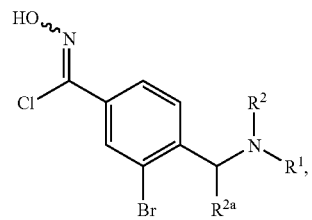
[3]-24
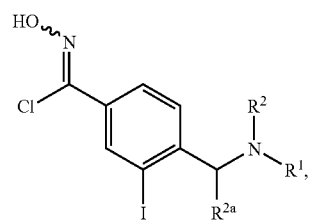
[3]-25
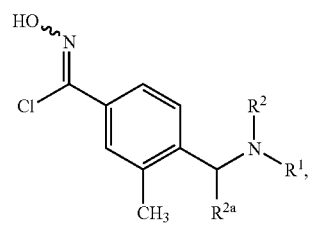
[3]-26
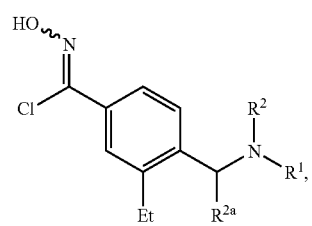
[3]-27
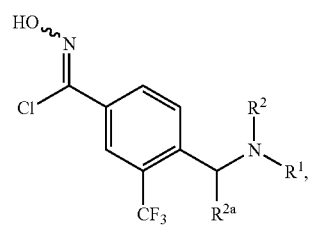
[3]-28
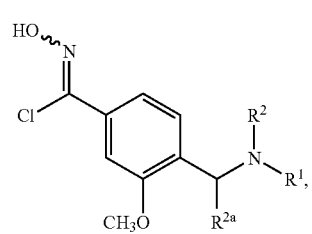

TABLE 4-continued

[3]-29, [3]-30, [3]-31, [3]-32, [3]-33, [3]-34, [3]-35, [3]-36, [3]-37, [3]-38

| R²ᵃ | R² | R¹ |
|---|---|---|
| H | H | CHO |
| H | H | C(O)CH₃ |
| H | H | C(O)Et |
| H | Et | C(O)Et |
| H | CH₂OCH₃ | C(O)Et |
| H | CH₂OC(O)CH₃ | C(O)Et |
| H | CH₂OC(O)OCH₃ | C(O)Et |
| H | CH₂CN | C(O)Et |
| H | CH₂C≡CH | C(O)Et |
| H | C(O)CH₃ | C(O)Et |
| H | C(O)OCH₃ | C(O)Et |
| H | H | C(O)Pr-n |
| H | Et | C(O)Pr-n |
| H | CH₂OCH₃ | C(O)Pr-n |
| H | CH₂OC(O)CH₃ | C(O)Pr-n |
| H | CH₂OC(O)OCH₃ | C(O)Pr-n |
| H | CH₂CN | C(O)Pr-n |
| H | CH₂C≡CH | C(O)Pr-n |
| H | C(O)CH₃ | C(O)Pr-n |
| H | C(O)OCH₃ | C(O)Pr-n |
| H | H | C(O)Pr-i |
| H | CH₃ | C(O)Pr-i |
| H | Et | C(O)Pr-i |
| H | CH₂OCH₃ | C(O)Pr-i |
| H | CH₂OEt | C(O)Pr-i |
| H | CH₂OCH₂CF₃ | C(O)Pr-i |
| H | CH₂OC(O)CH₃ | C(O)Pr-i |
| H | CH₂OC(O)OCH₃ | C(O)Pr-i |
| H | CH₂CN | C(O)Pr-i |
| H | CH₂C≡CH | C(O)Pr-i |

TABLE 4-continued

| | | |
|---|---|---|
| H | C(O)CH₃ | C(O)Pr-i |
| H | C(O)OCH₃ | C(O)Pr-i |
| H | H | C(O)Pr-c |
| H | CH₃ | C(O)Pr-c |
| H | Et | C(O)Pr-c |
| H | CH₂OCH₃ | C(O)Pr-c |
| H | CH₂OEt | C(O)Pr-c |
| H | CH₂OCH₂CF₃ | C(O)Pr-c |
| H | CH₂OC(O)CH₃ | C(O)Pr-c |
| H | CH₂OC(O)OCH₃ | C(O)Pr-c |
| H | CH₂CN | C(O)Pr-c |
| H | CH₂C≡CH | C(O)Pr-c |
| H | C(O)CH₃ | C(O)Pr-c |
| H | C(O)OCH₃ | C(O)Pr-c |
| H | H | C(O)Bu-i |
| H | H | C(O)CH₂Pr-c |
| H | Et | C(O)CH₂Pr-c |
| H | CH₂OCH₃ | C(O)OH₂Pr-c |
| H | CH₂OC(O)CH₃ | C(O)OH₂Pr-c |
| H | CH₂OC(O)OCH₃ | C(O)CH₂Pr-c |
| H | CH₂CN | C(O)CH₂Pr-c |
| H | CH₂C≡CH | C(O)CH₂Pr-c |
| H | C(O)CH₃ | C(O)CH₂Pr-c |
| H | C(O)OCH₃ | C(O)CH₂Pr-c |
| H | H | C(O)Bu-s |
| H | H | C(O)CF₃ |
| H | Et | C(O)CH₂CH₂Cl |
| H | CH₂OCH₃ | C(O)CH₂CH₂Cl |
| H | CH₂OC(O)CH₃ | C(O)CH₂CH₂Cl |
| H | CH₂OC(O)OCH₃ | C(O)CH₂CH₂Cl |
| H | CH₂CN | C(O)CH₂CH₂Cl |
| H | CH₂O≡CH | C(O)OH₂CH₂Cl |
| H | C(O)CH₃ | C(O)OH₂CH₂Cl |
| H | C(O)OCH₃ | C(O)OH₂CH₂Cl |
| H | H | C(O)CH₂CF₃ |
| H | CH₃ | C(O)CH₂CF₃ |
| H | Et | C(O)CH₂CF₃ |
| H | CH₂OCH₃ | C(O)CH₂CF₃ |
| H | CH₂OEt | C(O)CH₂CF₃ |
| H | CH₂OCH₂CF₃ | C(O)CH₂CF₃ |
| H | CH₂OC(O)CH₃ | C(O)CH₂CF₃ |
| H | CH₂OC(O)Et | C(O)CH₂CF₃ |
| H | CH₂OC(O)Pr-i | C(O)CH₂CF₃ |
| H | CH₂OC(O)Pr-c | C(O)CH₂CF₃ |
| H | CH₂OC(O)Bu-t | C(O)CH₂CF₃ |
| H | CH₂OC(O)Ph | C(O)CH₂CF₃ |
| H | CH₂OC(O)OCH₃ | C(O)CH₂CF₃ |
| H | CH₂CN | C(O)CH₂CF₃ |
| H | CH₂C≡CH | C(O)CH₂CF₃ |
| H | C(O)CH₃ | C(O)CH₂CF₃ |
| H | C(O)Et | C(O)CH₂CF₃ |
| H | C(O)Pr-i | C(O)CH₂CF₃ |
| H | C(O)Pr-c | C(O)CH₂CF₃ |
| H | C(O)Bu-t | C(O)CH₂CF₃ |
| H | C(O)CH₂OCH₃ | C(O)CH₂CF₃ |
| H | C(O)OCH₃ | C(O)CH₂CF₃ |
| H | C(O)OEt | C(O)CH₂CF₃ |
| H | C(O)OPr-i | C(O)CH₂CF₃ |
| H | C(O)OPr-c | C(O)CH₂CF₃ |
| H | C(O)OCH₂Cl | C(O)CH₂CF₃ |
| H | C(O)OCH₂CH₂Cl | C(O)CH₂CF₃ |
| H | C(O)OCH₂CH₂OCH₃ | C(O)CH₂CF₃ |
| H | C(O)OCH₂CH=CH₂ | C(O)CH₂CF₃ |
| H | C(O)OCH₂C≡CH | C(O)CH₂CF₃ |
| H | H | C(O)CF₂CHF₂ |
| H | H | C(O)CF₂CF₃ |
| H | H | C(O)CH₂CH₂OCH₃ |
| H | H | C(O)(E-5a) |
| H | H | C(O)CH=C(CH₃)₂ |
| H | H | C(O)CH₂CH₂C≡CH |
| H | H | C(O)(Ph-3-F) |
| H | H | C(O)(Ph-2,4-F₂) |
| H | H | C(O)(Ph-3,5-F₂) |
| H | H | C(O)NHEt |
| H | H | C(O)NHPr-i |
| H | H | C(O)NHPr-c |
| H | H | C(O)NHCH₂CF₃ |
| H | H | C(O)NHOCH₃ |
| CH₃ | H | C(O)Et |
| CH₃ | H | C(O)Pr-n |
| CH₃ | H | C(O)Pr-i |
| CH₃ | H | C(O)Pr-c |
| CH₃ | H | C(O)CH₂Pr-c |
| CH₃ | H | C(O)CF₃ |
| CH₃ | H | C(O)CH₂CH₂Cl |
| CH₃ | H | C(O)CH₂CF₃ |
| CH₃ | H | C(O)CF₂CHF₂ |
| CH₃ | H | C(O)CF₂CF₃ |
| CH₃ | H | C(O)(Ph-2,4-F₂) |
| CH₃ | H | C(O)NHEt |
| CH₃ | H | C(O)NHPr-i |
| CH₃ | H | O(O)NHCH₂CF₃ |
| CF₃ | H | C(O)Et |
| CF₃ | H | C(O)Pr-n |
| CF₃ | H | C(O)Pr-i |
| CF₃ | H | C(O)Pr-c |
| CF₃ | H | C(O)CH₂Pr-c |
| CF₃ | H | C(O)CH₂CH₂Cl |
| CF₃ | H | C(O)CH₂CF₃ |
| CN | H | C(O)Et |
| CN | H | C(O)Pr-n |
| CN | H | C(O)Pr-i |
| CN | H | C(O)Pr-c |
| CN | H | C(O)CH₂Pr-c |
| CN | H | C(O)CF₃ |
| CN | H | C(O)CH₂CH₂Cl |
| CN | H | C(O)CH₂CF₃ |
| CN | H | C(O)CF₂CHF₂ |
| CN | H | C(O)CF₂CF₃ |
| CN | H | C(O)(Ph-2,4-F₂) |
| CN | H | C(O)NHEt |
| CN | H | C(O)NHPr-i |
| CN | H | C(O)NHCH₂CF₃ |

The compounds of the present invention can effectively control in a low concentration so-called agricultural insects injuring agricultural and horticultural crops and trees, so-called domestic animal pests parasitizing domestic animals and domestic fowls, so-called hygienic pests having an adverse affect on human being's environment such as houses, insects as so-called stored grain insects injuring grains and the like stored in storehouses, and any pests of acarids, crustaceans, mollusks and nematodes generating in the similar scenes.

The insects, acarids, crustaceans, mollusks and nematodos that the compounds of the present invention can control concretely include for example the followings:

Lepidoptera insects, such as *Adoxophyes honmai, Adoxophyes orana faciata, Archips breviplicanus, Archips fuscocupreanus, Grapholita molesta, Homona magnanima, Leguminivora glycinivorella, Matsumuraeses phaseoli, Pandemis heparana, Bucculatrix pyrivorella, Lyonetia clerkella, Lyonetia prunifoliella malinella, Caloptilia theivora, Phyllonorycter ringoniella, Phyllocnistis citrella, Acrolepiopsis sapporensis, Acrolepiopsis suzukiella, Plutella xylostella, Stathmopoda masinissa, Helcystogramma triannulella, Pectinophora gossypiella, Carposina sasakii, Cydla pomonella, Chilo suppressalis, Cnaphalocrocis medinalis, Conogethes punctiferalis, Diaphania indica, Etiella zinckenella, Glyphodes pyloalis, Hellula undalis, Ostrinia furnacalis, Ostrinia scapulalis, Ostrinia nubilalis, Parapediasia teterrella, Parnara guttata, Pieris brassicae, Pieris rapae crucivora, Ascotis selenaria, Pseudoplusia includens, Euproctis pseudoconspersa, Lymantria dispar, Orgyia thyellina, Hyphantria cunea, Lemyra imparilis, Adris tyrannus, Aedia leucomelas, Agrotis ipsilon, Agrotis segetum, Autographa nigrisigna, Ctenoplusia agnata, Helicoverpa armigera, Helicoverpa assulta, Helicoverpa zea, Heliothis virescens, Mamestra brassicae, Mythimna separata, Naranga aenescens, Spodoptera eridania, Spodoptera exigua, Spodoptera*

*frugiperda, Spodoptera littoralis, Spodoptera litura, Spodoptera depravata, Trichoplusia ni, Endopiza viteana, Manduca quinquemaculata, Manduca sexta*, or the like;

Thysanoptera insects, such as *Frankliniella intonsa, Frankliniella occidentalis, Heliothrips haemorrhoidalis, Scirtothrips dorsalis, Thrips palmi, Thrips tabaci, Ponticulothrips diospyrosi*, or the like;

Hemiptera insects, such as *Dolycoris baccarum, Eurydema rugosum, Eysarcoris aeneus, Eysarcoris lewisi, Eysarcoris ventralis, Glaucias subpunctatus, Halyomorpha halys, Nezara antennata, Nezara viridula, Piezodorus hybneri, Plautia crossota, Scotinophora lurida, Cletus punctiger, Leptocorisa chinensis, Riptortus clavatus, Rhopalus msculatus, Cavelerius saccharivorus, Togo hemipterus, Dysdercus cingulatus, Stephanitis pyrioides, Halticus insularis, Lygus lineolaris, Stenodema sibiricum, Stenotus rubrovittatus, Trigonotylus caelestialium, Arboridia apicalis, Balclutha saltuella, Epicanthus stramineus, Empoasca fabae, Empoasca nipponica, Empoasca onukii, Empoasca sakaii, Macrosteles striifrons, Nephotettix cinctinceps, Psuedatomoscelis seriatus, Laodelphax striatella, Nilaparvata lugens, Sogatella furcifera, Diaphorina citri, Psylla pyrisuga, Aleurocanthus spiniferus, Bemisia argentifolii, Bemisia tabaci, Dialeurodes citri, Trialeurodes vaporariorum, Viteus vitifolii, Aphis gossypii, Aphis spiraecola, Myzus persicae, Toxoptera aurantii, Drosicha corpulenta, Icerya purchasi, Phenacoccus solani, Planococcus citri, Planococcus kuraunhiae, Pseudococcus comstocki, Ceroplastes ceriferus, Ceroplastes rubens, Aonidiella aurantii, Comstockaspis perniciosa, Fiorinia theae, Pseudaonidia paeoniae, Pseudaulacaspis pentagona, Pseudaulacaspis prunicola, Unaspis euonymi, Unaspis yanonensis, Cimex lectularius*, or the like;

Coleoptera insects, such as *Anomala cuprea, Anomala rufocuprea, Gametis jucunda, Heptophylla picea, Popillia japonica, Lepinotarsa decemlineata, Melanotus fortnumi, Melanotus tamsuyensis, Lasioderma serricorne, Epuraea domina, Epilachna varivestis, Epilachna vigintioctopunctata, Tenebrio molitor, Tribolium castaneum, Anoplophora malasiaca, Monochamus alternatus, Psacothea hilaris, Xylotrechus pyrrhoderus, Callosobruchus chinensis, Aulacophora femoralis, Chaetocnema concinna, Diabrotica undecimpunctata, Diabrotica virgifera, Diabrotica barberi, Oulema oryzae, Phyllotreta striolata, Psylliodes angusticollis, Rhynchites heros, Cylas formicarius, Anthonomus grandis, Echinocnemus squameus, Euscepes posffasciatus, Hypera postica, Lissohoptrus oryzophilus, Otiorhynchus sulcatus, Sitophilus granarius, Sitophilus zeamais, Sphenophorus venatus vestitus, Paederus fuscipes*, or the like;

Diptera insects, such as *Asphondylia yushimai, Sitodiplosis mosellana, Bactrocera cucurbitae, Bactrocera dorsalis, Ceratitis capitata, Hydrellia griseola, Drosophila suzukii, Agromyza oryzae, Chromatomyia horticola, Liriomyza bryoniae, Liriomyza chinensis, Liriomyza sativae, Liriomyza trifolii, Delia platura, Pegomya cunicularia, Rhagoletis pomonella, Mayetiola destructor, Musca domestica, Stomoxys calcitrans, Melophagus ovinus, Hypoderma bovis, Hypoderma lineatum, Oestrus ovis, Glossina palpalis, Glossina morsitans, Prosimulium yezoensis, Tabanus trigonus, Telmatoscopus albipunctatus, Leptoconops nipponensis, Culex pipiens pallens, Aedes aegypti, Aedes albopicutus, Anopheles hyracanus sinesis*, or the like;

Hymenoptera insects, such as *Apethymus kuri, Athalia rosae, Arge pagana, Neodiprion sertifer, Dryocosmus kuriphilus, Eciton burchelli, Eciton schmitti, Camponotus japonicus, Vespa mandarina, Myrmecia* spp., *Solenopsis* spp., *Monomorium pharaonis*, or the like;

Orthoptera insects, such as *Teleogryllus emma, Gryllotalpa orientalis, Locusta migratoria, Oxya yezoensis, Schistocerca gregaria*, or the like;

Collembola insects, such as *Onychiurus folsomi, Onychiurus sibiricus, Bourletiella hortensis*, or the like;

Dictyoptera insect, such as *Periplaneta fuliginosa, Periplaneta japonica, Blattella germanica*, or the like;

Isoptera insects, such as *Coptotermes formosanus, Reticulitermes speratus, Odontotermes formosanus*, or the like;

Siphonaptera insects, such as *Ctenocephalidae felis, Ctenocephalides canis, Echidnophaga gallinacea, Pulex irritans, Xenopsylla cheopis*, or the like;

Mallophaga insects, such as *Menacanthus stramineus, Bovicola bovis*, or the like;

Anoplura insects, such as *Haematopinus eurysternus, Haematopinus suis, Linognathus vituli, Solenopotes capillatus*, or the like;

Tarsonemid mites, such as *Phytonemus pallidus, Polyphagotarsonemus latus, Tarsonemus bilobatus*, or the like;

Eupodid mites, such as *Penthaleus erythrocephalus, Penthaleus major*, or the like;

Spider mites, such as *Oligonychus shinkajii, Panonychus citri, Panonychus mori, Panonychus ulmi, Tetranychus kanzawai, Tetranychus urticae*, or the like;

Eriophyid mites, such as *Acaphylla theavagrans, Aceria tulipae, Aculops lycopersici, Aculops pelekassi, Aculus schlechtendali, Eriophyes chibaensis, Phyllocoptruta oleivora*, or the like;

Acarid mites, such as *Rhizoglyphus robini, Tyrophagus putrescentiae, Tyrophagus similis*, or the like;

Bee brood mites, such as *Varroa jacobsoni*, or the like;

Ixodides, such as *Boophilus microplus, Rhipicephalus sanguineus, Haemaphysalis longicornis, Haemophysalis flava, Haemophysalis campanulata, Ixodes ovatus, Ixodes persulcatus, Amblyomma* spp., *Dermacentor* spp., or the like;

Cheyletidae, such as *Cheyletiella yasguri, Cheyletiella blakei*, or the like;

Demodicidae, such as *Demodex canis, Demodex cati*, or the like;

Psoroptidae, such as *Psoroptes ovis*, or the like;

Scarcoptidae, such as *Sarcoptes scabiei, Notoedres cati, Knemidocoptes* spp., or the like;

Crustacea, such as *Armadillidium vulgare*, or the like;

Gastropoda, such as *Pomacea canaliculata, Achatina fulica, Meghimatium bilineatum, Limax Valentiana, Acusta despecta sieboldiana, Euhadra peliomphala*, or the like;

Nematodes, such as *Prathylenchus coffeae, Prathylenchus penetrans, Prathylenchus vulnus, Globodera rostochiensis, Heterodera glycines, Meloidogyne hapla, Meloidogyne incognita, Aphelenchoides besseyi, Bursaphelenchus xylophilus*, or the like. But the present invention is not limited thereto.

The endo-parasites of domestic animals, domestic fowls, pets and the like that the compounds of the present invention can control concretely include for example the followings:

Nematodes, such as *Haemonchus, Trichostrongylus, Ostertagia, Nematodirus, Cooperia, Ascaris, Bunostomum, Oesophagostomum, Chabertia, Trichuris, Storongylus, Trichonema, Dictyocaulus, Capillaria, Heterakis, Toxocara, Ascaridia, Oxyuris, Ancylostoma, Uncinaria, Toxascaris, Parascaris*, or the like;

Filariidae in nematodes, such as *Wuchereria, Brugia, Onchoceca, Dirofilaria, Loa*, or the like;

Dracunculidae in nematodes, such as *Deacunculus*, or the like;

Cestoda, such as *Dipylidium caninum, Taenia taeniaeformis, Taenia solium, Taenia saginata, Hymenolepis diminuta,*

*Moniezia benedeni, Diphyllobothrium latum, Diphyllobothrium erinacei, Echinococcus granulosus, Echinococcus multilocularis*, or the like;
Trematoda, such as *Fasciola hepatica, F. gigantica, Paragonimus westermanii, Fasciolopsic bruski, Eurytrema pancreaticum, E. coelomaticum, Clonorchis sinensis, Schistosoma japonicum, Schistosoma haematobium, Schistosoma mansoni*, or the like;
*Eimeria* spp., such as *Eimeria tenella, Eimeria acervulina, Eimeria brunetti, Eimeria maxima, Eimeria necatrix, Eimeria bovis, Eimeria ovinoidalis*, or the like;
*Trypanosomsa cruzi, Leishmania* spp., *Plasmodium* spp., *Babesis* spp., *Trichomonadidae* spp., *Histomanas* spp., *Giardia* spp., *Toxoplasma* spp., *Entamoeba histolytica, Theileria* spp., or the like. But the present invention is not limited thereto.

Further, the compounds of the present invention are effective for pests acquiring high resistance against existing insecticides such as organic phosphorus compounds, carbamate compounds or pyrethroid compounds, etc.

That is, the compounds of the present invention can effectively control pests that belong to insects such as Collembola, Dictyoptera, Orthoptera, Isoptera, Thysanoptera, Hemiptera, Lepidoptera, Coleoptera, Hymenoptera, Diptera, Isoptera and Anoplura, Acarina, Gastropoda and Nematoda, in a low concentration. On the other hand, the compounds of the present invention have an extremely useful characteristic that they have little adverse affect on mammals, fishes, crustaceans and useful insects (beneficial insect such as honeybee, bumblebee or the like, or, natural enemies such as *Aphytis lingnanensis, Aphidius colemani, Orius strigicollis, Amblyseius californicus*, or the like).

When the compounds of the present invention are used, they can be generally mixed with a suitable solid carrier or liquid carrier, optionally along with surfactant, penetrating agent, spreading agent, thickener, anti-freezing agent, binder, anti-caking agent, disintegrating agent, anti-foaming agent, preservative, stabilizer, and the like, and can be formulated into any desired forms for practical use, such as soluble concentrates, emulsifiable concentrates, wettable powders, water soluble powders, water dispersible granules, water soluble granules, suspension concentrates, concentrated emulsions, suspoemulsions, microemulsions, dustable powders, granules, tablets and emulsifiable gels. From the viewpoint of an elimination or reduction of labor and an improvement of safety, the formulations in any desired forms described above may be included into a water-soluble bag made of water-soluble capsule or water-soluble film.

The solid carrier includes, for example, natural minerals such as quartz, calcite, sepiolite, dolomaite, chalk, kaolinite, pyrofilite, celicite, halocite, methahalocite, kibushi clay, gairome clay, pottery stone, zeaklite, allophane, white sand, mica, talc, bentonite, activated earth, acid china clay, pumice, attapulgite, zeolite and diatomaceous earth, etc., calcined products of natural minerals such as calcined clay, perlite, white sand balloon (loam balloon), vermiculite, attapulgus clay and calcined diatomaceous earth, etc., inorganic salts such as magnesium carbonate, calcium carbonate, sodium carbonate, sodium hydrogen carbonate, ammonium sulfate, sodium sulfate, magnesium sulfate, diammonium hydrogen phosphate, ammonium dihydrogen phosphate and potassium chloride, etc., saccharides such as glucose, fructose, sucrose and lactose, etc., polysaccharides such as starch, powder cellulose and dextrin, etc., organic materials such as urea, urea derivatives, benzoic acid and a salt of benzoic acid, etc., plants such as wood powder, cork powder, corn head stem, walnut shell and tobacco stem, etc., fly ash, white carbon (e.g., hydrated synthetic silica, anhydrous synthetic silica and hydrated synthetic silicate, etc.) and fertilizers, etc.

As the liquid carrier, there may be mentioned, for example, aromatic hydrocarbons such as xylene, alkyl($C_9$ or $C_{10}$, etc.) benzene, phenylxylylethane and alkyl($C_1$ or $C_3$, etc.)naphthalene, etc., aliphatic hydrocarbons such as machine oil, normal paraffin, isoparaffin and naphthene, etc., a mixture of aromatic hydrocarbons and aliphatic hydrocarbons such as kerosene, etc., alcohols such as ethanol, isopropanol, cyclohexanol, phenoxyethanol and benzylalcohol, etc., polyvalent alcohols such as ethylene glycol, propyleneglycol, diethylene glycol, hexylene glycol, polyethylene glycol and polypropyleneglycol, etc., ethers such as propyl cellosolve, butyl cellosolve, phenyl cellosolve, propyleneglycol monomethyl ether, propyleneglycol monoethyl ether, propyleneglycol monopropyl ether, propyleneglycol monobutyl ether and propyleneglycol monophenyl ether, etc., ketones such as acetophenone, cyclohexanone and γ-butyrolactone, etc., esters such as aliphatic acid methyl ester, dialkyl succinate, dialkyl glutamate, dialkyl adipate and dialkyl phthalate, etc., acid amides such as N-alkyl($C_1$, $C_8$ or $C_{12}$, etc.)pyrrolidone, etc., oil and fats such as soybean oil, linseed oil, rapeseed oil, coconut oil, cottonseed oil and caster oil, etc., dimethylsulfoxide and water.

These solid and liquid carriers may be used alone or in combination of two or more kinds in combination.

As the surfactant, there may be mentioned, for example, nonionic surfactants such as polyoxyethylene alkyl ether, polyoxyethylene alkyl (mono- or di-)phenyl ether, polyoxyethylene (mono-, di- or tri-)styrylphenyl ether, polyoxyethylene polyoxypropylene block copolymer, polyoxyethylene fatty acid (mono- or di-)ester, sorbitan fatty acid ester, polyoxyethylene sorbitan fatty acid ester, caster oil-ethylene oxide adducts, acetylene glycol, acetylene alcohol, ethylene oxide adducts of acetylene glycol, ethylene oxide adducts of acetylene alcohol and alkyl glycoside, etc., anionic surfactants such as alkyl sulfate, alkylbenzenesulfonate, lignine sulfonate, alkylsulfosuccinate, naphthalene sulfonate, alkylnaphthalene sulfonate, formalin condensate salt of naphthalene sulfonic acid, formalin condensate salt of alkylnaphthalene sulfonic acid, polyoxyethylene alkyl ether sulfate or phosphate, polyoxyethylene (mono- or di-)alkylphenyl ether sulfate or phosphate, polyoxyethylene (mono-, di- or tri-)styrylphenyl ether sulfate or phosphate, polycarboxylate (e.g., polyacryaltes, polymaleates and copolymer materials of maleic acid and olefin, etc.) and polystyrenesulfonate, etc., cationic surfactants such as alkylamine salt and alkyl quaternary ammonium salt; etc., amphoteric surfactants such as amino acid type and betaine type, etc., silicone type surfactants and fluorine type surfactants.

A content of these surfactants is not specifically limited, and it is desirably in the range of 0.05 to 20 parts by weight in general based on 100 parts by weight of the preparation according to the present invention. Also, these surfactants may be used alone or in combination of two or more kinds in combination.

A dose of the compound of the present invention to be applied may vary depending on the place to be applied, time to be applied, method to be applied, crops to cultivate, etc., and in general, it is suitable in an amount of about 0.005 to 50 kg or so per a hectare (ha) as an amount of the effective ingredient.

On the other hand, when the compound of the present invention is used for controlling ecto- or endo-parasites of mammals and birds as domestic animals and pets, the effective amount of the compound of the present invention together with additives for formulations can be administered through oral administration, parenteral administration such as injection (intramuscular, subcutaneous, intravenous, intraperitoneal) or the like; transdermal administration such as dipping, spray, bathing, washing, pouring-on and spotting-on, and dusting, or the like; transnasal administration. The compound of the present invention can be also administered through a formed product by use of a strip, a plate, a band, a collar, an ear mark, a limb band, a labe apparatus, or the like. In administration, the compound of the present invention can be formed in an arbitrary dosage form that is suited for the administration route.

The arbitrary dosage form includes solid preparations such as a dustable powder, a granule, wettable powder, a pellete, a tablet, a bolus, a capsule, a formed product containing an active compound; liquid formulations such as an injectable liquid formulation, an oral liquid formulation, a liquid formulation used on skin or in body cavity; solution preparations such as a pour-on agent, a spot-on agent, a flowable agent, an emulsifiable concentrate; semi-solid preparations such as an ointment, gel or the like.

The solid preparations can be mainly used through oral administration or transdermal administration by diluting with water or the like, or by environmental treatment. The solid preparations can be prepared by mixing the active compound with suitable excipients and optionally auxiliary substances and converting to a desired form. The suitable excipients include for example inorganic substances such as carbonates, hydrogen carbonates, phosphates, aluminum oxide, silica, clay or the like, organic substances such as sugar, cellulose, milled cereal, starch or the like.

The injectable liquid formulation can be administered intravenously, intramuscularly and subcutaneously. The injectable liquid formulation can be prepared by dissolving an active compound in a suitable solvent and optionally by adding an additive such as a solubilizing agent, an acid, a base, a buffering salt, an antioxidant, and a protective agent or the like. Suitable solvent is for example water, ethanol, butanol, benzyl alcohol, glycerin, propylene glycol, poethylene glycol, N-methylpyrrolidone, and a mixture thereof, a physiologically permissible vegetable oil, a synthetic oil suitable for injection, or the like. The solubilizing agent includes polyvinyl pyrrolidone, polyoxyethylated castor oil and polyoxyethylated sorbitan ester, or the like. The protective agent includes benzyl alcohol, trichlorobutanol, p-hydroxybenzoic acid ester and n-butanol or the like.

The oral liquid formulation can be administered directly or after dilution. It can be prepared similarly to the injectable liquid formulation.

The flowable agent and the emulsifiable concentrate can be administered directly or after dilution through transdermal administration or environmental treatment.

The liquid formulation used on skin can be administered by pouring on, spreading, rubbing, atomizing, spraying, or dipping (dipping, bathing or washing). These liquid can be prepared similarly to the injectable liquid formulation.

The pour-on agent and the spot-on agent are poured or atomized on the limited spot on the skin, thereby the active compound can be penetrated into the skin and act in the whole body. The pour-on agent and the spot-on agent can be prepared by dissolving, suspending or emulsifying an active ingredient in a suitable skin-fitted solvent or solvent mixture. If required, an auxiliary substance such as a surfactant, a colorant, an absorption promoting agent, an antioxidant, a light stabilizer and an adhesive, etc. may be added.

Suitable solvent includes water, alkanol, glycol, polyethylene glycol, polypropylene glycol, glycerin, benzyl alcohol, phenylethanol, phenoxyethanol, ethyl acetate, butyl acetate, benzyl benzoate, dipropylene glycol monomethyl ether, diethylene glycol monobutyl ether, acetone, methyl ethyl ketone, aromatic and/or aliphatic hydrocarbon, vegetable or synthetic oil, DMF, liquid paraffin, light-duty liquid paraffin, silicone, dimethylacetamide, N-methylpyrrolidone or 2,2-dimethyl-4-oxy-methylene-1,3-dioxolane. The absorption promoting agent includes DMSO, isopropyl myristate, dipropylene glycol pelargonate, silicone oil, aliphatic ester, triglyceride and fatty alcohol. The antioxidant includes sulfite, metabisulfite, ascorbic acid, butylhydroxytoluene, butylhydroxyanisole and tocopherol.

The emulsifiable concentrate can be administrated orally, subcutaneously or injectably. The emulsifiable concentrate can be prepared by dissolving an active ingredient in a hydrophobic phase or a hydrophilic phase, and then homogenating the resulting solution with a suitable emulsifying agent optionally with further an auxiliary substance such as a colorant, an absorption promoting agent, a protective agent, an antioxidant, a light screen and a thickening agent.

The hydrophobic phase (oil) includes paraffin oil, silicone oil, sesame-seed oil, oil of almonds, castor oil, synthetic triglyceride, ethyl stearate, di-n-butyryl adipate, hexyl laurate, dipropylene glycol pelargonate, ester of branched short chain length aliphatic acid with saturated aliphatic acid of chain length C16 to C18, isopropyl myristate, isopropyl palmitate, capryl/caprylic acid ester of saturated fatty alcohol of chain length C12 to C18, isopropyl stearate, oleyl oleate, decyl oleate, ethyl oleate, ethyl lactate, wax-like fatty acid ester, dibutyl phthalate, diisopropyl adipate, isotridecyl alcohol, 2-octyldodecanol, cetylstearyl alcohol, oleyl alcohol.

The hydrophilic phase includes water, propylene glycol, glycerin, sorbitol.

The emulsifying agent includes non-ionic surfactants such as polyoxyethylated castor oil, polyoxyethylated sorbitan mono-olefinate, sorbitan monostearate, glycerin monostearate, polyoxyethyl stearate, alkylphenol polyglycol ether; amphoteric surfactants such as di-sodium N-lauryl β-iminodipropionate, lecithin or the like; anionic surfactants such as sodium lauryl sulfate, fatty alcohol sulfric acid ether, monoethanol amine salt of mono/dialkylpolyglycol orthophosphate or the like; cationic surfactants such as cetyl chloride trimethylammonium or the like.

The other auxiliary substance includes carbocymethylcellulose, methylcellulose, polyacrylate, arginate, gelatin, gum arabic, polyvinyl pyrrolidone, polyvinyl alcohol, methylvinyl ether, copolymer of maleic anhydride, polyethylene glycol, wax, colloidal silica.

The semi-solid preparation can be administered by coating or spreading on the skin, or by introducing in body cavity. The gel can be prepared by adding a thickener in an amount enough to provide a clear substance having a viscosity of ointment in a solution prepared for the injectable liquid formulation as mentioned above.

Next, formulation examples of the preparation in case where the compound of the present invention is used are shown below. Provided that formulation examples of the present invention are not limited only thereto. In the interim, in the following Formulation Examples, "part(s)" mean part(s) by weight.

| (Wettable powder) | |
|---|---|
| Compound of the present invention | 0.1 to 80 parts |
| Solid carrier | 5 to 98.9 parts |
| Surfactant | 1 to 10 parts |
| Others | 0 to 5 parts |

As other components, there may be mentioned, for example, a non-caking agent, a decomposition preventing agent, and the like.

| (Emulsifiable concentrate) | |
| --- | --- |
| Compound of the present invention | 0.1 to 30 parts |
| Liquid carrier | 45 to 95 parts |
| Surfactant | 4.9 to 15 parts |
| Others | 0 to 10 parts |

As other components, there may be mentioned, for example, a spreading agent, a decomposition preventing agent, and the like.

| (Suspension concentrate) | |
| --- | --- |
| Compound of the present invention | 0.1 to 70 parts |
| Liquid carrier | 15 to 98.89 parts |
| Surfactant | 1 to 12 parts |
| Others | 0.01 to 30 parts |

As other components, there may be mentioned, for example, an antifreezing agent, a thickening agent, and the like.

| (Water dispersible granule) | |
| --- | --- |
| Compound of the present invention | 0.1 to 90 parts |
| Solid carrier | 0 to 98.9 parts |
| Surfactant | 1 to 20 parts |
| Others | 0 to 10 parts |

As other components, there may be mentioned, for example, a binder, a decomposition preventing agent, and the like.

| (Soluble concentrate) | |
| --- | --- |
| Compound of the present invention | 0.01 to 70 parts |
| Liquid carrier | 20 to 99.99 parts |
| Others | 0 to 10 parts |

As other components, there may be mentioned, for example, an antifreezing agent, a spreading agent, and the like.

| (Granule) | |
| --- | --- |
| Compound of the present invention | 0.01 to 80 parts |
| Solid carrier | 10 to 99.99 parts |
| Others | 0 to 10 parts |

As other components, there may be mentioned, for example, a binder, a decomposition preventing agent, and the like.

| (Dustable powder) | |
| --- | --- |
| Compound of the present invention | 0.01 to 30 parts |
| Solid carrier | 65 to 99.99 parts |
| Others | 0 to 5 parts |

As other components, there may be mentioned, for example, a drift preventing agent, a decomposition preventing agent, and the like.

Next, formulation examples using the compound of the present invention as an effective ingredient are described in more detail, but the present invention is not limited thereto. In the interim, in the following Formulation Examples, "part(s)" mean part(s) by weight.

| (Formulation Example 1) Wettable powder | |
| --- | --- |
| Compound of the present invention No. 2-032 | 20 parts |
| Pyrophylite | 74 parts |
| Solpol 5039 | 4 parts |
| (A mixture of a nonionic surfactant and an anionic surfactant: available from TOHO Chemical Industry Co., LTD, Tradename) | |
| CARPREX #80D | 2 parts |
| (Synthetic hydrated silicic acid: available from Shionogi & Co., Ltd., Tradename) | |

The above materials are uniformly mixed and pulverized to make wettable powder.

| (Formulation Example 2) Emulsion | |
| --- | --- |
| Compound of the present invention No. 2-032 | 5 parts |
| Xylene | 75 parts |
| N-methylpyrrolidone | 15 parts |
| Solpol 2680 | 5 parts |
| (A mixture of a nonionic surfactant and an anionic surfactant: available from TOHO Chemical Industry Co., LTD, Tradename) | |

The above materials are uniformly mixed to make emulsifiable concentrate.

| (Formulation Example 3) Suspension concentrate | |
| --- | --- |
| Compound of the present invention No. 2-032 | 25 parts |
| Agrisol S-710 | 10 parts |
| (a nonionic surfactant: available from KAO CORPORATION, Tradename) | |
| Lunox 1000C | 0.5 part |
| (an anionic surfactant: available from TOHO Chemical Industry Co., LTD, Tradename) | |
| Xanthan gum | 0.2 part |
| Water | 64.3 parts |

The above materials are uniformly mixed, and then, wet pulverized to make suspension concentrate.

| (Formulation Example 4) Water dispersible granule | |
| --- | --- |
| Compound of the present invention No. 2-032 | 75 parts |
| HITENOL NE-15 | 5 parts |
| (an anionic surfactant: available from DAI-ICHI KOGYO SEIYAKU CO., LTD., Tradename) | |
| VANILLEX N | 10 parts |
| (an anionic surfactant: available from Nippon Paper Chemicals Co., Ltd., Tradename) | |
| CARPREX #80D | 10 parts |
| (Synthetic hydrated silicic acid: available from Shionogi & Co., Ltd., Tradename) | |

The above materials are uniformly mixed and pulverized, and then, a small amount of water is added to the mixture and the resulting mixture is mixed under stirring, granulated by an extrusion granulator, and dried to make water dispersible granule.

(Formulation Example 5) Granule

| Compound of the present invention No. 2-032 | 5 parts |
|---|---|
| Bentonite | 50 parts |
| Talc | 45 parts |

The above materials are uniformly mixed and pulverized, and then, a small amount of water is added to the mixture and the resulting mixture is mixed under stirring, granulated by an extrusion granulator, and dried to make granule.

(Formulation Example 6) Dustable powder

| Compound of the present invention No. 2-032 | 3 parts |
|---|---|
| CARPREX #80D | 0.5 parts |
| (Synthetic hydrated silicic acid: available from Shionogi & Co., Ltd., Tradename) | |
| Kaolinite | 95 parts |
| Diisopropyl phosphate | 1.5 parts |

The above materials are uniformly mixed and pulverized to make dustable powder. When the formulation is used, it is sprayed by diluting with water in 1- to 10000-fold concentration, or directly without dilution.

(Formulation Example 7) Wettable powder preparation

| Compound of the present invention No. 2-032 | 25 parts |
|---|---|
| Sodium diisobutylnaphthalenesulfonate | 1 part |
| Calcium n-dodecylbenzenesulfonate | 10 parts |
| Alkylaryl polyglycol ether | 12 parts |
| Sodium salt of naphthalenesulfonic acid formalin condensate | 3 parts |
| Emulsion type silicone | 1 part |
| Silicon dioxide | 3 parts |
| Kaoline | 45 parts |

(Formulation Example 8) Water-soluble concentrate preparation

| Compound of the present invention No. 2-032 | 20 parts |
|---|---|
| Polyoxyethylene lauryl ether | 3 parts |
| Sodium dioctylsulfosuccinate | 3.5 parts |
| Dimethylsulfoxide | 37 parts |
| 2-Propanol | 36.5 parts |

(Formulation Example 9) Liquid formulation for atomization

| Compound of the present invention No. 2-032 | 2 parts |
|---|---|
| Dimethylsulfoxide | 10 parts |
| 2-Propanol | 35 parts |
| Acetone | 53 parts |

(Formulation Example 10) Liquid formulation for transdermal administration

| Compound of the present invention No. 2-032 | 5 parts |
|---|---|
| Hexylene glycol | 50 parts |
| Isopropanol | 45 parts |

(Formulation Example 11) Liquid formulation for transdermal administration

| Compound of the present invention No. 2-032 | 5 parts |
|---|---|
| Propylene glycol monomethyl ether | 50 parts |
| Dipropylene glycol | 45 parts |

(Formulation Example 12) Liquid formulation for transdermal administration (pouring-on)

| Compound of the present invention No. 2-032 | 2 parts |
|---|---|
| Light-duty liquid paraffin | 98 parts |

(Formulation Example 13) Liquid formulation for transdermal administration (pouring-on)

| Compound of the present invention No. 2-032 | 2 parts |
|---|---|
| Light-duty liquid paraffin | 58 parts |
| Olive oil | 30 parts |
| ODO-H | 9 parts |
| Shinetsu silicone | 1 part |

Also, when the compound of the present invention is used as an agricultural chemicals, it may be mixed with other kinds of herbicides, various kinds of insecticides, acaricides, nematocides, fungicides, vegetable growth regulators, synergists, fertilizers, soil improvers, etc., and applied, at the time of preparing the formulation or at the time of spreading, if necessary.

In particular, by mixing with the other agricultural chemicals or plant hormones and applying the mixture, it can be expected that a cost is reduced due to reduction in a dose to be applied, enlargement in insecticidal spectrum or higher prevention and extinction effect of noxious organisms due to synergistic effect by mixing agricultural chemicals. At this time, it is possible to use the compound with a plural number of the conventionally known agricultural chemicals in combination simultaneously. As the kinds of the agricultural chemicals to be used in admixture with the compound of the present invention, there may be mentioned, for example, the compounds described in Farm Chemicals Handbook, 2005 ed. and the like. Specific examples of the general names can be enumerated below, but the invention is not necessarily limited only thereto.

Fungicide: acibenzolar-5-methyl, acylaminobenzamide, acypetacs, aldimorph, amisulbrom, amobam, ampropylos, anilazine, azaconazole, azithiram, azoxystrobin, barium polysulfide, benalaxy, benodanil, benomyl, benquinox, bentaluron, benthiavalicarb, benthiazole, benzamacril, benzamorf, bethoxazine, binapacryl, biphenyl, bitertanol, blasticidin-S, bordeaux mixture, boscalid, bromoconazole, bupirimate, buthiobate, calcium polysulfide, captafol, captan, carpropamid, carbamorph, carbendazim, carboxin, carvone, cheshunt mixture, chinomethionat, chlobenthiazone, chloraniformethane, chloranil, chlorfenazol, chloroneb, chloropicrin, chlorothalonil, chlorquinox, chlozolinate, climbazole, clotrimazole, copper acetate, copper carbonate, basic, copper hydroxide, copper naphthenate, copper oleate, copper oxychloride, copper sulfate, copper sulfate, basic, copper zinc chromate, cufraneb, cuprobam, cyazofamid, cyclafuramid, cycloheximide, cyflufenamid, cymoxanil, cypendazole, cyproconazol, cyprodinil, cyprofuram, dazomet, debacarb, decafentin, dehydroacetic acid, dichlofluanid, dichlone, dichlorophen, dichlozoline, diclobutrazol, diclocymet, diclomedine, dicloran, diethofencarb, difenoconazole, diflumetorim, dimethirimol, dimethomorph, dimoxystrobin, diniconazole, diniconazole-M, dinobuton, dinocap, dinocap-4, dinocap-6, dinocton, dinosulfon, dinoterbon, diphenylamine, dipyrithione, ditalimfos, dithianon, dodemorph, dodine, drazoxolon, edifenphos, epoxiconazole, etaconazole, etem, ethirimol, ethoxyquin, etridiazole, famoxadone, fenarimol, febuconazole, fenamidone, fenaminosulf, fenapanil, fendazosulam, fenfuram, fenhexamid, fenitropan, fenoxanil, fenpiclonil, fenpropidin, fenpropimorph, fentin, ferbam, ferimzone, fluazinam, fludioxonil, flumetover, flumorph, fluoroimide, fluotrimazole, fluoxastrobin, fluquinconazole, flusilazole, flusulfamide, flutolanil, flutriafol, folpet, fosetyl-aluminium, fuberidazole, furalaxyl, furametpyr, furcarbanil, furconazole, furconazole-cis, furmecyclox, furphanate, glyodin, griseofulvin, guazatine, halacrinate, hexachlorobenzene, hexaconazole, hexylthiofos, 8-hydroxyquinoline sulfate, hymexazol, imazalil, imibenconazole, iminoctadine, ipconazole, iprobenfos, iprodione, iprovalicarb, isoprothiolane, isovaledione, kasugamycin, kresoxim-methyl, mancopper, mancozeb, maneb, mebenil, mecarbinzid, mepanipyrim, mepronil, metalaxyl, metalaxyl-M, metam, metazoxolon, metconazole, methasulfocarb, methfuroxam, methyl isothiocyanate, metiram, metominostrobin, metrafenone, metsulfovax, milneb, myclobutanil, myclozolin, nabam, natamycin, nickel bis(dimethyldithiocarbamate), nitrostyrene, nitrothal-isopropyl, nuarimol, OCH, octhilinone, ofurace, orysastrobin, oxadixyl, oxine copper, oxycarboxin, oxpoconazole fumarate, pefurzoate, penconazole, pencycuron, penthiopyrad, o-phenylphenol, phosdiphen, phthalide, picoxystrobin, piperalin, polycarbamate, polyoxins, polyoxorim, potassium azide, potassium hydrogen carbonate, proquinazid, probenazole, prochloraz, procymidone, propamocarb hydrochloride, propiconazole, propineb, prothiocarb, prothioconazole, pyra-carbolid, pyraclostrobin, pyrazophos, pyridinitril, pyrifenox, pyrimethanil, pyroquilon, pyroxychlor, pyroxyfur, quinomethionate, quinoxyfen, quintozene, quinacetol-sulfate, quinazamid, quinconazole, rabenzazole, sodium azide, sodium hydrogen carbonate, sodium hypochlorite, sulfur, spiroxamine, salycylanilide, silthiofam, simeconazole, tebuconazole, tecnazene, tecoram, tetraconazole, thiabendazole, thiadifluor, thicyofen, thifluzamide, thiochlorfenphim, thiophanate, thiophanate-methyl, thioquinox, thiram, tiadinil, tioxymid, tolclofos-methyl, tolylfluanid, triadimefon, toriadimenol, triamiphos, triarimol, triazoxide, triazbutil, tributyltin oxide, trichlamide, tricyclazole, tridemorph, trifloxystrobin, triflumizole, triforine, triticonazole, validamycin, vinclozolin, zarilamide, zinc sulfate, zineb, ziram, zoxamide, and shiitake mushroom hyphae extract, etc.;
Bactericides: benzalkonium chloride, bithionol, bronopol, cresol, formaldehyde, nitrapyrin, oxolinic acid, oxyterracycline, streptomycin and tecloftalam, etc.;
Nematocides: aldoxycarb, cadusafos, DBCP, dichlofenthion, DSP, ethoprophos, fenamiphos, fensulfothion, fosthiazate, fosthietan, imicyafos, isamidofos, isazofos, oxamyl and thionazin, etc.;

Acaricides: acequinocyl, acrinathrin, amitraz, BCI-033 (test name), bifenazate, bromopropylate, chinomethionat, chlorobezilate, clofentezine, cyenopyrafen, cyflumetofen, cyhexatine, dicofol, dienochlor, DNOC, etoxazole, fenazaquin, fenbutatin oxide, fenothiocarb, fenpropathrin, fenpyroximate, fluacrypyrim, halfenprox, hexythiazox, milbemectin, propargite, pyridaben, pyrimidifen), S-1870 (test name), spirodiclofen, spyromesifen and ebufenpyrad, etc.;
Insecticides: abamectin, acephate, acetamipirid, alanycarb, aldicarb, allethrin, azinphos-methyl, *bacillus thuringiensis*, bendiocarb, benfuracarb, bensultap, bifenthrin, buprofezin, butocarboxim, carbaryl, carbofuran, carbosulfan, cartap, chlorfenapyr, chlorfenvinphos, chlorfluazuron, chlorpyrifos, chlorpyrifos-methyl, chromafenozide, clothianidin, cycloprothrin, cyflumetofen, cyfluthrin, beta-cyfluthrin, cyhalothrin, lambda-cyhalothrin, cypermethrin, cyromazine, deltamethrin, diacloden, diafenthiuron, diazinon, dichlorvos, diflubenzuron, dimethylvinphos, dinotefuran, diofenolan, disulfoton, dimethoate, emamectin-benzoate, EPN, esfenvalerate, ethiofencarb, ethiprole, etofenprox, etrimfos, fenitrothion, fenobucarb, fenoxycarb, fenpropathrin, fenthion, fenvalerate, fipronil, flonicamid, flubendiamide, flucythrinate, flufenerim, flufenoxuron, flufenprox, fluvalinate, tau-fluvalinate, fonophos, formetanate, formothion, furathiocarb, halofenozide, hexaflumuron, hydramethylnon, imidacloprid, isofenphos, indoxacarb, isoprocarb, isoxathion, lepimectin, lufenuron, malathion, metaldehyde, methamidophos, methidathion, methacrifos, metaflumizone, metalcarb, methomyl, methoprene, methoxychlor, methoxyfenozide, methyl bromide, monocrotophos, muscalure, nitenpyram, NNH-0101 (test name), omethoate, oxamyl, oxydemeton-methyl, oxydeprofos, parathion, parathion-methyl, pentachlorophenol (PCP), permethrin, phenthoate, phoxim, phorate, phosalone, phosmet, phosphamidon, pirimicarb, pirimiphos-methyl, profenofos, prothiofos, propaphos, protrifenbute, pymetrozine, pyraclofos, pyridalyl, pyriproxyfen, rotenone, rynaxypyr, SI-0405 (test name), sulprofos, silafluofen, spinosad, sulfotep, SYJ-0159 (test name), tebfenozide, teflubenzuron, tefluthorin, terbufos, tetrachlorvinphos, thiacloprid, thiocyclam, thiodicarb, thiamethoxam, thiofanox, thiometon, tolfenpyrad, tralomethrin, trichlorfon, triazuron, triflumuron and vamidothion, etc.

EXAMPLES

Hereinafter, the present invention will be explained in more detail by specifically referring to Synthetic Examples and Test Examples of the compound of the present invention as working examples to which the present invention is not limited.

Synthetic Examples

Synthetic Example 1

Production of the Compound of the Present Invention with L-COS (a Parallel Liquid-Phase Synthesizer Manufactured by Moritex Corporation)

Step 1: Production of 3,5-dichloro-1-(1-trifluoromethylethenyl)benzene

In a solution of 25.0 g of 3,5-dichlorophenyl boric acid in 200 mL of tetrahydrofuran and 100 mL of water, 27.5 g of 2-bromo-3,3,3-trifluoropropene, 38.0 g of potassium carbonate and 1.84 g of dichlorobis(triphenylphosphine) palladium (II) were added, and stirred under reflux with heat for 3 hours.

After the completion of the reaction, the reaction mixture was left and cooled to room temperature, 500 mL of ice water was added, and extracted with ethyl acetate (500 mL×1). The organic phase was washed with water, dried over anhydrous sodium sulfate, the solvent was distilled off under reduced pressure. The residue was purified with silica gel column chromatography that was eluted with hexane to obtain 25.7 g of the aimed product as colorless oily substance.

$^1$H NMR (CDCl$_3$, Me$_4$Si, 300 MHz) δ7.41 (t, J=2.0 Hz, 1H), 7.3-7.35 (m, 2H), 6.05 (q, J=3.2 Hz, 1H), 5.82 (q, J=3.2 Hz, 1H).

Step 2: Production of methyl 4-[5-(3,5-dichlorophenyl)-5-trifluoromethyl-4,5-dihydroisoxazol-3-yl]benzoate In a solution of 2.70 g of methyl 4-(hydroxyiminomethyl) benzoate in 15 mL of N,N-dimethylformamide, 2.04 g of N-chlorosuccinimide was added, and stirred at 40° C. for 40 minutes. Then, the reaction mixture was cooled to 0° C., 3.40 g of 3,5-dichloro-1-(1-trifluoromethylethenyl)benzene and 1.72 g of triethylamine were added, and continued to stir at room temperature further for 18 hours. After the completion of the reaction, the reaction mixture was poured into 100 mL of ice water, extracted with ethyl acetate (50 mL×2), the organic phase was washed with water and then dehydrated with and dried over saturated sodium chloride aqueous solution and anhydrous sodium sulfate in that order, and the solvent was distilled off under reduced pressure. The residual solid was purified with medium pressure preparative liquid chromatography (medium pressure collection apparatus: YFLC-Wprep manufactured by Yamazen Corporation) that was eluted with ethyl acetate-hexane (gradient of 1:1 to 1:3) to obtain 4.05 g of the aimed products as white crystal.

Melting point: 94.0 to 96.0° C.

$^1$H NMR (CDCl$_3$, Me$_4$Si, 300 MHz) δ8.10 (d, J=8.4 Hz, 2H), 7.74 (d, J=8.4 Hz, 2H), 7.43 (s, 2H), 7.26 (s, 1H), 4.12 (d, J=17.3 Hz, 1H), 3.94 (s, 3H), 3.74 (d, J=17.3 Hz, 1H).

Step 3: Production of 5-(3,5-dichlorophenyl)-3-[4-(hydroxymethyl)phenyl]-5-trifluoromethyl-4,5-dihydro-isoxazole In a solution of 5.00 g of methyl 4-[5-(3,5-dichlorophenyl)-5-trifluoromethyl-4,5-dihydroisoisoxazol-3-yl]benzoate in 50 mL of tetrahydrofuran, 0.64 g of sodium boron hydride was added, and 10 mL of methanol was added dropwise in five additions with stirring at 50° C. After the completion of addition dropwise, it was continued to stir at the same temperature further for 3 hours. After the completion of the reaction, the reaction mixture was poured into 70 mL of water, dilute hydrochloric acid was added to be adjusted to pH3, and then extracted with ethyl acetate (50 mL×3), the organic phase was washed with water and then dehydrated with and dried over saturated sodium chloride aqueous solution and anhydrous sodium sulfate in that order, and the solvent was distilled off under reduced pressure to obtain 5.00 g of the crude aimed product as colorless resinous substance. The resulting product was used as such without purification for the next step.

Melting point: 108.0 to 110.0° C.

$^1$H NMR (CDCl$_3$, Me$_4$Si, 400 MHz) δ7.64 (d, J=8.0 Hz, 2H), 7.52 (d, J=1.6 Hz, 2H), 7.4-7.45 (m, 3H), 4.74 (s, 2H), 4.09 (d, J=17.2 Hz, 1H), 3.71 (d, J=17.2 Hz, 1H), 1.93 (bs, 1H).

Step 4: Production of 3-[4-(chloromethyl)phenyl]-5-(3,5-dichlorophenyl)-5-trifluoromethyl-4,5-dihydro-isoxazole In a solution of 4.2 g of 5-(3,5-dichlorophenyl)-3-[4-(hydroxymethyl)phenyl]-5-trifluoromethyl-4,5-dihydro-isoxazole in 100 mL of dichloromethane, 1.2 mL of thionyl chloride and a catalytic amount (2 to 3 drops) of N,N-dimethylformamide were added, and stirred under reflux with heating for 3 hours. After the completion of the reaction, the reaction mixture was poured into 30 mL of ice water, the organic phase was collected, washed with water (50 mL×1) and saturated sodium hydrogen carbonate aqueous solution (30 mL×3), and thereafter dehydrated with and dried over saturated sodium chloride aqueous solution and anhydrous sodium sulfate in that order, and the solvent was distilled off under reduced pressure. The residue was purified with silica gel column chromatography that was eluted with ethyl acetate-hexane (1:5) to obtain 4.1 g of the aimed product as pale yellow crystal.

Melting point: 98.0 to 100.0° C.

$^1$H NMR (CDCl$_3$, Me$_4$Si, 300 MHz) δ7.65 (d, J=7.8 Hz, 2H), 7.51 (s, 2H), 7.4-7.5 (m, 3H), 4.59 (s, 2H), 4.08 (d, J=17.4 Hz, 1H), 3.69 (d, J=17.4 Hz, 1H).

Step 5: Production of N-[4-[5-(3,5-dichlorophenyl)-5-trifluoromethyl-4,5-dihydroisoxazol-3-yl]phenyl-methyl]phthalimide In a solution of 1.20 g of 3-[4-(chloromethyl)phenyl]-5-(3,5-dichlorophenyl)-5-trifluoromethyl-4,5-dihydroisoxazole in 20 mL of N,N-dimethylformamide, 0.54 g of potassium phthalimide was added and stirred at room temperature for 20 hours. After the completion of the reaction, the reaction mixture was diluted with 100 mL of ethyl acetate, washed with water (50 mL×3) and then dehydrated with and dried over saturated sodium chloride aqueous solution and anhydrous magnesium sulfate in that order, and the solvent was distilled off under reduced pressure to obtain 1.50 g of the aimed product as white crystal.

Melting point: 190.0 to 192.0° C.

$^1$H NMR (CDCl$_3$, Me$_4$Si, 400 MHz) δ7.8-7.95 (m, 2H), 7.7-7.8 (m, 2H), 7.55-7.65 (m, 2H), 7.35-7.5 (m, 5H), 4.90 (s, 2H), 4.05 (t, J=17.6 Hz, 1H), 3.65 (d, J=17.6 Hz, 1H).

Step 6: Production of 3-[4-(aminomethyl)phenyl]-5-(3,5-dichlorophenyl)-5-trifluoromethyl-4,5-dihydro-isoxazole (Compound of the present invention No. 9-001)

In a suspension of 1.4 g of N-[4-[5-(3,5-dichlorophenyl)-5-trifluoromethyl-4,5-dihydroisoxazol-3-yl]phenylmethyl] phthalimide in 20 mL of ethanol, 1.0 mL of 80% hydrazine monohydrate aqueous solution was added, and stirred under reflux with heating for 1.5 hour. After the completion of the reaction, the reaction mixture was left and cooled to room temperature, 50 mL of chloroform was added therein, insoluble material was filtered off, and the solvent was distilled off under reduced pressure. The procedure comprising adding 50 mL of chloroform in the residue, filtering off insoluble material and distilling off the solvent was repeated twice to obtain 1.1 g of the aimed product as yellow resinous substance.

$^1$H NMR (CDCl$_3$, Me$_4$Si, 300 MHz) δ7.61 (d, J=8.1 Hz, 2H), 7.51 (s, 2H), 7.35-7.5 (m, 3H), 4.09 (d, J=17.4 Hz, 1H), 3.93 (s, 2H), 3.68 (d, J=17.4 Hz, 1H).

Step 7: Production of the compound of the present invention with L-COS (a Parallel Liquid-Phase Synthesizer Manufactured by Moritex Corporation)

In each of 13 L-COS reaction tubes in which stirrers were placed, and which were covered with lids and placed in L-COS reactor, 1 mL of chloroform solution (0.26 mmol/mL) of 3-[4-(aminomethyl)phenyl]-5-(3,5-dichlorophenyl)-5-trifluoromethyl-4,5-dihydroiso-oxazole and 1 mL of chloroform solution (0.28 mmol/mL) of triethylamine were pipetted. With stirring at room temperature, each 0.39 mmol of 4-chlorobenzoyl=chloride, 3-chlorobenzoyl=chloride, 2-chlorobenzoyl=chloride, acetyl=chloride, propionyl=chloride, chloroacetyl=chloride, phenyl chloroformate, methyl chloroformate, ethyl chloroformate, isobutyryl=chloride, isobutyl chloroformate, methoxyacetyl=chloride and cyclopropanecarbonyl=chloride was pipetted in each reaction tube. It was continued to stir at the same temperature for 24 hours. After the completion of the reaction, 3 mL of cool water was added in each reaction tube, and the organic phase was collected, and purified with medium pressure preparative liquid chromatography (medium pressure collection apparatus: YFLC-Wprep manufactured by Yamazen Corporation) that was eluted with ethyl acetate-hexane (gradient of 1:10 to 1:1) to obtain the aimed products. The products were confirmed by use of LC-MS (Waters LC-MS system, detector: ZMD, analysis condition: 254 nm, 83% $CH_3CN$-17% $H_2O$-0.1% HCOOH, ionization method: positive electrospray or negative electrospray).

4-Chloro-N-[4-[5-(3,5-dichlorophenyl)-5-trifluoromethyl-4,5-dihydroisoxazol-3-yl]phenylmethyl]benzamide; 0.104 g, $[M^+-H]=524.98$.

3-Chloro-N-[4-[5-(3,5-dichlorophenyl)-5-trifluoromethyl-4,5-dihydroisoxazol-3-yl]phenylmethyl]benzamide; 0.111 g, $[M^+-H]=524.98$.

2-Chloro-N-[4-[5-(3,5-dichlorophenyl)-5-trifluoromethyl-4,5-dihydroisoxazol-3-yl]phenylmethyl]benzamide; 0.107 g, $[M^++H]=527.06$.

N-[4-[5-(3,5-Dichlorophenyl)-5-trifluoromethyl-4,5-dihydroisoxazol-3-yl]phenylmethyl]acetamide; 0.044 g, $[M^++H]=431.06$.

N-[4-[5-(3,5-Dichlorophenyl)-5-trifluoromethyl-4,5-dihydroisoxazol-3-yl]phenylmethyl]propionamide; 0.089 g, $[M^++H]=445.13$.

Chloro-N-[4-[5-(3,5-dichlorophenyl)-5-trifluoromethyl-4,5-dihydroisoxazol-3-yl]phenylmethyl]acetamide; 0.083 g, $[M^+-H]=463.01$.

Phenyl N-[4-[5-(3,5-dichlorophenyl)-5-trifluoromethyl-4,5-dihydroisoxazol-3-yl]phenylmethyl]carbamate; 0.105 g, $[M^++H]=509.09$.

Methyl N-[4-[5-(3,5-dichlorophenyl)-5-trifluoromethyl-4,5-dihydroisoxazol-3-yl]phenylmethyl]carbamate; 0.049 g, $[M^++H]=447.14$.

Ethyl N-[4-[5-(3,5-dichlorophenyl)-5-trifluoromethyl-4,5-dihydroisoxazol-3-yl]phenylmethyl]carbamate; 0.101 g, $[M^++H]=461.12$.

N-[4-[5-(3,5-dichlorophenyl)-5-trifluoromethyl-4,5-dihydroisoxazol-3-yl]phenylmethyl]isobutyrylamide; 0.087 g, $[M^++H]=459.11$.

Isobutyl N-[4-[5-(3,5-dichlorophenyl)-5-trifluoromethyl-4,5-dihydroisoxazol-3-yl]phenylmethyl]carbamate; 0.101 g, $[M^++H]=489.17$.

N-[4-[5-(3,5-dichlorophenyl)-5-trifluoromethyl-4,5-dihydroisoxazol-3-yl]phenylmethyl]-2-methoxyacetamide; 0.079 g, $[M^++H]=461.10$.

N-[4-[5-(3,5-dichlorophenyl)-5-trifluoromethyl-4,5-dihydroisoxazol-3-yl]phenylmethyl]cyclopropanecarboxamide; 0.087 g, $[M^++H]=457.10$.

Synthetic Example 2

1-[4-[5-(3,5-Dichlorophenyl)-5-trifluoromethyl-4,5-dihydroisoxazol-3-yl]phenylmethyl]-3-(2,2,2-trifluoroethyl)urea (Compound of the present invention No. 5-001)

In a solution of 0.32 g of 1,1'-carbonylbis-1H-imidazole in 7.0 mL of tetrahydrofuran, 0.20 g of 2,2,2-trifluoroethylamine was added, and stirred at room temperature for 1.5 hour. Then, in the reaction mixture, a solution of 0.39 g of 3-[4-(aminomethyl)phenyl]-5-(3,5-dichlorophenyl)-5-trifluoromethyl-4,5-dihydro-isoxazole synthesized in Step 6 of Synthetic Example 1 in 5.0 mL of tetrahydrofuran was added, and continued to stir at room temperature further for 2.5 hours. After the completion of the reaction, the reaction mixture was diluted with 20 mL of ethyl acetate, washed with water (15 mL×2), and dehydrated with and dried over saturated sodium chloride aqueous solution and anhydrous magnesium sulfate in that order, and the solvent was distilled off under reduced pressure. The residue was purified with medium pressure preparative liquid chromatography (medium pressure collection apparatus: YFLC-Wprep manufactured by Yamazen Corporation) that was eluted with ethyl acetate-hexane (gradient of 1:8 to 1:1) to obtain 0.43 g of the aimed products as colorless resinous substance.

$^1$H NMR (CDCl$_3$, Me$_4$Si, 300 MHz) δ7.63 (d, J=8.1 Hz, 2H), 7.51 (s, 2H), 7.43 (s, 1H), 7.34 (d, J=8.1 Hz, 2H), 4.81 (bs, 1H), 4.63 (bs, 1H), 4.44 (d, J=6.0 Hz, 2H), 4.07 (d, J=17.4 Hz, 1H), 3.8-3.95 (m, 3H), 3.66 (d, J=17.4 Hz, 1H).

Synthetic Example 3

N-[2-Chloro-4-[5-(3,5-dichlorophenyl)-5-trifluoromethyl-4,5-dihydroisoxazol-3-yl]phenylmethyl]-1H-imidazole-1-carboxamide (Compound of the present invention No. 2-040)

In a solution of 1.0 g of 3-(4-(aminomethyl-3-chlorophenyl)-5-(3,5-dichlorophenyl)-5-trifluoromethyl-4,5-dihydroisoxazole synthesized similarly to Steps 1 to 6 of Synthetic Example 1 in 20 mL of tetrahydrofuran, a solution of 0.32 g of 1,1'-carbonylbis-1H-imidazole in 7 mL of tetrahydrofuran and 0.40 g of 2,2,2-trifluoroethylamine were added, and stirred at room temperature for 3 hours. After the completion of the reaction, the reaction mixture was diluted with 50 mL of ethyl acetate, washed with water (15 mL×2), and the organic phase was dehydrated with and dried over saturated sodium chloride aqueous solution and anhydrous magnesium sulfate in that order, and the solvent was distilled off under reduced pressure. The residue was purified with medium pressure preparative liquid chromatography (medium pressure collection apparatus: YFLC-Wprep manufactured by Yamazen Corporation) that was eluted with ethyl acetate-hexane (gradient of 1:5 to 1:1) to obtain 0.75 g of the aimed products as yellow resinous substance.

$^1$H NMR (CDCl$_3$, Me$_4$Si, 300 MHz) δ8.10 (s, 1H), 7.73 (s, 1H), 7.54 (s, 2H), 7.45-7.5 (m, 2H), 7.43 (t, J=1.5 Hz, 1H), 7.31 (t, J=1.5 Hz, 1H), 7.08 (s, 1H), 6.43 (bs, 1H), 4.69 (d, J=5.7 Hz, 2H), 4.05 (d, J=17.4 Hz, 1H), 3.07 (d, J=17.4 Hz, 1H).

Synthetic Example 4

2,2,2-Trifluoroethyl N-[2-chloro-4-[5-(3,5-dichlorophenyl)-5-trifluoromethyl-4,5-dihydroisoxazol-3-yl]phenylmethyl]carbamate (Compound of the present invention No. 4-004)

In a solution of 0.091 g of 2,2,2-trifluoroethanol in 4.0 mL of N,N-dimethylformamide, 0.033 g of 55% oily sodium hydride was added under cooling with ice and with stirring and stirred at the same temperature for 10 minutes. After ceasing the generation of hydrogen gas, a solution of 0.19 g of N-[2-chloro-4-[5-(3,5-dichlorophenyl)-5-trifluoromethyl-4,5-dihydroisoxazol-3-yl]phenylmethyl]-1H-imidazole-1-carboxamine (Compound of the present invention No. 2-040) in 1.0 mL of N,N-dimethylformamide was added, and continued to stir at the same temperature further for 2.5 hours. After the completion of the reaction, the reaction mixture was diluted with 30 mL of ethyl acetate, washed with water (20 mL×1), the organic phase was dehydrated with and dried over saturated sodium chloride aqueous solution and anhydrous magnesium sulfate in that order, and the solvent was distilled off under reduced pressure. The residue was purified with medium pressure preparative liquid chromatography (medium pressure collection apparatus: YFLC-Wprep manufactured by Yamazen Corporation) that was eluted with ethyl acetate-hexane (gradient of 1:5 to 1:2) to obtain 0.091 g of the aimed product as yellow resinous substance.

$^1$H NMR (CDCl$_3$, Me$_4$Si, 300 MHz) δ7.69 (d, J=1.8 Hz, 1H), 7.54 (dd, J=8.1 Hz, 1.8 Hz, 1H), 7.49 (d, J=1.5 Hz, 2H), 7.44 (d, J=8.1 Hz, 1H), 7.42 (t, J=1.5 Hz, 1H), 5.43 (t, J=6.3 Hz, 1H), 4.4-4.45 (m, 4H), 4.06 (d, J=17.4 Hz, 1H), 3.67 (d, J=17.4 Hz, 1H).

Synthetic Example 5

N-[4-[5-(3,5-Dichlorophenyl)-5-trifluoromethyl-4,5-dihydroisoxazol-3-yl]phenylmethyl]-2,2,2-trifluoropropionic acid thioamide (Compound of the present invention No. 3-001)

A solution of 0.25 g of N-[4-[5-(3,5-dichlorophenyl)-5-trifluoromethyl]-4,5-dihydroisoxazol-3-yl]phenylmethyl]-2,2,2-trifluoropropionic acid amide (Compound of the present invention No. 2-005) synthesized similarly to Synthetic Example 1 and 0.40 g of Lawesson's Reagent (2,4-bis(4-methoxyphenyl)-1,3,2,4-dithiadiphosphetane-2,4-disulfide) in 10 mL of toluene was stirred under reflux with heating for 3 hours. After the completion of the reaction, the reaction mixture was left and cooled to room temperature, diluted with 20 mL of ethyl acetate, washed with water (10 mL×1), and dehydrated with and dried over saturated sodium chloride aqueous solution and anhydrous sodium sulfate in that order, and then the solvent was distilled off under reduced pressure. The residue was purified with medium pressure preparative liquid chromatography (medium pressure collection apparatus: Purif-α2 manufactured by Moritex Corporation) that was eluted with ethyl acetate-hexane (gradient of 1:9 to 1:1) to obtain 0.80 g of the aimed product as yellow resinous substance.

$^1$H NMR (CDCl$_3$, Me$_4$Si, 300 MHz) δ7.87 (bs, 1H), 7.66 (d, J=8.4 Hz, 2H), 7.48 (s, 2H), 7.42 (t, J=1.5 Hz, 1H), 7.34 (d, J=8.4 Hz, 2H), 4.90 (d, J=5.4 Hz, 2H), 4.07 (d, J=17.4 Hz, 1H), 3.55-3.75 (m, 3H).

Synthetic Example 6

N-[1-[2-Chloro-4-[5-(3,5-dichlorophenyl)-5-trifluoromethyl-4,5-dihydroisoxazol-3-yl]phenyl]ethyl]cyclopropanecarboxamide (Compound of the present invention No. 2-041)

Step 1: Production of 3-chloro-4-methylbenzaldoxime

In a solution of 5.0 g of 3-chloro-4-methylbenzaldehyde in 40 mL of methanol and 30 mL of water, 4.7 g of hydroxylamine hydrochloride was added, and stirred at room temperature for 2 hours. After the completion of the reaction, the reaction mixture was diluted with 70 mL of ethyl acetate, washed with water (30 mL×1), and then dehydrated with and dried over saturated sodium chloride and anhydrous sodium sulfate in that order, and the solvent was distilled off under reduced pressure to obtain 5.1 g of the aimed product as white crystal. The resulting product was used as such without purification for the next step.

Melting point: 66.0 to 68.0° C.

$^1$H NMR (CDCl$_3$, Me$_4$Si, 300 MHz) δ8.12 (bs, 1H), 8.07 (s, 1H), 7.56 (s, 1H), 7.37 (d, J=7.8 Hz, 1H), 7.23 (d, J=7.8 Hz, 1H), 2.39 (s, 3H).

Step 2: Production of 3-(3-chloro-4-methylphenyl)-5-(3,5-dichlorophenyl)-5-trifluoromethyl-4,5-dihydro-isoxazole In a solution of 10.6 g of 3-chloro-4-methylbenzaldoxime in 60 mL of 1,2-dimethoxyethane, 9.2 g of N-chlorosuccinimide was added, and stirred at 70° C. for 2 hours. Then, the reaction mixture was left and cooled to room temperature, 11.3 g of 3,5-dichloro-1-(1-trifluoromethylethenyl)benzene synthesized in Step 1 of Synthetic Example 1, 15.6 g of potassium hydrogen carbonate and 10 mL of water were added, and continued to stir at room temperature further for 20 hours. After the completion of the reaction, the reaction mixture was diluted with 70 mL of ethyl acetate, washed with water (50 mL×1), and dehydrated with and dried over saturated sodium chloride aqueous solution and anhydrous sodium sulfate in that order, and then the solvent was distilled off under reduced pressure. The residual solid was washed with diisopropyl ether to obtain 13.8 g of the aimed product as white crystal.

Melting point: 97.0 to 99.0° C.

$^1$H NMR (CDCl$_3$, Me$_4$Si, 300 MHz) δ7.62 (d, J=1.5 Hz, 1H), 7.49 (s, 2H), 7.47 (dd, J=7.8, 1.5 Hz, 1H), 7.42 (t, J=1.5 Hz, 1H), 7.28 (d, J=7.8 Hz, 1H), 4.05 (d, J=17.4 Hz, 1H), 3.67 (d, J=17.4 Hz, 1H), 2.41 (s, 3H).

Step 3: Production of 3-(4-bromomethyl-3-chlorophenyl)-5-(3,5-dichlorophenyl)-5-trifluoromethyl-4,5-dihydro-isoxazole In a solution of 13.7 g of 3-(3-chloro-4-methylphenyl)-5-(3,5-dichlorophenyl)-5-trifluoromethyl-4,5-dihydro-isoxazole in 100 mL of 1,2-dichloroethane, 6.6 g of N-bromosuccinimide and 0.1 g of α,α'-azobisisobutyronitrile were added, and stirred at 70° C. for 3 hours. After the completion of the reaction, the reaction mixture was left and cooled to room temperature, washed with water (70 mL×2), and dehydrated with and dried over saturated sodium chloride aqueous solution and anhydrous sodium sulfate in that order, and then the solvent was distilled off under reduced pressure. The residual solid was washed with diisopropyl ether to obtain 12.1 g of the aimed product as pale yellow crystal.

Melting point: 94.0 to 97.0° C.

$^1$H NMR (CDCl$_3$, Me$_4$Si, 300 MHz) δ7.68 (d, J=1.8 Hz, 1H), 7.58 (dd, J=8.1, 1.8 Hz, 1H), 7.45-7.55 (m, 3H), 7.43 (t, J=1.8 Hz, 1H), 4.58 (s, 2H), 4.06 (d, J=17.4 Hz, 1H), 3.67 (d, J=17.4 Hz, 1H).

Step 4: Production of 2-chloro-4-[5-(3,5-dichlorophenyl)-5-trifluoromethyl-4,5-dihydro-isoxazol-3-yl]benzyl=acetate In a suspension of 7.9 g of 3-(4-bromomethyl-3-chlorophenyl)-5-(3,5-dichlorophenyl)-5-trifluoromethyl-4,5-dihydro-isoxazole in 40 mL of acetic acid, 3.8 g of potassium acetate was added, and stirred at 120° C. for 2 hours. After the completion of the reaction, the reaction mixture was left and cooled to room temperature, diluted with 100 mL of chloroform, washed with water (50 mL×2) and saturated sodium hydrogen carbonate aqueous solution (50 mL×4), and then dehydrated with and dried over saturated sodium chloride aqueous solution and anhydrous sodium sulfate in that order, and then the solvent was distilled off under reduced pressure. The residue was purified with silica gel chromatography that was eluted with ethyl acetate-hexane (1:6) to obtain 6.4 g of the aimed product as colorless oily substance.

$^1$H NMR (CDCl$_3$, Me$_4$Si, 300 MHz) δ7.68 (d, J=1.8 Hz, 1H), 7.58 (d, J=8.1, 1.8 Hz, 1H), 7.45-7.55 (m, 3H), 7.43 (t, J=1.8 Hz, 1H), 5.22 (s, 2H), 4.06 (d, J=17.4 Hz, 1H), 3.68 (d, J=17.4 Hz, 1H), 2.15 (s, 3H).

Step 5: Production of 3-[3-chloro-4-(hydroxymethyl)phenyl]-5-(3,5-dichlorophenyl)-5-trifluoromethyl-4,5-dihydroisoxazole In a solution of 6.4 g of 2-chloro-4-[5-(3,5-dichlorophenyl)-5-trifluoromethyl-4,5-dihydroisoxazol-3-yl]benzyl=acetate in 20 mL of ethanol and 40 mL of water, 1.4 g of sodium hydroxide was added, and stirred at 100° C. for 1 hour. After the completion of the reaction, the reaction mixture was left and cooled to room temperature, diluted with 80 mL of ethyl acetate, washed with water (40 mL×2), and the organic phase was dehydrated with and dried over saturated sodium chloride aqueous solution and anhydrous magnesium sulfate in that order, and then the solvent was distilled off under reduced pressure to obtain 4.5 g of the aimed product as yellow crystal.

Melting point: 32.0 to 35.0° C.

$^1$H NMR (CDCl$_3$, Me$_4$Si, 300 MHz) δ7.68 (d, J=1.8 Hz, 1H), 7.55-7.65 (m, 2H), 7.50 (d, J=1.8 Hz, 2H), 7.43 (t, J=1.8 Hz, 1H), 4.81 (s, 2H), 4.06 (d, J=17.4 Hz, 1H), 3.67 (d, J=17.4 Hz, 1H).

Step 6: Production of 2-chloro-4-[5-(3,5-dichlorophenyl)-5-trifluoromethyl-4,5-dihydro-isoxazol-3-yl]benzaldehyde In a solution of 2.0 g of 3-[3-chloro-4-(hydroxymethyl)phenyl]-5-(3,5-dichlorophenyl)-5-trifluoromethyl-4,5-dihydroisoxazole in 60 mL of dichloromethane, 4.0 g of silica gel and 1.3 g of pyridinium chlorochromate were added, and stirred at room temperature for 20 hours. After the completion of the reaction, the reaction mixture was filtered through glass filter in which silica gel was packed to separate a solid with a solvent. The solvent was distilled off under reduced pressure. The residual solid was washed with diisopropyl ether to obtain 1.45 g of the aimed product as pale yellow crystal.

Melting point: 129.0 to 130.0° C.

$^1$H NMR (CDCl$_3$, Me$_4$Si, 300 MHz) δ10.48 (s, 1H), 7.98 (d, J=7.8 Hz, 1H), 7.77 (s, 1H), 7.68 (d, J=7.8 Hz, 1H), 7.50 (s, 2H), 7.44 (s, 1H), 4.06 (d, J=17.4 Hz, 1H), 3.67 (d, J=17.4 Hz, 1H).

Step 7: Production of 3-[3-chloro-4-(1-hydroxyethyl)phenyl]-5-(3,5-dichlorophenyl)-5-trifluoromethyl-4,5-dihydroisoxazole In a solution of 1.4 g of 2-chloro-4-[5-(3,5-dichlorophenyl)-5-trifluoromethyl-4,5-dihydro-isoxazol-3-yl]benzaldehyde in 50 mL of diethyl ether under nitrogen atmosphere, 6.6 mL of a solution (0.87 mol/L) of methyl magnesium bromide in tetrahydrofuran was added dropwise with stirring at room temperature. After the completion of the addition dropwise, the mixture was continued to stir under reflux with heating further for 30 minutes. After the completion of the reaction, 5 mL of ammonium chloride aqueous solution was added in the reaction mixture under cooling with ice and with stirring, the mixture was extracted with ethyl acetate (50 mL×1), the organic phase was washed with water (30 mL×2), and dehydrated with and dried over saturated sodium chloride aqueous solution and anhydrous magnesium sulfate in that order, and then the solvent was distilled off under reduced pressure to obtain 1.5 g of the aimed product as pale yellow resinous substance.

$^1$H NMR (CDCl$_3$, Me$_4$Si, 300 MHz) δ7.55-7.75 (m, 3H), 7.50 (d, J=1.5 Hz, 2H), 7.43 (t, J=1.5 Hz, 1H), 5.29 (q, J=6.3 Hz, 1H), 4.06 (d, J=17.4 Hz, 1H), 3.67 (d, J=17.4 Hz, 1H), 1.48 (d, J=6.3 Hz, 3H).

Step 8: Production of 3-[3-chloro-4-(1-chloroethyl)phenyl]-5-(3,5-dichlorophenyl)-5-trifluoromethyl-4,5-dihydroisoxazole In a solution of 0.96 g of 3-[3-chloro-4-(1-hydroxyethyl)phenyl]-5-(3,5-dichlorophenyl)-5-trifluoromethyl-4,5-dihydroisoxazole in 20 mL of dichloromethane, 0.2 mL of thionyl chloride and a catalytic amount (2 to 3 drops) of N,N-dimethylformamide were added, and stirred at room temperature for 1 hour. After the completion of the reaction, the reaction mixture was poured into 20 mL of ice water, and the organic phase was collected, washed with water (20 mL×1) and then saturated sodium hydrogen carbonate aqueous solution (20 mL×3), and dehydrated with and dried over saturated sodium chloride aqueous solution and anhydrous sodium sulfate in that order, and then the solvent was distilled off under reduced pressure to obtain 0.88 g of the aimed product as yellow oily substance.

$^1$H NMR (CDCl$_3$, Me$_4$Si, 300 MHz) δ7.55-7.75 (m, 3H), 7.50 (s, 2H), 7.43 (s, 1H), 5.52 (q, J=6.3 Hz, 1H), 4.06 (d, J=17.4 Hz, 1H), 3.67 (d, J=17.4 Hz, 1H), 1.82 (d, J=6.3 Hz, 3H).

Step 9: Production of N-[1-[2-chloro-4-[5-(3,5-dichlorophenyl)-5-trifluoromethyl-4,5-dihydroisoxazol-3-yl]phenyl]ethyl]phthalimide In a solution of 0.88 g of 3-[3-chloro-4-(1-chloroethyl)phenyl]-5-(3,5-dichlorophenyl)-5-trifluoromethyl-4,5-dihydroisoxazole in 5 mL of N,N-dimethylformamide, 0.36 g of potassium phthalimide was added, and stirred at 100° C. for 1.5 hour. After the completion of the reaction, the reaction mixture was left and cooled to room temperature, and diluted with 20 mL of ethyl acetate, washed with water (10 mL×3), and then dehydrated with and dried over saturated sodium chloride aqueous solution and anhydrous magnesium sulfate in that order, and the solvent was distilled off under reduced pressure. The residue was purified with medium pressure preparative liquid chromatography (medium pressure collection apparatus: YFLC-Wprep manufactured by Yamazen Corporation) that was eluted with ethyl acetate-hexane (gradient of 1:10 to 1:3) to obtain 0.45 g of the aimed product as pale yellow resinous substance.

$^1$H NMR (CDCl$_3$, Me$_4$Si, 300 MHz) δ7.75-7.9 (m, 3H), 7.55-7.75 (m, 4H), 7.49 (d, J=1.5 Hz, 2H), 7.42 (d, J=1.5 Hz, 1H), 5.83 (q, J=7.2 Hz, 1H), 4.03 (d, J=17.4 Hz, 1H), 3.65 (d, J=17.4 Hz, 1H), 1.86 (d, J=7.2 Hz, 3H).

Step 10: Production of 3-[3-chloro-4-(1-aminoethyl)phenyl]-5-(3,5-dichlorophenyl)-5-trifluoromethyl-4,5-dihydroisoxazole (Compound of the present invention No. 9-016)

In a solution of 0.40 g of N-[1-[2-chloro-4-[5-(3,5-dichlorophenyl)-5-trifluoromethyl-4,5-dihydroisoxazol-3-yl]phenyl]ethyl]phthalimide in 10 mL of ethanol, 1.0 mL of 80% hydrazine monohydrate aqueous solution was added, and stirred under reflux with heating for 1 hour. After the completion of the reaction, the reaction mixture was left and cooled to room temperature, 20 mL of chloroform was added therein and insoluble substance was filtered off, and the solvent was distilled off under reduced pressure. The procedure comprising adding 20 mL of chloroform in the residue, filtering off insoluble material and distilling off the solvent under reduced pressure was repeated twice to obtain 0.26 g of the aimed product as yellow resinous substance.

$^1$H NMR (CDCl$_3$, Me$_4$Si, 300 MHz) δ7.5-7.7 (m, 3H), 7.51 (d, J=1.5 Hz, 2H), 7.43 (t, J=1.5 Hz, 1H), 4.56 (q, J=6.6 Hz, 1H), 4.06 (d, J=17.4 Hz, 1H), 3.67 (d, J=17.4 Hz, 1H), 1.37 (d, J=6.6 Hz, 3H).

Step 11: Production of N-[1-[2-chloro-4-[5-(3,5-dichlorophenyl)-5-trifluoromethyl-4,5-dihydroisoxazol-3-yl]phenyl]ethyl]cyclopropanecarboxamide In a solution of 0.22 g of 3-[3-chloro-4-(1-aminoethyl)phenyl]-5-(3,5-dichlorophenyl)-5-trifluoromethyl-4,5-dihydroisoxazole and 0.07 g of triethyl amine in 1.5 mL of chloroform, 0.08 g of cyclopropanecarbonyl=chloride was added dropwise under cooling with ice and with stirring, and after the completion of the addition dropwise, it was continued to stir at room temperature further for 20 minutes. After the completion of the reaction, 1 mL of water was added in the reaction mixture, and the organic phase was collected, and as such purified with medium pressure preparative liquid chromatography (medium pressure collection apparatus: YFLC-Wprep manufactured by Yamazen Corporation) that was eluted with ethyl acetate-hexane (gradient of 1:8 to 1:1) to obtain 0.14 g of the aimed product as colorless resinous substance.

$^1$H NMR (CDCl$_3$, Me$_4$Si, 300 MHz) δ7.5-7.65 (m, 2H), 7.49 (d, J=1.5 Hz, 2H), 7.43 (t, J=1.5 Hz, 1H), 7.39 (d, J=8.1 Hz, 1H), 6.12 (d, J=6.6 Hz, 1H), 5.3-5.45 (m, 1H), 4.04 (d, J=17.4 Hz, 1H), 3.65 (d, J=17.4 Hz, 1H), 1.48 (d, J=6.9 Hz, 3H), 1.35-1.45 (m, 1H), 0.70-1.05 (m, 4H).

Synthetic Example 7

N-[2-Chloro-4-[5-(3,5-dichlorophenyl)-5-trifluoromethyl-4,5-dihydroisoxazol-3-yl]phenyl(cyano)methyl]cyclopropanecarboxamide (Compound of the present invention No. 2-042)

Step 1: Production of amino[2-chloro-4-[5-(3,5-dichlorophenyl)-5-trifluoromethyl-4,5-dihydroisoxazol-3-yl]phenyl]acetonitrile (Compound of the present invention No. 9-017)

In a solution of 0.18 g of sodium cyanide and 0.29 g of ammonium chloride in 5 mL of 28% ammonia water, a solution of 1.0 g of 2-chloro-4-[5-(3,5-dichlorophenyl)-5-trifluoromethyl-4,5-dihydro-isoxazol-3-yl]benzaldehyde synthesized in Step 6 of Synthetic Example 6 in 30 mL of methanol was added, and stirred at 60° C. for 2 hours. After the completion of the reaction, the reaction mixture was left and cooled to room temperature, diluted with 60 mL of ethyl acetate, washed with water (30 mL×2), and the organic phase was dehydrated with and dried over saturated sodium chloride aqueous solution and anhydrous magnesium sulfate in that order, and the solvent was distilled off under reduced pressure to obtain 1.10 g of the aimed product as pale brown resinous substance.

$^1$H NMR (CDCl$_3$, Me$_4$Si, 300 MHz) δ7.7-7.8 (m, 3H), 7.50 (s, 2H), 7.44 (t, J=1.5 Hz, 1H), 5.25 (t, J=7.8 Hz, 1H), 4.06 (d, J=17.4 Hz, 1H), 3.69 (d, J=17.4 Hz, 1H).

Step 2: Production of N-[2-chloro-4-[5-(3,5-dichlorophenyl)-5-trifluoromethyl-4,5-dihydroisoxazol-3-yl]phenyl(cyano)methyl]cyclopropanecarboxamide In a solution of 0.20 g of amino[2-chloro-4-[5-(3,5-dichlorophenyl)-5-trifluoromethyl-4,5-dihydroisoxazol-3-yl]phenyl]acetonitrile and 0.06 g of triethyl amine in 1.5 mL of chloroform, 0.06 g of cyclopropanecarbonyl=chloride was added dropwise under cooling with ice and with stirring, and after the completion of the addition dropwise, it was continued to stir at room temperature further for 30 minutes. After the completion of the reaction, 1 mL of water was added in the reaction mixture, and the organic phase was collected, and as such purified with medium pressure preparative liquid chromatography (medium pressure collection apparatus: YFLC-Wprep manufactured by Yamazen Corporation) that was eluted with ethyl acetate-hexane (gradient of 1:8 to 1:1) to obtain 0.14 g of the aimed product as colorless resinous substance.

$^1$H NMR (CDCl$_3$, Me$_4$Si, 300 MHz) δ7.75-7.8 (m, 1H), 7.72 (d, J=8.1 Hz, 1H), 7.6-7.65 (m, 1H), 7.50 (d, J=1.5 Hz, 2H), 7.44 (t, 1.5 Hz, 1H), 6.52 (d, J=8.1 Hz, 1H), 6.30 (d, J=7.2 Hz, 1H), 4.07 (d, J=17.4 Hz, 1H), 3.67 (d, J=17.4 Hz, 1H), 1.35-1.5 (m, 1H), 0.80-1.15 (m, 4H).

Synthetic Example 8

N-[1-[2-Chloro-4-[5-(3,5-dichlorophenyl)-5-trifluoromethyl-4,5-dihydroisoxazol-3-yl]phenyl]-2,2,2-trifluoroethyl]isobutyramide (Compound of the present invention No. 2-026)

Step 1: Production of N-[1-(4-bromophenyl)-2,2,2-trifluoroethyl]isobutyramide

In 20 mL of a suspension of 1.10 g of 1-(4-bromophenyl)-2,2,2-trifluoroethyl amine hydrochloride and 0.79 g of triethyl amine in chloroform, 0.43 g of isobutyryl=chloride was added under cooling with ice and with stirring, and stirred at room temperature for 1 hour. After the completion of the reaction, the reaction mixture was washed with 20 mL of water, then with 20 mL of saturated sodium hydrogen carbonate aqueous solution, and the organic phase was dehydrated with and dried over saturated sodium chloride aqueous solution and anhydrous magnesium sulfate in that order, and the solvent was distilled off under reduced pressure to obtain 1.30 g of the aimed product as white crystal.

Melting point 176.0 to 178.0° C.

$^1$H NMR (CDCl$_3$, Me$_4$Si, 300 MHz) δ7.53 (d, J=8.1 Hz, 2H), 7.25 (d, J=8.1 Hz, 2H), 6.20 (d, J=9.0 Hz, 1H), 5.6-5.75 (m, 1H), 2.4-2.5 (m, 1H), 1.15 and 1.20 (d, J=6.6 Hz, 6H).

Step 2: Production of N-[2,2,2-trifluoro-1-(4-formylphenyl)ethyl]isobutyramide In a solution of 0.51 g of N-[1-(4-bromophenyl)-2,2,2-trifluoroethyl]isobutyramide and 0.16 g of sodium formate in 10 mL of N,N-dimethylformamide, 0.065 g of dichlorobis(triphenylphosphine) palladium(II) was added, and stirred under carbon monoxide atmosphere of 1.5 MPa at 120° C. for 1.5 hour. After the completion of the reaction, the reaction mixture was left and cooled to room temperature, diluted with 50 mL of ethyl acetate, washed with water (50 mL×2), and the organic phase was dehydrated with and dried over saturated sodium chloride aqueous solution and anhydrous magnesium sulfate in that order, and the solvent was distilled off under reduced pressure. The residue was purified with medium pressure preparative liquid chromatography (medium pressure collection apparatus: YFLC-Wprep manufactured by Yamazen Corporation) that was eluted with ethyl acetate-hexane (gradient of 1:3 to 1:1) to obtain 0.18 g of the aimed product as white crystal.

Melting point: 132.0 to 133.0° C.

$^1$H NMR (CDCl$_3$, Me$_4$Si, 300 MHz) δ10.04 (s, 1H), 7.93 (d, J=7.8 Hz, 2H), 7.70 (d, J=7.8 Hz, 2H), 6.15 (d, J=9.0 Hz, 1H), 5.75-5.9 (m, 1H), 2.4-2.55 (m, 1H), 1.17 and 1.22 (d, J=6.9 Hz, 6H).

Step 3: Production of N-[2,2,2-trifluoro-1-(4-hydroxyiminomethylphenyl)ethyl]isobutyramide In a solution of 0.16 g of N-[2,2,2-trifluoro-1-(4-formylphenyl)ethyl]isobutyramide in 4.0 mL of methanol and 1.0 mL of water, 0.075 g of hydroxylamine hydrochloride was added, and stirred at room temperature for 1.5 hour. After the completion of the reaction, the reaction mixture was diluted with 20 mL of ethyl acetate, washed with water (10 mL×1), and the organic phase was dehydrated with and dried over saturated sodium chloride aqueous solution and anhydrous magnesium sulfate in that order, and the solvent was distilled off under reduced pressure to obtain 0.20 g of the aimed product as white crystal.

Melting point 169.0 to 171.0° C.

$^1$H NMR (CDCl$_3$-DMSO-d$_6$, Me$_4$Si, 300 MHz) δ10.23 (s, 1H), 8.11 (s, 1H), 7.60 (d, J=8.1 Hz, 2H), 7.43 (d, J=8.1 Hz, 2H), 7.1-7.3 (m, 1H), 5.65-5.85 (m, 1H), 2.45-2.6 (m, 1H), 1.12 and 1.19 (d, J=6.9 Hz, 6H).

Step 4: Production of N-[1-[2-chloro-4-[5-(3,5-dichlorophenyl)-5-trifluoromethyl-4,5-dihydroisoxazol-3-yl]phenyl]-2,2,2-trifluoroethyl]isobutyramide In a solution of 0.14 g of N-[2,2,2-trifluoro-1-(4-hydroxyiminomethylphenyl)ethyl]isobutyramide in 10 mL of 1,2-dimethoxyethane, 0.086 g of N-chlorosuccinimide was added, and stirred at 80° C. for 1 hour. Then, the reaction mixture was left and cooled to room temperature, and 0.14 g of 3,5-dichloro-1-(1-trifluoromethylethenyl)benzene synthesized in Step 1 of Synthetic Example 1, 0.074 g of potassium hydrogen carbonate and 3 drops of water were added and continued to stir at room temperature further for 1.5 hour. After the completion of the reaction, the reaction mixture was diluted with 30 mL of ethyl acetate, washed with water (10 mL×1), and the organic phase was dehydrated with and dried over saturated sodium chloride aqueous solution and anhydrous sodium sulfate in that order, and the solvent was distilled off under reduced pressure. The residue was purified with medium pressure preparative liquid chromatography (medium pressure collection apparatus: YFLC-Wprep manufactured by Yamazen Corporation) that was eluted with ethyl acetate-hexane (gradient of 1:3 to 1:1) to obtain 0.044 g of the aimed product as colorless resinous substance.

$^1$H NMR (CDCl$_3$, Me$_4$Si, 300 MHz) δ7.69 (d, J=8.1 Hz, 2H), 7.4-7.55 (m, 5H), 6.32 (d, J=9.3 Hz, 1H), 5.75-5.85 (m, 1H), 4.08 (d, J=17.4 Hz, 1H), 3.70 (d, J=17.4 Hz, 1H), 2.4-2.55 (m, 1H), 1.15 and 1.20 (d, J=6.9 Hz, 6H).

Synthetic Example 9

N-[4-[5-(3,5-Dichlorophenyl)-5-trifluoromethyl-4,5-dihydroisoxazol-3-yl]phenyl(phenyl)methyl]cyclopropanecarboxamide (Compound of the present invention No. 2-060)

In a solution of 0.80 g of 4-[5-(3,5-dichlorophenyl)-5-trifluoromethyl-4,5-dihydroisoxazol-3-yl]benzonitrile in 10 mL of tetrahydrofuran under nitrogen atmosphere, 1.0 mL of 32% tetrahydrofuran solution of phenyl magnesium bromide was added dropwise with stirring at room temperature, after the completion of the addition dropwise, it was continued to stir at room temperature further for 3.5 hours. After the completion of the reaction, the solvent was distilled off under reduced pressure, the residue was dissolved in 10 mL of methanol, 0.075 g of sodium boron hydride was added, and stirred at room temperature for 2 hours. The reaction mixture was diluted with 20 mL of ethyl acetate, washed with water (10 mL×2), and the organic phase was dehydrated with and dried over saturated sodium chloride aqueous solution and anhydrous magnesium sulfate in that order, and the solvent was distilled off under reduced pressure. The residue was dissolved in 20 mL of chloroform, and under cooling with ice and with stirring, 0.20 g of triethyl amine and 0.21 g of cyclopropanecarbonyl=chloride were added dropwise, after the completion of the addition dropwise, it was continued to stir at room temperature further for 1 hour. After the completion of the reaction, the reaction mixture was washed with water (10 mL×1), and the organic phase was dehydrated with and dried over saturated sodium chloride aqueous solution and anhydrous magnesium sulfate in that order, and the solvent was distilled off under reduced pressure. The residue was purified with medium pressure preparative liquid chromatography (medium pressure collection apparatus: YFLC-Wprep manufactured by Yamazen Corporation) that was eluted with ethyl acetate-hexane (gradient of 1:9 to 1:2) to obtain 0.16 g of the aimed products as colorless resinous substance.

$^1$H NMR (CDCl$_3$, Me$_4$Si, 300 MHz) δ7.62 (d, J=8.1 Hz, 2H), 7.50 (s, 2H), 7.42 (t, J=1.5 Hz, 1H), 7.25-7.4 (m, 5H), 7.15-7.25 (m, 2H), 6.15-6.3 (m, 2H), 4.06 (d, J=17.4 Hz, 1H), 3.67 (d, J=17.4 Hz, 1H), 1.35-1.5 (m, 1H), 0.95-1.05 (m, 2H), 0.75-0.85 (m, 2H).

Synthetic Example 10

N-[3-Chloro-5-[5-(3,5-dichlorophenyl)-5-trifluoromethyl-4,5-dihydroisoxazol-3-yl]pyridin-2-yl]cyclopropanecarboxamide (Compound of the present invention No. 3-002)

Step 1: Production of 5-(3,5-dichlorophenyl)-3-(5,6-dichloro-3-pyridyl)-5-trifluoromethyl-4,5-dihydroisoxazole In a solution of 2.1 g of 5,6-dichloronicotine aldehyde oxime in 30 mL of 1,2-dimethoxyethane, 2.3 g of N-chlorosuccinimide was added, and stirred at 70° C. for 4 hours. Then, the reaction mixture was left and cooled to room temperature, 2.5 g of 3,5-dichloro-1-(1-trifluoromethylethenyl)benzene synthesized in Step 1 of Synthetic Example 1, 1.4 g of potassium hydrogen carbonate and 2.0 mL of water were added and continued to stir at room temperature further for 20 hours. After the completion of the reaction, the reaction mixture was diluted with 70 mL of ethyl acetate, washed with water (50 mL×1), and the organic was dehydrated with and dried over saturated sodium chloride aqueous solution and anhydrous sodium sulfate in that order, and the solvent was distilled off under reduced pressure. The residue was purified with medium pressure preparative liquid chromatography (medium pressure collection apparatus: YFLC-Wprep manufactured by Yamazen Corporation) that was eluted with ethyl acetate-hexane (gradient of 1:10 to 1:5) to obtain 1.7 g of the aimed products as white crystal.

Melting point: 155.0-157.0° C.
$^1$H NMR (CDCl$_3$, Me$_4$Si, 300 MHz) δ8.48 (d, J=1.8 Hz, 1H), 8.16 (d, J=1.8 Hz, 1H), 7.49 (s, 2H), 7.45 (t, J=1.5 Hz, 1H), 4.07 (d, J=17.4 Hz, 1H), 3.69 (d, J=17.4 Hz, 1H).

Step 2: Production of 3-(5-chloro-6-cyano-3-pyridyl)-5-(3,5-dichlorophenyl)-5-trifluoromethyl-4,5-dihydroisoxazole In a solution of 1.40 g of 5-(3,5-dichlorophenyl)-3-(5,6-dichloro-3-pyridyl)-5-trifluoromethyl-4,5-dihydroisoxazole in 30 mL of N,N-dimethylacetamide, 0.075 g of zinc cyanide and 0.37 g of tetrakis(triphenylphosphine) palladium(0) were added, and stirred at 80° C. to 120° C. for 4.5 hours under nitrogen atmosphere. After the completion of the reaction, the reaction mixture was left and cooled to room temperature, 5 mL of ammonia water and 50 mL of water were added, and extracted with ethyl acetate (50 mL×1). The organic phase were dehydrated with and dried over saturated sodium chloride aqueous solution and anhydrous magnesium sulfate in that order, and the solvent was distilled off under reduced pressure. The residue was purified with medium pressure preparative liquid chromatography (medium pressure collection apparatus: YFLC-Wprep manufactured by Yamazen Corporation) that was eluted with ethyl acetate-hexane (gradient of 1:8 to 1:3) to obtain 1.20 g of the aimed products as yellow resinous substance.

$^1$H NMR (CDCl$_3$, Me$_4$Si, 400 MHz) δ8.83 (d, J=1.8 Hz, 1H), 8.19 (d, J=1.8 Hz, 1H), 7.48 (s, 2H), 7.45-7.5 (m, 1H), 4.09 (t, J=17.4 Hz, 1H), 3.72 (d, J=17.4 Hz, 1H).

Step 3: Production of 3-(6-aminomethyl-5-chloro-3-pyridyl)-5-(3,5-dichlorophenyl)-5-trifluoromethyl-4,5-dihydroisoxazole (Compound of the present invention No. 10-001)

In a solution of 0.32 g of 3-(5-chloro-6-cyano-3-pyridyl)-5-(3,5-dichlorophenyl)-5-trifluoromethyl-4,5-dihydro-isoxazole in 12 mL of methanol, 0.5 mL of concentrated hydrochloric acid and 0.10 g of 5% palladium carbon were added, and stirred at room temperature under hydrogen atmosphere of normal pressure for 2.5 hours. After the completion of the reaction, the reaction mixture was filtered through Celite, and the solvent was distilled off under reduced pressure to obtain 0.30 g of the aimed product as brown resinous substance.

$^1$H NMR (CDCl$_3$-DMSO-d$_6$, Me$_4$Si, 300 MHz) δ8.89 (s, 1H), 8.59 (bs, 2H), 8.32 (s, 1H), 7.83 (s, 1H), 7.60 (s, 2H), 4.53 (d, J=18.6 Hz, 1H), 4.3-4.45 (m, 3H).

Step 4: Production of N-[3-chloro-5-[5-(3,5-dichlorophenyl)-5-trifluoromethyl-4,5-dihydroisoxazol-3-yl]pyridin-2-yl methyl]cyclopropanecarboxamide In a solution of 0.10 g of 3-(6-aminomethyl-5-chloro-3-pyridyl)-5-(3,5-dichlorophenyl)-5-trifluoromethyl-4,5-dihydroisoxazole and 0.03 g of triethyl amine in 2.0 mL of chloroform, 0.03 g of cyclopropanecarbonyl=chloride was added dropwise under cooling with ice and with stirring, after the completion of the addition dropwise, it was continued to stir at room temperature further for 1 hour. After the completion of the reaction, the reaction mixture was washed with 5 mL of saturated sodium hydrogen carbonate aqueous solution and then with 5 mL of water, and the organic phase was dehydrated with and dried over saturated sodium chloride aqueous solution and anhydrous magnesium sulfate in that order, and the solvent was distilled off under reduced pressure. The residue was purified with medium pressure preparative liquid chromatography (medium pressure collection apparatus: YFLC-Wprep manufactured by Yamazen Corporation) that was eluted with ethyl acetate-hexane (gradient of 1:5 to 1:1) to obtain 0.071 g of the aimed products as yellow resinous substance.

$^1$H NMR (CDCl$_3$, Me$_4$Si, 300 MHz) δ8.68 (d, J=1.8 Hz, 1H), 8.04 (d, J=1.8 Hz, 1H), 7.50 (s, 2H), 7.45 (t, J=1.5 Hz, 1H), 7.12 (bs, 1H), 4.71 (d, J=4.8 Hz, 2H), 4.08 (d, J=17.4 Hz, 1H), 3.70 (d, J=17.4 Hz, 1H), 1.5-1.65 (m, 1H), 1.0-1.1 (m, 2H), 0.75-0.85 (m, 2H).

Synthetic Example 11

N-[2-Chloro-4-[5-(3,5-bis(trifluoromethyl)phenyl)-5-trifluoromethyl-4,5-dihydroisoxazol-3-yl]phenylmethyl]cyclopropanecarboxamide (Compound of the present invention No. 2-081)

Step 1: Production of N-[(2-chloro-4-iodophenyl)methyl]phthalimide

In a solution of 7.6 g of 1-bromomethyl-2-chloro-4-iodobenzene in 50 mL of N,N-dimethylformamide, 3.7 g of potassium phthalimide was added, and stirred at room temperature for 1 hour. After the completion of the reaction, the reaction mixture was diluted with 80 mL of ethyl acetate, washed with water (30 mL×2), and then dehydrated with and dried over saturated sodium chloride aqueous solution and anhydrous sodium sulfate in that order, and the solvent was distilled off under reduced pressure to obtain 5.7 g of the aimed product as white crystal.

Melting point: 140.0-142.0° C.
$^1$H NMR (CDCl$_3$, Me$_4$Si, 300 MHz) δ7.85-7.9 (m, 2H), 7.7-7.8 (m, 3H), 7.51 (dd, J=8.1, 1.5 Hz, 1H), 6.95 (d, J=8.1 Hz, 1H), 4.92 (s, 2H).

Step 2: Production of 2-chloro-4-iodobenzylamine

In a solution of 2.9 g of N-[(2-chloro-4-iodophenyl)methyl]phthalimide in 60 mL of ethanol, 3.0 mL of 80% hydrazine monohydrate aqueous solution was added, and stirred at 70° C. for 30 minutes. After the completion of the reaction, the reaction mixture was left and cooled to room temperature, 100 mL of chloroform was added therein and insoluble substance was filtered off, and the solvent was distilled off under reduced pressure. The procedure comprising adding 30 mL of chloroform in the residue, filtering off insoluble material and distilling off the solvent under reduced pressure was repeated twice to obtain 2.8 g of the aimed product as yellow oily substance.

$^1$H NMR (CDCl$_3$, Me$_4$Si, 300 MHz) δ7.70 (d, J=1.5 Hz, 1H), 7.58 (t, J=8.1 Hz, 1H), 7.13 (d, J=8.1 Hz, 1H), 3.89 (s, 2H).

Step 3: Production of N-[(2-chloro-4-iodophenyl)methyl]cyclopropanecarboxamide

In 25 mL of a suspension of 2.80 g of 2-chloro-4-iodobenzylamine and 0.76 g of triethyl amine in chloroform, 0.77 g of cyclopropanecarbonyl=chloride was added under cooling with ice and with stirring, and stirred at room temperature for 1 hour. After the completion of the reaction, the reaction mixture was washed with 20 mL of saturated sodium hydrogen carbonate aqueous solution and then with 20 mL of water, and the organic phase was dehydrated with and dried over saturated sodium chloride aqueous solution and anhydrous sodium sulfate in that order, and the solvent was distilled off under reduced pressure to obtain 2.20 g of the aimed product as white crystal.

Melting point 158.0 to 160.0° C.

$^1$H NMR (CDCl$_3$, Me$_4$Si, 300 MHz) δ7.72 (d, J=1.5 Hz, 1H), 7.55 (d, J=8.1 Hz, 1H), 7.13 (d, J=8.1 Hz, 1H), 6.05 (bs, 1H), 4.47 (d, J=6.0 Hz, 2H), 1.3-1.4 (m, 1H), 0.95-1.05 (m, 2H), 0.7-0.8 (m, 2H).

Step 4: Production of N-[(2-chloro-4-formylphenyl)methyl]cyclopropanecarboxamide In a solution of 2.20 g of N-[(2-chloro-4-iodophenyl)methyl]cyclopropanecarboxamide and 0.57 g of sodium formate in 20 mL of N,N-dimethylformamide in an autoclave, 0.26 g of dichlorobis(triphenylphosphine) palladium (II) was added, and stirred under carbon monoxide atmosphere of 1.5 MPa at 90° C. for 1 hour. After the completion of the reaction, the reaction mixture was left and cooled to room temperature, and diluted with 60 mL of ethyl acetate and washed with water (30 mL×2). The organic phase was dehydrated with and dried over saturated sodium chloride aqueous solution and anhydrous magnesium sulfate in that order, the solvent was distilled off under reduced pressure. The residue was purified with silica gel column chromatography that was eluted with ethyl acetate to obtain 1.20 g of the aimed product as white crystal.

Melting point: 143.0 to 145.0° C.

$^1$H NMR (CDCl$_3$, Me$_4$Si, 300 MHz) δ9.96 (s, 1H), 7.88 (d, J=1.5 Hz, 1H), 7.74 (dd, J=8.1, 1.5 Hz, 1H), 7.57 (d, J=8.1 Hz, 1H), 6.13 (bs, 1H), 4.50 (d, J=6.3 Hz, 2H), 1.35-1.45 (m, 1H), 0.95-1.05 (m, 2H), 0.75-0.85 (m, 2H).

Step 5: Production of N-[(2-chloro-4-hydroxyiminomethylphenyl)methyl]cyclopropanecarboxamide In a solution of 1.20 g of N-[(2-chloro-4-formylphenyl)methyl]cyclopropanecarboxamide in 40 mL of methanol and 10 mL of water, 0.50 g of hydroxylamine hydrochloride was added, and stirred at room temperature for 1 hour. After the completion of the reaction, the reaction mixture was diluted with 50 mL of ethyl acetate, washed with water (30 mL×1), and the organic phase was dehydrated with and dried over saturated sodium chloride aqueous solution and anhydrous magnesium sulfate in that order, and the solvent was distilled off under reduced pressure to obtain 0.95 g of the aimed product as white crystal. Melting point 163.0 to 166.0° C.

$^1$H NMR (CDCl$_3$-DMSO-d$_6$, Me$_4$Si, 300 MHz) δ11.40 (s, 1H), 8.60 (t, J=5.7 Hz, 1H), 8.11 (s, 1H), 7.62 (s, 1H), 7.55 (d, J=8.1 Hz, 1H), 7.33 (d, J=8.1 Hz, 1H), 4.32 (d, J=5.7 Hz, 2H), 1.6-1.7 (m, 1H), 0.65-0.7 (m, 4H).

Step 6: Production of N-[(2-chloro-4-chlorohydroxyiminomethylphenyl)methyl]cyclopropanecarboxamide In a solution of 0.45 g of N-[(2-chloro-4-hydroxyiminomethylphenyl)methyl]cyclopropanecarboxamide in 20 mL of 1,2-dimethoxyethane, 0.29 g of N-chlorosuccinimide was added, and stirred at 70° C. for 1.5 hour. After the completion of the reaction, the reaction mixture was diluted with 50 mL of ethyl acetate, washed with water (10 mL×1), and the organic phase was dehydrated with and dried over saturated sodium chloride aqueous solution and anhydrous magnesium sulfate in that order, and the solvent was distilled off under reduced pressure to obtain 0.55 g of the aimed product as yellow resinous substance. The resulting product was used as such without purification for the next step.

Step 7: Production of N-[2-chloro-4-[5-[3,5-bis(trifluoromethyl)phenyl]-5-trifluoromethyl-4,5-dihydroisooxazol-3-yl]phenylmethyl)cyclopropanecarboxamide In a solution of 0.15 g of N-[(2-chloro-4-chlorohydroxyiminomethylphenyl)methyl]cyclopropanecarboxamide in 4.0 mL of 1,2-dimethoxyethane, 0.13 g of 3,5-bis(trifluoromethyl)-1-(1-trifluoromethylethenyl)benzene synthesized similarly to Step 1 of Synthetic Example 1, 0.080 g of potassium hydrogen carbonate and 3 drops of water were added, and stirred at room temperature for 15 hours. After the completion of the reaction, the reaction mixture was diluted with 5 mL of ethyl acetate, washed with water (2 mL×1), and the organic phase was dehydrated with and dried over saturated sodium chloride aqueous solution and anhydrous magnesium sulfate in that order, and the solvent was distilled off under reduced pressure. The residue was purified with medium pressure preparative liquid chromatography (medium pressure collection apparatus: YFLC-Wprep manufactured by Yamazen Corporation) that was eluted with ethyl acetate-hexane (gradient of 1:3 to 1:1) to obtain 0.037 g of the aimed products as colorless resinous substance.

$^1$H NMR (CDCl$_3$, Me$_4$Si, 300 MHz) δ8.07 (s, 2H), 7.97 (s, 1H), 7.70 (d, J=1.5 Hz, 1H), 7.53 (dd, J=8.1, 1.5 Hz, 1H), 7.47 (d, J=8.1 Hz, 1H), 6.10 (bs, 1H), 4.55 (d, J=6.3 Hz, 2H), 4.16 (d, J=17.4 Hz, 1H), 3.71 (d, J=17.4 Hz, 1H), 1.35-1.45 (m, 1H), 0.95-1.05 (m, 2H), 0.75-0.8 (m, 2H).

Synthetic Example 12

N-Butyryl-2-chloro-4-[5-(3,5-dibromo-4-fluorophenyl)-5-trifluoromethyl-4,5-dihydro-isoxazol-3-yl]benzylamine (Compound of the present invention No. 2-390)

Step 1: Preparation of 1-(3,5-dibromo-4-fluorophenyl)-2,2,2-trifluoroethanone

To a stirred solution of 1-(4-fluorophenyl)-2,2,2-trifluoroethanone (1.00 g) in glacial acetic acid (0.2 mL) and concentrated sulfuric acid (1.0 mL) at 0° C. was added 1,3-dibromo-5,5-dimethylhydantoin (1.79 g). After stirring at 45° C. for 3 hours, the reaction mixture was poured into ice-water (5 mL), neutralized with 2N aqueous sodium hydroxide solution, and then extracted with ethyl acetate (3 mL×2). The organic extracts were combined, washed with water and brine, dried over anhydrous sodium sulfate, and concentrated under reduced pressure to afford the title compound as a colorless oil (0.99 g).

$^1$H NMR (CDCl$_3$, Me$_4$Si, 300 MHz) δ 8.23 (dd, J=6.0, 0.9 Hz, 2H).

Step 2: Preparation of 1-(3-chloro-4-methylphenyl)-3-(3,5-dibromo-4-fluorophenyl)-4,4,4-trifluoro-3-hydroxy-butan-1-one To a stirred solution of 1-(3,5-dibromo-4-fluorophenyl)-2,2,2-trifluoroethanone (0.99 g) and 1-(3-chloro-4-methylphenyl)ethanone (0.48 g) in ethyl acetate (3 mL) was added dithylamine (0.062 g). The mixture was stirred at 50° C. for 2 hours. The reaction mixture was then concentrated under reduced pressure and the crude product was purified by liquid chromatography (medium pressure collection apparatus: Purif-α2 manufactured by Moritex Corporation) eluted with ethyl acetate-hexane (1:10) to afford the title compound as a pale yellow oil (1.40 g).

$^1$H NMR (CDCl$_3$, Me$_4$Si, 300 MHz) δ 7.90 (d, J=1.5 Hz, 1H), 7.75 (d, J=6.0 Hz, 2H), 7.72 (s, 1H), 7.39 (d, J=7.8 Hz, 1H), 5.76 (s, 1H), 3.80 (d, J=17.4 Hz, 1H), 3.69 (d, J=17.4 Hz, 1H), 2.47 (s, 3H).

Step 3: Preparation of 1-(3-chloro-4-methylphenyl)-3-(3,5-dibromo-4-fluorophenyl)-4,4,4-trifluoro-2-buten-1-one To a stirred solution of 1-(3-chloro-4-methylphenyl)-3-(3,5-dibromo-4-fluorophenyl)-4,4,4-trifluoro-3-hydroxy-butan-1-one (1.40 g) in toluene (3 mL) at 80° C. was added thionyl chloride (0.68 g) and pyridine (0.46 g). The mixture was stirred at same temperature for 2 hours. The resulting mixture was then cooled to 5° C. and water (3 mL) was added, and the mixture was allowed to stir and warm to ambient temperature. The layers were separated, and the organic phase was poured into 2N aqueous sodium hydroxide solution (3 mL). After stirring 0.5 hour at room temperature, the organic layer was separated, washed with brine, dried over anhydrous magnesium sulfate, and concentrated under reduced pressure to afford the crude title compound as a yellow oil (1.37 g), which was used in the next step without purification.

$^1$H NMR (CDCl$_3$, Me$_4$Si, 300 MHz) δ 7.55-7.8 (m, 2H), 7.25-7.4 (m, 4H), 2.44 (s, 3H).

Step 4: Preparation of 3-(3-chloro-4-methylphenyl)-5-(3,5-dibromo-4-fluorophenyl)-5-trifluoromethyl-4,5-dihydroisoxazole To a stirred solution of 1-(3-chloro-4-methylphenyl)-3-(3,5-dibromo-4-fluorophenyl)-4,4,4-trifluoro-2-buten-1-+one (1.37 g) and tetrabutylammonium bromide (0.27 g) in toluene (8 mL) at 5° C. was added dropwise a solution of hydroxylamine sulfate (0.32 g) and sodium hydroxide (0.33 g) in water (1.3 mL). After stirring at room temperature for 15 hours, 3N hydrochloric acid (5 mL) was added to the reaction mixture at 5° C., and the resulting two layers were separated. The organic layer was sequentially washed with water (5 mL), saturated aqueous sodium hydrogencarbonate solution (5 mL) and brine, dried over anhydrous sodium sulfate and concentrated under reduced pressure to provide a residue. The residue was purified by liquid chromatography (medium pressure collection apparatus: Purif-α2 manufactured by Moritex Corporation) eluted with ethyl acetate-hexane (1:10) to afford the title compound as a pale yellow resin (1.10 g).

$^1$H NMR (CDCl$_3$, Me$_4$Si, 300 MHz) δ 7.75 (d, J=5.7 Hz, 2H), 7.61 (d, J=1.8 Hz, 1H), 7.4-7.5 (m, 1H), 7.25-7.35 (m, 1H), 4.06 (d, J=17.4 Hz, 1H), 3.66 (d, J=17.4 Hz, 1H), 2.41 (s, 3H).

Step 5: Preparation of N-[[2-chloro-4-[5-(3,5-dibromo-4-fluorophenyl)-5-trifluoromethyl-4,5-dihydroisoxazol-3-yl]phenyl]methyl]phthalimide To a solution of 3-(3-chloro-4-methylphenyl)-5-(3,5-dibromo-4-fluorophenyl)-5-trifluoromethyl-4,5-dihydroisoxazole (1.1 g) in 1,2-dichloroethane (7 mL) was added N-bromosuccinimide (0.38 g) and 2,2'-azobis(2-methylpropionitrile) (0.028 g). The mixture was heated to reflux for 3 hours and then cooled to room temperature. The resulting mixture was diluted with 1,2-dichloroethane (10 mL), washed with water (30 mL) and brine, dried over anhydrous sodium sulfate and concentrated under reduced pressure to provide a residue. The residue was dissolved in N,N-dimethylformamide (7 mL), and potassium phthalimide (0.40 g) was added. The mixture was stirred at room temperature for 15 hours. The reaction mixture was then poured into water (10 mL) and extracted with ethyl acetate (10 mL×2). The organic extracts were combined, washed with brine, dried over anhydrous magnesium sulfate and concentrated under reduced pressure to afford the crude title compound as a pale yellow resin (0.75 g), which was used in the next step without purification.

$^1$H NMR (CDCl$_3$, Me$_4$Si, 300 MHz) δ 7.90 (dd, J=5.7, 3.0 Hz, 2H), 7.77 (dd, J=5.7, 3.0 Hz, 2H), 7.74 (d, J=6.0 Hz, 2H), 7.67 (d, J=1.8 Hz, 1H), 7.45-7.55 (m, 1H), 7.25-7.35 (m, 1H), 5.00 (s, 2H), 4.03 (d, J=17.4 Hz, 1H), 3.64 (d, J=17.4 Hz, 1H).

Step 6: Preparation of 3-(4-aminomethyl-3-chlorophenyl)-5-(3,5-dibromo-4-fluorophenyl)-5-trifluoromethyl-4,5-dihydroisoxazole To a solution of N-[[2-chloro-4-[5-(3,5-dibromo-4-fluorophenyl)-5-trifluoromethyl-4,5-dihydroisoxazol-3-yl]phenyl]methyl]phthalimide (0.75 g) in ethanol (10 mL) was added hydrazine monohydrate (1.07 g). The mixture was heated to reflux for 1 hour and then cooled to room temperature. The resulting mixture was filtered and concentrated under reduced pressure. The residue was dissolved in chloroform (10 mL) and filtered, and the filtrate was washed with water (10 mL) and brine, dried over anhydrous sodium sulfate and concentrated under reduced pressure to provide a residue. The residue was purified by column chromatography on silica gel eluted with methanol-ethyl:acetate (1:9) to afford the title compound as a pale yellow resin (0.51 g).

$^1$H NMR (CDCl$_3$, Me$_4$Si, 300 MHz) δ 7.76 (d, J=5.7 Hz, 2H), 7.65 (d, J=1.5 Hz, 1H), 7.45-7.6 (m, 2H), 4.07 (d, J=17.4 Hz, 1H), 3.96 (s, 2H), 3.68 (d, J=17.4 Hz, 1H), 1.67 (bs, 2H).

Step 7: Preparation of N-butyryl-2-chloro-4-[5-(3,5-dibromo-4-fluorophenyl)-5-trifluoromethyl-4,5-dihydro-isoxazol-3-yl]benzylamine To a solution of 3-(4-aminomethyl-3-chlorophenyl)-5-(3,5-dibromo-4-fluorophenyl)-5-trifluoromethyl-4,5-dihydroisoxazole (70.0 mg) and triethylamine (15.0 mg) in dichloromethane (2 mL) was added butyryl chloride (15.4 mg) at 5° C. The reaction mixture was then stirred at room temperature for 1 hour. The resulting mixture was diluted with chloroform (2 mL) and washed with saturated aqueous sodium hydrogencarbonate solution (3 mL) and brine. The organic layer was dried over anhydrous magnesium sulfate and concentrated under reduced pressure to provide a residue. The residue was purified by liquid chromatography (medium pressure collection apparatus: Purif-α2 manufactured by Moritex Corporation) eluted with ethyl acetate-hexane (1:10) to afford the title compound as a colorless resin (42.0 mg).

$^1$H NMR (CDCl$_3$, Me$_4$Si, 300 MHz) δ 7.75 (d, J=5.4 Hz, 2H), 7.67 (d, J=1.2 Hz, 1H), 7.4-7.55 (m, 2H), 5.98 (bs, 1H), 4.53 (d, J=6.0 Hz, 2H), 4.05 (d, J=17.4 Hz, 1H), 3.66 (d, J=17.4 Hz, 1H), 2.20 (t, J=7.5 Hz, 2H), 1.67 (sxt, J=7.5 Hz, 2H), 0.94 (t, J=7.5 Hz, 3H).

Reference Example 1

4-Chloro-3-trifluoromethyl-1-[1-(trifluoromethyl)ethenyl]benzene

To 1M solution of 1-(trifluoromethyl)ethenyl zinc bromide in tetrahydrofuran (see J. Org. Chem. 1991, 56, 7336 for preparation) (53 mL) under nitrogen atmosphere was added 2-chloro-5-iodobenzotrifluoride (7.1 g), followed by the addition of dichlorobis(triphenylphosphine)palladium(II) (0.65 g). The mixture was stirred under reflux for 2.5 hours and then cooled to room temperature. To the resulting mixture was added hexane (100 mL) and filtered, and the filtrate was washed with water (50 mL) and brine, dried over anhydrous sodium sulfate and concentrated under reduced pressure to provide a residue. The residue was purified by column chromatography on silica gel eluted with hexane to afford the title compound as colorless oil (4.8 g).

$^1$H NMR (CDCl$_3$, Me$_4$Si, 300 MHz) δ 7.75 (s, 1H), 7.57 (d, J=8.8 Hz, 1H), 7.54 (d, J=8.8 Hz, 1H), 6.08 (s, 1H), 5.84 (s, 1H).

Reference Example 2

3,5-Bis(trifluoromethyl)-1-[1-(trifluoromethyl)ethenyl]benzene

To a stirred solution of 3,5-bis(trifluoromethyl)phenyl boric acid (20.0 g) in tetrahydrofuran (100 mL) and water (40 mL) was added 2-bromo-3,3,3-trifluoropropene (20.2 g) and potassium carbonate (30.0 g), followed by the addition of 1,3-bis(2,6-diisopropylphenyl)imidazol-2-ylidene(1,4-naphthoquinone)palladium(0) dimer (0.023 g). The reaction mixture was stirred at 60° C. for 3 hours under nitrogen atmosphere and then cooled to room temperature. The resulting mixture was poured into ice-water (100 mL) and extracted with ethyl acetate (100 mL×2). The organic extracts were combined, washed with water and brine, dried over anhydrous sodium sulfate and concentrated under reduced pressure to provide a residue. The residue was purified by column chromatography on silica gel eluted with hexane to afford the title compound as orange oil (21.9 g).

$^1$H NMR (CDCl$_3$, Me$_4$Si, 300 MHz) δ 7.75 (s, 1H), 7.57 (d, J=8.8 Hz, 1H), 7.54 (d, J=8.8 Hz, 1H), 6.08 (s, 1H), 5.84 (s, 1H).

Reference Example 3

3,4-Dichloro-5-methyl-1-[1-(trifluoromethyl)ethenyl]benzene

To 1M solution of 1-(trifluoromethyl)ethenyl zinc bromide in tetrahydrofuran (see J. Org. Chem. 1991, 56, 7336 for preparation) (19 mL) was added a solution of 5-bromo-2,3-dichlorotoluene (2.2 g) in N,N-dimethylformamide (10 mL), then tetrahydrofuran was distilled off under reduced pressure. Dichlorobis(triphenylphosphine)palladium(II) (0.26 g) was added to the residual N,N-dimethylformamide solution, which was stirred at 100° C. for 3.5 hours under nitrogen atmosphere and then cooled to room temperature. To the resulting mixture was added tetrahydrofuran-hexane 2:5 mixture (200 mL) and filtered, and the filtrate was washed with water (100 mL) and brine, dried over anhydrous sodium sulfate and concentrated under reduced pressure to provide a residue. The residue was purified by column chromatography on silica gel eluted with hexane to afford the title compound as a brown oil (2.3 g).

$^1$H NMR (CDCl$_3$, Me$_4$Si, 300 MHz) δ 7.40 (s, 1H), 7.22 (s, 1H), 5.99 (s, 1H), 5.77 (s, 1H), 2.44 (s, 3H).

Reference Example 4

3,4-Dichloro-5-trifluoromethyl-1-[1-(trifluoromethyl)ethenyl]benzene

To a stirred solution of 5-bromo-2,3-dichlorobenzotrifluoride (26.2 g) and diisopropyl ether (9.1 g) in hexane (250 mL) at −10° C. was added dropwise 1.55M n-butyllithium in hexane (57.5 mL). After stirring at same temperature for 0.5 hour, trimethoxyborane (9.26 g) in tetrahydrofuran (30 mL) was added dropwise. After a further 10 minutes, water (150 mL), 2-bromo-3,3,3-trifluoropropene (23.4 g), potassium carbonate (36.9 g) and 1,3-bis(2,6-diisopropylphenyl)imidazol-2-ylidene(1,4-naphthoquinone)palladium(0) dimer (0.131 g) were added to the reaction mixture, which was stirred at 60° C. for 4 hours. After the completion of the reaction, the reaction mixture was cooled to room temperature, poured into ice-water (50 mL) and ethyl acetate (75 mL) and filtered. The filtrate was separated, and the organic layer was washed with water and brine, dried over anhydrous sodium sulfate and concentrated under reduced pressure to provide a residue. The residue was purified by column chromatography on silica gel eluted with hexane to afford the title compound as a colorless oil (21.8 g).

$^1$H NMR (CDCl$_3$, Me$_4$Si, 300 MHz) δ 7.73 (s, 1H), 7.68 (s, 1H), 6.12 (s, 1H), 5.87 (s, 1H).

Reference Example 5

3,5-Dichloro-4-difluoromethoxy-1-[1-(trifluoromethyl)ethenyl]benzene

Step 1: Preparation of 4-bromo-2,6-dichloro-1-(difluoromethoxy)benzene

To a stirred solution of 4-bromo-2,6-dichlorophenol (2.3 g) in acetonitrile (25 mL) was added potassium carbonate (1.3 g) and ethyl bromodifluoroacetate (3.8 g). The mixture was heated to reflux for 4 hours and then cooled to room temperature. The resulting mixture was poured into water (100 mL) and extracted with ethyl acetate (100 mL×1). The organic layer was washed with water and brine, dried over anhydrous sodium sulfate and concentrated under reduced pressure to provide a residue. The residue was purified by column chromatography on silica gel eluted with ethyl acetate-hexane (1:4) to afford the title compound as yellow oil (2.4 g).

$^1$H NMR (CDCl$_3$, Me$_4$Si, 300 MHz) δ 7.54 (s, 2H), 6.56 (t, J=73.6 Hz, 1H).

Step 2: Preparation of 3,5-dichloro-4-difluoromethoxy-1-[1-(trifluoromethyl)ethenyl]benzene To 1M solution of 1-(trifluoromethyl)ethenyl zinc bromide in tetrahydrofuran (see J. Org. Chem. 1991, 56, 7336 for preparation) (21 mL) was added a solution of 4-bromo-2,6-dichloro-1-(difluoromethoxy)benzene (2.4 g) in N,N-dimethylformamide (12 mL), then the bulk of the tetrahydrofuran was removed in vacuo. Dichlorobis(triphenylphosphine)palladium(II) (0.23 g) was added to the residual N,N-dimethylformamide solution, which was stirred at 100° C. for 3 hours under nitrogen atmosphere and then cooled to room temperature. The resulting mixture was poured into water (100 mL) and extracted with diethyl ether (100 mL×1). The organic layer was washed with water and brine, dried over anhydrous sodium sulfate and concentrated under reduced pressure to provide a residue. The residue was purified by column chromatography on silica gel eluted with hexane to afford the title compound as a brown oil (1.8 g).

$^1$H NMR (CDCl$_3$, Me$_4$Si, 300 MHz) δ 7.47 (s, 2H), 6.61 (t, J=73.6 Hz, 1H), 6.08 (s, 1H), 5.83 (s, 1H).

Reference Example 6

1-[3-Bromo-5-(trifluoromethyl)phenyl]-2,2,2-trifluoroethanone

To a stirred solution of 2,2,2-trifluoro-1-[3-(trifluoromethyl)phenyl]ethanone (5.00 g) in glacial acetic acid (1.0 mL) and concentrated sulfuric acid (6.0 mL) at 0° C. was added 1,3-dibromo-5,5-dimethylhydantoin (3.54 g). After stirring at 35° C. for 3.5 hours, the reaction mixture was poured into ice-water (60 mL) and extracted with chloroform (30 mL×2). The organic extracts were combined, washed with saturated aqueous sodium hydrogencarbonate solution (50 mL×1) and brine, dried over anhydrous magnesium sulfate, and concentrated under reduced pressure. The resulting residue was dissolved in hexane (20 mL) and filtered, and the filtrate was concentrated under reduced pressure to provide the title compound as a yellow oil (6.50 g).

$^1$H NMR (CDCl$_3$, Me$_4$Si, 300 MHz) δ 8.36 (s, 1H), 8.23 (s, 1H), 8.11 (s, 1H).

Reference Example 7

1-[3,5-Bromo-4-chlorophenyl]-2,2,2-trifluoroethanone

To a stirred solution of 1-(4-chlorophenyl)-2,2,2-trifluoroethanone (2.00 g) in glacial acetic acid (0.5 mL) and concentrated sulfuric acid (2.8 mL) at 0° C. was added 1,3-dibromo-5,5-dimethylhydantoin (3.02 g). After stirring at 35° C. for 3 hours, more glacial acetic acid (0.7 mL), concentrated sulfuric acid (2.0 mL) and 1,3-dibromo-5,5-dimethylhydantoin (3.02 g) was added. After stirring additional 3 hours, the reaction mixture was poured into ice-water (50 mL) and extracted with chloroform (50 mL×1). The organic layer was washed with saturated aqueous sodium hydrogencarbonate solution (50 mL×1) and brine, dried over anhydrous magnesium sulfate, and concentrated under reduced pressure. The resulting residue was dissolved in hexane (20 mL) and filtered, and the filtrate was concentrated under reduced pressure to provide the title compound as a yellow oil (3.89 g).

$^1$H NMR (CDCl$_3$, Me$_4$Si, 300 MHz) δ 8.24 (s, 2H).

Reference Example 8

2,2,2-Trifluoro-1-[3-iodo-5-(trifluoromethyl)phenyl]ethanone

A mixture of 2,2,2-trifluoro-1-[3-(trifluoromethyl)phenyl]ethanone (2.42 g), 30% fuming sulfuric acid (6.0 mL) and iodine (1.90 g) was stirred at 50° C. for 5 hours. After the completion of the reaction, the mixture was poured into ice-water (10 g) and extracted with diethyl ether (20 mL×1). The organic layer was washed with saturated aqueous sodium sulfite solution (10 mL×1) and brine, dried over anhydrous sodium sulfate, and concentrated under reduced pressure to provide the title compound as a pale yellow oil (2.56 g).

$^1$H NMR (CDCl$_3$, Me$_4$Si, 300 MHz) δ 8.53 (s, 1H), 8.28 (s, 1H), 8.25 (s, 1H).

The compounds of the present invention can be produced according to the above-mentioned production methods and working examples. The examples of the compounds according to the present invention that were produced similarly to Synthetic Examples 1 to 11 are shown in Tables 5 to 15 to which the present invention is not limited. In the meantime, in Tables, the indication "Et" means ethyl, hereinafter similarly thereto, "n-Pr" and "Pr-n" mean normal propyl, "i-Pr" and "Pr-i" mean isopropyl, "c-Pr" and "Pr-c" mean cyclopropyl, "n-Bu" and "Bu-n" mean normal butyl, "i-Bu" and "Bu-i" mean isobutyl, "s-Bu" and "Bu-s" mean secondary butyl, "c-Bu" and "Bu-c" mean cyclobutyl, "t-Bu" and "Bu-t" mean tertiary butyl, "c-Pen" and "Pen-c" mean cyclopentyl, "c-Hex" and "Hex-c" mean cyclohexyl, "Ph" means phenyl, and in tables, aromatic heterocyclic rings of D-1d to D-58a are the following structures, respectively D-1d:

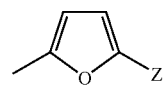

D-3a:

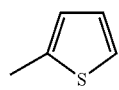

D-3b:

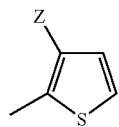

D-3e:

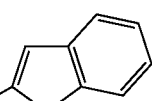

D-4a:

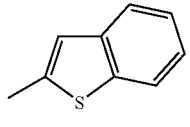

D-4c:

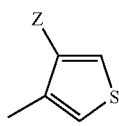

D-16c:
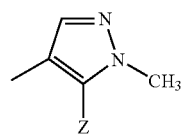
D-16d:
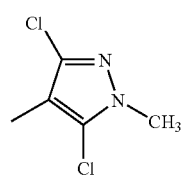
D-16e:
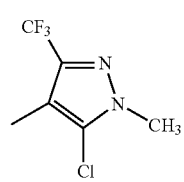
D-17b:
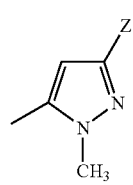
D-21a:
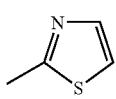
D-21a:
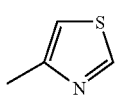
D-24a:
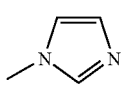
D-52a:
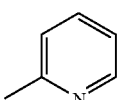
D-52b:
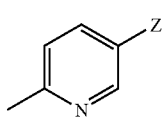
D-53a:
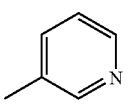
D-53b:
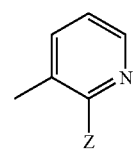
D-53e:
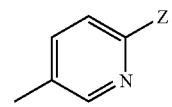
D-54a:
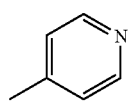
D-54b:
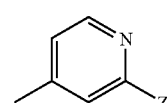
D-54d:
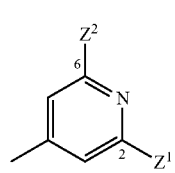
D-55a:
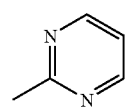
D-58a:
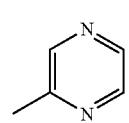
in Tables, saturated heterocyclic rings of E-4-a to E-26c are the following structures, respectively,
E-4a:
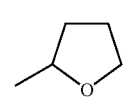
E-5a:
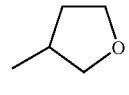
E-20a:
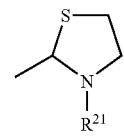

E-21a:

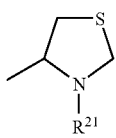

E-26a:

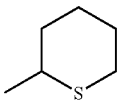

E-26b:

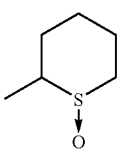

E-26c:

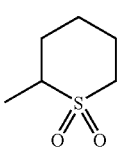

In Tables, partially saturated heterocyclic ring of M-7a to M-14a are the following structure M-7a:

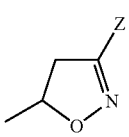

M-11a:

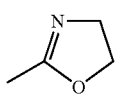

M-14a:

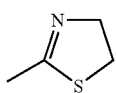

In Tables, T-6 to T-34 are the following structures, respectively

T-6:

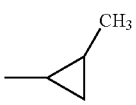

T-7:

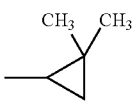

T-8:

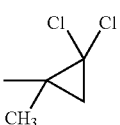

T-13:

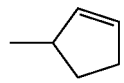

T-17:

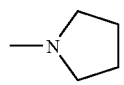

T-24:

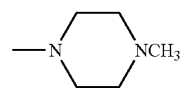

T-28:

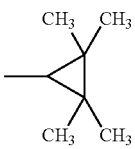

T-29:

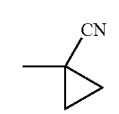

T-30:

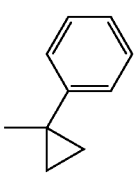

T-31:

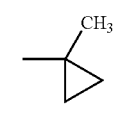

T-32:

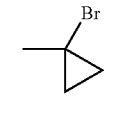

T-33:

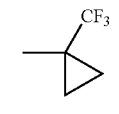

T-34:

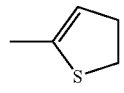

In addition, in Tables, the number showing the substitution position of substituents $(X)_m$ and $(Y)_n$ correspond to the position number indicated in the following structural formulae. The indication "-" means no-substitution.

Further, in Tables, the indication of "Mw" shows the calculated value of molecular weight, the indication of "M$^+$+H" shows the measured value of molecular ion peak measured with positive mode, and "*1" means "resinous" and "*2" means "oily".

TABLE 5

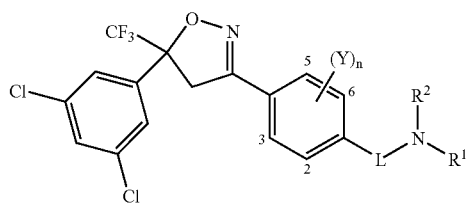

| No. | (Y)ₙ | L | R² | R¹ | Mw | M⁺ + H |
|---|---|---|---|---|---|---|
| 1-001 | — | CH₂ | H | C(O)Pr-i | 459.29 | 459.11 |
| 1-002 | — | CH₂ | H | C(O)Pr-c | 457.27 | 457.10 |
| 1-003 | — | CH₂ | H | C(O)CH₂Pr-c | 471.30 | 470.95 |
| 1-004 | — | CH₂ | H | C(O)CH₂Cl | 465.68 | 463.01* |
| 1-005 | — | CH₂ | H | C(O)CHF₂ | 467.22 | 466.90 |
| 1-006 | — | CH₂ | H | C(O)CH₂OCH₃ | 461.26 | 461.10 |
| 1-007 | — | CH₂ | H | C(O)CH₂OEt | 475.29 | 474.95 |
| 1-008 | — | CH₂ | H | C(O)CH=C(CH₃)₂ | 471.30 | 470.95 |
| 1-009 | — | CH₂ | H | C(O)OEt | 461.26 | 461.12 |
| 1-010 | — | CH₂ | H | C(O)OPh | 509.31 | 509.09 |
| 1-011 | — | CH₂ | H | C(O)NH(Ph-2-F) | 526.31 | 525.87 |
| 1-012 | — | CH₂ | H | C(O)NH(Ph-4-F) | 526.31 | 523.84* |
| 1-013 | — | CH₂ | H | C(O)NH(Ph-2-Cl) | 542.77 | 541.72 |
| 1-014 | — | CH₂ | H | C(O)NH(Ph-3-Cl) | 542.77 | 541.89 |
| 1-015 | — | CH₂ | H | C(O)NH(Ph-4-Cl) | 542.77 | 541.87 |
| 1-016 | — | CH₂ | H | C(O)NH(Ph-2-Bu-t) | 564.43 | 563.94 |
| 1-017 | — | CH₂ | H | C(O)NH(Ph-2-OCH₃) | 538.35 | 537.89 |
| 1-018 | — | CH₂ | H | C(O)NH(Ph-4-CN) | 533.33 | 532.84 |
| 1-019 | — | CH₂ | H | C(O)NH[(D-54d)-2,6-Cl₂] | 578.20 | 576.78 |
| 1-020 | — | CH₂ | H | C(O)(Ph-2-Cl) | 527.75 | 527.06 |
| 1-021 | — | CH₂ | H | C(O)(Ph-3-Cl) | 527.75 | 524.98* |
| 1-022 | — | CH₂ | H | C(O)(Ph-4-Cl) | 527.75 | 524.98* |
| 1-023 | — | CH₂ | H | C(O)(Ph-2-CH₃) | 507.33 | 506.80 |
| 1-024 | — | CH₂ | H | C(O)(Ph-2-CF₃) | 561.30 | 560.73 |
| 1-025 | — | CH₂ | H | C(O)NH(Ph-2-OEt) | 552.37 | 550.57* |
| 1-026 | — | CH₂ | H | C(O)(Ph-2-NO₂) | 538.30 | 537.75 |
| 1-027 | — | CH₂ | H | C(O)(Ph-2-CN) | 518.32 | 517.76 |
| 1-028 | — | CH₂ | H | C(O)(D-3a) | 499.33 | 498.73 |
| 1-029 | — | CH₂ | H | C(O)(D-4a) | 499.33 | 498.73 |
| 1-030 | — | CH₂ | H | C(O)(D-16d) | 599.74 | 598.67 |
| 1-031 | — | CH₂ | H | C(O)(D-17b)Cl | 531.74 | 530.71 |
| 1-032 | — | CH₂ | H | C(O)(D-53b)Cl | 528.74 | 527.72 |
| 1-033 | — | CH₂ | H | C(O)(D-54b)Cl | 528.74 | 527.73 |
| 1-034 | — | CH₂ | CH₃ | C(O)Et | 459.29 | 458.83 |
| 1-035 | — | CH₂ | CH₃ | C(O)Pr-n | 473.32 | 472.85 |
| 1-036 | — | CH₂ | CH₃ | C(O)Pr-i | 473.32 | 472.83 |
| 1-037 | — | CH₂ | CH₃ | C(O)Pr-c | 471.30 | 470.82 |
| 1-038 | — | CH₂ | CH₃ | C(O)CH₂CH₂Cl | 493.73 | 492.76 |
| 1-039 | — | CH₂ | CH₃ | C(O)OCH₃ | 461.26 | 460.81 |
| 1-040 | — | CH₂ | CH₃ | C(O)OEt | 475.29 | 474.82 |
| 1-041 | — | CH₂ | CH₃ | C(O)NHEt | 474.30 | 473.84 |
| 1-042 | — | CH₂ | Et | C(O)Et | 473.32 | 472.74 |
| 1-043 | — | CH₂ | Et | C(O)Pr-c | 485.33 | 484.74 |
| 1-044 | — | CH₂ | Et | C(O)CF₃ | 513.26 | 512.68 |
| 1-045 | — | CH₂ | Et | C(O)CF₂CF₃ | 563.27 | 562.65 |
| 1-046 | — | CH₂ | Et | C(O)OCH₃ | 475.29 | 474.72 |
| 1-047 | — | CH₂ | Et | C(O)OEt | 489.32 | 488.67 |
| 1-048 | — | CH₂ | i-Pr | C(O)CH₃ | 473.32 | 472.81 |
| 1-049 | — | CH₂ | i-Pr | C(O)Et | 487.34 | 486.81 |
| 1-050 | — | CH₂ | i-Pr | C(O)OCH₃ | 489.32 | 488.79 |
| 1-051 | — | CH₂ | i-Pr | C(O)OEt | 503.34 | 502.80 |
| 1-052 | — | CH₂ | i-Pr | C(O)NHEt | 502.36 | 501.81 |
| 1-053 | — | CH(CH₃) | H | C(O)Pr-n | 473.32 | 472.87 |
| 1-054 | — | CH(CH₃) | H | C(O)CH₂Bu-t | 501.37 | 500.88 |
| 1-055 | — | CH(CH₃) | | —C(O)CH₂CH(CH₃)C(O)— | 499.31 | 498.90 |
| 1-056 | — | CH(CH₃) | | —C(O)CH(CH₃)C(CH₃)₂C(O)— | 527.36 | 526.86 |
| 1-057 | — | CH(CH₃) | | —C(O)CH₂SC(O)— | 503.32 | 500.73 |
| 1-058 | — | CH(CH₃) | | —C(O)CH₂CH₂CH₂C(O)— | 499.31 | 498.87 |
| 1-059 | — | CH(CH₃) | | —C(O)CH₂OCH₂C(O)— | 527.36 | 500.86 |

TABLE 5-continued

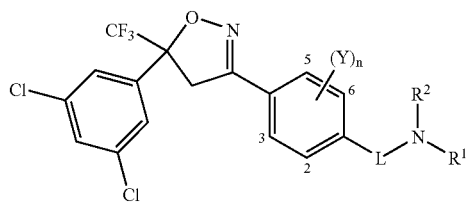

| No. | $(Y)_n$ | L | $R^2$ | $R^1$ | Mw | $M^+ + H$ |
|---|---|---|---|---|---|---|
| 1-060 | — | CH(Et) | H | C(O)Et | 473.32 | 472.80 |
| 1-061 | — | CH(Et) | H | C(O)NHEt | 488.33 | 487.81 |
| 1-062 | 2-Cl | $CH_2$ | H | C(O)Et | 479.71 | 478.84 |
| 1-063 | 2-Cl | $CH_2$ | H | C(O)Pr-n | 493.73 | 492.72 |
| 1-064 | 2-Cl | $CH_2$ | H | C(O)Bu-i | 507.76 | 506.73 |
| 1-065 | 2-Cl | $CH_2$ | H | C(O)Bu-s | 507.76 | 506.73 |
| 1-066 | 2-Cl | $CH_2$ | H | C(O)Bu-c | 505.75 | 504.67 |
| 1-067 | 2-Cl | $CH_2$ | H | C(O)Pen-c | 519.77 | 518.72 |
| 1-068 | 2-Cl | $CH_2$ | H | $C(O)CF_3$ | 519.65 | 518.65 |
| 1-069 | 2-Cl | $CH_2$ | H | $C(O)CH_2CH_2Cl$ | 514.15 | 512.59 |
| 1-070 | 2-Cl | $CH_2$ | H | $C(O)CH_2CH_2Br$ | 558.60 | 556.53 |
| 1-071 | 2-Cl | $CH_2$ | H | $C(O)CHClCH_3$ | 514.15 | 512.61 |
| 1-072 | 2-Cl | $CH_2$ | H | $C(O)CF_2CHF_2$ | 551.67 | 550.53 |
| 1-073 | 2-Cl | $CH_2$ | H | $C(O)CF_2CF_3$ | 569.66 | 568.63 |
| 1-074 | 2-Cl | $CH_2$ | H | $C(O)CF_2CF_2CF_3$ | 619.67 | 618.46 |
| 1-075 | 2-Cl | $CH_2$ | H | $C(O)CH_2CH_2SCH_3$ | 525.80 | 524.67 |
| 1-076 | 2-Cl | $CH_2$ | H | $C(O)CH_2C(O)OCH_3$ | 523.72 | 522.64 |
| 1-077 | 2-Cl | $CH_2$ | H | $C(O)CH_2CH_2C(O)OCH_3$ | 537.74 | 536.64 |
| 1-078 | 2-Cl | $CH_2$ | H | $C(O)CH=C(CH_3)_2$ | 505.75 | 506.66 |
| 1-079 | 2-Cl | $CH_2$ | H | C(O)CH=CHEt | 505.75 | 504.56 |
| 1-080 | 2-Cl | $CH_2$ | H | $C(O)CH_2CH=CHCH_3$ | 505.75 | 506.66 |
| 1-081 | 2-Cl | $CH_2$ | H | $C(O)CH_2CH_2CH=CH_2$ | 505.75 | 504.67 |
| 1-082 | 2-Cl | $CH_2$ | H | C(O)(Ph-2-F) | 545.74 | 544.62 |
| 1-083 | 2-Cl | $CH_2$ | H | C(O)(Ph-2-Cl) | 562.20 | 560.58 |
| 1-084 | 2-Cl | $CH_2$ | H | C(O)(Ph-2-Br) | 606.65 | 604.51 |
| 1-085 | 2-Cl | $CH_2$ | H | C(O)(Ph-2-I) | 653.65 | 652.45 |
| 1-086 | 2-Cl | $CH_2$ | H | $C(O)(Ph-2,4-F_2)$ | 563.73 | 562.62 |
| 1-087 | 2-Cl | $CH_2$ | H | C(O)(D-52a) | 528.74 | 527.63 |
| 1-088 | 2-Cl | $CH_2$ | H | $C(O)OCH_3$ | 481.68 | 480.63 |
| 1-089 | 2-Cl | $CH_2$ | H | C(O)OEt | 495.71 | 494.70 |
| 1-090 | 2-Cl | $CH_2$ | H | C(O)OPr-i | 509.73 | 508.69 |
| 1-091 | 2-Cl | $CH_2$ | H | C(O)NHEt | 494.72 | 493.89 |
| 1-092 | 2-Cl | $CH_2$ | H | $C(O)N(Et)_2$ | 522.78 | 521.68 |
| 1-093 | 2-Cl | $CH_2$ | H | C(O)NHPr-i | 508.75 | 507.68 |
| 1-094 | 2-Cl | $CH_2$ | H | C(S)NHPr-c | 522.80 | 521.63 |
| 1-095 | 2-I | $CH_2$ | H | C(O)Pr-n | 585.19 | 584.56 |
| 1-096 | 2-I | $CH_2$ | H | C(O)Pr-c | 583.17 | 582.55 |
| 1-097 | 2-I | $CH_2$ | H | $C(O)CF_3$ | 611.10 | 608.40 |
| 1-098 | 2-I | $CH_2$ | H | $C(O)CF_2CF_3$ | 661.11 | 658.36 |
| 1-099 | 2-I | $CH_2$ | H | $C(O)C(CH_3)=CHCH_3$ | 597.20 | 596.55 |
| 1-100 | 2-I | $CH_2$ | H | C(O)(Ph-2-Cl) | 653.65 | 652.47 |
| 1-101 | 2-I | $CH_2$ | H | C(O)(D-53b)Cl | 654.64 | 655.43 |
| 1-102 | 2-I | $CH_2$ | H | C(O)OEt | 587.16 | 586.55 |
| 1-103 | 2-I | $CH_2$ | H | C(O)NHEt | 586.17 | 585.55 |
| 1-104 | $2-CH_3$ | $CH_2$ | H | C(O)Pr-i | 473.32 | 472.93 |
| 1-105 | 2-(Ph-4-F) | $CH_2$ | H | C(O)Et | 539.35 | 538.83 |
| 1-106 | 2-(Ph-2-Cl) | $CH_2$ | H | C(O)Et | 555.80 | 554.79 |
| 1-107 | 2-(Ph-3-Cl) | $CH_2$ | H | C(O)Et | 555.80 | 554.80 |
| 1-108 | 2-(Ph-4-Cl) | $CH_2$ | H | C(O)Et | 555.80 | 554.78 |
| 1-109 | $2-(Ph-2-CH_3)$ | $CH_2$ | H | C(O)Et | 535.39 | 534.86 |
| 1-110 | $2-(Ph-3-CH_3)$ | $CH_2$ | H | C(O)Et | 535.39 | 534.87 |
| 1-111 | $2-(Ph-4-CH_3)$ | $CH_2$ | H | C(O)Et | 535.39 | 534.87 |
| 1-112 | 2-(Ph-3-CN) | $CH_2$ | H | C(O)Et | 546.37 | 545.82 |
| 1-113 | 2-(Ph-4-CN) | $CH_2$ | H | C(O)Et | 546.37 | 545.83 |

TABLE 5-continued

| No. | (Y)$_n$ | L | R$^2$ | R$^1$ | Mw | M$^+$ + H |
|---|---|---|---|---|---|---|
| 1-114 | 2-(Ph-3-NH$_2$) | CH$_2$ | H | C(O)Et | 536.37 | 535.85 |
| 1-115 | 2-[Ph-3-NHC(O)CH$_3$] | H | H | C(O)Et | 578.41 | 577.84 |
| 1-116 | 2-[Ph-4-N(CH$_3$)$_2$] | H | H | C(O)Et | 564.43 | 563.88 |
| 1-117 | 2-(1-Naph) | CH$_2$ | H | C(O)Et | 571.42 | 570.85 |
| 1-118 | 2-(D-3a) | CH$_2$ | H | C(O)Et | 527.39 | 526.81 |
| 1-119 | 2-(D-53e)Cl | CH$_2$ | H | C(O)Et | 556.79 | 555.79 |

In Table above, the indication of "*" shows the measured value of molecular ion peak of M$^+$–H measured with negative mode.

TABLE 6

| No. | (X)$_m$ | (Y)$_n$ | R$^{2a}$ | R$^{1a}$ | m.p. (°C.) |
|---|---|---|---|---|---|
| 2-001 | 3,5-Cl$_2$ | — | H | CH$_3$ | 171.0-173.0 |
| 2-002 | 3,5-Cl$_2$ | — | H | Et | 143.0-145.0 |
| 2-003 | 3,5-Cl$_2$ | — | H | CH$_2$Pen-c | 133.0-135.0 |
| 2-004 | 3,5-Cl$_2$ | — | H | CH$_2$Hex-c | 112.0-114.0 |
| 2-005 | 3,5-Cl$_2$ | — | H | CH$_2$CF$_3$ | *1 |
| 2-006 | 3,5-Cl$_2$ | — | H | CH$_2$CH$_2$OCH$_3$ | 134.0-136.0 |
| 2-007 | 3,5-Cl$_2$ | — | H | E-5a | 149.0-151.0 |
| 2-008 | 3,5-Cl$_2$ | — | H | CH$_2$(T-13) | 130.0-132.0 |
| 2-009 | 3,5-Cl$_2$ | — | H | CH$_2$CH$_2$C≡CH | 126.0-127.0 |
| 2-010 | 3,5-Cl$_2$ | — | H | CH$_2$(D-52a) | *1 |
| 2-011 | 3,5-Cl$_2$ | — | H | CH$_2$(D-53a) | 169.0-171.0 |
| 2-012 | 3,5-Cl$_2$ | — | H | CH$_2$(D-54a) | 65.0-72.0 |
| 2-013 | 3,5-Cl$_2$ | — | H | C(O)CH$_3$ | 168.0-170.0 |
| 2-014 | 3,5-Cl$_2$ | — | H | (D-4c)OCH$_3$ | *1 |
| 2-015 | 3,5-Cl$_2$ | — | H | D-52a | 78.0-82.5 |
| 2-016 | 3,5-Cl$_2$ | — | CH$_3$ | Et | 121.0-124.0 |
| 2-017 | 3,5-Cl$_2$ | — | CH$_3$ | i-Pr | 89.0-91.0 |
| 2-017(a) | | 99% d.e. | [α]$_D^{23.9}$ + 158.72° | (EtOH, c = 0.346) | 176.0-179.0 |
| 2-017(b) | | 99% d.e. | [α]$_D^{24.0}$ + 28.77° | (EtOH, c = 0.285) | 170.0-172.0 |
| 2-017(c) | | 99% d.e. | [α]$_D^{24.0}$ − 157.33° | (EtOH, c = 0.334) | 174.0-177.0 |
| 2-017(d) | | 99% d.e. | [α]$_D^{24.0}$ − 29.02° | (EtOH, c = 0.317) | 170.0-172.0 |
| 2-018 | 3,5-Cl$_2$ | — | CH$_3$ | c-Pr | 139.0-141.0 |
| 2-019 | 3,5-Cl$_2$ | — | CH$_3$ | n-Bu | 109.0-111.0 |
| 2-020 | 3,5-Cl$_2$ | — | CH$_3$ | t-Bu | 125.0-128.0 |
| 2-021 | 3,5-Cl$_2$ | — | CH$_3$ | CH$_2$CF$_3$ | *1 |
| 2-022 | 3,5-Cl$_2$ | — | CH$_3$ | CH$_2$CH$_2$CH$_2$Cl | 95.0-98.0 |
| 2-023 | 3,5-Cl$_2$ | — | CH$_3$ | C(CH$_3$)$_2$CH$_2$Cl | 113.0-116.0 |
| 2-024 | 3,5-Cl$_2$ | — | Et | i-Pr | 135.0-138.0 |
| 2-025 | 3,5-Cl$_2$ | — | Et | CH$_2$CF$_3$ | *1 |
| 2-026 | 3,5-Cl$_2$ | — | CF$_3$ | i-Pr | *1 |
| 2-027 | 3,5-Cl$_2$ | — | CN | c-Pr | 202.0-204.0 |
| 2-028 | 3,5-Cl$_2$ | — | CN | CH$_2$CF$_3$ | 164.0-166.0 |
| 2-029 | 3,5-Cl$_2$ | 2-F | H | CH$_2$CF$_3$ | *1 |
| 2-030 | 3,5-Cl$_2$ | 2-Cl | H | i-Pr | 155.0-157.0 |
| 2-031 | 3,5-Cl$_2$ | 2-Cl | H | c-Pr | 155.0-157.0 |
| 2-032 | 3,5-Cl$_2$ | 2-Cl | H | CH$_2$CF$_3$ | 135.0-139.0 |
| 2-033 | 3,5-Cl$_2$ | 2-Cl | H | E-4a | *1 |
| 2-034 | 3,5-Cl$_2$ | 2-Cl | H | E-5a | 149.0-152.0 |
| 2-035 | 3,5-Cl$_2$ | 2-Cl | H | CH$_2$CN | *1 |

TABLE 6-continued

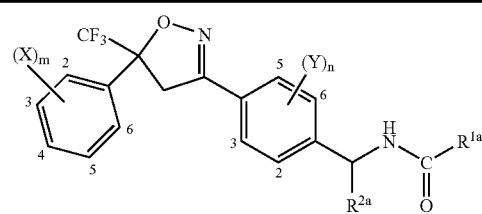

| No. | $(X)_m$ | $(Y)_n$ | $R^{2a}$ | $R^{1a}$ | m.p. (°C.) |
|---|---|---|---|---|---|
| 2-036 | 3,5-Cl$_2$ | 2-Cl | H | Ph-3-F | *1 |
| 2-037 | 3,5-Cl$_2$ | 2-Cl | H | Ph-4-F | *1 |
| 2-038 | 3,5-Cl$_2$ | 2-Cl | H | Ph-3,5-F$_2$ | *1 |
| 2-039 | 3,5-Cl$_2$ | 2-Cl | H | Ph-2, 6-Cl$_2$ | 259.0-262.0 |
| 2-040 | 3,5-Cl$_2$ | 2-Cl | H | D-24a | *1 |
| 2-041 | 3,5-Cl$_2$ | 2-Cl | CH$_3$ | c-Pr | *1 |
| 2-042 | 3,5-Cl$_2$ | 2-Cl | CN | c-Pr | *1 |
| 2-043 | 3,5-Cl$_2$ | 2-Br | H | i-Pr | 167.0-170.0 |
| 2-044 | 3,5-Cl$_2$ | 2-Br | H | c-Pr | *1 |
| 2-045 | 3,5-Cl$_2$ | 2-Br | H | CH$_2$CF$_3$ | *1 |
| 2-046 | 3,5-Cl$_2$ | 2-I | H | Et | *1 |
| 2-047 | 3,5-Cl$_2$ | 2-I | H | i-Pr | 173.0-175.0 |
| 2-048 | 3,5-Cl$_2$ | 2-I | H | i-Bu | 79.0-82.0 |
| 2-049 | 3,5-Cl$_2$ | 2-I | H | c-Bu | 84.0-86.0 |
| 2-050 | 3,5-Cl$_2$ | 2-I | H | CH$_2$CH$_2$Cl | 155.0-158.0 |
| 2-051 | 3,5-Cl$_2$ | 2-I | H | CH$_2$CF$_3$ | 150.0-152.0 |
| 2-052 | 3,5-Cl$_2$ | 2-I | H | CH$_2$CH$_2$SCH$_3$ | 74.0-77.0 |
| 2-053 | 3,5-Cl$_2$ | 2-CH$_3$ | H | Et | 159.0-161.0 |
| 2-054 | 3,5-Cl$_2$ | 2-CH$_3$ | H | CH$_2$CF$_3$ | 171.0-173.0 |
| 2-055 | 3,5-Cl$_2$ | 2-CH$_3$ | H | CH$_2$(D-52a) | *1 |
| 2-056 | 3,5-Cl$_2$ | 2-NH$_2$ | H | CH$_2$CF$_3$ | *1 |
| 2-057 | 3,5-Cl$_2$ | 2-NO$_2$ | H | CH$_2$CF$_3$ | *1 |
| 2-058 | 3,5-Cl$_2$ | 2-(Ph-2-F) | H | Et | *1 |
| 2-059 | 3,4,5-Cl$_3$ | 2-Cl | H | c-Pr | *1 |
| 2-060 | 3,5-Cl$_2$ | — | Ph | c-Pr | *1 |
| 2-061 | 3,5-Cl$_2$ | 2-Cl | H | CH$_2$Pr-c | *1 |
| 2-062 | 3,5-Cl$_2$ | 2-Cl | H | CH$_2$CH(CH$_3$)CF$_3$ | *1 |
| 2-063 | 3,5-Cl$_2$ | 2-Cl | H | CH$_2$CH(CF$_3$)$_2$ | *1 |
| 2-064 | 3,5-Cl$_2$ | 2-Cl | H | T-28 | *1 |
| 2-065 | 3,5-Cl$_2$ | 2-Cl | H | T-8 | *1 |
| 2-066 | 3,5-Cl$_2$ | 2-Cl | H | CH$_2$OCH$_3$ | *1 |
| 2-067 | 3,5-Cl$_2$ | 2-Cl | H | CH$_2$O(Ph-4-F) | *1 |
| 2-068 | 3,5-Cl$_2$ | 2-Cl | H | CH$_2$CH$_2$OCH$_3$ | *1 |
| 2-069 | 3,5-Cl$_2$ | 2-Cl | H | CH$_2$SCH$_3$ | *1 |
| 2-070 | 3,5-Cl$_2$ | 2-Cl | H | CH$_2$SO$_2$CH$_3$ | *1 |
| 2-071 | 3,5-Cl$_2$ | 2-Cl | H | CH$_2$NHC(O)Ph | *1 |
| 2-072 | 3,5-Cl$_2$ | 2-Cl | H | T-29 | *1 |
| 2-073 | 3,5-Cl$_2$ | 2-Cl | H | CH$_2$CH$_2$C≡CH | *1 |
| 2-074 | 3,5-Cl$_2$ | 2-Cl | H | CH$_2$(Ph-4-F) | 91.0-92.0 |
| 2-075 | 3,5-Cl$_2$ | 2-Cl | H | T-30 | *1 |
| 2-076 | 3,5-Cl$_2$ | 2-Cl | H | Ph-4-Cl | *1 |
| 2-077 | 3,5-Cl$_2$ | 2-Cl | H | Ph-4-CF$_3$ | *1 |
| 2-078 | 3,5-Cl$_2$ | 2-Cl | H | Ph-2,4-Cl$_2$ | 206.0-208.0 |
| 2-079 | 3,5-Br$_2$ | 2-Cl | H | c-Pr | *1 |
| 2-080 | 3-Cl-5-CF$_3$ | 2-Cl | H | c-Pr | *1 |
| 2-081 | 3,5-(CF$_3$)$_2$ | 2-Cl | H | c-Pr | *1 |
| 2-082 | 3,5-Cl$_2$-4-F | 2-Cl | H | c-Pr | *1 |
| 2-083 | 3,5-Cl$_2$ | — | CN | i-Pr | *1 |
| 2-084 | 3,5-Cl$_2$ | — | C(O)NH$_2$ | i-Pr | 114.0-117.0 |
| 2-085 | 3,5-Cl$_2$ | — | C(S)NH$_2$ | i-Pr | 118.0-121.0 |
| 2-086 | 3,5-Cl$_2$ | — | D-21a | c-Pr | *1 |
| 2-087 | 3,5-Cl$_2$ | 2-Cl | H | T-6 | *1 |
| 2-088 | 3,5-Cl$_2$ | 2-Cl | H | CF(CH$_3$)$_2$ | 143.0-145.0 |
| 2-089 | 3,5-Cl$_2$ | 2-Cl | H | CH$_2$NH$_2$ | 69.0-72.0 |
| 2-090 | 3,5-Cl$_2$ | 2-Cl | H | CH$_2$NHC(O)Pr-c | 92.0-95.0 |
| 2-091 | 3,5-Cl$_2$ | 2-Cl | H | CH$_2$NHC(O)OBu-t | *1 |
| 2-092 | 3,5-Cl$_2$ | 2-Cl | H | CH=NOCH$_3$ | *1 |
| 2-093 | 3,5-Cl$_2$ | 2-Cl | H | Ph-4-CN | *1 |
| 2-094 | 3,5-Cl$_2$ | 2-Cl | H | Ph-2-C(O)NHPr-c | 228.0-231.0 |
| 2-095 | 3,5-Cl$_2$ | 2-Br | H | CH$_2$Pr-c | 70.0-74.0 |
| 2-096 | 3,5-Cl$_2$ | 2-Br | H | E-4a | 53.0-59.0 |
| 2-097 | 3,5-Cl$_2$ | 2-Br | H | E-5a | 174.0-178.0 |
| 2-098 | 3,5-Cl$_2$ | 2-Br | H | Ph-2,4-F$_2$ | *1 |
| 2-099 | 3,5-Cl$_2$ | 2-CH$_3$ | H | c-Pr | 140.0-143.0 |
| 2-100 | 3,5-Cl$_2$ | 2-NO$_2$ | H | c-Pr | *1 |
| 2-101 | 3,5-Cl$_2$ | 2-NHC(O)CH$_3$ | H | CH$_2$CF$_3$ | 112.0-115.0 |
| 2-102 | 3,5-Cl$_2$ | 2-N=C(CH$_3$)OCH$_3$ | H | CH$_2$CF$_3$ | *1 |

TABLE 6-continued

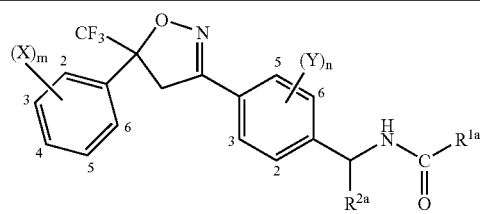

| No. | (X)$_m$ | (Y)$_n$ | R$^{2a}$ | R$^{1a}$ | m.p. (°C.) |
|---|---|---|---|---|---|
| 2-103 | 3,4,5-Cl$_3$ | 2-Cl | H | H | *1 |
| 2-104 | 3,5-(CF$_3$)$_2$ | 2-Cl | H | Et | *1 |
| 2-105 | 3,4,5-Cl$_3$ | 2-Cl | H | Et | *1 |
| 2-106 | 3,5-Cl$_2$ | 2-Br | H | Et | *1 |
| 2-107 | 3,4,5-Cl$_3$ | 2-Br | H | Et | *1 |
| 2-108 | 3,4,5-Cl$_3$ | 2-NO$_2$ | H | Et | *1 |
| 2-109 | 3,4,5-Cl$_3$ | — | CH$_3$ | Et | *1 |
| 2-110 | 3,5-(CF$_3$)$_2$ | 2-Cl | H | n-Pr | 150.0-152.0 |
| 2-111 | 3,4,5-Cl$_3$ | 2-Cl | H | n-Pr | *1 |
| 2-112 | 3,4,5-Cl$_3$ | 2-Br | H | n-Pr | *1 |
| 2-113 | 3,4,5-Cl$_3$ | 2-NO$_2$ | H | n-Pr | *1 |
| 2-114 | 3,4,5-Cl$_3$ | — | CH$_3$ | n-Pr | *1 |
| 2-115 | 3,4,5-Cl$_3$ | 2-Cl | H | i-Pr | 156.0-157.0 |
| 2-116 | 3,4,5-Cl$_3$ | 2-Br | H | i-Pr | 135.0-138.0 |
| 2-117 | 3,5-Cl$_2$ | 2-NO$_2$ | H | i-Pr | 176.0-177.0 |
| 2-118 | 3,4,5-Cl$_3$ | 2-NO$_2$ | H | i-Pr | *1 |
| 2-119 | 3,4,5-Cl$_3$ | — | CH$_3$ | i-Pr | 103.0-107.0 |
| 2-120 | 3,4,5-Cl$_3$ | — | H | c-Pr | *1 |
| 2-121 | 3-CF$_3$ | 2-Cl | H | c-Pr | *1 |
| 2-122 | 3,4-Cl$_2$-5-CH$_3$ | 2-Cl | H | c-Pr | 132.0-135.0 |
| 2-123 | 3,5-Cl$_2$-4-OH | 2-Cl | H | c-Pr | *1 |
| 2-124 | 3,5-Cl$_2$-4-OCHF$_2$ | 2-Cl | H | c-Pr | *1 |
| 2-125 | 3,5-Cl$_2$-4-OSO$_2$CH$_3$ | 2-Cl | H | c-Pr | *1 |
| 2-126 | 3,5-Cl$_2$-4-SCH$_3$ | 2-Cl | H | c-Pr | *1 |
| 2-127 | 3,5-Cl$_2$-4-S(O)CH$_3$ | 2-Cl | H | c-Pr | *1 |
| 2-128 | 3,5-Cl$_2$-4-SO$_2$CH$_3$ | 2-Cl | H | c-Pr | *1 |
| 2-129 | 3,4,5-Cl$_3$ | 2-Br | H | c-Pr | 128.5-132.0 |
| 2-130 | 3,4,5-Cl$_3$ | 2-NO$_2$ | H | c-Pr | *1 |
| 2-131 | 3,5-Cl$_2$ | 2-CN | H | c-Pr | *1 |
| 2-132 | 3,5-Cl$_2$ | 2-C(S)NH$_2$ | H | c-Pr | *1 |
| 2-133 | 3,5-Cl$_2$ | 2-CH=CHCH=CH-3 | H | c-Pr | 199.0-201.0 |
| 2-134 | 3,5-(CF$_3$)$_2$ | — | CH$_3$ | c-Pr | *1 |
| 2-135 | 3,4,5-Cl$_3$ | — | CH$_3$ | c-Pr | *1 |
| 2-136 | 3,5-Cl$_2$ | 2-CH$_3$ | CH$_3$ | c-Pr | *1 |
| 2-137 | 3,5-Cl$_2$ | — | c-Pr | c-Pr | *1 |
| 2-138 | 3,4,5-Cl$_3$ | — | CN | c-Pr | 203.0-207.0 |
| 2-139 | 3,4,5-Cl$_3$ | — | C(S)NH$_2$ | c-Pr | *1 |
| 2-140 | 3,5-(CF$_3$)$_2$ | 2-Cl | H | i-Bu | 164.0-166.0 |
| 2-141 | 3,4,5-Cl$_3$ | 2-Cl | H | i-Bu | *1 |
| 2-142 | 3,4,5-Cl$_3$ | 2-Br | H | i-Bu | *1 |
| 2-143 | 3,4,5-Cl$_3$ | — | CH$_3$ | i-Bu | *1 |
| 2-144 | 3,5-(CF$_3$)$_2$ | 2-Cl | H | CH$_2$Pr-c | 150.0-152.0 |
| 2-145 | 3,4,5-Cl$_3$ | 2-Cl | H | CH$_2$Pr-c | *1 |
| 2-146 | 3,4,5-Cl$_3$ | 2-Br | H | CH$_2$Pr-c | *1 |
| 2-147 | 3,4,5-Cl$_3$ | 2-NO$_2$ | H | CH$_2$Pr-c | *1 |
| 2-148 | 3,5-(CF$_3$)$_2$ | — | CH$_3$ | CH$_2$Pr-c | *1 |
| 2-149 | 3,4,5-Cl$_3$ | — | CH$_3$ | CH$_2$Pr-c | *1 |
| 2-150 | 3,4,5-Cl$_3$ | — | CN | CH$_2$Pr-c | *1 |
| 2-151 | 3,5-(CF$_3$)$_2$ | 2-Cl | H | T-6 | 163.0-165.0 |
| 2-152 | 3,4,5-Cl$_3$ | 2-Cl | H | T-6 | *1 |
| 2-153 | 3,4,5-Cl$_3$ | — | CH$_3$ | T-6 | 130.0-135.0 |
| 2-154 | 3,4,5-Cl$_3$ | 2-Cl | H | c-Bu | *1 |
| 2-155 | 3,4,5-Cl$_3$ | 2-Br | H | c-Bu | *1 |
| 2-156 | 3,4,5-Cl$_3$ | 2-Cl | H | T-31 | 176.0-178.0 |
| 2-157 | 3,4,5-Cl$_3$ | 2-Cl | H | T-7 | *1 |
| 2-158 | 3,5-Cl$_2$ | 2-Cl | H | CH$_2$Br | 160.0-163.0 |
| 2-159 | 3,4,5-Cl$_3$ | 2-Cl | H | CH$_2$Br | *1 |
| 2-160 | 3,4,5-Cl$_3$ | 2-Cl | H | CF$_3$ | *1 |
| 2-161 | 3,4,5-Cl$_3$ | 2-Br | H | CF$_3$ | *1 |
| 2-162 | 3,4,5-Cl$_3$ | 2-Cl | H | CF$_2$Cl | *1 |
| 2-163 | 3-Cl-4,5-(SCH$_3$)$_2$ | 2-Cl | H | CF$_2$Cl | *1 |
| 2-164 | 3,4,5-Cl$_3$ | 2-Cl | H | CH$_2$CH$_2$Cl | *1 |
| 2-165 | 3,4,5-Cl$_3$ | 2-Cl | H | CH$_2$CF$_3$ | *1 |
| 2-166 | 3,4,5-Cl$_3$ | 2-Br | H | CH$_2$CF$_3$ | 78.5-81.0 |
| 2-167 | 3,4,5-Cl$_3$ | 2-NO$_2$ | H | CH$_2$CF$_3$ | 183.0-185.0 |
| 2-168 | 3,4,5-Cl$_3$ | — | CH$_3$ | CH$_2$CF$_3$ | *1 |
| 2-169 | 3,4,5-Cl$_3$ | — | CN | CH$_2$CF$_3$ | *1 |

TABLE 6-continued

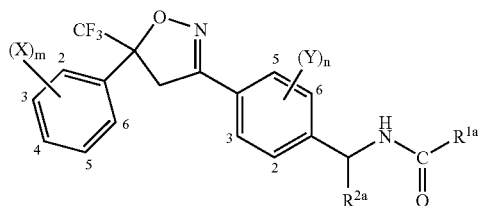

| No. | $(X)_m$ | $(Y)_n$ | $R^{2a}$ | $R^{1a}$ | m.p. (°C.) |
|---|---|---|---|---|---|
| 2-170 | 3,4,5-Cl$_3$ | 2-Cl | H | CF$_2$CF$_3$ | *1 |
| 2-171 | 3,4,5-Cl$_3$ | 2-Br | H | CF$_2$CF$_3$ | 100.0-112.5 |
| 2-172 | 3,4,5-Cl$_3$ | 2-Cl | H | CH$_2$CH$_2$CF$_3$ | *1 |
| 2-173 | 3,5-Cl$_2$ | — | CH$_3$ | CH$_2$CH$_2$CF$_3$ | 138.0-143.0 |
| 2-174 | 3,4,5-Cl$_3$ | — | CH$_3$ | CH$_2$CH$_2$CF$_3$ | *1 |
| 2-175 | 3,4,5-Cl$_3$ | 2-Cl | H | CH$_2$OCH$_2$CF$_3$ | *1 |
| 2-176 | 3,4,5-Cl$_3$ | 2-Cl | H | CH$_2$OCH$_2$C≡CH | *1 |
| 2-177 | 3,4,5-Cl$_3$ | — | H | E-5a | *1 |
| 2-178 | 3,5-(CF$_3$)$_2$ | 2-Cl | H | E-5a | 172.0-174.0 |
| 2-179 | 3,4,5-Cl$_3$ | 2-Cl | H | E-5a | *1 |
| 2-180 | 3,4,5-Cl$_3$ | 2-Br | H | E-5a | *1 |
| 2-181 | 3,4,5-Cl$_3$ | 2-NO$_2$ | H | E-5a | *1 |
| 2-182 | 3,4,5-Cl$_3$ | — | CH$_3$ | E-5a | *1 |
| 2-183 | 3,5-Cl$_2$ | 2-Br | H | CH$_2$SO$_2$CH$_3$ | *1 |
| 2-184 | 3,5-Cl$_2$ | 2-Cl | H | CH$_2$SEt | *1 |
| 2-185 | 3,5-Cl$_2$ | 2-Cl | H | CH$_2$S(O)Et | *1 |
| 2-186 | 3,5-Cl$_2$ | 2-Cl | H | CH$_2$SO$_2$Et | *1 |
| 2-187 | 3,5-Cl$_2$ | 2-Cl | H | CH$_2$SPr-n | *1 |
| 2-188 | 3,5-Cl$_2$ | 2-Cl | H | CH$_2$SPr-i | *1 |
| 2-189 | 3,5-Cl$_2$ | 2-Cl | H | CH$_2$SCH$_2$Ph | *1 |
| 2-190 | 3,5-Cl$_2$ | 2-Cl | H | CH$_2$SO$_2$CH$_2$Ph | *1 |
| 2-191 | 3,5-Cl$_2$ | 2-Cl | H | CH$_2$SPh | *1 |
| 2-192 | 3,5-Cl$_2$ | 2-Cl | H | CH$_2$SO$_2$Ph | *1 |
| 2-193 | 3,5-Cl$_2$ | 2-Cl | H | CH(CH$_3$)SCH$_3$ | 131.0-133.0 |
| 2-194 | 3,5-Cl$_2$ | 2-Cl | H | CH(CH$_3$)S(O)CH$_3$ | *1 |
| 2-195 | 3,5-Cl$_2$ | 2-Cl | H | CH(CH$_3$)SO$_2$CH$_3$ | *1 |
| 2-196 | 3,5-Cl$_2$ | 2-Cl | H | C(CH$_3$)$_2$SCH$_3$ | *1 |
| 2-197 | 3,5-Cl$_2$ | 2-Cl | H | C(CH$_3$)$_2$SO$_2$CH$_3$ | *1 |
| 2-198 | 3,4,5-Cl$_3$ | 2-Cl | H | CH$_2$CH$_2$SCH$_3$ | *1 |
| 2-199 | 3,4,5-Cl$_3$ | — | CN | CH$_2$CH$_2$SCH$_3$ | *1 |
| 2-200 | 3,4,5-Cl$_3$ | 2-Cl | H | CH$_2$N(CH$_3$)$_2$ | *1 |
| 2-201 | 3,4,5-Cl$_3$ | 2-Cl | H | CH$_2$N(CH$_3$)Et | *1 |
| 2-202 | 3,4,5-Cl$_3$ | 2-Cl | H | CH$_2$N(Et)$_2$ | *1 |
| 2-203 | 3,4,5-Cl$_3$ | 2-Cl | H | CH$_2$NHCH$_2$CF$_3$ | *1 |
| 2-204 | 3,4,5-Cl$_3$ | 2-Cl | H | CH$_2$NHCH$_2$CN | *1 |
| 2-205 | 3,4,5-Cl$_3$ | 2-Cl | H | CH$_2$NHCH$_2$C≡CH | *1 |
| 2-206 | 3,4,5-Cl$_3$ | 2-Cl | H | CH$_2$(T-17) | *1 |
| 2-207 | 3,4,5-Cl$_3$ | 2-Cl | H | CH$_2$NHC(O)OCH$_3$ | *1 |
| 2-208 | 3,4,5-Cl$_3$ | 2-Cl | H | CH$_2$N(CH$_3$)C(O)OCH$_3$ | *1 |
| 2-209 | 3,4,5-Cl$_3$ | 2-Cl | H | CH$_2$N(Et)C(O)OCH$_3$ | *1 |
| 2-210 | 3,4,5-Cl$_3$ | 2-Cl | H | CH$_2$N(CH$_2$CN)C(O)OCH$_3$ | *1 |
| 2-211 | 3,5-Cl$_2$ | 2-Cl | H | (E-20a)H | *1 |
| 2-212 | 3,5-Cl$_2$ | 2-Cl | H | (E-20a)C(O)CH$_3$ | *1 |
| 2-213 | 3,5-Cl$_2$ | 2-Cl | H | (E-20a)C(O)OCH$_3$ | *1 |
| 2-214 | 3,5-Cl$_2$ | 2-Cl | H | (E-21a)H | *1 |
| 2-215 | 3,5-Cl$_2$ | 2-Cl | H | (E-21a)C(O)CH$_3$ | *1 |
| 2-216 | 3,4,5-Cl$_3$ | 2-Cl | H | CH$_2$CN | *1 |
| 2-217 | 3,4,5-Cl$_3$ | 2-Cl | H | CH$_2$CH$_2$C(O)OCH$_3$ | *1 |
| 2-218 | 3,4,5-Cl$_3$ | 2-Cl | H | CH$_2$C(O)NHCH$_3$ | *1 |
| 2-219 | 3,4,5-Cl$_3$ | 2-Cl | H | CH$_2$C(O)NHEt | *1 |
| 2-220 | 3,4,5-Cl$_3$ | 2-Cl | H | CH$_2$C(O)NHCH$_2$Pr-c | *1 |
| 2-221 | 3,5-Cl$_2$ | 2-Cl | H | CH$_2$C(O)NHCH$_2$CF$_3$ | *1 |
| 2-222 | 3,4,5-Cl$_3$ | 2-Cl | H | CH$_2$C(O)(T-17) | *1 |
| 2-223 | 3,4,5-Cl$_3$ | 2-Cl | H | CH=CH$_2$ | *1 |
| 2-224 | 3,4,5-Cl$_3$ | 2-Br | H | CH=CH$_2$ | *1 |
| 2-225 | 3,4,5-Cl$_3$ | 2-Cl | H | CH$_2$CH=CH$_2$ | *1 |
| 2-226 | 3,4,5-Cl$_3$ | 2-Cl | H | CH=CHCH$_3$ | *1 |
| 2-227 | 3,4,5-Cl$_3$ | 2-Cl | H | C(CH$_3$)=CH$_2$ | *1 |
| 2-228 | 3,4,5-Cl$_3$ | 2-Cl | H | C(CF$_3$)=CH$_2$ | *1 |
| 2-229 | 3,4,5-Cl$_3$ | 2-Cl | H | CH=CHPh | *1 |
| 2-230 | 3,4,5-Cl$_3$ | 2-Cl | H | C≡CH | *1 |
| 2-231 | 3,4,5-Cl$_3$ | 2-Cl | H | C≡CCH$_3$ | *1 |
| 2-232 | 3,4,5-Cl$_3$ | 2-Cl | H | CH$_2$CH$_2$C≡CH | *1 |
| 2-233 | 3,4,5-Cl$_3$ | 2-Br | H | CH$_2$CH$_2$C≡CH | *1 |
| 2-234 | 3,4,5-Cl$_3$ | 2-NO$_2$ | H | CH$_2$CH$_2$C≡CH | *1 |
| 2-235 | 3,4,5-Cl$_3$ | — | CH$_3$ | CH$_2$CH$_2$C≡CH | *1 |
| 2-236 | 3,4,5-Cl$_3$ | — | CN | CH$_2$CH$_2$C≡CH | *1 |

TABLE 6-continued

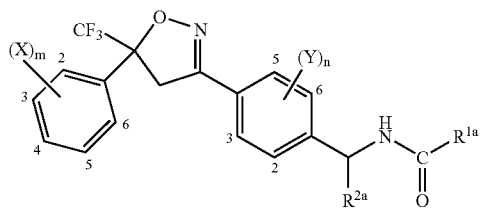

| No. | $(X)_m$ | $(Y)_n$ | $R^{2a}$ | $R^{1a}$ | m.p. (°C.) |
|---|---|---|---|---|---|
| 2-237 | 3,4,5-Cl₃ | — | CH₃ | CH₂(Ph-2,4-F₂) | *1 |
| 2-238 | 3,5-Cl₂ | — | CH₃ | CH₂CH₂Ph | 151.0-155.0 |
| 2-239 | 3,4,5-Cl₃ | — | CH₃ | CH₂(D-52a) | *1 |
| 2-240 | 3,5-Cl₂ | 2-Br | H | C(O)Pr-i | *1 |
| 2-241 | 3,4,5-Cl₃ | 2-Cl | H | C(O)NHCH₃ | *1 |
| 2-242 | 3,4,5-Cl₃ | 2-Cl | H | C(O)NHEt | *1 |
| 2-243 | 3,5-Cl₂ | — | CH₃ | Ph | 95.0-100.0 |
| 2-244 | 3,5-Cl₂ | — | CH₃ | Ph-2-F | *1 |
| 2-245 | 3,5-Cl₂ | — | CH₃ | Ph-3-F | 136.0-141.0 |
| 2-246 | 3,4,5-Cl₃ | 2-Cl | H | Ph-4-F | *1 |
| 2-247 | 3,4,5-Cl₃ | 2-Br | H | Ph-4-F | *1 |
| 2-248 | 3,5-Cl₂ | — | CH₃ | Ph-4-F | 123.0-128.0 |
| 2-249 | 3,4,5-Cl₃ | 2-Cl | H | Ph-2-Cl | *1 |
| 2-250 | 3,4,5-Cl₃ | 2-Br | H | Ph-2-Cl | *1 |
| 2-251 | 3,5-Cl₂ | — | CH₃ | Ph-2-Cl | *1 |
| 2-252 | 3,5-Cl₂ | — | CH₃ | Ph-3-Cl | 131.0-134.0 |
| 2-253 | 3,5-Cl₂ | — | CH₃ | Ph-4-Cl | 159.0-161.0 |
| 2-254 | 3,4,5-Cl₃ | 2-Br | H | Ph-2-Br | *1 |
| 2-255 | 3,4,5-Cl₃ | 2-Cl | H | Ph-2-CH₃ | *1 |
| 2-256 | 3,4,5-Cl₃ | 2-Cl | H | Ph-2-CF₃ | *1 |
| 2-257 | 3,5-Cl₂ | 2-Cl | H | Ph-4-CF(CF₃)₂ | *1 |
| 2-258 | 3,5-Cl₂ | 2-Cl | H | Ph-4-OPh | *1 |
| 2-259 | 3,4,5-Cl₃ | 2-Cl | H | Ph-2-SCH₃ | *1 |
| 2-260 | 3,5-Cl₂ | 2-Cl | H | Ph-4-SCH₃ | *1 |
| 2-261 | 3,5-Cl₂ | — | CH₃ | Ph-4-SO₂CH₃ | 163.0-165.0 |
| 2-262 | 3,5-Cl₂ | 2-Cl | H | Ph-4-SCF₃ | *1 |
| 2-263 | 3,4,5-Cl₃ | 2-Cl | H | Ph-2-NO₂ | *1 |
| 2-264 | 3,4,5-Cl₃ | 2-Cl | H | Ph-4-NO₂ | *1 |
| 2-265 | 3,4,5-Cl₃ | 2-Cl | H | Ph-2-CN | *1 |
| 2-266 | 3,4,5-Cl₃ | 2-Cl | H | Ph-4-CN | *1 |
| 2-267 | 3,4,5-Cl₃ | — | CH₃ | Ph-4-CN | *1 |
| 2-268 | 3,4,5-Cl₃ | 2-Cl | H | Ph-2,4-F₂ | *1 |
| 2-269 | 3,4,5-Cl₃ | 2-Br | H | Ph-2,4-F₂ | *1 |
| 2-270 | 3,5-Cl₂ | 2-NO₂ | H | Ph-2,4-F₂ | *1 |
| 2-271 | 3,4,5-Cl₃ | 2-NO₂ | H | Ph-2,4-F₂ | *1 |
| 2-272 | 3,5-Cl₂ | 2-CH=CHCH=CH-3 | H | Ph-2,4-F₂ | 169.0-171.0 |
| 2-273 | 3,5-Cl₂ | — | CH₃ | Ph-2,4-F₂ | *1 |
| 2-274 | 3,4,5-Cl₃ | — | CH₃ | Ph-2,4-F₂ | *1 |
| 2-275 | 3,4,5-Cl₃ | — | CN | Ph-2,4-F₂ | *1 |
| 2-276 | 3,5-Cl₂ | 2-Cl | H | Ph-2,6-F₂ | *1 |
| 2-277 | 3,4,5-Cl₃ | 2-Cl | H | Ph-2,6-F₂ | *1 |
| 2-278 | 3,5-Cl₂ | — | CH₃ | Ph-2,6-F₂ | *1 |
| 2-279 | 3,4,5-Cl₃ | — | CH₃ | Ph-2,6-F₂ | *1 |
| 2-280 | 3,4,5-Cl₃ | 2-Cl | H | Ph-3,4-F₂ | *1 |
| 2-281 | 3,4,5-Cl₃ | 2-Cl | H | Ph-2-Cl-4-F | *1 |
| 2-282 | 3,5-Cl₂ | — | CH₃ | Ph-2-Cl-4-F | *1 |
| 2-283 | 3,4,5-Cl₃ | — | CH₃ | Ph-2-Cl-4-F | *1 |
| 2-284 | 3,4,5-Cl₃ | 2-Cl | H | Ph-2-F-4-CN | *1 |
| 2-285 | 3,5-Cl₂ | — | CH₃ | Ph-2-F-4-CN | *1 |
| 2-286 | 3,5-Cl₂ | 2-Cl | H | Ph-2,4,6-F₃ | *1 |
| 2-287 | 3,5-(CF₃)₂ | 2-Cl | H | Ph-2,4,6-F₃ | 189.0-191.0 |
| 2-288 | 3,4,5-Cl₃ | 2-Cl | H | Ph-2,4,6-F₃ | *1 |
| 2-289 | 3,4,5-Cl₃ | 2-Br | H | Ph-2,4,6-F₃ | 141.0-144.5 |
| 2-290 | 3,5-Cl₂ | — | CH₃ | Ph-2,4,6-F₃ | *1 |
| 2-291 | 3,5-(CF₃)₂ | — | CH₃ | Ph-2,4,6-F₃ | *1 |
| 2-292 | 3,4,5-Cl₃ | — | CH₃ | Ph-2,4,6-F₃ | *1 |
| 2-293 | 3,4,5-Cl₃ | — | CH₃ | Ph-2,3,4,5,6-F₅ | *1 |
| 2-294 | 3,5-Cl₂ | — | CH₃ | (D-1d)Br | *1 |
| 2-295 | 3,5-Cl₂ | 2-Cl | H | D-3a | *1 |
| 2-296 | 3,4,5-Cl₃ | 2-Cl | H | (D-3b)Cl | *1 |
| 2-297 | 3,5-Cl₂ | — | CH₃ | (D-3b)Cl | *1 |
| 2-298 | 3,4,5-Cl₃ | 2-Cl | H | (D-16c)Cl | *1 |
| 2-299 | 3,5-Cl₂ | — | CH₃ | (D-16c)Cl | 115.0-120.0 |
| 2-300 | 3,4,5-Cl₃ | 2-Cl | H | D-16d | 175.0-180.0 |
| 2-301 | 3,4,5-Cl₃ | 2-Cl | H | (D-17b)Cl | *1 |
| 2-302 | 3,5-Cl₂ | — | CH₃ | (D-17b)Cl | 161.0-164.0 |
| 2-303 | 3,4,5-Cl₃ | — | CH₃ | D-22a | *1 |

TABLE 6-continued

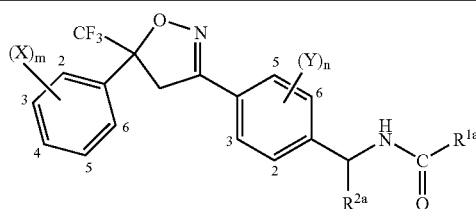

| No. | $(X)_m$ | $(Y)_n$ | $R^{2a}$ | $R^{1a}$ | m.p. (°C.) |
|---|---|---|---|---|---|
| 2-304 | 3,4,5-Cl$_3$ | 2-Cl | H | D-24a | *1 |
| 2-305 | 3,5-Cl$_2$ | 2-Cl | H | (D-52d)Cl | 65.0-70.0 |
| 2-306 | 3,4,5-Cl$_3$ | 2-Cl | H | (D-53b)Cl | *1 |
| 2-307 | 3,4,5-Cl$_3$ | 2-Br | H | (D-53b)Cl | *1 |
| 2-308 | 3,5-Cl$_2$ | — | CH$_3$ | (D-53b)Cl | *1 |
| 2-309 | 3,4,5-Cl$_3$ | — | CH$_3$ | (D-53b)Cl | *1 |
| 2-310 | 3,5-Cl$_2$ | 2-Cl | H | (D-53e)Cl | *1 |
| 2-311 | 3,4,5-Cl$_3$ | 2-Cl | H | (D-53e)Cl | *1 |
| 2-312 | 3,4,5-Cl$_3$ | 2-Br | H | (D-53e)Cl | *1 |
| 2-313 | 3,4,5-Cl$_3$ | — | CH$_3$ | (D-53e)Cl | 125.0-130.0 |
| 2-314 | 3,4,5-Cl$_3$ | — | CH$_3$ | D-55a | *1 |
| 2-315 | 3,5-Cl$_2$ | 2-Cl | H | D-58a | *1 |
| 2-316 | 3,5-(CF$_3$)$_2$ | 2-Br | H | Et | *1 |
| 2-317 | 3,5-(CF$_3$)$_2$ | — | CH$_3$ | Et | *1 |
| 2-318 | 3-CF$_3$-4-Cl | 2-Cl | H | n-Pr | *1 |
| 2-319 | 3,5-(CF$_3$)$_2$ | 2-Br | H | n-Pr | *1 |
| 2-320 | 3,5-(CF$_3$)$_2$ | — | CH$_3$ | n-Pr | *1 |
| 2-321 | 3,5-(CF$_3$)$_2$ | 2-Br | H | i-Pr | *1 |
| 2-322 | 3,5-(CF$_3$)$_2$ | — | CH$_3$ | i-Pr | *1 |
| 2-323 | 3-CF$_3$-4-Cl | 2-Cl | H | c-Pr | *1 |
| 2-324 | 3,5-(CF$_3$)$_2$ | 2-Br | H | c-Pr | *1 |
| 2-325 | 3,5-(CF$_3$)$_2$ | — | CN | c-Pr | 157.0-162.0 |
| 2-326 | 3-CF$_3$-4-Cl | 2-Cl | H | CH$_2$Pr-c | *1 |
| 2-327 | 3,5-Cl$_2$-4-OCHF$_2$ | 2-Cl | H | CH$_2$Pr-c | *1 |
| 2-328 | 3,5-(CF$_3$)$_2$ | 2-Br | H | CH$_2$Pr-c | *1 |
| 2-329 | 3,5-(CF$_3$)$_2$ | — | CN | CH$_2$Pr-c | 137.0-139.0 |
| 2-330 | 3-CF$_3$-4-Cl | 2-Cl | H | CH$_2$CF$_3$ | *1 |
| 2-331 | 3-CF$_3$-4-Cl | 2-Cl | H | E-5a | *1 |
| 2-332 | 3,5-(CF$_3$)$_2$ | 2-Br | H | E-5a | *1 |
| 2-333 | 3,5-(CF$_3$)$_2$ | — | CH$_3$ | E-5a | *1 |
| 2-334 | 3,4,5-Cl$_3$ | 2-Cl | H | CH$_2$NHCH$_2$Pr-c | *1 |
| 2-335 | 3,4,5-Cl$_3$ | 2-Cl | H | CH$_2$NHC(O)CF$_3$ | 176.0-180.0 |
| 2-336 | 3,4,5-Cl$_3$ | 2-Cl | H | CH$_2$N(CH$_3$)C(O)CF$_3$ | *1 |
| 2-337 | 3,4,5-Cl$_3$ | 2-Cl | H | CH$_2$N(CH$_2$Pr-c)C(O)CF$_3$ | *1 |
| 2-338 | 3,4,5-Cl$_3$ | 2-Cl | H | CH$_2$N(CH$_2$C≡CH)C(O)CF$_3$ | *1 |
| 2-339 | 3,4,5-Cl$_3$ | 2-Cl | H | CH$_2$N(CH$_2$Pr-c)C(O)OCH$_3$ | *1 |
| 2-340 | 3,4,5-Cl$_3$ | 2-Cl | H | CH$_2$N(CH$_2$C≡CH)C(O)OCH$_3$ | *1 |
| 2-341 | 3,4,5-Cl$_3$ | 2-Cl | H | CH$_2$N(CH$_3$)C(O)OEt | *1 |
| 2-342 | 3,4,5-Cl$_3$ | 2-Cl | H | CH$_2$N(CH$_3$)C(O)NHEt | *1 |
| 2-343 | 3,4,5-Cl$_3$ | 2-Cl | H | CH$_2$C(O)NHPr-n | *1 |
| 2-344 | 3,5-(CF$_3$)$_2$ | 2-Cl | H | CH$_2$CH$_2$C≡CH | *1 |
| 2-345 | 3,5-(CF$_3$)$_2$ | 2-Br | H | CH$_2$CH$_2$C≡CH | *1 |
| 2-346 | 3,5-(CF$_3$)$_2$ | — | CH$_3$ | CH$_2$CH$_2$C≡CH | *1 |
| 2-347 | 3-CF$_3$-4-Cl | 2-Cl | H | Ph-2,4,6-F$_3$ | 137.0-140.0 |
| 2-348 | 3,5-Cl$_2$ | — | CH$_3$ | T-33 | *1 |
| 2-349 | 3,5-(CF$_3$)$_2$ | 2-F | H | CH$_3$ | 151.0-153.0 |
| 2-350 | 3-Br-5-CF$_3$ | 2-Cl | H | CH$_3$ | *1 |
| 2-351 | 3-I-5-CF$_3$ | 2-Cl | H | CH$_3$ | 92.0-94.0 |
| 2-352 | 3,5-Br$_2$-4-F | 2-Cl | H | CH$_3$ | *1 |
| 2-353 | 3,5-Br$_2$-4-Cl | 2-Cl | H | CH$_3$ | *1 |
| 2-354 | 3-Cl-5-CF$_3$ | 2-Br | H | CH$_3$ | *1 |
| 2-355 | 3-Br-5-CF$_3$ | 2-Br | H | CH$_3$ | 106.0-107.0 |
| 2-356 | 3,5-Br$_2$-4-F | 2-Br | H | CH$_3$ | *1 |
| 2-357 | 3,5-Br$_2$-4-F | 2-I | H | CH$_3$ | *1 |
| 2-358 | 3,5-(CF$_3$)$_2$ | 2-NO$_2$ | H | CH$_3$ | *1 |
| 2-359 | 3-Cl-5-CF$_3$ | — | CH$_3$ | CH$_3$ | 148.0-154.0 |
| 2-360 | 3-I-5-CF$_3$ | — | CH$_3$ | CH$_3$ | 114.0-116.0 |
| 2-361 | 3,5-Br$_2$-4-F | — | CH$_3$ | CH$_3$ | 131.0-134.0 |
| 2-362 | 3,5-(CF$_3$)$_2$ | 2-F | H | Et | *1 |
| 2-363 | 3-CF$_3$ | 2-Cl | H | Et | 100.0-103.0 |
| 2-364 | 3-Br-5-CF$_3$ | 2-Cl | H | Et | *1 |
| 2-365 | 3-I-5-CF$_3$ | 2-Cl | H | Et | 138.0-140.0 |
| 2-366 | 3,5-Br$_2$-4-F | 2-Cl | H | Et | *1 |
| 2-367 | 3,5-Br$_2$-4-Cl | 2-Cl | H | Et | *1 |
| 2-368 | 3,4-Cl$_2$-5-CF$_3$ | 2-Cl | H | Et | *1 |
| 2-369 | 3-CF$_3$ | 2-Br | H | Et | 98.0-101.0 |
| 2-370 | 3-Cl-5-CF$_3$ | 2-Br | H | Et | *1 |

TABLE 6-continued

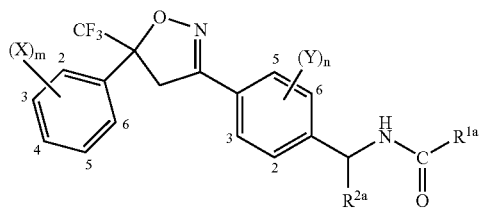

| No. | $(X)_m$ | $(Y)_n$ | $R^{2a}$ | $R^{1a}$ | m.p. (°C.) |
|---|---|---|---|---|---|
| 2-371 | 3-Br-5-$CF_3$ | 2-Br | H | Et | *1 |
| 2-372 | 3,5-$Br_2$-4-F | 2-Br | H | Et | *1 |
| 2-373 | 3,4-$Cl_2$-5-$CF_3$ | 2-Br | H | Et | *1 |
| 2-374 | 3,5-$(CF_3)_2$ | 2-I | H | Et | 154.0-156.0 |
| 2-375 | 3,5-$Br_2$-4-F | 2-I | H | Et | *1 |
| 2-376 | 3,5-$(CF_3)_2$ | 2-$NO_2$ | H | Et | 103.0-105.0 |
| 2-377 | 3-Cl-5-$CF_3$ | — | $CH_3$ | Et | 97.0-100.0 |
| 2-378 | 3-Br-5-$CF_3$ | — | $CH_3$ | Et | *1 |
| 2-379 | 3-I-5-$CF_3$ | — | $CH_3$ | Et | 105.0-108.0 |
| 2-380 | 3,5-$(CF_3)_2$ | — | $CH_3$(S) | Et | *1 |
| 2-381 | 3,5-$Br_2$-4-F | — | $CH_3$ | Et | 194.0-197.0 |
| 2-382 | 3,5-$(CF_3)_2$ | — | CN | Et | *1 |
| 2-383 | 3,4-$Cl_2$-5-$CF_3$ | — | CN | Et | 193.0-194.0 |
| 2-384 | 3,5-$(CF_3)_2$ | 2-Br | CN | Et | 165.0-167.0 |
| 2-385 | 3,5-$Cl_2$ | 2-$CH_3$ | CN | Et | *1 |
| 2-386 | 3,5-$(CF_3)_2$ | 2-F | H | n-Pr | *1 |
| 2-387 | 3-$CF_3$ | 2-Cl | H | n-Pr | *1 |
| 2-388 | 3-Br-5-$CF_3$ | 2-Cl | H | n-Pr | *1 |
| 2-389 | 3-I-5-$CF_3$ | 2-Cl | H | n-Pr | 154.0-156.0 |
| 2-390 | 3,5-$Br_2$-4-F | 2-Cl | H | n-Pr | *1 |
| 2-391 | 3,5-$Br_2$-4-Cl | 2-Cl | H | n-Pr | *1 |
| 2-392 | 3,4-$Cl_2$-5-$CF_3$ | 2-Cl | H | n-Pr | *1 |
| 2-393 | 3-$CF_3$ | 2-Br | H | n-Pr | *1 |
| 2-394 | 3-Cl-5-$CF_3$ | 2-Br | H | n-Pr | *1 |
| 2-395 | 3,5-$Br_2$-4-F | 2-Br | H | n-Pr | *1 |
| 2-396 | 3,5-$(CF_3)_2$ | 2-I | H | n-Pr | 165.0-167.0 |
| 2-397 | 3,5-$Br_2$-4-F | 2-I | H | n-Pr | *1 |
| 2-398 | 3,5-$(CF_3)_2$ | 2-$NO_2$ | H | n-Pr | *1 |
| 2-399 | 3-Cl-5-$CF_3$ | — | $CH_3$ | n-Pr | 88.0-90.0 |
| 2-400 | 3-I-5-$CF_3$ | — | $CH_3$ | n-Pr | 102.0-105.0 |
| 2-401 | 3,5-$Br_2$-4-F | — | $CH_3$ | n-Pr | 160.0-162.0 |
| 2-402 | 3,5-$(CF_3)_2$ | — | CN | n-Pr | 145.0-148.0 |
| 2-403 | 3,5-$(CF_3)_2$ | 2-F | H | i-Pr | *1 |
| 2-404 | 3-Br-5-$CF_3$ | 2-Cl | H | i-Pr | *1 |
| 2-405 | 3-I-5-$CF_3$ | 2-Cl | H | i-Pr | 160.0-162.0 |
| 2-406 | 3,5-$Br_2$-4-F | 2-Cl | H | i-Pr | *1 |
| 2-407 | 3,5-$Br_2$-4-Cl | 2-Cl | H | i-Pr | *1 |
| 2-408 | 3,4-$Cl_2$-5-$CF_3$ | 2-Cl | H | i-Pr | *1 |
| 2-409 | 3-Cl-5-$CF_3$ | 2-Br | H | i-Pr | *1 |
| 2-410 | 3-Br-5-$CF_3$ | 2-Br | H | i-Pr | *1 |
| 2-411 | 3,5-$Br_2$-4-F | 2-Br | H | i-Pr | *1 |
| 2-412 | 3,4-$Cl_2$-5-$CF_3$ | 2-Br | H | i-Pr | *1 |
| 2-413 | 3,5-$(CF_3)_2$ | 2-I | H | i-Pr | 150.0-152.0 |
| 2-414 | 3,5-$Br_2$-4-F | 2-I | H | i-Pr | *1 |
| 2-415 | 3,5-$(CF_3)_2$ | 2-$NO_2$ | H | i-Pr | *1 |
| 2-416 | 3-Cl-5-$CF_3$ | — | $CH_3$ | i-Pr | 109.0-113.0 |
| 2-417 | 3-Br-5-$CF_3$ | — | $CH_3$ | i-Pr | 125.0-127.0 |
| 2-418 | 3-I-5-$CF_3$ | — | $CH_3$ | i-Pr | 125.0-127.0 |
| 2-419 | 3,5-$Br_2$-4-F | — | $CH_3$ | i-Pr | 177.0-179.0 |
| 2-420 | 3,5-$(CF_3)_2$ | — | CN | i-Pr | *1 |
| 2-421 | 3,5-$(CF_3)_2$ | 2-F | H | c-Pr | *1 |
| 2-422 | 3-Br-4-F | 2-Cl | H | c-Pr | *1 |
| 2-423 | 3-Br-5-$CF_3$ | 2-Cl | H | c-Pr | *1 |
| 2-424 | 3-I-5-$CF_3$ | 2-Cl | H | c-Pr | 179.0-181.0 |
| 2-425 | 3,5-$Br_2$-4-F | 2-Cl | H | c-Pr | *1 |
| 2-426 | 3,5-$Br_2$-4-Cl | 2-Cl | H | c-Pr | *1 |
| 2-427 | 3,4-$Cl_2$-5-$CF_3$ | 2-Cl | H | c-Pr | *1 |
| 2-428 | 3-$CF_3$ | 2-Br | H | c-Pr | *1 |
| 2-429 | 3-Cl-5-$CF_3$ | 2-Br | H | c-Pr | *1 |
| 2-430 | 3-Br-5-$CF_3$ | 2-Br | H | c-Pr | 170.0-172.0 |
| 2-431 | 3,5-$Br_2$-4-F | 2-Br | H | c-Pr | *1 |
| 2-432 | 3,4-$Cl_2$-5-$CF_3$ | 2-Br | H | c-Pr | *1 |
| 2-433 | 3,5-$(CF_3)_2$ | 2-I | H | c-Pr | 160.0-161.0 |
| 2-434 | 3,5-$Br_2$-4-F | 2-I | H | c-Pr | *1 |
| 2-435 | 3,5-$(CF_3)_2$ | 2-C≡CH | H | c-Pr | *1 |
| 2-436 | 3,5-$(CF_3)_2$ | 2-CN | H | c-Pr | 147.0-148.0 |
| 2-437 | 3,5-$(CF_3)_2$ | 2-$NO_2$ | H | c-Pr | *1 |

TABLE 6-continued

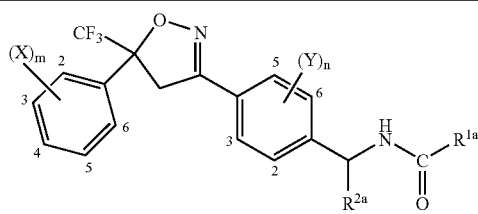

| No. | (X)$_m$ | (Y)$_n$ | R$^{2a}$ | R$^{1a}$ | m.p. (°C.) |
|---|---|---|---|---|---|
| 2-438 | 3-Cl-5-CF$_3$ | — | CH$_3$ | c-Pr | 105.0-108.0 |
| 2-439 | 3-Br-5-CF$_3$ | — | CH$_3$ | c-Pr | *1 |
| 2-440 | 3-I-5-CF$_3$ | — | CH$_3$ | c-Pr | 124.0-126.0 |
| 2-441 | 3,5-(CF$_3$)$_2$ | — | CH$_3$(S) | c-Pr | *1 |
| 2-442 | 3,5-Br$_2$-4-F | — | CH$_3$ | c-Pr | 208.0-210.0 |
| 2-443 | 3,4-Cl$_2$-5-CF$_3$ | — | CH$_3$ | c-Pr | *1 |
| 2-444 | 3,5-(CF$_3$)$_2$ | 2-Br | CH$_3$ | c-Pr | 101.0-105.0 |
| 2-445 | 3,5-(CF$_3$)$_2$ | 2-I | CH$_3$ | c-Pr | 177.0-179.0 |
| 2-446 | 3,5-(CF$_3$)$_2$ | 2-NO$_2$ | CH$_3$ | c-Pr | 172.0-175.0 |
| 2-447 | 3,5-Cl$_2$ | — | CH$_2$SCH$_3$ | c-Pr | *1 |
| 2-448 | 3,5-(CF$_3$)$_2$ | — | C≡CH | c-Pr | *1 |
| 2-449 | 3,4-Cl$_2$-5-CF$_3$ | — | CN | c-Pr | 185.0-186.0 |
| 2-450 | 3,5-(CF$_3$)$_2$ | 2-Cl | CN | c-Pr | *1 |
| 2-451 | 3,5-(CF$_3$)$_2$ | 2-Br | CN | c-Pr | *1 |
| 2-452 | 3,5-Cl$_2$ | 2-I | CN | c-Pr | *1 |
| 2-453 | 3,5-(CF$_3$)$_2$ | 2-I | CN | c-Pr | *1 |
| 2-454 | 3,5-Cl$_2$ | 2-CH$_3$ | CN | c-Pr | *1 |
| 2-455 | 3,5-Cl$_2$ | — | C(O)NH$_2$ | c-Pr | *1 |
| 2-456 | 3,5-(CF$_3$)$_2$ | 2-F | H | i-Bu | *1 |
| 2-457 | 3-Br-5-CF$_3$ | 2-Cl | H | i-Bu | *1 |
| 2-458 | 3-I-5-CF$_3$ | 2-Cl | H | i-Bu | 162.0-164.0 |
| 2-459 | 3,5-Br$_2$-4-F | 2-Cl | H | i-Bu | *1 |
| 2-460 | 3,5-Br$_2$-4-Cl | 2-Cl | H | i-Bu | *1 |
| 2-461 | 3,4-Cl$_2$-5-CF$_3$ | 2-Cl | H | i-Bu | *1 |
| 2-462 | 3-Cl-5-CF$_3$ | 2-Br | H | i-Bu | 148.0-150.0 |
| 2-463 | 3-Br-5-CF$_3$ | 2-Br | H | i-Bu | *1 |
| 2-464 | 3,5-Br$_2$-4-F | 2-Br | H | i-Bu | *1 |
| 2-465 | 3,4-Cl$_2$-5-CF$_3$ | 2-Br | H | i-Bu | *1 |
| 2-466 | 3,5-Br$_2$-4-F | 2-I | H | i-Bu | *1 |
| 2-467 | 3,5-(CF$_3$)$_2$ | 2-NO$_2$ | H | i-Bu | *1 |
| 2-468 | 3-Cl-5-CF$_3$ | — | CH$_3$ | i-Bu | 98.0-100.0 |
| 2-469 | 3-Br-5-CF$_3$ | — | CH$_3$ | i-Bu | 104.0-107.0 |
| 2-470 | 3-I-5-CF$_3$ | — | CH$_3$ | i-Bu | 103.0-105.0 |
| 2-471 | 3,5-Br$_2$-4-F | — | CH$_3$ | i-Bu | 167.0-170.0 |
| 2-472 | 3-CF$_3$ | 2-Cl | H | CH$_2$Pr-c | *1 |
| 2-473 | 3-Br-5-CF$_3$ | 2-Cl | H | CH$_2$Pr-c | 124.0-127.0 |
| 2-474 | 3-I-5-CF$_3$ | 2-Cl | H | CH$_2$Pr-c | 148.0-150.0 |
| 2-475 | 3,5-Br$_2$-4-F | 2-Cl | H | CH$_2$Pr-c | *1 |
| 2-476 | 3,5-Br$_2$-4-Cl | 2-Cl | H | CH$_2$Pr-c | *1 |
| 2-477 | 3-CF$_3$ | 2-Br | H | CH$_2$Pr-c | *1 |
| 2-478 | 3-Cl-5-CF$_3$ | 2-Br | H | CH$_2$Pr-c | *1 |
| 2-479 | 3-Br-5-CF$_3$ | 2-Br | H | CH$_2$Pr-c | 152.0-153.0 |
| 2-480 | 3,5-(CF$_3$)$_2$ | 2-I | H | CH$_2$Pr-c | 160.0-161.0 |
| 2-481 | 3-Cl-5-CF$_3$ | — | CH$_3$ | CH$_2$Pr-c | *1 |
| 2-482 | 3-I-5-CF$_3$ | — | CH$_3$ | CH$_2$Pr-c | *1 |
| 2-483 | 3,5-(CF$_3$)$_2$ | — | CH$_3$(R) [α]$_D^{20.0}$ + 31.70° | CH$_2$Pr-c (CH$_3$CN, c = 1.217) | 97.0-98.0 |
| 2-484 | 3,5-(CF$_3$)$_2$ | — | CH$_3$(S) [α]$_D^{20.0}$ − 32.92° | CH$_2$Pr-c (CH$_3$CN, c = 1.253) | 97.0-99.0 |
| 2-485 | 3,5-Cl$_2$ | 2-Cl | CN | CH$_2$Pr-c | *1 |
| 2-486 | 3,5-Cl$_2$ | 2-CH$_3$ | CN | CH$_2$Pr-c | *1 |
| 2-487 | 3-Br-5-CF$_3$ | 2-Cl | H | s-Bu | 154.0-157.5 |
| 2-488 | 3,5-(CF$_3$)$_2$ | 2-Cl | H | CHBr$_2$ | 107.0-109.0 |
| 2-489 | 3-I-5-CF$_3$ | 2-Cl | H | CH$_2$CF$_3$ | 174.0-176.0 |
| 2-490 | 3-Cl-5-CF$_3$ | 2-Br | H | CH$_2$CF$_3$ | 150.0-152.0 |
| 2-491 | 3-Cl-5-CF$_3$ | — | CH$_3$ | CH$_2$CF$_3$ | 127.0-128.0 |
| 2-492 | 3-I-5-CF$_3$ | — | CH$_3$ | CH$_2$CF$_3$ | 154.0-156.0 |
| 2-493 | 3,5-(CF$_3$)$_2$ | 2-Cl | H | T-32 | *1 |
| 2-494 | 3,5-(CF$_3$)$_2$ | 2-Cl | H | E-4a | *1 |
| 2-495 | 3-CF$_3$ | 2-Cl | H | E-5a | 133.0-136.5 |
| 2-496 | 3-Br-5-CF$_3$ | 2-Cl | H | E-5a | 152.5-156.0 |
| 2-497 | 3-I-5-CF$_3$ | 2-Cl | H | E-5a | 184.0-186.0 |
| 2-498 | 3-Cl-5-CF$_3$ | 2-Br | H | E-5a | 160.0-163.0 |
| 2-499 | 3-Br-5-CF$_3$ | 2-Br | H | E-5a | 173.0-175.0 |
| 2-500 | 3,5-(CF$_3$)$_2$ | 2-I | H | E-5a | *1 |
| 2-501 | 3,5-(CF$_3$)$_2$ | 2-NO$_2$ | H | E-5a | *1 |
| 2-502 | 3-Cl-5-CF$_3$ | — | CH$_3$ | E-5a | *1 |

TABLE 6-continued

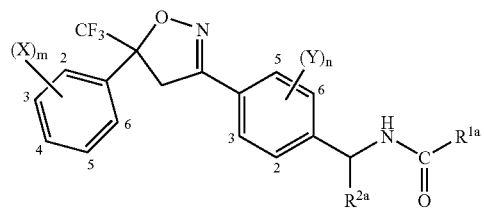

| No. | $(X)_m$ | $(Y)_n$ | $R^{2a}$ | $R^{1a}$ | m.p. (°C.) |
|---|---|---|---|---|---|
| 2-503 | 3,5-$(CF_3)_2$ | — | CN | E-5a | *1 |
| 2-504 | 3,5-$Cl_2$ | 2-$CH_3$ | CN | $CH_2SEt$ | *1 |
| 2-505 | 3,5-$Cl_2$ | 2-$CH_3$ | CN | $CH_2S(O)Et$ | *1 |
| 2-506 | 3,5-$Cl_2$ | 2-$CH_3$ | CN | $CH_2SO_2Et$ | *1 |
| 2-507 | 3,5-$Cl_2$ | 2-$CH_3$ | CN | $CH_2S(O)(Et)=NH$ | *1 |
| 2-508 | 3,5-$(CF_3)_2$ | 2-Cl | H | T-34 | *1 |
| 2-509 | 3,5-$(CF_3)_2$ | 2-Cl | H | $CH_2$(E-26a) | *1 |
| 2-510 | 3,5-$(CF_3)_2$ | 2-Cl | H | $CH_2$(E-26b) | *1 |
| 2-511 | 3,5-$(CF_3)_2$ | 2-Cl | H | $CH_2$(E-26c) | *1 |
| 2-512 | 3,4,5-$Cl_3$ | 2-Cl | H | $CH_2N(CH_3)C(O)CH_3$ | *1 |
| 2-513 | 3,5-$(CF_3)_2$ | 2-Cl | H | $CH_2N(CH_3)C(O)CH_2OCH_3$ | *1 |
| 2-514 | 3,5-$(CF_3)_2$ | 2-Cl | H | $CH_2N(CH_3)C(O)OCH_3$ | *1 |
| 2-515 | 3,4,5-$Cl_3$ | 2-Cl | H | $CH_2N(Pr-c)C(O)OCH_3$ | *1 |
| 2-516 | 3,4,5-$Cl_3$ | 2-Cl | H | $CH_2N(CH_3)C(O)OPr-i$ | *1 |
| 2-517 | 3,4,5-$Cl_3$ | 2-Cl | H | $CH_2N(CH_3)C(O)SCH_3$ | *1 |
| 2-518 | 3,4,5-$Cl_3$ | 2-Cl | H | $CH_2N(CH_3)SO_2CH_3$ | *1 |
| 2-519 | 3,5-$(CF_3)_2$ | 2-Cl | H | $CH_2N(CH_3)SO_2CF_3$ | 181.0-187.0 |
| 2-520 | 3,4,5-$Cl_3$ | 2-Cl | H | $CH(CH_3)NHCH_3$ | *1 |
| 2-521 | 3,4,5-$Cl_3$ | 2-Cl | H | $CH(CH_3)N(CH_3)C(O)OCH_3$ | *1 |
| 2-522 | 3,5-$(CF_3)_2$ | 2-Cl | H | (M-7a)$CH_3$ | *1 |
| 2-523 | 3,4,5-$Cl_3$ | 2-Cl | H | $CH_2C(O)NH_2$ | *1 |
| 2-524 | 3,5-$(CF_3)_2$ | 2-Cl | H | $CH_2C(NH_2)=NOH$ | *1 |
| 2-525 | 3,4,5-$Cl_3$ | 2-Cl | H | $CH_2C(NH_2)=NOEt$ | *1 |
| 2-526 | 3,4,5-$Cl_3$ | 2-Cl | H | $CH_2C(=NOEt)NHC(O)CF_3$ | 156.0-158.0 |
| 2-527 | 3,5-$(CF_3)_2$ | 2-Cl | H | $CH_2CH=CH_2$ | 140.0-141.0 |
| 2-528 | 3-$CF_3$ | 2-Cl | H | $CH_2CH_2C≡CH$ | 91.0-93.5 |
| 2-529 | 3,5-$(CF_3)_2$ | 2-I | H | $CH_2CH_2C≡CH$ | *1 |
| 2-530 | 3,5-$(CF_3)_2$ | — | CN | $CH_2CH_2C≡CH$ | *1 |
| 2-531 | 3,5-$(CF_3)_2$ | 2-Cl | H | $CH_2$(D-3a) | 175.0-178.0 |
| 2-532 | 3,5-$(CF_3)_2$ | 2-Cl | H | $CH_2$(D-3e) | 189.0-191.0 |
| 2-533 | 3-$CF_3$ | 2-Cl | H | Ph-2,4,6-$F_3$ | 128.0-131.0 |
| 2-534 | 3-$CF_3$ | 2-Br | H | Ph-2,4,6-$F_3$ | 159.0-161.0 |
| 2-535 | 3,5-$(CF_3)_2$ | 2-Cl | H | D-24a | *1 |
| 2-536 | 3-Br-5-$CF_3$ | 2-Cl | H | (D-53b)Cl | *1 |
| 2-537 | 3-I-5-$CF_3$ | 2-Cl | H | (D-53b)Cl | *1 |
| 2-538 | 3-Cl-5-$CF_3$ | 2-Br | H | (D-53b)Cl | *1 |

TABLE 7

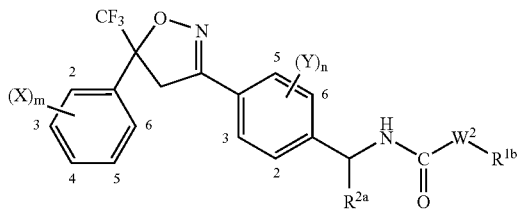

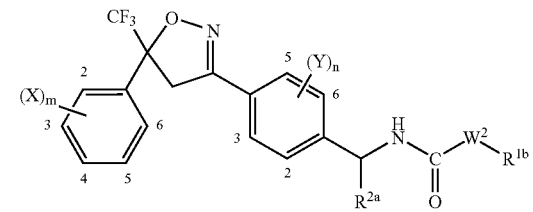

| No. | $(X)_m$ | $(Y)_n$ | $R^{2a}$ | $W^2$ | $R^{1b}$ | m.p. (° C.) |
|---|---|---|---|---|---|---|
| 3-001 | 3,5-$Cl_2$ | — | H | O | $CH_3$ | 122.0-124.0 |
| 3-002 | 3,5-$Cl_2$ | — | H | I | i-Bu | 108.0-110.0 |
| 3-003 | 3,5-$Cl_2$ | — | H | O | $CH_2CH_2Cl$ | *2 |
| 3-004 | 3,5-$Cl_2$ | 2-Cl | H | O | $CH_2CF_3$ | *1 |
| 3-005 | 3,5-$Cl_2$ | 2-Cl | H | S | Et | 122.0-124.0 |
| 3-006 | 3,4,5-$Cl_3$ | 2-$NO_2$ | H | O | t-Bu | *1 |
| 3-007 | 3,4,5-$Cl_3$ | 2-Cl | H | O | $CH_2CF_3$ | *1 |
| 3-008 | 3,5-$Cl_2$ | 2-Br | H | O | $CH_2CF_3$ | *1 |
| 3-009 | 3,4,5-$Cl_3$ | — | $CH_3$ | O | $CH_2CF_3$ | *1 |
| 3-010 | 3,4,5-$Cl_2$ | 2-Cl | H | O | $CH_2C≡CH$ | *1 |
| 3-011 | 3,4,5-$Cl_2$ | 2-Cl | H | S | $CH_3$ | *1 |
| 3-012 | 3,4,5-$Cl_2$ | 2-Cl | H | S | Et | *1 |
| 3-013 | 3,5-$(CF_3)_2$ | 2-Br | H | S | $CH_3$ | *1 |
| 3-014 | 3,5-$(CF_3)_2$ | — | $CH_3$(R) | O | t-Bu | *1 |
| 3-015 | 3,5-$(CF_3)_2$ | — | $CH_3$(S) | O | t-Bu | *1 |

TABLE 8

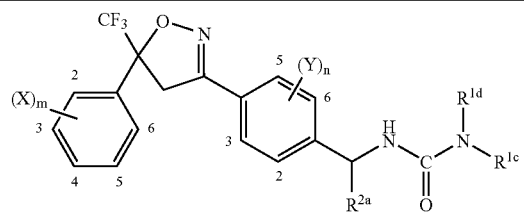

| No. | (X)$_m$ | (Y)$_n$ | R$^{2a}$ | R$^{1d}$ | R$^{1c}$ | m.p. (° C.) |
|---|---|---|---|---|---|---|
| 4-001 | 3,5-Cl$_2$ | — | H | H | CH$_2$CF$_3$ | *1 |
| 4-002 | 3,5-Cl$_2$ | — | CH$_3$ | H | Et | *2 |
| 4-003 | 3,5-Cl$_2$ | — | CH$_3$ | H | i-Pr | *1 |
| 4-004 | 3,5-Cl$_2$ | — | CH$_3$ | H | CH$_2$CH$_2$Cl | *1 |
| 4-005 | 3,5-Cl$_2$ | — | CN | H | Et | 169.0-170.0 |
| 4-006 | 3,5-Cl$_2$ | — | CN | H | i-Pr | 172.0-175.0 |
| 4-007 | 3,5-Cl$_2$ | 2-Cl | H | H | OCH$_3$ | *2 |
| 4-008 | 3,5-Cl$_2$ | 2-Br | H | H | CH$_2$CF$_3$ | 202.0-204.0 |
| 4-009 | 3,5-Cl$_2$ | 2-I | H | H | CH$_2$CF$_3$ | *1 |
| 4-010 | 3,5-Cl$_2$ | 2-CH$_3$ | H | H | Et | 128.0-132.0 |
| 4-011 | 3,5-Cl$_2$ | 2-Cl | H | CH$_3$ | CH$_3$ | *2 |
| 4-012 | 3,5-Cl$_2$ | 2-Cl | H | H | c-Pr | *1 |
| 4-013 | 3,5-Cl$_2$ | 2-Cl | H | H | CH$_2$CF$_3$ | *1 |
| 4-014 | 3,5-Cl$_2$ | 2-Cl | H | H | H | *1 |
| 4-015 | 3,4,5-Cl$_3$ | 2-Cl | H | H | Et | *1 |
| 4-016 | 3,5-Cl$_2$ | 2-Br | H | H | Et | *1 |
| 4-017 | 3,4,5-Cl$_3$ | — | CH$_3$ | H | Et | * |
| 4-018 | 3,4,5-Cl$_3$ | 2-Cl | H | Et | Et | *1 |
| 4-019 | 3,4,5-Cl$_3$ | 2-NO$_2$ | H | Et | Et | *1 |
| 4-020 | 3,4,5-Cl$_3$ | 2-Cl | H | H | i-Pr | *1 |
| 4-021 | 3,5-Cl$_2$ | 2-Br | H | H | i-Pr | *1 |
| 4-022 | 3,4,5-Cl$_3$ | — | CH$_3$ | H | i-Pr | *1 |
| 4-023 | 3,5-(CF$_3$)$_2$ | 2-Cl | H | H | c-Pr | *1 |
| 4-024 | 3,4,5-Cl$_3$ | 2-Cl | H | H | c-Pr | *1 |
| 4-025 | 3,4,5-Cl$_3$ | 2-Br | H | H | c-Pr | *1 |
| 4-026 | 3,4,5-Cl$_3$ | 2-NO$_2$ | H | H | c-Pr | 157.0-161.0 |
| 4-027 | 3,5-(CF$_3$)$_2$ | — | CH$_3$ | H | c-Pr | *1 |
| 4-028 | 3,4,5-Cl$_3$ | — | CH$_3$ | H | c-Pr | *1 |
| 4-029 | 3,4,5-Cl$_3$ | 2-Cl | H | H | i-Bu | *1 |
| 4-030 | 3,5-Cl$_2$ | 2-Cl | H | H | CH$_2$Pr-c | *1 |
| 4-031 | 3,4,5-Cl$_3$ | 2-Cl | H | H | CH$_2$Pr-c | *1 |
| 4-032 | 3,4,5-Cl$_3$ | 2-Cl | H | H | c-Bu | *1 |
| 4-033 | 3,4,5-Cl$_3$ | 2-Cl | H | H | CH$_2$Bu-t | *1 |
| 4-034 | 3,4,5-Cl$_3$ | 2-Cl | H | H | c-Pen | *1 |
| 4-035 | 3,4,5-Cl$_3$ | — | CH$_3$ | H | CH$_2$CH$_2$Cl | *1 |
| 4-036 | 3,4,5-Cl$_3$ | 2-Cl | H | H | CH$_2$CF$_3$ | *1 |
| 4-037 | 3,4,5-Cl$_3$ | 2-Br | H | H | CH$_2$CF$_3$ | 193.0-196.0 |
| 4-038 | 3,4,5-Cl$_3$ | 2-NO$_2$ | H | H | CH$_2$CF$_3$ | 229.0-231.0 |
| 4-039 | 3,4,5-Cl$_3$ | — | CH$_3$ | H | CH$_2$CF$_3$ | *1 |
| 4-040 | 3,4,5-Cl$_3$ | 2-Cl | H | H | CH$_2$CH$_2$OCH$_3$ | *1 |
| 4-041 | 3,4,5-Cl$_3$ | 2-Cl | H | H | CH$_2$CH$_2$SCH$_3$ | *1 |
| 4-042 | 3,4,5-Cl$_3$ | 2-Cl | H | H | CH$_2$CH$_2$SO$_2$CH$_3$ | 228.0-231.0 |
| 4-043 | 3,4,5-Cl$_3$ | 2-Cl | H | H | CH$_2$CH$_2$SEt | *1 |
| 4-044 | 3,4,5-Cl$_3$ | 2-Cl | H | H | CH$_2$CH$_2$SO$_2$Et | *1 |
| 4-045 | 3,4,5-Cl$_3$ | 2-Cl | H | H | CH$_2$CH$_2$N(CH$_3$)$_2$ | *1 |
| 4-046 | 3,4,5-Cl$_3$ | 2-Cl | H | H | CH$_2$CN | 217.0-220.0 |
| 4-047 | 3,4,5-Cl$_3$ | 2-Cl | H | H | CH$_2$C(O)OCH$_3$ | *1 |
| 4-048 | 3,4,5-Cl$_3$ | 2-Cl | H | H | CH$_2$C(O)OEt | *1 |
| 4-049 | 3,4,5-Cl$_3$ | 2-Br | H | H | CH$_2$C(O)NHCH$_2$CF$_3$ | *1 |
| 4-050 | 3,4,5-Cl$_3$ | 2-Cl | H | H | CH$_2$Si(CH$_3$)$_3$ | *1 |
| 4-051 | 3,4,5-Cl$_3$ | 2-Cl | H | H | CH$_2$CH=CH$_2$ | *1 |
| 4-052 | 3,5-Cl$_2$ | 2-Cl | H | H | CH$_2$C≡CH | *1 |
| 4-053 | 3,4,5-Cl$_3$ | 2-Cl | H | H | CH$_2$C≡CH | *1 |
| 4-054 | 3,4,5-Cl$_3$ | 2-NO$_2$ | H | H | CH$_2$C≡CH | 128.0-131.0 |
| 4-055 | 3,4,5-Cl$_3$ | — | CH$_3$ | H | CH$_2$C≡CH | *1 |
| 4-056 | 3,4,5-Cl$_3$ | 2-Cl | H | CH$_3$ | CH$_2$C≡CH | *1 |
| 4-057 | 3,4,5-Cl$_3$ | 2-Cl | H | H | CH$_2$Ph | *1 |
| 4-058 | 3,4,5-Cl$_3$ | — | CH$_3$ | H | CH$_2$Ph | *1 |
| 4-059 | 3,4,5-Cl$_3$ | 2-Cl | H | H | CH$_2$(Ph-2-F) | 161.0-165.0 |
| 4-060 | 3,4,5-Cl$_3$ | 2-Cl | H | H | CH$_2$(Ph-3-F) | 188.0-191.0 |
| 4-061 | 3,4,5-Cl$_3$ | 2-Cl | H | H | CH$_2$(Ph-4-F) | 193.0-195.0 |
| 4-062 | 3,4,5-Cl$_3$ | 2-Cl | H | H | CH$_2$(Ph-4-Cl) | *1 |
| 4-063 | 3,4,5-Cl$_3$ | 2-Cl | H | H | CH$_2$(Ph-2-CF$_3$) | *1 |
| 4-064 | 3,4,5-Cl$_3$ | 2-Cl | H | H | CH$_2$(Ph-3-CF$_3$) | *1 |
| 4-065 | 3,4,5-Cl$_3$ | 2-Cl | H | H | CH$_2$(Ph-4-CF$_3$) | *1 |
| 4-066 | 3,4,5-Cl$_3$ | 2-Cl | H | H | CH$_2$(D-1d)CH$_3$ | *1 |
| 4-067 | 3,4,5-Cl$_3$ | 2-Cl | H | H | CH$_2$(D-3a) | *1 |

TABLE 8-continued

| No. | $(X)_m$ | $(Y)_n$ | $R^{2a}$ | $R^{1d}$ | $R^{1c}$ | m.p. (° C.) |
|---|---|---|---|---|---|---|
| 4-068 | 3,4,5-Cl₃ | 2-Cl | H | H | CH₂(D-22a) | 232.0-236.0 |
| 4-069 | 3,4,5-Cl₃ | 2-Cl | H | H | CH₂(D-52a) | *1 |
| 4-070 | 3,4,5-Cl₃ | — | CH₃ | H | CH₂(D-52a) | *1 |
| 4-071 | 3,4,5-Cl₃ | 2-Cl | H | H | CH₂(D-53a) | *1 |
| 4-072 | 3,4,5-Cl₃ | 2-Cl | H | H | CH₂(D-54a) | *1 |
| 4-073 | 3,4,5-Cl₃ | — | CH₃ | H | CH(CN)Ph | 106.5-109.0 |
| 4-074 | 3,4,5-Cl₃ | 2-Cl | H | —CH₂CH₂CH₂CH₂— | | *1 |
| 4-075 | 3,4,5-Cl₃ | — | CH₃ | —CH₂CH₂CH₂CH₂— | | *1 |
| 4-076 | 3,4,5-Cl₃ | 2-Cl | H | —CH[C(O)OCH₃]CH₂CH₂CH₂— | | *1 |
| 4-077 | 3,4,5-Cl₃ | 2-Cl | H | —CH[C(O)NHCH₃]CH₂CH₂CH₂— | | *1 |
| 4-078 | 3,4,5-Cl₃ | 2-Cl | H | —CH₂CH₂CH₂CH₂CH₂— | | *1 |
| 4-079 | 3,4,5-Cl₃ | 2-Cl | H | —CH₂CH₂OCH₂CH₂— | | 114.0-116.0 |
| 4-080 | 3,5-Cl₂ | 2-Cl | H | —CH₂CH₂SCH₂— | | *1 |
| 4-081 | 3,4,5-Cl₃ | 2-Cl | H | —CH₂CH₂SCH₂CH₂— | | *1 |
| 4-082 | 3,4,5-Cl₃ | 2-Cl | H | —CH₂CH₂S(O)CH₂CH₂— | | *1 |
| 4-083 | 3,4,5-Cl₃ | 2-Cl | H | —CH₂CH₂SO₂CH₂CH₂— | | *1 |
| 4-084 | 3,4,5-Cl₃ | — | CH₃ | —CH₂CH₂SCH₂CH₂— | | *1 |
| 4-085 | 3,4,5-Cl₃ | — | CH₃ | —CH₂CH₂N(Ph)CH₂CH₂— | | *1 |
| 4-086 | 3,4,5-Cl₃ | 2-Cl | H | —CH₂CH₂CH₂C(O)— | | *1 |
| 4-087 | 3,4,5-Cl₃ | 2-Cl | H | H | C(O)OCH₃ | *1 |
| 4-088 | 3,5-Cl₂ | 2-Cl | H | —CH₂CH₂OC(O)— | | *1 |
| 4-089 | 3,4,5-Cl₃ | 2-Cl | H | H | M-14a | *1 |
| 4-090 | 3,4,5-Cl₃ | 2-Cl | H | H | Ph | *1 |
| 4-091 | 3,4,5-Cl₃ | 2-Cl | H | H | Ph-4-F | 193.0-195.0 |
| 4-092 | 3,4,5-Cl₃ | 2-Cl | H | H | Ph-4-Cl | 208.0-210.0 |
| 4-093 | 3,4,5-Cl₃ | 2-Cl | H | H | Ph-2-CF₃ | *1 |
| 4-094 | 3,4,5-Cl₃ | 2-Cl | H | H | Ph-4-CF₃ | *1 |
| 4-095 | 3,4,5-Cl₃ | 2-Cl | H | H | Ph-4-OCH₃ | 185.0-187.0 |
| 4-096 | 3,4,5-Cl₃ | 2-Cl | H | H | OCH₃ | *1 |
| 4-097 | 3,4,5-Cl₃ | 2-Cl | H | CH₃ | OCH₃ | *1 |
| 4-098 | 3,5-Cl₂ | 2-Cl | H | H | OEt | *1 |
| 4-099 | 3,5-Cl₂ | 2-Cl | H | H | SO₂CH₃ | *1 |
| 4-100 | 3,4,5-Cl₃ | 2-Cl | H | H | NH₂ | *1 |
| 4-101 | 3,4,5-Cl₃ | 2-Cl | H | Et | NH₂ | *1 |
| 4-102 | 3,4,5-Cl₃ | 2-Cl | H | t-Bu | NH₂ | *1 |
| 4-103 | 3,4,5-Cl₃ | 2-Cl | H | CH₂Ph | NH₂ | *1 |
| 4-104 | 3,5-Cl₂ | 2-Cl | H | H | N(CH₃)₂ | *1 |
| 4-105 | 3,4,5-Cl₃ | 2-Cl | H | H | N(CH₃)₂ | *1 |
| 4-106 | 3,4,5-Cl₃ | — | CH₃ | H | N(CH₃)₂ | *1 |
| 4-107 | 3,4,5-Cl₃ | 2-Cl | H | H | NHBu-t | *1 |
| 4-108 | 3,4,5-Cl₃ | 2-Cl | H | H | T-24 | *1 |
| 4-109 | 3,4,5-Cl₃ | 2-Cl | H | H | NHC(O)CH₃ | 128.0-130.0 |
| 4-110 | 3,4,5-Cl₃ | 2-Cl | H | H | NHC(O)Pr-n | *1 |
| 4-111 | 3,4,5-Cl₃ | 2-Cl | H | H | NHC(O)Pr-i | *1 |
| 4-112 | 3,4,5-Cl₃ | 2-Cl | H | H | NHC(O)Pr | 130.0-133.0 |
| 4-113 | 3,5-(CF₃)₂ | 2-Cl | H | H | NHC(O)OCH₃ | *1 |
| 4-114 | 3,4,5-Cl₃ | 2-Cl | H | H | NHC(O)OCH₃ | *1 |
| 4-115 | 3,4,5-Cl₃ | 2-Cl | H | H | NHC(O)OEt | 103.0-107.0 |
| 4-116 | 3,4,5-Cl₃ | 2-Cl | H | H | NHC(O)NH₂ | *1 |
| 4-117 | 3,4,5-Cl₃ | 2-Cl | H | H | NHC(S)NHCH₃ | 210.0-213.0 |
| 4-118 | 3,4,5-Cl₃ | 2-Cl | H | H | N(CH₃)Ph | *1 |
| 4-119 | 3,4,5-Cl₃ | 2-Cl | H | H | NH(Ph-4-CH₃) | *1 |
| 4-120 | 3,5-(CF₃)₂ | 2-Cl | H | H | Et | *1 |
| 4-121 | 3,5-(CF₃)₂ | 2-Br | H | H | Et | *1 |
| 4-122 | 3,5-(CF₃)₂ | — | CH₃ | H | Et | *1 |
| 4-123 | 3-CF₃-4-Cl | 2-Cl | H | H | c-Pr | *1 |
| 4-124 | 3,5-(CF₃)₂ | 2-Br | H | H | c-Pr | *1 |
| 4-125 | 3,5-(CF₃)₂ | 2-I | H | H | c-Pr | 177.0-181.0 |
| 4-126 | 3-CF₃-4-Cl | 2-Cl | H | H | CH₂CF₃ | 214.0-216.0 |
| 4-127 | 3,5-(CF₃)₂ | 2-Cl | H | H | CH₂C≡CH | *1 |
| 4-128 | 3,5-(CF₃)₂ | 2-Br | H | H | CH₂C≡CH | *1 |
| 4-129 | 3,5-(CF₃)₂ | — | CH₃ | H | CH₂C≡CH | *1 |
| 4-130 | 3,5-(CF₃)₂ | 2-F | H | H | Et | *1 |
| 4-131 | 3-Br-5-CF₃ | 2-Cl | H | H | Et | *1 |
| 4-132 | 3,5-Br₂-4-F | 2-Cl | H | H | Et | *1 |
| 4-133 | 3,5-Br₂-4-Cl | 2-Cl | H | H | Et | *1 |
| 4-134 | 3,4-Cl₂-5-CF₃ | 2-Cl | H | H | Et | *1 |

TABLE 8-continued

| No. | (X)$_m$ | (Y)$_n$ | R$^{2a}$ | R$^{1d}$ | R$^{1c}$ | m.p. (° C.) |
|---|---|---|---|---|---|---|
| 4-135 | 3-Br-5-CF$_3$ | 2-Br | H | H | Et | *1 |
| 4-136 | 3,4-Cl$_2$-5-CF$_3$ | 2-Br | H | H | Et | *1 |
| 4-137 | 3,5-(CF$_3$)$_2$ | 2-I | H | H | Et | *1 |
| 4-138 | 3-Br-5-CF$_3$ | — | CH$_3$ | H | Et | *1 |
| 4-139 | 3,5-Br$_2$-4-F | — | CH$_3$ | H | Et | *1 |
| 4-140 | 3,5-(CF$_3$)$_2$ | — | CN | H | Et | *1 |
| 4-141 | 3,5-(CF$_3$)$_2$ | — | CH$_3$(S) | H | c-Pr | *1 |
| 4-142 | 3,4-Cl$_2$-5-CF$_3$ | — | CH$_3$ | H | c-Pr | *1 |
| 4-143 | 3,5-(CF$_3$)$_2$ | 2-I | H | H | CH$_2$C≡CH | 169.0-171.0 |
| 4-144 | 3,5-Cl$_2$ | 2-Cl | H | H | CH=NOCH$_3$ | 230.0-231.0 |
| 4-145 | 3,5-Cl$_2$ | 2-Cl | H | —CH[N(CH$_3$)$_2$]— | | *1 |
| 4-146 | 3,5-(CF$_3$)$_2$ | 2-Br | H | CH$_3$ | SO$_2$CH$_3$ | *1 |
| 4-147 | 3,5-(CF$_3$)$_2$ | 2-Br | H | —CH(CH$_3$)CH$_2$CH$_2$SO$_2$— | | *1 |

TABLE 9

| No. | (X)$_m$ | A$^1$ | A$^2$ | (Y)$_n$ | R$^{1a}$ | R$^1$ | m.p. (° C.) |
|---|---|---|---|---|---|---|---|
| 5-001 | 3,5-Cl$_2$ | N | CH | 2-Cl | H | C(O)Pr-c | 136.0-138.0 |
| 5-002 | 3,4,5-Cl$_3$ | N | CH | — | H | C(O)Pr-c | *1 |
| 5-003 | 3,4,5-Cl$_3$ | N(O) | CH | — | H | C(O)Pr-c | *1 |
| 5-004 | 3,5-Cl$_2$ | N | CH | — | CH$_3$ | C(O)Pr-c | 196.0-200.0 |
| 5-005 | 3,5-Cl$_2$ | N | CH | — | CH$_3$ | C(O)CH$_2$CF$_3$ | 185.0-192.0 |
| 5-006 | 3,5-Cl$_2$ | N | CH | — | CH$_3$ | C(O)CH$_2$SCH$_3$ | *1 |
| 5-007 | 3,4,5-Cl$_3$ | N | CH | — | H | C*(O)(Ph-2,4,6-F$_3$) | *1 |
| 5-008 | 3,5-Cl$_2$ | N | CH | — | CH$_3$ | C(O)(Ph-2,4,6-F$_3$) | 97.0-101.0 |
| 5-009 | 3,4,5-Cl$_3$ | CH | N | — | CH$_3$ | C(O)Pr-c | *1 |
| 5-010 | 3,4,5-Cl$_3$ | CH | N | — | CH$_3$ | C(O)(Ph-2,4,6-F$_3$) | *1 |
| 5-011 | 3,4,5-Cl$_3$ | CH | N | — | CH$_3$ | C(O)NHCH$_2$CF$_3$ | *1 |
| 5-012 | 3,5-Cl$_2$ | CH | CH | — | H | C(S)CH$_2$CF$_3$ | *1 |
| 5-013 | 3,5-Cl$_2$ | CH | CH | 2-Cl | H | C(S)OCH$_2$CF$_3$ | *1 |
| 5-014 | 3,5-Cl$_2$ | CH | CH | 2-Cl | H | C(S)SCH$_3$ | *1 |
| 5-015 | 3,4,5-Cl$_3$ | CH | CH | 2-Cl | H | C(S)NHCH$_3$ | *1 |
| 5-016 | 3,4,5-Cl$_3$ | CH | CH | 2-Cl | H | C(S)NHPr-c | *1 |
| 5-017 | 3,4,5-Cl$_3$ | CH | CH | — | CH$_3$ | C(S)NHPr-c | *1 |
| 5-018 | 3,4,5-Cl$_3$ | CH | CH | 2-Cl | H | C(S)NHBu-s | *1 |
| 5-019 | 3,4,5-Cl$_3$ | CH | CH | 2-Cl | H | C(S)NHCH$_2$Ph | *1 |
| 5-020 | 3,4,5-Cl$_3$ | CH | CH | 2-Cl | H | C(S)NHC(O)OEt | *1 |

TABLE 10

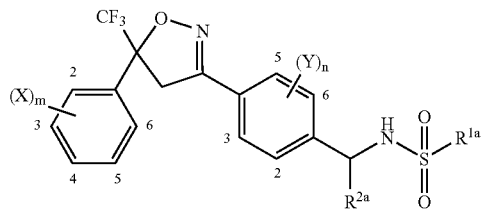

| No. | (X)$_m$ | (Y)$_n$ | R$^{2a}$ | R$^{1a}$ | m.p. (° C.) |
|---|---|---|---|---|---|
| 6-001 | 3,5-Cl$_2$ | — | H | Et | 139.0-141.0 |
| 6-002 | 3,5-Cl$_2$ | — | CH$_3$ | Ph-2,4-F$_2$ | *1 |
| 6-003 | 3,4,5-Cl$_3$ | — | CH$_3$ | Ph-2,4-F$_2$ | *1 |

TABLE 11

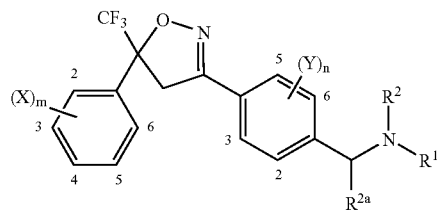

| No. | (X)$_m$ | (Y)$_n$ | R$^{2a}$ | R$^2$ | R$^1$ | m.p. (° C.) |
|---|---|---|---|---|---|---|
| 7-001 | 3,5-Cl$_2$ | — | H | —C(O)CH$_2$CH(Ph)C(O)— | | *1 |
| 7-002 | 3,5-Cl$_2$ | — | CH$_3$ | —C(O)CH$_2$CH$_2$C(O)— | | 191.0-194.0 |
| 7-003 | 3,5-Cl$_2$ | 2-Cl | H | Et | C(O)Pr-c | *1 |
| 7-004 | 3,5-Cl$_2$ | 2-Cl | H | OCH$_3$ | C(O)Pr-c | *1 |
| 7-005 | 3,5-Cl$_2$ | 2-Cl | H | OEt | C(O)Pr-c | *1 |
| 7-006 | 3,5-Cl$_2$ | 2-Cl | H | CH$_2$CF$_3$ | C(O)CH$_3$ | *1 |
| 7-007 | 3,5-Cl$_2$ | 2-Cl | H | CH$_2$CF$_3$ | C(O)Et | *1 |
| 7-008 | 3,5-Cl$_2$ | 2-Cl | H | c-Pr | C(O)Pr-c | *1 |
| 7-009 | 3,5-Cl$_2$ | 2-Cl | H | CH$_2$Pr-c | C(O)Pr-c | *1 |
| 7-010 | 3,5-Cl$_2$ | 2-Cl | H | CH$_2$CF$_3$ | C(O)Pr-c | *1 |
| 7-011 | 3,5-Cl$_2$ | 2-Cl | H | CH$_2$CH$_2$OCH$_3$ | C(O)Pr-c | *1 |
| 7-012 | 3,5-Cl$_2$ | 2-Cl | H | CH$_3$ | C(O)Pr-c | *1 |
| 7-013 | 3,5-Cl$_2$ | 2-Cl | H | CH$_2$OCH$_3$ | C(O)Pr-c | *1 |
| 7-014 | 3,5-Cl$_2$ | 2-Cl | H | C(O)OCH$_3$ | C(O)Pr-c | 163.0-165.0 |
| 7-015 | 3,5-Cl$_2$ | 2-Cl | H | CH$_2$C(O)NHCH$_2$CF$_3$ | C(O)Pr-c | *1 |
| 7-016 | 3,5-Cl$_2$ | 2-Cl | H | (D-52d)Cl | C(O)Pr-c | *1 |
| 7-017 | 3,5-Cl$_2$ | 2-Cl | H | CH$_3$ | C(O)CH$_2$Pr-c | *1 |
| 7-018 | 3,5-Cl$_2$ | 2-Cl | H | CH$_2$C(O)NHCH$_2$CF$_3$ | C(O)OCH$_3$ | *1 |
| 7-019 | 3,4,5-Cl$_3$ | — | CH$_3$ | C(O)Et | C(O)Et | *1 |
| 7-020 | 3,4,5-Cl$_3$ | 2-Cl | H | CH$_3$ | C(O)Pr-n | *1 |
| 7-021 | 3,4,5-Cl$_3$ | 2-Cl | H | CH$_3$ | C(O)Pr-c | *1 |
| 7-022 | 3,4,5-Cl$_3$ | 2-Cl | H | Et | C(O)Pr-c | *1 |
| 7-023 | 3,4,5-Cl$_3$ | — | CH$_3$ | Et | C(O)Pr-c | *1 |
| 7-024 | 3,4,5-Cl$_3$ | 2-Cl | H | CH$_2$Pr-c | C(O)Pr-c | *1 |
| 7-025 | 3,4,5-Cl$_3$ | — | CH$_3$ | CH$_2$Pr-c | C(O)Pr-c | *1 |
| 7-026 | 3,4,5-Cl$_3$ | 2-Cl | H | CH$_2$OCH$_3$ | C(O)Pr-c | *1 |
| 7-027 | 3,5-Cl$_2$ | 2-Cl | H | CH$_2$CH$_2$SCH$_3$ | C(O)Pr-c | *1 |
| 7-028 | 3,4,5-Cl$_3$ | 2-Cl | H | CH$_2$CN | C(O)Pr-c | *1 |
| 7-029 | 3,4,5-Cl$_3$ | — | CH$_3$ | CH$_2$C(O)OCH$_3$ | C(O)Pr-c | *1 |
| 7-030 | 3,4,5-Cl$_3$ | 2-Cl | H | CH$_2$C≡CH | C(O)Pr-c | *1 |
| 7-031 | 3,4,5-Cl$_3$ | 2-Cl | H | CN | C(O)Pr-c | *1 |
| 7-032 | 3,5-Cl$_2$ | 2-Br | H | C(O)OBu-t | C(O)Pr-c | *1 |
| 7-033 | 3,5-Cl$_2$ | 2-I | H | C(O)OBu-t | C(O)Pr-c | *1 |
| 7-034 | 3,5-Cl$_2$ | 2-CN | H | C(O)OBu-t | C(O)Pr-c | *1 |
| 7-035 | 3,5-Cl$_2$ | — | CH$_3$ | Ph-2,4,6-F$_3$ | C(O)Pr-c | *1 |
| 7-036 | 3,4,5-Cl$_3$ | 2-Cl | H | CH$_3$ | C(O)(E-5a) | *1 |
| 7-037 | 3,5-Cl$_2$ | 2-Cl | H | —CH$_2$CH$_2$CH$_2$C(O)— | | *1 |
| 7-038 | 3,5-Cl$_2$ | 2-Cl | H | —CH$_2$CH$_2$CH$_2$CH$_2$C(O)— | | *1 |
| 7-039 | 3,5-Cl$_2$ | 2-Cl | H | —CH$_2$CH$_2$CH$_2$CH$_2$CH$_2$C(O)— | | *1 |
| 7-040 | 3,4,5-Cl$_3$ | 2-Cl | H | CH$_3$ | C(O)(Ph-2,4,6-F$_3$) | 209.0-211.0 |
| 7-041 | 3,5-Cl$_2$ | — | CH$_3$ | CH$_3$ | C(O)(Ph-2,4,6-F$_3$) | *1 |
| 7-042 | 3,4,5-Cl$_3$ | 2-Cl | H | Et | C(O)(Ph-2,4,6-F$_3$) | *1 |
| 7-043 | 3,4,5-Cl$_3$ | 2-Cl | H | CH$_2$OCH$_3$ | C(O)(Ph-2,4,6-F$_3$) | 169.0-172.0 |
| 7-044 | 3,5-Cl$_2$ | 2-Cl | H | —CH$_2$CH$_2$OC(O)— | | *1 |
| 7-045 | 3,4,5-Cl$_3$ | 2-Cl | H | —C(=CH$_2$)CH$_2$OC(O)— | | *1 |
| 7-046 | 3,5-Cl$_2$ | 2-Cl | H | CH$_2$CH$_2$SCH$_3$ | C(O)NHEt | *1 |

TABLE 11-continued

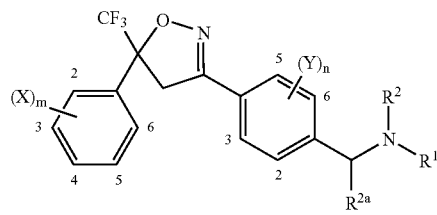

| No. | (X)$_m$ | (Y)$_n$ | R$^{2a}$ | R$^2$ | R$^1$ | m.p. (° C.) |
|---|---|---|---|---|---|---|
| 7-047 | 3,4,5-Cl$_3$ | 2-Cl | H | —C(O)CH$_2$NHC(O)— | | *1 |
| 7-048 | 3,5-(CF$_3$)$_2$ | 2-Cl | H | CH$_3$ | C(O)CH$_2$Pr-c | *1 |
| 7-049 | 3,5-(CF$_3$)$_2$ | 2-Cl | H | Et | C(O)CH$_2$Pr-c | *1 |
| 7-050 | 3,5-(CF$_3$)$_2$ | 2-Cl | H | n-Pr | C(O)CH$_2$Pr-c | *1 |
| 7-051 | 3,5-(CF$_3$)$_2$ | 2-Cl | H | CH$_2$Pr-c | C(O)CH$_2$Pr-c | *1 |
| 7-052 | 3,5-(CF$_3$)$_2$ | 2-Cl | H | CH$_2$C≡CH | C(O)CH$_2$Pr-c | *1 |
| 7-053 | 3,5-(CF$_3$)$_2$ | 2-Cl | H | CH$_3$ | C(O)(D-24a) | *1 |
| 7-054 | 3,5-(CF$_3$)$_2$ | 2-Cl | H | CH$_3$ | C(O)NHEt | 172.0-174.0 |
| 7-055 | 3,5-(CF$_3$)$_2$ | 2-Cl | H | Et | C(O)NHEt | 180.0-182.0 |
| 7-056 | 3,5-(CF$_3$)$_2$ | 2-Cl | H | n-Pr | C(O)NHEt | 133.0-135.0 |
| 7-057 | 3,5-(CF$_3$)$_2$ | 2-Cl | H | CH$_2$Pr-c | C(O)NHEt | 147.0-150.0 |
| 7-058 | 3,5-(CF$_3$)$_2$ | 2-Cl | H | CH$_2$C≡CH | C(O)NHEt | 150.0-153.0 |
| 7-059 | 3-Br-5-CF$_3$ | 2-Br | H | Et | C(O)CH$_3$ | 120.0-122.0 |
| 7-060 | 3,5-(CF$_3$)$_2$ | 2-Cl | H | Et | C(O)Et | *1 |
| 7-061 | 3,4-Cl$_2$-5-CF$_3$ | 2-Cl | H | Et | C(O)Et | *1 |
| 7-062 | 3-Br-5-CF$_3$ | 2-Br | H | Et | C(O)Et | 69.0-71.0 |
| 7-063 | 3,5-(CF$_3$)$_2$ | 2-Cl | H | n-Pr | C(O)Et | *1 |
| 7-064 | 3,5-(CF$_3$)$_2$ | 2-Cl | H | CH$_2$CN | C(O)Et | *1 |
| 7-065 | 3,4-Cl$_2$-5-CF$_3$ | 2-Cl | H | CH$_2$CN | C(O)Et | *1 |
| 7-066 | 3,5-(CF$_3$)$_2$ | 2-Cl | H | CH$_2$CH=CH$_2$ | C(O)Et | *1 |
| 7-067 | 3,4-Cl$_2$-5-CF$_3$ | 2-Cl | H | CH$_2$CH=CH$_2$ | C(O)Et | *1 |
| 7-068 | 3,5-(CF$_3$)$_2$ | 2-Cl | H | CH$_2$C≡CH | C(O)Et | *1 |
| 7-069 | 3,5-(CF$_3$)$_2$ | 2-Cl | H | Et | C(O)Pr-n | *1 |
| 7-070 | 3,4-Cl$_2$-5-CF$_3$ | 2-Cl | H | Et | C(O)Pr-n | *1 |
| 7-071 | 3,5-(CF$_3$)$_2$ | 2-Cl | H | n-Pr | C(O)Pr-n | *1 |
| 7-072 | 3,5-(CF$_3$)$_2$ | 2-Cl | H | CH$_2$CN | C(O)Pr-n | *1 |
| 7-073 | 3,4-Cl$_2$-5-CF$_3$ | 2-Cl | H | CH$_2$CN | C(O)Pr-n | *1 |
| 7-074 | 3,4-Cl$_2$-5-CF$_3$ | 2-Cl | H | CH$_2$CH=CH$_2$ | C(O)Pr-n | *1 |
| 7-075 | 3,5-(CF$_3$)$_2$ | 2-Cl | H | CH$_2$C≡CH | C(O)Pr-n | *1 |
| 7-076 | 3-Br-5-CF$_3$ | 2-Br | H | Et | C(O)Pr-i | 68.0-70.0 |
| 7-077 | 3,4-Cl$_2$-5-CF$_3$ | 2-Cl | H | CH$_3$ | C(O)Pr-c | *1 |
| 7-078 | 3,4-Cl$_2$-5-CF$_3$ | 2-Br | H | CH$_3$ | C(O)Pr-c | *1 |
| 7-079 | 3,4-Cl$_2$-5-CF$_3$ | — | CH$_3$ | CH$_3$ | C(O)Pr-c | *1 |
| 7-080 | 3,5-(CF$_3$)$_2$ | 2-Cl | H | Et | C(O)Pr-c | *1 |
| 7-081 | 3,4-Cl$_2$-5-CF$_3$ | 2-Cl | H | Et | C(O)Pr-c | *1 |
| 7-082 | 3-Br-5-CF$_3$ | 2-Br | H | Et | C(O)Pr-c | 61.0-62.0 |
| 7-083 | 3,4-Cl$_2$-5-CF$_3$ | 2-Br | H | Et | C(O)Pr-c | *1 |
| 7-084 | 3,4-Cl$_2$-5-CF$_3$ | — | CH$_3$ | Et | C(O)Pr-c | *1 |
| 7-085 | 3,5-(CF$_3$)$_2$ | 2-Cl | H | n-Pr | C(O)Pr-c | *1 |
| 7-086 | 3,4-Cl$_2$-5-CF$_3$ | 2-Cl | H | n-Pr | C(O)Pr-c | *1 |
| 7-087 | 3,4-Cl$_2$-5-CF$_3$ | 2-Br | H | n-Pr | C(O)Pr-c | *1 |
| 7-088 | 3,4-Cl$_2$-5-CF$_3$ | — | CH$_3$ | n-Pr | C(O)Pr-c | *1 |
| 7-089 | 3-Br-5-CF$_3$ | 2-Br | H | CH$_2$CH$_2$SCH$_3$ | C(O)Pr-c | 49.0-51.0 |
| 7-090 | 3-Br-5-CF$_3$ | 2-Br | H | CH$_2$CH$_2$S(O)CH$_3$ | C(O)Pr-c | *1 |
| 7-091 | 3-Br-5-CF$_3$ | 2-Br | H | CH$_2$CH$_2$SO$_2$CH$_3$ | C(O)Pr-c | *1 |
| 7-092 | 3-Br-5-CF$_3$ | 2-Br | H | CH$_2$CH$_2$NHC(O)CH$_3$ | C(O)Pr-c | *1 |
| 7-093 | 3,5-Cl$_2$ | 2-Cl | H | CH$_2$CH$_2$NHC(O)OBu-t | C(O)Pr-c | *1 |
| 7-094 | 3,5-Cl$_2$ | 2-Cl | H | CH$_2$CH$_2$NHC(O)NHEt | C(O)Pr-c | *1 |
| 7-095 | 3,5-(CF$_3$)$_2$ | 2-Cl | H | CH$_2$CN | C(O)Pr-c | *1 |
| 7-096 | 3,4-Cl$_2$-5-CF$_3$ | 2-Cl | H | CH$_2$CN | C(O)Pr-c | *1 |
| 7-097 | 3,4-Cl$_2$-5-CF$_3$ | 2-Br | H | CH$_2$CN | C(O)Pr-c | *1 |
| 7-098 | 3,4-Cl$_2$-5-CF$_3$ | — | CH$_3$ | CH$_2$CN | C(O)Pr-c | *1 |
| 7-099 | 3,5-(CF$_3$)$_2$ | 2-Cl | H | CH$_2$CH=CH$_2$ | C(O)Pr-c | *1 |
| 7-100 | 3,4-Cl$_2$-5-CF$_3$ | 2-Cl | H | CH$_2$CH=CH$_2$ | C(O)Pr-c | *1 |
| 7-101 | 3,4-Cl$_2$-5-CF$_3$ | 2-Br | H | CH$_2$CH=CH$_2$ | C(O)Pr-c | *1 |
| 7-102 | 3,4-Cl$_2$-5-CF$_3$ | — | CH$_3$ | CH$_2$CH=CH$_2$ | C(O)Pr-c | *1 |
| 7-103 | 3,5-(CF$_3$)$_2$ | 2-Cl | H | CH$_2$C≡CH | C(O)Pr-c | *1 |
| 7-104 | 3,4-Cl$_2$-5-CF$_3$ | 2-Cl | H | CH$_2$C≡CH | C(O)Pr-c | *1 |
| 7-105 | 3,4-Cl$_2$-5-CF$_3$ | 2-Br | H | CH$_2$C≡CH | C(O)Pr-c | *1 |
| 7-106 | 3,4-Cl$_2$-5-CF$_3$ | — | CH$_3$ | CH$_2$C≡CH | C(O)Pr-c | *1 |
| 7-107 | 3,5-(CF$_3$)$_2$ | 2-Cl | H | Et | C(O)Bu-i | *1 |
| 7-108 | 3,5-(CF$_3$)$_2$ | 2-Cl | H | n-Pr | C(O)Bu-i | *1 |
| 7-109 | 3,5-(CF$_3$)$_2$ | 2-Cl | H | CH$_2$CN | C(O)Bu-i | *1 |
| 7-110 | 3,5-(CF$_3$)$_2$ | 2-Cl | H | CH$_2$C≡CH | C(O)Bu-i | *1 |
| 7-111 | 3,5-(CF$_3$)$_2$ | 2-Cl | H | i-Bu | C(O)CH$_2$Pr-c | 144.0-146.0 |
| 7-112 | 3,5-(CF$_3$)$_2$ | 2-Cl | H | CH$_2$CH=CH$_2$ | C(O)CH$_2$Pr-c | *1 |
| 7-113 | 3,5-(CF$_3$)$_2$ | 2-Cl | H | CH$_2$Ph | C(O)CH$_2$Pr-c | *1 |

TABLE 11-continued
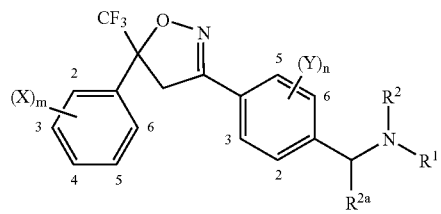
| No. | $(X)_m$ | $(Y)_n$ | $R^{2a}$ | $R^2$ | $R^1$ | m.p. (° C.) |
|---|---|---|---|---|---|---|
| 7-114 | 3,5-$(CF_3)_2$ | 2-Cl | H | i-Bu | C(O)NHEt | 145.0-147.0 |
| 7-115 | 3,5-$(CF_3)_2$ | 2-Cl | H | $CH_2CN$ | C(O)NHEt | *1 |
| 7-116 | 3,5-$(CF_3)_2$ | 2-Cl | H | $CH_2CH=CH_2$ | C(O)NHEt | *1 |
| 7-117 | 3,5-$(CF_3)_2$ | 2-Cl | H | $CH_2Ph$ | C(O)NHEt | 162.0-164.0 |
| 7-118 | 3,5-$(CF_3)_2$ | 2-Cl | H | $CH_2Pr$-c | C(O)C(O)NHPr-c | *1 |
| 7-119 | 3,5-$(CF_3)_2$ | 2-Br | H | $CH_3$ | $SO_2$(Ph-2,4-$F_2$) | 142.0-144.0 |
TABLE 12
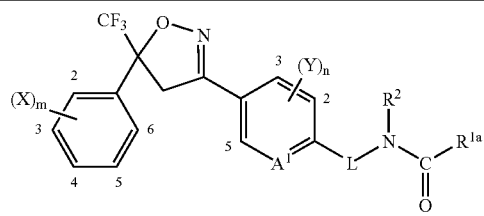
In table, L-6, L-7, L-8, L-9, L-10, L-13, L-16, L-22 and L-25 are the following structures, respectively.
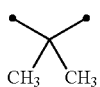
L-6
L-7
L-8
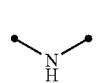
L-9
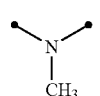
L-10
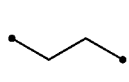
L-13
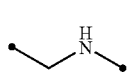
L-16
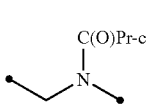
L-22

TABLE 12-continued

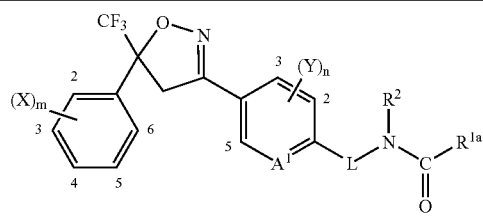

In table, L-6, L-7, L-8, L-9, L-10, L-13, L-16, L-22 and L-25 are the following structures, respectively.

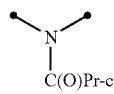

L-25

| No. | $(X)_m$ | $A^1$ | $(Y)_n$ | L | $R^2$ | $R^{1a}$ | m.p. (° C.) |
|---|---|---|---|---|---|---|---|
| 8-001 | 3,5-Cl$_2$ | CH | — | L-9 | H | c-Pr | 140.0-143.0 |
| 8-002 | 3,5-Cl$_2$ | CH | 2-NO$_2$ | L-9 | H | c-Pr | 128.0-131.0 |
| 8-003 | 3,5-Cl$_2$ | CH | 2-NO$_2$ | L-25 | H | c-Pr | *1 |
| 8-004 | 3,5-Cl$_2$ | N | — | L-10 | H | c-Pr | *1 |
| 8-005 | 3,5-Cl$_2$ | CH | — | L-13 | H | CH$_2$CF$_3$ | *1 |
| 8-006 | 3,5-Cl$_2$ | CH | 2-Cl | L-16 | H | i-Pr | *1 |
| 8-007 | 3,5-Cl$_2$ | CH | 2-Cl | L-22 | H | i-Pr | *1 |
| 8-008 | 3,5-Cl$_2$ | CH | — | L-6 | H | CH$_3$ | 166.0-168.0 |
| 8-009 | 3,5-Cl$_2$ | CH | — | L-7 | C(O)Pr-i | i-Pr | *1 |
| 8-010 | 3,5-Cl$_2$ | CH | — | L-7 | H | c-Pr | *1 |
| 8-011 | 3,5-Cl$_2$ | CH | — | L-6 | H | Et | 157.0-159.0 |
| 8-012 | 3,5-Cl$_2$ | CH | — | L-6 | H | n-Pr | 81.0-85.0 |
| 8-013 | 3,5-Cl$_2$ | CH | — | L-6 | H | c-Pr | 135.0-139.0 |
| 8-014 | 3,5-Cl$_2$ | CH | — | L-7 | H | i-Pr | *1 |
| 8-015 | 3,5-Cl$_2$ | CH | — | L-7 | H | CH$_2$Pr-c | *1 |
| 8-016 | 3,5-Cl$_2$ | CH | — | L-7 | H | CH$_2$SCH$_3$ | *1 |
| 8-017 | 3,5-Cl$_2$ | CH | — | L-7 | H | Ph-2,4-F$_2$ | *1 |
| 8-018 | 3,5-Cl$_2$ | CH | — | L-7 | H | Ph-2,4,6-F$_3$ | *1 |
| 8-019 | 3,5-Cl$_2$ | CH | — | L-7 | H | D-58a | 122.0-125.0 |
| 8-020 | 3,4,5-Cl$_3$ | CH | — | L-8 | H | c-Pr | *1 |

TABLE 13

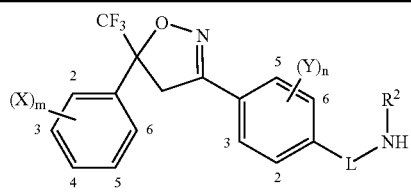

In table, L-1, L-2, L-4, L-9, L-26 and L-27 are the following structures, respectively.

L-1

L-2

L-4

L-9

TABLE 13-continued

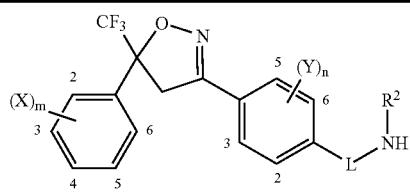

In table, L-1, L-2, L-4, L-9, L-26 and L-27 are the following structures, respectively.

L-26

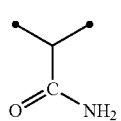
L-27

| No. | (X)$_m$ | (Y)$_n$ | L | R$^2$ | m.p. (° C.) |
|---|---|---|---|---|---|
| 9-001 | 3,5-Cl$_2$ | — | L-1 | H | *1 |
| 9-002 | 3,5-Cl$_2$ | — | L-1 | CH$_3$ | *1 |
| 9-003 | 3,5-Cl$_2$ | — | L-1 | Et | *1 |
| 9-004 | 3,5-Cl$_2$ | — | L-1 | i-Pr | *1 |
| 9-005 | 3,5-Cl$_2$ | — | L-1 | CH$_2$(D-52a) | *2 |
| 9-006 | 3,5-Cl$_2$ | — | L-1 | Ph-4-F | *1 |
| 9-007 | 3,5-Cl$_2$ | — | L-2 | H | *1 |
| 9-008 | 3,5-Cl$_2$ | — | L-2 | M-11a | *1 |
| 9-009 | 3,5-Cl$_2$ | — | L-26 | H | *1 |
| 9-010 | 3,5-Cl$_2$ | 2-F | L-1 | H | *2 |
| 9-011 | 3,5-Cl$_2$ | 2-Cl | L-1 | H | *1 |
| 9-012 | 3,5-Cl$_2$ | 2-Cl | L-1 | Et | *1 |
| 9-013 | 3,5-Cl$_2$ | 2-Cl | L-1 | CH$_2$C(O)NHCH$_2$CF$_3$ | *1 |
| 9-014 | 3,5-Cl$_2$ | 2-Cl | L-1 | OCH$_3$ | *1 |
| 9-015 | 3,5-Cl$_2$ | 2-Cl | L-1 | OEt | *1 |
| 9-016 | 3,5-Cl$_2$ | 2-Cl | L-2 | H | *1 |
| 9-017 | 3,5-Cl$_2$ | 2-Cl | L-4 | H | *1 |
| 9-018 | 3,5-Cl$_2$ | 2-Br | L-1 | H | *1 |
| 9-019 | 3,5-Cl$_2$ | 2-I | L-1 | H | 125.0-127.0 |
| 9-020 | 3,5-Cl$_2$ | 2-CH$_3$ | L-1 | H | *1 |
| 9-021 | 3,5-Cl$_2$ | 2-NO$_2$ | L-1 | H | *1 |
| 9-022 | 3,4,5-Cl$_3$ | 2-Cl | L-1 | H | *1 |
| 9-023 | 3,5-Cl$_2$ | 2-Cl | L-1 | CH$_3$ | *1 |
| 9-024 | 3,5-Cl$_2$ | 2-Cl | L-1 | c-Pr | *1 |
| 9-025 | 3,5-Cl$_2$ | 2-Cl | L-1 | CH$_2$Pr-c | *1 |
| 9-026 | 3,5-Cl$_2$ | 2-Cl | L-1 | CH$_2$CF$_3$ | 101.0-103.0 |
| 9-027 | 3,5-Cl$_2$ | 2-Cl | L-1 | CH$_2$CH$_2$OCH$_3$ | *1 |
| 9-028 | 3,5-Cl$_2$ | 2-NO$_2$ | L-9 | H | 202.0-205.0 |
| 9-029 | 3,5-Cl$_2$ | 2-Cl | L-1 | (D-52d)Cl | *1 |
| 9-030 | 3,5-Cl$_2$ | 2-I | L-1 | Et | *1 |
| 9-031 | 3,4,5-Cl$_3$ | — | L-1 | H | 113.0-117.0 |
| 9-032 | 3,5-(CF$_3$)$_2$ | 2-Cl | L-1 | H | *1 |
| 9-033 | 3,4,5-Cl$_3$ | 2-Br | L-1 | H | *1 |
| 9-034 | 3,4,5-Cl$_3$ | 2-NO$_2$ | L-1 | H | *1 |
| 9-035 | 3,5-Cl$_2$ | 2-CH=CHCH=CH-3 | L-1 | H | *1 |
| 9-036 | 3,4,5-Cl$_3$ | 2-Cl | L-1 | CH$_3$ | *1 |
| 9-037 | 3,4,5-Cl$_3$ | 2-Cl | L-1 | Et | *1 |
| 9-038 | 3,4,5-Cl$_3$ | 2-Cl | L-1 | n-Pr | *1 |
| 9-039 | 3,4,5-Cl$_3$ | 2-Cl | L-1 | n-Bu | *1 |
| 9-040 | 3,4,5-Cl$_3$ | 2-Cl | L-1 | CH$_2$Pr-c | *1 |
| 9-041 | 3,5-Cl$_2$ | 2-Cl | L-1 | CH$_2$CH$_2$SCH$_3$ | *1 |
| 9-042 | 3,4,5-Cl$_3$ | 2-Cl | L-1 | CH$_2$C≡CH | *1 |
| 9-043 | 3,5-Cl$_2$ | 2-Cl | L-1 | CH$_2$(Ph-4-F) | *1 |
| 9-044 | 3,4,5-Cl$_3$ | 2-Cl | L-1 | CN | *1 |
| 9-045 | 3,4,5-Cl$_3$ | 2-Cl | L-1 | N(CH$_3$)$_2$ | *1 |
| 9-046 | 3,4,5-Cl$_3$ | — | L-2 | H | 57.0-61.0 |
| 9-047 | 3,5-Cl$_2$ | — | L-2 | Et | *1 |
| 9-048 | 3,4,5-Cl$_3$ | — | L-4 | H | *1 |
| 9-049 | 3-CF$_3$-4-Cl | 2-Cl | L-1 | H | *1 |

TABLE 13-continued

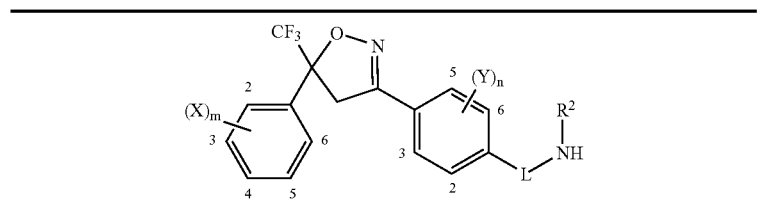

In table, L-1, L-2, L-4, L-9, L-26 and L-27 are the following structures, respectively.

| No. | $(X)_m$ | $(Y)_n$ | L | $R^2$ | m.p. (° C.) |
|---|---|---|---|---|---|
| 9-050 | 3,5-$Cl_2$-4-$OCHF_2$ | 2-Cl | L-1 | H | *1 |
| 9-051 | 3,5-$(CF_3)_2$ | 2-Cl | L-1 | $CH_3$ | *1 |
| 9-052 | 3,5-$(CF_3)_2$ | 2-Cl | L-1 | Et | *1 |
| 9-053 | 3,5-$(CF_3)_2$ | 2-Cl | L-1 | n-Pr | *1 |
| 9-054 | 3,5-$(CF_3)_2$ | 2-Cl | L-1 | $CH_2$Pr-c | *1 |
| 9-055 | 3,5-$(CF_3)_2$ | 2-Cl | L-1 | $CH_2C\equiv CH$ | *1 |
| 9-056 | 3,4-$Cl_2$-5-$CF_3$ | 2-Cl | L-1 | Et | *1 |
| 9-057 | 3,4-$Cl_2$-5-$CF_3$ | 2-Cl | L-1 | n-Pr | *1 |
| 9-058 | 3,5-$(CF_3)_2$ | 2-Cl | L-1 | i-Bu | *1 |
| 9-059 | 3,5-$Cl_2$ | 2-Cl | L-1 | $CH_2CH_2NHC(O)CH_3$ | *1 |
| 9-060 | 3-Br-5-$CF_3$ | 2-Br | L-1 | $CH_2CH_2NHC(O)CH_3$ | *1 |
| 9-061 | 3,5-$Cl_2$ | 2-Cl | L-1 | $CH_2CH_2NHC(O)OBu$-t | *1 |
| 9-062 | 3,5-$(CF_3)_2$ | 2-Cl | L-1 | $CH_2CN$ | *1 |
| 9-063 | 3,4-$Cl_2$-5-$CF_3$ | 2-Cl | L-1 | $CH_2CN$ | *1 |
| 9-064 | 3,5-$(CF_3)_2$ | 2-Cl | L-1 | $CH_2C(O)OCH_3$ | *1 |
| 9-065 | 3,5-$(CF_3)_2$ | 2-Cl | L-1 | $CH_2CH=CH_2$ | *1 |
| 9-066 | 3,4-$Cl_2$-5-$CF_3$ | 2-Cl | L-1 | $CH_2CH=CH_2$ | *1 |
| 9-067 | 3,4-$Cl_2$-5-$CF_3$ | 2-Cl | L-1 | $CH_2C\equiv CH$ | *1 |
| 9-068 | 3,5-$(CF_3)_2$ | 2-Cl | L-1 | $CH_2$Ph | 109.0-111.0 |
| 9-069 | 3,5-$(CF_3)_2$ | 2-Cl | L-4 | H | *1 |
| 9-070 | 3,5-$Cl_2$ | 2-$CH_3$ | L-4 | H | *1 |
| 9-071 | 3,5-$Cl_2$ | — | L-27 | H | *1 |

TABLE 14

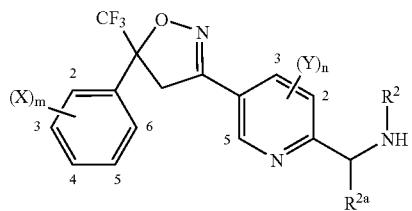

| No. | $(X)_m$ | $(Y)_n$ | $R^{2a}$ | $R^2$ | m.p. (° C.) |
|---|---|---|---|---|---|
| 10-001 | 3,5-$Cl_2$ | 2-Cl | H | H | *1 |

TABLE 15

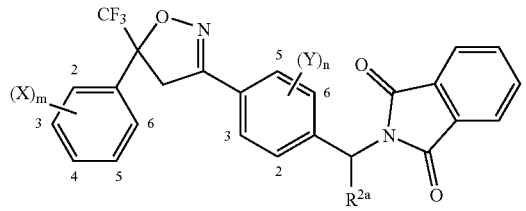

| No. | $(X)_m$ | $(Y)_n$ | $R^{2a}$ | m.p. (° C.) |
|---|---|---|---|---|
| 11-001 | 3,5-$Cl_2$ | — | H | 190.0-192.0 |
| 11-002 | 3,5-$Cl_2$ | — | $CH_3$ | *1 |
| 11-003 | 3,5-$Cl_2$ | — | Et | *1 |
| 11-004 | 3,5-$Cl_2$ | 2-F | H | *1 |
| 11-005 | 3,5-$Cl_2$ | 2-Cl | H | *1 |
| 11-006 | 3,5-$Cl_2$ | 2-Cl | $CH_3$ | *1 |
| 11-007 | 3,5-$Cl_2$ | 2-Br | H | *1 |

TABLE 15-continued

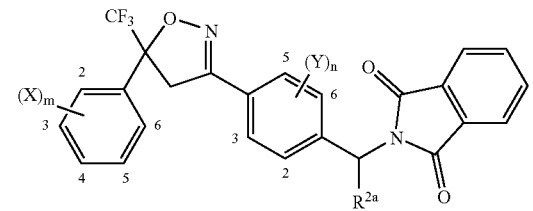

| No. | $(X)_m$ | $(Y)_n$ | $R^{2a}$ | m.p. (° C.) |
|---|---|---|---|---|
| 11-008 | 3,5-$Cl_2$ | 2-I | H | 59.0-61.0 |
| 11-009 | 3,5-$Cl_2$ | 2-$CH_3$ | H | *1 |
| 11-010 | 3,5-$Cl_2$ | 2-$NO_2$ | H | 115.0-118.0 |
| 11-011 | 3,4,5-$Cl_3$ | 2-Cl | H | *1 |
| 11-012 | 3,4,5-$Cl_3$ | — | H | 164.0-167.0 |
| 11-013 | 3,5-$(CF_3)_2$ | 2-Cl | H | *1 |
| 11-014 | 3,4,5-$Cl_3$ | 2-$NO_2$ | H | 91.0-94.0 |
| 11-015 | 3,5-$Cl_2$ | 2-CN | H | *1 |
| 11-016 | 3,5-$Cl_2$ | 2-CH=CHCH=CH-3 | H | 238.0-239.0 |
| 11-017 | 3,5-$(CF_3)_2$ | — | $CH_3$ | *1 |
| 11-018 | 3,4,5-$Cl_3$ | — | $CH_3$ | *1 |
| 11-019 | 3-$CF_3$-4-Cl | 2-Cl | H | *1 |
| 11-020 | 3,5-$Cl_2$-4-$OCHF_2$ | 2-Cl | H | *1 |
| 11-021 | 3,4-$Cl_2$-5-$CF_3$ | 2-Cl | H | *1 |

Among the compounds of the present invention, $^1$H NMR data of the compounds that the measured value of molecular ion peak, melting point or refractive index is not shown are shown in Table 16.

In the meantime, the indication of "(A)" in the table shows a condition in which tetramethylsilane is used as standard substance in deuterated chloroform solvent and measurement is carried out at 300 MHz ($CDCl_3$, $Me_4Si$, 300 MHz), and the indication "(B)" shows the measurement condition of ($CDCl_3$, $Me_4Si$, 400 MHz), and the indication of "(C)" shows the measurement condition of ($CDCl_3$, $Me_4Si$, 500 MHz).

TABLE 16

| No. | ¹H NMR |
|---|---|
| 2-005 | (A) δ 7.63 (d, J = 8.1 Hz, 2H), 7.51 (d, J = 1.5 Hz, 2H), 7.42 (t, J = 1.5 Hz, 1H), 7.33 (d, J = 8.1 Hz, 2H), 6.12 (bs, 1H), 4.52 (d, J = 6.0 Hz, 2H), 4.07 (d, J = 17.4 Hz, 1H), 3.69 (d, J = 17.4 Hz, 1H), 3.13 (q, J = 10.8 Hz, 2H). |
| 2-010 | (A) δ 8.52 (d, J = 4.7 Hz, 1H), 7.96 (bs, 1H), 7.65-7.8 (m, 1H), 7.58 (d, J = 8.2 Hz, 2H), 7.50 (s, 2H), 7.41 (s, 1H), 7.15-7.35 (m, 4H), 4.49 (d, J = 6.0 Hz, 2H), 4.09 (d, J = 17.4 Hz, 1H), 3.80 (s, 2H), 3.69 (d, J = 17.4 Hz, 1H). |
| 2-014 | (A) δ 8.14 (d, J = 3.9 Hz, 1H), 7.76 (bs, 1H), 7.63 (d, J = 8.2 Hz, 2H), 7.50 (d, J = 1.5 Hz, 1H), 7.35-7.5 (m, 3H), 6.36 (d, J = 3.9 Hz, 1H), 4.65 (d, J = 6.0 Hz, 2H), 4.09 (d, J = 17.4 Hz, 1H), 3.91 (s, 3H), 3.68 (d, J = 17.4 Hz, 1H). |
| 2-021 | (A) δ 7.64 (d, J = 8.1 Hz, 2H), 7.51 (d, J = 1.5 Hz, 2H), 7.42 (t, J = 1.5 Hz, 1H), 7.36 (d, J = 8.1 Hz, 2H), 5.97 (d, J = 7.2 Hz, 1H), 5.1-5.25 (m, 1H), 4.07 (d, J = 17.4 Hz, 1H), 3.68 (d, J = 17.4 Hz, 1H), 3.08 (q, J = 10.8 Hz, 2H), 1.52 (d, J = 6.6 Hz, 3H). |
| 2-025 | (A) δ 7.64 (d, J = 8.1 Hz, 2H), 7.51 (d, J = 1.5 Hz, 2H), 7.42 (t, J = 1.5 Hz, 1H), 7.32 (d, J = 8.1 Hz, 2H), 6.05 (d, J = 7.5 Hz, 1H), 4.89 (d, J = 7.5 Hz, 1H), 4.07 (d, J = 17.4 Hz, 1H), 3.67 (d, J = 17.4 Hz, 1H), 3.08 (q, J = 10.8 Hz, 2H), 1.75-1.95 (m, 2H), 0.91 (t, J = 7.2 Hz, 3H). |
| 2-029 | (A) δ 7.3-7.55 (m, 6H), 6.17 (bs, 1H), 4.55 (d, J = 6.0 Hz, 2H), 4.08 (d, J = 17.4 Hz, 1H), 3.66 (d, J = 17.4 Hz, 1H), 3.11 (q, J = 10.8 Hz, 2H). |
| 2-033 | (A) δ 7.69 (s, 1H), 7.45-7.6 (m, 3H), 7.4-7.5 (m, 2H), 7.1-7.3 (m, 1H), 4.55 (d, J = 6.0 Hz, 2H), 4.35-4.5 (m, 1H), 4.07 (d, J = 17.4 Hz, 1H), 3.8-4.0 (m, 2H), 3.69 (d, J = 17.4 Hz, 1H), 2.2-2.4 (m, 1H), 2.0-2.15 (m, 1H), 1.8-2.0 (m, 2H). |
| 2-035 | (A) δ 7.72 (d, J = 1.5 Hz, 1H), 7.54 (dd, J = 8.1, 1.5 Hz, 1H), 7.49 (s, 2H), 7.45 (d, J = 8.1 Hz, 1H), 7.43 (t, J = 1.5 Hz, 1H), 6.58 (bs, 1H), 4.59 (d, J = 6.3 Hz, 2H), 4.05 (d, J = 17.4 Hz, 1H), 3.67 (d, J = 17.4 Hz, 1H), 3.41 (s, 2H). |
| 2-036 | (A) δ 7.72 (s, 1H), 7.35-7.55 (m, 8H), 7.15-7.25 (m, 1H), 6.63 (bs, 1H), 4.74 (d, J = 6.0 Hz, 2H), 4.05 (d, J = 17.4 Hz, 1H), 3.67 (d, J = 17.4 Hz, 1H). |
| 2-037 | (A) δ 7.75-7.85 (m, 2H), 7.71 (s, 1H), 7.45-7.55 (m, 4H), 7.43 (t, J = 1.5 Hz, 1H), 7.05-7.15 (m, 2H), 6.63 (t, J = 6.0 Hz, 1H), 4.72 (d, J = 6.0 Hz, 2H), 4.05 (d, J = 17.4 Hz, 1H), 3.67 (d, J = 17.4 Hz, 1H). |
| 2-038 | (A) δ 7.69 (s, 1H), 7.4-7.55 (m, 5H), 7.25-7.35 (m, 2H), 6.9-7.0 (m, 1H), 6.89 (t, J = 6.0 Hz, 1H), 4.69 (d, J = 6.0 Hz, 2H), 4.05 (d, J = 17.4 Hz, 1H), 3.69 (d, J = 17.4 Hz, 1H). |
| 2-044 | (A) δ 7.83 (s, 1H), 7.4-7.6 (m, 5H), 6.33 (t, J = 6.0 Hz, 1H), 4.51 (d, J = 6.0 Hz, 2H), 4.05 (d, J = 17.4 Hz, 1H), 3.67 (d, J = 17.4 Hz, 1H), 1.35-1.5 (m, 1H), 0.85-1.1 (m, 4H). |
| 2-045 | (A) δ 7.89 (s, 1H), 7.58 (dd, J = 8.1, 1.5 Hz, 1H), 7.50 (s, 2H), 7.4-7.5 (m, 2H), 6.25 (bs, 1H), 4.57 (d, J = 6.0 Hz, 2H), 4.09 (d, J = 17.4 Hz, 1H), 3.66 (d, J = 17.4 Hz, 1H), 3.12 (q, J = 10.8 Hz, 2H). |
| 2-046 | (A) δ 8.11 (s, 1H), 7.61 (dd, J = 8.1, 1.5 Hz, 1H), 7.50 (s, 2H), 7.35-7.5 (m, 2H), 5.94 (bs, 1H), 4.47 (d, J = 6.0 Hz, 2H), 4.04 (d, J = 17.4 Hz, 1H), 3.65 (d, J = 17.4 Hz, 1H), 2.26 (d, J = 7.7 Hz, 2H), 1.18 (t, J = 7.7 Hz, 3H). |
| 2-055 | (A) δ 8.51 (d, J = 3.9 Hz, 1H), 7.89 (bs, 1H), 7.7-7.8 (m, 1H), 7.35-7.55 (m, 5H), 7.32 (d, J = 7.8 Hz, 1H), 7.15-7.3 (m, 2H), 4.46 (d, J = 6.0 Hz, 2H), 4.06 (d, J = 17.4 Hz, 1H), 3.82 (s, 2H), 3.67 (d, J = 17.4 Hz, 1H), 2.30 (s, 3H). |
| 2-056 | (A) δ 7.49 (d, J = 1.5 Hz, 2H), 7.42 (t, J = 1.5 Hz, 1H), 7.09 (d, J = 8.1 Hz, 1H), 6.98 (s, 1H), 6.91 (d, J = 8.1 Hz, 1H), 6.10 (bs, 1H), 4.42 (d, J = 6.0 Hz, 2H), 4.34 (bs, 2H), 4.09 (d, J = 17.4 Hz, 1H), 3.66 (d, J = 17.4 Hz, 1H), 3.09 (d, J = 10.8 Hz, 2H). |
| 2-057 | (A) δ 8.32 (d, J = 1.5 Hz, 1H), 7.95 (dd, J = 8.1, 1.5 Hz, 1H), 7.75 (d, J = 8.1 Hz, 1H), 7.50 (d, J = 1.5 Hz, 2H), 7.44 (t, J = 1.5 Hz, 1H), 6.63 (t, J = 7.8 Hz, 1H), 4.74 (d, J = 6.0 Hz, 2H), 4.09 (d, J = 17.4 Hz, 1H), 3.72 (d, J = 17.4 Hz, 1H), 3.09 (q, J = 10.8 Hz, 2H). |
| 2-058 | (A) δ 7.70 (dd, J = 8.1, 1.5 Hz, 1H), 7.45-7.55 (m, 4H), 7.4-7.45 (m, 2H), 7.1-7.25 (m, 3H), 5.63 (bs, 1H), 4.36 (bs, 2H), 4.08 (d, J = 17.4 Hz, 1H), 3.69 (d, J = 17.4 Hz, 1H), 2.17 (q, J = 7.7 Hz, 2H), 1.11 (t, J = 7.7 Hz, 3H). |
| 2-059 | (A) δ 7.69 (d, J = 1.5 Hz, 1H), 7.64 (s, 2H), 7.45-7.55 (m, 2H), 6.10 (bs, 1H), 4.56 (d, J = 6.0 Hz, 2H), 4.05 (d, J = 17.4 Hz, 1H), 3.65 (d, J = 17.4 Hz, 1H), 1.3-1.45 (m, 1H), 0.95-1.0 (m, 2H), 0.7-0.8 (m, 2H). |
| 2-061 | (A) δ 7.69 (d, J = 1.5 Hz, 1H), 7.45-7.55 (m, 3H), 7.46 (d, J = 8.1 Hz, 1H), 7.42 (t, J = 1.5 Hz, 1H), 6.44 (bs, 1H), 4.56 (d, J = 6.6 Hz, 2H), 4.05 (d, J = 17.4 Hz, 1H), 3.66 (d, J = 17.4 Hz, 1H), 2.20 (d, J = 7.2 Hz, 2H), 0.9-1.05 (m, 1H), 0.6-0.7 (m, 2H), 0.15-0.25 (m, 2H). |
| 2-062 | (A) δ 7.69 (d, J = 1.5 Hz, 1H), 7.45-7.55 (m, 4H), 7.42 (t, J = 1.5 Hz, 1H), 6.00 (bs, 1H), 4.55 (d, J = 6.3 Hz, 2H), 4.05 (d, J = 17.4 Hz, 1H), 3.66 (d, J = 17.4 Hz, 1H), 2.75-2.95 (m, 1H), 2.59 (dd, J = 15.0, 4.8 Hz, 1H), 2.14 (dd, J = 15.0, 9.3 Hz, 1H), 1.13 (d, J = 7.2 Hz, 3H). |

TABLE 16-continued

| No. | ¹H NMR |
|---|---|
| 2-063 | (A) δ 7.70 (d, J = 1.5 Hz, 1H), 7.45-7.55 (m, 3H), 7.40-7.45 (m, 2H), 6.08 (bs, 1H), 4.57 (d, J = 6.0 Hz, 2H), 4.05 (d, J = 17.4 Hz, 1H), 3.8-3.95 (m, 1H), 3.66 (d, J = 17.4 Hz, 1H), 2.64 (d, J = 6.0 Hz, 2H). |
| 2-064 | (A) δ 7.67 (d, J = 1.5 Hz, 1H), 7.45-7.55 (m, 3H), 7.45 (d, J = 8.1 Hz, 1H), 7.42 (t, J = 1.5 Hz, 1H), 5.87 (bs, 1H), 4.51 (d, J = 6.3 Hz, 2H), 4.05 (d, J = 17.4 Hz, 1H), 3.66 (d, J = 17.4 Hz, 1H), 1.24 (s, 6H), 1.16 (s, 6H), 0.88 (s, 1H). |
| 2-065 | (A) δ 7.70 (d, J = 1.5 Hz, 1H), 7.45-7.5 (m, 4H), 7.42 (t, J = 1.5 Hz, 1H), 6.20 (bs, 1H), 4.60 (d, J = 6.3 Hz, 2H), 4.05 (d, J = 17.4 Hz, 1H), 3.66 (d, J = 17.4 Hz, 1H), 2.23 (d, J = 7.8 Hz, 1H), 1.60 (s, 3H), 1.69 (d, J = 7.8 Hz, 1H). |
| 2-066 | (A) δ 7.68 (d, J = 1.5 Hz, 1H), 7.52 (dd, J = 8.1, 1.5 Hz, 1H), 7.49 (d, J = 1.5 Hz, 2H), 7.44 (d, J = 8.1 Hz, 1H), 7.42 (t, J = 1.5 Hz, 1H), 7.00 (t, J = 6.0 Hz, 1H), 4.58 (d, J = 6.3 Hz, 2H), 4.05 (d, J = 17.4 Hz, 1H), 3.94 (s, 2H), 3.67 (d, J = 17.4 Hz, 1H), 3.42 (s, 3H). |
| 2-067 | (A) δ 7.68 (d, J = 1.5 Hz, 1H), 7.45-7.5 (m, 3H), 7.4-7.45 (m, 2H), 6.95-7.1 (m, 3H), 6.8-6.9 (m, 2H), 6.64 (d, J = 6.0 Hz, 2H), 4.50 (s, 2H), 4.05 (d, J = 17.4 Hz, 1H), 3.66 (d, J = 17.4 Hz, 1H). |
| 2-068 | (A) δ 7.68 (s, 1H), 7.45-7.55 (m, 3H), 7.45 (d, J = 8.1 Hz, 1H), 7.42 (t, J = 1.5 Hz, 1H), 6.80 (bs, 1H), 4.54 (d, J = 6.3 Hz, 2H), 4.05 (d, J = 17.4 Hz, 1H), 3.66 (d, J = 17.4 Hz, 1H), 3.64 (t, J = 5.7 Hz, 2H), 3.38 (s, 3H), 2.51 (t, J = 5.7 Hz, 2H). |
| 2-069 | (A) δ 7.70 (d, J = 1.5 Hz, 1H), 7.52 (dd, J = 8.1, 1.5 Hz, 1H), 7.49 (d, J = 1.5 Hz, 2H), 7.46 (d, J = 8.1 Hz, 1H), 7.42 (t, J = 1.5 Hz, 1H), 7.35-7.45 (m, 1H), 4.58 (d, J = 6.3 Hz, 2H), 4.05 (d, J = 17.4 Hz, 1H), 3.66 (d, J = 17.4 Hz, 1H), 3.23 (s, 2H), 2.01 (s, 3H). |
| 2-070 | (A) δ 7.70 (d, J = 1.5 Hz, 1H), 7.54 (dd, J = 8.1, 1.5 Hz, 1H), 7.45-7.5 (m, 3H), 7.42 (t, J = 1.5 Hz, 1H), 6.84 (bs, 1H), 4.60 (d, J = 6.0 Hz, 2H), 4.05 (d, J = 17.4 Hz, 1H), 3.91 (s, 2H), 3.66 (d, J = 17.4 Hz, 1H), 3.04 (s, 3H). |
| 2-071 | (A) δ 7.75-7.8 (m, 2H), 7.67 (d, J = 1.5 Hz, 1H), 7.4-7.55 (m, 8H), 6.92 (s, 1H), 6.79 (bs, 1H), 4.57 (d, J = 6.0 Hz, 2H), 4.17 (d, J = 6.0 Hz, 2H), 4.03 (d, J = 17.4 Hz, 1H), 3.64 (d, J = 17.4 Hz, 1H). |
| 2-072 | (A) δ 7.70 (d, J = 1.5 Hz, 1H), 7.54 (dd, J = 8.1, 1.5 Hz, 1H), 7.49 (t, J = 1.5 Hz, 2H), 7.4-7.45 (m, 2H), 6.88 (t, J = 6.0 Hz, 1H), 4.59 (d, J = 9.0 Hz, 2H), 4.05 (d, J = 17.4 Hz, 1H), 3.67 (d, J = 17.4 Hz, 1H), 1.65-1.75 (m, 2H), 1.5-1.6 (m, 2H). |
| 2-073 | (A) δ 7.69 (s, 1H), 7.45-7.55 (m, 4H), 7.42 (t, J = 1.5 Hz, 1H), 6.11 (bs, 1H), 4.56 (d, J = 6.6 Hz, 2H), 4.05 (d, J = 17.4 Hz, 1H), 3.66 (d, J = 17.4 Hz, 1H), 2.5-2.6 (m, 2H), 2.4-2.5 (m, 2H), 2.00 (t, J = 2.4 Hz, 1H). |
| 2-075 | (A) δ 7.62 (d, J = 1.5 Hz, 1H), 7.45-7.5 (m, 3H), 7.3-7.45 (m, 7H), 5.84 (bs, 1H), 4.42 (d, J = 6.0 Hz, 2H), 4.03 (d, J = 17.4 Hz, 1H), 3.64 (d, J = 17.4 Hz, 1H), 1.55-1.65 (m, 2H), 1.05-1.15 (m, 2H). |
| 2-076 | (A) δ 7.65-7.75 (m, 3H), 7.45-7.55 (m, 4H), 7.35-7.45 (m, 3H), 6.59 (bs, 1H), 4.72 (d, J = 6.0 Hz, 2H), 4.04 (d, J = 17.4 Hz, 1H), 3.66 (d, J = 17.4 Hz, 1H). |
| 2-077 | (A) δ 7.88 (d, J = 8.4 Hz, 2H), 7.7-7.75 (m, 3H), 7.45-7.6 (m, 4H), 7.42 (t, J = 1.5 Hz, 1H), 6.66 (bs, 1H), 4.75 (d, J = 6.3 Hz, 2H), 4.05 (d, J = 17.4 Hz, 1H), 3.67 (d, J = 17.4 Hz, 1H). |
| 2-079 | (A) δ 7.65-7.8 (m, 4H), 7.51 (dd, J = 8.1, 1.5 Hz, 1H), 7.45 (d, J = 8.1 Hz, 1H), 6.12 (t, J = 6.0 Hz, 1H), 4.55 (d, J = 6.0 Hz, 2H), 4.04 (d, J = 17.4 Hz, 1H), 3.66 (d, J = 17.4 Hz, 1H), 1.35-1.45 (m, 1H), 0.95-1.05 (m, 2H), 0.75-0.8 (m, 2H). |
| 2-080 | (A) δ 7.80 (s, 1H), 7.74 (s, 1H), 7.65-7.7 (m, 2H), 7.52 (dd, J = 8.1, 1.5 Hz, 1H), 7.46 (d, J = 8.1 Hz, 1H), 6.11 (bs, 1H), 4.55 (d, J = 6.3 Hz, 2H), 4.10 (d, J = 17.4 Hz, 1H), 3.68 (d, J = 17.4 Hz, 1H), 1.35-1.45 (m, 1H), 0.95-1.05 (m, 2H), 0.75-0.8 (m, 2H). |
| 2-082 | (A) δ 7.68 (d, J = 1.5 Hz, 1H), 7.57 (s, 1H), 7.56 (s, 1H), 7.51 (dd, J = 8.1, 1.5 Hz, 1H), 7.45 (d, J = 8.1 Hz, 1H), 6.10 (bs, 1H), 4.55 (d, J = 6.0 Hz, 2H), 4.05 (d, J = 17.4 Hz, 1H), 3.65 (d, J = 17.4 Hz, 1H), 1.35-1.45 (m, 1H), 0.95-1.05 (m, 2H), 0.75-0.8 (m, 2H). |
| 2-083 | (A) δ 7.72 (d, J = 8.7 Hz, 2H), 7.45-7.6 (m, 4H), 7.42 (t, J = 1.5 Hz, 1H), 6.24 (d, J = 8.7 Hz, 1H), 6.05 (d, J = 8.7 Hz, 1H), 4.07 (d, J = 17.4 Hz, 1H), 3.69 (d, J = 17.4 Hz, 1H), 2.35-2.5 (m, 1H), 1.18 and 1.21 (d, J = 6.9 Hz, 6H). |
| 2-086 | (A) δ 7.76 (d, J = 3.6 Hz, 1H), 7.63 (d, J = 8.1 Hz, 2H), 7.49 (d, J = 1.5 Hz, 2H), 7.45 (d, J = 8.1 Hz, 2H), 7.41 (t, J = 1.5 Hz, 1H), 7.32 (d, J = 3.6 Hz, 1H), 7.20 (d, J = 6.6 Hz, 1H), 6.43 (d, J = 6.6 Hz, 1H), 4.04 (d, J = 17.4 Hz, 1H), 3.65 (d, J = 17.4 Hz, 1H), 1.45-1.55 (m, 1H), 0.9-1.05 (m, 2H), 0.75-0.85 (m, 2H). |
| 2-087 | (A) δ 7.69 (s, 1H), 7.45-7.55 (m, 4H), 7.42 (t, J = 1.5 Hz, 1H), 6.02 (bs, 1H), 4.54 (d, J = 6.0 Hz, 2H), 4.04 (d, J = 17.4 Hz, 1H), 3.66 (d, J = 17.4 Hz, 1H), 1.3-1.4 (m, 1H), 1.1-1.2 (m, 2H), 1.09 (d, J = 6.0 Hz, 3H), 0.55-0.65 (m, 1H). |
| 2-091 | (A) δ 7.68 (d, J = 1.5 Hz, 1H), 7.4-7.55 (m, 5H), 6.68 (bs, 1H), 5.08 (bs, 1H), 4.56 (d, J = 6.0 Hz, 2H), 4.05 (d, J = 17.4 Hz, 1H), 3.81 (d, J = 6.0 Hz, 2H), 3.66 (d, J = 17.4 Hz, 1H), 1.44 (s, 9H). |

TABLE 16-continued

| No. | ¹H NMR |
|---|---|
| 2-092 | (A) δ 7.70 (d, J = 1.5 Hz, 1H), 7.53 (dd, J = 8.1, 1.5 Hz, 1H), 7.50 (d, J = 1.5 Hz, 1H), 7.45 (d, J = 8.1 Hz, 1H), 7.4-7.45 (m, 2H), 6.96 (bs, 1H), 4.62 (d, J = 6.6 Hz, 2H), 4.05 (d, J = 17.4 Hz, 1H), 3.98 (s, 3H), 3.66 (d, J = 17.4 Hz, 1H). |
| 2-093 | (A) δ 7.87 (d, J = 6.9 Hz, 2H), 7.7-7.75 (m, 3H), 7.45-7.55 (m, 4H), 7.42 (t, J = 1.5 Hz, 1H), 6.65 (t, J = 6.0 Hz, 1H), 4.75 (d, J = 6.3 Hz, 2H), 4.05 (d, J = 17.4 Hz, 1H), 3.66 (d, J = 17.4 Hz, 1H). |
| 2-098 | (A) δ 8.05-8.2 (m, 1H), 7.87 (s, 1H), 7.15-7.65 (m, 6H), 6.8-7.05 (m, 2H), 7.43 (d, J = 5.7 Hz, 2H), 4.05 (d, J = 17.4 Hz, 1H), 3.67 (d, J = 17.4 Hz, 1H). |
| 2-100 | (A) δ 8.29 (d, J = 1.5 Hz, 1H), 7.92 (dd, J = 8.1, 1.5 Hz, 1H), 7.75 (d, J = 1.5 Hz, 1H), 7.50 (d, J = 1.5 Hz, 2H), 7.44 (t, J = 1.5 Hz, 1H), 6.45 (t, J = 6.3 Hz, 1H), 4.71 (d, J = 6.3 Hz, 2H), 4.11 (d, J = 17.4 Hz, 1H), 3.71 (d, J = 17.4 Hz, 1H), 1.3-1.45 (m, 1H), 0.9-1.0 (m, 2H), 0.7-0.8 (m, 2H). |
| 2-102 | (A) δ 7.50 (s, 2H), 7.4-7.45 (m, 1H), 7.32 (d, J = 7.5 Hz, 1H), 7.24 (dd, J = 7.5, 1.5 Hz, 1H), 7.08 (d, J = 1.5 Hz, 1H), 6.37 (bs, 1H), 4.37 (d, J = 5.7 Hz, 2H), 4.06 (d, J = 17.4 Hz, 1H), 3.81 (s, 3H), 3.67 (d, J = 17.4 Hz, 1H), 3.08 (q, J = 10.5 Hz, 2H), 1.87 (s, 3H). |
| 2-103 | (A) δ 8.26 (s, 1H), 7.35-7.7 (m, 5H), 6.50 (t, J = 6.3 Hz, 1H), 4.55 (d, J = 6.3 Hz, 2H), 4.07 (d, J = 17.4 Hz, 1H), 3.70 (d, J = 17.4 Hz, 1H). |
| 2-104 | (A) δ 8.07 (s, 2H), 7.96 (s, 1H), 7.69 (d, J = 1.5 Hz, 1H), 7.52 (dd, J = 7.8, 1.5 Hz, 1H), 7.45 (d, J = 7.8 Hz, 1H), 5.99 (t, J = 6.0 Hz, 1H), 4.53 (d, J = 6.3 Hz, 2H), 4.16 (d, J = 17.4 Hz, 1H), 3.71 (d, J = 17.4 Hz, 1H), 2.26 (q, J = 7.5 Hz, 2H), 1.17 (t, J = 7.6 Hz, 3H). |
| 2-105 | (A) δ 7.68 (d, J = 1.5 Hz, 1H), 7.63 (s, 2H), 7.49 (dd, J = 7.8, 1.5 Hz, 1H), 7.44 (d, J = 7.8 Hz, 1H), 5.96 (bs, 1H), 4.53 (d, J = 6.3 Hz, 2H), 4.05 (d, J = 17.4 Hz, 1H), 3.65 (d, J = 17.4 Hz, 1H), 2.26 (q, J = 7.8 Hz, 2H), 1.17 (t, J = 7.8 Hz, 3H). |
| 2-106 | (A) δ 7.83 (s, 1H), 7.3-7.6 (m, 5H), 6.10 (t, J = 6.6 Hz, 1H), 4.50 (d, J = 6.6 Hz, 2H), 4.04 (d, J = 17.4 Hz, 1H), 3.67 (d, J = 17.4 Hz, 1H), 2.26 (q, J = 7.8 Hz, 2H), 1.17 (t, J = 7.8 Hz, 3H). |
| 2-107 | (A) δ 7.85 (d, J = 1.8 Hz, 1H), 7.62 (s, 2H), 7.55 (dd, J = 8.1, 1.8 Hz, 1H), 7.45 (d, J = 8.1 Hz, 1H), 5.96 (t, J = 6.2 Hz, 1H), 4.52 (d, J = 6.2 Hz, 2H), 4.05 (d, J = 17.2 Hz, 1H), 3.65 (d, J = 17.2 Hz, 1H), 2.26 (q, J = 7.5 Hz, 2H), 1.17 (t, J = 7.5 Hz, 3H). |
| 2-108 | (A) δ 8.28 (s, 1H), 7.92 (d, J = 8.4 Hz, 1H), 7.77 (d, J = 8.4 Hz, 1H), 7.64 (s, 2H), 6.29 (t, J = 6.6 Hz, 1H), 4.69 (d, J = 6.6 Hz, 2H), 4.10 (d, J = 17.4 Hz, 1H), 3.71 (d, J = 17.4 Hz, 1H), 2.28 (q, J = 7.8 Hz, 2H), 1.14 (t, J = 7.8 Hz, 3H). |
| 2-109 | (A) δ 7.65 (s, 2H), 7.60 (d, J = 8.1 Hz, 2H), 7.35 (d, J = 8.1 Hz, 2H), 5.85 (d, J = 7.8 Hz, 1H), 5.05-5.2 (m, 1H), 4.05 (d, J = 17.4 Hz, 1H), 3.65 (d, J = 17.4 Hz, 1H), 2.20 (q, J = 7.5 Hz, 2H), 1.45 (d, J = 7.2 Hz, 3H), 1.15 (t, J = 7.5 Hz, 3H). |
| 2-112 | (A) δ 7.85 (d, J = 1.8 Hz, 1H), 7.62 (s, 2H), 7.55 (dd, J = 8.1, 1.8 Hz, 1H), 7.45 (d, J = 8.1 Hz, 1H), 5.95 (t, J = 6.2 Hz, 1H), 4.52 (d, J = 6.2 Hz, 2H), 4.05 (d, J = 17.2 Hz, 1H), 3.65 (d, J = 17.2 Hz, 1H), 2.20 (t, J = 7.5 Hz, 2H), 1.6-1.75 (m, 2H), 0.94 (t, J = 7.4 Hz, 3H). |
| 2-113 | (A) δ 8.27 (s, 1H), 7.91 (d, J = 8.4 Hz, 1H), 7.76 (d, J = 8.4 Hz, 1H), 7.64 (s, 2H), 6.35 (t, J = 6.3 Hz, 1H), 4.69 (d, J = 6.3 Hz, 2H), 4.11 (d, J = 17.7 Hz, 1H), 3.73 (d, J = 17.7 Hz, 1H), 2.18 (t, J = 7.5 Hz, 2H), 1.5-1.8 (m, 2H), 0.91 (t, J = 7.5 Hz, 3H). |
| 2-114 | (A) δ 7.65 (s, 2H), 7.60 (d, J = 8.1 Hz, 2H), 7.35 (d, J = 8.1 Hz, 2H), 5.75 (d, J = 7.5 Hz, 1H), 5.1-5.2 (m, 1H), 4.05 (d, J = 17.4 Hz, 1H), 3.65 (d, J = 17.4 Hz, 1H), 2.15 (t, J = 7.5 Hz, 2H), 1.65 (q, J = 7.5 Hz, 2H), 1.50 (d, J = 7.2 Hz, 3H), 0.95 (t, J = 7.5 Hz, 3H). |
| 2-118 | (A) δ 8.27 (s, 1H), 7.91 (d, J = 8.4 Hz, 1H), 7.76 (d, J = 8.4 Hz, 1H), 7.64 (s, 2H), 6.29 (t, J = 6.0 Hz, 1H), 4.68 (d, J = 6.0 Hz, 2H), 4.10 (d, J = 17.4 Hz, 1H), 3.71 (d, J = 17.4 Hz, 1H), 2.38 (sep, J = 7.2 Hz, 1H), 1.12 (d, J = 7.2 Hz, 6H). |
| 2-120 | (A) δ 7.64 (s, 2H), 7.62 (d, J = 8.4 Hz, 2H), 7.35 (d, J = 8.4 Hz, 2H), 5.93 (bs, 1H), 4.49 (d, J = 5.7 Hz, 2H), 4.08 (d, J = 17.4 Hz, 1H), 3.67 (d, J = 17.4 Hz, 1H), 1.3-1.45 (m, 1H), 0.95-1.05 (m, 2H), 0.75-0.85 (m, 2H). |
| 2-121 | (A) δ 7.86 (s, 1H), 7.80 (d, J = 7.5 Hz, 1H), 7.70 (d, J = 1.8 Hz, 1H), 7.69 (d, J = 7.5 Hz, 1H), 7.59 (t, J = 7.5 Hz, 1H), 7.51 (dd, J = 8.0, 1.8 Hz, 1H), 7.45 (d, J = 8.0 Hz, 1H), 6.12 (t, J = 6.1 Hz, 1H), 4.55 (d, J = 6.1 Hz, 2H), 4.10 (d, J = 17.5 Hz, 1H), 3.71 (d, J = 17.5 Hz, 1H), 1.3-1.45 (m, 1H), 0.95-1.1 (m, 2H), 0.7-0.85 (m, 2H). |
| 2-123 | (A) δ 7.68 (d, J = 1.5 Hz, 1H), 7.50 (s, 2H), 7.45-7.5 (m, 1H), 7.45 (d, J = 8.1 Hz, 1H), 6.13 (bs, 2H), 4.55 (d, J = 6.3 Hz, 2H), 4.01 (d, J = 17.4 Hz, 1H), 3.65 (d, J = 17.4 Hz, 1H), 1.35-1.45 (m, 1H), 0.95-1.05 (m, 2H), 0.7-0.85 (m, 2H). |
| 2-124 | (A) δ 7.67 (d, J = 1.5 Hz, 1H), 7.64 (s, 2H), 7.50 (dd, J = 8.1, 1.5 Hz, 1H), 7.46 (d, J = 8.1 Hz, 1H), 6.61 (t, J = 73.5 Hz, 1H), 6.17 (t, J = 6.0 Hz, 1H), 4.54 (d, J = 6.0 Hz, 2H), 4.06 (d, J = 17.4 Hz, 1H), 3.67 (d, J = 17.4 Hz, 1H), 1.35-1.45 (m, 1H), 0.95-1.05 (m, 2H), 0.7-0.85 (m, 2H). |

TABLE 16-continued

| No. | ¹H NMR |
|---|---|
| 2-125 | (A) δ 7.67 (d, J = 1.5 Hz, 1H), 7.66 (s, 2H), 7.49 (dd, J = 7.8, 1.5 Hz, 1H), 7.45 (d, J = 7.8 Hz, 1H), 6.21 (bs, 1H), 4.54 (d, J = 6.0 Hz, 2H), 4.06 (d, J = 17.4 Hz, 1H), 3.68 (d, J = 17.4 Hz, 1H), 3.48 (s, 3H), 1.35-1.45 (m, 1H), 0.95-1.05 (m, 2H), 0.7-0.85 (m, 2H). |
| 2-126 | (A) δ 7.68 (d, J = 1.5 Hz, 1H), 7.60 (s, 2H), 7.50 (dd, J = 8.4, 1.5 Hz, 1H), 7.46 (d, J = 8.4 Hz, 1H), 6.09 (bs, 1H), 4.55 (d, J = 6.0 Hz, 2H), 4.04 (d, J = 17.4 Hz, 1H), 3.65 (d, J = 17.4 Hz, 1H), 2.46 (s, 3H), 1.3-1.45 (m, 1H), 0.95-1.05 (m, 2H), 0.7-0.85 (m, 2H). |
| 2-127 | (A) δ 7.67 (d, J = 1.5 Hz, 1H), 7.60 (s, 2H), 7.50 (dd, J = 8.4, 1.5 Hz, 1H), 7.45 (d, J = 8.4 Hz, 1H), 6.23 (t, J = 6.0 Hz, 1H), 4.54 (d, J = 6.3 Hz, 2H), 4.07 (d, J = 17.4 Hz, 1H), 3.67 and 3.66 (d, J = 17.4 Hz, 1H), 3.07 and 3.06 (s, 3H), 1.35-1.45 (m, 1H), 0.9-1.05 (m, 2H), 0.7-0.8 (m, 2H). |
| 2-128 | (A) δ 7.73 (s, 2H), 7.67 (d, J = 1.5 Hz, 1H), 7.50 (dd, J = 8.4, 1.5 Hz, 1H), 7.46 (d, J = 8.1 Hz, 1H), 6.16 (t, J = 6.0 Hz, 1H), 4.50 (d, J = 6.6 Hz, 2H), 4.09 (d, J = 17.4 Hz, 1H), 3.67 (d, J = 17.4 Hz, 1H), 3.35 (s, 3H), 1.35-1.45 (m, 1H), 0.95-1.05 (m, 2H), 0.7-0.85 (m, 2H). |
| 2-130 | (A) δ 8.29 (s, 1H), 7.92 (d, J = 8.4 Hz, 1H), 7.76 (d, J = 8.4 Hz, 1H), 7.64 (s, 2H), 6.48 (t, J = 6.3 Hz, 1H), 4.71 (d, J = 6.3 Hz, 2H), 4.10 (d, J = 17.4 Hz, 1H), 3.72 (d, J = 17.4 Hz, 1H), 1.3-1.5 (m, 1H), 0.9-1.1 (m, 2H), 0.7-0.9 (m, 2H). |
| 2-132 | (A) δ 9.90 (bs, 1H), 8.00 (bs, 1H), 7.81 (dd, J = 8.4, 1.5 Hz, 1H), 7.75 (d, J = 1.5 Hz, 1H), 7.48 (s, 2H), 7.42 (t, J = 1.5 Hz, 1H), 7.37 (d, J = 8.4 Hz, 1H), 6.71 (bs, 1H), 4.41 (d, J = 5.1 Hz, 2H), 4.09 (d, J = 17.4 Hz, 1H), 3.71 (d, J = 17.4 Hz, 1H), 1.35-1.45 (m, 1H), 0.85-0.95 (m, 2H), 0.75-0.85 (m, 2H). |
| 2-134 | (A) δ 8.08 (s, 2H), 7.95 (s, 1H), 7.63 (d, J = 8.7 Hz, 2H), 7.38 (d, J = 8.7 Hz, 2H), 5.95 (d, J = 7.2 Hz, 1H), 5.05-5.2 (m, 1H), 4.17 (d, J = 17.4 Hz, 1H), 3.73 (d, J = 17.4 Hz, 1H), 1.49 (d, J = 7.2 Hz, 3H), 1.3-1.45 (m, 1H), 0.85-1.05 (m, 2H), 0.65-0.8 (m, 2H). |
| 2-135 | (A) δ 7.63 (s, 2H), 7.62 (d, J = 8.7 Hz, 2H), 7.38 (d, J = 8.7 Hz, 2H), 5.83 (d, J = 7.2 Hz, 1H), 5.05-5.2 (m, 1H), 4.06 (d, J = 17.4 Hz, 1H), 3.66 (d, J = 17.4 Hz, 1H), 1.49 (d, J = 7.2 Hz, 3H), 1.25-1.4 (m, 1H), 0.85-1.0 (m, 2H), 0.7-0.8 (m, 2H). |
| 2-136 | (A) δ 7.3-7.6 (m, 6H), 5.84 (d, J = 6.9 Hz, 1H), 5.2-5.35 (m, 1H), 4.06 (d, J = 17.4 Hz, 1H), 3.66 (d, J = 17.4 Hz, 1H), 2.42 (s, 3H), 1.45 (d, J = 6.9 Hz, 3H), 1.2-1.4 (m, 1H), 0.8-1.05 (m, 2H), 0.65-0.8 (m, 2H). |
| 2-137 | (B) δ 7.55-7.6 (m, 2H), 7.5-7.55 (m, 2H), 7.35-7.4 (m, 3H), 6.46 (d, J = 12.0 Hz, 1H), 6.2-6.3 (m, 1H), 5.72 (bs, 1H), 4.36 (q, J = 6.0 Hz, 2H), 4.08 (d, J = 17.3 Hz, 1H), 3.69 (d, J = 17.3 Hz, 1H), 2.46 (q, J = 6.0 Hz, 2H), 1.25-1.4 (m, 1H), 0.9-1.0 (m, 2H), 0.7-0.8 (m, 2H). |
| 2-139 | (A) δ 8.85 and 8.77 (d, J = 3.0 Hz, 1H), 7.6-7.7 (m, 3H), 7.4-7.6 (m, 5H), 6.12 and 6.10 (d, J = 7.8 Hz, 1H), 4.06 and 4.05 (d, J = 17.4 Hz, 1H), 3.67 and 3.65 (d, J = 17.4 Hz, 1H), 1.55-1.7 (m, 1H), 0.8-0.95 (m, 4H). |
| 2-141 | (A) δ 7.67 (d, J = 1.5 Hz, 1H), 7.62 (s, 2H), 7.50 (dd, J = 7.8, 1.5 Hz, 1H), 7.45 (d, J = 7.8 Hz, 1H), 5.96 (t, J = 6.0 Hz, 1H), 4.53 (d, J = 6.0 Hz, 2H), 4.05 (d, J = 17.4 Hz, 1H), 3.66 (d, J = 17.4 Hz, 1H), 2.05-2.2 (m, 3H), 0.93 (t, J = 6.6 Hz, 6H). |
| 2-142 | (A) δ 7.85 (d, J = 1.8 Hz, 1H), 7.62 (s, 2H), 7.55 (dd, J = 8.1, 1.8 Hz, 1H), 7.46 (d, J = 8.1 Hz, 1H), 5.93 (t, J = 6.2 Hz, 1H), 4.52 (d, J = 6.2 Hz, 2H), 4.05 (d, J = 17.5 Hz, 1H), 3.65 (d, J = 17.5 Hz, 1H), 2.0-2.2 (m, 3H), 0.94 (d, J = 6.2 Hz, 6H). |
| 2-143 | (A) δ 7.65 (s, 2H), 7.60 (d, J = 8.4 Hz, 2H), 7.35 (d, J = 8.4 Hz, 2H), 5.70 (d, J = 7.5 Hz, 1H), 5.1-5.15 (m, 1H), 4.05 (d, J = 17.4 Hz, 1H), 3.65 (d, J = 17.4 Hz, 1H), 2.05-2.15 (m, 3H), 1.45 (d, J = 6.9 Hz, 3H), 0.95 (d, J = 6.3 Hz, 3H), 0.90 (d, J = 6.3 Hz, 3H). |
| 2-145 | (A) δ 7.69 (d, J = 1.5 Hz, 1H), 7.63 (s, 2H), 7.50 (dd, J = 7.8, 1.5 Hz, 1H), 7.46 (d, J = 7.8 Hz, 1H), 6.45 (t, J = 6.0 Hz, 1H), 4.56 (d, J = 6.3 Hz, 2H), 4.05 (d, J = 17.4 Hz, 1H), 3.66 (d, J = 17.4 Hz, 1H), 2.20 (d, J = 7.2 Hz, 2H), 0.9-1.05 (m, 1H), 0.55-0.7 (m, 2H), 0.15-0.25 (m, 2H). |
| 2-146 | (A) δ 7.86 (d, J = 1.8 Hz, 1H), 7.62 (s, 2H), 7.55 (dd, J = 8.1, 1.8 Hz, 1H), 7.46 (d, J = 8.1 Hz, 1H), 6.49 (t, J = 6.2 Hz, 1H), 4.54 (d, J = 6.2 Hz, 2H), 4.05 (d, J = 17.4 Hz, 1H), 3.65 (d, J = 17.4 Hz, 1H), 2.20 (d, J = 7.2 Hz, 2H), 0.9-1.05 (m, 1H), 1.55-1.7 (m, 2H), 0.15-0.35 (m, 2H). |
| 2-147 | (A) δ 8.28 (s, 1H), 7.92 (d, J = 8.4 Hz, 1H), 7.77 (d, J = 8.4 Hz, 1H), 7.64 (s, 2H), 6.78 (t, J = 6.3 Hz, 1H), 4.72 (d, J = 6.3 Hz, 2H), 4.10 (d, J = 17.4 Hz, 1H), 3.71 (d, J = 17.4 Hz, 1H), 2.16 (d, J = 7.2 Hz, 2H), 0.8-1.0 (m, 1H), 0.55-0.7 (m, 2H), 0.15-0.25 (m, 2H). |
| 2-148 | (A) δ 8.08 (s, 2H), 7.96 (s, 1H), 7.65 (d, J = 8.4 Hz, 2H), 7.39 (d, J = 8.4 Hz, 2H), 6.09 (d, J = 8.1 Hz, 1H), 5.1-5.2 (m, 1H), 4.18 (d, J = 17.1 Hz, 1H), 3.73 (d, J = 17.1 Hz, 1H), 2.17 (d, J = 7.2 Hz, 2H), 1.50 (d, J = 6.9 Hz, 3H), 0.9-1.0 (m, 1H), 0.6-0.65 (m, 2H), 0.15-0.25 (m, 2H). |

TABLE 16-continued

| No. | $^1$H NMR |
|---|---|
| 2-149 | (A) δ 7.65 (s, 2H), 7.60 (d, J = 8.1 Hz, 2H), 7.40 (d, J = 8.1 Hz, 2H), 6.10 (d, J = 7.8 Hz, 1H), 5.15-5.25 (m, 1H), 4.05 (d, J = 17.1 Hz, 1H), 3.70 (d, J = 17.1 Hz, 1H), 2.20 (d, J = 7.2 Hz, 2H), 1.50 (d, J = 7.2 Hz, 3H), 0.95-1.0 (m, 1H), 0.6-0.65 (m, 2H), 0.2-0.25 (m, 2H). |
| 2-150 | (A) δ 7.72 (d, J = 8.4 Hz, 2H), 7.63 (s, 2H), 7.55 (d, J = 8.4 Hz, 2H), 6.49 (d, J = 9.0 Hz, 1H), 6.26 (d, J = 9.0 Hz, 1H), 4.08 (d, J = 17.4 Hz, 1H), 3.68 (d, J = 17.4 Hz, 1H), 2.26 (d, J = 7.2 Hz, 2H), 0.9-1.05 (m, 1H), 0.55-0.7 (m, 2H), 0.15-0.3 (m, 2H). |
| 2-152 | (A) δ 7.68 (s, 1H), 7.63 (s, 2H), 7.4-7.55 (m, 2H), 6.03 (bs, 1H), 4.54 (d, J = 6.0 Hz, 2H), 4.05 (d, J = 17.4 Hz, 1H), 3.65 (d, J = 17.4 Hz, 1H), 1.3-1.45 (m, 1H), 1.1-1.2 (m, 2H), 1.09 (d, J = 6.0 Hz, 3H), 0.55-0.65 (m, 1H). |
| 2-154 | (A) δ 7.4-7.75 (m, 5H), 6.00 (bs, 1H), 4.50 (d, J = 6.3 Hz, 2H), 4.05 (d, J = 17.3 Hz, 1H), 3.67 (d, J = 17.3 Hz, 1H), 3.04 (qui, J = 8.4 Hz, 1H), 1.75-2.35 (m, 6H). |
| 2-155 | (A) δ 7.84 (d, J = 1.8 Hz, 1H), 7.62 (s, 2H), 7.55 (dd, J = 8.1, 1.8 Hz, 1H), 7.43 (d, J = 8.1 Hz, 1H), 5.85 (t, J = 6.3 Hz, 1H), 4.50 (d, J = 6.3 Hz, 2H), 4.04 (d, J = 17.7 Hz, 1H), 3.64 (d, J = 17.7 Hz, 1H), 2.95-3.1 (m, 1H), 1.8-2.35 (m, 6H). |
| 2-157 | (A) δ 7.67 (s, 1H), 7.62 (s, 2H), 7.48 (d, J = 7.8 Hz, 1H), 7.44 (d, J = 7.8 Hz, 1H), 6.06 (t, J = 6.0 Hz, 1H), 4.57 (dd, J = 15.6, 6.3 Hz, 1H), 4.51 (dd, J = 15.6, 6.3 Hz, 1H), 4.05 (d, J = 17.4 Hz, 1H), 3.65 (d, J = 17.4 Hz, 1H), 1.2-1.35 (m, 1H), 1.15 (s, 3H), 1.14 (s, 3H), 1.1-1.15 (m, 1H), 0.76 (dd, J = 8.1, 4.5 Hz, 1H). |
| 2-159 | (A) δ 7.6-7.7 (m, 3H), 7.4-7.55 (m, 2H), 7.13 (bs, 1H), 4.59 (d, J = 6.0 Hz, 2H), 4.09 (s, 2H), 4.06 (d, J = 17.3 Hz, 1H), 3.67 (d, J = 17.3 Hz, 1H). |
| 2-160 | (A) δ 7.35-7.7 (m, 5H), 7.05 (bs, 1H), 4.63 (d, J = 6.3 Hz, 2H), 4.07 (d, J = 17.3 Hz, 1H), 3.68 (d, J = 17.3 Hz, 1H). |
| 2-161 | (A) δ 7.90 (d, J = 1.8 Hz, 1H), 7.62 (s, 2H), 7.59 (dd, J = 8.1, 1.8 Hz, 1H), 7.45 (d, J = 8.1 Hz, 1H), 6.80 (bs, 1H), 4.63 (d, J = 6.2 Hz, 2H), 4.06 (d, J = 17.2 Hz, 1H), 3.66 (d, J = 17.2 Hz, 1H). |
| 2-162 | (A) δ 7.74 (d, J = 1.2 Hz, 1H), 7.62 (s, 2H), 7.45-7.6 (m, 2H), 6.73 (bs, 1H), 4.64 (d, J = 6.3 Hz, 2H), 4.05 (d, J = 17.4 Hz, 1H), 3.66 (d, J = 17.4 Hz, 1H). |
| 2-163 | (A) δ 7.71 (t, J = 1.8 Hz, 1H), 7.5-7.55 (m, 1H), 7.35-7.45 (m, 2H), 7.21 (s, 1H), 6.91 (bs, 1H), 4.63 (d, J = 6.3 Hz, 2H), 4.06 (d, J = 17.4 Hz, 1H), 3.71 (d, J = 17.4 Hz, 1H), 2.48 (s, 3H), 2.39 (d, J = 0.6 Hz, 3H). |
| 2-164 | (A) δ 7.6-7.7 (m, 3H), 7.4-7.5 (m, 2H), 6.29 (bs, 1H), 4.5-4.6 (m, 2H), 4.05 (d, J = 17.3 Hz, 1H), 3.81 (td, J = 6.3, 2.1 Hz, 2H), 3.66 (d, J = 17.3 Hz, 1H), 2.68 (t, J = 6.3 Hz, 2H). |
| 2-165 | (A) δ 7.6-7.7 (m, 3H), 7.4-7.5 (m, 1H), 7.3-7.4 (m, 1H), 6.68 (bs, 1H), 4.52 (d, J = 6.0 Hz, 2H), 4.06 (d, J = 17.3 Hz, 1H), 3.68 (d, J = 17.3 Hz, 1H), 3.11 (q, J = 10.8 Hz, 2H). |
| 2-168 | (A) δ 7.65 (s, 2H), 7.60 (d, J = 8.7 Hz, 2H), 7.35 (d, J = 8.7 Hz, 2H), 6.05 (d, J = 7.5 Hz, 1H), 5.1-5.2 (m, 1H), 4.05 (d, J = 17.8 Hz, 1H), 3.65 (d, J = 17.8 Hz, 1H), 3.10 (q, J = 10.5 Hz, 2H), 1.50 (d, J = 7.2 Hz, 3H). |
| 2-169 | (A) δ 7.73 (d, J = 8.4 Hz, 2H), 7.63 (s, 2H), 7.53 (d, J = 8.4 Hz, 2H), 6.75 (d, J = 8.7 Hz, 1H), 6.20 (d, J = 8.7 Hz, 1H), 4.08 (d, J = 17.4 Hz, 1H), 3.69 (d, J = 17.4 Hz, 1H), 3.1-3.25 (m, 2H). |
| 2-170 | (A) δ 7.73 (d, J = 1.5 Hz, 1H), 7.62 (s, 2H), 7.52 (dd, J = 7.8, 1.5 Hz, 1H), 7.43 (d, J = 7.8 Hz, 1H), 6.92 (bs, 1H), 4.66 (d, J = 6.0 Hz, 2H), 4.05 (d, J = 17.4 Hz, 1H), 3.66 (d, J = 17.4 Hz, 1H). |
| 2-172 | (A) δ 7.6-7.7 (m, 3H), 7.45-7.55 (m, 1H), 7.3-7.4 (m, 1H), 6.38 (bs, 1H), 4.51 (q, J = 3.0 Hz, 2H), 4.06 (d, J = 17.3 Hz, 1H), 3.66 (d, J = 17.3 Hz, 1H), 2.4-2.65 (m, 4H). |
| 2-174 | (A) δ 7.65 (s, 2H), 7.60 (d, J = 8.4 Hz, 2H), 7.35 (d, J = 8.4 Hz, 2H), 5.80 (d, J = 7.8 Hz, 1H), 5.05-5.15 (m, 1H), 4.05 (d, J = 17.1 Hz, 1H), 3.65 (d, J = 17.1 Hz, 1H), 2.35-2.55 (m, 4H), 1.50 (d, J = 6.6 Hz, 3H). |
| 2-175 | (A) δ 7.6-7.7 (m, 3H), 7.4-7.5 (m, 2H), 7.00 (bs, 1H), 4.59 (d, J = 6.0 Hz, 2H), 4.17 (s, 2H), 4.06 (d, J = 17.3 Hz, 1H), 3.93 (q, J = 8.4 Hz, 2H), 3.68 (d, J = 17.3 Hz, 1H). |
| 2-176 | (A) δ 7.6-7.75 (m, 3H), 7.4-7.5 (m, 2H), 7.00 (bs, 1H), 4.58 (d, J = 6.0 Hz, 2H), 4.24 (d, J = 2.4 Hz, 2H), 4.10 (s, 2H), 4.06 (d, J = 17.3 Hz, 1H), 3.67 (d, J = 17.3 Hz, 1H), 2.50 (t, J = 2.4 Hz, 1H). |
| 2-177 | (A) δ 7.64 (m, 2H), 7.62 (d, J = 8.4 Hz, 2H), 7.46 (d, J = 8.4 Hz, 2H), 6.04 (bs, 1H), 4.46 (d, J = 6.0 Hz, 2H), 4.07 (d, J = 17.4 Hz, 1H), 3.75-4.0 (m, 4H), 3.67 (d, J = 17.4 Hz, 1H), 2.9-3.0 (m, 1H), 2.1-2.25 (m, 2H). |
| 2-179 | (A) δ 7.69 (d, J = 1.5 Hz, 1H), 7.62 (s, 2H), 7.50 (dd, J = 7.8, 1.5 Hz, 1H), 7.44 (d, J = 7.8 Hz, 1H), 6.17 (bs, 1H), 4.52 (d, J = 6.0 Hz, 2H), 4.05 (d, J = 17.4 Hz, 1H), 3.66 (d, J = 17.4 Hz, 1H), 3.75-4.0 (m, 4H), 2.85-3.0 (m, 1H), 2.1-2.25 (m, 2H). |

TABLE 16-continued

| No. | $^1$H NMR |
|---|---|
| 2-180 | (A) δ 7.86 (s, 1H), 7.63 (s, 2H), 7.56 (d, J = 8.1 Hz, 1H), 7.43 (d, J = 8.1 Hz, 1H), 6.22 (bs, 1H), 4.51 (d, J = 6.0 Hz, 2H), 4.05 (d, J = 17.3 Hz, 1H), 3.75-4.0 (m, 4H), 3.65 (d, J = 17.3 Hz, 1H), 2.85-3.0 (m, 1H), 2.05-2.25 (m, 2H). |
| 2-181 | (A) δ 8.28 (s, 1H), 7.93 (d, J = 8.4 Hz, 1H), 7.75 (d, J = 8.4 Hz, 1H), 7.64 (s, 2H), 6.49 (t, J = 6.3 Hz, 1H), 4.69 (d, J = 6.3 Hz, 2H), 4.11 (d, J = 17.4 Hz, 1H), 3.7-4.05 (m, 4H), 3.72 (d, J = 17.4 Hz, 1H), 2.85-2.95 (m, 1H), 2.0-2.3 (m, 2H). |
| 2-182 | (A) δ 7.63 (s, 2H), 7.62 (d, J = 8.1 Hz, 2H), 7.35 (dd, J = 8.1, 2.1 Hz, 2H), 5.90 (d, J = 7.8 Hz, 1H), 5.05-5.15 (m, 1H), 4.05 (d, J = 17.7 Hz, 1H), 3.75-4.15 (m, 4H), 3.65 (d, J = 17.7 Hz, 1H), 2.85-2.95 (m, 1H), 2.05-2.15 (m, 2H), 1.45-1.5 (m, 3H). |
| 2-183 | (A) δ 7.80 (s, 1H), 7.35-7.6 (m, 5H), 7.26 (t, J = 5.7 Hz, 1H), 4.52 (d, J = 5.7 Hz, 2H), 4.05 (d, J = 17.4 Hz, 1H), 3.97 (s, 2H), 3.68 (d, J = 17.4 Hz, 1H), 3.07 (s, 3H). |
| 2-184 | (A) δ 7.4-7.8 (m, 7H), 4.56 (d, J = 6.3 Hz, 2H), 4.06 (d, J = 17.3 Hz, 1H), 3.68 (d, J = 17.3 Hz, 1H), 3.26 (s, 2H), 2.53 (q, J = 7.4 Hz, 2H), 1.23 (t, J = 7.4 Hz, 3H). |
| 2-185 | (A) δ 7.75-7.8 (m, 1H), 7.67 (s, 1H), 7.35-7.5 (m, 2H), 7.1-7.3 (m, 3H), 4.53 (d, J = 6.0 Hz, 2H), 4.03 (d, J = 17.3 Hz, 1H), 3.68 (d, J = 13.6 Hz, 1H), 3.66 (d, J = 17.3 Hz, 1H), 3.40 (d, J = 13.6 Hz, 1H), 2.75-2.85 (m, 2H), 1.29 (t, J = 7.4 Hz, 3H). |
| 2-186 | (A) δ 7.9-8.1 (m, 2H), 7.2-7.7 (m, 5H), 4.58 (d, J = 6.0 Hz, 2H), 4.04 (d, J = 17.3 Hz, 1H), 3.97 (s, 2H), 3.66 (d, J = 17.3 Hz, 1H), 3.20 (q, J = 7.5 Hz, 2H), 1.41 (t, J = 7.5 Hz, 3H). |
| 2-187 | (A) δ 7.70 (s, 1H), 7.4-7.55 (m, 6H), 4.57 (d, J = 6.0 Hz, 2H), 4.06 (d, J = 17.3 Hz, 1H), 3.69 (d, J = 17.3 Hz, 1H), 3.25 (s, 2H), 2.48 (t, J = 4.5 Hz, 2H), 1.58 (sxt, J = 4.5 Hz, 2H), 0.94 (t, J = 4.5 Hz, 3H). |
| 2-188 | (A) δ 7.70 (s, 1H), 7.4-7.55 (m, 6H), 4.56 (d, J = 6.0 Hz, 2H), 4.06 (d, J = 17.3 Hz, 1H), 3.69 (d, J = 17.3 Hz, 1H), 3.28 (s, 2H), 2.88 (sep, J = 6.5 Hz, 1H), 1.22 (d, J = 6.5 Hz, 6H). |
| 2-189 | (A) δ 7.68 (s, 1H), 7.1-7.55 (m, 11H), 4.44 (d, J = 6.0 Hz, 2H), 4.05 (d, J = 17.3 Hz, 1H), 3.69 (s, 2H), 3.67 (d, J = 17.3 Hz, 1H), 3.16 (s, 2H). |
| 2-190 | (A) δ 7.62 (s, 1H), 7.35-7.55 (m, 10H), 7.26 (bs, 1H), 4.51 (d, J = 5.7 Hz, 2H), 4.41 (s, 2H), 4.03 (d, J = 17.3 Hz, 1H), 3.81 (s, 2H), 3.65 (d, J = 17.3 Hz, 1H). |
| 2-191 | (A) δ 7.05-7.6 (m, 12H), 4.50 (d, J = 6.3 Hz, 2H), 4.02 (d, J = 17.3 Hz, 1H), 3.67 (s, 2H), 3.64 (d, J = 17.3 Hz, 1H). |
| 2-192 | (A) δ 7.3-7.85 (m, 12H), 4.45-4.55 (m, 2H), 4.07 (s, 2H), 4.06 (d, J = 17.3 Hz, 1H), 3.68 (d, J = 17.3 Hz, 1H). |
| 2-194 | (A) δ 7.4-7.7 (m, 7H), 4.59 (d, J = 5.7 Hz, 2H), 4.05 (d, J = 17.3 Hz, 1H), 3.66 (d, J = 17.3 Hz, 1H), 3.23 (q, J = 7.1 Hz, 1H), 2.59 (s, 3H), 1.63 (d, J = 7.1 Hz, 3H). |
| 2-195 | (A) δ 7.35-7.65 (m, 6H), 7.27 (bs, 1H), 4.4-4.65 (m, 2H), 4.05 (d, J = 17.3 Hz, 1H), 3.84 (q, J = 7.2 Hz, 1H), 3.68 (d, J = 17.3 Hz, 1H), 2.88 (s, 3H), 1.62 (d, J = 7.2 Hz, 3H). |
| 2-196 | (A) δ 7.4-7.75 (m, 6H), 4.81 (d, J = 6.0 Hz, 2H), 4.05 (d, J = 17.3 Hz, 1H), 3.67 (d, J = 17.3 Hz, 1H), 1.96 (s, 3H), 1.50 (s, 6H). |
| 2-197 | (A) δ 7.4-7.7 (m, 6H), 7.2-7.3 (m, 1H), 4.57 (d, J = 6.0 Hz, 2H), 4.05 (d, J = 17.3 Hz, 1H), 3.67 (d, J = 17.3 Hz, 1H), 2.85 (s, 3H), 1.65 (s, 6H). |
| 2-198 | (A) δ 7.68 (s, 1H), 7.62 (s, 2H), 7.50 (s, 2H), 6.21 (bs, 1H), 4.55 (d, J = 6.3 Hz, 2H), 4.05 (d, J = 17.4 Hz, 1H), 3.65 (d, J = 17.4 Hz, 1H), 2.80 (t, J = 7.2 Hz, 2H), 2.52 (t, J = 7.2 Hz, 2H), 2.11 (s, 3H). |
| 2-199 | (A) δ 7.72 (d, J = 8.4 Hz, 2H), 7.63 (s, 2H), 7.56 (d, J = 8.4 Hz, 2H), 6.50 (bs, 1H), 6.23 (d, J = 9.0 Hz, 1H), 4.08 (d, J = 17.4 Hz, 1H), 3.68 (d, J = 17.4 Hz, 1H), 2.75-2.85 (m, 2H), 2.5-2.65 (m, 2H), 2.13 (s, 3H). |
| 2-200 | (A) δ 7.6-7.7 (m, 3H), 7.4-7.55 (m, 2H), 4.56 (d, J = 6.6 Hz, 2H), 4.05 (d, J = 17.3 Hz, 1H), 3.66 (d, J = 17.3 Hz, 1H), 2.99 (s, 2H), 2.28 (s, 6H). |
| 2-201 | (A) δ 7.80 (t, J = 6.0 Hz, 1H), 7.69 (d, J = 1.5 Hz, 1H), 7.64 (s, 2H), 7.4-7.55 (m, 2H), 4.56 (d, J = 6.0 Hz, 2H), 4.07 (d, J = 17.4 Hz, 1H), 3.68 (d, J = 17.4 Hz, 1H), 3.03 (s, 2H), 248 (q, J = 7.2 Hz, 2H), 2.27 (s, 3H), 1.04 (t, J = 7.2 Hz, 3H). |
| 2-202 | (A) δ 7.95 (bs, 1H), 7.6-7.75 (m, 3H), 7.35-7.55 (m, 2H), 4.55 (d, J = 6.6 Hz, 2H), 4.06 (d, J = 17.4 Hz, 1H), 3.68 (d, J = 17.4 Hz, 1H), 3.07 (s, 2H), 2.55 (q, J = 7.2 Hz, 4H), 1.01 (t, J = 7.2 Hz, 6H). |
| 2-203 | (A) δ 7.4-7.75 (m, 6H), 4.56 (dd, J = 6.3, 2.4 Hz, 2H), 4.06 (d, J = 17.4 Hz, 1H), 3.67 (d, J = 17.4 Hz, 1H), 3.44 (s, 2H), 3.21 (q, J = 9.3 Hz, 2H), 1.93 (bs, 1H). |
| 2-204 | (A) δ 7.69 (d, J = 0.9 Hz, 1H), 7.62 (s, 2H), 7.4-7.55 (m, 2H), 7.23 (t, J = 6.3 Hz, 1H), 4.56 (d, J = 6.3 Hz, 2H), 4.05 (d, J = 17.4 Hz, 1H), 3.66 (d, J = 17.4 Hz, 1H), 3.61 (s, 2H), 3.46 (s, 2H), 1.99 (bs, 1H). |
| 2-205 | (A) δ 7.6-7.7 (m, 3H), 7.3-7.5 (m, 2H), 4.45-4.6 (m, 2H), 4.05 (d, J = 17.3 Hz, 1H), 3.67 (d, J = 17.3 Hz, 1H), 3.43 (s, 2H), 3.42 (d, J = 2.4 Hz, 2H), 2.23 (t, J = 2.4 Hz, 1H). |

TABLE 16-continued

| No. | ¹H NMR |
|---|---|
| 2-206 | (A) δ 7.35-7.8 (m, 6H), 4.56 (d, J = 6.0 Hz, 2H), 4.07 (d, J = 17.4 Hz, 1H), 3.69 (d, J = 17.4 Hz, 1H), 3.20 (s, 2H), 2.5-2.7 (m, 4H), 1.7-1.9 (m, 4H). |
| 2-207 | (A) δ 7.6-7.7 (m, 3H), 7.35-7.5 (m, 2H), 6.89 (bs, 1H), 4.57 (bs, 1H), 4.52 (d, J = 6.0 Hz, 2H), 4.05 (d, J = 17.3 Hz, 1H), 3.88 (d, J = 5.4 Hz, 2H), 3.69 (d, J = 17.3 Hz, 1H), 3.68 (s, 3H). |
| 2-208 | (A) δ 7.65-7.7 (m, 3H), 7.45-7.55 (m, 1H), 7.35-7.45 (m, 1H), 6.80 (bs, 1H), 4.53 (d, J = 6.0 Hz, 2H), 4.06 (d, J = 17.4 Hz, 1H), 3.93 (s, 2H), 3.71 (s, 3H), 3.68 (d, J = 17.4 Hz, 1H), 2.98 (t, J = 1.5 Hz, 3H). |
| 2-209 | (A) δ 7.66 (s, 1H), 7.63 (s, 2H), 7.35-7.55 (m, 2H), 6.88 (bs, 1H), 4.53 (d, J = 6.3 Hz, 2H), 4.06 (d, J = 17.4 Hz, 1H), 3.91 (s, 2H), 3.72 (s, 3H), 3.67 (d, J = 17.4 Hz, 1H), 3.66 (q, J = 7.2 Hz, 2H), 1.11 (t, J = 7.2 Hz, 3H). |
| 2-210 | (A) δ 7.69 (s, 1H), 7.62 (s, 2H), 7.4-7.55 (m, 2H), 6.2-6.5 (m, 1H), 4.55 (d, J = 6.0 Hz, 2H), 4.36 (s, 2H), 4.06 (d, J = 17.4 Hz, 1H), 4.04 (s, 2H), 3.79 (bs, 3H), 3.67 (d, J = 17.4 Hz, 1H). |
| 2-211 | (A) δ 7.67 (s, 1H), 7.4-7.55 (m, 5H), 5.01 (s, 1H), 4.53 (dd, J = 6.3, 2.7 Hz, 2H), 4.49 (d, J = 17.3 Hz, 1H), 3.67 (d, J = 17.3 Hz, 1H), 3.4-3.5 (m, 1H), 2.95-3.05 (m, 2H), 2.75-2.85 (m, 1H), 2.42 (bs, 1H). |
| 2-212 | (A) δ 7.4-7.7 (m, 6H), 7.05 (bs, 1H), 5.55 (s, 1H), 4.50 (d, J = 5.7 Hz, 2H), 4.05 (d, J = 17.3 Hz, 1H), 3.9-4.05 (m, 1H), 3.7-3.85 (m, 1H), 3.68 (d, J = 17.3 Hz, 1H), 3.45-3.55 (m, 1H), 3.05-3.15 (m, 1H), 2.13 (s, 3H). |
| 2-213 | (A) δ 7.64 (s, 1H), 7.4-7.55 (m, 5H), 6.79 (bs, 1H), 5.36 (s, 1H), 4.51 (dd, J = 6.0, 4.2 Hz, 2H), 4.06 (d, J = 17.3 Hz, 1H), 3.8-3.95 (m, 2H), 3.71 (s, 3H), 3.68 (d, J = 17.3 Hz, 1H), 3.24 (bs, 1H), 2.95-3.05 (m, 1H). |
| 2-214 | (A) δ 7.35-7.7 (m, 7H), 4.4-4.6 (m, 2H), 4.15-4.3 (m, 2H), 4.05 (d, J = 17.3 Hz, 1H), 3.95 (d, J = 9.8 Hz, 1H), 3.67 (d, J = 17.3 Hz, 1H), 3.4-3.5 (m, 1H), 3.05-3.15 (m, 1H), 2.44 (bs, 1H). |
| 2-215 | (A) δ 7.3-7.7 (m, 6H), 6.92 (bs, 1H), 4.95-5.05 (m, 1H), 4.4-4.7 (m, 4H), 4.05 (d, J = 17.3 Hz, 1H), 3.67 (d, J = 17.3 Hz, 1H), 3.57 (d, J = 10.4 Hz, 1H), 3.05-3.15 (m, 1H), 2.31 (s, 3H). |
| 2-216 | (A) δ 7.71 (d, J = 1.5 Hz, 1H), 7.62 (s, 2H), 7.54 (dd, J = 8.1, 1.5 Hz, 1H), 7.46 (d, J = 8.1 Hz, 1H), 6.58 (bs, 1H), 4.59 (d, J = 6.3 Hz, 2H), 4.04 (d, J = 17.4 Hz, 1H), 3.65 (d, J = 17.4 Hz, 1H), 3.41 (s, 2H). |
| 2-217 | (A) δ 7.66 (d, J = 1.5 Hz, 1H), 7.63 (s, 2H), 7.4-7.5 (m, 2H), 6.32 (bs, 1H), 4.53 (d, J = 6.3 Hz, 2H), 4.06 (d, J = 17.4 Hz, 1H), 3.68 (s, 3H), 3.67 (d, J = 17.4 Hz, 1H), 2.69 (t, J = 6.6 Hz, 2H), 2.53 (t, J = 6.6 Hz, 2H). |
| 2-218 | (A) δ 7.96 (bs, 1H), 7.55-7.65 (m, 3H), 7.45-7.5 (m, 1H), 7.35-7.4 (m, 1H), 7.02 (bs, 1H), 4.51 (d, J = 6.0 Hz, 2H), 4.05 (d, J = 17.4 Hz, 1H), 3.67 (d, J = 17.4 Hz, 1H), 3.24 (s, 2H), 2.80 (dd, J = 4.8, 0.9 Hz, 3H). |
| 2-219 | (A) δ 7.92 (d, J = 5.4 Hz, 1H), 7.64 (s, 1H), 7.63 (s, 2H), 7.55-7.65 (m, 1H), 7.45-7.55 (m, 1H), 6.28 (bs, 1H), 4.53 (d, J = 6.0 Hz, 2H), 4.05 (d, J = 17.4 Hz, 1H), 3.67 (d, J = 17.4 Hz, 1H), 3.28 (qd, J = 7.2, 5.4 Hz, 2H), 3.22 (s, 2H), 1.42 (t, J = 7.2 Hz, 3H). |
| 2-220 | (A) δ 7.96 (t, J = 5.7 Hz, 1H), 7.6-7.7 (m, 3H), 7.45-7.55 (m, 1H), 7.35-7.45 (m, 1H), 6.91 (bs, 1H), 4.53 (d, J = 6.3 Hz, 2H), 4.05 (d, J = 17.4 Hz, 1H), 3.66 (d, J = 17.4 Hz, 1H), 3.25 (s, 2H), 3.05-3.15 (m, 2H), 0.90-1.05 (m, 1H), 0.5-0.6 (m, 2H), 0.15-0.25 (m, 2H). |
| 2-221 | (A) δ 7.69 (s, 1H), 7.56 (t, J = 8.1 Hz, 1H), 7.25-7.55 (m, 5H), 7.14 (t, J = 6.6 Hz, 1H), 4.55 (d, J = 6.3 Hz, 2H), 4.05 (d, J = 17.1 Hz, 1H), 3.85-4.0 (m, 2H), 3.65 (d, J = 17.1 Hz, 1H), 3.30 (s, 2H). |
| 2-222 | (A) δ 7.6-7.7 (m, 3H), 7.4-7.55 (m, 2H), 4.58 (d, J = 6.0 Hz, 2H), 4.05 (d, J = 17.4 Hz, 1H), 3.67 (d, J = 17.4 Hz, 1H), 3.45-3.55 (m, 4H), 3.32 (s, 2H), 1.85-2.05 (m, 4H). |
| 2-223 | (A) δ 7.68 (s, 1H), 7.62 (s, 2H), 7.45-7.55 (m, 2H), 6.32 (dd, J = 17.1, 1.2 Hz, 1H), 6.12 (dd, J = 17.1, 10.2 Hz, 1H), 6.10 (bs, 1H), 5.70 (dd, J = 10.2, 1.2 Hz, 1H), 4.61 (d, J = 6.6 Hz, 2H), 4.05 (d, J = 17.4 Hz, 1H), 3.65 (d, J = 17.4 Hz, 1H). |
| 2-224 | (A) δ 7.85 (d, J = 1.8 Hz, 1H), 7.62 (s, 2H), 7.55 (dd, J = 8.1, 1.8 Hz, 1H), 7.47 (d, J = 8.1 Hz, 1H), 6.32 (dd, J = 17.0, 1.2 Hz, 1H), 6.12 (dd, J = 17.0, 10.2 Hz, 1H), 6.09 (bs, 1H), 5.69 (dd, J = 10.2, 1.2 Hz, 1H), 4.61 (d, J = 6.5 Hz, 2H), 4.05 (d, J = 17.3 Hz, 1H), 3.65 (d, J = 17.3 Hz, 1H). |
| 2-225 | (A) δ 7.6-7.75 (m, 3H), 7.4-7.55 (m, 2H), 6.18 (t, J = 6.0 Hz, 1H), 5.8-6.05 (m, 1H), 5.15-5.3 (m, 2H), 4.52 (d, J = 6.0 Hz, 2H), 4.05 (d, J = 17.3 Hz, 1H), 3.66 (d, J = 17.3 Hz, 1H), 3.05 (d, J = 6.6 Hz, 2H). |
| 2-226 | (A) δ 7.6-7.7 (m, 3H), 7.35-7.5 (m, 2H), 6.85 (dq, J = 15.3, 6.9 Hz, 1H), 6.31 (t, J = 6.0 Hz, 1H), 5.86 (dd, J = 15.3, 1.8 Hz, 1H), 4.54 (d, J = 6.0 Hz, 2H), 4.05 (d, J = 17.3 Hz, 1H), 3.67 (d, J = 17.3 Hz, 1H), 1.84 (dd, J = 6.9, 1.8 Hz, 3H). |

TABLE 16-continued

| No. | ¹H NMR |
|---|---|
| 2-227 | (A) δ 7.68 (s, 1H), 7.62 (s, 2H), 7.4-7.55 (m, 2H), 6.34 (bs, 1H), 5.72 (s, 1H), 5.37 (s, 1H), 4.58 (d, J = 6.3 Hz, 2H), 4.05 (d, J = 17.4 Hz, 1H), 3.65 (d, J = 17.4 Hz, 1H), 1.98 (s, 3H). |
| 2-228 | (A) δ 7.96 (ddd, J = 8.1, 5.7, 1.2 Hz, 1H), 7.4-7.7 (m, 6H), 6.75 (bs, 1H), 4.63 (d, J = 6.3 Hz, 2H), 4.07 (d, J = 17.4 Hz, 1H), 3.69 (d, J = 17.4 Hz, 1H). |
| 2-229 | (A) δ 7.55-7.65 (m, 4H), 7.4-7.5 (m, 4H), 7.25-7.35 (m, 3H), 6.69 (bs, 1H), 6.48 (dd, J = 15.6, 2.4 Hz, 1H), 4.61 (d, J = 6.0 Hz, 2H), 4.00 (d, J = 17.3 Hz, 1H), 3.61 (d, J = 17.3 Hz, 1H). |
| 2-230 | (A) δ 7.4-7.75 (m, 5H), 6.59 (bs, 1H), 4.58 (d, J = 6.0 Hz, 2H), 4.06 (d, J = 17.3 Hz, 1H), 3.67 (d, J = 17.3 Hz, 1H), 2.89 (s, 1H). |
| 2-231 | (A) δ 7.4-7.7 (m, 5H), 6.25 (bs, 1H), 4.55 (d, J = 6.0 Hz, 2H), 4.05 (d, J = 17.3 Hz, 1H), 3.67 (d, J = 17.3 Hz, 1H), 2.95 (s, 3H). |
| 2-232 | (A) δ 7.6-7.7 (m, 3H), 7.4-7.6 (m, 2H), 6.30 (d, J = 6.0 Hz, 1H), 4.54 (d, J = 6.0 Hz, 2H), 4.04 (d, J = 17.3 Hz, 1H), 3.67 (d, J = 17.3 Hz, 1H), 2.4-2.6 (m, 4H), 1.99 (t, J = 1.8 Hz, 1H). |
| 2-233 | (A) δ 7.85 (d, J = 1.8 Hz, 1H), 7.62 (s, 2H), 7.55 (dd, J = 8.1, 1.8 Hz, 1H), 7.48 (d, J = 8.1 Hz, 1H), 6.18 (t, J = 6.2 Hz, 1H), 4.54 (d, J = 6.2 Hz, 2H), 4.05 (d, J = 17.3 Hz, 1H), 3.65 (d, J = 17.3 Hz, 1H), 2.4-2.65 (m, 4H), 2.0-2.05 (m, 1H). |
| 2-234 | (A) δ 8.27 (s, 1H), 7.91 (d, J = 7.8 Hz, 1H), 7.76 (d, J = 7.8 Hz, 1H), 7.63 (s, 2H), 6.62 (t, J = 6.0 Hz, 1H), 4.72 (d, J = 6.0 Hz, 2H), 4.11 (d, J = 17.4 Hz, 1H), 3.74 (d, J = 17.4 Hz, 1H), 2.35-2.6 (m, 4H), 1.98 (s, 1H). |
| 2-235 | (A) δ 7.65 (s, 2H), 7.60 (d, J = 8.7 Hz, 2H), 7.40 (d, J = 8.7 Hz, 2H), 6.00 (d, J = 7.5 Hz, 1H), 5.05-5.2 (m, 1H), 4.05 (d, J = 17.4 Hz, 1H), 3.65 (d, J = 17.4 Hz, 1H), 2.35-2.6 (m, 4H), 2.00 (s, 1H), 1.50 (d, J = 7.2 Hz, 3H). |
| 2-236 | (A) δ 7.72 (d, J = 8.4 Hz, 2H), 7.63 (s, 2H), 7.55 (d, J = 8.4 Hz, 2H), 6.38 (d, J = 8.7 Hz, 1H), 6.23 (d, J = 8.7 Hz, 1H), 4.08 (d, J = 17.4 Hz, 1H), 3.68 (d, J = 17.4 Hz, 1H), 2.45-2.65 (m, 4H), 2.0-2.05 (m, 1H). |
| 2-237 | (A) δ 7.63 (s, 2H), 7.58 (d, J = 8.7 Hz, 2H), 7.28 (d, J = 8.7 Hz, 2H), 7.25-7.3 (m, 1H), 6.75-6.9 (m, 2H), 5.80 (d, J = 7.5 Hz, 1H), 5.05-5.15 (m, 1H), 4.05 (d, J = 17.4 Hz, 1H), 3.65 (d, J = 17.4 Hz, 1H), 3.50 (s, 2H), 1.45 (d, J = 7.1 Hz, 3H). |
| 2-239 | (A) δ 8.55 (d, J = 4.8 Hz, 1H), 7.90 (d, J = 7.5 Hz, 1H), 7.2-7.7 (m, 9H), 5.0-5.15 (m, 1H), 4.05 (d, J = 17.1 Hz, 1H), 3.70 (d, J = 3.0 Hz, 2H), 3.65 (d, J = 17.1 Hz, 1H), 1.45 (d, J = 6.9 Hz, 3H). |
| 2-240 | (A) δ 7.86 (s, 1H), 7.3-7.65 (m, 6H), 4.58 (d, J = 6.3 Hz, 2H), 4.05 (d, J = 17.4 Hz, 1H), 3.67 (d, J = 17.4 Hz, 1H), 3.59 (sep, J = 6.9 Hz, 1H), 1.14 (d, J = 6.9 Hz, 6H). |
| 2-241 | (A) δ 8.07 (bs, 1H), 7.35-7.7 (m, 6H), 4.59 (d, J = 6.3 Hz, 2H), 4.06 (d, J = 17.3 Hz, 1H), 3.67 (d, J = 17.3 Hz, 1H), 2.92 (dd, J = 5.1, 3.6 Hz, 3H). |
| 2-242 | (A) δ 8.14 (bs, 1H), 7.35-7.7 (m, 6H), 4.59 (d, J = 6.3 Hz, 2H), 4.06 (d, J = 17.3 Hz, 1H), 3.66 (d, J = 17.3 Hz, 1H), 2.36 (qui, J = 6.9 Hz, 2H), 1.21 (t, J = 6.9 Hz, 3H). |
| 2-244 | (A) δ 8.0-8.1 (m, 1H), 7.64 (d, J = 8.4 Hz, 2H), 7.50 (d, J = 1.2 Hz, 2H), 7.4-7.5 (m, 1H), 7.44 (d, J = 8.4 Hz, 2H), 7.41 (t, J = 1.5 Hz, 1H), 7.2-7.3 (m, 1H), 7.1-7.15 (m, 1H), 7.0-7.1 (m, 1H), 5.3-5.4 (m, 1H), 4.05 (d, J = 17.4 Hz, 1H), 3.70 (d, J = 17.4 Hz, 1H), 1.60 (d, J = 6.9 Hz, 3H). |
| 2-246 | (A) δ 7.75-7.85 (m, 2H), 7.68 (s, 1H), 7.62 (s, 2H), 7.48 (s, 2H), 7.0-7.15 (m, 2H), 6.77 (bs, 1H), 4.70 (dd, J = 6.0, 1.5 Hz, 2H), 4.05 (d, J = 17.3 Hz, 1H), 3.68 (d, J = 17.3 Hz, 1H). |
| 2-247 | (A) δ 7.87 (d, J = 1.2 Hz, 1H), 7.78 (dd, J = 8.6, 5.4 Hz, 2H), 7.62 (s, 2H), 7.57 (dd, J = 8.1, 1.2 Hz, 1H), 7.52 (d, J = 8.1 Hz, 1H), 7.11 (t, J = 8.6 Hz, 2H), 6.64 (t, J = 6.0 Hz, 1H), 4.71 (d, J = 6.0 Hz, 2H), 4.05 (d, J = 17.3 Hz, 1H), 3.65 (d, J = 17.3 Hz, 1H). |
| 2-249 | (A) δ 7.25-7.75 (m, 9H), 6.87 (bs, 1H), 4.73 (d, J = 6.3 Hz, 2H), 4.07 (d, J = 17.3 Hz, 1H), 3.68 (d, J = 17.3 Hz, 1H). |
| 2-250 | (A) δ 7.89 (s, 1H), 7.55-7.75 (m, 5H), 7.25-7.45 (m, 3H), 6.82 (t, J = 6.0 Hz, 1H), 4.74 (d, J = 6.0 Hz, 2H), 4.06 (d, J = 17.3 Hz, 1H), 3.66 (d, J = 17.3 Hz, 1H). |
| 2-251 | (A) δ 7.25-7.7 (m, 11H), 6.55 (d, J = 7.5 Hz, 1H), 5.25-5.4 (m, 1H), 4.05 (d, J = 17.1 Hz, 1H), 3.70 (d, J = 17.1 Hz, 1H), 1.60 (d, J = 6.9 Hz, 3H). |
| 2-254 | (A) δ 7.89 (d, J = 1.7 Hz, 1H), 7.5-7.7 (m, 6H), 7.25-7.4 (m, 2H), 6.57 (t, J = 6.2 Hz, 1H), 4.74 (d, J = 6.2 Hz, 2H), 4.06 (d, J = 17.3 Hz, 1H), 3.67 (d, J = 17.3 Hz, 1H). |
| 2-255 | (A) δ 7.69 (d, J = 1.5 Hz, 1H), 7.63 (s, 2H), 7.52 (t, J = 2.1 Hz, 2H), 7.1-7.4 (m, 4H), 6.37 (bs, 1H), 4.69 (d, J = 6.0 Hz, 2H), 4.06 (d, J = 17.4 Hz, 1H), 3.67 (d, J = 17.4 Hz, 1H), 2.40 (s, 3H). |
| 2-256 | (A) δ 7.5-7.85 (m, 9H), 6.32 (bs, 1H), 4.72 (dd, J = 6.0, 1.8 Hz, 2H), 4.07 (d, J = 17.4 Hz, 1H), 3.68 (d, J = 17.4 Hz, 1H). |
| 2-257 | (A) δ 7.2-7.95 (m, 10H), 6.6-6.65 (m, 1H), 4.75 (d, J = 6.3 Hz, 2H), 4.05 (d, J = 17.4 Hz, 1H), 3.65 (d, J = 17.4 Hz, 1H). |
| 2-258 | (A) δ 7.0-7.75 (m, 15H), 6.5-6.6 (m, 1H), 4.70 (d, J = 6.3 Hz, 2H), 4.05 (d, J = 17.1 Hz, 1H), 3.65 (d, J = 17.1 Hz, 1H). |

TABLE 16-continued

| No. | ¹H NMR |
|---|---|
| 2-259 | (A) δ 7.5-7.7 (m, 6H), 7.15-7.45 (m, 3H), 7.04 (bs, 1H), 4.73 (t, J = 5.4 Hz, 2H), 4.06 (d, J = 17.4 Hz, 1H), 3.67 (d, J = 17.4 Hz, 1H), 2.42 (s, 3H). |
| 2-260 | (A) δ 7.70 (s, 1H), 7.86 (d, J = 8.4 Hz, 2H), 7.50 (d, J = 9.6 Hz, 4H), 7.42 (t, J = 1.8 Hz, 1H), 7.25 (d, J = 8.1 Hz, 2H), 6.55-6.65 (m, 1H), 4.70 (d, J = 6.3 Hz, 2H), 4.05 (d, J = 17.1 Hz, 1H), 3.65 (d, J = 17.1 Hz, 1H), 2.50 (s, 3H). |
| 2-262 | (A) δ 7.80 (d, J = 8.1 Hz, 2H), 7.72 (s, 1H), 7.71 (d, J = 8.1 Hz, 2H), 7.53 (d, J = 2.4 Hz, 2H), 7.49 (s, 2H), 7.42 (t, J = 2.1 Hz, 1H), 6.65 (t, J = 6.0 Hz, 1H), 4.75 (d, J = 6.0 Hz, 2H), 4.05 (d, J = 17.7 Hz, 1H), 3.65 (d, J = 17.7 Hz, 1H). |
| 2-263 | (A) δ 8.03 (d, J = 7.8 Hz, 1H), 7.45-7.7 (m, 8H), 6.53 (bs, 1H), 4.70 (d, J = 6.0 Hz, 2H), 4.07 (d, J = 17.4 Hz, 1H), 3.69 (d, J = 17.4 Hz, 1H). |
| 2-264 | (A) δ 7.26 (d, J = 8.4 Hz, 2H), 7.94 (d, J = 8.4 Hz, 2H), 7.70 (s, 1H), 7.63 (s, 2H), 7.52 (s, 2H), 6.97 (bs, 1H), 4.74 (d, J = 5.7 Hz, 2H), 4.06 (d, J = 17.3 Hz, 1H), 3.68 (d, J = 17.3 Hz, 1H). |
| 2-265 | (A) δ 7.4-7.85 (m, 9H), 6.81 (bs, 1H), 4.78 (d, J = 6.0 Hz, 2H), 4.06 (d, J = 17.4 Hz, 1H), 3.67 (d, J = 17.4 Hz, 1H). |
| 2-266 | (A) δ 7.85-7.9 (m, 2H), 7.7-7.75 (m, 3H), 7.62 (s, 2H), 7.51 (d, J = 5.4 Hz, 2H), 6.75-7.05 (m, 1H), 4.73 (dd, J = 6.0, 3.4 Hz, 2H), 4.05 (d, J = 17.3 Hz, 1H), 3.67 (d, J = 17.3 Hz, 1H). |
| 2-267 | (A) δ 7.86 (d, J = 8.4 Hz, 2H), 7.72 (d, J = 8.4 Hz, 2H), 7.64 (d, J = 8.4 Hz, 2H), 7.63 (s, 2H), 7.43 (d, J = 8.4 Hz, 2H), 6.49 (d, J = 7.2 Hz, 1H), 5.25-5.35 (m, 1H), 4.07 (d, J = 17.1 Hz, 1H), 3.77 (d, J = 17.1 Hz, 1H), 1.62 (d, J = 7.2 Hz, 3H). |
| 2-268 | (A) δ 8.05-8.2 (m, 1H), 7.70 (s, 1H), 7.62 (s, 2H), 7.53 (s, 2H), 7.1-7.25 (m, 1H), 6.95-7.05 (m, 1H), 6.8-6.95 (m, 1H), 4.75 (d, J = 6.0 Hz, 2H), 4.05 (d, J = 17.4 Hz, 1H), 3.66 (d, J = 17.4 Hz, 1H). |
| 2-269 | (A) δ 8.05-8.2 (m, 1H), 7.87 (d, J = 1.5 Hz, 1H), 7.62 (s, 2H), 7.57 (dd, J = 7.8, 1.5 Hz, 1H), 7.52 (d, J = 7.8 Hz, 1H), 7.21 (bs, 1H), 6.8-7.05 (m, 2H), 4.73 (d, J = 6.2 Hz, 2H), 4.05 (d, J = 17.6 Hz, 1H), 3.65 (d, J = 17.6 Hz, 1H). |
| 2-270 | (A) δ 8.31 (d, J = 1.8 Hz, 1H), 8.0-8.15 (m, 1H), 7.96 (dd, J = 8.4, 1.8 Hz, 1H), 7.83 (d, J = 8.4 Hz, 1H), 7.45-7.55 (m, 3H), 7.43 (t, J = 1.8 Hz, 1H), 6.95-7.05 (m, 1H), 6.8-6.95 (m, 1H), 4.93 (d, J = 5.1 Hz, 2H), 4.06 (d, J = 17.4 Hz, 1H), 3.72 (d, J = 17.4 Hz, 1H). |
| 2-271 | (A) δ 8.31 (s, 1H), 7.8-8.15 (m, 3H), 7.63 (s, 2H), 7.45-7.7 (m, 1H), 6.8-7.05 (m, 2H), 4.92 (d, J = 6.6 Hz, 2H), 4.11 (d, J = 17.4 Hz, 1H), 3.73 (d, J = 17.4 Hz, 1H). |
| 2-273 | (A) δ 8.05-8.15 (m, 1H), 7.65 (d, J = 8.1 Hz, 2H), 7.51 (s, 2H), 7.4-7.45 (m, 3H), 6.85-7.0 (m, 3H), 5.25-5.35 (m, 1H), 4.05 (d, J = 17.1 Hz, 1H), 3.70 (d, J = 17.1 Hz, 1H), 1.60 (d, J = 6.9 Hz, 3H). |
| 2-274 | (A) δ 8.05-8.15 (m, 1H), 7.64 (d, J = 8.7 Hz, 2H), 7.63 (s, 2H), 7.44 (d, J = 8.7 Hz, 2H), 6.8-7.05 (m, 3H), 5.25-5.35 (m, 1H), 4.07 (d, J = 17.4 Hz, 1H), 3.67 (d, J = 17.4 Hz, 1H), 1.59 (d, J = 7.2 Hz, 3H). |
| 2-275 | (A) δ 8.1-8.25 (m, 1H), 7.75 (d, J = 8.4 Hz, 2H), 7.63 (s, 2H), 7.62 (d, J = 8.4 Hz, 2H), 7.1-7.2 (m, 1H), 7.0-7.1 (m, 1H), 6.85-6.95 (m, 1H), 6.39 (d, J = 6.6 Hz, 1H), 4.09 (d, J = 17.4 Hz, 1H), 3.69 (d, J = 17.4 Hz, 1H). |
| 2-276 | (A) δ 7.25-7.7 (m, 7H), 6.8-6.95 (m, 3H), 4.67 (d, J = 6.0 Hz, 2H), 4.06 (d, J = 17.3 Hz, 1H), 3.66 (d, J = 17.3 Hz, 1H). |
| 2-277 | (A) δ 7.7-7.8 (m, 3H), 7.40 (s, 2H), 7.3-7.4 (m, 1H), 6.85-7.0 (m, 2H), 6.76 (bs, 1H), 4.69 (d, J = 6.0 Hz, 2H), 4.06 (d, J = 17.3 Hz, 1H), 3.70 (d, J = 17.3 Hz, 1H). |
| 2-278 | (A) δ 7.65 (d, J = 8.4 Hz, 2H), 7.51 (d, J = 1.8 Hz, 2H), 7.45 (d, J = 8.4 Hz, 2H), 7.41 (t, J = 1.8 Hz, 1H), 7.3-7.4 (m, 1H), 6.9-7.0 (m, 2H), 6.30 (d, J = 7.8 Hz, 1H), 5.3-5.4 (m, 1H), 4.05 (d, J = 17.4 Hz, 1H), 3.70 (d, J = 17.4 Hz, 1H), 1.55 (d, J = 6.9 Hz, 3H). |
| 2-279 | (A) δ 7.65 (s, 2H), 7.60 (d, J = 8.1 Hz, 2H), 7.45 (d, J = 8.1 Hz, 2H), 7.3-7.4 (m, 1H), 6.85-7.0 (m, 2H), 6.30 (d, J = 7.5 Hz, 1H), 5.25-5.4 (m, 1H), 4.05 (d, J = 17.4 Hz, 1H), 3.70 (d, J = 17.4 Hz, 1H), 1.60 (d, J = 6.9 Hz, 3H). |
| 2-280 | (A) δ 7.71 (s, 1H), 7.55-7.7 (m, 3H), 7.45-7.55 (m, 3H), 7.15-7.25 (m, 1H), 6.61 (t, J = 6.0 Hz, 1H), 4.71 (d, J = 6.0 Hz, 2H), 4.05 (d, J = 17.4 Hz, 1H), 3.66 (d, J = 17.4 Hz, 1H). |
| 2-281 | (A) δ 7.65-7.7 (m, 2H), 7.63 (s, 2H), 7.5-7.6 (m, 2H), 7.1-7.15 (m, 1H), 7.0-7.1 (m, 1H), 6.92 (t, J = 6.0 Hz, 1H), 4.72 (t, J = 6.0 Hz, 2H), 4.07 (d, J = 17.4 Hz, 1H), 3.68 (d, J = 17.4 Hz, 1H). |
| 2-282 | (A) δ 7.6-7.7 (m, 1H), 7.64 (d, J = 8.1 Hz, 2H), 7.51 (d, J = 1.8 Hz, 2H), 7.44 (d, J = 8.1 Hz, 2H), 7.41 (t, J = 1.8 Hz, 1H), 7.12 (dd, J = 8.4, 2.4 Hz, 1H), 7.10 (td, J = 8.4, 2.4 Hz, 1H), 6.60 (d, J = 7.5 Hz, 1H), 5.25-5.35 (m, 1H), 4.10 (d, J = 17.4 Hz, 1H), 3.70 (d, J = 17.4 Hz, 1H), 1.60 (d, J = 7.2 Hz, 3H). |
| 2-283 | (A) δ 7.71 (dd, J = 9.0, 6.3 Hz, 1H), 7.65 (d, J = 7.8 Hz, 2H), 7.64 (s, 2H), 7.46 (d, J = 7.8 Hz, 2H), 7.15 (dd, J = 8.4, 2.7 Hz, 1H), 7.05 (td, J = 8.1, 2.7 Hz, 1H), 6.82 (d, J = 7.2 Hz, 1H), 5.25-5.35 (m, 1H), 4.07 (d, J = 17.4 Hz, 1H), 3.67 (d, J = 17.4 Hz, 1H), 1.61 (d, J = 7.2 Hz, 3H). |

TABLE 16-continued

| No. | ¹H NMR |
|---|---|
| 2-284 | (A) δ 8.12 (t, J = 7.8 Hz, 1H), 7.4-7.55 (m, 8H), 4.76 (d, J = 5.7 Hz, 2H), 4.05 (d, J = 17.4 Hz, 1H), 3.67 (d, J = 17.4 Hz, 1H). |
| 2-285 | (A) δ 8.16 (t, J = 7.8 Hz, 1H), 7.65 (d, J = 8.4 Hz, 2H), 7.58 (d, J = 4.5 Hz, 1H), 7.50 (s, 2H), 7.4-7.45 (m, 4H), 6.97 (dd, J = 10.5, 7.8 Hz, 1H), 5.25-5.4 (m, 1H), 4.08 (d, J = 17.1 Hz, 1H), 3.68 (d, J = 17.1 Hz, 1H), 1.61 (d, J = 6.9 Hz, 3H). |
| 2-286 | (A) δ 7.72 (s, 1H), 7.55 (d, J = 1.8 Hz, 2H), 7.49 (s, 2H), 7.42 (t, J = 1.8 Hz, 1H), 6.7-6.8 (m, 2H), 6.35-6.45 (m, 1H), 4.75 (d, J = 6.3 Hz, 2H), 4.05 (d, J = 17.4 Hz, 1H), 3.70 (d, J = 17.4 Hz, 1H). |
| 2-288 | (A) δ 7.70 (s, 1H), 7.65 (s, 2H), 7.55 (s, 2H), 6.65-6.75 (m, 2H), 6.55 (t, J = 6.0 Hz, 1H), 4.70 (d, J = 6.0 Hz, 2H), 4.05 (d, J = 17.4 Hz, 1H), 3.65 (d, J = 17.4 Hz, 1H). |
| 2-290 | (A) δ 7.66 (d, J = 8.1 Hz, 2H), 7.51 (d, J = 2.1 Hz, 2H), 7.4-7.45 (m, 3H), 6.65-6.75 (m, 2H), 6.20 (d, J = 7.8 Hz, 1H), 5.3-5.4 (m, 1H), 4.10 (d, J = 17.1 Hz, 1H), 3.70 (d, J = 17.1 Hz, 1H), 1.60 (d, J = 6.9 Hz, 3H). |
| 2-291 | (A) δ 8.08 (s, 2H), 7.95 (s, 1H), 7.67 (d, J = 8.7 Hz, 2H), 7.45 (d, J = 8.7 Hz, 2H), 6.72 (t, J = 8.4 Hz, 2H), 6.16 (d, J = 7.2 Hz, 1H), 5.25-5.4 (m, 1H), 4.19 (d, J = 17.4 Hz, 1H), 3.73 (d, J = 17.4 Hz, 1H), 1.59 (d, J = 6.9 Hz, 3H). |
| 2-292 | (A) δ 7.65 (s, 2H), 7.60 (d, J = 8.4 Hz, 2H), 7.40 (d, J = 8.4 Hz, 2H), 6.65-6.75 (m, 2H), 6.25 (d, J = 6.6 Hz, 1H), 5.25-5.35 (m, 1H), 4.05 (d, J = 17.7 Hz, 1H), 3.70 (d, J = 17.7 Hz, 1H), 1.60 (d, J = 7.2 Hz, 3H). |
| 2-293 | (A) δ 7.65 (d, J = 8.4 Hz, 2H), 7.64 (s, 2H), 7.40 (d, J = 8.4 Hz, 2H), 6.40 (d, J = 7.8 Hz, 1H), 5.25-5.35 (m, 1H), 4.10 (d, J = 17.4 Hz, 1H), 3.70 (d, J = 17.4 Hz, 1H), 1.60 (d, J = 6.6 Hz, 3H). |
| 2-294 | (A) δ 7.63 (d, J = 8.4 Hz, 2H), 7.51 (d, J = 1.5 Hz, 2H), 7.4-7.45 (m, 3H), 7.05 (d, J = 3.6 Hz, 1H), 6.55 (d, J = 7.5 Hz, 1H), 6.45 (d, J = 3.6 Hz, 1H), 5.2-5.3 (m, 1H), 4.05 (d, J = 17.4 Hz, 1H), 3.70 (d, J = 17.4 Hz, 1H), 1.60 (d, J = 7.2 Hz, 3H). |
| 2-295 | (A) δ 7.08 (s, 1H), 7.45-7.6 (m, 7H), 7.06 (dd, J = 4.5, 4.2 Hz, 1H), 6.67 (d, J = 6.0 Hz, 1H), 4.68 (d, J = 6.0 Hz, 2H), 4.04 (d, J = 17.3 Hz, 1H), 3.66 (d, J = 17.3 Hz, 1H). |
| 2-296 | (A) δ 7.65-7.7 (m, 1H), 7.62 (s, 2H), 7.4-7.6 (m, 4H), 6.97 (d, J = 5.1 Hz, 1H), 4.74 (d, J = 6.6 Hz, 2H), 4.05 (d, J = 17.3 Hz, 1H), 3.65 (d, J = 17.3 Hz, 1H). |
| 2-297 | (A) δ 7.64 (d, J = 8.7 Hz, 2H), 7.50 (d, J = 1.8 Hz, 2H), 7.46 (d, J = 5.1 Hz, 1H), 7.44 (d, J = 8.7 Hz, 2H), 7.41 (t, J = 1.8 Hz, 1H), 7.25 (d, J = 7.2 Hz, 1H), 7.00 (d, J = 5.1 Hz, 1H), 5.2-5.35 (m, 1H), 4.05 (d, J = 17.1 Hz, 1H), 3.65 (d, J = 17.1 Hz, 1H), 1.60 (d, J = 7.2 Hz, 3H). |
| 2-298 | (A) δ 7.92 (d, J = 1.5 Hz, 1H), 7.69 (d, J = 1.2 Hz, 1H), 7.63 (s, 2H), 7.45-7.55 (m, 2H), 6.76 (t, J = 6.3 Hz, 1H), 4.68 (d, J = 6.3 Hz, 2H), 4.05 (d, J = 17.4 Hz, 1H), 3.87 (s, 3H), 3.67 (d, J = 17.4 Hz, 1H). |
| 2-301 | (A) δ 7.71 (d, J = 1.5 Hz, 1H), 7.63 (s, 2H), 7.45-7.55 (m, 2H), 6.55 (bs, 1H), 6.44 (d, J = 1.2 Hz, 1H), 4.66 (d, J = 6.3 Hz, 2H), 4.09 (s, 3H), 4.06 (d, J = 17.4 Hz, 1H), 3.67 (d, J = 17.4 Hz, 1H). |
| 2-303 | (A) δ 8.75 (d, J = 2.1 Hz, 1H), 8.15 (d, J = 2.1 Hz, 1H), 7.6-7.65 (m, 5H), 7.45 (d, J = 8.1 Hz, 2H), 5.25-5.35 (m, 1H), 4.05 (d, J = 17.1 Hz, 1H), 3.65 (d, J = 17.1 Hz, 1H), 1.60 (d, J = 7.2 Hz, 3H). |
| 2-304 | (A) δ 8.10 (s, 1H), 7.73 (s, 1H), 7.62 (s, 2H), 7.54 (d, J = 1.2 Hz, 2H), 7.32 (t, J = 1.2 Hz, 1H), 7.08 (s, 1H), 6.44 (bs, 1H), 4.70 (d, J = 6.0 Hz, 2H), 4.05 (d, J = 17.3 Hz, 1H), 3.65 (d, J = 17.3 Hz, 1H). |
| 2-306 | (A) δ 8.4-8.45 (m, 1H), 8.05-8.15 (m, 1H), 7.5-7.7 (m, 5H), 7.25-7.35 (m, 1H), 7.18 (bs, 1H), 4.74 (d, J = 6.3 Hz, 2H), 4.07 (d, J = 17.3 Hz, 1H), 3.69 (d, J = 17.3 Hz, 1H). |
| 2-307 | (A) δ 8.47 (dd, J = 4.8, 2.1 Hz, 1H), 8.15 (dd, J = 7.8, 2.1 Hz, 1H), 7.89 (s, 1H), 7.55-7.7 (m, 4H), 7.35 (dd, J = 7.8, 4.8 Hz, 1H), 7.15 (t, J = 5.9 Hz, 1H), 4.75 (d, J = 6.2 Hz, 2H), 4.06 (d, J = 17.5 Hz, 1H), 3.67 (d, J = 17.5 Hz, 1H). |
| 2-308 | (A) δ 7.7-7.85 (m, 4H), 7.63 (d, J = 8.4 Hz, 2H), 7.55 (d, J = 8.4 Hz, 2H), 7.49 (s, 2H), 7.41 (t, J = 1.8 Hz, 1H), 5.55-5.65 (m, 1H), 4.05 (d, J = 17.1 Hz, 1H), 3.65 (d, J = 17.1 Hz, 1H), 1.90 (d, J = 7.5 Hz, 3H). |
| 2-309 | (A) δ 8.46 (dd, J = 4.8, 1.8 Hz, 1H), 8.11 (dd, J = 7.8, 1.8 Hz, 1H), 7.66 (d, J = 8.7 Hz, 2H), 7.64 (s, 2H), 7.47 (d, J = 8.7 Hz, 2H), 7.35 (dd, J = 7.8, 1.8 Hz, 1H), 6.83 (d, J = 7.5 Hz, 1H), 5.25-5.4 (m, 1H), 4.08 (d, J = 17.4 Hz, 1H), 3.68 (d, J = 17.4 Hz, 1H), 1.62 (d, J = 6.9 Hz, 3H). |
| 2-310 | (A) δ 8.06 (dd, J = 8.0, 2.3 Hz, 1H), 7.68 (s, 1H), 7.35-7.6 (m, 7H), 6.98 (bs, 1H), 4.71 (d, J = 6.0 Hz, 2H), 4.51 (d, J = 17.3 Hz, 1H), 3.68 (d, J = 17.3 Hz, 1H). |
| 2-311 | (A) δ 8.0-8.1 (m, 1H), 7.35-7.75 (m, 7H), 6.92 (t, J = 6.0 Hz, 1H), 4.72 (d, J = 6.0 Hz, 2H), 4.06 (d, J = 17.3 Hz, 1H), 3.67 (d, J = 17.3 Hz, 1H). |
| 2-312 | (A) δ 8.73 (d, J = 2.4 Hz, 1H), 8.06 (dd, J = 8.1, 2.4 Hz, 1H), 7.85 (d, J = 1.8 Hz, 1H), 7.62 (s, 2H), 7.56 (dd, J = 8.1, 1.8 Hz, 1H), 7.48 (d, J = 8.1 Hz, 1H), 7.39 (d, J = 8.1 Hz, 1H), 6.93 (t, J = 5.7 Hz, 1H), 4.69 (d, J = 5.7 Hz, 2H), 4.05 (d, J = 17.2 Hz, 1H), 3.67 (d, J = 17.2 Hz, 1H). |
| 2-314 | (A) δ 8.90 (d, J = 4.8 Hz, 2H), 8.30 (d, J = 5.4 Hz, 1H), 7.63 (s, 2H), 7.62 (d, J = 8.1 Hz, 2H), 7.47 (d, J = 8.1 Hz, 2H), 7.46 (t, J = 4.8 Hz, 1H), 5.35-5.45 (m, 1H), 4.05 (d, J = 17.1 Hz, 1H), 3.65 (d, J = 17.1 Hz, 1H), 1.65 (d, J = 7.2 Hz, 3H). |

TABLE 16-continued

| No. | ¹H NMR |
|---|---|
| 2-315 | (A) δ 9.40 (d, J = 1.5 Hz, 1H), 8.77 (d, J = 2.4 Hz, 1H), 8.53 (dd, J = 2.4, 1.5 Hz, 1H), 8.25-8.3 (m, 1H), 7.71 (s, 1H), 7.53 (d, J = 1.5 Hz, 2H), 7.48 (s, 2H), 7.42 (t, J = 1.8 Hz, 1H), 4.80 (d, J = 6.3 Hz, 2H), 4.10 (d, J = 17.1 Hz, 1H), 3.65 (d, J = 17.1 Hz, 1H). |
| 2-316 | (A) δ 8.07 (s, 2H), 7.96 (s, 1H), 7.86 (d, J = 1.5 Hz, 1H), 7.56 (dd, J = 7.8, 1.5 Hz, 1H), 7.44 (d, J = 7.8 Hz, 1H), 6.02 (t, J = 6.3 Hz, 1H), 4.51 (d, J = 6.3 Hz, 2H), 4.16 (d, J = 17.4 Hz, 1H), 3.72 (d, J = 17.4 Hz, 1H), 2.26 (q, J = 7.5 Hz, 2H), 1.17 (t, J = 7.5 Hz, 3H). |
| 2-317 | (A) δ 8.07 (s, 2H), 7.95 (s, 1H), 7.63 (d, J = 8.1 Hz, 2H), 7.37 (d, J = 8.1 Hz, 2H), 5.65 (d, J = 7.8 Hz, 1H), 5.05-5.2 (m, 1H), 4.17 (d, J = 17.5 Hz, 1H), 3.72 (d, J = 17.5 Hz, 1H), 2.22 (q, J = 7.8 Hz, 2H), 1.48 (d, J = 6.9 Hz, 3H), 1.15 (t, J = 7.8 Hz, 3H). |
| 2-318 | (A) δ 7.91 (d, J = 1.5 Hz, 1H), 7.73 (dd, J = 8.4, 1.5 Hz, 1H), 7.66 (d, J = 1.5 Hz, 1H), 7.61 (d, J = 8.4 Hz, 1H), 7.49 (dd, J = 8.1, 1.5 Hz, 1H), 7.41 (d, J = 8.1 Hz, 1H), 6.22 (bs, 1H), 4.50 (d, J = 6.0 Hz, 2H), 4.11 (d, J = 17.4 Hz, 1H), 3.70 (d, J = 17.4 Hz, 1H), 2.21 (t, J = 6.9 Hz, 2H), 1.6-1.75 (m, 2H), 0.93 (t, J = 6.9 Hz, 3H). |
| 2-319 | (A) δ 8.06 (s, 2H), 7.96 (s, 1H), 7.87 (d, J = 1.8 Hz, 1H), 7.57 (dd, J = 7.8, 1.5 Hz, 1H), 7.46 (d, J = 7.8 Hz, 1H), 5.94 (t, J = 5.8 Hz, 1H), 4.52 (d, J = 6.0 Hz, 2H), 4.16 (d, J = 17.4 Hz, 1H), 3.71 (d, J = 17.4 Hz, 1H), 2.20 (t, J = 7.2 Hz, 2H), 1.6-1.75 (m, 2H), 0.94 (t, J = 7.2 Hz, 3H). |
| 2-320 | (A) δ 8.07 (s, 2H), 7.95 (s, 1H), 7.63 (d, J = 8.1 Hz, 2H), 7.37 (d, J = 8.1 Hz, 2H), 5.64 (d, J = 7.5 Hz, 1H), 5.1-5.2 (m, 1H), 4.18 (d, J = 17.1 Hz, 1H), 3.72 (d, J = 17.1 Hz, 1H), 2.17 (t, J = 7.8 Hz, 2H), 1.6-1.7 (m, 2H), 1.48 (d, J = 6.9 Hz, 3H), 0.93 (t, J = 7.5 Hz, 3H). |
| 2-321 | (A) δ 8.07 (s, 2H), 7.96 (s, 1H), 7.87 (d, J = 1.5 Hz, 1H), 7.57 (dd, J = 7.8, 1.5 Hz, 1H), 7.44 (d, J = 7.8 Hz, 1H), 6.00 (t, J = 6.9 Hz, 1H), 4.50 (d, J = 6.3 Hz, 2H), 4.16 (d, J = 17.4 Hz, 1H), 3.71 (d, J = 17.4 Hz, 1H), 2.35-2.45 (m, 1H), 1.17 (d, J = 6.6 Hz, 6H). |
| 2-322 | (A) δ 8.09 (s, 2H), 7.97 (s, 1H), 7.65 (d, J = 7.8 Hz, 2H), 7.37 (d, J = 7.8 Hz, 2H), 5.65 (d, J = 7.2 Hz, 1H), 5.05-5.2 (m, 1H), 4.19 (d, J = 17.1 Hz, 1H), 3.74 (d, J = 17.1 Hz, 1H), 2.3-2.45 (m, 1H), 1.49 (d, J = 6.9 Hz, 3H), 1.16 (t, J = 7.5 Hz, 6H). |
| 2-323 | (A) δ 7.91 (d, J = 1.5 Hz, 1H), 7.73 (dd, J = 8.4, 1.5 Hz, 1H), 7.70 (d, J = 1.5 Hz, 1H), 7.61 (d, J = 8.4 Hz, 1H), 7.51 (dd, J = 8.1, 1.5 Hz, 1H), 7.47 (d, J = 8.1 Hz, 1H), 6.09 (bs, 1H), 4.56 (d, J = 6.3 Hz, 2H), 4.10 (d, J = 17.4 Hz, 1H), 3.68 (d, J = 17.4 Hz, 1H), 1.3-1.45 (m, 1H), 0.95-1.05 (m, 2H), 0.7-0.85 (m, 2H). |
| 2-324 | (A) δ 8.07 (s, 2H), 7.97 (s, 1H), 7.88 (d, J = 1.8 Hz, 1H), 7.58 (dd, J = 8.1, 1.8 Hz, 1H), 7.47 (d, J = 8.1 Hz, 1H), 6.14 (t, J = 6.3 Hz, 1H), 4.54 (d, J = 6.0 Hz, 2H), 4.16 (d, J = 17.4 Hz, 1H), 3.72 (d, J = 17.4 Hz, 1H), 1.35-1.45 (m, 1H), 0.95-1.05 (m, 2H), 0.75-0.8 (m, 2H). |
| 2-326 | (A) δ 7.90 (d, J = 1.5 Hz, 1H), 7.74 (dd, J = 8.4, 1.5 Hz, 1H), 7.70 (d, J = 1.5 Hz, 1H), 7.61 (d, J = 8.4 Hz, 1H), 7.52 (dd, J = 8.1, 1.5 Hz, 1H), 7.47 (d, J = 8.1 Hz, 1H), 6.46 (t, J = 6.0 Hz, 1H), 4.56 (d, J = 6.0 Hz, 2H), 4.10 (d, J = 17.4 Hz, 1H), 3.68 (d, J = 17.4 Hz, 1H), 2.20 (d, J = 7.2 Hz, 2H), 0.9-1.05 (m, 1H), 0.55-0.7 (m, 2H), 0.15-0.25 (m, 2H). |
| 2-327 | (A) δ 7.70 (d, J = 1.5 Hz, 1H), 7.64 (s, 2H), 7.51 (dd, J = 7.8, 1.5 Hz, 1H), 7.47 (d, J = 7.8 Hz, 1H), 6.61 (t, J = 73.5 Hz, 1H), 6.45 (bs, 1H), 4.57 (d, J = 6.0 Hz, 2H), 4.07 (d, J = 17.4 Hz, 1H), 3.67 (d, J = 17.4 Hz, 1H), 2.20 (d, J = 7.2 Hz, 2H), 0.9-1.05 (m, 1H), 0.55-0.7 (m, 2H), 0.15-0.25 (m, 2H). |
| 2-328 | (A) δ 8.07 (s, 2H), 7.97 (s, 1H), 7.89 (d, J = 1.8 Hz, 1H), 7.58 (dd, J = 8.1, 1.8 Hz, 1H), 7.47 (d, J = 8.1 Hz, 1H), 6.49 (t, J = 6.0 Hz, 1H), 4.55 (d, J = 6.3 Hz, 2H), 4.16 (d, J = 17.4 Hz, 1H), 3.71 (d, J = 17.4 Hz, 1H), 2.20 (d, J = 7.2 Hz, 2H), 0.95-1.0 (m, 1H), 0.6-0.7 (m, 2H), 0.15-0.25 (m, 2H). |
| 2-330 | (A) δ 7.90 (d, J = 1.5 Hz, 1H), 7.72 (dd, J = 8.4, 1.5 Hz, 1H), 7.65 (d, J = 1.5 Hz, 1H), 7.60 (d, J = 8.4 Hz, 1H), 7.47 (dd, J = 8.1, 1.5 Hz, 1H), 7.35 (d, J = 8.1 Hz, 1H), 6.69 (t, J = 6.3 Hz, 1H), 4.52 (d, J = 6.3 Hz, 2H), 4.10 (d, J = 17.4 Hz, 1H), 3.69 (d, J = 17.4 Hz, 1H), 3.11 (q, J = 10.5 Hz, 2H). |
| 2-331 | (A) δ 7.91 (d, J = 1.5 Hz, 1H), 7.73 (dd, J = 8.4, 1.5 Hz, 1H), 7.69 (d, J = 1.5 Hz, 1H), 7.61 (d, J = 8.4 Hz, 1H), 7.51 (dd, J = 8.1, 1.5 Hz, 1H), 7.43 (d, J = 8.1 Hz, 1H), 6.28 (bs, 1H), 4.46 (d, J = 6.0 Hz, 2H), 4.10 (d, J = 17.4 Hz, 1H), 3.75-4.0 (m, 4H), 3.68 (d, J = 17.4 Hz, 1H), 2.85-3.0 (m, 1H), 2.1-2.25 (m, 2H). |
| 2-332 | (A) δ 8.07 (s, 2H), 7.97 (s, 1H), 7.89 (d, J = 1.5 Hz, 1H), 7.59 (dd, J = 8.1, 1.8 Hz, 1H), 7.45 (d, J = 8.1 Hz, 1H), 6.25 (t, J = 6.6 Hz, 1H), 4.51 (d, J = 6.0 Hz, 2H), 4.16 (d, J = 17.1 Hz, 1H), 3.75-4.0 (m, 4H), 3.71 (d, J = 17.1 Hz, 1H), 2.9-3.0 (m, 1H), 2.1-2.2 (m, 2H). |

TABLE 16-continued

| No. | $^1$H NMR |
|---|---|
| 2-333 | (A) δ 8.07 (s, 2H), 7.96 (s, 1H), 7.64 (d, J = 8.1 Hz, 2H), 7.37 and 7.35 (d, J = 8.1 Hz, 2H), 5.90 (d, J = 7.5 Hz, 1H), 5.05-5.15 (m, 1H), 4.18 (d, J = 17.4 Hz, 1H), 3.75-4.0 (m, 4H), 3.72 (d, J = 17.4 Hz, 1H), 2.85-2.95 (m, 1H), 2.1-2.2 (m, 2H), 1.49 and 1.48 (d, J = 6.9 Hz, 3H). |
| 2-334 | (A) δ 7.94 (t, J = 6.0 Hz, 1H), 7.74 (d, J = 1.2 Hz, 1H), 7.63 (s, 2H), 7.4-7.55 (m, 2H), 4.56 (d, J = 6.0 Hz, 2H), 4.06 (d, J = 17.4 Hz, 1H), 3.67 (d, J = 17.4 Hz, 1H), 3.36 (s, 2H), 2.47 (d, J = 6.9 Hz, 2H), 2.46 (bs, 1H), 0.85-1.0 (m, 1H), 0.4-0.5 (m, 2H), 0.05-0.15 (m, 2H). |
| 2-336 | (A) δ 7.70 (d, J = 1.5 Hz, 1H), 7.63 (s, 2H), 7.4-7.55 (m, 2H), 6.41 (bs, 1H), 4.55 (d, J = 6.0 Hz, 2H), 4.06 (s, 2H), 4.06 (d, J = 17.4 Hz, 1H), 3.66 (d, J = 17.4 Hz, 1H), 3.26 (t, J = 1.5 Hz, 3H). |
| 2-337 | (A) δ 7.68 (s, 2H), 7.64 (s, 1H), 7.4-7.6 (m, 2H), 6.74 (bs, 1H), 4.53 (d, J = 6.0 Hz, 2H), 4.06 (d, J = 17.4 Hz, 1H), 3.93 (s, 2H), 3.68 (d, J = 17.4 Hz, 1H), 3.42 (d, J = 6.9 Hz, 2H), 0.95-1.05 (m, 1H), 0.55-0.65 (m, 2H), 0.25-0.35 (m, 2H). |
| 2-338 | (A) δ 7.7-7.75 (m, 1H), 7.63 (s, 2H), 7.4-7.55 (m, 2H), 6.34 and 6.17 (t, J = 6.3 Hz, 1H), 4.59 and 4.55 (d, J = 6.3 Hz, 2H), 4.39 and 4.37 (t, J = 2.4 Hz, 2H), 4.27 and 4.19 (s, 2H), 4.05 (d, J = 17.4 Hz, 1H), 3.66 (d, J = 17.4 Hz, 1H), 2.35 and 2.31 (t, J = 2.4 Hz, 1H). |
| 2-339 | (A) δ 7.67 (s, 1H), 7.64 (s, 2H), 7.4-7.55 (m, 2H), 6.89 (bs, 1H), 4.55 (d, J = 6.3 Hz, 2H), 4.07 (d, J = 17.4 Hz, 1H), 4.05 (s, 2H), 3.73 (s, 3H), 3.68 (d, J = 17.4 Hz, 1H), 3.23 (d, J = 7.2 Hz, 2H), 0.9-1.05 (m, 1H), 0.45-0.55 (m, 2H), 0.2-0.3 (m, 2H). |
| 2-340 | (A) δ 7.68 (d, J = 1.5 Hz, 1H), 7.63 (s, 2H), 7.4-7.55 (m, 2H), 6.40 (bs, 1H), 4.56 (d, J = 6.3 Hz, 2H), 4.19 (s, 2H), 4.06 (d, J = 17.4 Hz, 1H), 4.05 (s, 2H), 3.76 (s, 3H), 3.66 (d, J = 17.4 Hz, 1H), 2.24 (t, J = 2.4 Hz, 1H). |
| 2-341 | (A) δ 7.69 (d, J = 1.5 Hz, 1H), 7.63 (s, 2H), 7.4-7.5 (m, 2H), 4.56 (d, J = 6.3 Hz, 2H), 4.16 (q, J = 6.9 Hz, 2H), 4.05 (d, J = 17.4 Hz, 1H), 3.94 (s, 2H), 3.65 (d, J = 17.4 Hz, 1H), 2.99 (s, 3H), 1.25 (t, J = 6.9 Hz, 3H). |
| 2-342 | (A) δ 7.65 (d, J = 1.2 Hz, 1H), 7.63 (s, 2H), 7.4-7.55 (m, 2H), 7.16 (t, J = 6.3 Hz, 1H), 4.59 (t, J = 5.4 Hz, 1H), 4.52 (d, J = 6.3 Hz, 2H), 4.05 (d, J = 17.4 Hz, 1H), 3.96 (s, 2H), 3.66 (d, J = 17.4 Hz, 1H), 3.27 (qd, J = 7.2, 5.4 Hz, 2H), 2.95 (s, 3H), 1.15 (t, J = 7.2 Hz, 3H). |
| 2-343 | (A) δ 7.80 (t, J = 6.0 Hz, 1H), 7.6-7.7 (m, 3H), 7.45-7.55 (m, 1H), 7.35-7.45 (m, 1H), 6.89 (bs, 1H), 4.54 (d, J = 6.0 Hz, 2H), 4.05 (d, J = 17.4 Hz, 1H), 3.66 (d, J = 17.4 Hz, 1H), 3.22 (s, 2H), 3.21 (q, J = 7.2 Hz, 2H), 1.53 (sxt, J = 7.2 Hz, 2H), 0.91 (t, J = 7.2 Hz, 3H). |
| 2-344 | (A) δ 8.07 (s, 2H), 7.96 (s, 1H), 7.68 (s, 1H), 7.4-7.55 (m, 2H), 6.31 (bs, 1H), 4.54 (d, J = 6.0 Hz, 2H), 4.17 (d, J = 17.4 Hz, 1H), 3.73 (d, J = 17.4 Hz, 1H), 2.4-2.6 (m, 4H), 2.00 (t, J = 2.4 Hz, 1H). |
| 2-345 | (A) δ 8.07 (s, 2H), 7.97 (s, 1H), 7.88 (d, J = 1.8 Hz, 1H), 7.58 (dd, J = 8.1, 1.8 Hz, 1H), 7.49 (d, J = 8.1 Hz, 1H), 6.16 (t, J = 6.0 Hz, 1H), 4.55 (d, J = 6.3 Hz, 2H), 4.16 (d, J = 17.4 Hz, 1H), 3.71 (d, J = 17.4 Hz, 1H), 2.5-2.6 (m, 2H), 2.4-2.5 (m, 2H), 2.00 (t, J = 2.4 Hz, 1H). |
| 2-346 | (A) δ 8.07 (s, 2H), 7.95 (s, 1H), 7.63 (d, J = 8.4 Hz, 2H), 7.39 (d, J = 8.4 Hz, 2H), 5.89 (d, J = 7.5 Hz, 1H), 5.1-5.2 (m, 1H), 4.18 (d, J = 17.4 Hz, 1H), 3.72 (d, J = 17.4 Hz, 1H), 2.5-2.55 (m, 2H), 2.35-2.45 (m, 2H), 2.01 (bs, 1H), 1.50 (d, J = 6.9 Hz, 3H). |
| 2-348 | (A) δ 7.64 (d, J = 8.4 Hz, 2H), 7.51 (s, 2H), 7.42 (t, J = 1.8 Hz, 1H), 7.36 (d, J = 8.4 Hz, 2H), 6.33 (d, J = 6.3 Hz, 1H), 5.05-5.15 (m, 1H), 4.07 (d, J = 17.1 Hz, 1H), 3.68 (d, J = 17.1 Hz, 1H), 1.53 (d, J = 6.9 Hz, 3H), 1.35-1.45 (m, 2H), 1.15-1.25 (m, 2H). |
| 2-350 | (A) δ 7.95 (s, 1H), 7.84 (s, 1H), 7.79 (s, 1H), 7.69 (d, J = 1.8 Hz, 1H), 7.51 (dd, J = 8.4, 1.8 Hz, 1H), 7.44 (d, J = 8.4 Hz, 1H), 5.96 (t, J = 6.2 Hz, 1H), 4.53 (d, J = 6.2 Hz, 2H), 4.10 (d, J = 17.5 Hz, 1H), 3.69 (d, J = 17.5 Hz, 1H), 2.04 (s, 3H). |
| 2-352 | (A) δ 7.75 (d, J = 5.7 Hz, 2H), 7.66 (s, 1H), 7.35-7.5 (m, 2H), 6.13 (bs, 1H), 4.51 (d, J = 6.3 Hz, 2H), 4.05 (d, J = 17.4 Hz, 1H), 3.67 (d, J = 17.4 Hz, 1H), 2.04 (s, 3H). |
| 2-353 | (A) δ 7.83 (s, 2H), 7.69 (d, J = 1.2 Hz, 1H), 7.45-7.55 (m, 2H), 5.94 (t, J = 6.0 Hz, 1H), 4.54 (d, J = 6.0 Hz, 2H), 4.05 (d, J = 17.4 Hz, 1H), 3.65 (d, J = 17.4 Hz, 1H), 2.04 (s, 3H). |
| 2-354 | (A) δ 7.87 (s, 1H), 7.80 (s, 1H), 7.75 (s, 1H), 7.69 (s, 1H), 7.58 (d, J = 8.1 Hz, 1H), 7.47 (d, J = 8.1 Hz, 1H), 5.96 (bs, 1H), 4.51 (d, J = 6.3 Hz, 2H), 4.10 (d, J = 17.4 Hz, 1H), 3.68 (d, J = 17.4 Hz, 1H), 2.04 (s, 3H). |
| 2-356 | (A) δ 7.75 (d, J = 5.4 Hz, 2H), 7.67 (s, 1H), 7.4-7.55 (m, 2H), 5.99 (bs, 1H), 4.52 (d, J = 6.0 Hz, 2H), 4.04 (d, J = 17.4 Hz, 1H), 3.65 (d, J = 17.4 Hz, 1H), 2.03 (s, 3H). |
| 2-357 | (A) δ 8.10 (d, J = 1.8 Hz, 1H), 7.75 (d, J = 5.7 Hz, 2H), 7.60 (dd, J = 7.8, 1.8 Hz, 1H), 7.42 (d, J = 7.8 Hz, 1H), 5.94 (t, J = 6.0 Hz, 1H), 4.47 (d, J = 6.0 Hz, 2H), 4.03 (d, J = 17.4 Hz, 1H), 3.64 (d, J = 17.4 Hz, 1H), 2.40 (s, 3H). |

TABLE 16-continued

| No. | ¹H NMR |
|---|---|
| 2-358 | (A) δ 8.31 (bs, 1H), 8.08 (s, 2H), 7.9-8.05 (m, 2H), 7.78 (d, J = 8.1 Hz, 1H), 6.2-6.35 (m, 1H), 4.72 (d, J = 6.6 Hz, 2H), 4.21 (d, J = 17.4 Hz, 1H), 3.76 (d, J = 17.4 Hz, 1H), 2.00 (s, 3H). |
| 2-362 | (A) δ 8.07 (s, 2H), 7.97 (s, 1H), 7.3-7.55 (m, 3H), 6.03 (bs, 1H), 4.49 (d, J = 6.0 Hz, 2H), 4.16 (d, J = 17.4 Hz, 1H), 3.73 (d, J = 17.4 Hz, 1H), 2.25 (q, J = 7.5 Hz, 2H), 1.16 (t, J = 7.5 Hz, 3H). |
| 2-364 | (A) δ 7.95 (s, 1H), 7.84 (s, 1H), 7.79 (s, 1H), 7.69 (d, J = 1.5 Hz, 1H), 7.51 (dd, J = 8.1, 1.5 Hz, 1H), 7.46 (d, J = 8.1 Hz, 1H), 5.93 (t, J = 6.3 Hz, 1H), 4.53 (d, J = 6.3 Hz, 2H), 4.10 (d, J = 17.4 Hz, 1H), 3.69 (d, J = 17.4 Hz, 1H), 2.25 (q, J = 7.6 Hz, 2H), 1.17 (t, J = 7.6 Hz, 3H). |
| 2-366 | (A) δ 7.75 (d, J = 6.0 Hz, 2H), 7.66 (d, J = 1.2 Hz, 1H), 7.4-7.55 (m, 2H), 5.95-6.15 (m, 1H), 4.52 (d, J = 6.0 Hz, 2H), 4.05 (d, J = 17.4 Hz, 1H), 3.66 (d, J = 17.4 Hz, 1H), 2.26 (q, J = 7.5 Hz, 2H), 1.19 (t, J = 7.5 Hz, 3H). |
| 2-367 | (A) δ 7.83 (s, 2H), 7.69 (d, J = 1.5 Hz, 1H), 7.45-7.55 (m, 2H), 5.91 (t, J = 6.0 Hz, 1H), 4.54 (d, J = 6.0 Hz, 2H), 4.04 (d, J = 17.4 Hz, 1H), 3.65 (d, J = 17.4 Hz, 1H), 2.26 (q, J = 7.5 Hz, 2H), 1.17 (t, J = 7.5 Hz, 3H). |
| 2-368 | (A) δ 7.93 (d, J = 1.8 Hz, 1H), 7.82 (s, 1H), 7.68 (d, J = 1.5 Hz, 1H), 7.4-7.55 (m, 2H), 5.60 (t, J = 6.0 Hz, 1H), 4.53 (d, J = 6.0 Hz, 2H), 4.10 (d, J = 17.4 Hz, 1H), 3.68 (d, J = 17.4 Hz, 1H), 2.26 (q, J = 7.8 Hz, 2H), 1.17 (t, J = 7.8 Hz, 3H). |
| 2-370 | (A) δ 7.87 (s, 1H), 7.80 (s, 1H), 7.75 (s, 1H), 7.69 (s, 1H), 7.58 (d, J = 8.1 Hz, 1H), 7.47 (d, J = 8.1 Hz, 1H), 5.92 (bs, 1H), 4.52 (d, J = 6.0 Hz, 2H), 4.10 (d, J = 17.4 Hz, 1H), 3.68 (d, J = 17.4 Hz, 1H), 2.26 (q, J = 7.5 Hz, 2H), 1.17 (t, J = 7.5 Hz, 3H). |
| 2-371 | (A) δ 7.96 (s, 1H), 7.88 (s, 1H), 7.84 (s, 1H), 7.80 (s, 1H), 7.58 (d, J = 8.1 Hz, 1H), 7.47 (d, J = 8.1 Hz, 1H), 5.94 (bs, 1H), 4.52 (d, J = 6.3 Hz, 2H), 4.10 (d, J = 17.4 Hz, 1H), 3.68 (d, J = 17.4 Hz, 1H), 2.26 (q, J = 7.5 Hz, 2H), 1.17 (t, J = 7.5 Hz, 3H). |
| 2-372 | (A) δ 7.75 (d, J = 5.4 Hz, 2H), 7.67 (d, J = 1.5 Hz, 1H), 7.4-7.55 (m, 2H), 5.99 (bs, 1H), 4.53 (d, J = 6.0 Hz, 2H), 4.05 (d, J = 17.4 Hz, 1H), 3.66 (d, J = 17.4 Hz, 1H), 2.26 (q, J = 7.5 Hz, 2H), 1.17 (t, J = 7.5 Hz, 3H). |
| 2-373 | (A) δ 7.94 (s, 1H), 7.87 (s, 1H), 7.83 (s, 1H), 7.58 (d, J = 8.1 Hz, 1H), 7.47 (d, J = 8.1 Hz, 1H), 5.93 (bs, 1H), 4.52 (d, J = 6.0 Hz, 2H), 4.10 (d, J = 17.4 Hz, 1H), 3.67 (d, J = 17.4 Hz, 1H), 2.27 (q, J = 7.5 Hz, 2H), 1.17 (t, J = 7.5 Hz, 3H). |
| 2-375 | (A) δ 8.10 (d, J = 1.8 Hz, 1H), 7.75 (d, J = 5.7 Hz, 2H), 7.60 (dd, J = 7.8, 1.8 Hz, 1H), 7.42 (d, J = 7.8 Hz, 1H), 5.93 (t, J = 6.0 Hz, 1H), 4.47 (d, J = 6.0 Hz, 2H), 4.03 (d, J = 17.4 Hz, 1H), 3.64 (d, J = 17.4 Hz, 1H), 2.27 (q, J = 7.5 Hz, 2H), 1.18 (t, J = 7.5 Hz, 3H). |
| 2-378 | (A) δ 7.97 (s, 1H), 7.84 (s, 1H), 7.80 (s, 1H), 7.64 (d, J = 8.1 Hz, 2H), 7.38 (d, J = 8.1 Hz, 2H), 5.63 (d, J = 7.2 Hz, 1H), 5.14 (qui, J = 7.2 Hz, 1H), 4.12 (d, J = 17.4 Hz, 1H), 3.70 (d, J = 17.4 Hz, 1H), 2.22 (q, J = 7.5 Hz, 2H), 1.48 (d, J = 7.2 Hz, 3H), 1.15 (t, J = 7.5 Hz, 3H). |
| 2-380 | (A) δ 8.07 (s, 2H), 7.95 (s, 1H), 7.63 (d, J = 8.1 Hz, 2H), 7.37 (d, J = 8.1 Hz, 2H), 5.65 (d, J = 7.8 Hz, 1H), 5.05-5.2 (m, 1H), 4.17 (d, J = 17.4 Hz, 1H), 3.72 (d, J = 17.4 Hz, 1H), 2.22 (q, J = 7.8 Hz, 2H), 1.48 (d, J = 6.9 Hz, 3H), 1.15 (t, J = 7.8 Hz, 3H). |
| 2-382 | (A) δ 8.08 (s, 2H), 7.98 (s, 1H), 7.75 (d, J = 8.4 Hz, 2H), 7.56 (d, J = 8.4 Hz, 2H), 6.26 (d, J = 8.4 Hz, 1H), 5.99 (d, J = 8.4 Hz, 1H), 4.20 (d, J = 17.4 Hz, 1H), 3.76 (d, J = 17.4 Hz, 1H), 2.32 (q, J = 7.5 Hz, 2H), 1.21 (t, J = 7.5 Hz, 3H). |
| 2-385 | (A) δ 7.64 (d, J = 8.4 Hz, 1H), 7.45-7.6 (m, 4H), 7.4-7.45 (m, 1H), 6.19 (s, 2H), 4.07 (d, J = 17.4 Hz, 1H), 3.70 (d, J = 17.4 Hz, 1H), 2.36 (s, 3H), 2.2-2.35 (m, 2H), 1.17 (t, J = 7.8 Hz, 3H). |
| 2-386 | (A) δ 8.07 (s, 2H), 7.96 (s, 1H), 7.3-7.45 (m, 3H), 6.10 (bs, 1H), 4.49 (d, J = 6.0 Hz, 2H), 4.17 (d, J = 17.4 Hz, 1H), 3.73 (d, J = 17.4 Hz, 1H), 2.20 (t, J = 7.5 Hz, 2H), 1.66 (sxt, J = 7.5 Hz, 2H), 0.93 (t, J = 7.5 Hz, 3H). |
| 2-387 | (A) δ 7.86 (s, 1H), 7.82 (d, J = 7.8 Hz, 1H), 7.65-7.75 (m, 2H), 7.59 (t, J = 7.8 Hz, 1H), 7.45-7.55 (m, 2H), 5.93 (t, J = 6.2 Hz, 1H), 4.53 (d, J = 6.2 Hz, 2H), 4.10 (d, J = 17.2 Hz, 1H), 3.71 (d, J = 17.2 Hz, 1H), 2.20 (t, J = 7.6 Hz, 2H), 1.55-1.75 (m, 2H), 0.94 (t, J = 7.4 Hz, 3H). |
| 2-388 | (A) δ 7.95 (s, 1H), 7.83 (s, 1H), 7.79 (s, 1H), 7.69 (d, J = 1.8 Hz, 1H), 7.51 (dd, J = 8.1, 1.8 Hz, 1H), 7.46 (d, J = 8.1 Hz, 1H), 5.92 (t, J = 6.0 Hz, 1H), 4.53 (d, J = 6.0 Hz, 2H), 4.10 (d, J = 17.4 Hz, 1H), 3.69 (d, J = 17.4 Hz, 1H), 2.20 (t, J = 7.7 Hz, 2H), 1.6-1.75 (m, 2H), 0.94 (t, J = 7.4 Hz, 3H). |
| 2-390 | (A) δ 7.75 (d, J = 5.4 Hz, 2H), 7.67 (d, J = 1.2 Hz, 1H), 7.4-7.55 (m, 2H), 5.98 (bs, 1H), 4.53 (d, J = 6.0 Hz, 2H), 4.05 (d, J = 17.4 Hz, 1H), 3.66 (d, J = 17.4 Hz, 1H), 2.20 (t, J = 7.5 Hz, 2H), 1.67 (sxt, J = 7.5 Hz, 2H), 0.94 (t, J = 7.5 Hz, 3H). |
| 2-391 | (A) δ 7.83 (s, 2H), 7.69 (d, J = 1.5 Hz, 1H), 7.45-7.55 (m, 2H), 5.91 (t, J = 6.0 Hz, 1H), 4.54 (d, J = 6.0 Hz, 2H), 4.05 (d, J = 17.4 Hz, 1H), 3.65 (d, J = 17.4 Hz, 1H), 2.20 (t, J = 7.2 Hz, 2H), 1.67 (sxt, J = 7.2 Hz, 2H), 0.94 (t, J = 7.2 Hz, 3H). |
| 2-392 | (A) δ 7.93 (d, J = 1.8 Hz, 1H), 7.83 (s, 1H), 7.68 (d, J = 1.5 Hz, 1H), 7.4-7.5 (m, 2H), 5.95 (t, J = 6.0 Hz, 1H), 4.53 (d, J = 6.0 Hz, 2H), 4.10 (d, J = 17.4 Hz, 1H), 3.67 (d, J = 17.4 Hz, 1H), 2.20 (t, J = 7.5 Hz, 2H), 1.67 (sxt, J = 7.5 Hz, 2H), 0.94 (t, J = 7.5 Hz, 3H). |

TABLE 16-continued

| No. | ¹H NMR |
|---|---|
| 2-393 | (A) δ 7.87 (d, J = 1.8 Hz, 1H), 7.86 (s, 1H), 7.80 (d, J = 7.8 Hz, 1H), 7.69 (d, J = 7.8 Hz, 1H), 7.59 (t, J = 7.8 Hz, 1H), 7.57 (dd, J = 7.8, 1.8 Hz, 1H), 7.44 (d, J = 7.8 Hz, 1H), 5.98 (t, J = 6.3 Hz, 1H), 4.51 (d, J = 6.3 Hz, 2H), 4.10 (d, J = 17.7 Hz, 1H), 3.71 (d, J = 17.7 Hz, 1H), 2.20 (t, J = 7.5 Hz, 2H), 1.6-1.75 (m, 2H), 0.94 (t, J = 7.5 Hz, 3H). |
| 2-394 | (A) δ 7.87 (s, 1H), 7.80 (s, 1H), 7.75 (s, 1H), 7.69 (s, 1H), 7.58 (d, J = 8.1 Hz, 1H), 7.47 (d, J = 8.1 Hz, 1H), 5.94 (bs, 1H), 4.52 (d, J = 6.0 Hz, 2H), 4.10 (d, J = 17.4 Hz, 1H), 3.68 (d, J = 17.4 Hz, 1H), 2.21 (t, J = 7.5 Hz, 2H), 1.68 (sxt, J = 7.5 Hz, 2H), 0.94 (t, J = 7.5 Hz, 3H). |
| 2-395 | (A) δ 7.75 (d, J = 5.4 Hz, 2H), 7.67 (d, J = 1.5 Hz, 1H), 7.4-7.55 (m, 2H), 5.98 (bs, 1H), 4.53 (d, J = 6.0 Hz, 2H), 4.05 (d, J = 17.4 Hz, 1H), 3.66 (d, J = 17.4 Hz, 1H), 2.20 (t, J = 7.5 Hz, 2H), 1.67 (sxt, J = 7.5 Hz, 2H), 0.93 (t, J = 7.5 Hz, 3H). |
| 2-397 | (A) δ 8.10 (d, J = 1.8 Hz, 1H), 7.75 (d, J = 5.7 Hz, 2H), 7.60 (dd, J = 7.8, 1.8 Hz, 1H), 7.42 (d, J = 7.8 Hz, 1H), 5.93 (t, J = 6.0 Hz, 1H), 4.47 (d, J = 6.0 Hz, 2H), 4.03 (d, J = 17.4 Hz, 1H), 3.64 (d, J = 17.4 Hz, 1H), 2.21 (t, J = 7.5 Hz, 2H), 1.68 (sxt, J = 7.5 Hz, 2H), 0.95 (t, J = 7.5 Hz, 3H). |
| 2-398 | (A) δ 8.30 (bs, 1H), 8.08 (s, 2H), 7.9-8.0 (m, 2H), 7.78 (d, J = 8.1 Hz, 1H), 6.25 (t, J = 6.6 Hz, 1H), 4.69 (d, J = 6.6 Hz, 2H), 4.21 (d, J = 17.4 Hz, 1H), 3.76 (d, J = 17.4 Hz, 1H), 2.16 (t, J = 7.8 Hz, 2H), 1.5-1.75 (m, 2H), 0.90 (t, J = 7.5 Hz, 3H). |
| 2-403 | (A) δ 8.07 (s, 2H), 7.96 (s, 1H), 7.3-7.45 (m, 3H), 6.10 (t, J = 6.0 Hz, 1H), 4.48 (d, J = 6.0 Hz, 2H), 4.17 (d, J = 17.4 Hz, 1H), 3.74 (d, J = 17.4 Hz, 1H), 2.40 (sep, J = 6.9 Hz, 1H), 1.16 (d, J = 6.9 Hz, 6H). |
| 2-404 | (A) δ 7.95 (s, 1H), 7.84 (s, 1H), 7.79 (s, 1H), 7.69 (d, J = 1.8 Hz, 1H), 7.51 (dd, J = 8.4, 1.8 Hz, 1H), 7.44 (d, J = 8.4 Hz, 1H), 5.95 (t, J = 6.0 Hz, 1H), 4.52 (d, J = 6.0 Hz, 2H), 4.10 (d, J = 17.1 Hz, 1H), 3.69 (d, J = 17.1 Hz, 1H), 2.3-2.5 (m, 1H), 1.17 (d, J = 6.9 Hz, 6H). |
| 2-406 | (A) δ 7.75 (d, J = 5.4 Hz, 2H), 7.67 (d, J = 1.2 Hz, 1H), 7.35-7.5 (m, 2H), 6.03 (bs, 1H), 4.52 (d, J = 6.3 Hz, 2H), 4.05 (d, J = 17.4 Hz, 1H), 3.66 (d, J = 17.4 Hz, 1H), 2.41 (sep, J = 6.9 Hz, 1H), 1.17 (d, J = 6.9 Hz, 6H). |
| 2-407 | (A) δ 7.83 (s, 2H), 7.69 (d, J = 1.5 Hz, 1H), 7.4-7.55 (m, 2H), 5.93 (t, J = 6.0 Hz, 1H), 4.53 (d, J = 6.0 Hz, 2H), 4.05 (d, J = 17.4 Hz, 1H), 3.65 (d, J = 17.4 Hz, 1H), 2.40 (sep, J = 6.9 Hz, 1H), 1.17 (t, J = 6.9 Hz, 6H). |
| 2-408 | (A) δ 7.93 (d, J = 1.8 Hz, 1H), 7.82 (s, 1H), 7.69 (d, J = 1.5 Hz, 1H), 7.4-7.5 (m, 2H), 5.96 (t, J = 6.3 Hz, 1H), 4.53 (d, J = 6.3 Hz, 2H), 4.10 (d, J = 17.4 Hz, 1H), 3.67 (d, J = 17.4 Hz, 1H), 2.40 (sep, J = 6.9 Hz, 1H), 1.17 (d, J = 6.9 Hz, 6H). |
| 2-409 | (A) δ 7.88 (s, 1H), 7.82 (s, 1H), 7.75 (s, 1H), 7.69 (s, 1H), 7.58 (d, J = 8.1 Hz, 1H), 7.46 (d, J = 8.1 Hz, 1H), 5.96 (bs, 1H), 4.51 (d, J = 6.0 Hz, 2H), 4.10 (d, J = 17.4 Hz, 1H), 3.68 (d, J = 17.4 Hz, 1H), 2.40 (sep, J = 6.9 Hz, 1H), 1.17 (d, J = 6.9 Hz, 6H). |
| 2-410 | (A) δ 7.96 (s, 1H), 7.88 (s, 1H), 7.84 (s, 1H), 7.80 (s, 1H), 7.58 (d, J = 8.1 Hz, 1H), 7.45 (d, J = 8.1 Hz, 1H), 5.69 (bs, 1H), 4.51 (d, J = 6.3 Hz, 2H), 4.10 (d, J = 17.4 Hz, 1H), 3.68 (d, J = 17.4 Hz, 1H), 2.40 (qui, J = 6.9 Hz, 1H), 1.17 (d, J = 6.9 Hz, 6H). |
| 2-411 | (A) δ 7.75 (d, J = 5.4 Hz, 2H), 7.68 (d, J = 1.5 Hz, 1H), 7.49 (dd, J = 7.8, 1.2 Hz, 1H), 7.44 (d, J = 7.8 Hz, 1H), 6.02 (bs, 1H), 4.52 (d, J = 6.0 Hz, 2H), 4.05 (d, J = 17.4 Hz, 1H), 3.66 (d, J = 17.4 Hz, 1H), 2.41 (sep, J = 6.9 Hz, 1H), 1.17 (d, J = 6.9 Hz, 6H). |
| 2-412 | (A) δ 7.94 (s, 1H), 7.87 (s, 1H), 7.83 (s, 1H), 7.58 (d, J = 8.1 Hz, 1H), 7.45 (d, J = 8.1 Hz, 1H), 5.98 (bs, 1H), 4.51 (d, J = 6.0 Hz, 2H), 4.10 (d, J = 17.4 Hz, 1H), 3.67 (d, J = 17.4 Hz, 1H), 2.41 (sep, J = 7.2 Hz, 1H), 1.17 (d, J = 7.2 Hz, 6H). |
| 2-414 | (A) δ 8.10 (d, J = 1.8 Hz, 1H), 7.75 (d, J = 5.7 Hz, 2H), 7.60 (dd, J = 7.8, 1.8 Hz, 1H), 7.42 (d, J = 7.8 Hz, 1H), 5.95 (t, J = 6.0 Hz, 1H), 4.46 (d, J = 6.0 Hz, 2H), 4.03 (d, J = 17.4 Hz, 1H), 3.64 (d, J = 17.4 Hz, 1H), 2.41 (sep, J = 6.9 Hz, 1H), 1.18 (d, J = 6.9 Hz, 6H). |
| 2-415 | (A) δ 8.30 (bs, 1H), 7.9-8.15 (m, 4H), 7.78 (d, J = 8.1 Hz, 1H), 6.25 (t, J = 6.6 Hz, 1H), 4.68 (d, J = 6.6 Hz, 2H), 4.21 (d, J = 17.4 Hz, 1H), 3.76 (d, J = 17.4 Hz, 1H), 2.3-2.45 (m, 1H), 1.13 (d, J = 6.9 Hz, 6H). |
| 2-420 | (A) δ 8.08 (s, 2H), 7.98 (s, 1H), 7.76 (d, J = 8.4 Hz, 2H), 7.56 (d, J = 8.4 Hz, 2H), 6.26 (d, J = 8.4 Hz, 1H), 6.01 (d, J = 8.4 Hz, 1H), 4.20 (d, J = 17.4 Hz, 1H), 3.76 (d, J = 17.4 Hz, 1H), 2.44 (sep, J = 6.9 Hz, 1H), 1.22 (d, J = 6.9 Hz, 3H), 1.19 (d, J = 6.9 Hz, 3H). |
| 2-421 | (A) δ 8.07 (s, 2H), 7.97 (s, 1H), 7.3-7.5 (m, 3H), 6.03 (t, J = 6.0 Hz, 1H), 4.52 (d, J = 6.0 Hz, 2H), 4.16 (d, J = 17.4 Hz, 1H), 3.71 (d, J = 17.4 Hz, 1H), 1.4-1.55 (m, 1H), 0.95-1.1 (m, 2H), 0.7-0.85 (m, 2H). |
| 2-422 | (A) δ 7.81 (d, J = 6.3 Hz, 1H), 7.66 (d, J = 1.2 Hz, 1H), 7.4-7.6 (m, 3H), 7.1-7.2 (m, 1H), 6.28 (t, J = 6.0 Hz, 1H), 4.53 (d, J = 6.0 Hz, 2H), 4.05 (d, J = 17.4 Hz, 1H), 3.67 (d, J = 17.4 Hz, 1H), 1.35-1.45 (m, 1H), 0.9-1.05 (m, 2H), 0.7-0.85 (m, 2H). |

TABLE 16-continued

| No. | ¹H NMR |
|---|---|
| 2-423 | (A) δ 7.95 (s, 1H), 7.83 (s, 1H), 7.79 (s, 1H), 7.69 (d, J = 1.5 Hz, 1H), 7.51 (dd, J = 8.4, 1.5 Hz, 1H), 7.46 (d, J = 8.4 Hz, 1H), 6.10 (t, J = 6.0 Hz, 1H), 4.55 (d, J = 6.0 Hz, 2H), 4.10 (d, J = 17.1 Hz, 1H), 3.69 (d, J = 17.1 Hz, 1H), 1.35-1.45 (m, 1H), 0.95-1.05 (m, 2H), 0.7-0.8 (m, 2H). |
| 2-425 | (A) δ 7.75 (d, J = 5.7 Hz, 2H), 7.66 (d, J = 1.2 Hz, 1H), 7.35-7.5 (m, 2H), 6.15-6.35 (m, 1H), 4.56 (d, J = 6.0 Hz, 2H), 4.04 (d, J = 17.4 Hz, 1H), 3.66 (d, J = 17.4 Hz, 1H), 1.35-1.45 (m, 1H), 0.9-1.05 (m, 2H), 0.7-0.9 (m, 2H). |
| 2-426 | (A) δ 7.82 (s, 2H), 7.67 (d, J = 1.2 Hz, 1H), 7.4-7.55 (m, 2H), 6.13 (t, J = 6.0 Hz, 1H), 4.55 (d, J = 6.0 Hz, 2H), 4.04 (d, J = 17.4 Hz, 1H), 3.62 (d, J = 17.4 Hz, 1H), 1.35-1.45 (m, 1H), 0.95-1.05 (m, 2H), 0.7-0.85 (m, 2H). |
| 2-427 | (A) δ 7.93 (s, 1H), 7.83 (s, 1H), 7.68 (s, 1H), 7.4-7.55 (m, 2H), 6.22 (bs, 1H), 4.54 (d, J = 6.0 Hz, 2H), 4.10 (d, J = 17.4 Hz, 1H), 3.68 (d, J = 17.4 Hz, 1H), 1.35-1.45 (m, 1H), 0.9-1.05 (m, 2H), 0.7-0.85 (m, 2H). |
| 2-428 | (A) δ 7.87 (d, J = 1.7 Hz, 1H), 7.86 (s, 1H), 7.80 (d, J = 7.8 Hz, 1H), 7.69 (d, J = 7.8 Hz, 1H), 7.59 (t, J = 7.8 Hz, 1H), 7.57 (dd, J = 8.1, 1.7 Hz, 1H), 7.45 (d, J = 8.1 Hz, 1H), 6.14 (t, J = 6.2 Hz, 1H), 4.53 (d, J = 6.2 Hz, 2H), 4.10 (d, J = 17.4 Hz, 1H), 3.71 (d, J = 17.4 Hz, 1H), 1.3-1.45 (m, 1H), 0.95-1.1 (m, 2H), 0.7-0.85 (m, 2H). |
| 2-429 | (A) δ 7.88 (s, 1H), 7.82 (s, 1H), 7.75 (s, 1H), 7.69 (s, 1H), 7.58 (d, J = 8.1 Hz, 1H), 7.47 (d, J = 8.1 Hz, 1H), 6.12 (bs, 1H), 4.54 (d, J = 6.0 Hz, 2H), 4.10 (d, J = 17.4 Hz, 1H), 3.68 (d, J = 17.4 Hz, 1H), 1.3-1.45 (m, 1H), 0.95-1.05 (m, 2H), 0.7-0.85 (m, 2H). |
| 2-431 | (A) δ 7.75 (d, J = 5.4 Hz, 2H), 7.66 (d, J = 1.5 Hz, 1H), 7.49 (dd, J = 7.8, 1.2 Hz, 1H), 7.44 (d, J = 7.8 Hz, 1H), 6.23 (bs, 1H), 4.54 (d, J = 6.0 Hz, 2H), 4.04 (d, J = 17.4 Hz, 1H), 3.65 (d, J = 17.4 Hz, 1H), 1.40 (qui, J = 7.5 Hz, 1H), 0.95-1.1 (m, 2H), 0.7-0.9 (m, 2H). |
| 2-432 | (A) δ 7.93 (s, 1H), 7.87 (s, 1H), 7.83 (s, 1H), 7.58 (d, J = 8.1 Hz, 1H), 7.47 (d, J = 8.1 Hz, 1H), 6.12 (bs, 1H), 4.54 (d, J = 6.0 Hz, 2H), 4.10 (d, J = 17.4 Hz, 1H), 3.67 (d, J = 17.4 Hz, 1H), 1.3-1.45 (m, 1H), 0.95-1.05 (m, 2H), 0.7-0.85 (m, 2H). |
| 2-434 | (A) δ 8.10 (d, J = 1.8 Hz, 1H), 7.76 (d, J = 5.7 Hz, 2H), 7.61 (dd, J = 7.8, 1.8 Hz, 1H), 7.43 (d, J = 7.8 Hz, 1H), 6.11 (t, J = 6.0 Hz, 1H), 4.49 (d, J = 6.0 Hz, 2H), 4.04 (d, J = 17.4 Hz, 1H), 3.64 (d, J = 17.4 Hz, 1H), 1.35-1.45 (m, 1H), 0.95-1.05 (m, 2H), 0.75-0.85 (m, 2H). |
| 2-435 | (A) δ 8.07 (s, 2H), 7.96 (s, 1H), 7.76 (d, J = 1.8 Hz, 1H), 7.65 (dd, J = 8.1, 1.8 Hz, 1H), 7.45 (d, J = 8.1 Hz, 1H), 6.14 (bs, 1H), 4.62 (d, J = 6.0 Hz, 2H), 4.18 (d, J = 17.4 Hz, 1H), 3.72 (d, J = 17.4 Hz, 1H), 3.41 (s, 1H), 1.3-1.4 (m, 1H), 0.95-1.05 (m, 2H), 0.7-0.85 (m, 2H). |
| 2-437 | (A) δ 8.31 (bs, 1H), 8.08 (s, 2H), 7.9-8.0 (m, 2H), 7.77 (d, J = 8.1 Hz, 1H), 6.45 (t, J = 6.6 Hz, 1H), 4.72 (d, J = 6.6 Hz, 2H), 4.21 (d, J = 17.4 Hz, 1H), 3.77 (d, J = 17.4 Hz, 1H), 1.3-1.45 (m, 1H), 0.9-1.0 (m, 2H), 0.7-0.85 (m, 2H). |
| 2-439 | (A) δ 7.97 (s, 1H), 7.84 (s, 1H), 7.80 (s, 1H), 7.64 (d, J = 8.1 Hz, 2H), 7.39 (d, J = 8.1 Hz, 2H), 5.63 (d, J = 7.2 Hz, 1H), 5.14 (qui, J = 7.2 Hz, 1H), 4.12 (d, J = 17.4 Hz, 1H), 3.70 (d, J = 17.4 Hz, 1H), 1.50 (d, J = 7.2 Hz, 3H), 1.3-1.4 (m, 1H), 0.9-1.05 (m, 2H), 0.7-0.8 (m, 2H). |
| 2-441 | (A) δ 8.08 (s, 2H), 7.96 (s, 1H), 7.63 (d, J = 8.1 Hz, 2H), 7.38 (d, J = 8.1 Hz, 2H), 5.94 (t, J = 7.5 Hz, 1H), 5.05-5.2 (m, 1H), 4.18 (d, J = 17.4 Hz, 1H), 3.73 (d, J = 17.4 Hz, 1H), 1.49 (d, J = 7.2 Hz, 3H), 1.3-1.4 (m, 1H), 0.9-1.0 (m, 2H), 0.7-0.8 (m, 2H). |
| 2-443 | (A) δ 7.94 (s, 1H), 7.84 (s, 1H), 7.63 (d, J = 8.1 Hz, 2H), 7.39 (d, J = 8.1 Hz, 2H), 5.83 (d, J = 7.2 Hz, 1H), 5.1-5.2 (m, 1H), 4.17 (d, J = 17.4 Hz, 1H), 3.68 (d, J = 17.4 Hz, 1H), 1.50 (d, J = 6.9 Hz, 3H), 1.25-1.4 (m, 1H), 0.9-1.05 (m, 2H), 0.65-0.85 (m, 2H). |
| 2-447 | (A) δ 7.58 (d, J = 8.4 Hz, 2H), 7.47 (s, 2H), 7.25-7.4 (m, 3H), 6.58 (d, J = 7.2 Hz, 1H), 5.14 (q, J = 6.9 Hz, 1H), 4.03 (d, J = 17.4 Hz, 1H), 3.65 (d, J = 17.4 Hz, 1H), 2.86 (d, J = 6.9 Hz, 2H), 1.98 (s, 3H), 1.35-1.5 (m, 1H), 0.85-1.0 (m, 2H), 0.6-0.8 (m, 2H). |
| 2-448 | (A) δ 8.08 (s, 2H), 7.97 (s, 1H), 7.68 (d, J = 8.4 Hz, 2H), 7.59 (d, J = 8.4 Hz, 2H), 6.05-6.15 (m, 1H), 6.10 (bs, 1H), 4.18 (d, J = 17.1 Hz, 1H), 3.74 (d, J = 17.1 Hz, 1H), 2.54 (d, J = 2.1 Hz, 1H), 1.3-1.4 (m, 1H), 0.95-1.1 (m, 2H), 0.75-0.85 (m, 2H). |
| 2-450 | (A) δ 8.07 (s, 2H), 7.98 (s, 1H), 7.6-7.85 (m, 3H), 6.45 (d, J = 8.1 Hz, 1H), 6.30 (d, J = 8.1 Hz, 1H), 4.18 (d, J = 17.4 Hz, 1H), 3.74 (d, J = 17.4 Hz, 1H), 1.35-1.45 (m, 1H), 0.8-1.15 (m, 4H). |
| 2-451 | (A) δ 8.07 (s, 2H), 7.9-8.1 (m, 2H), 7.65-7.8 (m, 2H), 6.40 (d, J = 6.9 Hz, 1H), 6.26 (d, J = 6.9 Hz, 1H), 4.18 (d, J = 17.4 Hz, 1H), 3.74 (d, J = 17.4 Hz, 1H), 1.35-1.5 (m, 1H), 0.95-1.1 (m, 2H), 0.75-0.95 (m, 2H). |

TABLE 16-continued

| No. | ¹H NMR |
|---|---|
| 2-452 | (A) δ 8.19 (d, J = 9.0 Hz, 1H), 7.73 (d, J = 3.3 Hz, 2H), 7.49 (d, J = 1.8 Hz, 2H), 7.44 (t, J = 1.8 Hz, 1H), 6.53 (d, J = 7.8 Hz, 1H), 6.11 (d, J = 7.8 Hz, 1H), 4.06 (d, J = 17.4 Hz, 1H), 3.69 (d, J = 17.4 Hz, 1H), 1.35-1.45 (m, 1H), 1.0-1.1 (m, 2H), 0.75-0.95 (m, 2H). |
| 2-453 | (A) δ 8.24 and 8.21 (s, 1H), 8.07 (s, 2H), 7.99 (s, 1H), 7.76 (s, 2H), 6.24 (d, J = 7.8 Hz, 1H), 6.13 (d, J = 7.8 Hz, 1H), 4.15 (d, J = 17.4 Hz, 1H), 3.73 (d, J = 17.4 Hz, 1H), 1.35-1.45 (m, 1H), 1.0-1.1 (m, 2H), 0.8-0.9 (m, 2H). |
| 2-454 | (A) δ 7.64 (d, J = 8.4 Hz, 1H), 7.45-7.6 (m, 4H), 7.4-7.45 (m, 1H), 6.62 (d, J = 8.4 Hz, 1H), 6.18 (d, J = 8.4 Hz, 1H), 4.08 (d, J = 17.4 Hz, 1H), 3.71 (d, J = 17.4 Hz, 1H), 2.36 (s, 3H), 1.35-1.5 (m, 1H), 0.95-1.1 (m, 2H), 0.75-0.95 (m, 2H). |
| 2-455 | (A) δ 7.78 (d, J = 7.5 Hz, 1H), 7.64 (d, J = 8.4 Hz, 2H), 7.55 (d, J = 8.4 Hz, 2H), 7.51 (s, 2H), 7.4-7.45 (m, 1H), 7.26 (s, 1H), 6.26 (s, 1H), 5.62 (d, J = 7.5 Hz, 1H), 4.10 (d, J = 17.4 Hz, 1H), 3.75 (d, J = 17.4 Hz, 1H), 1.55-1.7 (m, 1H), 0.8-1.0 (m, 2H), 0.65-0.8 (m, 2H). |
| 2-456 | (A) δ 8.07 (s, 2H), 7.96 (s, 1H), 7.3-7.45 (m, 3H), 6.07 (bs, 1H), 4.49 (d, J = 6.0 Hz, 2H), 4.17 (d, J = 17.4 Hz, 1H), 3.74 (d, J = 17.4 Hz, 1H), 2.0-2.2 (m, 3H), 0.93 (d, J = 6.6 Hz, 6H). |
| 2-457 | (A) δ 7.95 (s, 1H), 7.84 (s, 1H), 7.79 (s, 1H), 7.69 (d, J = 1.8 Hz, 1H), 7.51 (dd, J = 8.4, 1.8 Hz, 1H), 7.44 (d, J = 8.4 Hz, 1H), 5.93 (t, J = 6.2 Hz, 1H), 4.54 (d, J = 6.2 Hz, 2H), 4.10 (d, J = 17.2 Hz, 1H), 3.69 (d, J = 17.2 Hz, 1H), 2.0-2.2 (m, 3H), 0.93 (d, J = 6.5 Hz, 6H). |
| 2-459 | (A) δ 7.75 (d, J = 6.0 Hz, 2H), 7.65 (d, J = 1.5 Hz, 1H), 7.35-7.5 (m, 2H), 6.14 (bs, 1H), 4.51 (d, J = 6.0 Hz, 2H), 4.05 (d, J = 17.4 Hz, 1H), 3.68 (d, J = 17.4 Hz, 1H), 2.0-2.2 (m, 3H), 0.93 (d, J = 6.3 Hz, 6H). |
| 2-460 | (A) δ 7.83 (s, 2H), 7.69 (d, J = 1.5 Hz, 1H), 7.4-7.55 (m, 2H), 5.89 (t, J = 6.0 Hz, 1H), 4.54 (d, J = 6.0 Hz, 2H), 4.05 (d, J = 17.4 Hz, 1H), 3.65 (d, J = 17.4 Hz, 1H), 2.0-2.2 (m, 3H), 0.94 (d, J = 6.3 Hz, 6H). |
| 2-461 | (A) δ 7.93 (d, J = 1.8 Hz, 1H), 7.82 (s, 1H), 7.68 (d, J = 1.5 Hz, 1H), 7.4-7.5 (m, 2H), 5.97 (t, J = 6.0 Hz, 1H), 4.53 (d, J = 6.0 Hz, 2H), 4.10 (d, J = 17.4 Hz, 1H), 3.68 (d, J = 17.4 Hz, 1H), 2.0-2.2 (m, 3H), 0.93 (d, J = 6.6 Hz, 6H). |
| 2-463 | (A) δ 7.96 (s, 1H), 7.88 (s, 1H), 7.84 (s, 1H), 7.81 (s, 1H), 7.58 (d, J = 8.1 Hz, 1H), 7.47 (d, J = 8.1 Hz, 1H), 5.92 (bs, 1H), 4.52 (d, J = 6.0 Hz, 2H), 4.10 (d, J = 17.4 Hz, 1H), 3.69 (d, J = 17.4 Hz, 1H), 2.05-2.2 (m, 3H), 0.94 (d, J = 6.6 Hz, 6H). |
| 2-464 | (A) δ 7.75 (d, J = 5.4 Hz, 2H), 7.68 (d, J = 1.5 Hz, 1H), 7.49 (dd, J = 7.8, 1.2 Hz, 1H), 7.44 (d, J = 7.8 Hz, 1H), 6.03 (bs, 1H), 4.52 (d, J = 6.0 Hz, 2H), 4.05 (d, J = 17.4 Hz, 1H), 3.66 (d, J = 17.4 Hz, 1H), 2.05-2.2 (m, 3H), 0.93 (d, J = 6.6 Hz, 6H). |
| 2-465 | (A) δ 7.93 (s, 1H), 7.87 (s, 1H), 7.83 (s, 1H), 7.58 (d, J = 8.1 Hz, 1H), 7.45 (d, J = 8.1 Hz, 1H), 5.98 (bs, 1H), 4.51 (d, J = 6.0 Hz, 2H), 4.10 (d, J = 17.4 Hz, 1H), 3.67 (d, J = 17.4 Hz, 1H), 2.05-2.2 (m, 3H), 0.93 (d, J = 6.6 Hz, 6H). |
| 2-467 | (A) δ 8.29 (bs, 1H), 7.9-8.2 (m, 4H), 7.79 (d, J = 8.1 Hz, 1H), 6.22 (t, J = 6.6 Hz, 1H), 4.69 (d, J = 6.6 Hz, 2H), 4.21 (d, J = 17.4 Hz, 1H), 3.76 (d, J = 17.4 Hz, 1H), 2.0-2.15 (m, 2H), 0.85-1.2 (m, 7H). |
| 2-472 | (A) δ 7.86 (s, 1H), 7.82 (d, J = 7.8 Hz, 1H), 7.65-7.75 (m, 2H), 7.59 (t, J = 7.8 Hz, 1H), 7.45-7.55 (m, 2H), 6.47 (t, J = 6.2 Hz, 1H), 4.56 (d, J = 6.2 Hz, 2H), 4.11 (d, J = 17.5 Hz, 1H), 3.72 (d, J = 17.5 Hz, 1H), 2.19 (d, J = 7.2 Hz, 2H), 0.9-1.1 (m, 1H), 0.55-0.7 (m, 2H), 0.15-0.3 (m, 2H). |
| 2-475 | (A) δ 7.75 (d, J = 5.7 Hz, 2H), 7.68 (s, 1H), 7.4-7.5 (m, 2H), 6.52 (bs, 1H), 4.56 (d, J = 6.0 Hz, 2H), 4.06 (d, J = 17.4 Hz, 1H), 3.67 (d, J = 17.4 Hz, 1H), 2.20 (d, J = 7.2 Hz, 2H), 0.9-1.05 (m, 1H), 0.55-0.7 (m, 2H), 0.2-0.35 (m, 2H). |
| 2-476 | (A) δ 7.83 (s, 2H), 7.69 (d, J = 1.5 Hz, 1H), 7.4-7.55 (m, 2H), 6.50 (t, J = 6.0 Hz, 1H), 4.54 (d, J = 6.0 Hz, 2H), 4.05 (d, J = 17.4 Hz, 1H), 3.65 (d, J = 17.4 Hz, 1H), 2.18 (d, J = 7.2 Hz, 2H), 0.9-1.05 (m, 1H), 0.45-0.7 (m, 2H), 0.15-0.3 (m, 2H). |
| 2-477 | (A) δ 7.88 (d, J = 1.8 Hz, 1H), 7.86 (s, 1H), 7.80 (d, J = 7.8 Hz, 1H), 7.69 (d, J = 7.8 Hz, 1H), 7.55-7.65 (m, 2H), 7.45 (d, J = 7.8 Hz, 1H), 6.49 (t, J = 6.0 Hz, 1H), 4.54 (d, J = 6.0 Hz, 2H), 4.10 (d, J = 17.7 Hz, 1H), 3.71 (d, J = 17.7 Hz, 1H), 2.19 (d, J = 7.2 Hz, 2H), 0.9-1.1 (m, 1H), 0.55-0.7 (m, 2H), 0.15-0.3 (m, 2H). |
| 2-478 | (A) δ 7.89 (s, 1H), 7.82 (s, 1H), 7.75 (s, 1H), 7.69 (s, 1H), 7.58 (d, J = 8.1 Hz, 1H), 7.45 (d, J = 8.1 Hz, 1H), 6.49 (t, J = 6.0 Hz, 1H), 4.54 (d, J = 6.0 Hz, 2H), 4.10 (d, J = 17.4 Hz, 1H), 3.69 (d, J = 17.4 Hz, 1H), 2.20 (d, J = 7.2 Hz, 2H), 0.85-1.05 (m, 1H), 0.6-0.65 (m, 2H), 0.2-0.3 (m, 2H). |
| 2-481 | (A) δ 7.81 (s, 1H), 7.76 (s, 1H), 7.68 (s, 1H), 7.65 (d, J = 8.4 Hz, 2H), 7.38 (d, J = 8.4 Hz, 2H), 6.08 (d, J = 7.5 Hz, 1H), 5.17 (qui, J = 7.5 Hz, 1H), 4.12 (d, J = 17.4 Hz, 1H), 3.70 (d, J = 17.4 Hz, 1H), 2.17 (d, J = 7.5 Hz, 2H), 1.50 (d, J = 6.9 Hz, 3H), 0.9-1.0 (m, 1H), 0.55-0.65 (m, 2H), 0.2-0.25 (m, 2H). |

TABLE 16-continued

| No. | ¹H NMR |
|---|---|
| 2-482 | (A) δ 8.15 (s, 1H), 8.02 (s, 1H), 7.83 (s, 1H), 7.64 (d, J = 8.4 Hz, 2H), 7.39 (d, J = 8.4 Hz, 2H), 6.09 (d, J = 7.5 Hz, 1H), 5.17 (qui, J = 7.5 Hz, 1H), 4.11 (d, J = 17.4 Hz, 1H), 3.69 (d, J = 17.4 Hz, 1H), 2.17 (d, J = 7.5 Hz, 2H), 1.50 (d, J = 7.5 Hz, 3H), 0.9-1.0 (m, 1H), 0.55-0.65 (m, 2H), 0.2-0.25 (m, 2H). |
| 2-485 | (A) δ 7.6-7.8 (m, 3H), 7.49 (s, 2H), 7.4-7.45 (m, 1H), 6.77 (d, J = 7.2 Hz, 1H), 6.28 (d, J = 7.2 Hz, 1H), 4.06 (d, J = 17.4 Hz, 1H), 3.69 (d, J = 17.4 Hz, 1H), 2.22 (d, J = 7.2 Hz, 2H), 0.85-1.05 (m, 1H), 0.6-0.7 (m, 2H), 0.2-0.3 (m, 2H). |
| 2-486 | (A) δ 7.66 (d, J = 8.4 Hz, 1H), 7.45-7.6 (m, 4H), 7.4-7.45 (m, 1H), 6.40 (d, J = 8.4 Hz, 1H), 6.22 (d, J = 8.4 Hz, 1H), 4.08 (d, J = 17.4 Hz, 1H), 3.70 (d, J = 17.4 Hz, 1H), 2.38 (s, 3H), 2.22 (d, J = 7.2 Hz, 2H), 0.85-1.05 (m, 1H), 0.55-0.65 (m, 2H), 0.15-0.25 (m, 2H). |
| 2-493 | (A) δ 8.07 (s, 2H), 7.97 (s, 1H), 7.72 (d, J = 1.5 Hz, 1H), 7.5-7.6 (m, 1H), 7.4-7.5 (m, 1H), 7.34 (t, J = 6.0 Hz, 1H), 4.56 (d, J = 6.0 Hz, 2H), 4.17 (d, J = 17.4 Hz, 1H), 3.72 (d, J = 17.4 Hz, 1H), 1.34 (dd, J = 6.0, 5.1 Hz, 2H), 1.70 (dd, J = 6.0, 5.1 Hz, 2H). |
| 2-494 | (A) δ 8.08 (s, 2H), 7.97 (s, 1H), 7.55 (s, 1H), 7.5-7.6 (m, 1H), 7.4-7.5 (m, 1H), 7.20 (t, J = 6.0 Hz, 1H), 4.55 (d, J = 6.0 Hz, 2H), 4.35-4.45 (m, 1H), 4.18 (d, J = 17.4 Hz, 1H), 3.85-4.05 (m, 2H), 3.75 (d, J = 17.4 Hz, 1H), 2.2-2.4 (m, 1H), 1.8-2.15 (m, 3H). |
| 2-500 | (A) δ 8.11 (s, 1H), 8.07 (s, 2H), 7.96 (s, 1H), 7.62 (d, J = 8.4 Hz, 1H), 7.39 (d, J = 8.4 Hz, 1H), 6.30 (bs, 1H), 4.45 (d, J = 6.0 Hz, 2H), 4.16 (d, J = 17.4 Hz, 1H), 3.75-4.0 (m, 4H), 3.72 (d, J = 17.4 Hz, 1H), 2.9-3.0 (m, 1H), 2.15-2.2 (m, 2H). |
| 2-501 | (A) δ 8.29 (bs, 1H), 8.08 (s, 2H), 7.9-8.0 (m, 2H), 7.75 (d, J = 8.1 Hz, 1H), 6.50 (t, J = 6.6 Hz, 1H), 4.69 (d, J = 6.6 Hz, 2H), 4.21 (d, J = 17.4 Hz, 1H), 3.7-4.0 (m, 5H), 2.85-3.0 (m, 1H), 2.0-2.2 (m, 2H). |
| 2-502 | (A) δ 7.81 (s, 1H), 7.76 (s, 1H), 7.68 (s, 1H), 7.64 (d, J = 8.4 Hz, 2H), 7.3-7.4 (m, 2H), 5.93 (d, J = 7.5 Hz, 1H), 5.11 (qui, J = 7.5 Hz, 1H), 4.12 (d, J = 17.4 Hz, 1H), 3.75-4.0 (m, 4H), 3.70 (d, J = 17.4 Hz, 1H), 2.90 (qui, J = 5.7 Hz, 1H), 2.05-2.2 (m, 2H), 1.49 and 1.48 (d, J = 6.9 Hz, 3H). |
| 2-503 | (A) δ 8.08 (s, 2H), 7.98 (s, 1H), 7.75 (d, J = 8.4 Hz, 1H), 7.56 (d, J = 8.4 Hz, 2H), 6.38 (d, J = 6.9 Hz, 1H), 6.21 (d, J = 8.4 Hz, 1H), 3.7-4.25 (m, 6H), 2.95-3.05 (m, 1H), 2.1-2.3 (m, 2H). |
| 2-504 | (A) δ 7.69 (d, J = 8.7 Hz, 1H), 7.55-7.65 (m, 2H), 7.4-7.55 (m, 3H), 7.30 (d, J = 8.7 Hz, 1H), 6.18 (d, J = 8.7 Hz, 1H), 4.08 (d, J = 17.4 Hz, 1H), 3.70 (d, J = 17.4 Hz, 1H), 3.34 (d, J = 17.8 Hz, 1H), 3.27 (d, J = 17.8 Hz, 1H), 2.54 (q, J = 7.5 Hz, 2H), 2.40 (s, 3H), 1.25 (t, J = 7.5 Hz, 3H). |
| 2-505 | (A) δ 7.95-8.1 (m, 1H), 7.4-7.7 (m, 6H), 6.14 (t, J = 7.5 Hz, 1H), 4.07 (d, J = 17.4 Hz, 1H), 3.65-3.8 (m, 2H), 3.25-3.4 (m, 1H), 2.4-3.0 (m, 2H), 2.47 and 2.41 (s, 3H), 1.26 (t, J = 7.2 Hz, 3H). |
| 2-506 | (A) δ 7.45-7.7 (m, 6H), 7.42 (s, 1H), 6.07 (d, J = 7.2 Hz, 1H), 4.08 (d, J = 17.4 Hz, 1H), 3.93 (s, 2H), 3.70 (d, J = 17.4 Hz, 1H), 3.16 (q, J = 7.5 Hz, 2H), 2.38 (s, 3H), 1.37 (t, J = 7.5 Hz, 3H). |
| 2-507 | (A) δ 8.62 and 8.56 (d, J = 7.8 Hz, 1H), 7.66 (d, J = 7.5 Hz, 1H), 7.45-7.6 (m, 4H), 7.4-7.45 (m, 1H), 6.09 (d, J = 7.5 Hz, 1H), 3.85-4.1 (m, 3H), 3.71 (d, J = 17.4 Hz, 1H), 3.05-3.25 (m, 3H), 2.40 and 2.39 (s, 3H), 1.37 and 1.35 (t, J = 7.5 Hz, 3H). |
| 2-508 | (A) δ 8.07 (s, 2H), 7.96 (s, 1H), 7.70 (s, 1H), 7.45-7.55 (m, 2H), 6.48 (td, J = 3.3, 0.9 Hz, 1H), 6.30 (t, J = 6.0 Hz, 1H), 4.60 (d, J = 6.0 Hz, 2H), 4.16 (d, J = 17.4 Hz, 1H), 3.72 (d, J = 17.4 Hz, 1H), 3.40 (t, J = 8.7 Hz, 2H), 2.91 (td, J = 8.7, 3.3 Hz, 2H). |
| 2-509 | (A) δ 8.07 (s, 2H), 7.97 (s, 1H), 7.66 (s, 1H), 7.4-7.55 (m, 2H), 7.38 (t, J = 6.0 Hz, 1H), 4.45-4.6 (m, 2H), 4.17 and 4.16 (d, J = 17.4 Hz, 1H), 3.63 (d, J = 17.4 Hz, 1H), 2.9-3.1 (m, 2H), 2.6-2.75 (m, 1H), 2.4-2.55 (m, 1H), 3.4-3.3 and 2.4-2.55 (m, 1H), 1.35-2.25 (m, 6H). |
| 2-510 | (A) δ 8.07 (s, 2H), 7.96 (s, 1H), 7.66 (s, 1H), 7.5-7.65 (m, 1H), 7.3-7.4 (m, 1H), 6.47 (t, J = 6.0 Hz, 1H), 4.45-4.6 (m, 2H), 4.17 (d, J = 17.4 Hz, 1H), 3.74 (d, J = 17.4 Hz, 1H), 3.1-3.25 (m, 1H), 2.65-2.85 (m, 2H), 2.3-2.45 (m, 2H), 1.75-2.05 (m, 3H), 1.35-1.65 (m, 3H). |
| 2-511 | (A) δ 8.07 (s, 2H), 7.97 (s, 1H), 7.65 (d, J = 1.8 Hz, 1H), 7.4-7.55 (m, 2H), 6.92 (t, J = 6.0 Hz, 1H), 4.4-4.6 (m, 2H), 4.20 (d, J = 17.4 Hz, 1H), 3.75 (d, J = 17.4 Hz, 1H), 3.4-3.55 (m, 1H), 2.9-3.15 (m, 3H), 2.36 (dd, J = 8.4, 7.2 Hz, 1H), 1.95-2.2 (m, 3H), 1.7-1.9 (m, 2H), 1.4-1.65 (m, 1H). |
| 2-512 | (A) δ 7.6-7.7 (m, 3H), 7.45-7.55 (m, 2H), 7.35-7.45 (m, 1H), 7.16 (t, J = 6.0 Hz, 1H), 4.55 (d, J = 6.0 Hz, 2H), 4.05 (d, J = 17.4 Hz, 1H), 4.02 (s, 2H), 3.68 (d, J = 17.4 Hz, 1H), 3.11 (s, 3H), 2.12 (s, 3H). |
| 2-513 | (A) δ 8.07 (s, 2H), 7.97 (s, 1H), 7.67 (d, J = 1.8 Hz, 1H), 7.4-7.6 (m, 2H), 7.00 (t, J = 6.3 Hz, 1H), 4.56 and 4.50 (d, J = 6.3 Hz, 2H), 4.20 and 4.14 (s, 2H), 4.08 and 4.04 (s, 2H), 4.04 (d, J = 17.4 Hz, 1H), 3.74 (d, J = 17.4 Hz, 1H), 3.42 (s, 3H), 3.09 and 2.96 (s, 3H). |

TABLE 16-continued

| No. | $^1$H NMR |
|---|---|
| 2-515 | (A) δ 7.67 (d, J = 1.5 Hz, 1H), 7.64 (s, 2H), 7.45-7.55 (m, 1H), 7.35-7.45 (m, 1H), 6.59 (bs, 1H), 4.52 (d, J = 6.0 Hz, 2H), 4.06 (d, J = 17.4 Hz, 1H), 3.94 (s, 2H), 3.74 (s, 3H), 3.67 (d, J = 17.4 Hz, 1H), 2.72 (sep, J = 3.6 Hz, 1H), 0.7-0.8 (m, 2H), 0.6-0.7 (m, 2H). |
| 2-516 | (A) δ 7.66 (d, J = 1.2 Hz, 1H), 7.63 (s, 2H), 7.45-7.55 (m, 1H), 7.35-7.45 (m, 1H), 6.77 and 6.49 (bs, 1H), 4.91 (sep, J = 6.3 Hz, 1H), 4.54 (d, J = 6.0 Hz, 2H), 4.05 (d, J = 17.4 Hz, 1H), 3.93 (s, 2H), 3.66 (d, J = 17.4 Hz, 1H), 2.97 (s, 3H), 1.24 (d, J = 6.3 Hz, 6H). |
| 2-517 | (A) δ 7.66 (s, 1H), 7.64 (s, 2H), 7.45-7.55 (m, 1H), 7.35-7.45 (m, 1H), 6.65 (bs, 1H), 4.53 (d, J = 6.0 Hz, 2H), 4.07 (d, J = 17.4 Hz, 1H), 4.07 (s, 2H), 3.67 (d, J = 17.4 Hz, 1H), 3.08 (s, 3H), 2.35 (s, 3H). |
| 2-518 | (A) δ 7.66 (d, J = 1.8 Hz, 1H), 7.64 (s, 2H), 7.5-7.55 (m, 1H), 7.35-7.45 (m, 1H), 7.02 (t, J = 6.3 Hz, 1H), 4.55 (d, J = 6.3 Hz, 2H), 4.07 (d, J = 17.4 Hz, 1H), 3.84 (s, 2H), 3.69 (d, J = 17.4 Hz, 1H), 2.94 (s, 3H), 2.91 (s, 3H). |
| 2-520 | (A) δ 7.77 (t, J = 6.3 Hz, 1H), 7.67 (t, J = 1.8 Hz, 1H), 7.63 (s, 2H), 7.52 and 7.49 (d, J = 1.8 Hz, 1H), 7.42 and 7.40 (s, 1H), 4.54 (d, J = 6.3 Hz, 2H), 4.06 (d, J = 17.4 Hz, 1H), 3.68 (d, J = 17.4 Hz, 1H), 3.10 (q, J = 7.2 Hz, 1H), 2.38 (s, 3H), 1.41 (bs, 1H), 1.31 (d, J = 7.2 Hz, 3H). |
| 2-521 | (A) δ 7.67 (t, J = 1.8 Hz, 1H), 7.63 (s, 2H), 7.52 and 7.49 (d, J = 1.8 Hz, 1H), 7.42 and 7.40 (s, 1H), 6.70 (bs, 1H), 4.78 (bs, 1H), 4.55 (dd, J = 15.9, 6.3 Hz, 1H), 4.47 (dd, J = 15.9, 6.3 Hz, 1H), 4.06 (d, J = 17.4 Hz, 1H), 3.73 (s, 3H), 3.67 (d, J = 17.4 Hz, 1H), 2.79 (s, 3H), 1.36 (d, J = 7.2 Hz, 3H). |
| 2-522 | (A) δ 8.07 (s, 2H), 7.97 (s, 1H), 7.70 (s, 1H), 7.55 (d, J = 7.8 Hz, 1H), 7.39 (d, J = 7.8 Hz, 1H), 7.24 (t, J = 6.0 Hz, 1H), 4.98 (dd, J = 11.1, 5.7 Hz, 1H), 4.61 (dd, J = 15.3, 6.0 Hz, 1H), 4.50 (dd, J = 15.3, 6.0 Hz, 1H), 4.11 (d, J = 17.7 Hz, 1H), 3.72 (d, J = 17.7 Hz, 1H), 3.33 (dd, J = 17.7, 11.1 Hz, 1H), 3.22 (dd, J = 17.7, 5.7 Hz, 1H), 2.02 (s, 3H). |
| 2-523 | (A) δ 7.6-7.8 (m, 4H), 7.45-7.55 (m, 1H), 7.35-7.45 (m, 1H), 6.89 (bs, 1H), 5.78 (bs, 1H), 4.53 (d, J = 6.3 Hz, 2H), 4.05 (d, J = 17.4 Hz, 1H), 3.66 (d, J = 17.4 Hz, 1H), 3.25 (s, 2H). |
| 2-524 | (A) δ 8.06 (s, 2H), 7.96 (s, 1H), 7.55 (d, J = 1.8 Hz, 1H), 7.35-7.5 (m, 1H), 7.15-7.35 (m, 2H), 5.18 (bs, 2H), 4.40 (d, J = 6.0 Hz, 2H), 4.17 (d, J = 17.4 Hz, 1H), 3.72 (d, J = 17.4 Hz, 1H), 3.05 (s, 3H). |
| 2-525 | (A) δ 7.64 (s, 1H), 7.63 (s, 2H), 7.35-7.5 (m, 2H), 7.17 (bs, 1H), 5.00 (s, 2H), 4.50 (d, J = 6.0 Hz, 2H), 4.05 (d, J = 17.4 Hz, 1H), 3.97 (q, J = 7.2 Hz, 2H), 3.67 (d, J = 17.4 Hz, 1H), 3.09 (s, 2H), 1.23 (t, J = 7.2 Hz, 3H). |
| 2-529 | (A) δ 8.11 (d, J = 1.8 Hz, 1H), 8.08 (s, 2H), 7.97 (s, 1H), 7.62 (dd, J = 8.4, 2.1 Hz, 1H), 7.45 (d, J = 8.4 Hz, 1H), 6.27 (t, J = 5.7 Hz, 1H), 4.48 (d, J = 6.3 Hz, 2H), 4.16 (d, J = 17.1 Hz, 1H), 3.72 (d, J = 17.1 Hz, 1H), 2.45-2.6 (m, 4H), 2.01 (d, J = 2.4 Hz, 1H). |
| 2-530 | (A) δ 8.08 (s, 2H), 7.98 (s, 1H), 7.75 (d, J = 8.4 Hz, 2H), 7.58 (d, J = 8.4 Hz, 2H), 6.2-6.35 (m, 2H), 4.21 (d, J = 17.4 Hz, 1H), 3.76 (d, J = 17.4 Hz, 1H), 2.4-2.65 (m, 4H), 2.02 (t, J = 2.4 Hz, 1H). |
| 2-535 | (A) δ 8.10 (d, J = 1.2 Hz, 1H), 8.06 (s, 2H), 7.97 (s, 1H), 7.76 (s, 1H), 7.5-7.6 (m, 2H), 7.32 (d, J = 1.2 Hz, 1H), 7.05-7.1 (m, 1H), 6.36 (t, J = 6.0 Hz, 1H), 4.70 (d, J = 6.0 Hz, 2H), 4.17 (d, J = 17.4 Hz, 1H), 3.72 (d, J = 17.4 Hz, 1H). |
| 2-536 | (A) δ 8.47 (dd, J = 4.8, 2.1 Hz, 1H), 8.15 (dd, J = 7.8, 2.1 Hz, 1H), 7.95 (s, 1H), 7.84 (s, 1H), 7.79 (s, 1H), 7.73 (d, J = 1.5 Hz, 1H), 7.59 (d, J = 8.1 Hz, 1H), 7.55 (dd, J = 8.1, 1.5 Hz, 1H), 7.35 (dd, J = 7.8, 4.8 Hz, 1H), 7.10 (t, J = 6.0 Hz, 1H), 4.76 (d, J = 6.0 Hz, 2H), 4.11 (d, J = 17.4 Hz, 1H), 3.70 (d, J = 17.4 Hz, 1H). |
| 2-537 | (A) δ 8.45-8.55 (m, 1H), 8.1-8.2 (m, 2H), 8.03 (s, 1H), 7.82 (s, 1H), 7.74 (s, 1H), 7.5-7.7 (m, 2H), 7.3-7.4 (m, 1H), 7.10 (bs, 1H), 4.77 (d, J = 6.3 Hz, 2H), 4.11 (d, J = 17.4 Hz, 1H), 3.69 (d, J = 17.4 Hz, 1H). |
| 2-538 | (A) δ 8.45-8.5 (m, 1H), 8.15-8.2 (m, 1H), 7.91 (s, 1H), 7.80 (s, 1H), 7.75 (s, 1H), 7.69 (s, 1H), 7.61 (s, 2H), 7.3-7.4 (m, 1H), 7.14 (bs, 1H), 4.76 (d, J = 6.0 Hz, 2H), 4.11 (d, J = 17.4 Hz, 1H), 3.70 (d, J = 17.4 Hz, 1H). |
| 3-003 | (A) δ 7.63 (d, J = 8.1 Hz, 2H), 7.51 (s, 2H), 7.42 (s, 1H), 7.33 (d, J = 8.1 Hz, 2H), 5.19 (bs, 1H), 4.3-4.5 (m, 3H), 3.69 (d, J = 17.4 Hz, 1H), 3.6-3.8 (m, 4H). |
| 3-006 | (A) δ 8.26 (s, 1H), 7.97 (d, J = 8.1 Hz, 1H), 7.75 (d, J = 8.1 Hz, 1H), 7.64 (s, 2H), 5.31 (t, J = 6.0 Hz, 1H), 4.60 (d, J = 6.0 Hz, 2H), 4.11 (d, J = 17.4 Hz, 1H), 3.71 (d, J = 17.4 Hz, 1H), 1.42 (s, 9H). |
| 3-007 | (A) δ 7.4-7.7 (m, 5H), 5.49 (t, J = 6.3 Hz, 1H), 4.4-4.55 (m, 4H), 4.06 (d, J = 17.3 Hz, 1H), 3.67 (d, J = 17.3 Hz, 1H). |
| 3-008 | (A) δ 7.85 (s, 1H), 7.35-7.6 (m, 5H), 5.55 (t, J = 6.9 Hz, 1H), 4.4-4.55 (m, 4H), 4.05 (d, J = 17.4 Hz, 1H), 3.67 (d, J = 17.4 Hz, 1H). |

TABLE 16-continued

| No. | ¹H NMR |
|---|---|
| 3-009 | (A) δ 7.65 (d, J = 8.4 Hz, 2H), 7.64 (s, 2H), 7.36 (d, J = 8.4 Hz, 2H), 5.38 (d, J = 7.8 Hz, 1H), 4.8-4.9 (m, 1H), 4.35-4.5 (m, 2H), 4.07 (d, J = 17.1 Hz, 1H), 3.67 (d, J = 17.1 Hz, 1H), 1.50 (d, J = 7.2 Hz, 3H). |
| 3-010 | (A) δ 7.55-7.7 (m, 3H), 7.4-7.55 (m, 2H), 5.39 (d, J = 6.0 Hz, 1H), 4.69 (d, J = 2.4 Hz, 2H), 4.47 (d, J = 6.0 Hz, 2H), 4.06 (d, J = 17.3 Hz, 1H), 3.67 (d, J = 17.3 Hz, 1H), 2.48 (t, J = 2.4 Hz, 1H). |
| 3-011 | (A) δ 7.67 (s, 1H), 7.63 (s, 2H), 7.4-7.55 (m, 2H), 5.92 (bs, 1H), 4.56 (d, J = 6.0 Hz, 2H), 4.05 (d, J = 17.4 Hz, 1H), 3.66 (d, J = 17.4 Hz, 1H), 2.34 (s, 3H). |
| 3-012 | (A) δ 7.67 (s, 1H), 7.63 (s, 2H), 7.4-7.55 (m, 2H), 5.93 (bs, 1H), 4.55 (d, J = 6.3 Hz, 2H), 4.06 (d, J = 17.4 Hz, 1H), 3.67 (d, J = 17.4 Hz, 1H), 2.92 (q, J = 7.5 Hz, 2H), 1.29 (t, J = 7.5 Hz, 3H). |
| 3-013 | (A) δ 8.08 (s, 2H), 7.98 (s, 1H), 7.88 (d, J = 1.8 Hz, 1H), 7.55-7.65 (m, 1H), 7.45-7.55 (m, 1H), 5.89 (t, J = 6.0 Hz, 1H), 4.56 (d, J = 6.0 Hz, 2H), 4.17 (d, J = 17.4 Hz, 1H), 3.73 (d, J = 17.4 Hz, 1H), 2.37 (s, 3H). |
| 3-014 | (A) δ 8.09 (s, 2H), 7.96 (s, 1H), 7.65 (d, J = 8.4 Hz, 2H), 7.37 (d, J = 8.4 Hz, 2H), 4.7-4.9 (m, 2H), 4.19 (d, J = 17.4 Hz, 1H), 3.74 (d, J = 17.4 Hz, 1H), 1.41 (bs, 12H). |
| 3-015 | (A) δ 8.08 (s, 2H), 7.95 (s, 1H), 7.64 (d, J = 8.4 Hz, 2H), 7.36 (d, J = 8.4 Hz, 2H), 4.85 (bs, 1H), 4.79 (bs, 1H), 4.19 (d, J = 17.1 Hz, 1H), 3.74 (d, J = 17.1 Hz, 1H), 1.41 (bs, 12H). |
| 4-002 | (A) δ 7.62 (d, J = 8.1 Hz, 2H), 7.51 (d, J = 1.5 Hz, 2H), 7.42 (t, J = 1.5 Hz, 1H), 7.36 (d, J = 8.1 Hz, 2H), 4.8-4.9 (m, 1H), 4.66 (d, J = 5.7 Hz, 1H), 4.27 (bs, 1H), 4.07 (d, J = 17.4 Hz, 1H), 3.68 (d, J = 17.4 Hz, 1H), 3.1-3.25 (m, 2H), 1.44 (d, J = 6.9 Hz, 3H), 1.07 (d, J = 6.9 Hz, 3H). |
| 4-003 | (A) δ 7.60 (d, J = 8.1 Hz, 2H), 7.50 (d, J = 1.5 Hz, 2H), 7.42 (t, J = 1.5 Hz, 1H), 7.36 (d, J = 8.1 Hz, 2H), 4.75-4.85 (m, 2H), 4.25-4.35 (m, 1H), 4.06 (d, J = 17.4 Hz, 1H), 3.75-3.9 (m, 1H), 3.68 (d, J = 17.4 Hz, 1H), 1.41 (d, J = 6.3 Hz, 3H), 1.08 and 1.06 (d, J = 6.3 Hz, 6H). |
| 4-004 | (A) δ 7.63 (d, J = 8.1 Hz, 2H), 7.50 (d, J = 1.5 Hz, 2H), 7.42 (t, J = 1.5 Hz, 1H), 7.38 (d, J = 8.1 Hz, 2H), 4.8-4.9 (m, 1H), 4.65-4.75 (m, 2H), 4.07 (d, J = 17.4 Hz, 1H), 3.68 (d, J = 17.4 Hz, 1H), 3.55-3.6 (m, 2H), 3.45-3.55 (m, 2H), 1.46 (d, J = 6.9 Hz, 3H). |
| 4-007 | (A) δ 7.69 (d, J = 1.5 Hz, 1H), 7.52 (dd, J = 8.1, 1.5 Hz, 1H), 7.45-7.55 (m, 3H), 7.42 (t, J = 1.5 Hz, 1H), 7.10 (s, 1H), 6.20 (t, J = 6.3 Hz, 1H), 4.57 (d, J = 6.3 Hz, 2H), 4.05 (d, J = 17.4 Hz, 1H), 3.71 (s, 3H), 3.66 (d, J = 17.4 Hz, 1H). |
| 4-009 | (A) δ 7.89 (s, 1H), 7.4-7.55 (m, 4H), 7.12 (d, J = 8.1 Hz, 1H), 5.97 (t, J = 6.0 Hz, 1H), 5.87 (t, J = 6.0 Hz, 1H), 4.05-4.3 (m, 2H), 4.07 (d, J = 17.4 Hz, 1H), 3.65-3.85 (m, 2H), 3.68 (d, J = 17.4 Hz, 1H). |
| 4-011 | (A) δ 7.69 (d, J = 1.5 Hz, 1H), 7.45-7.55 (m, 4H), 7.42 (t, J = 1.5 Hz, 1H), 4.96 (t, J = 6.3 Hz, 1H), 4.50 (d, J = 6.3 Hz, 2H), 4.04 (d, J = 17.4 Hz, 1H), 3.66 (d, J = 17.4 Hz, 1H), 2.92 (s, 6H). |
| 4-012 | (A) δ 7.68 (s, 1H), 7.4-7.55 (m, 5H), 5.57 (bs, 1H), 4.82 (bs, 1H), 4.53 (d, J = 6.0 Hz, 2H), 4.06 (d, J = 17.4 Hz, 1H), 3.66 (d, J = 17.4 Hz, 1H), 2.35-2.5 (m, 1H), 0.7-0.8 (m, 2H), 0.5-0.65 (m, 2H). |
| 4-013 | (A) δ 7.69 (d, J = 1.5 Hz, 1H), 7.45-7.55 (m, 4H), 7.43 (t, J = 1.5 Hz, 1H), 5.01 (bs, 1H), 4.68 (bs, 1H), 4.50 (d, J = 6.3 Hz, 2H), 4.05 (d, J = 17.4 Hz, 1H), 3.85-3.95 (m, 2H), 3.68 (d, J = 17.4 Hz, 1H). |
| 4-014 | (A) δ 7.2-7.55 (m, 6H), 6.14 (bs, 1H), 5.19 (bs, 2H), 4.22 (s, 2H), 4.03 (d, J = 17.3 Hz, 1H), 3.67 (d, J = 17.3 Hz, 1H). |
| 4-015 | (A) δ 7.25-7.65 (m, 5H), 5.70 (bs, 1H), 5.26 (bs, 1H), 4.28 (d, J = 6.3 Hz, 2H), 4.04 (d, J = 17.3 Hz, 1H), 3.67 (d, J = 17.3 Hz, 1H), 3.14 (t, J = 6.8 Hz, 2H), 1.04 (t, J = 6.8 Hz, 3H). |
| 4-016 | (A) δ 7.63 (s, 1H), 7.2-7.5 (m, 5H), 5.75 (t, J = 6.0 Hz, 1H), 5.30 (t, J = 7.2 Hz, 1H), 4.23 (d, J = 6.6 Hz, 2H), 4.04 (d, J = 17.7 Hz, 1H), 3.67 (d, J = 17.7 Hz, 1H), 3.14 (qui, J = 7.2 Hz, 2H), 1.06 (t, J = 7.2 Hz, 3H). |
| 4-017 | (A) δ 7.63 (s, 2H), 7.59 (d, J = 8.4 Hz, 2H), 7.35 (d, J = 2.4 Hz, 2H), 4.75-4.85 (m, 2H), 4.42 (t, J = 6.0 Hz, 1H), 4.06 (d, J = 17.4 Hz, 1H), 3.66 (d, J = 17.4 Hz, 1H), 3.1-3.2 (m, 2H), 1.42 (d, J = 6.6 Hz, 3H), 1.06 (t, J = 7.2 Hz, 3H). |
| 4-018 | (A) δ 7.66 (s, 1H), 7.63 (s, 2H), 7.45-7.55 (m, 2H), 4.93 (t, J = 6.0 Hz, 1H), 4.50 (d, J = 6.3 Hz, 2H), 4.05 (d, J = 17.4 Hz, 1H), 3.65 (d, J = 17.4 Hz, 1H), 3.26 (q, J = 7.2 Hz, 4H), 1.14 (t, J = 7.2 Hz, 6H). |
| 4-019 | (A) δ 8.24 (s, 1H), 7.89 (d, J = 8.4 Hz, 1H), 7.79 (d, J = 8.4 Hz, 1H), 7.63 (s, 2H), 5.27 (t, J = 6.0 Hz, 1H), 4.66 (d, J = 6.0 Hz, 2H), 4.10 (d, J = 17.4 Hz, 1H), 3.72 (d, J = 17.4 Hz, 1H), 3.24 (q, J = 7.2 Hz, 4H), 1.12 (t, J = 7.2 Hz, 6H). |
| 4-020 | (A) δ 7.6-7.7 (m, 3H), 7.50 (s, 2H), 4.69 (t, J = 6.3 Hz, 1H), 4.47 (d, J = 6.3 Hz, 2H), 4.05 (d, J = 17.3 Hz, 1H), 3.75-3.95 (m, 1H), 3.65 (d, J = 17.3 Hz, 1H), 1.14 (d, J = 6.6 Hz, 6H). |
| 4-021 | (A) δ 7.4-7.6 (m, 5H), 7.2-7.3 (m, 1H), 5.72 (t, J = 6.0 Hz, 1H), 5.14 (d, J = 7.8 Hz, 1H), 4.1-4.25 (m, 2H), 4.04 (d, J = 17.7 Hz, 1H), 3.7-3.85 (m, 1H), 3.67 (d, J = 17.7 Hz, 1H), 1.08 (d, J = 6.6 Hz, 6H). |

TABLE 16-continued

| No. | $^1$H NMR |
|---|---|
| 4-022 | (A) δ 7.65 (s, 2H), 7.60 (d, J = 8.1 Hz, 2H), 7.35 (d, J = 8.1 Hz, 2H), 4.8-4.9 (m, 1H), 4.75 (d, J = 7.2 Hz, 1H), 4.25 (d, J = 7.8 Hz, 1H), 4.05 (d, J = 17.1 Hz, 1H), 3.75-3.85 (m, 1H), 3.65 (d, J = 17.1 Hz, 1H), 1.40 (d, J = 6.6 Hz, 3H), 1.10 (d, J = 6.0 Hz, 3H), 1.05 (d, J = 6.0 Hz, 3H). |
| 4-023 | (A) δ 8.07 (s, 2H), 7.96 (s, 1H), 7.68 (d, J = 1.5 Hz, 1H), 7.45-7.55 (m, 2H), 5.62 (t, J = 1.5 Hz, 1H), 4.91 (bs, 1H), 4.52 (d, J = 6.0 Hz, 1H), 4.17 (d, J = 17.4 Hz, 1H), 3.73 (d, J = 17.4 Hz, 1H), 2.4-2.5 (m, 1H), 0.7-0.8 (m, 2H), 0.55-0.65 (m, 2H). |
| 4-025 | (A) δ 7.85 (d, J = 1.5 Hz, 1H), 7.63 (s, 2H), 7.55 (dd, J = 8.1, 1.5 Hz, 1H), 7.48 (d, J = 8.1 Hz, 1H), 5.62 (t, J = 6.2 Hz, 1H), 4.77 (s, 1H), 4.50 (d, J = 6.2 Hz, 1H), 4.05 (d, J = 17.1 Hz, 1H), 3.65 (d, J = 17.1 Hz, 1H), 2.4-2.55 (m, 1H), 0.7-0.85 (m, 2H), 0.55-0.65 (m, 2H). |
| 4-027 | (A) δ 8.09 (s, 1H), 7.96 (s, 2H), 7.65 (d, J = 8.4 Hz, 2H), 7.41 (d, J = 8.4 Hz, 2H), 5.21 (bs, 1H), 5.02 (bs, 1H), 4.69 (bs, 1H), 4.19 (d, J = 17.4 Hz, 1H), 3.73 (d, J = 17.4 Hz, 1H), 2.4-2.5 (m, 1H), 1.51 (d, J = 7.2 Hz, 3H), 0.7-0.8 (m, 2H), 0.55-0.6 (m, 2H). |
| 4-028 | (A) δ 7.65 (s, 2H), 7.60 (d, J = 8.4 Hz, 2H), 7.40 (d, J = 8.4 Hz, 2H), 5.25 (d, J = 7.5 Hz, 1H), 4.95-5.05 (m, 1H), 4.80 (bs, 1H), 4.05 (d, J = 17.4 Hz, 1H), 3.65 (d, J = 17.4 Hz, 1H), 2.4-2.5 (m, 1H), 1.50 (d, J = 6.9 Hz, 3H), 0.7-0.8 (m, 2H), 0.55-0.6 (m, 2H). |
| 4-029 | (A) δ 7.63 (s, 2H), 7.45-7.5 (m, 1H), 7.35-7.4 (m, 1H), 7.25-7.3 (m, 1H), 5.68 (bs, 1H), 5.29 (bs, 1H), 4.28 (d, J = 5.4 Hz, 2H), 4.04 (d, J = 17.3 Hz, 1H), 3.66 (d, J = 17.3 Hz, 1H), 2.92 (t, J = 6.6 Hz, 2H), 1.65 (sep, J = 6.6 Hz, 1H), 0.83 (d, J = 6.6 Hz, 6H). |
| 4-030 | (A) δ 7.15-7.5 (m, 6H), 5.75 (bs, 1H), 5.39 (bs, 1H), 4.30 (s, 2H), 4.04 (d, J = 17.3 Hz, 1H), 3.67 (d, J = 17.3 Hz, 1H), 2.99 (t, J = 5.6 Hz, 2H), 0.8-0.95 (m, 1H), 0.35-0.45 (m, 2H), 0.05-0.15 (m, 2H). |
| 4-031 | (A) δ 7.63 (s, 2H), 7.5-7.55 (m, 1H), 7.3-7.45 (m, 2H), 5.40 (bs, 1H), 5.05 (bs, 1H), 4.37 (d, J = 5.7 Hz, 2H), 4.05 (d, J = 17.3 Hz, 1H), 3.66 (d, J = 17.3 Hz, 1H), 3.01 (t, J = 6.0 Hz, 2H), 0.8-0.95 (m, 1H), 0.4-0.5 (m, 2H), 0.05-0.15 (m, 2H). |
| 4-032 | (A) δ 7.5-7.65 (m, 3H), 7.3-7.5 (m, 2H), 5.13 (bs, 1H), 4.92 (bs, 1H), 4.3-4.45 (m, 2H), 4.04 (d, J = 17.3 Hz, 1H), 4.11 (qui, J = 10.3 Hz, 1H), 3.65 (d, J = 17.3 Hz, 1H), 2.2-2.35 (m, 2H), 1.55-1.9 (m, 4H). |
| 4-033 | (A) δ 7.55-7.65 (m, 3H), 7.50 (s, 2H), 4.78 (t, J = 6.3 Hz, 1H), 4.48 (d, J = 6.3 Hz, 2H), 4.36 (t, J = 6.3 Hz, 1H), 4.05 (d, J = 17.3 Hz, 1H), 3.65 (d, J = 17.3 Hz, 1H), 2.97 (d, J = 6.3 Hz, 2H), 0.89 (s, 9H). |
| 4-034 | (A) δ 7.65-7.7 (m, 3H), 7.4-7.5 (m, 2H), 5.10 (t, J = 6.3 Hz, 1H), 4.63 (d, J = 6.3 Hz, 1H), 4.41 (d, J = 6.3 Hz, 2H), 4.04 (d, J = 17.3 Hz, 1H), 3.93 (qui, J = 6.8 Hz, 1H), 3.65 (d, J = 17.3 Hz, 1H), 1.85-2.0 (m, 2H), 1.5-1.65 (m, 4H), 1.2-1.4 (m, 2H). |
| 4-035 | (A) δ 7.64 (s, 2H), 7.61 (d, J = 8.4 Hz, 2H), 7.40 (d, J = 8.4 Hz, 2H), 4.6-5.0 (m, 3H), 4.06 (d, J = 17.1 Hz, 1H), 3.4-3.75 (m, 5H), 1.46 (d, J = 6.3 Hz, 3H). |
| 4-036 | (A) δ 7.15-7.7 (m, 5H), 5.7-6.15 (m, 2H), 4.27 (d, J = 6.3 Hz, 2H), 4.04 (d, J = 17.3 Hz, 1H), 3.65-3.85 (m, 2H), 3.66 (d, J = 17.3 Hz, 1H). |
| 4-039 | (A) δ 7.64 (d, J = 1.5 Hz, 2H), 7.56 (d, J = 8.1 Hz, 2H), 7.26 (dd, J = 8.4, 2.4 Hz, 2H), 5.65 (d, J = 7.2 Hz, 1H), 5.5-5.55 (m, 1H), 4.75-4.9 (m, 1H), 4.05 (d, J = 17.4 Hz, 1H), 3.6-3.75 (m, 3H), 1.35 (d, J = 6.9 Hz, 3H). |
| 4-040 | (A) δ 7.63 (s, 2H), 7.56 (s, 1H), 7.35-7.45 (m, 2H), 5.72 (bs, 1H), 5.38 (bs, 1H), 4.38 (d, J = 6.3 Hz, 2H), 4.05 (d, J = 17.3 Hz, 1H), 3.67 (d, J = 17.3 Hz, 1H), 3.43 (t, J = 5.1 Hz, 2H), 3.34 (t, J = 5.1 Hz, 2H), 3.32 (s, 3H). |
| 4-041 | (A) δ 7.45-7.7 (m, 5H), 4.85 (bs, 1H), 4.77 (bs, 1H), 4.48 (d, J = 6.0 Hz, 2H), 4.05 (d, J = 17.3 Hz, 1H), 3.65 (d, J = 17.3 Hz, 1H), 3.41 (q, J = 6.0 Hz, 2H), 2.63 (t, J = 6.0 Hz, 2H), 2.09 (s, 3H). |
| 4-043 | (A) δ 7.35-7.6 (m, 5H), 5.46 (bs, 1H), 5.30 (bs, 1H), 4.38 (d, J = 6.0 Hz, 2H), 4.05 (d, J = 17.3 Hz, 1H), 3.67 (d, J = 17.3 Hz, 1H), 3.35 (q, J = 6.3 Hz, 2H), 2.61 (t, J = 6.3 Hz, 2H), 2.50 (q, J = 7.1 Hz, 2H), 1.22 (t, J = 7.1 Hz, 3H). |
| 4-044 | (A) δ 7.63 (s, 2H), 7.52 (s, 1H), 7.3-7.45 (m, 2H), 5.75-5.9 (m, 2H), 4.33 (d, J = 6.3 Hz, 2H), 4.06 (d, J = 17.3 Hz, 1H), 3.69 (d, J = 17.3 Hz, 1H), 3.64 (t, J = 6.0 Hz, 2H), 3.16 (t, J = 6.0 Hz, 2H), 3.00 (q, J = 7.4 Hz, 2H), 1.34 (t, J = 7.4 Hz, 3H). |
| 4-045 | (A) δ 7.55-7.65 (m, 3H), 7.4-7.5 (m, 2H), 7.28 (bs, 1H), 5.64 (bs, 1H), 4.40 (d, J = 4.5 Hz, 2H), 4.05 (d, J = 17.3 Hz, 1H), 3.66 (d, J = 17.3 Hz, 1H), 3.26 (d, J = 5.1 Hz, 2H), 2.47 (t, J = 5.1 Hz, 2H), 2.25 (s, 6H). |
| 4-047 | (A) δ 7.63 (s, 2H), 7.56 (s, 1H), 7.35-7.5 (m, 2H), 5.59 (t, J = 6.0 Hz, 1H), 5.47 (t, J = 5.7 Hz, 1H), 4.39 (d, J = 6.0 Hz, 2H), 4.04 (d, J = 17.4 Hz, 1H), 3.96 (d, J = 5.7 Hz, 2H), 3.71 (s, 3H), 3.66 (d, J = 17.4 Hz, 1H). |
| 4-048 | (A) δ 7.64 (s, 2H), 7.5-7.55 (m, 1H), 7.3-7.45 (m, 2H), 5.85 (bs, 1H), 5.71 (bs, 1H), 4.35 (d, J = 6.0 Hz, 2H), 4.14 (q, J = 7.2 Hz, 2H), 4.05 (d, J = 17.4 Hz, 1H), 3.93 (d, J = 5.4 Hz, 2H), 3.67 (d, J = 17.4 Hz, 1H), 1.24 (t, J = 7.2 Hz, 3H). |

TABLE 16-continued

| No. | ¹H NMR |
|---|---|
| 4-049 | (A) δ 7.68 (t, J = 6.0 Hz, 1H), 7.63 (s, 2H), 7.61 (d, J = 1.5 Hz, 1H), 7.41 (dd, J = 8.4, 1.5 Hz, 1H), 7.19 (d, J = 8.4 Hz, 1H), 6.16 (t, J = 6.0 Hz, 1H), 5.94 (t, J = 6.0 Hz, 1H), 4.23 (d, J = 6.0 Hz, 2H), 4.02 (d, J = 17.1 Hz, 1H), 4.00 (d, J = 6.0 Hz, 2H), 3.75-3.9 (m, 2H), 3.64 (d, J = 17.1 Hz, 1H). |
| 4-050 | (A) δ 7.55-7.65 (m, 3H), 7.51 (s, 2H), 4.95 (bs, 1H), 4.50 (d, J = 6.3 Hz, 2H), 4.10 (bs, 1H), 4.05 (d, J = 17.3 Hz, 1H), 3.65 (d, J = 17.3 Hz, 1H), 2.56 (d, J = 4.8 Hz, 2H), 0.08 (s, 9H). |
| 4-051 | (A) δ 7.63 (s, 2H), 7.45-7.55 (m, 1H), 7.35-7.45 (m, 1H), 7.25-7.35 (m, 1H), 5.65-5.85 (m, 2H), 5.35 (bs, 1H), 5.0-5.2 (m, 2H), 4.29 (s, 2H), 4.04 (d, J = 17.3 Hz, 1H), 3.65-3.75 (m, 2H), 3.66 (d, J = 17.3 Hz, 1H). |
| 4-052 | (A) δ 7.45-7.75 (m, 6H), 6.48 (t, J = 6.0 Hz, 1H), 6.33 (t, J = 6.0 Hz, 1H), 4.41 (d, J = 6.0 Hz, 2H), 4.18 (d, J = 17.3 Hz, 1H), 3.93 (d, J = 17.3 Hz, 1H), 3.9-3.95 (m, 2H), 2.43 (s, 1H). |
| 4-053 | (D) δ 7.6-7.8 (m, 4H), 7.35-7.45 (m, 1H), 6.59 (t, J = 6.3 Hz, 1H), 6.45 (t, J = 6.0 Hz, 1H), 4.2-4.4 (m, 4H), 3.83 (dd, J = 6.0, 2.4 Hz, 2H), 2.92 (d, J = 2.4 Hz, 1H). |
| 4-055 | (A) δ 7.61 (s, 2H), 7.57 (d, J = 8.1 Hz, 2H), 7.32 (d, J = 8.1 Hz, 2H), 5.30 (d, J = 7.2 Hz, 1H), 5.05 (t, J = 5.4 Hz, 1H), 4.8-4.9 (m, 1H), 4.06 (d, J = 17.4 Hz, 1H), 3.85-3.95 (m, 2H), 3.67 (d, J = 17.4 Hz, 1H), 2.18 (t, J = 2.4 Hz, 1H), 1.40 (d, J = 6.6 Hz, 3H). |
| 4-056 | (A) δ 7.63 (s, 3H), 7.47 (d, J = 6.0 Hz, 2H), 5.25 (t, J = 6.0 Hz, 1H), 4.49 (d, J = 6.0 Hz, 2H), 4.10 (d, J = 2.4 Hz, 2H), 4.05 (d, J = 17.3 Hz, 1H), 3.67 (d, J = 17.3 Hz, 1H), 2.97 (s, 3H), 2.26 (t, J = 2.4 Hz, 1H). |
| 4-057 | (A) δ 7.63 (s, 2H), 7.0-7.45 (m, 8H), 5.89 (bs, 2H), 4.0-4.2 (m, 4H), 3.98 (d, J = 17.3 Hz, 1H), 3.59 (d, J = 17.3 Hz, 1H). |
| 4-058 | (A) δ 7.64 (s, 2H), 7.58 (d, J = 8.4 Hz, 2H), 7.15-7.35 (m, 7H), 4.8-4.95 (m, 1H), 4.76 (d, J = 6.6 Hz, 1H), 4.71 (t, J = 5.7 Hz, 1H), 4.33 (dd, J = 15.0, 5.7 Hz, 1H), 4.27 (dd, J = 15.0, 5.7 Hz, 1H), 4.05 (d, J = 17.1 Hz, 1H), 3.65 (d, J = 17.1 Hz, 1H), 1.40 (d, J = 6.6 Hz, 3H). |
| 4-062 | (A) δ 7.6-7.7 (m, 3H), 7.4-7.5 (m, 2H), 7.15-7.3 (m, 4H), 4.94 (t, J = 6.3 Hz, 1H), 4.80 (t, J = 6.0 Hz, 1H), 4.45 (d, J = 6.3 Hz, 2H), 4.31 (d, J = 6.0 Hz, 2H), 4.05 (d, J = 17.3 Hz, 1H), 3.65 (d, J = 17.3 Hz, 1H). |
| 4-063 | (A) δ 7.3-7.65 (m, 9H), 5.15 (t, J = 6.0 Hz, 1H), 5.04 (t, J = 6.0 Hz, 1H), 4.89 (d, J = 6.0 Hz, 2H), 4.40 (d, J = 6.0 Hz, 2H), 4.03 (d, J = 17.3 Hz, 1H), 3.64 (d, J = 17.3 Hz, 1H). |
| 4-064 | (A) δ 7.64 (s, 2H), 7.52 (s, 1H), 7.25-7.5 (m, 6H), 5.3-5.45 (m, 2H), 4.35 (d, J = 5.7 Hz, 2H), 4.32 (d, J = 5.7 Hz, 2H), 4.08 (d, J = 17.3 Hz, 1H), 3.64 (d, J = 17.3 Hz, 1H). |
| 4-065 | (A) δ 7.62 (s, 2H), 7.25-7.45 (m, 4H), 7.05-7.2 (m, 3H), 6.00 (bs, 1H), 5.83 (bs, 1H), 4.05-4.2 (m, 4H), 3.99 (d, J = 17.3 Hz, 1H), 3.62 (d, J = 17.3 Hz, 1H). |
| 4-066 | (A) δ 7.55-7.7 (m, 3H), 7.35-7.5 (m, 2H), 6.04 (d, J = 3.3 Hz, 1H), 5.84 (dd, J = 3.3, 1.2 Hz, 1H), 5.18 (t, J = 6.0 Hz, 1H), 4.97 (t, J = 5.7 Hz, 1H), 4.41 (d, J = 6.0 Hz, 2H), 4.25 (d, J = 5.7 Hz, 2H), 4.04 (d, J = 17.3 Hz, 1H), 3.64 (d, J = 17.3 Hz, 1H), 2.21 (s, 3H). |
| 4-067 | (A) δ 7.3-7.7 (m, 5H), 7.1-7.2 (m, 1H), 6.8-6.95 (m, 2H), 5.42 (bs, 2H), 4.25-4.5 (m, 4H), 4.03 (d, J = 17.3 Hz, 1H), 3.64 (d, J = 17.3 Hz, 1H). |
| 4-069 | (A) δ 8.45 (d, J = 4.5 Hz, 1H), 7.70 (s, 2H), 7.55-7.7 (m, 3H), 7.42 (s, 2H), 7.1-7.3 (m, 1H), 6.07 (bs, 1H), 5.93 (bs, 1H), 4.45-4.5 (m, 4H), 4.03 (d, J = 17.3 Hz, 1H), 3.64 (d, J = 17.3 Hz, 1H). |
| 4-070 | (A) δ 8.45 (d, J = 4.8 Hz, 1H), 7.55-7.75 (m, 5H), 7.37 (d, J = 8.1 Hz, 2H), 7.1-7.3 (m, 2H), 5.68 (t, J = 4.8 Hz, 1H), 5.38 (bs, 1H), 4.8-5.0 (m, 1H), 4.66 (dd, J = 16.7, 4.8 Hz, 1H), 4.40 (dd, J = 16.7, 4.8 Hz, 1H), 4.06 (d, J = 17.2 Hz, 1H), 3.66 (d, J = 17.2 Hz, 1H), 1.43 (d, J = 6.9 Hz, 3H). |
| 4-071 | (A) δ 8.38 (bs, 1H), 7.5-7.7 (m, 4H), 7.1-7.4 (m, 3H), 7.14 (s, 1H), 5.85-6.2 (m, 2H), 4.33 (d, J = 5.1 Hz, 2H), 4.27 (bs, 2H), 4.03 (d, J = 17.3 Hz, 1H), 3.66 (d, J = 17.3 Hz, 1H). |
| 4-072 | (A) δ 8.42 (d, J = 5.4 Hz, 1H), 7.55-7.7 (m, 4H), 7.3-7.45 (m, 2H), 7.05-7.2 (m, 2H), 5.77 (t, J = 6.3 Hz, 2H), 4.39 (d, J = 6.3 Hz, 2H), 4.30 (d, J = 5.7 Hz, 2H), 4.04 (d, J = 17.3 Hz, 1H), 3.66 (d, J = 17.3 Hz, 1H). |
| 4-074 | (A) δ 7.6-7.7 (m, 3H), 7.45-7.55 (m, 2H), 4.79 (t, J = 6.0 Hz, 1H), 4.51 (d, J = 6.0 Hz, 2H), 4.04 (d, J = 17.3 Hz, 1H), 3.65 (d, J = 17.3 Hz, 1H), 3.34 (t, J = 6.6 Hz, 4H), 1.8-2.0 (m, 4H). |
| 4-075 | (A) δ 7.63 (s, 2H), 7.60 (d, J = 8.4 Hz, 2H), 7.40 (d, J = 8.4 Hz, 2H), 5.0-5.1 (m, 1H), 4.41 (d, J = 7.2 Hz, 1H), 4.06 (d, J = 17.4 Hz, 1H), 3.66 (d, J = 17.4 Hz, 1H), 3.3-3.35 (m, 4H), 1.85-1.95 (m, 4H), 1.48 (d, J = 6.9 Hz, 3H). |
| 4-076 | (A) δ 7.63 (s, 3H), 7.48 (s, 2H), 5.11 (t, J = 6.0 Hz, 1H), 4.4-4.6 (m, 3H), 4.05 (d, J = 17.4 Hz, 1H), 3.72 (s, 3H), 3.66 (d, J = 17.4 Hz, 1H), 3.45-3.55 (m, 1H), 3.35-3.45 (m, 1H), 1.95-2.2 (m, 4H). |

TABLE 16-continued

| No. | ¹H NMR |
|---|---|
| 4-077 | (A) δ 7.6-7.7 (m, 3H), 7.55-7.65 (m, 2H), 6.99 (bs, 1H), 5.11 (t, J = 6.0 Hz, 1H), 4.35-4.65 (m, 3H), 4.06 (d, J = 17.4 Hz, 1H), 3.67 (d, J = 17.4 Hz, 1H), 3.43 (dt, J = 8.1, 2.7 Hz, 1H), 3.29 (q, J = 2.7 Hz, 1H), 2.76 (d, J = 4.8 Hz, 3H), 2.25-2.35 (m, 1H), 1.8-2.15 (m, 3H). |
| 4-078 | (A) δ 7.6-7.7 (m, 3H), 7.48 (s, 2H), 5.05 (t, J = 6.0 Hz, 1H), 4.49 (d, J = 6.0 Hz, 2H), 4.04 (d, J = 17.3 Hz, 1H), 3.65 (d, J = 17.3 Hz, 1H), 3.3-3.4 (m, 4H), 1.45-1.7 (m, 6H). |
| 4-080 | (A) δ 7.77 (s, 1H), 7.35-7.5 (m, 5H), 5.09 (bs, 1H), 4.49 (d, J = 5.7 Hz, 2H), 4.46 (s, 2H), 4.04 (d, J = 17.3 Hz, 1H), 3.66 (d, J = 17.3 Hz, 1H), 3.66 (t, J = 6.3 Hz, 2H), 3.04 (t, J = 6.3 Hz, 2H). |
| 4-081 | (A) δ 7.6-7.75 (m, 3H), 7.49 (s, 2H), 4.98 (t, J = 6.0 Hz, 1H), 4.51 (d, J = 6.0 Hz, 2H), 4.04 (d, J = 17.3 Hz, 1H), 3.68 (t, J = 4.8 Hz, 4H), 3.64 (d, J = 17.3 Hz, 1H), 2.60 (t, J = 4.8 Hz, 4H). |
| 4-082 | (A) δ 7.67 (s, 1H), 7.63 (s, 2H), 7.35-7.6 (m, 2H), 5.42 and 5.33 (bs, 1H), 5.45-5.55 (m, 2H), 4.05 (d, J = 17.4 Hz, 1H), 4.8-4.95 (m, 4H), 3.65 (d, J = 17.4 Hz, 1H), 2.65-2.85 (m, 4H). |
| 4-083 | (A) δ 7.35-7.7 (m, 5H), 5.32 (bs, 1H), 4.51 (d, J = 5.7 Hz, 2H), 4.04 (d, J = 17.4 Hz, 1H), 3.89 (t, J = 5.1 Hz, 4H), 3.64 (d, J = 17.4 Hz, 1H), 3.03 (t, J = 5.1 Hz, 4H). |
| 4-084 | (A) δ 7.63 (s, 2H), 7.60 (d, J = 8.7 Hz, 2H), 7.37 (d, J = 8.7 Hz, 2H), 4.5-5.05 (m, 1H), 4.68 (d, J = 6.6 Hz, 1H), 4.07 (d, J = 17.1 Hz, 1H), 3.6-3.75 (m, 5H), 2.55-2.6 (m, 4H), 1.47 (d, J = 7.2 Hz, 3H). |
| 4-085 | (A) δ 7.64 (s, 2H), 7.61 (d, J = 8.4 Hz, 2H), 7.40 (d, J = 8.4 Hz, 2H), 7.2-7.35 (m, 3H), 6.85-6.95 (m, 2H), 4.95-5.05 (m, 1H), 4.69 (d, J = 6.9 Hz, 1H), 4.05 (d, J = 17.4 Hz, 1H), 3.67 (d, J = 17.4 Hz, 1H), 3.56 (t, J = 4.5 Hz, 4H), 3.18 (t, J = 5.1 Hz, 4H), 1.50 (d, J = 6.9 Hz, 3H). |
| 4-086 | (A) δ 7.58 (d, J = 1.2 Hz, 1H), 7.55 (s, 2H), 7.35-7.5 (m, 2H), 4.51 (d, J = 6.0 Hz, 2H), 4.06 (d, J = 17.4 Hz, 1H), 3.97 (t, J = 7.2 Hz, 2H), 3.67 (d, J = 17.4 Hz, 1H), 2.55 (t, J = 8.1 Hz, 2H), 1.98 (tt, J = 8.1, 7.2 Hz, 2H). |
| 4-087 | (A) δ 7.72 (d, J = 1.8 Hz, 1H), 7.63 (s, 2H), 7.52 (dd, J = 8.4, 1.8 Hz, 1H), 7.16 (d, J = 8.4 Hz, 1H), 6.65 (s, 1H), 4.90 (s, 2H), 4.07 (d, J = 17.3 Hz, 1H), 3.67 (d, J = 17.3 Hz, 1H), 1.90 (s, 3H). |
| 4-088 | (A) δ 8.33 (t, J = 2.7 Hz, 1H), 7.67 (s, 1H), 7.4-7.55 (m, 5H), 4.59 (d, J = 6.0 Hz, 2H), 4.45 (t, J = 8.1 Hz, 2H), 4.06 (d, J = 8.1 Hz, 2H), 4.05 (d, J = 17.3 Hz, 1H), 3.68 (d, J = 17.3 Hz, 1H). |
| 4-089 | (A) δ 7.55-7.7 (m, 4H), 7.4-7.55 (m, 2H), 4.56 (d, J = 6.0 Hz, 2H), 4.26 (t, J = 6.9 Hz, 2H), 4.05 (d, J = 17.4 Hz, 1H), 3.66 (d, J = 17.4 Hz, 1H), 3.17 (t, J = 6.9 Hz, 2H). |
| 4-090 | (A) δ 7.61 (s, 3H), 7.0-7.45 (m, 7H), 6.8-6.95 (m, 1H), 6.22 (bs, 1H), 4.15-4.3 (m, 2H), 3.95 (d, J = 17.3 Hz, 1H), 3.55 (d, J = 17.3 Hz, 1H). |
| 4-093 | (A) δ 7.55-7.65 (m, 3H), 7.4-7.5 (m, 7H), 5.00 (t, J = 6.3 Hz, 1H), 4.44 (d, J = 6.3 Hz, 2H), 4.05 (d, J = 17.3 Hz, 1H), 3.65 (d, J = 17.3 Hz, 1H). |
| 4-094 | (A) δ 7.55-7.65 (m, 3H), 7.3-7.5 (m, 4H), 7.04 (s, 1H), 6.69 (d, J = 8.0 Hz, 2H), 5.61 (t, J = 6.3 Hz, 1H), 4.46 (d, J = 6.3 Hz, 2H), 4.02 (d, J = 17.3 Hz, 1H), 3.63 (d, J = 17.3 Hz, 1H). |
| 4-096 | (A) δ 7.4-7.7 (m, 6H), 6.24 (bs, 1H), 4.55 (d, J = 6.6 Hz, 2H), 4.05 (d, J = 17.3 Hz, 1H), 3.70 (s, 3H), 3.67 (d, J = 17.3 Hz, 1H). |
| 4-097 | (A) δ 7.6-7.7 (m, 3H), 7.4-7.5 (m, 2H), 6.32 (t, J = 6.3 Hz, 1H), 4.51 (d, J = 6.3 Hz, 2H), 4.05 (d, J = 17.3 Hz, 1H), 3.67 (s, 3H), 3.65 (d, J = 17.3 Hz, 1H), 3.10 (s, 3H). |
| 4-098 | (A) δ 7.69 (d, J = 1.5 Hz, 1H), 7.4-7.55 (m, 5H), 7.13 (bs, 1H), 6.24 (t, J = 6.3 Hz, 1H), 4.57 (d, J = 6.3 Hz, 2H), 4.06 (d, J = 17.3 Hz, 1H), 3.89 (q, J = 7.1 Hz, 2H), 3.67 (d, J = 17.3 Hz, 1H), 1.26 (t, J = 7.1 Hz, 3H). |
| 4-099 | (A) δ 7.68 (d, J = 1.5 Hz, 1H), 7.45-7.55 (m, 3H), 7.4-7.45 (m, 2H), 6.89 (t, J = 5.7 Hz, 1H), 4.51 (d, J = 6.0 Hz, 2H), 4.05 (d, J = 17.4 Hz, 1H), 3.67 (d, J = 17.3 Hz, 1H), 3.19 (s, 3H). |
| 4-100 | (A) δ 7.6-7.7 (m, 3H), 7.4-7.5 (m, 2H), 7.06 (bs, 1H), 6.6-6.7 (m, 1H), 5.21 (bs, 2H), 4.58 (d, J = 6.6 Hz, 1H), 4.50 (d, J = 6.6 Hz, 1H), 4.05 (d, J = 17.3 Hz, 1H), 3.67 (d, J = 17.3 Hz, 1H). |
| 4-101 | (A) δ 7.6-7.7 (m, 3H), 7.49 (s, 2H), 6.89 (bs, 1H), 4.49 (d, J = 6.8 Hz, 2H), 4.04 (d, J = 17.3 Hz, 1H), 3.64 (d, J = 17.3 Hz, 1H), 3.55 (q, J = 7.1 Hz, 2H), 1.15 (t, J = 7.1 Hz, 3H). |
| 4-102 | (A) δ 7.6-7.7 (m, 3H), 7.4-7.55 (m, 2H), 7.13 (t, J = 6.3 Hz, 1H), 4.46 (d, J = 6.3 Hz, 2H), 4.05 (d, J = 17.3 Hz, 1H), 3.66 (d, J = 17.3 Hz, 1H), 3.58 (s, 2H), 1.47 (s, 9H). |
| 4-103 | (A) δ 7.6-7.7 (m, 3H), 7.45-7.55 (m, 2H), 7.2-7.4 (m, 5H), 7.00 (t, J = 6.3 Hz, 1H), 4.69 (s, 2H), 4.53 (d, J = 6.3 Hz, 2H), 4.06 (d, J = 17.3 Hz, 1H), 3.67 (d, J = 17.3 Hz, 1H), 3.47 (s, 2H). |
| 4-104 | (A) δ 7.67 (d, J = 3.0 Hz, 1H), 7.4-7.55 (m, 5H), 6.57 (t, J = 6.0 Hz, 1H), 5.18 (d, J = 6.0 Hz, 1H), 4.53 (d, J = 6.0 Hz, 2H), 4.05 (d, J = 17.3 Hz, 1H), 3.67 (d, J = 17.3 Hz, 1H), 2.49 (s, 6H). |
| 4-105 | (A) δ 7.6-7.7 (m, 3H), 7.4-7.55 (m, 2H), 6.58 (t, J = 6.3 Hz, 1H), 5.30 (bs, 1H), 4.53 (d, J = 6.3 Hz, 2H), 4.06 (d, J = 17.3 Hz, 1H), 3.67 (d, J = 17.3 Hz, 1H), 2.52 (s, 6H). |

TABLE 16-continued

| No. | $^1$H NMR |
|---|---|
| 4-106 | (A) δ 7.64 (s, 2H), 7.61 (d, J = 8.4 Hz, 2H), 7.40 (d, J = 8.4 Hz, 2H), 4.9-5.1 (m, 1H), 4.59 (d, J = 6.3 Hz, 1H), 4.06 (d, J = 17.1 Hz, 1H), 3.66 (d, J = 17.1 Hz, 1H), 2.91 (s, 6H), 1.48 (d, J = 6.9 Hz, 3H). |
| 4-107 | (A) δ 7.6-7.7 (m, 3H), 7.4-7.55 (m, 2H), 6.61 (t, J = 6.3 Hz, 1H), 5.91 (bs, 1H), 4.53 (d, J = 6.3 Hz, 2H), 4.06 (d, J = 17.3 Hz, 1H), 3.66 (d, J = 17.3 Hz, 1H), 3.31 (bs, 1H), 1.08 (s, 9H). |
| 4-108 | (A) δ 7.55-7.7 (m, 3H), 7.4-7.5 (m, 2H), 6.59 (t, J = 6.0 Hz, 1H), 5.62 (bs, 1H), 4.51 (d, J = 6.0 Hz, 2H), 4.06 (d, J = 17.3 Hz, 1H), 3.68 (d, J = 17.3 Hz, 1H), 2.1-3.05 (m, 8H), 2.29 (s, 3H). |
| 4-110 | (A) δ 8.39 (bs, 1H), 7.99 (bs, 1H), 7.62 (s, 2H), 7.51 (s, 1H), 7.25-7.45 (m, 2H), 6.29 (d, J = 6.0 Hz, 1H), 4.39 (d, J = 6.0 Hz, 2H), 4.02 (d, J = 17.3 Hz, 1H), 3.64 (d, J = 17.3 Hz, 1H), 2.19 (t, J = 7.4 Hz, 2H), 1.63 (sxt, J = 7.4 Hz, 2H), 0.91 (t, J = 7.4 Hz, 3H). |
| 4-111 | (A) δ 8.65 (bs, 1H), 8.22 (bs, 1H), 7.62 (s, 2H), 7.50 (s, 1H), 7.2-7.4 (m, 2H), 6.44 (bs, 1H), 4.37 (d, J = 6.3 Hz, 2H), 4.01 (d, J = 17.3 Hz, 1H), 3.64 (d, J = 17.3 Hz, 1H), 2.49 (sep, J = 6.8 Hz, 1H), 1.11 (d, J = 6.8 Hz, 6H). |
| 4-113 | (A) δ 8.07 (s, 2H), 7.96 (s, 1H), 7.67 (s, 1H), 7.45-7.55 (m, 2H), 6.48 (bs, 1H), 6.34 (bs, 1H), 5.81 (bs, 1H), 4.52 (d, J = 6.0 Hz, 2H), 4.16 (d, J = 17.4 Hz, 1H), 3.78 (s, 3H), 3.73 (d, J = 17.4 Hz, 1H). |
| 4-114 | (E) δ 7.7-7.8 (m, 3H), 7.63 (d, J = 8.4 Hz, 1H), 7.49 (d, J = 8.4 Hz, 1H), 4.59 (s, 1H), 4.45 (s, 2H), 4.25 (d, J = 18.0 Hz, 1H), 3.99 (d, J = 18.0 Hz, 1H), 3.74 (s, 3H). |
| 4-116 | (A) δ 7.6-7.65 (m, 3H), 7.4-7.5 (m, 2H), 5.07 (bs, 1H), 4.44 (d, J = 6.0 Hz, 2H), 4.05 (d, J = 17.3 Hz, 1H), 3.65 (d, J = 17.3 Hz, 1H). |
| 4-118 | (A) δ 7.6-7.7 (m, 3H), 7.2-7.55 (m, 4H), 6.85-7.0 (m, 3H), 6.2-6.35 (m, 2H), 4.51 (d, J = 6.3 Hz, 2H), 4.04 (d, J = 17.3 Hz, 1H), 3.65 (d, J = 17.3 Hz, 1H), 3.12 (s, 3H). |
| 4-119 | (A) δ 7.6-7.7 (m, 3H), 7.35-7.5 (m, 2H), 7.0-7.1 (m, 2H), 6.7-6.8 (m, 2H), 6.41 (t, J = 6.3 Hz, 1H), 6.32 (bs, 1H), 5.68 (bs, 1H), 4.51 (d, J = 6.3 Hz, 2H), 4.04 (d, J = 17.3 Hz, 1H), 3.65 (d, J = 17.3 Hz, 1H), 2.27 (s, 3H). |
| 4-120 | (A) δ 8.07 (s, 2H), 7.97 (s, 1H), 7.45 (d, J = 1.8 Hz, 1H), 7.2-7.4 (m, 2H), 5.75 (bs, 1H), 5.31 (bs, 1H), 4.26 (d, J = 6.0 Hz, 2H), 4.15 (d, J = 17.4 Hz, 1H), 3.72 (d, J = 17.4 Hz, 1H), 3.1-3.2 (m, 2H), 1.06 (t, J = 7.2 Hz, 3H). |
| 4-121 | (A) δ 8.08 (s, 2H), 7.97 (s, 1H), 7.81 (d, J = 1.5 Hz, 1H), 7.54 (dd, J = 8.1, 1.5 Hz, 1H), 7.45 (d, J = 8.1 Hz, 1H), 5.06 (bs, 1H), 4.45-4.7 (m, 1H), 4.41 (s, 2H), 4.16 (d, J = 17.1 Hz, 1H), 3.71 (d, J = 17.1 Hz, 1H), 3.20 (q, J = 7.2 Hz, 2H), 1.12 (t, J = 7.2 Hz, 3H). |
| 4-122 | (A) δ 8.08 (s, 2H), 7.96 (s, 1H), 7.64 (d, J = 8.4 Hz, 2H), 7.39 (d, J = 8.4 Hz, 2H), 4.8-4.9 (m, 1H), 4.58 (bs, 1H), 4.18 (d, J = 17.4 Hz, 1H), 3.73 (d, J = 17.4 Hz, 1H), 3.17 (q, J = 7.2 Hz, 2H), 1.44 (d, J = 6.9 Hz, 3H), 1.08 (t, J = 7.2 Hz, 3H). |
| 4-123 | (A) δ 7.91 (d, J = 1.5 Hz, 1H), 7.73 (dd, J = 8.4, 1.5 Hz, 1H), 7.70 (s, 1H), 7.61 (d, J = 8.4 Hz, 1H), 7.45-7.55 (m, 2H), 5.59 (t, J = 6.3 Hz, 1H), 4.78 (s, 1H), 4.53 (d, J = 6.3 Hz, 2H), 4.10 (d, J = 17.4 Hz, 1H), 3.68 (d, J = 17.4 Hz, 1H), 2.4-2.5 (m, 1H), 0.7-0.85 (m, 2H), 0.55-0.65 (m, 2H). |
| 4-124 | (A) δ 8.07 (s, 2H), 7.97 (s, 1H), 7.88 (d, J = 1.8 Hz, 1H), 7.58 (dd, J = 8.1, 1.8 Hz, 1H), 7.49 (d, J = 8.1 Hz, 1H), 5.64 (t, J = 6.0 Hz, 1H), 4.78 (bs, 1H), 4.51 (d, J = 6.3 Hz, 2H), 4.16 (d, J = 17.1 Hz, 1H), 3.71 (d, J = 17.1 Hz, 1H), 2.4-2.55 (m, 1H), 0.7-0.85 (m, 2H), 0.55-0.65 (m, 2H). |
| 4-127 | (A) δ 8.17 (s, 2H), 8.06 (s, 1H), 7.61 (d, J = 1.5 Hz, 1H), 7.35-7.5 (m, 2H), 5.32 (t, J = 6.0 Hz, 1H), 4.99 (t, J = 5.4 Hz, 1H), 4.43 (d, J = 6.0 Hz, 2H), 4.16 (d, J = 17.4 Hz, 1H), 3.96 (dd, J = 5.4, 2.4 Hz, 2H), 3.72 (d, J = 17.4 Hz, 1H), 2.21 (t, J = 2.4 Hz, 1H). |
| 4-128 | (A) δ 8.07 (s, 2H), 7.97 (s, 1H), 7.76 (d, J = 1.5 Hz, 1H), 7.52 (dd, J = 8.1, 1.5 Hz, 1H), 7.38 (d, J = 8.1 Hz, 1H), 5.46 (t, J = 6.0 Hz, 1H), 5.13 (t, J = 5.4 Hz, 1H), 4.37 (d, J = 6.0 Hz, 2H), 4.16 (d, J = 17.1 Hz, 1H), 3.96 (dd, J = 5.4, 2.4 Hz, 2H), 3.72 (d, J = 17.1 Hz, 1H), 2.20 (t, J = 2.4 Hz, 1H). |
| 4-129 | (A) δ 8.08 (s, 2H), 7.96 (s, 1H), 7.64 (d, J = 8.4 Hz, 2H), 7.39 (d, J = 8.4 Hz, 2H), 4.85-4.95 (m, 1H), 4.75 (d, J = 6.6 Hz, 1H), 4.48 (t, J = 5.7 Hz, 1H), 4.18 (d, J = 17.1 Hz, 1H), 3.95 (dd, J = 5.4, 2.4 Hz, 2H), 3.73 (d, J = 17.1 Hz, 1H), 2.21 (d, J = 2.4 Hz, 1H), 1.45 (d, J = 6.9 Hz, 3H). |
| 4-130 | (A) δ 8.07 (s, 2H), 7.96 (s, 1H), 7.25-7.45 (m, 3H), 5.35 (t, J = 5.4 Hz, 1H), 4.93 (t, J = 6.0 Hz, 1H), 4.36 (d, J = 6.0 Hz, 2H), 4.15 (d, J = 17.4 Hz, 1H), 3.72 (d, J = 17.4 Hz, 1H), 3.16 (qd, J = 7.2, 5.4 Hz, 2H), 1.08 (t, J = 7.2 Hz, 3H). |
| 4-131 | (A) δ 7.95 (s, 1H), 7.84 (s, 1H), 7.79 (s, 1H), 7.66 (s, 1H), 7.49 (s, 2H), 4.86 (t, J = 6.0 Hz, 1H), 4.46 (d, J = 6.0 Hz, 2H), 4.37 (t, J = 6.0 Hz, 1H), 4.10 (d, J = 17.4 Hz, 1H), 3.68 (d, J = 17.4 Hz, 1H), 3.15-3.25 (m, 2H), 1.13 (t, J = 7.2 Hz, 3H). |

TABLE 16-continued

| No. | ¹H NMR |
|---|---|
| 4-132 | (A) δ 7.76 (d, J = 5.4 Hz, 2H), 7.55 (s, 1H), 7.3-7.45 (m, 2H), 5.39 (bs, 1H), 4.93 (bs, 1H), 4.34 (d, J = 6.0 Hz, 2H), 4.04 (d, J = 17.4 Hz, 1H), 3.66 (d, J = 17.4 Hz, 1H), 3.17 (qd, J = 7.2, 5.4 Hz, 2H), 1.09 (t, J = 7.2 Hz, 3H). |
| 4-133 | (A) δ 7.82 (s, 2H), 7.57 (d, J = 1.5 Hz, 1H), 7.35-7.5 (m, 2H), 5.29 (t, J = 6.3 Hz, 1H), 4.83 (t, J = 5.4 Hz, 1H), 4.38 (d, J = 6.3 Hz, 2H), 4.03 (d, J = 17.4 Hz, 1H), 3.65 (d, J = 17.4 Hz, 1H), 3.18 (qd, J = 7.2, 5.4 Hz, 2H), 1.10 (t, J = 7.2 Hz, 3H). |
| 4-134 | (A) δ 7.94 (s, 1H), 7.84 (s, 1H), 7.58 (s, 1H), 7.45-7.55 (m, 2H), 5.30 (t, J = 6.0 Hz, 1H), 4.83 (t, J = 5.4 Hz, 1H), 4.39 (t, J = 6.0 Hz, 2H), 4.10 (d, J = 17.4 Hz, 1H), 3.69 (d, J = 17.4 Hz, 1H), 3.19 (qd, J = 7.2, 5.4 Hz, 2H), 1.11 (t, J = 7.2 Hz, 3H). |
| 4-136 | (A) δ 7.93 (s, 1H), 7.85 (s, 1H), 7.83 (s, 1H), 7.56 (d, J = 8.1 Hz, 1H), 7.50 (d, J = 8.1 Hz, 1H), 4.82 (bs, 1H), 4.45 (d, J = 6.0 Hz, 2H), 4.2-4.3 (m, 1H), 4.10 (d, J = 17.4 Hz, 1H), 3.67 (d, J = 17.4 Hz, 1H), 3.15-3.3 (m, 2H), 1.14 (t, J = 7.2 Hz, 3H). |
| 4-137 | (A) δ 8.07 (s, 3H), 7.96 (s, 1H), 7.60 (dd, J = 7.8, 1.8 Hz, 1H), 7.43 (d, J = 7.8 Hz, 1H), 4.97 (t, J = 6.3 Hz, 1H), 4.44 (t, J = 5.8 Hz, 1H), 4.36 (d, J = 6.3 Hz, 2H), 4.15 (d, J = 17.4 Hz, 1H), 3.71 (d, J = 17.4 Hz, 1H), 3.21 (qd, J = 7.2, 5.8 Hz, 2H), 1.13 (t, J = 7.2 Hz, 3H). |
| 4-138 | (A) δ 7.97 (s, 1H), 7.83 (s, 1H), 7.80 (s, 1H), 7.64 (d, J = 8.1 Hz, 2H), 7.39 (d, J = 8.1 Hz, 2H), 4.87 (qui, J = 7.2 Hz, 1H), 4.50 (d, J = 7.2 Hz, 1H), 4.12 (d, J = 17.4 Hz, 1H), 3.70 (d, J = 17.4 Hz, 1H), 3.18 (qui, J = 7.2 Hz, 2H), 1.46 (d, J = 7.2 Hz, 3H), 1.08 (t, J = 7.2 Hz, 3H). |
| 4-139 | (A) δ 7.76 (d, J = 5.4 Hz, 2H), 7.59 (dd, J = 8.7, 1.5 Hz, 2H), 7.35 (d, J = 8.7 Hz, 2H), 4.85 (bs, 1H), 4.84 (qui, J = 4.8 Hz, 1H), 4.46 (bs, 1H), 4.06 (d, J = 17.4 Hz, 1H), 3.67 (d, J = 17.4 Hz, 1H), 3.15 (qd, J = 7.2, 5.4 Hz, 2H), 1.42 (d, J = 4.8 Hz, 3H), 1.07 (t, J = 7.2 Hz, 3H). |
| 4-140 | (A) δ 8.08 (s, 2H), 7.97 (s, 1H), 7.74 (d, J = 8.4 Hz, 2H), 7.58 (d, J = 8.4 Hz, 2H), 6.14 (d, J = 8.4 Hz, 1H), 4.85 (d, J = 8.4 Hz, 1H), 4.4-4.55 (m, 1H), 4.20 (d, J = 17.4 Hz, 1H), 3.76 (d, J = 17.4 Hz, 1H), 3.2-3.35 (m, 2H), 1.17 (t, J = 7.2 Hz, 3H). |
| 4-141 | (A) δ 8.08 (s, 2H), 7.95 (s, 1H), 7.64 (d, J = 8.4 Hz, 2H), 7.40 (d, J = 8.4 Hz, 2H), 5.21 (d, J = 7.5 Hz, 1H), 4.95-5.05 (m, 1H), 4.70 (bs, 1H), 4.18 (d, J = 17.4 Hz, 1H), 3.73 (d, J = 17.4 Hz, 1H), 2.4-2.5 (m, 1H), 1.50 (d, J = 6.6 Hz, 3H), 0.7-0.8 (m, 2H), 0.55-0.6 (m, 2H). |
| 4-142 | (A) δ 7.94 (s, 1H), 7.84 (s, 1H), 7.64 (d, J = 8.4 Hz, 2H), 7.41 (d, J = 8.4 Hz, 2H), 5.15-5.2 (m, 1H), 4.95-5.05 (m, 1H), 4.6-4.7 (m, 1H), 4.16 (d, J = 17.1 Hz, 1H), 3.69 (d, J = 17.1 Hz, 1H), 2.4-2.5 (m, 1H), 1.51 (d, J = 6.9 Hz, 3H), 0.75-0.8 (m, 2H), 0.55-0.6 (m, 2H). |
| 4-145 | (A) δ 8.45 (s, 1H), 8.01 (s, 1H), 7.4-7.55 (m, 5H), 5.83 (t, J = 6.0 Hz, 1H), 4.54 (d, J = 6.0 Hz, 2H), 4.05 (d, J = 17.4 Hz, 1H), 3.67 (d, J = 17.4 Hz, 1H), 3.08 (s, 3H), 3.03 (s, 3H). |
| 4-146 | (A) δ 8.08 (s, 2H), 7.98 (s, 1H), 7.90 (s, 1H), 7.68 (t, J = 5.8 Hz, 1H), 7.61 (dd, J = 8.1, 1.5 Hz, 1H), 7.48 (d, J = 8.1 Hz, 1H), 4.51 (d, J = 5.8 Hz, 2H), 4.17 (d, J = 17.4 Hz, 1H), 3.72 (d, J = 17.4 Hz, 1H), 3.24 (s, 3H), 3.05 (s, 3H). |
| 4-147 | (A) δ 8.07 (s, 2H), 7.96 (s, 1H), 7.86 (t, J = 1.8 Hz, 1H), 7.61 (d, J = 7.8 Hz, 1H), 7.48 (d, J = 7.8 Hz, 1H), 6.64 (t, J = 6.0 Hz, 1H), 4.35-4.6 (m, 3H), 4.16 (d, J = 17.4 Hz, 1H), 3.71 (d, J = 17.4 Hz, 1H), 3.25-3.5 (m, 2H), 2.55-2.7 (m, 1H), 2.05-2.15 (m, 1H), 1.43 (d, J = 6.3 Hz, 3H). |
| 5-002 | (A) δ 8.75 (d, J = 2.1 Hz, 1H), 8.00 (dd, J = 8.1, 2.1 Hz, 1H), 7.65 (s, 2H), 7.36 (d, J = 8.1 Hz, 1H), 6.82 (bs, 1H), 6.20 (d, J = 5.4 Hz, 2H), 4.09 (d, J = 17.1 Hz, 1H), 3.71 (d, J = 17.1 Hz, 1H), 1.45-1.5 (m, 1H), 0.95-1.05 (m, 2H), 0.75-0.85 (m, 2H). |
| 5-003 | (A) δ 8.52 (s, 1H), 7.61 (s, 2H), 7.51 (d, J = 1.2 Hz, 2H), 6.96 (bs, 1H), 4.62 (d, J = 6.3 Hz, 2H), 4.01 (d, J = 17.1 Hz, 1H), 3.62 (d, J = 17.1 Hz, 1H), 1.35-1.45 (m, 1H), 0.9-0.95 (m, 2H), 0.7-0.8 (m, 2H). |
| 5-006 | (A) δ 8.77 (s, 1H), 8.01 (dt, J = 8.1, 2.4 Hz, 1H), 7.94 (d, J = 6.9 Hz, 1H), 7.50 (d, J = 1.5 Hz, 2H), 7.43 (t, J = 1.8 Hz, 1H), 7.33 (d, J = 8.1 Hz, 1H), 5.15-5.25 (m, 1H), 4.08 (d, J = 17.7 Hz, 1H), 3.69 (d, J = 17.7 Hz, 1H), 3.26 (d, J = 16.5 Hz, 1H), 3.19 (d, J = 16.5 Hz, 1H), 2.13 (d, J = 1.5 Hz, 3H), 1.50 (d, J = 6.9 Hz, 3H). |
| 5-007 | (A) δ 8.75 (d, J = 2.1 Hz, 1H), 8.04 (dd, J = 8.1, 2.1 Hz, 1H), 7.65 (s, 2H), 7.43 (d, J = 8.1 Hz, 1H), 7.25 (bs, 1H), 6.7-6.8 (m, 2H), 4.82 (d, J = 4.8 Hz, 2H), 4.09 (d, J = 17.1 Hz, 1H), 3.70 (d, J = 17.1 Hz, 1H). |
| 5-009 | (A) δ 8.56 (s, 1H), 7.96 (d, J = 8.4 Hz, 1H), 7.69 (dd, J = 8.4, 2.4 Hz, 1H), 7.64 (s, 2H), 6.33 (d, J = 7.2 Hz, 1H), 5.05-5.15 (m, 1H), 4.25 (d, J = 18.6 Hz, 1H), 3.87 (d, J = 18.6 Hz, 1H), 1.51 (d, J = 7.2 Hz, 3H), 1.35-1.45 (m, 1H), 0.85-1.0 (m, 2H), 0.7-0.8 (m, 2H). |
| 5-010 | (A) δ 8.63 (s, 1H), 7.99 (d, J = 8.1 Hz, 1H), 7.75 (dd, J = 8.1, 2.1 Hz, 1H), 7.65 (s, 2H), 6.65-6.75 (m, 2H), 6.55 (d, J = 7.2 Hz, 1H), 5.25-5.35 (m, 1H), 4.26 (d, J = 18.6 Hz, 1H), 3.88 (d, J = 18.6 Hz, 1H), 1.59 (d, J = 6.9 Hz, 3H). |

TABLE 16-continued

| No. | ¹H NMR |
|---|---|
| 5-011 | (A) δ 8.52 (s, 1H), 7.94 (d, J = 8.4 Hz, 1H), 7.64 (dd, J = 7.8, 2.4 Hz, 1H), 7.64 (s, 2H), 5.44 (dd, J = 7.2, 3.0 Hz, 1H), 5.35 (t, J = 4.8 Hz, 1H), 4.9-5.0 (m, 1H), 4.23 (d, J = 18.3 Hz, 1H), 3.85 (d, J = 18.3 Hz, 1H), 3.65-3.85 (m, 2H), 1.43 (d, J = 7.2 Hz, 3H). |
| 5-013 | (A) δ 7.68 (s, 1H), 7.45-7.55 (m, 4H), 7.35-7.45 (m, 2H), 5.03 (d, J = 6.0 Hz, 2H), 4.04 (d, J = 17.4 Hz, 1H), 3.66 (d, J = 17.4 Hz, 1H), 2.64 (s, 3H). |
| 5-014 | (A) δ 7.71 (s, 1H), 7.5-7.6 (m, 2H), 7.49 (d, J = 1.5 Hz, 2H), 7.42 (t, J = 1.5 Hz, 1H), 6.93 (bs, 1H), 4.75-4.9 (m, 4H), 4.05 (d, J = 17.4 Hz, 1H), 3.66 (d, J = 17.4 Hz, 1H). |
| 5-015 | (A) δ 7.70 (s, 1H), 7.65 (s, 2H), 7.4-7.55 (m, 2H), 6.3-6.45 (m, 2H), 4.80 (d, J = 6.0 Hz, 2H), 4.05 (d, J = 17.4 Hz, 1H), 3.70 (d, J = 17.4 Hz, 1H), 3.00 (d, J = 5.1 Hz, 3H). |
| 5-016 | (A) δ 7.45-7.75 (m, 5H), 6.85 (t, J = 6.0 Hz, 1H), 6.71 (bs, 1H), 4.98 (d, J = 6.0 Hz, 2H), 4.06 (d, J = 17.3 Hz, 1H), 3.69 (d, J = 17.3 Hz, 1H), 2.49 (bs, 1H), 0.8-0.9 (m, 2H), 0.65-0.75 (m, 2H). |
| 5-017 | (A) δ 7.64 (s, 2H), 7.61 (d, J = 8.4 Hz, 2H), 7.40 (d, J = 8.4 Hz, 2H), 6.41 (d, J = 7.8 Hz, 1H), 6.31 (bs, 1H), 5.68 (t, J = 6.3 Hz, 1H), 4.08 (d, J = 17.4 Hz, 1H), 3.67 (d, J = 17.4 Hz, 1H), 2.50 (bs, 1H), 1.61 (d, J = 6.9 Hz, 3H), 0.75-1.0 (m, 2H), 0.65-0.75 (m, 2H). |
| 5-018 | (A) δ 7.6-7.7 (m, 3H), 7.4-7.55 (m, 2H), 6.35 (bs, 1H), 5.94 (bs, 1H), 4.84 (d, J = 5.7 Hz, 2H), 4.07 (d, J = 17.3 Hz, 1H), 3.69 (d, J = 17.3 Hz, 1H), 1.7-1.8 (m, 1H), 1.54 (dt, J = 7.4, 3.9 Hz, 2H), 1.19 (d, J = 6.0 Hz, 3H), 0.92 (t, J = 7.4 Hz, 3H). |
| 5-019 | (A) δ 7.55-7.65 (m, 3H), 7.2-7.4 (m, 7H), 6.63 (bs, 1H), 6.47 (bs, 1H), 4.76 (d, J = 6.0 Hz, 2H), 4.55 (d, J = 4.8 Hz, 2H), 4.02 (d, J = 17.3 Hz, 1H), 3.65 (d, J = 17.3 Hz, 1H). |
| 5-020 | (A) δ 10.18 (bs, 1H), 8.26 (bs, 1H), 7.5-7.75 (m, 5H), 4.98 (d, J = 5.7 Hz, 2H), 4.21 (q, J = 7.1 Hz, 2H), 4.05 (d, J = 17.3 Hz, 1H), 3.67 (d, J = 17.3 Hz, 1H), 1.31 (t, J = 7.1 Hz, 3H). |
| 6-002 | (A) δ 7.7-7.75 (m, 1H), 7.50 (d, J = 1.5 Hz, 2H), 7.46 (d, J = 8.4 Hz, 2H), 7.43 (t, J = 1.8 Hz, 1H), 7.21 (d, J = 8.4 Hz, 2H), 6.75-6.9 (m, 2H), 5.20 (d, J = 6.9 Hz, 1H), 4.5-4.6 (m, 1H), 4.00 (d, J = 17.1 Hz, 1H), 3.65 (d, J = 17.1 Hz, 1H), 1.45 (d, J = 6.9 Hz, 3H). |
| 6-003 | (A) δ 7.7-7.75 (m, 1H), 7.65 (s, 2H), 7.50 (d, J = 8.7 Hz, 2H), 7.20 (d, J = 8.7 Hz, 2H), 6.75-6.9 (m, 2H), 5.30 (d, J = 7.5 Hz, 1H), 4.5-4.6 (m, 1H), 4.05 (d, J = 17.4 Hz, 1H), 3.65 (d, J = 17.4 Hz, 1H), 1.50 (d, J = 6.9 Hz, 3H). |
| 7-001 | (A) δ 7.61 (d, J = 8.1 Hz, 2H), 7.4-7.55 (m, 4H), 7.3-7.4 (m, 3H), 7.1-7.3 (m, 3H), 4.7-4.8 (m, 2H), 3.95-4.15 (m, 2H), 3.68 (d, J = 17.4 Hz, 1H), 3.15-3.35 (m, 1H), 2.75-2.95 (m, 1H). |
| 7-003 | (A) δ 7.64 and 7.75 (s, 1H), 7.4-7.6 (m, 4H), 7.25-7.35 (m, 1H), 4.72 and 4.77 (s, 2H), 4.04 and 4.06 (d, J = 17.4 Hz, 1H), 3.65 and 3.68 (d, J = 17.4 Hz, 1H), 3.45-3.55 (m, 2H), 0.6-1.5 (m, 8H). |
| 7-004 | (A) δ 7.67 (d, J = 1.5 Hz, 1H), 7.54 (dd, J = 8.1, 1.5 Hz, 1H), 7.49 (s, 2H), 7.43 (t, J = 1.5 Hz, 1H), 7.39 (d, J = 8.1 Hz, 1H), 4.98 (s, 2H), 4.05 (d, J = 17.4 Hz, 1H), 3.75 (s, 3H), 3.66 (d, J = 17.4 Hz, 1H), 1.55-1.65 (m, 1H), 1.0-1.1 (m, 2H), 0.85-0.95 (m, 2H). |
| 7-005 | (A) δ 7.67 (d, J = 1.5 Hz, 1H), 7.54 (dd, J = 8.1, 1.5 Hz, 1H), 7.50 (s, 2H), 7.35-7.45 (m, 2H), 4.98 (s, 2H), 4.05 (d, J = 17.4 Hz, 1H), 3.97 (q, J = 6.9 Hz, 2H), 3.66 (d, J = 17.4 Hz, 1H), 1.55-1.65 (m, 1H), 1.23 (t, J = 6.9 Hz, 3H), 1.0-1.1 (m, 2H), 0.8-0.95 (m, 2H). |
| 7-006 | (A) δ 7.67 and 7.76 (d, J = 1.5 Hz, 1H), 7.53 and 7.58 (dd, J = 8.1, 1.5 Hz, 1H), 7.49 (s, 2H), 7.43 (t, J = 1.5 Hz, 1H), 7.15 and 7.31 (d, J = 8.1 Hz, 1H), 4.77 and 4.83 (s, 2H), 3.8-4.15 (m, 3H), 3.66 and 3.68 (d, J = 17.4 Hz, 1H), 2.13 and 2.25 (s, 3H). |
| 7-007 | (A) δ 7.67 and 7.76 (s, 1H), 7.45-7.55 (m, 3H), 7.43 (s, 1H), 7.11 and 7.29 (d, J = 8.1 Hz, 1H), 4.76 and 4.83 (s, 2H), 3.85-4.15 (m, 3H), 3.66 and 3.67 (d, J = 17.4 Hz, 1H), 2.33 and 2.47 (q, J = 7.2 Hz, 2H), 1.1-1.25 (m, 3H). |
| 7-008 | (A) δ 7.63 (s, 1H), 7.45-7.6 (m, 3H), 7.49 (t, J = 1.5 Hz, 1H), 7.17 (d, J = 8.1 Hz, 1H), 4.72 (s, 2H), 4.04 (d, J = 17.4 Hz, 1H), 3.66 (d, J = 17.4 Hz, 1H), 2.75-2.85 (m, 1H), 2.25-2.4 (m, 1H), 1.0-1.1 (m, 2H), 0.75-0.95 (m, 6H). |
| 7-009 | (A) δ 7.63 and 7.74 (d, J = 1.5 Hz, 1H), 7.45-7.6 (m, 3H), 7.42 (s, 1H), 7.24 and 7.35 (d, J = 8.1 Hz, 1H), 4.82 and 4.89 (s, 2H), 4.04 and 4.06 (d, J = 17.4 Hz, 1H), 3.65 and 3.68 (d, J = 17.4 Hz, 1H), 3.35 and 3.37 (d, J = 6.0 Hz, 2H), 1.4-1.5 and 1.85-1.95 (m, 1H), 0.95-1.1 (m, 3H), 0.75-0.85 and 0.8-0.9 (m, 2H), 0.4-0.5 and 0.5-0.6 (m, 2H), 0.15-0.25 (m, 2H). |
| 7-010 | (A) δ 7.67 and 7.76 (s, 1H), 7.4-7.6 (m, 4H), 7.2-7.35 (m, 1H), 4.84 and 4.94 (s, 2H), 4.0-4.2 (m, 3H), 3.66 and 3.68 (d, J = 17.4 Hz, 1H), 1.65-1.85 (m, 1H), 1.0-1.1 (m, 2H), 0.75-0.85 and 0.85-0.95 (m, 2H). |

TABLE 16-continued

| No. | ¹H NMR |
|---|---|
| 7-011 | (A) δ 7.64 and 7.73 (d, J = 1.5 Hz, 1H), 7.45-7.6 (m, 3H), 7.43 (t, J = 1.5 Hz, 1H), 7.2-7.35 (m, 1H), 4.76 and 4.9 (s, 2H), 4.04 and 4.07 (d, J = 17.4 Hz, 1H), 3.6 and 3.75 (m, 3H), 3.5-3.6 (m, 2H), 3.29 and 3.33 (s, 3H), 1.35-1.5 and 1.85-2.0 (m, 1H), 0.95-1.1 (m, 2H), 0.65-0.8 and 0.8-0.9 (m, 2H). |
| 7-012 | (A) δ 7.65 and 7.75 (d, J = 1.5 Hz, 1H), 7.4-7.6 (m, 4H), 7.2-7.3 (m, 1H), 4.74 and 4.80 (s, 2H), 4.05 and 4.07 (d, J = 17.4 Hz, 1H), 3.66 and 3.69 (d, J = 17.4 Hz, 1H), 3.03 and 3.17 (s, 3H), 1.45-1.55 and 1.8-1.9 (m, 1H), 1.0-1.1 (m, 2H), 0.65-0.75 and 0.8-0.9 (m, 2H). |
| 7-013 | (A) δ 7.65 and 7.74 (d, J = 1.5 Hz, 1H), 7.5-7.6 (m, 3H), 7.25-7.45 (m, 2H), 4.75-4.95 (m, 4H), 4.04 and 4.07 (d, J = 17.4 Hz, 1H), 3.66 and 3.68 (d, J = 17.4 Hz, 1H), 3.35 (s, 3H), 1.4-1.5 and 1.9-2.0 (m, 1H), 1.0-1.1 (m, 2H), 0.7-0.8 and 0.85-0.95 (m, 2H). |
| 7-015 | (A) δ 7.73 (s, 1H), 7.57 (d, J = 8.1 Hz, 1H), 7.50 (d, J = 1.5 Hz, 2H), 7.43 (t, J = 1.5 Hz, 1H), 7.28 (d, J = 8.1 Hz, 1H), 7.14 (bs, 1H), 4.91 (s, 2H), 3.95-4.25 (m, 3H), 3.8-3.9 (m, 2H), 3.67 (d, J = 17.4 Hz, 1H), 1.5-1.65 (m, 1H), 1.0-1.1 (m, 2H), 0.8-0.9 (m, 2H). |
| 7-016 | (A) δ 8.39 (d, J = 2.7 Hz, 1H), 7.66 (dd, J = 8.4, 2.7 Hz, 1H), 7.61 (d, J = 1.5 Hz, 1H), 7.4-7.55 (m, 6H), 5.27 (s, 2H), 4.03 (d, J = 17.4 Hz, 1H), 3.65 (d, J = 17.4 Hz, 1H), 1.55-1.6 (m, 1H), 1.1-1.2 (m, 2H), 0.75-0.85 (m, 2H). |
| 7-017 | (A) δ 7.66 and 7.74 (d, J = 1.5 Hz, 1H), 7.4-7.6 (m, 4H), 7.16 and 7.20 (d, J = 8.1 Hz, 1H), 4.60 and 4.75 (s, 2H), 4.05 and 4.06 (d, J = 17.4 Hz, 1H), 3.68 and 3.69 (d, J = 17.4 Hz, 1H), 2.98 and 3.00 (s, 3H), 2.20 and 2.37 (d, J = 6.6 Hz, 2H), 1.0-1.2 (m, 1H), 0.5-0.65 (m, 2H), 0.05-0.15 and 0.15-0.25 (m, 2H). |
| 7-018 | (A) δ 7.68 (d, J = 1.5 Hz, 1H), 7.55 (dd, J = 8.1, 1.5 Hz, 1H), 7.4-7.5 (m, 4H), 6.58 (bs, 1H), 4.70 (s, 2H), 4.05 (d, J = 17.4 Hz, 1H), 3.85-4.0 (m, 4H), 3.78 (s, 3H), 3.67 (d, J = 17.4 Hz, 1H). |
| 7-019 | (A) δ 7.65 (s, 2H), 7.60 (d, J = 8.1 Hz, 2H), 7.30 (d, J = 8.1 Hz, 2H), 5.6-5.7 (m, 1H), 4.05 (d, J = 17.1 Hz, 1H), 3.65 (d, J = 17.1 Hz, 1H), 2.5-2.65 (m, 4H), 1.75 (d, J = 7.2 Hz, 3H), 1.10 (t, J = 7.5 Hz, 6H). |
| 7-020 | (A) δ 7.75 (s, 1H), 7.1-7.7 (m, 4H), 4.73 and 4.62 (s, 2H), 4.08 and 4.06 (d, J = 17.4 Hz, 1H), 3.69 and 3.68 (d, J = 17.4 Hz, 1H), 3.00 and 2.99 (s, 3H), 2.40 and 2.34 (t, J = 7.5 Hz, 2H), 1.71 (sep, J = 7.5 Hz, 2H), 1.00 and 0.91 (t, J = 7.5 Hz, 3H). |
| 7-021 | (A) δ 7.74 (s, 1H), 7.5-7.65 (m, 3H), 7.27 (s, 1H), 4.81 and 4.74 (s, 2H), 4.09 and 4.06 (d, J = 17.4 Hz, 1H), 3.70 and 3.67 (d, J = 17.4 Hz, 1H), 3.49 and 3.39 (q, J = 7.2 Hz, 1H), 3.17 and 3.03 (s, 3H), 0.95-1.1 (m, 4H). |
| 7-023 | (A) δ 7.70 (s, 2H), 7.67 (d, J = 8.1 Hz, 2H), 7.37 (d, J = 8.1 Hz, 2H), 6.02 and 5.47 (bs, 1H), 4.09 (d, J = 17.7 Hz, 1H), 3.68 (d, J = 17.7 Hz, 1H), 3.05-3.45 (m, 2H), 1.65-1.8 (m, 1H), 1.54 (d, J = 6.9 Hz, 3H), 0.95-1.15 (m, 5H), 0.65-0.95 (m, 2H). |
| 7-024 | (A) δ 7.74 and 7.63 (s, 1H), 7.63 (s, 2H), 7.45-7.55 (m, 1H), 7.2-7.4 (m, 1H), 4.90 and 4.82 (s, 2H), 4.07 and 4.04 (d, J = 17.4 Hz, 1H), 3.67 and 3.65 (d, J = 17.4 Hz, 1H), 3.3-3.5 (m, 2H), 1.75-1.9 and 1.35-1.5 (m, 1H), 0.95-1.15 (m, 2H), 0.85-1.0 (m, 1H), 0.75-0.9 (m, 1H), 0.6-0.75 (m, 1H), 0.4-0.6 (m, 2H), 0.15-0.3 (m, 2H). |
| 7-025 | (A) δ 7.65 (s, 2H), 7.62 (d, J = 8.1 Hz, 2H), 7.37 (d, J = 8.1 Hz, 2H), 5.94 and 5.45 (bs, 1H), 4.08 (d, J = 17.1 Hz, 1H), 3.68 (d, J = 17.1 Hz, 1H), 3.25 (dd, J = 15.6, 6.0 Hz, 1H), 2.97 (dd, J = 15.6, 6.0 Hz, 1H), 1.45-2.95 (m, 4H), 0.6-1.15 (m, 5H), 0.35-0.6 (m, 2H), 0.05-0.2 (m, 2H). |
| 7-026 | (A) δ 7.73 and 7.63 (s, 1H), 7.63 (s, 2H), 7.45-7.6 (m, 1H), 7.25-7.4 (m, 1H), 4.87 and 4.78 (s, 2H), 4.86 and 4.78 (s, 2H), 4.08 and 4.05 (d, J = 17.4 Hz, 1H), 3.68 and 3.66 (d, J = 17.4 Hz, 1H), 3.35 (s, 3H), 1.4-1.55 and 1.9-2.0 (m, 1H), 1.0-1.15 (m, 2H), 0.8-0.95 and 0.65-0.8 (m, 2H). |
| 7-027 | (A) δ 7.74 and 7.65 (d, J = 1.5 Hz, 1H), 7.4-7.6 (m, 4H), 7.25-7.35 (m, 1H), 4.85 and 4.77 (s, 2H), 4.06 and 4.04 (d, J = 17.4 Hz, 1H), 3.55-3.75 (m, 3H), 2.65-2.75 (m, 2H), 2.14 and 2.12 (s, 3H), 1.75-1.85 and 1.4-1.55 (m, 1H), 1.0-1.15 (m, 2H), 0.8-0.9 and 0.65-0.8 (m, 2H). |
| 7-029 | (A) δ 7.67 and 7.61 (d, J = 8.1 Hz, 2H), 7.64 (bs, 2H), 7.41 and 7.36 (d, J = 8.1 Hz, 2H), 6.05-6.1 and 5.5-5.6 (m, 1H), 4.0-4.15 (m, 2H), 3.5-3.85 (m, 2H), 3.67 (s, 3H), 1.8-1.85 (m, 1H), 1.69 and 1.48 (d, J = 6.9 Hz, 3H), 1.05-1.1 (m, 2H), 0.75-0.85 (m, 2H). |
| 7-030 | (A) δ 7.74 and 7.63 (s, 1H), 7.63 (s, 2H), 7.45-7.6 (m, 1H), 7.25-7.4 (m, 1H), 4.94 and 4.80 (s, 2H), 4.30 and 4.23 (s, 2H), 4.09 and 4.06 (d, J = 17.4 Hz, 1H), 3.70 and 3.68 (d, J = 17.4 Hz, 1H), 2.32 and 2.20 (s, 1H), 1.4-1.6 and 1.85-2.0 (m, 1H), 1.0-1.15 (m, 2H), 0.8-0.95 and 0.65-0.8 (m, 2H). |

TABLE 16-continued

| No. | ¹H NMR |
|---|---|
| 7-031 | (A) δ 7.73 (d, J = 1.8 Hz, 1H), 7.63 (s, 2H), 7.59 (dd, J = 7.8, 1.8 Hz, 1H), 7.44 (d, J = 7.8 Hz, 1H), 4.87 (s, 2H), 4.06 (d, J = 17.4 Hz, 1H), 3.67 (d, J = 17.4 Hz, 1H), 2.25-2.35 (m, 1H), 1.15-1.25 (m, 2H), 1.05-1.15 (m, 2H). |
| 7-032 | (A) δ 7.82 (s, 1H), 7.56 (d, J = 8.1 Hz, 1H), 7.49 (s, 2H), 7.42 (s, 1H), 7.05 (d, J = 8.1 Hz, 1H), 4.95 (s, 2H), 4.04 (d, J = 17.1 Hz, 1H), 3.65 (d, J = 17.1 Hz, 1H), 2.85-2.95 (m, 1H), 1.44 (s, 9H), 1.1-1.2 (m, 2H), 0.95-1.05 (m, 2H). |
| 7-035 | (A) δ 7.54 (d, J = 8.4 Hz, 2H), 7.50 (d, J = 1.5 Hz, 2H), 7.42 (t, J = 1.8 Hz, 1H), 7.31 (d, J = 8.4 Hz, 2H), 6.75-6.85 (m, 1H), 6.5-6.6 (m, 1H), 5.95-6.05 (m, 1H), 4.05 (d, J = 17.1 Hz, 1H), 3.65 (d, J = 17.1 Hz, 1H), 1.45-1.55 (m, 3H), 1.0-1.05 (m, 2H), 1.05-1.1 (m, 1H), 0.6-0.65 (m, 2H). |
| 7-036 | (A) δ 7.5-7.75 (m, 4H), 7.1-7.3 (m, 1H), 4.74 and 4.68 (s, 2H), 4.0-4.15 (m, 2H), 3.85-3.95 (m, 3H), 3.70 and 3.68 (d, J = 17.4 Hz, 1H), 3.34 and 3.09 (qui, J = 7.8 Hz, 1H), 3.04 and 3.02 (s, 3H), 2.1-2.3 (m, 2H). |
| 7-037 | (A) δ 7.67 (s, 1H), 7.53 (d, J = 8.4 Hz, 1H), 7.49 (s, 2H), 7.42 (s, 1H), 7.33 (d, J = 8.4 Hz, 1H), 4.61 (s, 2H), 4.06 (d, J = 17.1 Hz, 1H), 3.67 (d, J = 17.1 Hz, 1H), 3.33 (t, J = 6.9 Hz, 2H), 2.46 (t, J = 8.4 Hz, 2H), 2.0-2.15 (m, 2H). |
| 7-038 | (A) δ 7.66 (s, 1H), 7.53 (d, J = 8.4 Hz, 1H), 7.49 (s, 2H), 7.42 (s, 1H), 7.24 (d, J = 8.4 Hz, 1H), 4.74 (s, 2H), 4.05 (d, J = 17.4 Hz, 1H), 3.66 (d, J = 17.4 Hz, 1H), 3.2-3.35 (m, 2H), 2.45-2.6 (m, 2H), 1.75-2.0 (m, 4H). |
| 7-039 | (A) δ 7.66 (s, 1H), 7.54 (d, J = 8.1 Hz, 1H), 7.50 (s, 2H), 7.43 (s, 1H), 7.36 (d, J = 8.1 Hz, 1H), 4.74 (s, 2H), 4.05 (d, J = 17.4 Hz, 1H), 3.66 (d, J = 17.4 Hz, 1H), 3.0-3.4 (m, 2H), 2.55-2.7 (m, 2H), 1.65-1.75 (m, 4H), 1.5-1.7 (m, 2H). |
| 7-041 | (A) δ 7.15-7.7 (m, 7H), 6.7-6.8 (m, 2H), 6.15-6.25 and 4.8-4.9 (m, 1H), 4.05-4.15 (m, 1H), 3.65-3.75 (m, 1H), 2.80 and 2.50 (s, 3H), 1.6-1.65 (m, 3H). |
| 7-042 | (A) δ 7.5-7.75 (m, 4H), 7.43 and 7.32 (d, J = 8.1 Hz, 1H), 6.77 and 6.67 (t, J = 7.2 Hz, 2H), 4.91 and 4.54 (s, 2H), 4.07 and 4.06 (d, J = 17.4 Hz, 1H), 3.69 and 3.67 (d, J = 17.4 Hz, 1H), 3.54 and 3.22 (q, J = 7.2 Hz, 2H), 1.11 and 0.88 (t, J = 7.2 Hz, 3H). |
| 7-044 | (A) δ 7.71 (s, 1H), 7.56 (d, J = 8.1 Hz, 1H), 7.50 (s, 2H), 7.4-7.5 (m, 2H), 4.60 (s, 2H), 4.35 (dd, J = 7.8, 6.9 Hz, 2H), 4.06 (d, J = 17.4 Hz, 1H), 3.67 (d, J = 17.4 Hz, 1H), 3.53 (dd, J = 7.8, 6.9 Hz, 2H). |
| 7-045 | (A) δ 7.6-7.75 (m, 3H), 7.5-7.65 (m, 1H), 7.15-7.25 (m, 1H), 4.96 (d, J = 2.1 Hz, 2H), 4.79 (s, 2H), 4.0-4.2 (m, 3H), 3.67 (d, J = 17.3 Hz, 1H). |
| 7-046 | (A) δ 7.70 (d, J = 1.8 Hz, 1H), 7.53 (dd, J = 8.4, 1.8 Hz, 1H), 7.49 (s, 2H), 7.42 (t, J = 1.8 Hz, 1H), 7.36 (d, J = 8.4 Hz, 1H), 4.59 (s, 2H), 4.5-4.6 (m, 1H), 4.05 (d, J = 17.4 Hz, 1H), 3.67 (d, J = 17.4 Hz, 1H), 3.49 (t, J = 7.2 Hz, 2H), 3.2-3.35 (m, 2H), 2.67 (t, J = 7.2 Hz, 2H), 2.15 (s, 3H), 1.10 (t, J = 7.2 Hz, 3H). |
| 7-047 | (A) δ 7.66 (d, J = 1.8 Hz, 1H), 7.63 (s, 2H), 7.5-7.6 (m, 1H), 7.30 (s, 1H), 6.02 (bs, 1H), 4.83 (s, 2H), 4.07 (s, 2H), 4.05 (d, J = 17.4 Hz, 1H), 3.65 (d, J = 17.4 Hz, 1H). |
| 7-048 | (A) δ 8.07 (s, 2H), 7.97 (s, 1H), 7.77 and 7.68 (d, J = 1.5 Hz, 1H), 7.5-7.6 (m, 1H), 7.32 and 7.18 (d, J = 8.4 Hz, 1H), 4.75 and 4.61 (s, 2H), 4.19 and 4.17 (d, J = 17.4 Hz, 1H), 3.74 and 3.73 (d, J = 17.4 Hz, 1H), 3.00 and 2.99 (s, 3H), 2.38 and 2.22 (d, J = 6.9 Hz, 2H), 1.0-1.2 (m, 1H), 0.4-0.55 (m, 2H), 0.15-0.25 and 0.05-0.15 (m, 2H). |
| 7-049 | (A) δ 8.07 (s, 2H), 7.97 (s, 1H), 7.76 and 7.67 (d, J = 1.8 Hz, 1H), 7.5-7.6 (m, 1H), 7.15-7.35 (m, 1H), 4.72 and 4.57 (s, 2H), 4.19 and 4.17 (d, J = 17.4 Hz, 1H), 3.75 and 3.73 (d, J = 17.4 Hz, 1H), 3.45 and 3.33 (q, J = 7.2 Hz, 2H), 2.38 and 2.16 (d, J = 6.9 Hz, 2H), 1.0-1.3 (m, 4H), 0.45-0.65 (m, 2H), 0.15-0.25 and 0.0-0.1 (m, 2H). |
| 7-050 | (A) δ 8.08 (s, 2H), 7.97 (s, 1H), 7.77 and 7.68 (d, J = 1.5 Hz, 1H), 7.45-7.55 (m, 1H), 7.3-7.4 and 7.15-7.3 (m, 1H), 4.74 and 4.59 (s, 2H), 4.20 and 4.18 (d, J = 17.4 Hz, 1H), 3.75 and 3.74 (d, J = 17.4 Hz, 1H), 3.56 and 3.21 (t, J = 7.8 Hz, 2H), 2.38 and 2.17 (d, J = 6.9 Hz, 2H), 1.61 and 1.59 (qui, J = 7.8 Hz, 2H), 1.0-1.2 (m, 1H), 0.91 (t, J = 7.8 Hz, 3H), 0.45-0.7 (m, 2H), 0.15-0.25 and 0.0-0.15 (m, 2H). |
| 7-051 | (A) δ 8.07 (s, 2H), 7.97 (s, 1H), 7.76 and 7.66 (d, J = 1.5 Hz, 1H), 7.5-7.6 (m, 1H), 7.2-7.3 (m, 1H), 4.84 and 4.70 (s, 2H), 4.19 and 4.17 (d, J = 17.4 Hz, 1H), 3.77 and 3.73 (d, J = 17.4 Hz, 1H), 3.34 and 3.18 (q, J = 6.9 Hz, 2H), 2.43 and 2.19 (d, J = 6.9 Hz, 2H), 0.85-1.2 (m, 4H), 0.45-0.7 (m, 2H), 0.05-0.3 (m, 4H). |
| 7-052 | (A) δ 8.08 (s, 2H), 7.97 (s, 1H), 7.76 and 7.68 (d, J = 1.5 Hz, 1H), 7.5-7.6 (m, 1H), 7.3-7.4 and 7.2-7.3 (m, 1H), 4.82 and 4.75 (s, 2H), 4.20 and 4.18 (d, J = 17.4 Hz, 1H), 4.29 and 4.03 (d, J = 2.4 Hz, 2H), 3.75 and 3.74 (d, J = 17.4 Hz, 1H), 2.46 and 2.28 (q, J = 6.9 Hz, 2H), 2.2-2.25 (m, 1H), 1.0-1.2 (m, 1H), 0.15-0.3 (m, 2H), 0.0-0.15 (m, 2H). |

TABLE 16-continued

| No. | ¹H NMR |
|---|---|
| 7-053 | (A) δ 8.08 (s, 2H), 7.97 (s, 1H), 7.90 (s, 1H), 7.77 (d, J = 1.5 Hz, 1H), 7.6-7.7 (m, 1H), 7.4-7.5 (m, 1H), 7.22 (s, 1H), 7.08 (t, J = 0.9 Hz, 1H), 4.77 (s, 2H), 4.20 (d, J = 17.4 Hz, 1H), 3.76 (d, J = 17.4 Hz, 1H), 3.09 (s, 3H). |
| 7-060 | (A) δ 8.08 (s, 2H), 7.97 (s, 1H), 7.77 and 7.67 (d, J = 1.8 Hz, 1H), 7.5-7.6 (m, 1H), 7.2-7.35 (m, 1H), 4.71 and 4.59 (s, 2H), 4.19 and 4.17 (d, J = 17.4 Hz, 1H), 3.75 and 3.73 (d, J = 17.4 Hz, 1H), 3.45 and 3.34 (q, J = 7.2 Hz, 2H), 2.47 and 2.23 (q, J = 7.2 Hz, 2H), 1.05-1.25 (m, 6H). |
| 7-061 | (A) δ 7.93 (s, 1H), 7.83 (s, 1H), 7.75 and 7.65 (s, 1H), 7.4-7.6 and 7.15-7.35 (m, 2H), 4.72 and 4.59 (s, 2H), 4.11 and 4.10 (d, J = 17.4 Hz, 1H), 3.69 and 3.67 (d, J = 17.4 Hz, 1H), 3.45 and 3.33 (q, J = 6.9 Hz, 2H), 2.46 and 2.40 (q, J = 7.8 Hz, 2H), 1.05-1.25 (m, 6H). |
| 7-063 | (A) δ 8.08 (s, 2H), 7.97 (s, 1H), 7.77 and 7.66 (d, J = 1.8 Hz, 1H), 7.5-7.6 (m, 1H), 7.15-7.3 (m, 1H), 4.72 and 4.60 (s, 2H), 4.19 and 4.17 (d, J = 17.4 Hz, 1H), 3.75 and 3.73 (d, J = 17.4 Hz, 1H), 3.35 and 3.22 (t, J = 7.5 Hz, 2H), 2.47 and 2.23 (q, J = 7.5 Hz, 2H), 1.5-1.7 (m, 2H), 1.21 and 1.11 (t, J = 7.5 Hz, 3H), 0.91 and 0.90 (t, J = 7.5 Hz, 3H). |
| 7-064 | (A) δ 8.07 (s, 2H), 7.97 (s, 1H), 7.80 (s, 1H), 7.55-7.65 (m, 1H), 7.2-7.3 (m, 1H), 4.77 (s, 2H), 4.32 (s, 2H), 4.19 (d, J = 17.4 Hz, 1H), 3.75 (d, J = 17.4 Hz, 1H), 2.41 (q, J = 7.2 Hz, 2H), 1.26 and 1.18 (t, J = 7.2 Hz, 3H). |
| 7-065 | (A) δ 7.93 (s, 1H), 7.82 (s, 1H), 7.78 (s, 1H), 7.5-7.6 (m, 1H), 7.15-7.25 (m, 1H), 4.77 (s, 2H), 4.32 (s, 2H), 4.12 (d, J = 17.4 Hz, 1H), 3.70 (d, J = 17.4 Hz, 1H), 2.35-2.45 (m, 2H), 1.18 and 1.16 (t, J = 7.2 Hz, 3H). |
| 7-066 | (A) δ 8.07 (s, 2H), 7.97 (s, 1H), 7.77 and 7.66 (d, J = 1.5 Hz, 1H), 7.5-7.6 (m, 1H), 7.15-7.35 (m, 1H), 5.65-5.85 (m, 1H), 5.05-5.3 (m, 2H), 4.71 and 4.56 (s, 2H), 4.19 and 4.17 (d, J = 17.4 Hz, 1H), 4.04 and 3.90 (d, J = 5.7 Hz, 2H), 3.75 and 3.73 (d, J = 17.4 Hz, 1H), 2.44 and 2.27 (q, J = 7.5 Hz, 2H), 1.20 and 1.13 (t, J = 7.5 Hz, 3H). |
| 7-067 | (A) δ 7.94 (s, 1H), 7.84 (s, 1H), 7.76 and 7.65 (s, 1H), 7.5-7.6 (m, 1H), 7.15-7.35 (m, 1H), 5.7-5.85 (m, 1H), 5.05-5.3 (m, 2H), 4.72 and 4.58 (s, 2H), 4.11 (d, J = 17.4 Hz, 1H), 4.04 and 3.90 (d, J = 6.0 Hz, 2H), 3.69 (d, J = 17.4 Hz, 1H), 2.45 and 2.28 (q, J = 7.5 Hz, 2H), 1.20 and 1.14 (t, J = 7.5 Hz, 3H). |
| 7-068 | (A) δ 8.08 (s, 2H), 7.97 (s, 1H), 7.77 and 7.68 (s, 1H), 7.5-7.6 (m, 1H), 7.35 and 7.26 (d, J = 7.8 Hz, 1H), 4.81 and 4.77 (s, 2H), 4.20 and 4.18 (d, J = 17.4 Hz, 1H), 4.29 and 4.04 (d, J = 2.4 Hz, 2H), 3.75 and 3.74 (d, J = 17.4 Hz, 1H), 2.55 and 2.39 (q, J = 7.5 Hz, 2H), 2.29 and 2.21 (t, J = 2.4 Hz, 1H), 1.22 and 1.16 (t, J = 7.5 Hz, 3H). |
| 7-069 | (A) δ 8.07 (s, 2H), 7.97 (s, 1H), 7.77 and 7.66 (d, J = 1.8 Hz, 1H), 7.5-7.6 (m, 1H), 7.2-7.35 (m, 1H), 4.71 and 4.59 (s, 2H), 4.20 and 4.17 (d, J = 17.4 Hz, 1H), 3.75 and 3.73 (d, J = 17.4 Hz, 1H), 3.44 and 3.35 (q, J = 7.2 Hz, 2H), 2.42 and 2.18 (t, J = 7.5 Hz, 2H), 1.6-1.85 (m, 2H), 1.19 and 1.14 (t, J = 6.9 Hz, 3H), 1.00 and 0.90 (t, J = 7.2 Hz, 3H). |
| 7-070 | (A) δ 7.94 (s, 1H), 7.83 (s, 1H), 7.76 and 7.66 (s, 1H), 7.45-7.6 and 7.15-7.35 (m, 2H), 4.72 and 4.59 (s, 2H), 4.11 and 4.10 (d, J = 17.4 Hz, 1H), 3.69 and 3.67 (d, J = 17.4 Hz, 1H), 3.44 and 3.34 (q, J = 7.2 Hz, 2H), 2.41 and 2.35 (t, J = 7.5 Hz, 2H), 1.6-1.8 (m, 2H), 1.18 and 1.14 (t, J = 7.2 Hz, 3H), 1.00 and 0.98 (t, J = 7.5 Hz, 3H). |
| 7-071 | (A) δ 8.08 (s, 2H), 7.97 (s, 1H), 7.77 and 7.67 (d, J = 1.8 Hz, 1H), 7.5-7.6 (m, 1H), 7.15-7.3 (m, 1H), 4.72 and 4.60 (s, 2H), 4.20 and 4.17 (d, J = 17.4 Hz, 1H), 3.76 and 3.74 (d, J = 17.4 Hz, 1H), 3.34 and 3.22 (t, J = 7.5 Hz, 2H), 2.41 and 2.18 (t, J = 7.2 Hz, 2H), 1.5-1.8 (m, 4H), 0.7-1.1 (m, 6H). |
| 7-072 | (A) δ 8.07 (s, 2H), 7.97 (s, 1H), 7.80 (s, 1H), 7.6-7.7 (m, 1H), 7.2-7.3 (m, 1H), 4.77 (s, 2H), 4.31 (s, 2H), 4.19 (d, J = 17.4 Hz, 1H), 3.75 (d, J = 17.4 Hz, 1H), 2.35 (t, J = 7.5 Hz, 2H), 1.71 (sxt, J = 7.5 Hz, 2H), 0.95 (t, J = 7.5 Hz, 3H). |
| 7-073 | (A) δ 7.93 (s, 1H), 7.82 (s, 1H), 7.78 (s, 1H), 7.55-7.65 (m, 1H), 7.2-7.3 (m, 1H), 4.77 (s, 2H), 4.31 (s, 2H), 4.11 (d, J = 17.4 Hz, 1H), 3.72 (d, J = 17.4 Hz, 1H), 2.35 (t, J = 7.2 Hz, 2H), 1.6-1.85 (m, 2H), 0.94 (t, J = 7.2 Hz, 3H). |
| 7-074 | (A) δ 7.94 (s, 1H), 7.83 (s, 1H), 7.75 and 7.65 (s, 1H), 7.5-7.6 (m, 1H), 7.15-7.35 (m, 1H), 5.7-5.85 (m, 1H), 5.05-5.3 (m, 2H), 4.71 and 4.58 (s, 2H), 4.13 and 4.11 (d, J = 17.4 Hz, 1H), 4.02 and 3.90 (d, J = 6.0 Hz, 2H), 3.70 and 3.68 (d, J = 17.4 Hz, 1H), 2.39 and 2.22 (t, J = 7.5 Hz, 2H), 1.6-1.8 (m, 2H), 0.98 and 0.91 (t, J = 7.5 Hz, 3H). |

TABLE 16-continued

| No. | ¹H NMR |
|---|---|
| 7-075 | (A) δ 8.08 (s, 2H), 7.97 (s, 1H), 7.78 and 7.68 (d, J = 1.5 Hz, 1H), 7.5-7.6 (m, 1H), 7.50 and 7.25 (d, J = 7.8 Hz, 1H), 4.81 and 4.77 (s, 2H), 4.20 and 4.17 (d, J = 17.4 Hz, 1H), 4.28 and 4.04 (d, J = 2.4 Hz, 2H), 3.75 and 3.73 (d, J = 17.4 Hz, 1H), 2.49 and 2.23 (t, J = 7.2 Hz, 2H), 2.29 and 2.21 (t, J = 2.4 Hz, 1H), 1.6-1.8 (m, 2H), 1.01 and 0.91 (t, J = 7.2 Hz, 3H). |
| 7-077 | (A) δ 7.93 (s, 1H), 7.82 (s, 1H), 7.76 and 7.66 (s, 1H), 7.55-7.6 (m, 1H), 7.2-7.3 (m, 1H), 4.80 and 4.74 (s, 2H), 4.16 and 4.10 (d, J = 17.4 Hz, 1H), 3.69 and 3.67 (d, J = 17.4 Hz, 1H), 3.17 and 3.03 (s, 3H), 1.45-1.65 (m, 1H), 1.0-1.1 (m, 2H), 0.8-0.9 and 0.7-0.8 (m, 2H). |
| 7-078 | (A) δ 7.94 (s, 1H), 7.83 (s, 1H), 7.55-7.65 (m, 1H), 7.2-7.4 (m, 2H), 4.74 (d, J = 8.1 Hz, 2H), 4.0-4.2 (m, 1H), 3.6-3.8 (m, 1H), 3.17 and 3.03 (s, 3H), 1.7-1.9 and 1.4-1.6 (m, 1H), 1.0-1.1 (m, 2H), 0.8-0.9 and 0.65-0.8 (m, 2H). |
| 7-079 | (A) δ 7.94 (d, J = 1.8 Hz, 1H), 7.84 (s, 1H), 7.62 (d, J = 8.4 Hz, 2H), 7.34 (d, J = 8.4 Hz, 2H), 6.0-6.05 and 5.5-5.55 (m, 1H), 4.14 (d, J = 17.1 Hz, 1H), 3.70 (d, J = 17.1 Hz, 1H), 2.82 and 2.69 (s, 3H), 1.7-1.8 (m, 1H), 1.50 (d, J = 7.2 Hz, 3H), 1.0-1.1 (m, 2H), 0.75-0.85 (m, 2H). |
| 7-080 | (A) δ 8.07 (s, 2H), 7.97 (s, 1H), 7.77 and 7.66 (d, J = 1.8 Hz, 1H), 7.5-7.6 (m, 1H), 7.35-7.45 (m, 1H), 4.78 and 4.72 (s, 2H), 4.20 and 4.17 (d, J = 17.4 Hz, 1H), 3.75 and 3.73 (d, J = 17.4 Hz, 1H), 3.53 and 3.48 (q, J = 7.2 Hz, 2H), 1.8-1.9 and 1.4-1.5 (m, 1H), 1.27 and 1.15 (t, J = 7.2 Hz, 3H), 0.95-1.1 (m, 2H), 0.8-0.95 and 0.65-0.75 (m, 2H). |
| 7-081 | (A) δ 7.94 (s, 1H), 7.83 (s, 1H), 7.76 and 7.65 (s, 1H), 7.45-7.6 and 7.15-7.35 (m, 2H), 4.77 and 4.72 (s, 2H), 4.11 and 4.10 (d, J = 17.4 Hz, 1H), 3.69 and 3.67 (d, J = 17.4 Hz, 1H), 3.52 and 3.48 (q, J = 6.9 Hz, 2H), 1.75-1.85 and 1.55-1.7 (m, 1H), 1.26 and 1.14 (t, J = 6.9 Hz, 3H), 0.95-1.10 (m, 2H), 0.8-0.9 and 0.65-0.75 (m, 2H). |
| 7-083 | (A) δ 7.94 (s, 2H), 7.83 (s, 1H), 7.5-7.65 (m, 1H), 7.2-7.4 (m, 1H), 4.71 and 4.69 (s, 2H), 4.05-4.2 (m, 1H), 3.6-3.75 (m, 1H), 3.4-3.6 (m, 2H), 1.8-2.0 and 1.4-1.6 (m, 1H), 1.26 (t, J = 6.9 Hz, 3H), 1.0-1.1 (m, 2H), 0.8-0.9 and 0.65-0.8 (m, 2H). |
| 7-084 | (A) δ 7.95 (d, J = 2.1 Hz, 1H), 7.84 (s, 1H), 7.62 (d, J = 7.8 Hz, 2H), 7.37 (d, J = 7.8 Hz, 2H), 5.95-6.1 and 5.45-5.55 (m, 1H), 4.14 (d, J = 17.4 Hz, 1H), 3.71 (d, J = 17.4 Hz, 1H), 3.1-3.45 (m, 2H), 1.65-1.75 (m, 1H), 1.54 (d, J = 7.2 Hz, 3H), 1.0-1.15 (m, 5H), 0.75-0.85 (m, 2H). |
| 7-085 | (A) δ 8.07 (s, 2H), 7.97 (s, 1H), 7.77 and 7.66 (d, J = 1.8 Hz, 1H), 7.5-7.6 (m, 1H), 7.25-7.35 (m, 1H), 4.78 and 4.72 (s, 2H), 4.19 and 4.17 (d, J = 17.4 Hz, 1H), 3.75 and 3.73 (d, J = 17.4 Hz, 1H), 3.41 and 3.38 (t, J = 7.8 Hz, 2H), 1.5-1.9 (m, 3H), 0.94 and 0.92 (t, J = 7.8 Hz, 3H), 0.8-1.1 (m, 4H). |
| 7-086 | (A) δ 7.93 (s, 1H), 7.83 (s, 1H), 7.75 and 7.65 (d, J = 1.5 Hz, 1H), 7.45-7.6 (m, 1H), 7.2-7.3 (m, 1H), 4.78 and 4.72 (s, 2H), 4.13 and 4.10 (d, J = 17.4 Hz, 1H), 3.70 and 3.67 (d, J = 17.4 Hz, 1H), 3.40 and 3.37 (t, J = 7.8 Hz, 2H), 1.69 and 1.58 (sxt, J = 7.8 Hz, 2H), 1.8-1.9 and 1.4-1.5 (m, 1H), 1.0-1.1 (m, 2H), 0.94 and 0.92 (t, J = 7.8 Hz, 3H), 0.8-0.9 (m, 2H). |
| 7-087 | (A) δ 7.94 (s, 2H), 7.83 (s, 1H), 7.5-7.65 (m, 1H), 7.2-7.4 (m, 1H), 4.73 and 4.70 (s, 2H), 4.05-4.2 (m, 1H), 3.6-3.75 (m, 1H), 3.40 and 3.37 (t, J = 7.5 Hz, 2H), 1.8-2.0 and 1.4-1.6 (m, 1H), 0.5-1.2 (m, 9H). |
| 7-088 | (A) δ 7.96 (s, 1H), 7.86 (s, 1H), 7.63 (d, J = 8.1 Hz, 2H), 7.37 (d, J = 8.1 Hz, 2H), 5.95-6.05 and 5.45-5.55 (m, 1H), 4.16 (d, J = 17.1 Hz, 1H), 3.72 (d, J = 17.1 Hz, 1H), 2.9-3.3 (m, 2H), 1.3-1.75 (m, 3H), 1.53 (d, J = 6.9 Hz, 3H), 1.0-1.1 (m, 2H), 0.7-0.85 (m, 5H). |
| 7-090 | (A) δ 7.96 (s, 1H), 7.93 (s, 1H), 7.85 (s, 1H), 7.80 (s, 1H), 7.55-7.7 (m, 1H), 7.15-7.3 (m, 1H), 4.95, 4.89, 4.83 and 4.77 (s, 2H), 4.08 (d, J = 17.4 Hz, 1H), 3.85-4.0 (m, 1H), 3.6-3.8 (m, 2H), 3.1-3.2 (m, 1H), 2.85-3.0 (m, 1H), 2.64 (s, 3H), 1.45-1.6 (m, 1H), 0.65-1.15 (m, 4H). |
| 7-091 | (A) δ 7.9-8.0 (m, 2H), 7.85 (s, 1H), 7.80 (s, 1H), 7.55-7.7 (m, 1H), 7.15-7.3 (m, 1H), 4.85 (s, 2H), 4.12 (d, J = 17.4 Hz, 1H), 3.82 (t, J = 6.6 Hz, 2H), 3.71 (d, J = 17.4 Hz, 1H), 3.34 (t, J = 6.6 Hz, 2H), 2.97 (s, 3H), 1.45-1.6 (m, 1H), 0.7-1.15 (m, 4H). |
| 7-092 | (A) δ 7.75-8.0 (m, 4H), 7.55-7.7 (m, 1H), 7.24 and 7.21 (s, 1H), 6.54 and 5.98 (bs, 1H), 4.76 and 4.72 (s, 2H), 4.05-4.2 (m, 1H), 3.35-3.75 (m, 5H), 1.94 and 1.92 (s, 3H), 1.4-1.55 (m, 1H), 0.7-1.1 (m, 4H). |

TABLE 16-continued

| No. | ¹H NMR |
|---|---|
| 7-093 | (A) δ 7.74 and 7.67 (s, 1H), 7.45-7.6 (m, 4H), 7.43 (s, 1H), 5.03 and 4.69 (bs, 1H), 4.82 and 4.74 (s, 2H), 4.0-4.15 (m, 1H), 3.5-3.75 (m, 4H), 3.25-3.4 (m, 2H), 1.43 (s, 9H), 0.95-1.1 (m, 2H), 0.8-0.9 (m, 1H), 0.65-0.75 (m, 1H). |
| 7-094 | (A) δ 7.73 and 7.67 (s, 1H), 7.4-7.6 (m, 5H), 5.22 (bs, 1H), 4.82 and 4.73 (s, 2H), 4.59 and 4.24 (bs, 1H), 4.06 and 4.04 (d, J = 17.4 Hz, 1H), 3.5-3.75 (m, 2H), 3.3-3.45 (m, 2H), 3.1-3.3 (m, 3H), 1.4-1.55 (m, 1H), 1.05-1.2 (m, 3H), 1.95-1.1 (m, 2H), 0.7-0.9 (m, 2H). |
| 7-095 | (A) δ 8.07 (s, 2H), 7.97 (s, 1H), 7.80 (s, 1H), 7.55-7.7 (m, 1H), 7.25-7.35 (m, 1H), 4.95 (s, 2H), 4.36 (s, 2H), 4.19 (d, J = 17.4 Hz, 1H), 3.75 (d, J = 17.4 Hz, 1H), 1.55-1.65 (m, 1H), 1.05-1.2 (m, 2H), 0.8-0.95 (m, 2H). |
| 7-096 | (A) δ 7.93 (d, J = 2.1 Hz, 1H), 7.75-7.85 (m, 2H), 7.55-7.65 (m, 1H), 7.25-7.35 (m, 1H), 4.94 (s, 2H), 4.35 (s, 2H), 4.11 (d, J = 17.4 Hz, 1H), 3.71 (d, J = 17.4 Hz, 1H), 1.55-1.7 (m, 1H), 1.05-1.15 (m, 2H), 0.8-0.9 (m, 2H). |
| 7-097 | (A) δ 7.96 (s, 1H), 7.94 (s, 1H), 7.83 (s, 1H), 7.68 (d, J = 6.6 Hz, 1H), 7.31 (d, J = 6.6 Hz, 1H), 4.90 (s, 2H), 4.37 (s, 2H), 4.10 (d, J = 17.4 Hz, 1H), 3.69 (d, J = 17.4 Hz, 1H), 1.5-1.7 (m, 1H), 1.1-1.2 (m, 2H), 0.75-0.9 (m, 2H). |
| 7-098 | (A) δ 7.94 (s, 1H), 7.84 (s, 1H), 7.70 (d, J = 7.8 Hz, 2H), 7.39 (d, J = 7.8 Hz, 2H), 5.9-6.2 and 5.65-5.8 (m, 1H), 4.05-4.25 (m, 1H), 4.15 (d, J = 17.1 Hz, 1H), 3.7-3.85 (m, 1H), 3.71 (d, J = 17.1 Hz, 1H), 1.6-1.9 (m, 4H), 1.1-1.2 (m, 2H), 0.85-0.95 (m, 2H). |
| 7-099 | (A) δ 8.07 (s, 2H), 7.97 (s, 1H), 7.77 and 7.66 (d, J = 1.5 Hz, 1H), 7.5-7.6 (m, 1H), 7.25-7.35 (m, 1H), 5.7-5.9 (m, 1H), 5.1-5.3 (m, 2H), 4.76 and 4.72 (s, 2H), 4.20 and 4.17 (d, J = 17.4 Hz, 1H), 4.0-4.1 (m, 2H), 3.75 and 3.73 (d, J = 17.4 Hz, 1H), 1.75-1.85 and 1.45-1.55 (m, 1H), 1.0-1.1 (m, 2H), 1.8-1.9 and 1.65-1.75 (m, 2H). |
| 7-100 | (A) δ 7.94 (s, 1H), 7.84 (s, 1H), 7.76 and 7.65 (d, J = 1.5 Hz, 1H), 7.5-7.6 (m, 1H), 7.25-7.35 (m, 1H), 5.7-5.95 (m, 1H), 5.1-5.3 (m, 2H), 4.76 and 4.72 (s, 2H), 4.08 (s, 2H), 4.07 (d, J = 17.4 Hz, 1H), 3.71 and 3.69 (d, J = 17.4 Hz, 1H), 1.7-1.85 (m, 1H), 0.95-1.1 (m, 2H), 0.75-0.9 and 0.65-0.75 (m, 2H). |
| 7-101 | (A) δ 7.94 (s, 2H), 7.82 (s, 1H), 7.55-7.7 (m, 1H), 7.2-7.4 (m, 1H), 5.7-6.0 (m, 1H), 5.1-5.35 (m, 2H), 4.70 (s, 2H), 4.0-4.2 (m, 3H), 3.70 and 3.67 (d, J = 17.4 Hz, 1H), 1.8-2.0 and 1.4-1.6 (m, 1H), 1.0-1.1 (m, 2H), 0.8-0.9 (m, 1H), 0.65-0.8 (m, 2H). |
| 7-102 | (A) δ 7.94 (s, 1H), 7.84 (s, 1H), 7.62 (d, J = 8.4 Hz, 2H), 7.36 (d, J = 8.4 Hz, 2H), 6.0-6.15 and 5.4-5.55 (m, 1H), 5.65-5.8 (m, 1H), 5.15 (bs, 1H), 5.10 (bs, 1H), 4.15 (d, J = 17.1 Hz, 1H), 3.9-4.05 (m, 1H), 3.6-3.75 (m, 1H), 3.71 (d, J = 17.1 Hz, 1H), 1.65-1.75 (m, 1H), 1.50 (d, J = 6.9 Hz, 3H), 1.0-1.1 (m, 2H), 0.75-0.85 (m, 2H). |
| 7-103 | (A) δ 8.08 (s, 2H), 7.97 (s, 1H), 7.77 and 7.67 (s, 1H), 7.5-7.6 (m, 1H), 7.3-7.45 (m, 1H), 4.94 and 4.81 (s, 2H), 4.31 and 4.22 (d, J = 2.4 Hz, 2H), 4.19 and 4.17 (d, J = 17.4 Hz, 1H), 3.75 and 3.73 (d, J = 17.4 Hz, 1H), 2.31 and 2.20 (t, J = 2.4 Hz, 1H), 1.85-1.95 and 1.45-1.55 (m, 1H), 1.0-1.2 (m, 2H), 0.9-1.0 and 0.7-0.85 (m, 2H). |
| 7-103 | (A) δ 7.93 (s, 1H), 7.83 (s, 1H), 7.75 and 7.66 (s, 1H), 7.45-7.6 (m, 1H), 7.3-7.4 (m, 1H), 4.94 and 4.81 (s, 2H), 4.31 and 4.23 (s, 2H), 4.13 and 4.11 (d, J = 17.4 Hz, 1H), 3.72 and 3.69 (d, J = 17.4 Hz, 1H), 2.31 and 2.20 (s, 1H), 1.55-1.75 (m, 1H), 1.0-1.1 (m, 2H), 0.99-1.0 and 0.7-0.8 (m, 2H). |
| 7-105 | (A) δ 7.94 (s, 2H), 7.83 (s, 1H), 7.55-7.7 (m, 1H), 7.2-7.4 (m, 1H), 4.88 and 4.79 (s, 2H), 4.31 and 4.20 (s, 2H), 4.1-4.2 (m, 1H), 3.6-3.75 (m, 1H), 2.32 and 2.20 (s, 1H), 1.8-2.0 and 1.4-1.6 (m, 1H), 1.0-1.1 (m, 2H), 0.8-0.9 and 0.65-0.8 (m, 2H). |
| 7-106 | (A) δ 7.95 (s, 1H), 7.85 (s, 1H), 7.64 (d, J = 7.8 Hz, 2H), 7.39 (d, J = 7.8 Hz, 2H), 6.0-6.15 and 5.5-5.6 (m, 1H), 3.9-4.4 (m, 2H), 4.16 (d, J = 17.4 Hz, 1H), 3.72 (d, J = 17.4 Hz, 1H), 2.23 (bs, 1H), 1.75-1.9 (m, 1H), 1.60 (bs, 3H), 1.05-1.15 (m, 2H), 0.85-1.0 (m, 2H). |
| 7-107 | (A) δ 8.08 (s, 2H), 7.97 (s, 1H), 7.78 and 7.67 (d, J = 1.8 Hz, 1H), 7.5-7.6 (m, 1H), 7.2-7.35 (m, 1H), 4.72 and 4.60 (s, 2H), 4.20 and 4.18 (d, J = 17.4 Hz, 1H), 3.76 and 3.74 (d, J = 17.4 Hz, 1H), 3.44 and 3.35 (q, J = 7.2 Hz, 2H), 2.05-2.3 (m, 3H), 1.19 and 1.15 (t, J = 7.2 Hz, 3H), 1.00 and 0.91 (d, J = 6.3 Hz, 6H). |
| 7-108 | (A) δ 8.08 (s, 2H), 7.97 (s, 1H), 7.77 and 7.67 (d, J = 1.8 Hz, 1H), 7.5-7.6 (m, 1H), 7.28 and 7.18 (d, J = 8.4 Hz, 1H), 4.73 and 4.60 (s, 2H), 4.20 and 4.17 (d, J = 17.4 Hz, 1H), 3.76 and 3.74 (d, J = 17.4 Hz, 1H), 3.34 and 3.22 (t, J = 7.5 Hz, 2H), 2.2-2.35 (m, 1H), 2.35-2.25 and 2.05-2.15 (m, 2H), 1.5-1.7 (m, 2H), 1.00 and 0.91 (d, J = 7.2 Hz, 6H), 0.92 (t, J = 7.5 Hz, 3H). |
| 7-109 | (A) δ 8.08 (s, 2H), 7.98 (s, 1H), 7.81 (s, 1H), 7.55-7.8 (m, 1H), 7.2-7.3 (m, 1H), 4.78 (s, 2H), 4.32 (s, 2H), 4.20 (d, J = 17.4 Hz, 1H), 3.76 (d, J = 17.4 Hz, 1H), 2.2-2.4 (m, 3H), 1.01 and 0.97 (t, J = 6.9 Hz, 6H). |

TABLE 16-continued

| No. | $^1$H NMR |
|---|---|
| 7-110 | (A) δ 8.08 (s, 2H), 7.97 (s, 1H), 7.78 and 7.68 (d, J = 1.5 Hz, 1H), 7.5-7.6 (m, 1H), 7.28 and 7.25 (d, J = 7.8 Hz, 1H), 4.82 and 4.77 (s, 2H), 4.20 and 4.18 (d, J = 17.4 Hz, 1H), 4.27 and 4.04 (d, J = 2.4 Hz, 2H), 3.76 and 3.74 (d, J = 17.4 Hz, 1H), 2.29 and 2.20 (t, J = 2.4 Hz, 1H), 2.15-2.3 (m, 1H), 2.38 and 2.13 (d, J = 6.6 Hz, 2H), 1.01 and 0.92 (d, J = 6.3 Hz, 6H). |
| 7-112 | (A) δ 8.07 (s, 2H), 7.97 (s, 1H), 7.75 and 7.67 (s, 1H), 7.5-7.6 (m, 1H), 7.3-7.4 and 7.2-7.25 (m, 1H), 5.65-5.9 (m, 1H), 5.1-5.3 (m, 2H), 4.72 and 4.56 (s, 2H), 4.19 and 4.17 (d, J = 17.4 Hz, 1H), 4.03 and 3.88 (d, J = 4.8 Hz, 2H), 3.73 and 3.72 (d, J = 17.4 Hz, 1H), 2.35 and 2.20 (d, J = 6.6 Hz, 2H), 1.1-1.2 (m, 1H), 0.5-0.7 (m, 2H), 0.05-0.25 (m, 2H). |
| 7-113 | (A) δ 8.08 (s, 2H), 7.97 (s, 1H), 7.55-7.8 (m, 2H), 7.1-7.45 (m, 6H), 4.73 and 4.62 (s, 2H), 4.52 (s, 2H), 4.19 and 4.17 (d, J = 17.4 Hz, 1H), 3.75 and 3.73 (d, J = 17.4 Hz, 1H), 2.41 and 2.25 (d, J = 6.6 Hz, 2H), 1.05-1.25 (m, 1H), 0.5-0.7 (m, 2H), 0.05-0.25 (m, 2H). |
| 7-115 | (A) δ 8.08 (s, 2H), 7.98 (s, 1H), 7.80 (d, J = 1.8 Hz, 1H), 7.55-7.65 (m, 1H), 7.38 and 7.36 (s, 1H), 4.61 (s, 2H), 4.54 (t, J = 5.4 Hz, 1H), 4.34 (s, 2H), 4.19 (d, J = 17.4 Hz, 1H), 3.75 (d, J = 17.4 Hz, 1H), 3.28 (qd, J = 7.2, 5.4 Hz, 2H), 1.10 (t, J = 7.2 Hz, 3H). |
| 7-116 | (A) δ 8.07 (s, 2H), 7.96 (s, 1H), 7.68 (d, J = 1.5 Hz, 1H), 7.5 and 7.6 (m, 1H), 7.35-7.45 (m, 1H), 5.7-5.9 (m, 1H), 5.15-5.35 (m, 2H), 4.61 (s, 2H), 4.42 (t, J = 4.8 Hz, 1H), 4.17 (d, J = 17.4 Hz, 1H), 3.85 (d, J = 4.8 Hz, 2H), 3.73 (d, J = 17.4 Hz, 1H), 3.26 (qd, J = 7.2, 4.8 Hz, 2H), 1.11 (t, J = 7.2 Hz, 3H). |
| 7-118 | (A) δ 8.07 (s, 2H), 7.97 (s, 1H), 7.57 (s, 1H), 7.25-7.55 (m, 3H), 5.28 and 4.84 (s, 2H), 4.16 (d, J = 17.4 Hz, 1H), 3.71 (d, J = 17.4 Hz, 1H), 3.75 and 3.25 (d, J = 7.2 Hz, 2H), 2.65-2.85 (m, 1H), 0.9-1.15 (m, 1H), 0.75-0.9 (m, 2H), 0.45-0.7 (m, 4H), 0.15-0.3 (m, 2H). |
| 8-003 | (A) δ 7.8-8.5 (m, 4H), 7.50 (s, 2H), 7.45 (s, 1H), 4.09 (d, J = 17.4 Hz, 1H), 3.72 (d, J = 17.4 Hz, 1H), 1.45-1.55 (m, 1H), 1.15-1.3 and 1.55-1.8 (m, 1H), 0.7-1.2 (m, 8H). |
| 8-004 | (A) δ 8.25 and 8.37 (d, J = 2.1 Hz, 1H), 7.85-7.95 (m, 2H), 7.50 (s, 2H), 7.41 (t, J = 1.5 Hz, 1H), 6.72 and 6.91 (d, J = 8.7 Hz, 1H), 4.01 and 4.05 (d, J = 17.4 Hz, 1H), 3.63 and 3.66 (d, J = 17.4 Hz, 1H), 3.38 and 3.49 (s, 3H), 1.45-1.55 and 1.75-1.85 (m, 1H), 1.05-1.15 (m, 2H), 0.85-0.95 (m, 2H). |
| 8-005 | (A) δ 7.60 (d, J = 8.1 Hz, 2H), 7.50 (s, 2H), 7.42 (s, 1H), 7.25 (d, J = 8.1 Hz, 2H), 5.92 (bs, 1H), 4.07 (d, J = 17.4 Hz, 1H), 3.67 (d, J = 17.4 Hz, 1H), 3.55 (q, J = 6.3 Hz, 2H), 3.01 (q, J = 10.8 Hz, 2H), 2.8-2.9 (m, 2H). |
| 8-006 | (A) δ 7.65 (d, J = 1.5 Hz, 1H), 7.56 (dd, J = 8.1, 1.5 Hz, 1H), 7.45-7.5 (m, 3H), 7.43 (t, J = 1.5 Hz, 1H), 6.94 (s, 1H), 5.00 (bs, 1H), 4.11 (s, 2H), 4.06 (d, J = 17.4 Hz, 1H), 3.67 (d, J = 17.4 Hz, 1H), 2.2-2.35 (m, 1H), 1.12 (d, J = 7.2 Hz, 6H). |
| 8-007 | (A) δ 7.69 (s, 1H), 7.45-7.55 (m, 4H), 7.43 (t, J = 1.5 Hz, 1H), 7.35 (bs, 1H), 4.05 (d, J = 17.4 Hz, 1H), 3.67 (d, J = 17.4 Hz, 1H), 2.3-2.45 (m, 1H), 1.75-1.9 (m, 1H), 1.15 (d, J = 7.2 Hz, 6H), 1.0-1.1 (m, 2H), 0.75-0.85 (m, 2H). |
| 8-009 | (A) δ 7.59 (d, J = 8.7 Hz, 2H), 7.50 (d, J = 1.5 Hz, 2H), 7.40 (t, J = 1.5 Hz, 1H), 7.06 (d, J = 8.7 Hz, 2H), 4.05 (d, J = 17.4 Hz, 1H), 3.66 (d, J = 17.4 Hz, 1H), 3.15-3.3 (m, 2H), 1.55-1.7 (m, 2H), 1.35-1.45 (m, 2H), 0.9-1.4 (m, 12H). |
| 8-010 | (C) δ 7.56 and 7.62 (d, J = 8.5 Hz, 2H), 7.50 (d, J = 1.5 Hz, 2H), 7.40 (t, J = 1.5 Hz, 1H), 7.2-7.3 (m, 2H), 6.11 and 6.31 (s, 1H), 4.04 and 4.07 (d, J = 17.5 Hz, 1H), 3.65 and 3.67 (d, J = 17.5 Hz, 1H), 1.65-1.75 and 1.25-1.55 (m, 5H), 0.95-1.05 (m, 2H), 0.65-0.8 (m, 2H). |
| 8-014 | (A) δ 7.55 (d, J = 9.0 Hz, 2H), 7.49 (bs, 2H), 7.40 (t, J = 2.1 Hz, 1H), 7.23 (d, J = 9.0 Hz, 2H), 6.17 (bs, 1H), 4.04 (d, J = 17.4 Hz, 1H), 3.65 (d, J = 17.4 Hz, 1H), 2.3-2.4 (m, 1H), 1.25-1.35 (m, 4H), 1.16 (d, J = 6.6 Hz, 6H). |
| 8-015 | (A) δ 7.56 (d, J = 8.4 Hz, 2H), 7.50 (d, J = 1.5 Hz, 2H), 7.41 (t, J = 1.8 Hz, 1H), 7.24 (d, J = 8.4 Hz, 2H), 6.55 (s, 1H), 4.05 (d, J = 17.4 Hz, 1H), 3.65 (d, J = 17.4 Hz, 1H), 2.20 (d, J = 6.8 Hz, 2H), 1.35 (s, 4H), 0.95-1.05 (m, 1H), 0.6-0.65 (m, 2H), 0.2-0.25 (m, 2H). |
| 8-016 | (A) δ 7.57 (d, J = 8.4 Hz, 2H), 7.50 (d, J = 1.5 Hz, 2H), 7.46 (s, 1H), 7.40 (t, J = 1.5 Hz, 1H), 7.27 (d, J = 8.4 Hz, 2H), 4.05 (d, J = 17.7 Hz, 1H), 3.65 (d, J = 17.7 Hz, 1H), 3.20 (s, 2H), 2.10 (s, 3H), 1.30 (bs, 4H). |
| 8-017 | (A) δ 8.1-8.15 (m, 1H), 7.81 (d, J = 8.4 Hz, 2H), 7.49 (d, J = 1.5 Hz, 2H), 7.40 (t, J = 1.8 Hz, 1H), 7.32 (d, J = 8.4 Hz, 2H), 6.95-7.05 (m, 1H), 6.85-6.9 (m, 1H), 4.05 (d, J = 17.4 Hz, 1H), 3.65 (d, J = 17.4 Hz, 1H), 1.45 (bs, 4H). |
| 8-020 | (A) δ 7.70 (d, J = 8.7 Hz, 2H), 7.64 (s, 2H), 7.61 (d, J = 8.7 Hz, 2H), 6.19 (s, 1H), 4.06 (d, J = 17.4 Hz, 1H), 3.66 (d, J = 17.4 Hz, 1H), 1.94 (s, 3H), 1.35-1.5 (m, 1H), 0.7-1.1 (m, 4H). |

TABLE 16-continued

| No. | ¹H NMR |
|---|---|
| 9-002 | (A) δ 7.65 (d, J = 8.1 Hz, 2H), 7.45-7.55 (m, 4H), 7.42 (t, J = 1.5 Hz, 1H), 5.20 (bs, 1H), 4.09 (d, J = 17.4 Hz, 1H), 3.91 (s, 2H), 3.68 (d, J = 17.4 Hz, 1H), 2.48 (s, 3H). |
| 9-003 | (A) δ 7.62 (d, J = 8.1 Hz, 2H), 7.51 (d, J = 1.5 Hz, 2H), 7.35-7.45 (m, 3H), 4.09 (d, J = 17.4 Hz, 1H), 3.84 (s, 2H), 3.68 (d, J = 17.4 Hz, 1H), 2.67 (q, J = 6.9 Hz, 2H), 1.14 (t, J = 6.9 Hz, 3H). |
| 9-004 | (A) δ 7.62 (d, J = 8.1 Hz, 2H), 7.51 (d, J = 1.5 Hz, 2H), 7.46 (s, 1H), 7.4-7.45 (m, 2H), 4.07 (d, J = 17.4 Hz, 1H), 3.85 (s, 2H), 3.68 (d, J = 17.4 Hz, 1H), 2.8-2.95 (m, 1H), 1.14 (d, J = 6.6 Hz, 6H). |
| 9-005 | (B) δ 8.56 (d, J = 4.8 Hz, 1H), 7.6-7.7 (m, 3H), 7.50 (s, 2H), 7.4-7.5 (m, 2H), 7.25-7.35 (m, 2H), 7.15-7.25 (m, 1H), 4.08 (d, J = 17.4 Hz, 1H), 3.92 (s, 2H), 3.89 (s, 2H), 3.68 (d, J = 17.4 Hz, 1H). |
| 9-006 | (A) δ 7.62 (d, J = 8.1 Hz, 2H), 7.51 (d, J = 1.5 Hz, 2H), 7.4-7.5 (m, 3H), 6.8-6.95 (m, 2H), 6.45-6.6 (m, 2H), 4.35 (s, 2H), 4.07 (d, J = 17.4 Hz, 1H), 3.68 (d, J = 17.4 Hz, 1H). |
| 9-007 | (A) δ 7.62 (d, J = 8.1 Hz, 2H), 7.51 (d, J = 1.5 Hz, 2H), 7.35-7.45 (m, 3H), 4.1-4.2 (m, 1H), 4.09 (d, J = 17.4 Hz, 1H), 3.68 (d, J = 17.4 Hz, 1H), 1.38 (d, J = 6.6 Hz, 3H). |
| 9-008 | (A) δ 7.63 (d, J = 8.1 Hz, 2H), 7.50 (d, J = 1.5 Hz, 2H), 7.35-7.45 (m, 3H), 4.75-4.85 (m, 1H), 4.15-4.3 (m, 2H), 4.07 (d, J = 17.4 Hz, 1H), 3.6-3.8 (m, 3H), 1.47 (d, J = 6.9 Hz, 3H). |
| 9-009 | (A) δ 7.62 (d, J = 8.1 Hz, 2H), 7.51 (d, J = 1.5 Hz, 2H), 7.41 (t, J = 1.5 Hz, 1H), 7.38 (d, J = 8.1 Hz, 2H), 4.09 (d, J = 17.4 Hz, 1H), 3.86 (t, J = 6.9 Hz, 1H), 3.68 (d, J = 17.4 Hz, 1H), 1.6-1.75 (m, 2H), 0.86 (t, J = 7.2 Hz, 3H). |
| 9-010 | (A) δ 7.35-7.55 (m, 6H), 4.05 (d, J = 17.4 Hz, 1H), 3.96 (s, 2H), 3.67 (d, J = 17.4 Hz, 1H). |
| 9-011 | (A) δ 7.66 (d, J = 1.5 Hz, 1H), 7.4-7.6 (m, 5H), 4.06 (d, J = 17.4 Hz, 1H), 3.99 (s, 2H), 3.67 (d, J = 17.4 Hz, 1H). |
| 9-012 | (A) δ 7.66 (d, J = 1.5 Hz, 1H), 7.54 (dd, J = 8.1, 1.5 Hz, 1H), 7.45-7.55 (m, 3H), 7.43 (t, J = 1.5 Hz, 1H), 4.06 (d, J = 17.4 Hz, 1H), 3.91 (s, 2H), 3.67 (d, J = 17.4 Hz, 1H), 2.68 (q, J = 7.2 Hz, 2H), 1.15 (t, J = 7.2 Hz, 3H). |
| 9-013 | (A) δ 7.71 (d, J = 1.5 Hz, 1H), 7.67 (bs, 1H), 7.56 (dd, J = 8.1, 1.5 Hz, 1H), 7.50 (s, 2H), 7.43 (t, J = 1.5 Hz, 1H), 7.38 (d, J = 8.1 Hz, 1H), 4.07 (d, J = 17.4 Hz, 1H), 3.85-4.0 (m, 4H), 3.68 (d, J = 17.4 Hz, 1H), 3.36 (s, 2H). |
| 9-014 | (A) δ 7.67 (d, J = 1.5 Hz, 1H), 7.54 (dd, J = 8.1, 1.5 Hz, 1H), 7.45-7.55 (m, 3H), 7.43 (t, J = 1.5 Hz, 1H), 5.90 (bs, 1H), 4.18 (s, 2H), 4.06 (d, J = 17.4 Hz, 1H), 3.68 (d, J = 17.4 Hz, 1H), 3.51 (s, 3H). |
| 9-015 | (A) δ 7.65 (d, J = 1.5 Hz, 1H), 7.54 (dd, J = 8.1, 1.5 Hz, 1H), 7.45-7.55 (m, 3H), 7.42 (t, J = 1.5 Hz, 1H), 5.78 (bs, 1H), 4.17 (s, 2H), 4.05 (d, J = 17.4 Hz, 1H), 3.6-3.75 (m, 3H), 1.12 (t, J = 6.9 Hz, 3H). |
| 9-018 | (A) δ 7.84 (d, J = 1.5 Hz, 1H), 7.62 (dd, J = 8.1, 1.5 Hz, 1H), 7.45-7.55 (m, 3H), 7.43 (t, J = 1.5 Hz, 1H), 4.06 (d, J = 17.4 Hz, 1H), 3.99 (s, 2H), 3.67 (d, J = 17.4 Hz, 1H). |
| 9-020 | (A) δ 7.35-7.55 (m, 6H), 4.08 (d, J = 17.4 Hz, 1H), 3.90 (s, 2H), 3.68 (d, J = 17.4 Hz, 1H), 2.35 (s, 3H). |
| 9-021 | (A) δ 8.19 (d, J = 1.5 Hz, 1H), 7.98 (dd, J = 7.8, 1.5 Hz, 1H), 7.78 (d, J = 7.8 Hz, 1H), 7.51 (d, J = 1.5 Hz, 2H), 7.44 (t, J = 1.5 Hz, 1H), 4.18 (s, 2H), 4.11 (d, J = 17.4 Hz, 1H), 3.73 (d, J = 17.4 Hz, 1H). |
| 9-022 | (A) δ 7.66 (d, J = 1.5 Hz, 1H), 7.64 (s, 2H), 7.56 (dd, J = 7.8, 1.5 Hz, 1H), 7.50 (d, J = 7.8 Hz, 1H), 4.07 (d, J = 17.4 Hz, 1H), 3.98 (s, 2H), 3.67 (d, J = 17.4 Hz, 1H). |
| 9-023 | (A) δ 7.66 (d, J = 1.5 Hz, 1H), 7.54 (dd, J = 8.1, 1.5 Hz, 1H), 7.50 (d, J = 1.5 Hz, 2H), 7.47 (d, J = 8.1 Hz, 1H), 7.42 (t, J = 1.5 Hz, 1H), 4.06 (d, J = 17.4 Hz, 1H), 3.87 (s, 2H), 3.67 (d, J = 17.4 Hz, 1H), 2.46 (s, 3H). |
| 9-024 | (A) δ 7.65 (d, J = 1.5 Hz, 1H), 7.4-7.55 (m, 5H), 4.07 (d, J = 17.4 Hz, 1H), 3.96 (s, 2H), 3.67 (d, J = 17.4 Hz, 1H), 2.05-2.15 (m, 1H), 0.35-0.5 (m, 4H). |
| 9-025 | (A) δ 7.65 (d, J = 1.5 Hz, 1H), 7.45-7.55 (m, 4H), 7.42 (t, J = 1.5 Hz, 1H), 4.07 (d, J = 17.4 Hz, 1H), 3.93 (s, 2H), 3.68 (d, J = 17.4 Hz, 1H), 2.48 (d, J = 6.9 Hz, 2H), 0.95-1.05 (m, 1H), 0.45-0.55 (m, 2H), 0.05-0.15 (m, 2H). |
| 9-027 | (A) δ 7.65 (s, 1H), 7.45-7.55 (m, 4H), 7.42 (t, J = 1.5 Hz, 1H), 4.06 (d, J = 17.4 Hz, 1H), 3.93 (s, 2H), 3.67 (d, J = 17.4 Hz, 1H), 3.52 (t, J = 5.1 Hz, 2H), 3.36 (s, 3H), 2.81 (t, J = 5.1 Hz, 2H). |
| 9-029 | (A) δ 7.87 (d, J = 2.4 Hz, 1H), 7.75 (s, 1H), 7.54 (dd, J = 9.6, 2.4 Hz, 1H), 7.45-7.55 (m, 4H), 7.25-7.45 (m, 2H), 6.58 (d, J = 9.6 Hz, 1H), 4.65 (s, 2H), 4.04 (d, J = 17.4 Hz, 1H), 3.66 (d, J = 17.4 Hz, 1H). |
| 9-030 | (A) δ 8.08 (d, J = 1.5 Hz, 1H), 7.63 (dd, J = 8.1, 1.5 Hz, 1H), 7.50 (d, J = 1.5 Hz, 2H), 7.45 (d, J = 8.1 Hz, 2H), 7.44 (t, J = 1.5 Hz, 1H), 4.05 (d, J = 17.4 Hz, 1H), 3.82 (s, 2H), 3.67 (d, J = 17.4 Hz, 1H), 3.47 (q, J = 7.2 Hz, 2H), 1.15 (t, J = 7.2 Hz, 3H). |

TABLE 16-continued

| No. | $^1$H NMR |
|---|---|
| 9-032 | (A) δ 8.07 (s, 2H), 7.96 (s, 1H), 7.67 (d, J = 1.5 Hz, 1H), 7.57 (dd, J = 8.1, 1.5 Hz, 1H), 7.50 (d, J = 8.1 Hz, 1H), 4.18 (d, J = 17.4 Hz, 1H), 3.98 (s, 2H), 3.72 (d, J = 17.4 Hz, 1H). |
| 9-033 | (A) δ 7.83 (d, J = 1.5 Hz, 1H), 7.63 (s, 2H), 7.60 (dd, J = 8.1, 1.5 Hz, 1H), 7.49 (d, J = 8.1 Hz, 1H), 4.06 (d, J = 17.4 Hz, 1H), 3.95 (s, 2H), 3.66 (d, J = 17.4 Hz, 1H). |
| 9-034 | (A) δ 8.18 (s, 1H), 7.97 (d, J = 8.4 Hz, 1H), 7.78 (d, J = 8.4 Hz, 1H), 7.64 (s, 2H), 4.18 (s, 2H), 4.11 (d, J = 17.4 Hz, 1H), 3.73 (d, J = 17.4 Hz, 1H). |
| 9-035 | (A) δ 8.85-9.0 (m, 1H), 8.05-8.2 (m, 1H), 7.55-7.7 (m, 2H), 7.55 (s, 2H), 7.45-7.55 (m, 2H), 7.43 (t, J = 1.8 Hz, 1H), 4.37 (s, 2H), 4.26 (d, J = 17.4 Hz, 1H), 3.98 (d, J = 17.4 Hz, 1H). |
| 9-036 | (A) δ 8.00 (d, J = 7.8 Hz, 1H), 7.82 (s, 1H), 7.64 (s, 2H), 7.62 (d, J = 7.8 Hz, 1H), 4.29 (s, 2H), 4.09 (d, J = 17.4 Hz, 1H), 3.74 (d, J = 17.4 Hz, 1H), 2.59 (s, 3H). |
| 9-038 | (A) δ 7.6-7.65 (m, 3H), 7.45-7.55 (m, 2H), 4.07 (d, J = 17.1 Hz, 1H), 3.90 (s, 2H), 3.67 (d, J = 17.1 Hz, 1H), 2.59 (t, J = 7.2 Hz, 2H), 1.54 (sxt, J = 7.2 Hz, 2H), 0.93 (t, J = 7.2 Hz, 3H). |
| 9-039 | (A) δ 7.64 (s, 1H), 7.63 (s, 2H), 7.45-7.55 (m, 2H), 4.06 (d, J = 17.1 Hz, 1H), 3.90 (s, 2H), 3.66 (d, J = 17.1 Hz, 1H), 2.62 (t, J = 7.2 Hz, 2H), 1.3-1.55 (m, 4H), 0.91 (t, J = 7.2 Hz, 3H). |
| 9-040 | (A) δ 7.64 (s, 1H), 7.63 (s, 2H), 7.54 (d, J = 9.0 Hz, 1H), 7.50 (d, J = 9.0 Hz, 1H), 4.06 (d, J = 17.1 Hz, 1H), 3.93 (s, 2H), 3.66 (d, J = 17.1 Hz, 1H), 2.48 (d, J = 6.9 Hz, 2H), 0.9-1.05 (m, 1H), 0.45-0.55 (m, 2H), 0.05-0.15 (m, 2H). |
| 9-041 | (A) δ 7.65 (s, 1H), 7.45-7.6 (m, 4H), 7.42 (t, J = 1.5 Hz, 1H), 4.05 (d, J = 17.4 Hz, 1H), 3.93 (s, 2H), 3.68 (d, J = 17.4 Hz, 1H), 2.83 (t, J = 6.0 Hz, 2H), 2.69 (t, J = 6.0 Hz, 2H), 2.08 (s, 3H). |
| 9-042 | (A) δ 7.66 (s, 1H), 7.63 (s, 2H), 7.53 (s, 2H), 4.06 (d, J = 17.1 Hz, 1H), 4.01 (s, 2H), 3.66 (d, J = 17.1 Hz, 1H), 3.46 (d, J = 2.4 Hz, 2H), 2.28 (t, J = 2.4 Hz, 1H). |
| 9-043 | (A) δ 7.65 (s, 1H), 7.45-7.55 (m, 4H), 7.40 (s, 1H), 7.2-7.35 (m, 2H), 6.95-7.05 (m, 2H), 4.07 (d, J = 17.4 Hz, 1H), 3.90 (s, 2H), 3.76 (s, 2H), 3.67 (d, J = 17.4 Hz, 1H), 1.81 (s, 1H). |
| 9-044 | (A) δ 7.75 (d, J = 1.5 Hz, 1H), 7.64 (s, 2H), 7.59 (dd, J = 7.8, 1.5 Hz, 1H), 7.51 (d, J = 7.8 Hz, 1H), 4.35 (d, J = 6.0 Hz, 2H), 4.05 (d, J = 17.4 Hz, 1H), 4.01 (bs, 1H), 3.68 (d, J = 17.4 Hz, 1H). |
| 9-045 | (A) δ 8.10 (d, J = 7.8 Hz, 1H), 7.87 (s, 1H), 7.66 (d, J = 7.8 Hz, 1H), 7.64 (s, 2H), 5.20 (s, 2H), 4.09 (d, J = 17.4 Hz, 1H), 3.73 (d, J = 17.4 Hz, 1H), 3.57 (s, 6H). |
| 9-047 | (A) δ 7.62 (d, J = 8.1 Hz, 2H), 7.52 (d, J = 1.5 Hz, 2H), 7.39 (d, J = 8.1 Hz, 2H), 7.41 (t, J = 1.5 Hz, 1H), 4.10 (d, J = 17.1 Hz, 1H), 3.75-3.85 (m, 1H), 3.70 (d, J = 17.1 Hz, 1H), 2.45-2.55 (m, 2H), 1.35 (d, J = 6.6 Hz, 3H), 1.05 (t, J = 6.9 Hz, 3H). |
| 9-048 | (A) δ 7.72 (d, J = 8.4 Hz, 2H), 7.64 (s, 2H), 7.63 (d, J = 8.4 Hz, 2H), 4.95 (s, 1H), 4.09 (d, J = 17.4 Hz, 1H), 3.69 (d, J = 17.4 Hz, 1H). |
| 9-049 | (A) δ 7.91 (d, J = 1.5 Hz, 1H), 7.73 (dd, J = 8.4, 1.5 Hz, 1H), 7.67 (d, J = 1.5 Hz, 1H), 7.61 (d, J = 8.4 Hz, 1H), 7.56 (dd, J = 8.1, 1.5 Hz, 1H), 7.50 (d, J = 8.1 Hz, 1H), 4.11 (d, J = 17.4 Hz, 1H), 3.97 (s, 2H), 3.69 (d, J = 17.4 Hz, 1H). |
| 9-050 | (A) δ 7.66 (d, J = 1.8 Hz, 1H), 7.64 (s, 2H), 7.56 (dd, J = 7.8, 1.8 Hz, 1H), 7.50 (d, J = 7.8 Hz, 1H), 6.61 (t, J = 73.5 Hz, 1H), 4.08 (d, J = 17.4 Hz, 1H), 3.98 (s, 2H), 3.68 (d, J = 17.4 Hz, 1H). |
| 9-051 | (A) δ 8.08 (s, 2H), 7.97 (s, 1H), 7.69 (d, J = 1.5 Hz, 1H), 7.56 (dd, J = 7.8, 1.5 Hz, 1H), 7.50 (d, J = 7.8 Hz, 1H), 4.19 (d, J = 17.4 Hz, 1H), 3.88 (s, 2H), 3.73 (d, J = 17.4 Hz, 1H), 2.47 (s, 3H). |
| 9-052 | (A) δ 8.08 (s, 2H), 7.97 (s, 1H), 7.68 (d, J = 1.5 Hz, 1H), 7.55 (dd, J = 8.1, 1.5 Hz, 1H), 7.51 (d, J = 8.1 Hz, 1H), 4.18 (d, J = 17.4 Hz, 1H), 3.92 (s, 2H), 3.73 (d, J = 17.4 Hz, 1H), 2.68 (q, J = 7.2 Hz, 2H), 1.15 (t, J = 7.2 Hz, 3H). |
| 9-053 | (A) δ 8.07 (s, 2H), 7.96 (s, 1H), 7.68 (d, J = 1.8 Hz, 1H), 7.45-7.6 (m, 2H), 4.18 (d, J = 17.4 Hz, 1H), 3.91 (s, 2H), 3.73 (d, J = 17.4 Hz, 1H), 2.59 (t, J = 7.2 Hz, 2H), 1.53 (qui, J = 7.2 Hz, 2H), 1.48 (bs, 1H), 0.93 (t, J = 7.2 Hz, 3H). |
| 9-054 | (A) δ 8.07 (s, 2H), 7.96 (s, 1H), 7.67 (d, J = 1.5 Hz, 1H), 7.5-7.6 (m, 2H), 4.18 (d, J = 17.4 Hz, 1H), 3.93 (s, 2H), 3.73 (d, J = 17.4 Hz, 1H), 2.49 (d, J = 6.9 Hz, 2H), 1.60 (bs, 1H), 0.9-1.05 (m, 1H), 0.45-0.55 (m, 2H), 0.05-0.15 (m, 2H). |
| 9-055 | (A) δ 8.07 (s, 2H), 7.96 (s, 1H), 7.68 (d, J = 1.5 Hz, 1H), 7.5-7.6 (m, 2H), 4.18 (d, J = 17.4 Hz, 1H), 4.01 (s, 2H), 3.73 (d, J = 17.4 Hz, 1H), 3.46 (d, J = 2.4 Hz, 2H), 2.28 (t, J = 2.4 Hz, 1H), 1.61 (bs, 1H). |
| 9-056 | (A) δ 7.94 (s, 1H), 7.83 (s, 1H), 7.67 (s, 1H), 7.5-7.6 (m, 2H), 4.12 (d, J = 17.4 Hz, 1H), 3.97 (s, 2H), 3.68 (d, J = 17.4 Hz, 1H), 2.74 (q, J = 7.2 Hz, 2H), 1.20 (t, J = 7.2 Hz, 3H). |
| 9-058 | (A) δ 8.08 (s, 2H), 7.96 (s, 1H), 7.67 (d, J = 1.8 Hz, 1H), 7.5-7.6 (m, 2H), 4.19 (d, J = 17.4 Hz, 1H), 3.90 (s, 2H), 3.75 (d, J = 17.4 Hz, 1H), 2.42 (d, J = 6.6 Hz, 2H), 1.77 (sep, J = 6.6 Hz, 1H), 0.92 (d, J = 6.6 Hz, 6H). |

TABLE 16-continued

| No. | ¹H NMR |
|---|---|
| 9-059 | (A) δ 7.67 (bs, 1H), 7.4-7.6 (m, 5H), 6.02 (bs, 1H), 4.06 (d, J = 17.4 Hz, 1H), 3.91 (s, 2H), 3.67 (d, J = 17.4 Hz, 1H), 3.36 (dd, J = 11.4, 5.7 Hz, 2H), 2.76 (t, J = 6.3 Hz, 2H), 1.99 (s, 3H). |
| 9-060 | (A) δ 7.97 (s, 1H), 7.8-7.9 (m, 2H), 7.80 (s, 1H), 7.55-7.7 (m, 1H), 7.4-7.5 (m, 1H), 5.96 (bs, 1H), 4.09 (d, J = 17.4 Hz, 1H), 3.89 (s, 2H), 3.70 (d, J = 17.4 Hz, 1H), 3.36 (dd, J = 11.4, 5.7 Hz, 2H), 2.7-2.85 (m, 2H), 1.96 (s, 3H). |
| 9-061 | (A) δ 7.67 (bs, 1H), 7.4-7.6 (m, 5H), 4.87 (bs, 1H), 4.06 (d, J = 17.4 Hz, 1H), 3.91 (s, 2H), 3.67 (d, J = 17.4 Hz, 1H), 3.25 (dd, J = 11.4, 5.7 Hz, 2H), 2.75 (t, J = 6.3 Hz, 2H), 1.44 (s, 9H). |
| 9-064 | (A) δ 8.08 (s, 2H), 7.97 (s, 1H), 7.68 (d, J = 0.9 Hz, 1H), 7.5-7.6 (m, 2H), 4.18 (d, J = 17.4 Hz, 1H), 3.94 (s, 2H), 3.74 (s, 3H), 3.73 (d, J = 17.4 Hz, 1H), 3.45 (s, 2H), 1.98 (bs, 1H). |
| 9-065 | (A) δ 8.09 (s, 2H), 7.97 (s, 1H), 7.68 (d, J = 1.8 Hz, 1H), 7.5-7.6 (m, 2H), 5.92 (ddt, J = 17.4, 10.5, 6.0 Hz, 1H), 5.1-5.3 (m, 2H), 4.21 (d, J = 17.4 Hz, 1H), 3.91 (s, 2H), 3.77 (d, J = 17.4 Hz, 1H), 3.28 (d, J = 6.0 Hz, 2H), 1.67 (bs, 1H). |
| 9-066 | (A) δ 7.94 (d, J = 1.5 Hz, 1H), 7.83 (s, 1H), 7.76 (s, 1H), 7.5-7.6 (m, 2H), 5.92 (ddt, J = 17.4, 10.5, 6.0 Hz, 1H), 5.1-5.3 (m, 2H), 4.12 (d, J = 17.4 Hz, 1H), 3.91 (s, 2H), 3.69 (d, J = 17.4 Hz, 1H), 3.28 (d, J = 6.0 Hz, 2H), 1.53 (bs, 1H). |
| 9-070 | (A) δ 7.64 (d, J = 7.8 Hz, 1H), 7.45-7.6 (m, 4H), 7.42 (t, J = 4.5 Hz, 1H), 5.02 (bs, 1H), 4.08 (d, J = 17.4 Hz, 1H), 3.69 (d, J = 17.4 Hz, 1H), 2.48 (s, 3H), 1.91 (bs, 2H). |
| 9-071 | (A) δ 7.60 (m, 2H), 7.45-7.5 (m, 4H), 7.4-7.45 (m, 1H), 6.97 (bs, 1H), 5.58 (bs, 1H), 4.58 (s, 1H), 4.07 (d, J = 17.4 Hz, 1H), 3.67 (d, J = 17.4 Hz, 1H), 1.77 (bs, 2H). |
| 11-002 | (A) δ 7.75-7.85 (m, 2H), 7.65-7.75 (m, 2H), 7.63 (d, J = 8.1 Hz, 2H), 7.45-7.6 (m, 4H), 5.58 (q, J = 7.5 Hz, 1H), 5.1-5.25 (m, 1H), 4.05 (d, J = 17.4 Hz, 1H), 3.66 (d, J = 17.4 Hz, 1H), 1.91 (d, J = 6.6 Hz, 3H). |
| 11-003 | (A) δ 7.75-7.85 (m, 2H), 7.65-7.75 (m, 2H), 7.55-7.65 (m, 4H), 7.49 (d, J = 1.5 Hz, 2H), 7.41 (t, J = 1.5 Hz, 1H), 5.26 (dd, J = 6.9, 6.6 Hz, 1H), 4.05 (d, J = 17.4 Hz, 1H), 3.66 (d, J = 17.4 Hz, 1H), 2.45-2.65 (m, 1H), 2.25-2.45 (m, 1H), 0.97 (t, J = 7.2 Hz, 3H). |
| 11-004 | (A) δ 7.8-7.95 (m, 2H), 7.7-7.8 (m, 2H), 7.48 (d, J = 1.5 Hz, 2H), 7.35-7.45 (m, 4H), 4.95 (s, 2H), 4.02 (d, J = 17.4 Hz, 1H), 3.64 (d, J = 17.4 Hz, 1H). |
| 11-005 | (A) δ 7.85-7.95 (m, 2H), 7.75-7.85 (m, 2H), 7.4-7.7 (m, 5H), 7.25-7.35 (m, 1H), 5.00 (s, 2H), 4.03 (d, J = 17.4 Hz, 1H), 3.65 (d, J = 17.4 Hz, 1H). |
| 11-007 | (A) δ 7.7-8.1 (m, 4H), 7.35-7.7 (m, 4H), 7.15-7.35 (m, 2H), 4.98 (s, 2H), 4.03 (d, J = 17.4 Hz, 1H), 3.65 (d, J = 17.4 Hz, 1H). |
| 11-009 | (A) δ 7.8-7.95 (m, 2H), 7.7-7.85 (m, 2H), 7.45-7.55 (m, 3H), 7.35-7.45 (m, 1H), 7.25-7.45 (m, 2H), 4.87 (s, 2H), 4.04 (d, J = 17.4 Hz, 1H), 3.65 (d, J = 17.4 Hz, 1H), 2.51 (s, 3H). |
| 11-011 | (A) δ 7.85-7.95 (m, 2H), 7.75-7.8 (m, 2H), 7.67 (d, J = 1.5 Hz, 1H), 7.62 (s, 2H), 7.50 (dd, J = 7.8, 1.5 Hz, 1H), 7.28 (d, J = 7.8 Hz, 1H), 5.00 (s, 2H), 4.03 (d, J = 17.4 Hz, 1H), 3.64 (d, J = 17.4 Hz, 1H). |
| 11-013 | (A) δ 8.05 (s, 2H), 7.95 (s, 1H), 7.85-7.95 (m, 2H), 7.7-7.8 (m, 2H), 7.68 (d, J = 1.5 Hz, 1H), 7.52 (dd, J = 8.1, 1.5 Hz, 1H), 7.28 (d, J = 8.1 Hz, 1H), 5.00 (s, 2H), 4.14 (d, J = 17.4 Hz, 1H), 3.69 (d, J = 17.4 Hz, 1H). |
| 11-015 | (A) δ 7.8-7.95 (m, 4H), 7.7-7.8 (m, 2H), 7.4-7.5 (m, 4H), 5.10 (s, 2H), 4.04 (d, J = 17.4 Hz, 1H), 3.67 (d, J = 17.4 Hz, 1H). |
| 11-017 | (A) δ 8.07 (s, 2H), 7.94 (s, 1H), 7.75-7.85 (m, 2H), 7.65-7.75 (m, 2H), 7.64 (d, J = 8.4 Hz, 2H), 7.55 (d, J = 8.4 Hz, 2H), 5.58 (q, J = 7.2 Hz, 1H), 4.17 and 4.16 (d, J = 17.4 Hz, 1H), 3.71 (d, J = 17.4 Hz, 1H), 1.92 (d, J = 7.2 Hz, 3H). |
| 11-018 | (A) δ 7.75-7.85 (m, 2H), 7.65-7.75 (m, 2H), 7.62 (s, 2H), 7.61 (d, J = 8.7 Hz, 2H), 7.55 (d, J = 8.7 Hz, 2H), 5.58 (q, 1H), 4.05 and 4.04 (d, J = 17.4 Hz, 1H), 3.65 (d, J = 17.4 Hz, 1H), 1.92 (d, J = 7.5 Hz, 3H). |
| 11-019 | (A) δ 7.85-7.95 (m, 3H), 7.75-7.85 (m, 2H), 7.72 (dd, J = 8.4, 1.5 Hz, 1H), 7.68 (d, J = 1.5 Hz, 1H), 7.60 (d, J = 8.1 Hz, 1H), 7.51 (dd, J = 8.1, 1.5 Hz, 1H), 7.28 (d, J = 8.1 Hz, 1H), 5.00 (s, 2H), 4.08 (d, J = 17.4 Hz, 1H), 3.66 (d, J = 17.4 Hz, 1H). |
| 11-020 | (A) δ 7.85-7.95 (m, 2H), 7.7-7.8 (m, 2H), 7.67 (d, J = 1.8 Hz, 1H), 7.62 (s, 2H), 7.49 (dd, J = 8.1, 1.8 Hz, 1H), 7.27 (d, J = 8.1 Hz, 1H), 6.59 (t, J = 74.1 Hz, 1H), 5.00 (s, 2H), 4.04 (d, J = 17.4 Hz, 1H), 3.64 (d, J = 17.4 Hz, 1H). |
| 11-021 | (A) δ 7.85-7.95 (m, 3H), 7.75-7.85 (m, 3H), 7.68 (d, J = 1.5 Hz, 1H), 7.51 (dd, J = 8.1, 1.5 Hz, 1H), 7.28 (d, J = 8.1 Hz, 1H), 5.00 (s, 2H), 4.09 (d, J = 17.4 Hz, 1H), 3.66 (d, J = 17.4 Hz, 1H). |

Test Examples

Next, usefulness of the compound of the present invention as a pesticide is specifically explained in the following Test Examples to which the present invention is not limited.

Test Example 1

Insecticidal Test Against Cabbage Moth

A 10% emulsifiable concentrate (depending on the compounds, 10% wettable powder was applied for the test) of the compound of the present invention was diluted with water containing a spreading agent to prepare a chemical solution with a concentration of 500 ppm. To the chemical solution was dipped leaves of cabbage for about 10 seconds, and after air-drying, they were placed in a laboratory dish, then 5-cabbage moth (*Plutella xylostella*) in the stage of second instar larva per the dish were released therein, and the dish was covered with a lid and contained at a thermostat chamber at 25° C. A number of dead insect(s) after 6 days was counted and a rate of dead insects was calculated by the following calculation equation. Incidentally, the test was carried out with two districts.

Rate of dead insects (%)=(Number of dead insects/Number of released insects)×100

As a result, the following compounds showed an insecticidal rate of 80% or more among the compounds tested.

The compounds of the present invention: No. 1-001*, 1-002*, 1-003*, 1-004, 1-005*, 1-006*, 1-007*, 1-008*, 1-009, 1-010, 1-011, 1-013 to 1-015, 1-017 to 1-019, 1-020, 1-021, 1-022*, 1-023*, 1-024*, 1-025, 1-026*, 1-027, 1-028*, 1-029*, 1-031, 1-032*, 1-033 to 1-052, 1-053*, 1-054 to 1-061, 1-062*, 1-063, 1-064, 1-065, 1-066, 1-067, 1-068, 1-069, 1-070, 1-071, 1-072, 1-073, 1074, 1-075, 1-076 to 1-078, 1-079*, 1-080 to 1-085, 1-086*, 1-087 to 1-090, 1-091*, 1-092, 1-093, 1-094, 1-095, 1-096, 1-097, 1-098, 1-099 to 1-103, 1-104, 1-105 to 1-114, 1-116*, 1-117, 1-118, 1-119, 2-001*, 2-002*, 2-003, 2-004, 2-005*, 2-006*, 2-007*, 2-008, 2-009*, 2-010*, 2-011, 2-012, 2-014, 2-015, 2-016*, 2-017*, 2-017(a), 2-017(d)**, 2-018*, 2-019, 2-020, 2-021*, 2-022*, 2-023 to 2-025, 2-026, 2-027, 2-028, 2-029, 2-030, 2-031, 2-032*, 2-033*, 2-034, 2-035, 2-036, 2-037, 2-038, 2-039, 2-040, 2-041, 2-042**, 2-043*, 2-044*, 2-045*, 2-046*, 2-047 to 2-050, 2-051*, 2-052, 2-053*, 2-054*, 2-055*, 2-056, 2-057*, 2-058, 2-059*, 2-060*, 2-061**, 2-062*, 2-063*, 2-064, 2-065*, 2-066*, 2-067, 2-068, 2-069, 2-070*, 2-071, 2-072*, 2-073*, 2-074, 2-075, 2-076*, 2-077*, 2-078*, 2-079, 2-080, 2-081*, 2-082, 2-083, 2-084, 2-085**, 2-086*, 2-087**, 2-089, 2-090*, 2-091, 2-092, 2-093, 2-094, 2-095**, 2-096*, 2-097**, 2-098, 2-099*, 2-100*, 2-101, 2-102, 2-103, 2-104, 2-105, 2-106, 2-107, 2-108, 2-109, 2-110, 2-111, 2-112, 2-113, 2-114, 2-115, 2-116, 2-117, 2-118, 2-119, 2-120, 2-121, 2-122, 2-124, 2-125 to 2-128, 2-129, 2-130, 2-131, 2-132**, 2-133*, 2-134, 2-135, 2-136*, 2-137, 2-138, 2-139, 2-140, 2-141, 2-142, 2-143, 2-144, 2-145, 2-146, 2-147, 2-148, 2-149, 2-150, 2-151, 2-152, 2-153, 2-154, 2-155, 2-156**, 2-157*, 2-158, 2-159, 2-160, 2-161, 2-162, 2-164, 2-165, 2-166, 2-167, 2-168, 2-169**, 2-170*, 2-171, 2-172, 2-173, 2-174, 2-175, 2-176, 2-177, 2-178, 2-179, 2-180, 2-181, 2-182, 2-183, 2-184, 2-185, 2-186, 2-187*, 2-188*, 2-189 to 2-192, 2-193, 2-194, 2-195, 2-196, 2-197, 2-198, 2-199, 2-200, 2-201, 2-202**, 2-203*, 2-204**, 2-205*, 2-206*, 2-207*, 2-208**, 2-209*, 2-210**, 2-211*, 2-212 to 2-215, 2-216, 2-217, 2-218, 2-219, 2-220, 2-221*, 2-222, 2-223, 2-224, 2-225, 2-226, 2-227, 2-228, 2-229, 2-230, 2-231, 2-232, 2-233, 2-234*, 2-235, 2-236, 2-237 to 2-240, 2-241*, 2-242, 2-243*, 2-244, 2-245*, 2-246*, 2-247, 2-248, 2-249, 2-250 to 2-253, 2-254, 2-255**, 2-256*, 2-257, 2-258, 2-259, 2-260 to 2-262, 2-263, 2-264, 2-265, 2-266, 2-267**, 2-268*, 2-269**, 2-270*, 2-271*, 2-273, 2-274, 2-275*, 2-276, 2-277, 2-278, 2-279, 2-280*, 2-281, 2-282, 2-283, 2-284, 2-285, 2-286, 2-287, 2-288, 2-289, 2-290, 2-291, 2-292, 2-293, 2-294, 2-295*, 2-296*, 2-297, 2-298, 2-299, 2-300, 2-301, 2-302, 2-303*, 2-304, 2-305, 2-306, 2-307, 2-308, 2-309*, 2-310*, 2-311, 2-312, 2-313, 2-314, 2-315*, 2-316, 2-317, 2-318, 2-319, 2-320, 2-321, 2-322, 2-323, 2-324, 2-325, 2-326, 2-327, 2-328, 2-329, 2-330, 2-331, 2-332, 2-333, 2-334*, 2-335, 2-336, 2-337*, 2-338*, 2-339*, 2-340*, 2-341*, 2-342*, 2-343**, 2-344*, 2-345, 2-346, 2-347**, 2-348, 2-349*, 2-350*, 2-351*, 2-352, 2-353, 2-354**, 2-355*, 2-358*, 2-359**, 2-360*, 2-361**, 2-362*, 2-363**, 2-364*, 2-365*, 2-366*, 2-367, 2-368, 2-369, 2-370, 2-371*, 2-373**, 2-374*, 2-376**, 2-377*, 2-378*, 2-379*, 2-380, 2-381, 2-382**, 2-383*, 2-384, 2-385, 2-386*, 2-387**, 2-388*, 2-389*, 2-390*, 2-391, 2-392, 2-393, 2-394, 2-396, 2-398, 2-399*, 2-400, 2-401, 2-402**, 2-403*, 2-404**, 2-405*, 2-406, 2-407, 2-408, 2-409, 2-410*, 2-412**, 2-413*, 2-415**, 2-416*, 2-417**, 2-418*, 2-419, 2-420, 2-421, 2-422, 2-423**, 2-424*, 2-425*, 2-426, 2-427, 2-428, 2-429, 2-430*, 2-432, 2-433, 2-435, 2-436, 2-437**, 2-438*, 2-439*, 2*440*, 2-441, 2-442, 2-443, 2-444, 2-445**, 2-446*, 2-447, 2-448, 2-449, 2-450*, 2-451, 2-452, 2-453, 2-454, 2-455, 2-456*, 2-457*, 2-458*, 2-459, 2-460, 2-461, 2-462, 2-463*, 2-465, 2-467, 2-468*, 2-469*, 2-470*, 2-471, 2-472, 2-473*, 2-474*, 2-475*, 2-476, 2-477, 2-478**, 2-479*, 2-480, 2-481, 2-482**, 2-483*, 2-484**, 2-485*, 2-486**, 2-487*, 2-488, 2-489*, 2490, 2-491, 2-492**, 2-493*, 2-494, 2-495, 2-496*, 2-497*, 2-498**, 2-499*, 2-500*, 2-501, 2-502, 2-503, 2-504, 2-505, 2-506, 2-507*, 2-508*, 2-509 to 2-511, 2-512*, 2-513*, 2-514**, 2-515, 2-516*, 2-517, 2-518, 2-519**, 2-520*, 2-521*, 2-522*, 2-523*, 2-524*, 2-525*, 2-526*, 2-527*, 2-528*, 2-529*, 2-530, 2-531, 2-532, 2-533, 2-534**, 2-535, 2-536*, 2-537*, 2-538**, 3-001*, 3-002, 3-003*, 3-004**, 3-005*, 3-006*, 3-007, 3-008, 3-009*, 3-010, 3-011, 3-012*, 3-013*, 3-014*, 3-015*, 4-001*, 4-002**, 4-003*, 4-004, 4-005, 4-006*, 4-007*, 4-008*, 4-009*, 4-010*, 4-011*, 4-012, 4-013, 4-014*, 4-015*, 4-016, 4-017, 4-018, 4-019, 4-020, 4-021, 4-022, 4-023, 4-024, 4-025, 4-026, 4-027, 4-028**, 4-029*, 4-030*, 4-031, 4-032, 4-033*, 4-034, 4-035, 4-036, 4-037, 4-038, 4-039, 4-040, 4-041*, 4-042 to 4-045, 4-046**, 4-047, 4-048, 4-049*, 4-050*, 4-051, 4-052, 4-053, 4-054, 4-055, 4-056, 4-058, 4-059, 4-060*, 4-061*, 4-062 to 4-064, 4-065*, 4-066*, 4-067, 4-068*, 4-069*, 4-070*, 4-071, 4-072*, 4-073, 4-074**, 4-075*, 4-076, 4-077*, 4-078, 4-079*, 4-080*, 4-081*, 4-082*, 4-083*, 4-084*, 4-085 to 4-088, 4-089*, 4-090 to 4-095, 4-096, 4-097, 4-098*, 4-100, 4-101*, 4-102*, 4-103*, 4-104, 4-105, 4-106**, 4-107*, 4-108 to 4-112, 4-113, 4-114, 4-115, 4-116 to 4-119, 4-120, 4-121, 4-122, 4-123**, 4-124*, 4-125, 4-126, 4-127, 4-128, 4-129**, 4-130*, 4-131*, 4-132*, 4-133, 4-134, 4-135*, 4-136*, 4-137*, 4-138*, 4-139, 4-140, 4-141, 4-142, 4-143*, 4-144*, 4-145**, 4-146*, 4-147*, 5-001**, 5-002*, 5-003*, 5-004**, 5-005*, 5-006, 5-007, 5-008, 5-009, 5-010, 5-011*, 5-012*, 5-013*, 5-014*, 5-015*, 5-016, 5-017, 5-018*, 5-019, 5-020, 6-001 to 6-003, 7-002, 7-003, 7-004, 7-005*, 7-006, 7-007*, 7-008, 7-009**, 7-010*, 7-011*, 7-012**, 7-013*, 7-015**, 7-017*, 7-018, 7-019, 7-020, 7-021, 7-022, 7-023, 7-024, 7-025, 7-026, 7-027, 7-028, 7-029, 7-030, 7-031, 7-034*, 7-036, 7-037 to 7-039, 7-040, 7-041, 7-042, 7-043**, 7-044, 7-045*, 7-046*, 7-048, 7-049, 7-050, 7-051, 7-052**, 7-053*, 7-054, 7-055, 7-056, 7-057, 7-058**, 7-059*, 7-060, 7-061, 7-062*, 7-063, 7-064, 7-065, 7-066, 7-067, 7-068, 7-069, 7-070, 7-071, 7-072, 7-073, 7-074, 7-075**, 7-076*, 7-077, 7-078, 7-079, 7-080, 7-081, 7-082, 7-083, 7-084, 7-085, 7-086, 7-087*, 7-088*, 7-089, 7-090*, 7-091*, 7-092*, 7-093*, 7-094, 7-095, 7-096, 7-097**, 7-098*, 7-099, 7-100, 7-101**, 7-102*, 7-103, 7-104, 7-105**, 7-106*, 7-107, 7-109, 7-110, 7-111, 7-112, 7-113, 7-114, 7-115, 7-116, 7-117, 7-118, 8-001 to 8-004, 8-005*, 8-006*, 8-007 to 8-009, 8-011*, 8-012 to 8-014, 8-015*, 8-016, 8-017, 8-018, 8-019, 8-020, 9-001, 9-005, 9-006, 9-007*, 9-008 to 9-010, 9-011*, 9-012**, 9-013*, 9-014 to 9-018, 9-019*, 9-020, 9-021, 9-022*, 9-023*, 9-024*, 9-025*, 9-026 to 9-029, 9-030*, 9-031, 9-032*, 9-033*, 9-034, 9-035*, 9-036, 9-037, 9-038*, 9-040, 9-041, 9-042*, 9-043*, 9-044*, 9-047 to 9-048, 9-049*, 9-050, 9-051*, 9-052**, 9-055*, 9-056**, 9-057*, 9-059*, 9-060*, 9-061, 9-062*, 9-063**, 9-065*, 9-066*, 9-067, 9-068, 9-069**, 9-070, 10-001, 11-001, 11-002, 11-005, 11-008, 11-011 to 11-015, 11-018, 11-019, 11-020.

In the interim, the indication of "*" shows that the insecticidal test was carried out by use of a chemical solution of a concentration of 100 ppm, and the indication "**" shows that the insecticidal test was carried out by use of a chemical solution of a concentration of 10 ppm.

Test Example 2

Insecticidal Test Against Common Cutworm

A 10% emulsifiable concentrate (depending on the compounds, 10% wettable powder was applied for the test) of the compound of the present invention was diluted with water containing a spreading agent to prepare a chemical solution with a concentration of 500 ppm. To the chemical solution was dipped leaves of cabbage for about 10 seconds, and after air-drying, they were placed in a laboratory dish, then 5-common cutworm (*Spodoptera litura*) in the stage of second instar larva per the dish were released therein, and the dish was covered with a lid and contained at a thermostat chamber at 25° C. A number of dead insect(s) after 6 days was counted and a rate of dead insects was calculated by the calculation equation similar to that in Test Example 1. Incidentally, the test was carried out with two districts.

As a result, the following compounds showed an insecticidal rate of 80% or more among the compounds tested.

The compounds of the present invention: No. 1-001*, 1-002*, 1-003*, 1-005*, 1-006*, 1-007*, 1-008*, 1-009**, 1-010, 1-011, 1-018, 1-020*, 1-021, 1-023*, 1-024*, 1-026*, 1-028*, 1-029*, 1-030*, 1-032*, 1-033 to 1-038, 1-040, 1-042 to 1-045, 1-047 to 1-052, 1-053*, 1-054, 1-056 to 1-058, 1-060, 1-061, 1-062*, 1-063, 1-064, 1-065, 1-066, 1-067, 1-068, 1-069, 1-070, 1-071, 1-072, 1-073**, 1-074*, 1-075**, 1-076, 1-078, 1-079*, 1-080 to 1-085, 1-086**, 1-087 to 1-090, 1-091*, 1-092, 1-093, 1-094, 1-095, 1-096, 1-097, 1-098**, 1-099 to 1-103, 1-104*, 1-105 to 1-107, 1-109 to 1-114, 1-116*, 1-117, 1-118**, 1-119, 2-001*, 2-002*, 2-003, 2-005*, 2-006*, 2-007*, 2-009*, 2-010*, 2-011, 2-012, 2-015, 2-016*, 2-017*, 2-017(a)*, 2-017(d)**, 2-018*, 2-019*, 2-021*, 2-022*, 2-024, 2-025, 2-026**, 2-027*, 2-028**, 2-029*, 2-030*, 2-031**, 2-032*, 2-033*, 2-034*, 2-036*, 2-037*, 2-038*, 2-039, 2-040, 2-041**, 2-042*, 2-043*, 2-044*, 2-045*, 2-046*, 2-047 to 2-050, 2-051*, 2-052, 2-053*, 2-054*, 2-055*, 2-056, 2-057*, 2-058, 2-059*, 2-060*, 2-061*, 2-062*, 2-063*, 2-064, 2-065*, 2-066*, 2-067, 2-068*, 2-069**, 2-070*, 2-071, 2-072*, 2-073*, 2-074, 2-077*, 2-078*, 2-079*, 2-080*, 2-081*, 2-082*, 2-083*, 2-085*, 2-086*, 2-087*, 2-089, 2-091, 2-092**, 2-093*, 2-095*, 2-096*, 2-097**, 2-098*, 2-099, 2-100, 2-101, 2-103, 2-104, 2-105, 2-106, 2-107, 2-108, 2-109, 2-110, 2-111, 2-112, 2-113, 2-114, 2-115, 2-116, 2-117, 2-118, 2-119, 2-120, 2-121, 2-122, 2-124, 2-125, 2-129, 2-130**, 2-131*, 2-132**, 2-133*, 2-134, 2-135, 2-136*, 2-137, 2-138, 2-139, 2-140, 2-141, 2-142, 2-143, 2-144, 2-145, 2-146, 2-147, 2-148, 2-149, 2-150, 2-151, 2-152, 2-153, 2-154, 2-155, 2-156**, 2-157*, 2-160, 2-161, 2-162, 2-164, 2-165, 2-166, 2-167, 2-168, 2-169**, 2-170*, 2-171, 2-172, 2-173, 2-174, 2-175**, 2-176*, 2-177, 2-178, 2-179, 2-180, 2-181**, 2-182*, 2-183*, 2-184, 2-185, 2-186**, 2-187*, 2-188*, 2-191, 2-192, 2-193*, 2-194, 2-195, 2-196, 2-197, 2-198, 2-199, 2-200, 2-201, 2-202, 2-203*, 2-204**, 2-205*, 2-206*, 2-207*, 2-208**, 2-209*, 2-210**, 2-211*, 2-214, 2-216, 2-218, 2-219, 2-220, 2-221*, 2-223*, 2-224**, 2-225*, 2-226, 2-227, 2-228, 2-231, 2-232, 2-233, 2-234*, 2-235, 2-236, 2-237, 2-239, 2-241*, 2-242, 2-243*, 2-244, 2-245*, 2-246*, 2-247, 2-248, 2-249, 2-250 to 2-253, 2-254, 2-255**, 2-256*, 2-257, 2-259**, 2-260, 2-262, 2-263*, 2-264, 2-266, 2-267**, 2-268*, 2-269**, 2-270*, 2-271*, 2-273**, 2-274*, 2-275*, 2-276*, 2-277, 2-278, 2-279*, 2-280*, 2-281, 2-282, 2-283, 2-284, 2-285, 2-286, 2-287, 2-288, 2-289, 2-290, 2-291, 2-292, 2-293, 2-295*, 2-297, 2-298*, 2-299, 2-300, 2-301**, 2-302, 2-303*, 2-304, 2-305, 2-306, 2-307, 2-309**, 2-310*, 2-311, 2-312, 2-313**, 2-314*, 2-315*, 2-316, 2-317, 2-318, 2-319, 2-320, 2-321, 2-322, 2-323, 2-324, 2-325, 2-326, 2-327, 2-328, 2-329, 2-330, 2-331, 2-332, 2-333, 2-334, 2-335, 2-336**, 2-337*, 2-338, 2-339, 2-340*, 2-341, 2-342, 2-343*, 2-344*, 2-345, 2-346, 2-347, 2-348, 2-349, 2-350*, 2-351*, 2-352, 2-353, 2-354**, 2-355*, 2-358**, 2-359*, 2-360*, 2-361, 2-362, 2-363**, 2-364*, 2-365*, 2-366*, 2-367**, 2-368*, 2-369, 2-370, 2-371*, 2-373**, 2-374*, 2-376, 2-377, 2-378**, 2-379*, 2-380, 2-381, 2-382**, 2-383*, 2-384, 2-385, 2-386*, 2-387**, 2-388*, 2-389*, 2-390*, 2-391, 2-392, 2-393, 2-394, 2-396*, 2-398*, 2-399*, 2-400*, 2-401*, 2-402*, 2-403*, 2-404*, 2-405*, 2-406, 2-407, 2-408**, 2-409*, 2-410*, 2-412, 2-413, 2-415**, 2-416*, 2-417*, 2-418*, 2-419*, 2-420**, 2-421*, 2-422*, 2-423*, 2-424*, 2-425*, 2-426*, 2-427*, 2-428*, 2-429*, 2-430*, 2-432**, 2-433*, 2-435*, 2-436*, 2-437*, 2-438*, 2-439*, 2-440*, 2-441, 2-442, 2-443, 2-444, 2-446*, 2-448**, 2-449*, 2-450*, 2-451*, 2-452, 2-453, 2-454**, 2-456*, 2-457*, 2-458*, 2-459, 2-460, 2-461, 2-462, 2-463*, 2-465, 2-467, 2-468*, 2-469*, 2-470*, 2-471%, 2-472**, 2-473*, 2-474*, 2-475*, 2-476*, 2-477, 2-478, 2-479*, 2-480*, 2-481, 2-482, 2-483*, 2-484*, 2-485*, 2-486*, 2-487*, 2-488, 2-489*, 2-490, 2-491, 2-492**, 2-493*, 2-494, 2-495, 2-496*, 2-497*, 2-498**, 2-499*, 2-500*, 2-501, 2-502, 2-503, 2-504, 2-505, 2-506, 2-507*, 2-508*, 2-509 to 2-511, 2-512*, 2-513*, 2-514**, 2-515, 2-516*, 2-517, 2-518, 2-519**, 2-520*, 2-521*, 2-523*, 2-524*, 2-525*, 2-526*, 2-527**, 2-528*, 2-529*, 2-530, 2-533, 2-534**, 2-535, 2-536*, 2-537*, 2-538*, 3-001*, 3-002, 3-003*, 3-004**, 3-005*, 3-006*, 3-007, 3-008, 3-009*, 3-010, 3-011, 3-012*, 3-013*, 3-014*, 3-015*, 4-001*, 4-002*, 4-003*, 4-004, 4-005, 4-006*, 4-007*, 4-008*, 4-009*, 4-010*, 4-011*, 4-012, 4-013, 4-014*, 4-015, 4-016, 4-017, 4-018, 4-019, 4-020, 4-021, 4-022, 4-023, 4-024, 4-025, 4-026, 4-027, 4-028, 4-029*, 4-030*, 4-033*, 4-034, 4-035, 4-036, 4-037, 4-038, 4-039, 4-040, 4-041*, 4-042 to 4-045, 4-046**, 4-047, 4-048, 4-049*, 4-050*, 4-051, 4-052, 4-053*, 4-054, 4-055, 4-056**, 4-058, 4-059, 4-060*, 4-062, 4-064, 4-065*, 4-066*, 4-067, 4-069*, 4-071, 4-072*, 4-074**, 4-076, 4-077*, 4-078, 4-079*, 4-080*, 4-082, 4-083*, 4-086, 4-088, 4-089*, 4-090, 4-091, 4-095, 4-096*, 4-097**, 4-098*, 4-100, 4-101*, 4-102*, 4-103*, 4-105, 4-106, 4-107*, 4-109 to 4-112, 4-114*, 4-115, 4-116 to 4-119, 4-120, 4-121, 4-122, 4-123, 4-124, 4-125, 4-126, 4-127, 4-128, 4-129**, 4-130*, 4-131*, 4-132*, 4-133, 4-134, 4-135*, 4-136**, 4-137*, 4-138*, 4-139, 4-140, 4-141**, 4-142*, 4-143*, 4-144*, 4-145*, 4-146*, 4-147*, 5-001**, 5-002*, 5-004*, 5-005*, 5-007, 5-009, 5-011*, 5-012**, 5-013*, 5-014*, 5-015*, 5-016*, 5-017**, 5-018*, 5-020, 6-001, 7-003*, 7-004, 7-005*, 7-006, 7-007*, 7-008, 7-009*, 7-010*, 7-011*, 7-012*, 7-013**, 7-014*, 7-015, 7-017, 7-019, 7-020**, 7-021*, 7-022, 7-023, 7-024, 7-025, 7-026, 7-028, 7-029, 7-030, 7-031, 7-032, 7-034*, 7-036, 7-037 to 7-039, 7-040, 7-041, 7-042, 7-043**, 7-045*, 7-046*, 7-048, 7-049, 7-050, 7-051, 7-052**, 7-053*, 7-054, 7-055, 7-056, 7-057, 7-058**, 7-059*, 7-060, 7-061, 7-062*, 7-063*, 7-064, 7-065, 7-066, 7-067, 7-068, 7-069, 7-070, 7-071, 7-072, 7-073, 7-074, 7-075, 7-076, 7-077, 7-078, 7-079, 7-080, 7-081, 7-082*, 7-083, 7-084, 7-085, 7-086, 7-087**, 7-088*, 7-089, 7-090*, 7-091*, 7-092*, 7-093*, 7-094, 7-095, 7-096, 7-097**, 7-098*, 7-099, 7-100, 7-101**, 7-102*, 7-103, 7-104, 7-105**, 7-106*, 7-107, 7-109, 7-110, 7-111, 7-112**, 7-113*, 7-114, 7-115, 7-116, 7-118, 8-002, 8-005, 8-006**, 8-007, 8-014, 8-015*, 8-018, 8-020, 9-007*, 9-010, 9-011*, 9-013*, 9-014 to 9-018, 9-019*, 9-020, 9-022*, 9-023*, 9-024*, 9-025*, 9-026, 9-027, 9-030*, 9-031, 9-032*, 9-033*, 9-034, 9-037**, 9-038*, 9-040, 9-041, 9-042*, 9-044*, 9-045*, 9-046**, 9-048, 9-049*, 9-050, 9-051*, 9-055*, 9-057*, 9-060*, 9-061, 9-062, 9-065, 9-066, 9-069, 11-001, 11-011, 11-012, 11-015.

In the interim, the indication of "**" shows that the insecticidal test was carried out by use of a chemical solution of a concentration of 100 ppm, and the indication "*" shows that the insecticidal test was carried out by use of a chemical solution of a concentration of 10 ppm.

Test Example 3

Insecticidal Test Against Beet Armyworm

A 10% emulsifiable concentrate (depending on the compounds, 10% wettable powder was applied for the test) of the compound of the present invention was diluted with water containing a spreading agent to prepare a chemical solution with a concentration of 100 ppm. To the chemical solution was dipped leaves of cabbage for about 10 seconds, and after air-drying, they were placed in a laboratory dish, then 5-beet armyworm (*Spodoptera exigua*) in the stage of second instar larva per the dish were released therein, and the dish was covered with a lid and contained at a thermostat chamber at 25° C. A number of dead insect(s) after 6 days was counted and a rate of dead insects was calculated by the calculation equation similar to that in Test Example 1. Incidentally, the test was carried out with two districts.

As a result, the following compounds showed an insecticidal rate of 80% or more among the compounds tested.

The compounds of the present invention: No. 2-031, 2-032, 2-035, 2-036, 2-044, 2-105, 2-106, 2-111, 2-141, 2-144, 2-145, 2-148, 2-149, 2-152, 2-178, 2-179, 2-259, 2-313, 2-317, 2-333, 2-390, 2436, 2-480, 2-538, 4-004, 4-008, 4-027, 4-074, 4-105, 4-114, 4-122, 5-001, 7-022, 7-024, 7-028, 7-049, 7-052, 7-058, 7-060, 7-061, 7-067, 7-068, 7-070, 7-073, 7-080, 7-081, 7-083, 7-095 to 7-097, 7-099, 7-100, 7-103, 7-112, 7-116.

Test Example 4

Insecticidal Test Against Oriental Tea Tortix

A 10% emulsifiable concentrate (depending on the compounds, 10% wettable powder was applied for the test) of the compound of the present invention was diluted with water containing a spreading agent to prepare a chemical solution with a concentration of 100 ppm. To the chemical solution was dipped leaves of cabbage for about 10 seconds, and after air-drying, they were placed in a laboratory dish, then 5-oriental tea tortix (*Homona magnanima*) in the stage of second instar larva per the dish were released therein, and the dish was covered with a lid and contained at a thermostat chamber at 25° C. A number of dead insect(s) after 6 days was counted and a rate of dead insects was calculated by the calculation equation similar to that in Test Example 1. Incidentally, the test was carried out with two districts.

As a result, the following compounds showed an insecticidal rate of 80% or more among the compounds tested.

The compounds of the present invention: No. 2-017(d), 2-028, 2-029, 2-031, 2-032, 2-034, 2-044, 2-051, 2-054, 2-057, 2-059, 2-061, 2-062, 2-069, 2-070, 2-073, 2-079 to 2-082, 2-095, 2-097, 2-100, 2-104 to 2-107, 2-110, 2-111, 2-118 to 2-122, 2-124, 2-129, 2-130, 2-135, 2-138, 2-139, 2-141, 2-144 to 2-149, 2-151, 2-152, 2-154, 2-165 to 2-169, 2-172, 2-173, 2-177 to 2-180, 2-183 to 2-186, 2-193 to 2-195, 2-198, 2-204, 2-218, 2-219, 2-223, 2-232, 2-233, 2-235, 2-267, 2-285, 2-286, 2-317, 2-318, 2-322, 2-323, 2-326, 2-329 to 2-333, 2-335, 2-347, 2-350, 2-352 to 2-355, 2-362, 2-364, 2-366 to 2-368, 2-370, 2-371, 2-373, 2-374, 2-378, 2-380, 2-383, 2-386, 2-388, 2-390, 2-392, 2-394, 2-396, 2403, 2404, 2406, 2408 to 2410, 2412, 2413, 2417, 2421, 2422, 2-425 to 2430, 2432, 2435 to 2437, 2439, 2-441, 2-449, 2456, 2457, 2459, 2-460, 2462, 2463, 2473, 2475, 2478 to 2480, 2-484, 2490, 2496, 2498 to 2-500, 2-523, 2-533, 2-534, 2-536, 2-538, 3-008, 4-012, 4-013, 4-015, 4-016, 4-018, 4-023, 4-024, 4-027, 4-028, 4-030, 4-036, 4-039, 4-052, 4-053, 4-055, 4-074, 4-081, 4-104, 4-105, 4-114, 4-123 to 4-131, 4-133 to 4-138, 4-141, 4-142, 5-001, 7-036, 7-059, 7-079, 9-022.

Test Example 5

Insecticidal Test Against Corn Earworm

A 10% emulsifiable concentrate (depending on the compounds, 10% wettable powder was applied for the test) of the compound of the present invention was diluted with water containing a spreading agent to prepare a chemical solution with a concentration of 100 ppm. To the chemical solution was dipped leaves of cabbage for about 10 seconds, and after air-drying, they were placed in a laboratory dish, then 1-corn earworm (*Helicoverpa armigera*) in the stage of second instar larva per the dish were released therein, and the dish was covered with a lid and contained at a thermostat chamber at 25° C. A number of dead insect(s) after 6 days was counted and a rate of dead insects was calculated by the calculation equation similar to that in Test Example 1. Incidentally, the test was carried out with twelve districts. As a result, the following compounds showed an insecticidal rate of 80% or more among the compounds tested.
The compounds of the present invention: No. 1-001 to 1-003, 1-005, 1-008 to 1-010, 1-015, 1-020, 1-022, 1-026, 1-029, 1-031, 1-032, 1-043, 1-053, 1-061 to 1-070, 1-072 to 1-076, 1-078 to 1-080, 1-082 to 1-104, 1-118, 2-002, 2-005 to 2-007, 2-009, 2-016, 2-017, 2-017(d), 2-018, 2-019, 2-021, 2-024 to 2-038, 2-040, 2-042 to 2-054, 2-057, 2-059, 2-061 to 2-063, 2-065, 2-069, 2-070, 2-072 to 2-074, 2-076 to 2-083, 2-085 to 2-088, 2-092, 2-093, 2-095, 2-097 to 2-100, 2-103, 2-104, 2-106 to 2-122, 2-124, 2-125, 2-129 to 2-135, 2-138 to 2-157, 2-160 to 2-162, 2-164 to 2-175, 2-177 to 2-181, 2-183 to 2-188, 2-191 to 2-195, 2-198, 2-200 to 2-211, 2-218 to 2-226, 2-228, 2-229, 2-231 to 2-235, 2-241, 2-245, 2-248 to 2-251, 2-253 to 2-256, 2-259, 2-263 to 2-292, 2-295, 2-296, 2-298, 2-300, 2-301, 2-303 to 2-307, 2-309 to 2-341, 2-343 to 2-347, 2-349 to 2-355, 2-358 to 2-368, 2-370, 2-371, 2-373, 2-374, 2-376 to 2-395, 2-398 to 2410, 2412, 2-413, 2415 to 2430, 2432 to 2434, 2436 to 2446, 2448 to 2454, 2456 to 2464, 2467 to 2-504, 2-506, 2-508, 2-512, 2-513, 2-516 to 2-521, 2-523 to 2-532, 2-534 to 2-538, 3-001, 3-004 to 3-013, 3-015, 4-001, 4-002, 4-004, 4-005, 4-007 to 4-010, 4-012 to 4-044, 4-046 to 4-057, 4-059 to 4-062, 4-064, 4-066, 4-068 to 4-075, 4-077 to 4-079, 4-081 to 4-084, 4-086, 4-088 to 4-092, 4-096 to 4-098, 4-100 to 4-115, 4-118 to 4-147, 5-001 to 5-005, 5-007 to 5-018, 5-020, 6-001, 7-003 to 7-005, 7-007, 7-009, 7-012 to 7-014, 7-017, 7-020 to 7-032, 7-034, 7-036, 7-038, 7-040 to 7-043, 7-045, 7-048 to 7-092, 7-095 to 7-118, 8-002, 8-016 to 8-018, 8-020, 9-001 to 9-004, 9-011 to 9-013, 9-015, 9-017 to 9-019, 9-022, 9-023, 9-025, 9-026, 9-028, 9-030, 9-032, 9-033, 9-035, 9-037 to 9-040, 9-042 to 9-045, 9-051, 9-052.

Test Example 6

Insecticidal Test Against *Frankliniella occidentalis*

A wet filter paper was laid in a styrol cup having an inner diameter of 7 cm, a leaf of a common bean cut out so as to have the same diameter was laid thereon, and 10-*Frankliniella occidentalis* with first instar larva per leaf was inoculated thereon. A 10% emulsifiable concentrate (depending on the compounds, 10% wettable powder was applied for the test) of the compound of the present invention was diluted with water containing a spreading agent to prepare a chemical solution with a concentration of 500 ppm. The chemical solution was sprayed with a rotating spray tower in an amount of 2.5 ml per styrol cup, and the styrol cups were covered with lids and contained at a thermostat chamber at 25° C. A number of dead insect(s) after 2 days was counted and a rate of dead insects was calculated by the calculation equation similar to that in Test Example 1. Incidentally, the test was carried out with two districts.
As a result, the following compounds showed an insecticidal rate of 80% or more among the compounds tested.
The compounds of the present invention: No. 1-001 to 1-003, 1-005 to 1-009, 1-034 to 1-038, 1-040, 1-042, 1-043, 1-048, 1-049, 1-052 to 1-054, 1-057, 1-060 to 1-073, 1-075 to 1-106, 1-113, 1-114, 1-116, 1-118, 2-001 to 2-003, 2-005 to 2-009, 2-011, 2-016, 2-017, 2-017(a), 2-017(d), 2-018, 2-019, 2-021, 2-022, 2-024, 2-026 to 2-038, 2-041 to 2-055, 2-057 to 2-059, 2-061, 2-062, 2-066, 2-068 to 2-070, 2-072, 2-073, 2-076, 2-078 to 2-083, 2-085 to 2-089, 2-092, 2-093, 2-095 to 2-100, 2-103 to 2-120, 2-122, 2-124, 2-126 to 2-132, 2-134, 2-135, 2-139 to 2-142, 2-144 to 2-146, 2-148, 2-149, 2-151 to 2-155, 2-159, 2-162, 2-164 to 2-169, 2-172, 2-177 to 2-180, 2-182 to 2-188, 2-193 to 2-196, 2-198, 2-199, 2-201, 2-203 to 2-205, 2-211, 2-212, 2-214, 2-216 to 2-218, 2-223 to 2-225, 2-227, 2-230 to 2-233, 2-239, 2-240, 2-247, 2-250, 2-255, 2-259, 2-268, 2-270, 2-281, 2-284, 2-286, 2-289, 2-295, 2-298, 2-301, 2-303, 2-305, 2-306, 2-310, 2-315 to 2-317, 2-319 to 2-322, 2-324, 2-325, 2-328, 2-329, 2-332, 2-333, 2-344, 2-345, 2-348 to 2-355, 2-358 to 2-362, 2-364 to 2-368, 2-370, 2-371, 2-373, 2-374, 2-376 to 2-381, 2-383 to 2-386, 2-388 to 2-392, 2-394, 2-396, 2-398 to 2401, 2-403 to 2410, 2412, 2413, 2415 to 2-420, 2422 to 2-427, 2429, 2-430, 2432, 2433, 2435, 2-438 to 2443, 2-448 to 2450, 2-452, 2-454, 2456 to 2463, 2465, 2467 to 2471, 2473 to 2476, 2478 to 2-482, 2-484 to 2487, 2489 to 2493, 2496 to 2-502, 2-522, 2-523, 2-527, 2-529, 2-531, 2-537, 2-538, 3-004, 3-005, 3-007, 3-008, 3-010, 3-012, 3-013, 4-002, 4-004 to 4-018, 4-021, 4-023, 4-025, 4-027, 4-028, 4-030, 4-034, 4-037, 4-039, 4-047, 4-052, 4-055, 4-056, 4-071, 4-074, 4-077, 4-078, 4-080 to 4-083, 4-086, 4-088, 4-098, 4-104, 4-106, 4-107, 4-109, 4-111, 4-120, 4-124, 4-127, 4-130 to 4-139, 4-141 to 4-146, 5-001, 5-002, 5-004, 5-006, 5-012, 5-013, 5-017, 7-002 to 7-006, 7-008, 7-009, 7-011 to 7-013, 7-017, 7-019 to 7-021, 7-023 to 7-026, 7-029 to 7-033, 7-036 to 7-039, 7-042, 7-043, 7-048 to 7-052, 7-059 to 7-071, 7-073 to 7-077, 7-080 to 7-085, 7-088, 7-089, 7-091, 7-092, 7-095, 7-096, 7-098 to 7-110, 7-112, 7-113, 8-006, 8-015, 8-017, 8-018, 9-007, 9-011 to 9-015, 9-017, 9-018, 9-022 to 9-027, 9-040, 9-041, 9-043, 9-057, 9-061, 9-063, 9-070, 10-001, 11-002.

Test Example 7

Insecticidal Test Against *Thrips palmi*

A wet filter paper was laid in a styrol cup having an inner diameter of 7 cm, a leaf of a common bean cut out so as to have the same diameter was laid thereon, and 10-*Thrips palmi* in the stage of adult per leaf was inoculated thereon. A 10% emulsifiable concentrate (depending on the compounds, 10% wettable powder was applied for the test) of the compound of the present invention was diluted with water containing a spreading agent to prepare a chemical solution with a concentration of 100 ppm. The chemical solution was sprayed with a rotating spray tower in an amount of 2.5 ml per styrol cup, and the styrol cups were covered with lids and contained at a thermostat chamber at 25° C. A number of dead insect(s) after 2 days was counted and a rate of dead insects was calculated by the calculation equation similar to that in Test Example 1. Incidentally, the test was carried out with two districts.

As a result, the following compounds showed an insecticidal rate of 80% or more among the compounds tested.

The compounds of the present invention: No. 1-001 to 1-003, 1-005, 1-006, 1-008, 1-043, 1-049, 1-053, 1-057, 1-060, 1-062 to 1-073, 1-075, 1-076, 1-078 to 1-082, 1-084 to 1-097, 1-100 to 1-103, 1-118, 2-002, 2-005 to 2-007, 2-009, 2-016, 2-017, 2-017(a), 2-017(d), 2-018, 2-019, 2-021, 2-022, 2-027 to 2-035, 2-037, 2-041 to 2-054, 2-057, 2-059, 2-062, 2-066, 2-068 to 2-070, 2-072, 2-073, 2-079 to 2-083, 2-085, 2-087, 2-092, 2-095 to 2-100, 2-103 to 2-122, 2-124, 2-126 to 2-132, 2-134, 2-135, 2-138 to 2-157, 2-159 to 2-162, 2-164 to 2-175, 2-177 to 2-188, 2-193 to 2-195, 2-198 to 2-209, 2-216 to 2-221, 2-223 to 2-228, 2-231 to 2-236, 2-240, 2-241, 2-247 to 2-250, 2-254, 2-255, 2-259, 2-263, 2-264, 2-266 to 2-271, 2-273 to 2-277, 2-280 to 2-292, 2-295, 2-298, 2-301, 2-305 to 2-307, 2-309 to 2-333, 2-335, 2-336, 2-339, 2-340, 2-344 to 2-347, 2-349 to 2-355, 2-358 to 2-368, 2-370, 2-371, 2-373, 2-374, 2-376 to 2-394, 2-396, 2-398 to 2410, 2412, 2413, 2415 to 2-430, 2432, 2433, 2435 to 2443, 2448 to 2450, 2452 to 2454, 2456 to 2463, 2465, 2467 to 2487, 2-489 to 2492, 2494 to 2496, 2498 to 2-503, 2-512 to 2-514, 2-518, 2-520, 2-522 to 2-530, 2-533, 2-534, 2-536 to 2-538, 3-004 to 3-012, 4-001 to 4-004, 4-007 to 4-009, 4-011 to 4-034, 4-036 to 4-044, 4-046, 4-049 to 4-053, 4-055 to 4-057, 4-061, 4-062, 4-065 to 4-069, 4-071, 4-072, 4-074, 4-078 to 4-083, 4-088, 4-091, 4-096 to 4-098, 4-104 to 4-107, 4-109 to 4-111, 4-113 to 4-115, 4-117, 4-120 to 4-139, 4-141 to 4-145, 4-147, 5-001 to 5-009, 5-012 to 5-020, 7-003 to 7-005, 7-008, 7-009, 7-011 to 7-013, 7-015, 7-017 to 7-032, 7-034, 7-036, 7-040 to 7-043, 7-045, 7-046, 7-048 to 7-052, 7-055, 7-057 to 7-077, 7-080 to 7-085, 7-088 to 7-091, 7-095 to 7-118, 8-006, 8-015, 8-017, 8-018, 8-020, 9-007, 9-010 to 9-013, 9-018 to 9-027, 9-030 to 9-033, 9-037 to 9-044, 9-046, 9-047, 9-052.

Test Example 8

Insecticidal Test Against *Eysarcoris lewisi*

A 10% emulsifiable concentrate (depending on the compounds, 10% wettable powder was applied for the test) of the compound of the present invention was diluted with water containing a spreading agent to prepare a chemical solution with a concentration of 500 ppm. To the chemical solution was dipped leave sheaths of rice for about 10 seconds, and after air-drying, they were placed in a test tube, then 5-*Eysarcoris lewisi* in the stage of first instar larva per the test tube were released therein, and the test tube was covered with a sponge and contained at a thermostat chamber at 25° C. A number of dead insect(s) after 2 days was counted and a rate of dead insects was calculated by the calculation equation similar to that in Test Example 1. Incidentally, the test was carried out with two districts.

As a result, the following compounds showed an insecticidal rate of 80% or more among the compounds tested.

The compounds of the present invention: No. 1-001 to 1-003, 1-006 to 1-009, 1-020, 1-053, 1-054, 1-062 to 1-065, 1-069, 1-072, 1-075, 1-079, 1-086, 1-091, 1-093, 1-096, 1-104, 2-002, 2-003, 2-005, 2-006, 2-008 to 2-013, 2-016, 2-017, 2-017(d), 2-018, 2-019, 2-021 to 2-023, 2-027 to 2-034, 2-041, 2-043 to 2-046, 2-051, 2-053 to 2-055, 2-057, 2-059, 2-061, 2-062, 2-066, 2-068 to 2-070, 2-073, 2-079 to 2-083, 2-085, 2-087, 2-092, 2-095 to 2-098, 2-100, 2-105, 2-106, 2-111, 2-115, 2-117, 2-119, 2-120, 2-135, 2-141, 2-145, 2-149, 2-152, 2-168, 2-179, 2-182 to 2-188, 2-193, 2-194, 2-198, 2-221, 2-227, 2-268, 2-286, 2-292, 2-303, 3-003, 3-004, 3-008, 4-001, 4-002, 4-005, 4-008 to 4-010, 4-012, 4-013, 4-015, 4-016, 4-018, 4-021, 4-028, 4-039, 4-080, 4-098, 4-104, 5-001, 7-003, 7-009, 7-013, 8-005, 8-006, 8-020, 9-016, 9-019, 9-020, 11-001.

Test Example 9

Insecticidal Test Against Brown Rice Planthopper

A 10% emulsifiable concentrate (depending on the compounds, 10% wettable powder was applied for the test) of the compound of the present invention was diluted with water containing a spreading agent to prepare a chemical solution with a concentration of 500 ppm. To the chemical solution was dipped leave sheaths of rice for about 10 seconds, and after air-drying, they were placed in a test tube, then 5-brown rice planthopper (*Nilaparvata lugens*) in the second instar larva per the test tube were released therein, and the test tube was covered with a sponge and contained at a thermostat chamber at 25° C. A number of dead insect(s) after 6 days was counted and a rate of dead insects was calculated by the calculation equation similar to that in Test Example 1. Incidentally, the test was carried out with two districts.

As a result, the following compounds showed an insecticidal rate of 80% or more among the compounds tested.

The compounds of the present invention: No. 1-001, 1-002, 1-034, 1-042 to 1-044, 1-046, 1-062 to 1-064, 1-066, 1-067, 1-069, 1-070, 1-075, 1-078, 1-079, 1-081, 1-082, 1-084, 1-086 to 1-089, 1-091 to 1-093, 1-095 to 1-097, 2-005, 2-010, 2-016, 2-018, 2-028, 2-029, 2-031 to 2-033, 2-035, 2-039, 2-044 to 2-046, 2-048, 2-049, 2-051, 2-054, 2-055, 2-059, 2-061, 2-066, 2-068 to 2-070, 2-073, 2-079 to 2-083, 2-085, 2-087, 2-092, 2-095, 2-096, 2-098, 2-100, 2-103, 2-105, 2-106, 2-107, 2-108, 2-109, 2-111, 2-112*, 2-113*, 2-119 to 2-122, 2-124, 2-126, 2-129*, 2-130*, 2-131, 2-135, 2-139, 2-141, 2-145, 2-146*, 2-149, 2-150*, 2-152, 2-164*, 2-165*, 2-166*, 2-168, 2-172, 2-177, 2-179, 2-182 to 2-185, 2-198, 2-203, 2-204, 2-209, 2-216 to 2-218, 2-220 to 2-223, 2-225*, 2-226*, 2-232*, 2-233*, 2-240, 2-286, 2-292, 2-306, 2-318*, 2-323*, 2-326*, 2-330*, 2-331*, 2-335, 2-343, 2-344, 2-347*, 2-350, 2-351, 2-352*, 2-353*, 2-355, 2-363*, 2-364, 2-366, 2-367*, 2-368*, 2-369*, 2-373*, 2-378, 2-387, 2-388, 2-390, 2-391, 2-392*, 2-399, 2-425, 2-426*, 2-427, 2-430, 2-432*, 2-438, 2-439, 2-441, 2-442*, 2-443*, 2-459*, 2-461*, 2-463, 2-465*, 2-475, 2-528*, 3-004, 3-007, 3-008, 3-010, 3-011, 4-011 to 4-013, 4-015, 4-016, 4-017, 4-018, 4-019, 4-021, 4-023, 4-025, 4-028, 4-030, 4-034, 4-039, 4-052, 4-055, 4-056, 4-074, 4-078, 4-082, 4-098, 4-104, 4-105, 4-113, 4-120, 4-123, 4-131, 4-132, 4-134, 4-135, 4-136, 4-138, 5-001, 5-002, 7-003 to 7-005, 7-008, 7-009, 7-011 to 7-013, 7-017, 7-020, 7-021, 7-022, 7-023*, 7-024*, 7-025, 7-026*, 7-028*, 7-029, 7-030*, 7-036, 7-038, 7-039, 7-042, 7-059, 7-061*, 7-062, 7-070*, 7-077*, 7-079*, 7-081*, 7-082, 7-084*, 7-086*, 7-088, 7-098, 7-102, 7-105*, 7-106, 8-006, 8-020, 9-014, 9-020, 11-009.

*means the compound tested at 100 ppm.

Test Example 10

Insecticidal Test Against Silverleaf Whitefly

A wet filter paper was laid in a styrol cup having an inner diameter of 7 cm, a leaf of a tomato cut out on which silverleaf whitefly (*Bemisia argentifolii*) laid eggs (10-egg/leaf) was laid thereon. A 10% emulsifiable concentrate (depending on the compounds, 10% wettable powder was applied for the test) of the compound of the present invention was diluted with water containing a spreading agent to prepare a chemical solution with a concentration of 500 ppm. The chemical solution was sprayed with a rotating spray tower in an amount of 2.5 ml per styrol cup, and the styrol cups were covered with lids and contained at a thermostat chamber at 25° C. A number of dead insect(s) after 6 days was counted and a rate of dead insects was calculated by the calculation equation similar to that in Test Example 1. Incidentally, the test was carried out with two districts.

As a result, the following compounds showed an insecticidal rate of 80% or more among the compounds tested.

The compounds of the present invention: No. 1-001, 1-002, 1-006 to 1-008, 1-035, 1-036, 1-038, 1-042, 1-043, 1-053, 1-054, 1-060, 1-062 to 1-067, 1-069 to 1-072, 1-075 to 1-086, 1-089 to 1-093, 1-095, 1-096, 1-099 to 1-103, 1-118, 2-003, 2-005, 2-006, 2-008, 2-009, 2-012, 2-016, 2-017, 2-017(d), 2-018, 2-019, 2-021, 2-024, 2-026, 2-029 to 2-034, 2-036, 2-037, 2-043 to 2-051, 2-055, 2-057, 2-059, 2-061, 2-062, 2-064, 2-066, 2-068 to 2-070, 2-073, 2-078 to 2-083, 2-087, 2-092, 2-093, 2-095, 2-096, 2-098, 2-100, 2-105, 2-106, 2-111, 2-112, 2-115, 2-119 to 2-122, 2-129, 2-135, 2-141, 2-145, 2-146, 2-148, 2-149, 2-152, 2-153, 2-162, 2-165, 2-177, 2-179, 2-180, 2-182 to 2-187, 2-191, 2-193, 2-194, 2-201, 2-209, 2-217, 2-223, 2-227, 2-240, 2-250, 2-255, 2-268, 2-281, 2-284, 2-286, 2-288, 2-289, 2-292, 2-295, 2-296, 2-306, 2-310, 2-315, 2-316, 2-318, 2-323, 2-326, 2-328, 2-330, 2-331, 2-344, 2-347, 2-350 to 2-355, 2-361 to 2-368, 2-370, 2-371, 2-373, 2-374, 2-377 to 2-379, 2-381, 2-386 to 2-388, 2-390 to 2-392, 2-394, 2-399 to 2401, 2403 to 2406, 2408, 2409, 2412, 2416 to 2419, 2422, 2423, 2425 to 2427, 2429, 2438 to 2-443, 2-456 to 2463, 2468 to 2479, 2481, 2482, 2489 to 2-491, 2496, 2498 to 2-500, 2-502, 2-523, 2-529, 2-536 to 2-538, 3-004, 3-005, 3-007, 3-008, 3-011, 3-012, 4-011, 4-012, 4-016, 4-018, 4-020, 4-021, 4-023, 4-027, 4-028, 4-034, 4-044, 4-078, 4-080, 4-132, 4-133, 4-138, 4-141, 5-001, 5-013, 7-003, 7-013, 7-017, 7-019, 7-020, 7-036, 7-037, 7-073, 7-082, 7-106, 8-006, 9-018, 9-022, 9-024, 9-031, 9-069.

Test Example 11

Insecticidal Test Against Green Peach Aphid

A wet cotton wool was laid in a laboratory dish having an inner diameter of 3 cm, a leaf of a cabbage cut out so as to have the same diameter was laid thereon, and 4-green peach aphid (*Myzus persicae*) in the stage of no-wing adult was left. After 1 day, a 10% emulsifiable concentrate (depending on the compounds, 10% wettable powder was applied for the test) of the compound of the present invention was diluted with water containing a spreading agent to prepare a chemical solution with a concentration of 500 ppm, and the chemical solution was sprayed with a rotating spray tower (2.5 mg/cm$^2$), and the laboratory dish was covered with lids and contained at a thermostat chamber at 25° C. A number of dead insect(s) after 6 days was counted and a rate of dead insects was calculated by the calculation equation similar to that in Test Example 1. Incidentally, the test was carried out with two districts.

As a result, the following compounds showed an insecticidal rate of 80% or more among the compounds tested.

The compounds of the present invention: No. 1-001, 1-042 to 1-044, 1-046, 1-047, 1-062 to 1-064, 1-066, 1-067, 1-069, 1-070, 1-072, 1-076 to 1-082, 1-084 to 1-087, 1-092 to 1-097, 1-099 to 1-101, 1-103, 1-105, 1-106, 1-113, 1-118, 2-010, 2-017, 2-021, 2-026, 2-029 to 2-033, 2-037, 2-039, 2-043, 2-044, 2-046 to 2-052, 2-054, 2-056, 2-057, 2-059, 2-061, 2-062, 2-066, 2-068, 2-073, 2-076, 2-077, 2-079 to 2-083, 2-085, 2-087, 2-092, 2-093, 2-095, 2-098, 2-100, 2-103, 2-105, 2-106, 2-107*, 2-111, 2-115, 2-119*, 2-120, 2-121, 2-124, 2-129*, 2-130*, 2-131, 2-135*, 2-141, 2-145, 2-148, 2-149, 2-154*, 2-158, 2-168, 2-182 to 2-185, 2-187, 2-188, 2-193, 2-196, 2-198, 2-204, 2-221, 2-225*, 2-226*, 2-257, 2-260, 2-268, 2-284, 2-286, 2-288*, 2-292, 2-306, 2-315, 2-318*, 2-323*, 2-326*, 2-330*, 2-331*, 2-344, 2-347*, 2-350, 2-351, 2-352*, 2-354*, 2-355, 2-360, 2-361*, 2-363*, 2-364 to 2-366, 2-367*, 2-368*, 2-369*, 2-370*, 2-371, 2-373*, 2-374, 2-376*, 2-377 to 2-379, 2-380*, 2-381*, 2-386, 2-387*, 2-388 to 2-390, 2-391*, 2-392*, 2-393*, 2-399, 2-400, 2-401*, 2403 to 2405, 2-406*, 2-408*, 2-409*, 2-412*, 2-416, 2-418, 2-421*, 2-422*, 2-425, 2-426*, 2-427, 2-430, 2-432*, 2-437*, 2-438 to 2-441, 2-442, 2-443, 2-458, 2-459, 2-460, 2-461*, 2-462, 2-463, 2-465, 2-468, 2-470, 2-472*, 2-473, 2-475, 2-476*, 2-478*, 2-479, 2-481*, 2-482*, 2-490*, 2-492*, 2-496, 2-523, 2-527*, 2-528*, 2-536, 2-538*, 3-004, 3-008, 4-009, 4-012, 4-013, 4-020*, 4-021, 4-023, 4-028, 4-030, 4-059, 4-080, 4-082, 4-088, 4-098, 4-111, 4-113, 4-120, 4-123, 4-131, 4-132, 4-134*, 4-135, 4-137, 4-138, 4-139*, 4-141*, 4-142*, 5-001, 5-002, 5-012, 5-013, 7-003, 7-004, 7-011 to 7-013, 7-017, 7-020, 7-021, 7-025, 7-030*, 7-036 to 7-038, 7-059, 7-061*, 7-062, 7-066, 7-067, 7-070, 7-072, 7-074*, 7-075, 7-076, 7-077*, 7-079, 7-080*, 7-081*, 7-082, 7-083, 7-084, 7-086, 7-087, 7-088, 7-092 to 7-094, 7-098, 7-100*, 7-102, 7-103*, 7-104*, 7-106, 7-109*, 8-006.

*means the compound tested at 100 ppm.

Test Example 12

Insecticidal Test Against Japanese Mealybug

A wet filter paper was laid in a styrol cup having an inner diameter of 7 cm, a leaf of a common bean cut out so as to have the same diameter was laid thereon, and 10-Japanese mealybug (*Planococcus kraunhiae*) in the first instar larva per leaf was inoculated thereon. A 10% emulsifiable concentrate (depending on the compounds, 10% wettable powder was applied for the test) of the compound of the present invention was diluted with water containing a spreading agent to prepare a chemical solution with a concentration of 500 ppm. The chemical solution was sprayed with a rotating spray tower in an amount of 2.5 ml per styrol cup, and the styrol cups were covered with lids and contained at a thermostat chamber at 25° C. A number of dead insect(s) after 6 days was counted and a rate of dead insects was calculated by the calculation equation similar to that in Test Example 1. Incidentally, the test was carried out with two districts.

As a result, the following compounds showed an insecticidal rate of 80% or more among the compounds tested.

The compounds of the present invention: No. 1-002, 1-007, 1-035, 1-042, 1-043, 1-049, 1-052, 1-062 to 1-064, 1-077, 1-079 to 1-081, 1-084 to 1-087, 1-091, 1-092, 1-095, 1-096, 1-100, 1-101, 1-103, 2-004, 2-006, 2-008, 2-009, 2-016, 2-017(d), 2-021, 2-027, 2-030, 2-032 to 2-034, 2-036, 2-043 to 2-047, 2-049, 2-050, 2-057, 2-059, 2-061, 2-062, 2-066, 2-068 to 2-070, 2-073, 2-079 to 2-083, 2-087, 2-088, 2-092, 2-093, 2-095 to 2-098, 2-105, 2-106, 2-111, 2-120, 2-135, 2-141, 2-145, 2-149, 2-152, 2-168, 2-182, 2-184, 2-186, 2-187, 2-191, 2-194, 2-258, 2-260, 2-268, 2-286, 2-305, 2-310, 2-315, 3-004, 3-008, 4-002, 4-004, 4-007, 4-008, 4-012, 4-013, 4-018, 4-021, 4-043, 4-080, 4-098, 5-001, 5-013, 7-003, 7-013, 7-014, 7-017, 8-006, 8-015, 9-010, 9-024, 9-031.

Test Example 13

Insecticidal Test Against Cucurbit Leaf Beetle

A 10% emulsifiable concentrate (depending on the compounds, 10% wettable powder was applied for the test) of the compound of the present invention was diluted with water containing a spreading agent to prepare a chemical solution with a concentration of 500 ppm. To the chemical solution was dipped leaves of cucumber for about 10 seconds, and after air-drying, they were placed in a laboratory dish, then 5-cucurbit leaf beetle (*Aulacophora femoralis*) in the stage of second instar larva per the dish were released therein, and the dish was covered with a lid and contained at a thermostat chamber at 25° C. A number of dead insect(s) after 6 days was counted and a rate of dead insects was calculated by the calculation equation similar to that in Test Example 1. Incidentally, the test was carried out with two districts.
As a result, the following compounds showed an insecticidal rate of 80% or more among the compounds tested.
The compounds of the present invention: No. 1-001 to 1-011, 1-017, 1-020 to 1-024, 1-026, 1-028 to 1-038, 1-041 to 1-055, 1-057, 1-059 to 1-119, 2-001 to 2-013, 2-016, 2-017, 2-017 (a), 2-017(d), 2-018, 2-019, 2-021, 2-022, 2-024 to 2-090, 2-092 to 2-102, 2-105, 2-106, 2-111, 2-115, 2-117, 2-119, 2-120, 2-135, 2-137, 2-141, 2-145, 2-149, 2-152, 2-158, 2-168, 2-170, 2-179, 2-182 to 2-198, 2-211 to 2-215, 2-221, 2-227, 2-237, 2-240 to 2-242, 2-257, 2-260, 2-262, 2-268, 2-270, 2-280, 2-286, 2-292, 2-295, 2-303, 2-305, 2-310, 2-314, 2-315, 3-001 to 3-005, 3-008, 4-001 to 4-016, 4-018, 4-021, 4-028, 4-030, 4-039, 4-041, 4-043, 4-052, 4-080, 4-088, 4-098, 4-099, 4-104, 5-001, 5-012 to 5-014, 6-001, 7-001, 7-003 to 7-015, 7-017, 7-018, 8-002 to 8-007, 8-009, 8-011 to 8-020, 9-006 to 9-008, 9-010 to 9-027, 9-030, 9-031, 9-046, 10-001.

Test Example 14

Insecticidal Test Against Serpentine Leaf Miner

A 10% emulsifiable concentrate (depending on the compounds, 10% wettable powder was applied for the test) of the compound of the present invention was diluted with water containing a spreading agent to prepare a chemical solution with a concentration of 500 ppm. To the chemical solution was dipped leaves of common bean on which serpentine leaf miner (*Liriomyza trifolii*) laid eggs (10 eggs/leaf) for about 10 seconds, and after air-drying, they were placed on a wet filter paper laid in a styrol cup having an inner diameter of 7 cm, and the styrol cup was covered with a lid and contained at a thermostat chamber at 25° C. A number of dead insect(s) after 6 days was counted and a rate of dead insects was calculated by the calculation equation similar to that in Test Example 1. Incidentally, the test was carried out with two districts.
As a result, the following compounds showed an insecticidal rate of 80% or more among the compounds tested.
The compounds of the present invention: No. 1-001, 1-002, 1-006 to 1-008, 1-032, 1-042, 1-043, 1-049, 1-053, 1-054, 1-062 to 1-067, 1-069 to 1-071, 1-075, 1-076, 1-078 to 1-081, 1-083, 1-086, 1-088, 1-089, 1-095, 1-096, 1-101, 1-104, 2-003, 2-005 to 2-007, 2-009, 2-016, 2-017, 2-017(d), 2-018, 2-019, 2-021, 2-027 to 2-035, 2-037, 2-042 to 2-054, 2-057 to 2-059, 2-061, 2-062, 2-066, 2-068 to 2-070, 2-073, 2-079 to 2-083, 2-085, 2-087, 2-090, 2-092, 2-093, 2-095 to 2-097, 2-100, 2-105, 2-106, 2-111, 2-122, 2-145, 2-179, 2-183, 2-185, 2-186, 2-223, 2-286, 2-326, 2-350 to 2-355, 2-364, 2-366 to 2-368, 2-370, 2-371, 2-374, 2-377 to 2-379, 2-388, 2-390, 2-391, 2404, 2406, 2425, 2427, 2438 to 2442, 2459, 2473, 2475, 2476, 2478, 2481, 2490, 2491, 2496, 2498, 2-500, 2-502, 2-523, 3-004, 4-002, 4-005, 4-007, 4-009, 4-011, 4-012, 4-027, 4-141, 5-001, 5-012, 8-006.

Test Example 15

Insecticidal Test Against Two-Spotted Spider Mite

A wet filter paper was laid in a styrol cup having an inner diameter of 7 cm, a leaf of a common bean cut out so as to have the same diameter was laid thereon, and 10 larvae of two-spotted spider mite (*Tetranychus urticae*) per leaf was inoculated thereon. A 10% emulsifiable concentrate (depending on the compounds, 10% wettable powder was applied for the test) of the compound of the present invention was diluted with water containing a spreading agent to prepare a chemical solution with a concentration of 500 ppm. The chemical solution was sprayed with a rotating spray tower in an amount of 2.5 ml per styrol cup, and the styrol cups were covered with lids and contained at a thermostat chamber at 25° C. A number of dead insect(s) after 6 days was counted and a rate of dead insects was calculated by the calculation equation similar to that in Test Example 1. Incidentally, the test was carried out with two districts.
As a result, the following compounds showed an insecticidal rate of 80% or more among the compounds tested.
The compounds of the present invention: No. 1-001 to 1-003, 1-006, 1-007, 1-042, 1-053, 1-054, 1-062 to 1-066, 1-069 to 1-071, 1-075 to 1-086, 1-088 to 1-090, 1-092 to 1-096, 1-100 to 1-104, 1-116, 1-118, 2-002, 2-003, 2-005 to 2-012, 2-016, 2-017, 2-017(d), 2-018, 2-019, 2-021, 2-022, 2-024, 2-026 to 2-037, 2-043 to 2-055, 2-057, 2-059, 2-061 to 2-063, 2-066, 2-068 to 2-070, 2-073, 2-076 to 2-083, 2-085, 2-087, 2-090, 2-092, 2-093, 2-095 to 2-100, 2-103, 2-104**, 2-105, 2-106, 2-107*, 2-108*, 2-109**, 2-111, 2-112*, 2-113*, 2-114**, 2-115, 2-116*, 2-117*, 2-118*, 2-119*, 2-120 to 2-122, 2-124, 2-126 to 2-128, 2-129*, 2-130*, 2-131, 2-132*, 2-134**, 2-135*, 2-138, 2-139, 2-140**, 2-141, 2-142*, 2-143, 2-144, 2-145, 2-146, 2-147, 2-148, 2-149, 2-150, 2-152, 2-153**, 2-154*, 2-155, 2-159, 2-164, 2-165*, 2-166**, 2-167*, 2-168, 2-169*, 2-170, 2-172, 2-174, 2-175*, 2-176*, 2-177, 2-178, 2-179, 2-180, 2-181*, 2-182 to 2-188, 2-191 to 2-199, 2-200*, 2-201 to 2-206, 2-207*, 2-208, 2-209, 2-210*, 2-211 to 2-213, 2-215 to 2-218, 2-219*, 2-220 to 2-223, 2-224*, 2-225*, 2-226*, 2-227 to 2-229, 2-232, 2-233, 2-234*, 2-235, 2-236, 2-237, 2-239, 2-240, 2-242, 2-246*, 2-247, 2-249*, 2-250, 2-251, 2-254*, 2-255, 2-256, 2-259, 2-260, 2-262, 2-263*, 2-264**, 2-266, 2-268, 2-269*, 2-276, 2-277, 2-280, 2-281, 2-283**, 2-284 to 2-286, 2-288*, 2-289*, 2-292, 2-298, 2-300, 2-301, 2-303, 2-306, 2-307*, 2-309**, 2-310, 2-311*, 2-312, 2-313, 2-315, 2-318, 2-326, 2-327, 2-331, 2-335, 2-343, 2-344, 2-345**, 2-349 to 2-351, 2-352*, 2-353*, 2-354*, 2-355, 2-359, 2-360, 2-361*, 2-362, 2-363*, 2-364 to 2-366, 2-367*, 2-368**, 2-370*, 2-371, 2-373**, 2-374, 2-377 to 2-379, 2-381*, 2-383*, 2-385*, 2-386, 2-387*, 2-388 to 2-390, 2-391*, 2-392*, 2-393**, 2-394*, 2-396, 2-399, 2-400, 2-401*, 2403 to 2-405, 2-406*, 2-407*, 2408*, 2409*, 2-410, 2-412*, 2-413, 2-416 to 2-418, 2-419*, 2-422*, 2-424, 2-425, 2-426*, 2-427, 2429*, 2-430, 2-432**, 2-435*, 2-438 to 2-441, 2-442*, 2-443**, 2-449, 2-456 to 2-458, 2-459*, 2-460*, 2-461*, 2-462*, 2-463, 2-465**, 2468 to 2-470, 2-471*, 2-472*, 2-473 to 2-475, 2-476*, 2-477**, 2-478*, 2-479, 2-480*, 2-481*, 2-482*, 2-484**, 2-485, 2-486*, 2-487, 2-489, 2-490*, 2-491*, 2-492*, 2-495*, 2496, 2-497, 2-498*, 2-499, 2-500, 2-502*, 2-509 to 2-511, 2-513, 2-515, 2-522, 2-523, 2-526*, 2-527*, 2-528*, 2-529, 2-533*, 2-536, 2-537, 2-538, 3-004, 3-007, 3-008, 3-010 to 3-012, 4-001, 4-003, 4-005, 4-008, 4-009, 4-012 to 4-016, 4-017**, 4-018, 4-019*, 4-020*, 4-021, 4-022*, 4-023, 4-024*, 4-025**, 4-026, 4-027*, 4-028, 4-029*, 4-030, 4-031, 4-033*, 4-034, 4-035, 4-036*, 4-037**, 4-038*, 4-039, 4-040*, 4-041, 4-043, 4-044, 4-047, 4-050*, 4-051*, 4-053, 4-054*, 4-055**, 4-056, 4-057*, 4-058, 4-059, 4-066 to 4-072, 4-074*, 4-076 to 4-078, 4-079*, 4-080, 4-081*, 4-082, 4-083, 4-090, 4-098, 4-101*, 4-102*, 4-103*, 4-104, 4-105*, 4-106*, 4-107*, 4-109 to 4-111, 4-113, 4-114*, 4-115*, 4-117, 4-120, 4-125*, 4-127*, 4-130 to 4-132, 4-133*, 4-134, 4-135, 4-136, 4-137, 4-138, 4-139*, 4-141*, 4-142*, 4-143, 4-144, 4-146, 4-147, 5-001, 5-002, 5-004, 5-005, 5-007*, 5-009, 5-011 to 5-013, 5-016*, 5-017, 5-018*, 5-019, 7-012, 7-017, 7-019 to 7-021, 7-036 to 7-038, 7-042, 7-044, 7-045, 7-059, 7-061*, 7-062, 7-070, 7-102, 7-106, 8-006, 8-015 to 8-017, 8-020, 9-013, 9-061, 9-069.

*means the compound tested at 100 ppm.
**means the compound tested at 10 ppm.

Test Example 16

Insecticidal Test Against Pink Citrus Rust Mite

A wet filter paper was laid in a styrol cup having an inner diameter of 7 cm, a leaf of a mandarin orange cut out so as to have the same diameter was laid thereon, and 10 larvae of pink citrus rust mite (*Aculops pelekassi*) per leaf was inoculated thereon. A 10% emulsifiable concentrate (depending on the compounds, 10% wettable powder was applied for the test) of the compound of the present invention was diluted with water containing a spreading agent to prepare a chemical solution with a concentration of 100 ppm. The chemical solution was sprayed with a rotating spray tower in an amount of 2.5 ml per styrol cup, and the styrol cups were covered with lids and contained at a thermostat chamber at 25° C. A number of dead insect(s) after 6 days was counted and a rate of dead insects was calculated by the calculation equation similar to that in Test Example 1. Incidentally, the test was carried out with two districts.
As a result, the following compounds showed an insecticidal rate of 80% or more among the compounds tested.
The compounds of the present invention: No. 2-017, 2-021, 2-031, 2-032, 2-034 to 2-036, 2-051, 2-059, 2-069, 2-079 to 2-082, 2-095, 2-104 to 2-106, 2-110, 2-111, 2-115, 2-124, 2-129, 2-134, 2-140, 2-141, 2-144 to 2-146, 2-148, 2-149, 2-151, 2-152, 2-154, 2-155, 2-165, 2-166, 2-168, 2-169, 2-172, 2-178 to 2-180, 2-183 to 2-185, 2-195, 2-208, 2-223, 2-226, 2-232, 2-233, 2-249, 2-276, 2-277, 2-281, 2-287, 2-291, 2-306, 2-311, 2-313, 2-316 to 2-319, 2-321, 2-322, 2-324, 2-326 to 2-329, 2-332, 2-333, 2-345, 2-346, 2-364, 2-373, 2-386, 2-388, 2-390, 2404, 2421, 2-433, 2436, 2-437, 2449, 2480, 3-007, 4-004, 4-008, 4-023, 4-025, 4-027, 4-037, 4-056, 4-074, 4-081, 4-097, 4-105, 4-120, 4-121, 4-124, 4-128, 5-001, 7-022, 7-024, 7-028, 7-030, 7-036, 7-042, 7-048, 7-049, 7-052, 7-058, 7-061, 7-067, 7-070, 7-073, 7-081, 7-100, 7-103, 7-116.

Test Example 17

Insecticidal Test Against Broad Mite

A wet filter paper was laid in a styrol cup having an inner diameter of 7 cm, a leaf of a common bean cut out so as to have the same diameter was laid thereon, and 10 adults of broad mite (*Polyphagotarsonemus latus*) per leaf was inoculated thereon. A 10% emulsifiable concentrate (depending on the compounds, 10% wettable powder was applied for the test) of the compound of the present invention was diluted with water containing a spreading agent to prepare a chemical solution with a concentration of 100 ppm. The chemical solution was sprayed with a rotating spray tower in an amount of 2.5 ml per styrol cup, and the styrol cups were covered with lids and contained at a thermostat chamber at 25° C. A number of dead insect(s) after 2 days was counted and a rate of dead insects was calculated by the calculation equation similar to that in Test Example 1. Incidentally, the test was carried out with two districts.
As a result, the following compounds showed an insecticidal rate of 80% or more among the compounds tested.
The compounds of the present invention: No. 2-031, 2-036, 2-069, 2-079 to 2-082, 2-104, 2-106, 2-110, 2-122, 2-124, 2-134, 2-140, 2-141, 2-144, 2-185, 2-259, 2-281, 2-318, 2-327, 2-386, 2-390, 2441, 2472, 2480, 2-533, 4-114, 4-121, 4-124, 4-127, 7-022, 7-024, 7-028, 7-049, 7-051, 7-052, 7-060, 7-061, 7-067, 7-070, 7-073, 7-081, 7-096, 7-100, 7-112, 7-116.

Test Example 18

Insecticidal Test Against Cat Flea

After 400 μl of acetone solution in which 4 mg of the compound of the present invention was dissolved in 40 ml of acetone (concentration 100 ppm) was coated on the bottom face and side face of a laboratory dish having an inner diameter of 5.3 cm, acetone was vaporized to prepare a thin film of the compound of the present invention on the inner wall of the laboratory dish. As the surface area of the inner wall is 40 cm$^2$, the treated dosage is 1 μg/cm$^2$. 10 adults of *Ctenocephalides felis* (male and female are mixed) were left in the laboratory dish, covered with lid and contained at a thermostat chamber at 25° C. A number of dead insect(s) after 4 days was counted and a rate of dead insects was calculated by the calculation equation similar to that in Test Example 1. Incidentally, the test was carried out with one district. As a result, the following compounds showed an insecticidal rate of 80% or more among the compounds tested.
The compounds of the present invention: No. 2-031, 2-032, 2-363, 2-369, 2-387, 2-393, 2428, 2433, 2441, 2472, 7-061, 7-065, 7-067, 7-068, 7-070, 7-073, 7-074, 7-080, 7-081, 7-085, 7-095, 7-096, 7-099, 7-100, 7-103.
In the interim, the indication of "*" shows that the insecticidal test was carried out by use of a chemical solution of a concentration of 0.1 μg/cm$^2$.

Test Example 19

Insecticidal Test Against American Dog Tick

After 400 μl of acetone solution in which 4 mg of the compound of the present invention was dissolved in 40 ml of acetone (concentration 100 ppm) was coated on the bottom face and side face of two laboratory dishes having an inner diameter of 5.3 cm, acetone was vaporized to prepare a thin film of the compound of the present invention on the inner wall of the laboratory dish. As the surface area of the inner wall is 40 cm$^2$, the treated dosage is 1 μg/cm$^2$. 10-American dog tick (*Dermacentor variabilis*) (male and female are mixed) in the stage of protonymph were left in the laboratory dishes, two laboratory dishes together were sealed with a tape so that ticks do not escape, and contained at a thermostat chamber at 25° C. A number of dead insect(s) after 4 days was counted and a rate of dead insects was calculated by the calculation equation similar to that in Test Example 1. Incidentally, the test was carried out with one district.

As a result, the following compounds showed an insecticidal rate of 80% or more among the compounds tested.

The compounds of the present invention: No. 2-021, 2-031, 2-032, 2-144, 2-363, 2-369, 2-374, 2-380, 2-382, 2-385, 2-387, 2-393, 2-396, 2-420, 2428, 2441, 2448, 2452, 2-454, 2472, 2477, 2480, 2484, 2486, 2495, 2-500, 2-503, 2-504, 2-506, 2-512, 2-527 to 2-530, 2-533, 2-534, 4-137, 4-143, 7-061, 7-063 to 7-075, 7-081, 7-085, 7-096, 7-100, 7-107, 7-108, 7-110, 7-111, 7-117.

In the interim, the indication of "1" shows that the insecticidal test was carried out by use of a chemical solution of a concentration of 0.1 μg/cm².

INDUSTRIAL APPLICABILITY

The substituted isoxazoline compounds according to the present invention are extremely useful compounds showing an excellent pesticidal activity, particularly an insecticidal and acaricidal activity, and causing little adverse effect against non-targeted beings such as mammals, fishes and useful insects.

The invention claimed is:

1. An isoxazoline compound of formula (I) or a salt thereof:

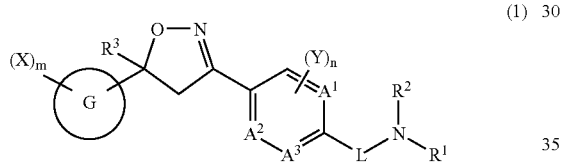

wherein $A^1$, $A^1$ and $A^3$ independently of one another are carbon atom or nitrogen atom, G is benzene ring, L is —C($R^{2a}$)($R^{2b}$)—, —C($R^{2a}$)($R^{2b}$)CH$_2$—, or —CH$_2$C($R^{2a}$)($R^{2b}$)—, X is halogen atom, cyano, nitro, azido, —SCN, —SF$_5$, C$_1$-C$_6$alkyl, C$_1$-C$_6$alkyl arbitrarily substituted with $R^4$, C$_3$-C$_8$cycloalkyl, C$_3$-C$_8$cycloalkyl arbitrarily substituted with $R^4$, E-1 to E-49, C$_2$-C$_6$alkenyl, C$_2$-C$_6$alkenyl arbitrarily substituted with $R^4$, C$_3$-C$_8$cycloalkenyl, C$_3$-C$_8$halocycloalkenyl, C$_2$-C$_6$alkynyl, C$_2$-C$_6$alkynyl arbitrarily substituted with $R^4$, —OH, —OR$^5$, —OSO$_2$R$^5$, —SH, —S(O)$_r$R$^5$, —NH$_2$, —N(R$^7$)R$^6$, —N=CHOR$^8$, —N=C(R$^9$)OR$^8$, —CHO, —C(O)R$^9$, —C(O)OR$^9$, —C(O)SR$^9$, —C(O)NH$_2$, —C(O)N(R$^{10}$)R$^9$, —C(S)OR$^9$, —C(S)SR$^9$, —C(S)NH$_2$, —C(S)N(R$^{10}$)R$^9$, —CH=NOR$^{11}$, —C(R$^9$)=NOR$^{11}$, S(O)$_2$OR$^9$, —S(O)$_2$NH$_2$, —S(O)$_2$N(R$^{10}$)R$^9$, —Si(R$_{12a}$)(R$^{12b}$)R$^{12}$, phenyl, phenyl substituted with (Z)$_{p1}$, or D-1 to D-65, when m is an integer of 2 or more, each X may be identical with or different from each other, further, when two Xs are adjacent, the adjacent two Xs may form 5-membered or 6-membered ring together with carbon atoms to which the two Xs are bonded by forming —CH$_2$CH$_2$CH$_2$—, —CH$_2$CH$_2$O—, —CH$_2$OCH$_2$—, —OCH$_2$O—, —CH$_2$CH$_2$S—, —CH$_2$SCH$_2$—, —CH$_2$CH$_2$N(R$^{13}$)—, —CH$_2$N(R$^{13}$)CH$_2$—, —CH$_2$CH$_2$CH$_2$CH$_2$—, —CH$_2$CH$_2$CH$_2$O—, —CH$_2$CH$_2$OCH$_2$—, —CH$_2$OCH$_2$O—, —OCH$_2$CH$_2$O—, —OCH$_2$CH$_2$S—, —CH$_2$CH=CH—, —OCH=CH—, —SCH=CH—, —N(R$^{13}$)CH=CH—, —OCH=N—, —SCH=N—, —N(R$^{13}$)CH=N—, —N(R$^{13}$)N=CH—, —CH=CHCH=CH—, —OCH$_2$CH=CH—, —N=CHCH=CH—, —N=CHCH=N— or —N=CHN=CH—, in this case, hydrogen atoms bonded to each carbon atom forming the ring may be arbitrarily substituted with Z, further when the hydrogen atoms are substituted with two or more Zs at the same time, each Z may be identical with or different from each other, Y is halogen atom, cyano, nitro, azido, —SCN, —SF$_5$, C$_1$-C$_6$alkyl, C$_1$-C$_6$alkyl arbitrarily substituted with $R^4$, C$_3$-C$_8$cycloalkyl, C$_3$-C$_8$cycloalkyl arbitrarily substituted with $R^4$, E-1 to E-49, C$_2$-C$_6$alkynyl, C$_2$-C$_6$alkynyl arbitrarily substituted with $R^4$, —OH, —OR$^5$, —OSO$_2$R$^5$, —SH, —S(O)$_r$R$^5$, —NH$_2$, —N(R$^7$)R$^6$, —N(R$^7$)C(O)R$^{9a}$, —N(R$^7$)C(O)OR$^{9a}$, —N(R$^7$)C(O)SR$^{9a}$, —N(R$^7$)C(S)OR$^{9a}$, —N(R$^7$)C(S)SR$^{9a}$, —N(R$^7$)S(O)$_2$R$^{9a}$, —N=CHOR$^8$, —N=C(R$^9$)OR$^8$, —C(O)NH$_2$, —C(O)N(R$^{10}$)R$^9$, —C(S)NH$_2$, —C(S)N(R$^{10}$)R$^9$, —Si(R$^{12a}$)(R$^{12b}$)R$^{12}$, phenyl, phenyl substituted with (Z)$_{p1}$, or D-1 to D-65, when n is an integer of 2 or more, each Y may be identical with or different from each other, further, when two Ys are adjacent, the adjacent two Ys may form 5-membered or 6-membered ring together with carbon atoms to which the two Ys are bonded by forming —CH$_2$CH$_2$CH$_2$—, —CH$_2$CH$_2$O—, —CH$_2$OCH$_2$—, —OCH$_2$O—, —CH$_2$CH$_2$S—, —CH$_2$SCH$_2$—, —SCH$_2$S—, —CH$_2$CH$_2$CH$_2$CH$_2$—, —CH$_2$CH$_2$CH$_2$O—, —CH$_2$CH$_2$OCH$_2$—, —CH$_2$OCH$_2$O—, —OCH$_2$CH$_2$O—, —OCH$_2$CH$_2$S—, —SCH$_2$CH$_2$S—, —OCH=N— or —SCH=N—, in this case, hydrogen atoms bonded to each carbon atom forming the ring may be arbitrarily substituted with Z, further when the hydrogen atoms are substituted with two or more Zs at the same time, each Z may be identical with or different from each other, $R^1$ is hydrogen atom, —CHO, —C(=W$^1$)R$^{1a}$, —C(=W$^1$)—W$^2$—R$^{1a}$, —C(=W$^1$)NH$_2$, —C(=W$^1$)N(R$^{1b}$)R$^{1a}$, —C(=W$^1$)NHC(O)R$^{1a}$, —C(=W$^1$)NHSO$_2$R$^{1a}$, —S(O)$_2$R$^{1a}$, —S(O)$_2$NH$_2$ or —S(O)$_2$N(R$^{1b}$)R$^{1a}$, W$^1$ and W$^2$ independently of each other are oxygen atom or sulfur atom, $R^{1a}$ is C$_1$-C$_{12}$alkyl, C$_1$-C$_{12}$alkyl arbitrarily substituted with $R^{14}$, C$_3$-C$_{12}$cycloalkyl, C$_3$-C$_{12}$cyloalkyl arbitrarily substituted with $R^{14}$, E-1 to E-49, C$_2$-C$_{12}$alkenyl, C$_2$-C$_{12}$alkenyl arbitrarily substituted with $R^{14}$, C$_3$-C$_{12}$cycloalkenyl, C$_3$-C$_{12}$halocycloalkenyl, C$_2$-C$_{12}$alkynyl, C$_2$-C$_{12}$alkynyl arbitrarily substituted with $R^{14}$, phenyl, phenyl substituted with (Z)$_{p1}$ or D-1 to D-65, $R^{1b}$ is hydrogen atom, C$_1$-C$_6$alkyl, C$_1$-C$_6$haloalkyl, C$_3$-C$_6$cycloalkyl C$_1$-C$_4$alkyl, C$_1$-C$_6$alkoxy C$_1$-C$_4$alkyl, C$_1$-C$_6$alkylthio C$_1$-C$_4$alkyl, cyano C$_1$-C$_6$alkyl, phenyl C$_1$-C$_4$alkyl, phenyl C$_1$-C$_4$alkyl substituted with (Z)$_{p1}$, C$_3$-C$_6$alkenyl or C$_3$-C$_6$alkynyl, or $R^{1b}$ together with $R^{1a}$ may form 3- to 7-membered ring together with the nitrogen atom bonding them by forming C$_2$-C$_6$alkylene chain, in this case, the alkylene chain may contain one oxygen atom, sulfur atom or nitrogen atom, and may be arbitrarily substituted with halogen atom, C$_1$-C$_6$alkyl, C$_1$-C$_6$alkoxy, —CHO, C$_1$-C$_6$alkylcarbonyl or C$_1$-C$_6$alkoxycarbonyl, $R^2$ is hydrogen atom, C$_1$-C$_{12}$alkyl, C$_1$-C$_{12}$haloalkyl, C$_1$-C$_6$alkyl arbitrarily substituted with $R^{14a}$, $C_3$-$C_2$cycloalkyl, $C_3$-$C_{12}$alkenyl, $C_3$-$C_{12}$haloalkenyl, $C_3$-$C_{12}$alkynyl, $C_3$-$C_{12}$haloalkynyl, —C(O)$R^{15}$, —C(O)O$R^{15}$, —C(O)S$R^{15}$, —CONH$_2$, —C(O)N($R^{16}$)$R^{15}$, —C(S)O$R^{15}$, —C(S)S$R^{15}$, C(S)NH$_2$, —C(S)N($R^{16}$)$R^{15}$, —S$R^{15}$, —S(O)$_2R^{15}$, —SN($R^{18}$)$R^{17}$, phenyl or phenyl substituted with $(Z)_{p1}$, or $R^2$ together with $R^1$ may form 5- to 7-membered ring together with the nitrogen atom bonding them by forming $C_4$-$C_6$alkylene chain, in this case, the alkylene chain may contain one oxygen atom, sulfur atom or nitrogen atom, and may be arbitrarily substituted with $C_1$-$C_6$alkyl, $C_1$-$C_6$haloalkyl, —CHO, $C_1$-$C_6$alkylcarbonyl, $C_1$-$C_6$haloalkylcarbonyl, $C_1$-$C_6$alkoxycarbonyl, $C_1$-$C_6$haloalkoxycarbonyl, $C_1$-$C_6$alkylaminocarbonyl, $C_1$-$C_6$haloalkylaminocarbonyl, phenyl, phenyl substituted with $(Z)_{p1}$, D-52, D-55, oxo or thioxo, or further when substituent Y is present on an adjacent position, $R^2$ together with Y may form 5- or 6-membered ring together with the atoms to which the $R^2$ and Y are bonded by forming —CH$_2$—, —CH$_2$CH$_2$—, —CH$_2$O—, —CH$_2$S— or —CH$_2$N($R^6$)—, $R^{2a}$ is hydrogen atom, cyano, $C_1$-$C_6$alkyl, $C_1$-$C_6$haloalkyl, or $C_1$-$C_6$alkoxycarbonyl, —C(O)NH$_2$—, or —C(S)NH$_2$, $R^{2b}$ is hydrogen atom or $C_1$-$C_6$alkyl, or $R^{2b}$ together with $R^{2a}$ may form 3- to 6-membered ring with the carbon atom bonding them by forming $C_2$-$C_5$alkylene chain, in this case, the alkylene chain may contain one oxygen atom, sulfur atom or nitrogen atom, $R^{2c}$ is hydrogen atom, $C_1$-$C_6$alkyl, $C_1$-$C_6$haloalkyl, $C_1$-$C_6$alkylcarbonyl, $C_1$-$C_6$haloalkylcarbonyl or $C_1$-$C_6$alkoxycarbonyl, $R^3$ is halogen atom, cyano, $C_1$-$C_6$alkyl, $C_1$-$C_6$alkyl arbitrarily substituted with $R^4$, $C_3$-$C_8$cycloalkyl, $C_3$-$C_8$cycloalkyl arbitrarily substituted with $R^4$, E-1 to E-49, $C_3$-$C_6$alkenyl, $C_2$-$C_6$alkenyl arbitrarily substituted with $R^4$, $C_3$-$C_6$alkynyl, $C_2$-$C_6$alkynyl arbitrarily substituted with $R^4$, —O$R^5$, —S(O)$_rR^5$, —N($R^{10}$)$R^9$, —N($R^{10}$)$R^{9a}$, —CHO, —C(O)$R^9$, —C(O)O$R^9$, —C(O)S$R^9$, —C(O)NH$_2$, —C(O)N($R^{10}$)$R^9$, —C(S)O$R^9$, —C(S)S$R^9$, —C(S)NH$_2$, —C(S)N($R^{10}$)$R^9$, —CH=NO$R^{11}$, —C($R^9$)=NO$R^{11}$, M 5, M 20, M 48, Si($R^{12a}$)($R^{12b}$)$R^{12}$, —P(O)(O$R^{19}$)$_2$, phenyl, phenyl substituted with $(Z)_{p1}$ or D-1 to D-65, D-1 to D-65 are aromatic heterocyclic rings of the following formulae, respectively

D-1

D-2

D-3

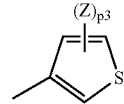

D-4

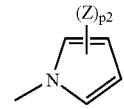

D-5

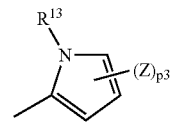

D-6

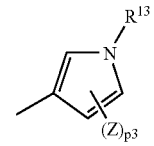

D-7

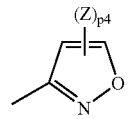

D-8

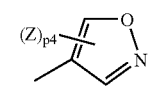

D-9

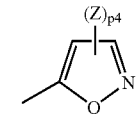

D-10

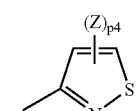

D-11

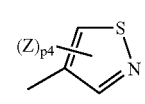

D-12

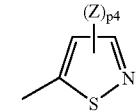

D-13

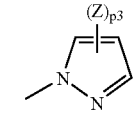

D-14

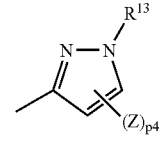

D-15

-continued
D-16 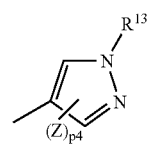
D-17 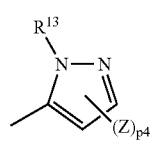
D-18 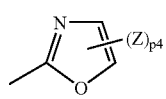
D-19 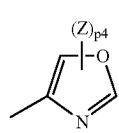
D-20 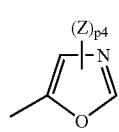
D-21 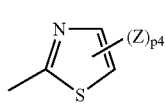
D-22 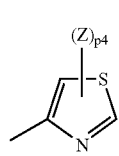
D-23 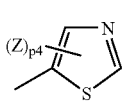
D-24 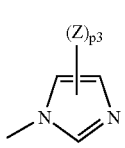
D-25 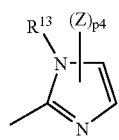
D-26 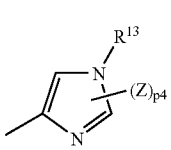
D-27 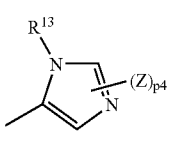
-continued
D-28 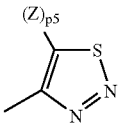
D-29 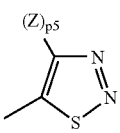
D-30 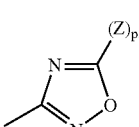
D-31 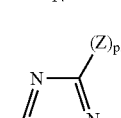
D-32 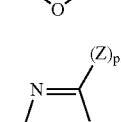
D-33 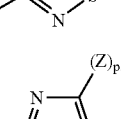
D-34 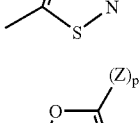
D-35 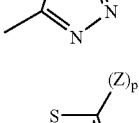
D-36 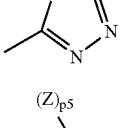
D-37 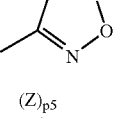
D-38 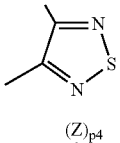
D-39 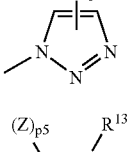

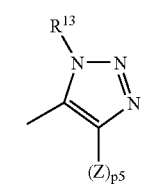 D-40
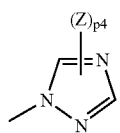 D-41
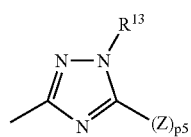 D-42
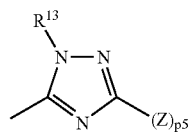 D-43
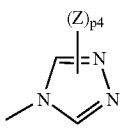 D-44
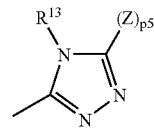 D-45
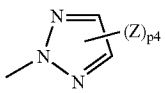 D-46
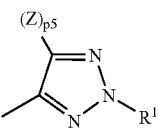 D-47
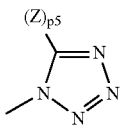 D-48
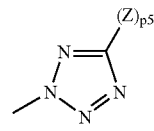 D-49
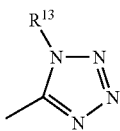 D-50
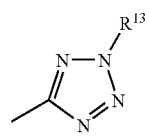 D-51
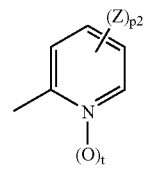 D-52
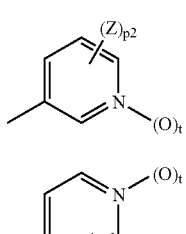 D-53
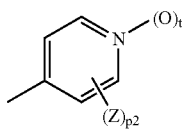 D-54
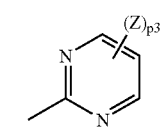 D-55
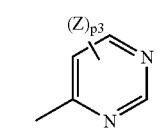 D-56
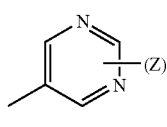 D-57
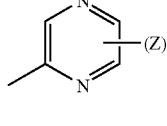 D-58
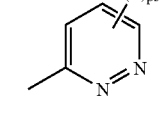 D-59
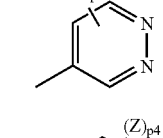 D-60
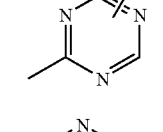 D-61
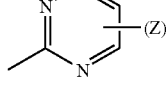 D-62

-continued

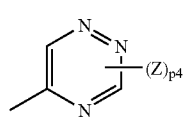
D-63

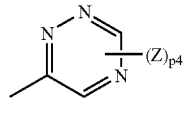
D-64

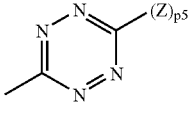
D-65

Z is halogen atom, cyano, nitro, $C_1$-$C_6$alkyl, $C_1$-$C_6$haloalkyl, $C_1$-$C_4$alkoxy $C_1$-$C_4$alkyl, $C_1$-$C_4$haloalkoxy $C_1$-$C_4$alkyl, $C_1$-$C_4$alkylthio $C_1$-$C_4$alkyl, $C_1$-$C_4$haloalkylthio $C_1$-$C_4$alkyl, $C_1$-$C_4$alkylsulfinyl $C_1$-$C_4$alkyl, $C_1$-$C_4$haloalkylsulfinyl $C_1$-$C_4$alkyl, $C_1$-$C_4$alkylsulfonyl $C_1$-$C_4$alkyl, $C_1$-$C_4$haloalkylsulfonyl $C_1$-$C_4$alkyl, $C_3$-$C_6$cycloalkyl, $C_3$-$C_6$halocycloalkyl, —OH, $C_1$-$C_6$alkoxy, $C_1$-$C_6$haloalkoxy, $C_1$-$C_6$alkylsulfonyloxy, $C_1$-$C_6$haloalkylsulfonyloxy, $C_1$-$C_6$alkylthio, $C_1$-$C_6$haloalkylthio, $C_1$-$C_6$alkylsulfinyl, $C_1$-$C_6$haloalkylsulfinyl, $C_1$-$C_6$alkylsulfonyl, $C_1$-$C_6$haloalkylsulfonyl, —$NH_2$, $C_1$-$C_6$alkylamino, di($C_1$-$C_6$alkyl)amino, $C_1$-$C_6$alkoxycarbonyl, $C_1$-$C_6$haloalkoxycarbonyl, —C(O)$NH_2$, $C_1$-$C_6$alkylaminocarbonyl, $C_1$-$C_6$haloalkylaminocarbonyl, di($C_1$-$C_6$alkyl)aminocarbonyl, —C(S)$NH_2$, —S(O)$_2NH_2$, $C_1$-$C_6$alkylaminosulfonyl, di($C_1$-$C_6$alkyl)aminosulfonyl, phenyl or phenyl arbitrarily substituted with halogen atom, when p1, p2, p3 or p4 is an integer of 2 or more, each Z may be identical with or different from each other, further, when two Zs are adjacent, the adjacent two Zs may form 5-membered or 6-membered ring together with carbon atoms to which the two Zs are bonded by forming —$CH_2CH_2CH_2$—, —$CH_2OCH_2$—, —$OCH_2O$—, —$CH_2CH_2S$—, —$CH_2SCH_2$—, —$CH_2CH_2CH_2CH_2$—, —$CH_2CH_2CH_2O$—, —$CH_2CH_2OCH_2$—, —$CH_2OCH_2O$—, —$OCH_2CH_2O$—, —$CH_2CH_2CH_2S$—, —$OCH_2CH_2S$— or —CH=CH—CH=CH—, in this case, hydrogen atoms bonded to each carbon atom forming the ring may be arbitrarily substituted with halogen atom, cyano, nitro, $C_1$-$C_4$alkyl, $C_1$-$C_4$haloalkyl, $C_1$-$C_4$alkoxy or $C_1$-$C_4$alkylthio, E-1 to E-49 are saturated heterocyclic rings of the following formulae, respectively

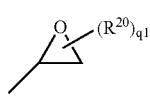
E-1

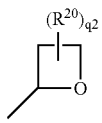
E-2

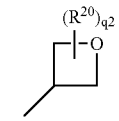
E-3

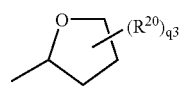
E-4

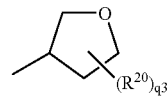
E-5

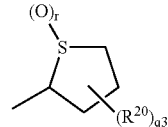
E-6

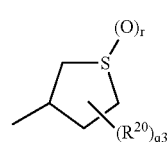
E-7

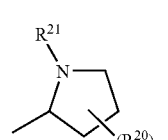
E-8

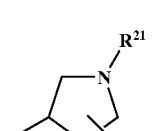
E-9

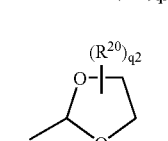
E-10

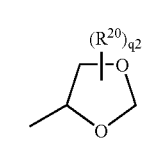
E-11

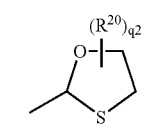
E-12

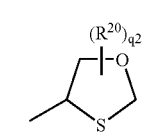
E-13

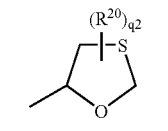
E-14

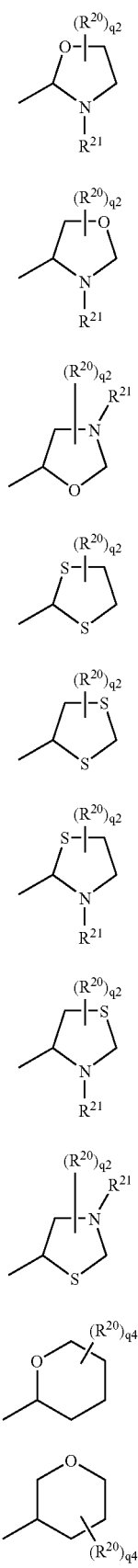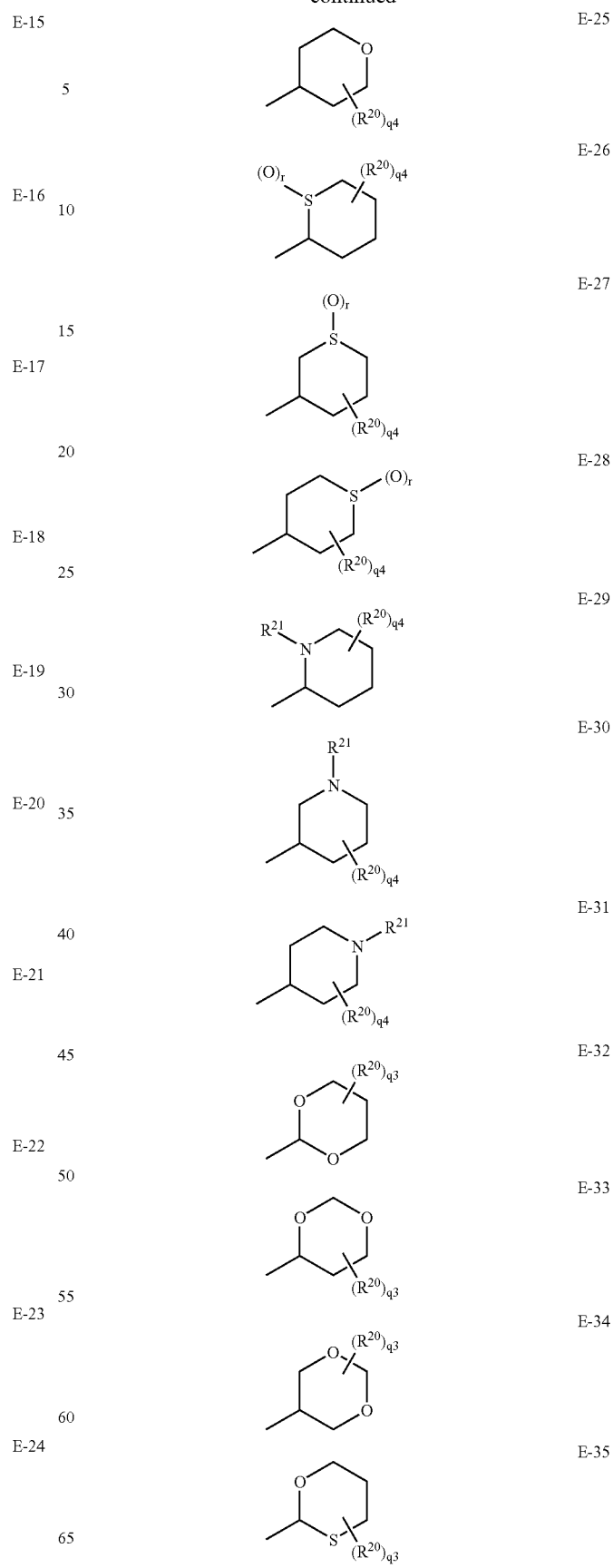

-continued

E-36 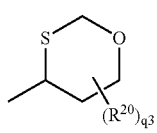

E-37 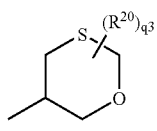

E-38 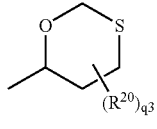

E-39 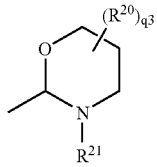

E-40 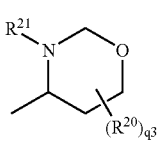

E-41 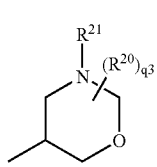

E-42 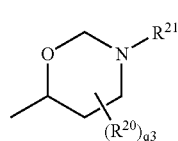

E-43 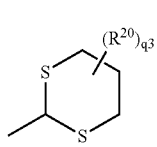

E-44 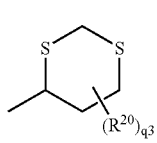

E-45 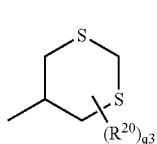

E-46 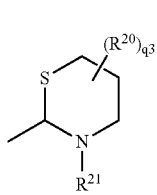

E-47 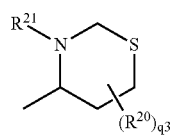

E-48 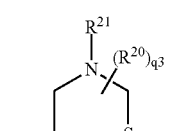

E-49 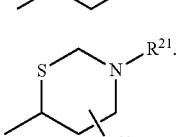

$R^4$ is halogen atom, cyano, $C_3$-$C_8$cycloalkyl, $C_3$-$C_8$halocycloalkyl, E-1 to E-49, —OH, —$OR^5$, —SH, —S(O)$_r R^5$, —N($R^7$)$R^6$, —N($R^7$)C(O)$R^{9a}$, —N($R^7$)C(O)$OR^{9a}$, —N($R^7$)C(O)$SR^{9a}$, —N($R^7$)C(S)$OR^{9a}$, —N($R^7$)C(S)$SR^{9a}$, —N($R^7$)S(O)$_2 R^{9a}$, —C(O)$OR^9$,)-C(O)N($R^{10}$)$R^9$, —Si($R^{12a}$)($R^{12b}$)$R^{12}$, phenyl, phenyl substituted with $(Z)_{p1}$ or D-1 to D-65, $R^5$ is $C_1$-$C_6$alkyl, $C_1$-$C_6$alkyl arbitrarily substituted with $R^{22}$, $C_3$-$C_8$cycloalkyl, $C_3$-$C_8$cycloalkyl arbitrarily substituted with $R^{22}$, E-3 to E-9, E-23 to E-31, E-34, E-45, $C_2$-$C_6$alkenyl, $C_2$-$C_6$alkenyl arbitrarily substituted with $R^{22}$, $C_3$-$C_8$cycloalkenyl, $C_3$-$C_8$halocycloalkenyl, $C_3$-$C_6$alkynyl, $C_3$-$C_6$alkynyl arbitrarily substituted with $R^{22}$, $C_1$-$C_6$alkylcarbonyl, $C_1$-$C_6$alkoxycarbonyl, phenyl, phenyl substituted with $(Z)_{p1}$, D-1 to D-4, D-6 to D-13, D-15 to D-23, D-25 to D-37, D-39, D-40, D-42, D-43, D-45, D-47, D-50 to D-64 or D-65, $R^6$ is $C_1$-$C_6$alkyl, $C_1$-$C_6$allyl arbitrarily substituted with $R^{22}$, $C_3$-$C_8$cycloalkyl, $C_3$-$C_8$halocycloalkyl, $C_3$-$C_6$alkenyl, $C_3$-$C_6$haloalkenyl, $C_3$-$C_6$alkynyl, $C_3$-$C_6$haloalkynyl, —CHO, —C(O)$R^9$, —C(O)$OR^9$, —C(O)$SR^9$, —C(O)$NH_2$, —C(O)N($R^{10}$)$R^9$, —C(S)$OR^9$, —C(S)$SR^9$, —C(S)$NH_2$, —C(S)N($R^{10}$)$R^9$, —C(O)C(O)$R^9$, —C(O)C(O)$OR^9$, —OH, —S(O)$_2 R^9$,)-S(O)$_2$N($R^{10}$)$R^9$, —P(O)(O$R^{19}$)$_2$ or —P(S)(O$R^{19}$)$_2$, $R^7$ is hydrogen atom, $C_1$-$C_6$alkyl, $C_1$-$C_6$alkyl arbitrarily substituted with $R^{22}$, $C_3$-$C_8$cycloalkyl, $C_3$-$C_6$alkenyl, $C_3$-$C_6$haloalkenyl, $C_3$-$C_6$alkynyl, $C_3$-$C_6$haloalkynyl, —CHO, $C_1$-$C_6$alkylcarbonyl, $C_1$-$C_6$haloalkylcarbonyl or $C_1$-$C_6$alkoxycarbonyl, or $R^7$ together with $R^6$ may form 3- to 7-membered ring together with the nitrogen atom bonding them by forming $C_2$-$C_6$alkylene chain, in this case, the alkylene chain may contain one oxygen atom, sulfur atom or nitrogen atom, and may be arbitrarily substituted with halogen atom, $C_1$-$C_6$alkyl, $C_1$-$C_6$haloalkyl, oxo or thioxo, $R^8$ is $C_1$-$C_6$alkyl, $C_1$-$C_6$haloalkyl, $C_3$-$C_6$alkenyl, phenyl or phenyl substituted with $(Z)_{p1}$, $R^9$ is $C_1$-$C_6$alkyl, $C_1$-$C_6$alkyl arbitrarily substituted with $R^{22}$, $C_3$-$C_8$cycloalkyl, $C_3$-$C_8$halocycloalkyl, E-1 to E-49, $C_3$-$C_6$alkenyl, $C_3$-$C_6$haloalkenyl, $C_3$-$C_6$alkynyl or $C_3$-$C_6$haloalkynyl, $R^{9a}$ is phenyl, phenyl substituted with $(Z)_{p1}$ or D-1 to D-65, $R^{10}$ is hydrogen atom, $C_1$-$C_6$allyl, $C_1$-$C_6$haloalkyl, $C_3$-$C_6$cycloalkyl $C_1$-$C_4$alkyl, $C_1$-$C_6$alkoxy $C_1$-$C_4$alkyl, $C_1$-$C_6$alkylthio $C_1$-$C_4$alkyl, cyano $C_1$-$C_6$alkyl, $C_3$-$C_6$alkenyl or $C_3$-$C_6$alkynyl, or $R^{10}$ together with $R^9$ may form 3- to 7-membered ring with the nitrogen atom bonding them by forming $C_2$-$C_6$alkylene chain, in this case, the alkylene chain may contain one oxygen atom, sulfur atom or nitrogen atom, and may be arbitrarily substituted with halogen atom, $C_1$-$C_6$alkyl, $C_1$-$C_6$alkoxy, —CHO, $C_1$-$C_6$alkylcarbonyl or $C_1$-$C_6$alkoxycarbonyl, $R^{11}$ is hydrogen atom, $C_1$-$C_6$alkyl, $C_1$-$C_6$haloalkyl, phenyl $C_1$-$C_4$alkyl, phenyl $C_1$-$C_4$alkyl substituted with $(Z)_{p1}$, $C_3$-$C_6$alkenyl, $C_3$-$C_6$haloalkenyl, $C_3$-$C_6$alkynyl or $C_3$-$C_6$haloalkynyl, $R^{12}$ is $C_1$-$C_6$alkyl, $C_1$-$C_6$haloalkyl, $C_1$-$C_6$alkoxy, phenyl or phenyl substituted with $(Z)_{p1}$, $R^{12a}$ and $R^{12b}$ independently of each other are $C_1$-$C_6$alkyl, $C_1$-$C_6$haloalkyl or $C_1$-$C_6$alkoxy, $R^{13}$ is hydrogen atom, $C_1$-$C_6$alkyl, $C_1$-$C_6$haloalkyl, $C_1$-$C_6$alkoxycarbonyl $C_1$-$C_4$alkyl, $C_1$-$C_6$haloalkoxycarbonyl $C_1$-$C_4$allyl, phenyl $C_1$-$C_4$alkyl, phenyl $C_1$-$C_4$alkyl substituted with $(Z)_{p1}$, $C_2$-$C_6$alkenyl, $C_2$-$C_6$haloalkenyl, $C_3$-$C_6$alkynyl, $C_3$-$C_6$haloalkynyl, $C_1$-$C_6$alkoxy, $C_1$-$C_6$alkoxycarbonyl, $C_1$-$C_6$haloalkoxycarbonyl, phenyl or phenyl substituted with $(Z)_{p1}$, further, in case where Z is present in an adjacent position of $R^{13}$, $R^{13}$ together with Z may form 6-membered ring together with the atom bonding them by forming —CH$_2$CH$_2$CH$_2$CH$_2$—, —CH=CH—CH=CH—, —N=CH—CH=CH—, —CH=N—CH=CH—, —CH=CH—N=CH— or —CH=CH—CH=N—, in this case, hydrogen atoms bonded to each carbon atom forming the ring may be arbitrarily substituted with halogen atom, $C_1$-$C_4$alkyl or $C_1$-$C_4$haloalkyl, $R^{14}$ is halogen atom, cyano, nitro, $C_3$-$C_8$cycloalkyl, $C_3$-$C_8$halocycloalkyl, E-4 to E-7, E-10 to E-11, E 32, $C_5$-$C_8$cycloalkenyl, $C_5$-$C_8$halocycloalkenyl, —OR$^{23}$, —N(R$^{24}$)R$^{23}$, —S(O)$_r$R$^{25}$, —C(O)R$^{26}$, —C(O)OR$^{26}$, —C(O)SR$^{26}$, —C(O)N(R$^{27}$)R$^{26}$, —C(S)OR$^{26}$, —C(S)SR$^{26}$, —C(S)N(R$^{27}$)R$^{26}$, Si(R$^{12a}$)(R$^{12b}$)R$^{12}$, phenyl, phenyl substituted with $(Z)_{p1}$ or D-1 to D-65,

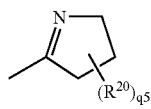
M-1

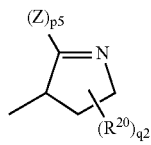
M-2

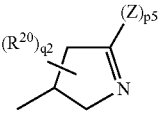
M-3

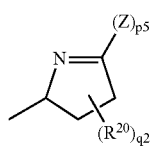
M-4

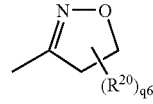
M-5

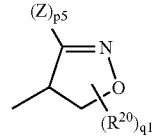
M-6

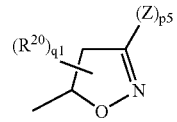
M-7

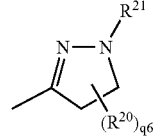
M-8

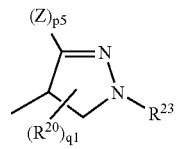
M-9

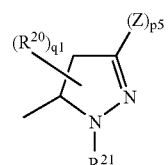
M-10

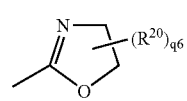
M-11

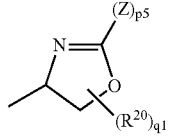
M-12

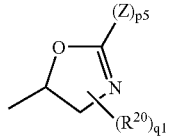
M-13

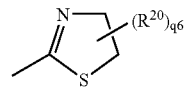
M-14

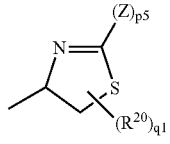
M-15

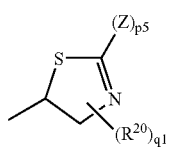 M-16
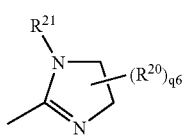 M-17
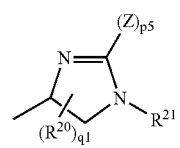 M-18
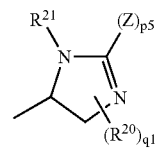 M-19
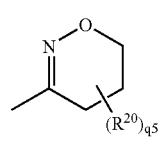 M-20
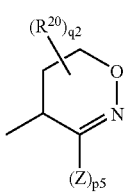 M-21
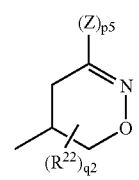 M-22
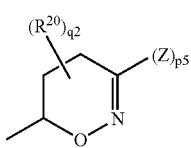 M-23
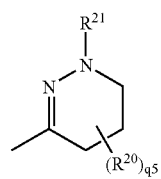 M-24
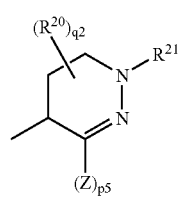 M-25
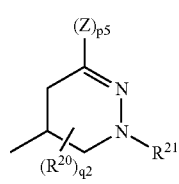 M-26
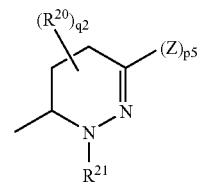 M-27
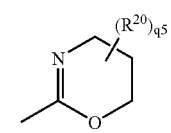 M-28
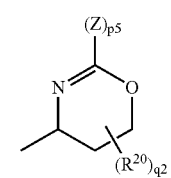 M-29
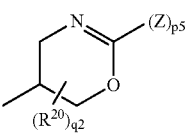 M-30
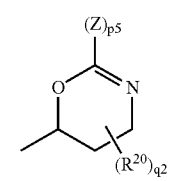 M-31
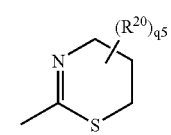 M-32
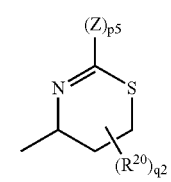 M-33
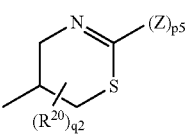 M-34
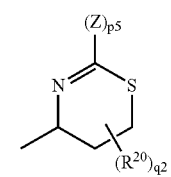 M-35

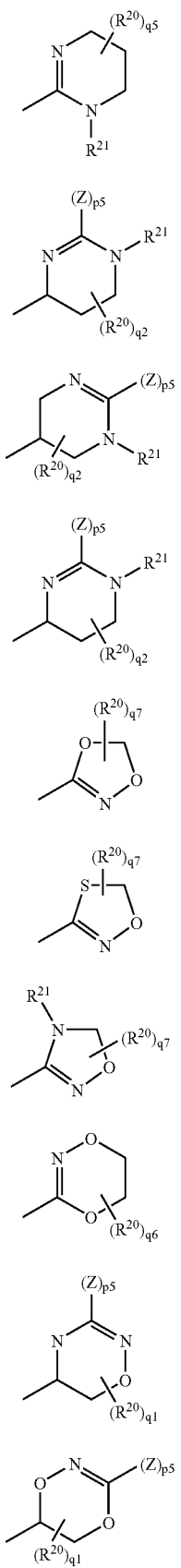

$R^{14a}$ is cyano, $OR^{23}$, —$N(R^{24})R^{23}$, —$S(O)_rR^{25}$, —$C(O)OR^{26}$, phenyl or phenyl substituted with $(Z)_{p1}$, $R^{15}$ is $C_1$-$C_6$alkyl, $C_1$-$C_6$alkyl arbitrarily substituted with $R^{29}$, $C_3$-$C_8$cycloalkyl, $C_3$-$C_8$halocycloalkyl, $C_2$-$C_6$alkenyl, $C_2$-$C_6$haloalkenyl, $C_2$-$C_6$alkynyl, $C_2$-$C_6$haloalkynyl, phenyl, phenyl substituted with $(Z)_{p1}$, naphthyl, D-52, D-53 or D 54, $R^{16}$ is hydrogen atom, $C_1$-$C_6$alkyl, $C_1$-$C_6$haloalkyl, $C_3$-$C_6$alkenyl or $C_3$-$C_6$alkynyl, or $R^{16}$ together with $R^{15}$ may form 5- to 6-membered ring with the nitrogen atom bonding them by forming $C_4$-$C_5$alkylene chain, in this case, the alkylene chain may contain one oxygen atom or sulfur atom, $R^{17}$ is $C_1$-$C_{12}$alkyl, $C_1$-$C_6$alkoxy $C_1$-$C_6$alkyl, $C_1$-$C_6$alkoxycarbonyl $C_1$-$C_6$alkyl, phenyl $C_1$-$C_6$alkyl, phenyl $C_1$-$C_6$alkyl substituted with $(Z)_{p1}$, $C_1$-$C_{12}$alkoxycarbonyl, —$C(O)ON=C(CH_3)SCH_3$ or —$C(O)ON=C(SCH_3)C(O)N(CH_3)_2$, $R^{18}$ is $C_1$-$C_{12}$alkyl, phenyl $C_1$-$C_6$alkyl or phenyl $C_1$-$C_6$alkyl substituted with $(Z)_{p1}$, or $R^{18}$ together with $R^{17}$ may form 5- to 6-membered ring with the nitrogen atom bonding them by forming $C_4$-$C_5$alkylene chain, in this case, the alkylene chain may contain one oxygen atom or sulfur atom, and may be arbitrarily substituted with $C_1$-$C_4$alkyl or $C_1$-$C_4$alkoxy, $R^{19}$ is $C_1$-$C_6$alkyl or $C_1$-$C_6$haloalkyl, $R^{20}$ is halogen atom, $C_1$-$C_6$alkyl or $C_1$-$C_6$haloalkyl, when q1 to q8 are an integer of 2 or more, each $R^{20}$ may be identical with or different from each other, further, when two $R^{20}$s are present on the same carbon atom, the two $R^{20}$s together may form oxo or thioxo, $R^{21}$ is hydrogen atom, $C_1$-$C_6$alkyl, $C_1$-$C_6$haloalkyl, —CHO, —$C(O)R^{30}$, —$C(O)OR^{30}$, —$C(O)SR^{30}$, —$C(O)NH_2$, —$C(O)N(R^{31})R^{30}$, or —$S(O)_2R^{30}$, $R^{22}$ is halogen atom, cyano, $C_3$-$C_8$cycloalkyl, $C_3$-$C_8$halocycloalkyl, E-1 to E-49, $C_1$-$C_6$alkoxy, $C_1$-$C_6$haloalkoxy, $C_1$-$C_6$alkylthio, $C_1$-$C_6$haloalkylthio, $C_1$-$C_6$alkylsulfonyl, $C_1$-$C_6$haloalkylsulfonyl, $C_1$-$C_6$alkylamino, di($C_1$-$C_6$alkyl)amino, —CHO, $C_1$-$C_6$alkylcarbonyl, $C_1$-$C_6$haloalkylcarbonyl, $C_1$-$C_6$alkoxycarbonyl, $C_1$-$C_6$haloalkoxycarbonyl, $C_1$-$C_6$alkylaminocarbonyl, di($C_1$-$C_6$alkyl)aminocarbonyl, phenyl, phenyl substituted with $(Z)_{p1}$, or D-1 to D-65, $R^{23}$ is hydrogen atom, $C_1$-$C_6$allyl, $C_1$-$C_6$allyl arbitrarily substituted with $R^{29}$, $C_3$-$C_6$alkenyl, $C_3$-$C_6$alkynyl, —$C(O)R^{30}$, —$C(O)OR^{30}$, —$C(O)SR^{30}$, —$C(O)NH_2$, —C(O)N(R$^{31}$)R$^{30}$, —C(S)R$^{30}$, —C(S)OR$^{30}$, —C(S)SR$^{30}$, —C(S)NH$_2$, —C(S)N(R$^{31}$)R$^{30}$, —S(O)$_2$R$^{30}$, —S(O)$_2$N(R$^{31}$)R$^{30}$, tri(C$_1$-C$_4$alkyl) silyl, di(C$_1$-C$_6$allyl) thiophosphoryl, phenyl or phenyl substituted with (Z)$_{p1}$, R$^{24}$ X is hydrogen atom, C$_1$-C$_6$alkyl, C$_1$-C$_6$haloalkyl, C$_3$-C$_6$alkenyl or C$_3$-C$_6$alkynyl, or R$^{24}$ together with R$^{23}$ may form 4- to 6-membered ring with the nitrogen atom bonding them by forming C$_3$-C$_5$alkylene chain, in this case, the alkylene chain may contain one oxygen atom, sulfur atom or nitrogen atom, R$^{25}$ is C$_1$-C$_6$alkyl, C$_1$-C$_6$alkyl arbitrarily substituted with R$^{29}$, —C(O)R$^{30}$, —C(O)NH$_2$, —C(O)N(R$^{31}$)R$^{30}$, —C(S)OR$^{30}$, —C(S)NH$_2$, —C(S)N(R$^{31}$)R$^{30}$, C$_1$-C$_6$alkylthio, phenyl, phenyl substituted with (Z)$_{p1}$, D-21, D-35, D-52 or D-55, R$^{26}$ is C$_1$-C$_6$alkyl, C$_1$-C$_6$alkyl arbitrarily substituted with R$^{29}$, C$_3$-C$_6$cycloalkyl, C$_3$-C$_6$halocycloalkyl, E-4, E-5, E-7, E-23, C$_2$-C$_6$alkenyl, C$_2$-C$_6$haloalkenyl, C$_2$-C$_6$alkynyl, C$_2$-C$_6$halolkynyl, phenyl, phenyl substituted with (Z)$_{p1}$, D-1 to D-4, D-21 to D-23, D-52 to D-56, D-58 or D-59, R$^{27}$ is hydrogen atom, C$_1$-C$_6$alkyl, C$_1$-C$_4$alkoxy C$_1$-C$_4$alkyl, C$_1$-C$_4$alkylthio C$_1$-C$_4$alkyl, cyano C$_1$-C$_4$alkyl, C$_3$-C$_6$alkenyl or C$_3$-C$_6$alkynyl, or R$^{27}$ together with R$^{26}$ may form 3- to 6-membered ring with the nitrogen atom bonding them by forming C$_2$-C$_5$alkylene chain, in this case, the alkylene chain may contain one oxygen atom, sulfur atom or nitrogen atom, R$^{29}$ is halogen atom, cyano, C$_3$-C$_8$cycloalkyl, C$_3$-C$_8$halocycloalkyl, E-4 to E-7, —OH, —OR$^{30}$, —S(O)$_r$R$^{30}$, —C(O)OR$^{30}$, —C(O)NH$_2$, —C(O)N(R$^{31}$)R$^{30}$, tri(C$_1$-C$_4$alkyl) silyl, phenyl, phenyl substituted with (Z)$_{p1}$, D-1 to D-4, D-21 to D-23, D-52, D-53 or D-54, R$^{30}$ is C$_1$-C$_6$alkyl, C$_1$-C$_6$haloalkyl, C$_1$-C$_4$alkyl arbitrarily substituted with R$^{32}$, C$_3$-C$_6$cycloalkyl, C$_3$-C$_6$halocycloalkyl, C$_2$-C$_6$alkenyl, C$_2$-C$_6$alkynyl, phenyl, or phenyl substituted with (Z)$_{p1}$, R$^{31}$ is hydrogen atom, C$_1$-C$_6$alkyl, C$_1$-C$_6$haloalkyl, C$_3$-C$_6$alkenyl or C$_3$-C$_6$alkynyl, or R$^{31}$ together with R$^{30}$ may form 3- to 6-membered ring with the nitrogen atom bonding them by forming C$_2$-C$_5$alkylene chain, in this case, the alkylene chain may contain one oxygen atom or sulfur atom, R$^{32}$ is C$_3$-C$_6$cycloalkyl, C$_1$-C$_4$alkoxy, C$_1$-C$_4$alkylthio, C$_1$-C$_4$alkylsulfonyl, phenyl or phenyl substituted with (Z)$_{p1}$, m is an integer of 0 to 5,
n is an integer of 0 to 4,
p1 is an integer of 1 to 5,
p2 is an integer of 0 to 4,
p3 is an integer of 0 to 3,
p4 is an integer of 0 to 2,
p5 is an integer of 0 or 1,
q1 is an integer of 0 to 3,
q2 is an integer of 0 to 5,
q3 is an integer of 0 to 7,
q4 is an integer of 0 to 9,
r is an integer of 0 to 2, and
t is an integer of 0 or 1.

2. The isoxazoline compound or the salt thereof according to claim 1, wherein
G is an aromatic 6-membered ring as shown below in G-1

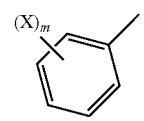

G-1

L is —CH(R$^{2a}$)— or —CH(R$^{2a}$)CH$_2$—
X is halogen atom, cyano, nitro, —SF$_5$, C$_1$-C$_6$alkyl, C$_1$-C$_6$alkyl arbitrarily substituted with R$^4$, C$_3$-C$_8$cycloalkyl, C$_3$-C$_8$haloycloalkyl, C$_2$-C$_6$alkenyl, C$_2$-C$_6$halolkenyl, C$_2$-C$_6$alkynyl, C$_2$-C$_6$halolkynyl, —OH, —OR$^5$, —OSO$_2$R$^5$, —S(O)$_r$R$^5$ or tri(C$_1$-C$_6$alkyl)silyl, when m is an integer of 2 or 3, each X may be identical with or different from each other, further, when two Xs are adjacent, the adjacent two Xs may form 5-membered or 6-membered ring together with carbon atoms to which the two Xs are bonded by forming —CF$_2$OCF$_2$—, —OCF$_2$O—, —CF$_2$OCF$_2$O— or —OCF$_2$CF$_2$O—, Y is halogen atom, cyano, nitro, C$_1$-C$_6$alkyl, C$_1$-C$_6$allyl arbitrarily substituted with R$^4$, C$_2$-C$_6$alkynyl, tri(C$_1$-C$_6$silylethynyl, —OR$^5$, —OSO$_2$R$^5$, —S(O)$_r$R$^5$, —NH$_2$, —N(R$^7$)R$^6$, —N=C(R$^9$)OR$^8$, —C(O)NH$_2$ or —C(S)NH$_2$, when n is 2, each Y may be identical with or different from each other, R$^1$ is hydrogen atom, —C(O)R$^{1a}$, —C(S)R$^{1a}$, —C(O)OR$^{1a}$, —C(O)SR$^{1a}$, —C(S)OR$^{1a}$, —C(S)SR$^{1a}$, —C(O)N(R$^{1b}$)R$^{1a}$, —C(S)N(R$^{1b}$)R$^{1a}$ or —S(O)$_2$R$^{1a}$, R$^{1a}$ is C$_1$-C$_6$alkyl, C$_1$-C$_6$haloalkyl, C$_1$-C$_4$alkyl arbitrarily substituted with R$^{14}$, C$_3$-C$_8$cycloalkyl, C$_3$-C$_6$halocycloalkyl, E 4 to E-7, C$_2$-C$_6$alkenyl, C$_2$-C$_6$haloalkenyl, C$_2$-C$_6$alkynyl, C$_2$-C$_6$haloalkynyl, phenyl, phenyl substituted with (Z)$_{p1}$, D-1 to D-4, D-15 to D-17, D-21 to D-23, D-52 to D-58 or D-59, R$^{1b}$ is hydrogen atom or C$_1$-C$_6$alkyl, or R$^{1b}$ together with R$^{1a}$ may form 3- to 7-membered ring together with the nitrogen atom bonding them by forming C$_2$-C$_6$alkylene chain, in this case, the alkylene chain may contain one oxygen atom or sulfur atom, R$^2$ is hydrogen atom, C$_1$-C$_6$alkyl, C$_1$-C$_6$haloalkyl, C$_1$-C$_4$alkyl arbitrarily substituted with R$^{14a}$, C$_3$-C$_6$cycloalkyl, C$_3$-C$_6$alkenyl, C$_3$-C$_6$alkynyl, —C(O)R$^{15}$, —C(O)OR$^{15}$, —C(O)SR$^{15}$, —C(S)OR$^{15}$, —C(S)SR$^{15}$, C$_1$-C$_6$haloalkylthio or —SN(R$^{18}$)R$^{17}$, or R$^2$ together with R$^1$ may form 5- to 7-membered ring together with the nitrogen atom bonding them by forming C$_4$-C$_6$alkylene chain, in this case, the alkylene chain may contain one oxygen atom, sulfur atom or nitrogen atom, and may be arbitrarily substituted with C$_1$-C$_6$alkyl, oxo or thioxo, R$^{2a}$ is hydrogen atom, cyano, C$_1$-C$_6$alkyl, C$_3$-C$_6$cycloalkyl, R$^{2c}$ is hydrogen atom, C$_1$-C$_6$alkyl, or C$_1$-C$_6$haloalkylcarbonyl, R$^3$ is C$_1$-C$_6$alkyl, C$_1$-C$_6$haloalkyl, C$_1$-C$_4$alkoxy C$_1$-C$_4$haloalkyl, C$_1$-C$_4$haloalkoxy C$_1$-C$_4$haloalkyl, C$_1$-C$_4$alkylthio C$_1$-C$_4$haloalkyl, C$_1$-C$_4$haloalkylthio C$_1$-C$_4$haloalkyl, cyano C$_1$-C$_6$haloalkyl, C$_3$-C$_6$cycloalkyl or C$_3$-C$_6$halocycloalkyl, Z is halogen atom, cyano, nitro, C$_1$-C$_6$alkyl, C$_1$-C$_6$haloalkyl, C$_1$-C$_6$alkoxy, C$_1$-C$_6$haloalkoxy, $C_1$-$C_6$alkylsulfonyloxy, $C_1$-$C_6$haloalkylsulfonyloxy, $C_1$-$C_6$alkylthio, $C_1$-$C_6$haloalkylthio, $C_1$-$C_6$alkylsulfinyl, $C_1$-$C_6$haloalkylsulfinyl, $C_1$-$C_6$alkylsulfonyl, $C_1$-$C_6$haloalkylsulfonyl, —C(O)NH$_2$, —C(S)NH$_2$ or —S(O)$_2$NH$_2$, when p1, p2, p3 or p4 is an integer of 2 or more, each Z may be identical with or different from each other, further, when two Zs are adjacent, the adjacent two Zs may form 5-membered or 6-membered ring together with carbon atoms to which the two Zs are bonded by forming —OCH$_2$O— or —OCH$_2$CH$_2$O—, in this case, hydrogen atoms bonded to each carbon atom forming the ring may be arbitrarily substituted with halogen atom, $R^4$ is halogen atom, —OH, $C_1$-$C_6$alkoxy, $C_1$-$C_6$haloalkoxy, $C_1$-$C_6$alkylthio, $C_1$-$C_6$haloalkylthio, $C_1$-$C_6$alkylsulfinyl, $C_1$-$C_6$haloalkylsulfinyl, $C_1$-$C_6$alkylsulfonyl or $C_1$-$C_6$haloalkylsulfonyl, $R^5$ is $C_1$-$C_6$alkyl, $C_1$-$C_6$haloalkyl, $C_1$-$C_4$haloalkoxy $C_1$-$C_4$haloalkyl, $C_2$-$C_6$alkenyl, $C_2$-$C_6$haloalkenyl, $C_3$-$C_6$alkynyl, $C_3$-$C_6$haloalkynyl or $C_1$-$C_6$alkoxycarbonyl, $R^6$ is $C_1$-$C_6$alkyl, $C_1$-$C_6$haloalkyl, —CHO, —C(O)$R^9$, —C(O)O$R^9$, —C(O)S$R^9$, —C(S)O$R^9$, —C(S)S$R^9$ or —S(O)$_2R^9$, $R^7$ is hydrogen atom, $C_1$-$C_6$alkyl or $C_1$-$C_6$haloalkyl, $R^8$ is $C_1$-$C_6$alkyl, $R^9$ is $C_1$-$C_6$alkyl, $C_1$-$C_6$haloalkyl, $C_3$-$C_6$cycloalkyl or $C_3$-$C_6$halocycloalkyl, $R^{13}$ is $C_1$-$C_6$alkyl or $C_1$-$C_6$haloalkyl, $R^{14}$ is cyano, $C_3$-$C_6$cycloalkyl, $C_1$-$C_6$alkoxy, $C_1$-$C_6$alkylthio, $C_1$-$C_6$alkylsulfinyl, $C_1$-$C_6$alkylsulfonyl, $C_1$-$C_6$alkoxycarbonyl, $C_5$-$C_6$cycloalkenyl, phenyl, phenyl substituted with $(Z)_{p1}$, D-52, D-53 or D-54, $R^{14a}$ is cyano, —OR$^{23}$, $C_1$-$C_6$alkylthio, $C_1$-$C_6$allylsulfonyl or phenyl, $R^{15}$ is $C_1$-$C_6$alkyl, $C_1$-$C_6$haloalkyl, $C_1$-$C_4$alkoxy $C_1$-$C_4$alkyl, $C_1$-$C_4$alkylthio $C_1$-$C_4$alkylsulfinyl $C_1C_4$allyl, $C_1$-$C_4$alkylsulfonyl $C_1$-$C_4$alkyl, $C_3$-$C_6$cycloalkyl, $C_2$-$C_6$alkenyl, $C_2$-$C_6$alkynyl or phenyl, $R^{17}$ is $C_1$-$C_6$alkyl, $C_1$-$C_6$alkoxycarbonyl $C_1$-$C_4$alkyl or $C_1$-$C_6$alkoxycarbonyl, $R^{18}$ is $C_1$-$C_6$alkyl or benzyl, $R^{23}$ is $C_1$-$C_6$alkyl, $C_1$-$C_6$haloalkyl, —C(O)$R^{30}$ or —C(O)OR$^{30}$, $R^{30}$ is $C_1$-$C_6$alkyl, or phenyl, m is an integer of 1 to 3, n is an integer of 0 to 2, and q3 is 0.

3. The isoxazoline compound or the salt thereof according to claim 2, wherein $A^1$ is carbon atom or nitrogen atom, $A^2$ and $A^3$ are carbon atoms, L is —CH$_2$—, —CH(CH$_3$)—, —CH(CF$_3$)— or —CH(CN)—, X is halogen atom, cyano, nitro, —SF$_5$, $C_1$-$C_6$alkyl, $C_1$-$C_6$haloalkyl, hydroxy $C_1$-$C_6$haloalkyl, $C_1$-$C_6$alkoxy $C_1$-$C_6$haloalkyl, $C_3$-$C_8$halocycloalkyl, —OR$^5$, —OSO$_2R^5$ or —S(O)$_nR^5$, when m is 2 or 3, each X may be identical with or different from each other, Y is halogen atom, cyano, nitro, $C_1$-$C_6$alkyl, $C_1$-$C_6$haloalkyl, $C_1$-$C_4$alkyl arbitrarily substituted with $R^4$, $C_3$-$C_6$alkynyl, —OR$^5$, —SR$^5$, —NH$_2$, —N(R$^7$)R$^6$ or —C(S)NH$_2$, $R^1$ is hydrogen atom, —C(O)R$^{1a}$, —C(O)OR$^{1a}$, or —C(O)N(R$^{1b}$)R$^{1a}$, $R^{1a}$ is $C_6$alkyl, $C_1$-$C_6$haloalkyl, $C_1$-$C_4$alkyl substituted with $R^{14}$, $C_3$-$C_6$cycloalkyl, $C_3$-$C_6$halocycloalkyl, E 4, E-5, E-7, $C_2$-$C_6$alkenyl, $C_2$-$C_6$alkenyl, phenyl or phenyl substituted with $(Z)_{p1}$, $R^{1b}$ is hydrogen atom or $C_1$-$C_6$alkyl, $R^2$ is hydrogen atom, $C_1$-$C_6$alkyl, $C_1$-$C_4$alkyl substituted with $R^{14a}$, $C_3$-$C_6$alkynyl, —C(O)R$^{15}$, —C(O)OR$^{15}$ or $C_1$-$C_6$haloalkylthio, $R^3$ is $C_1$-$C_6$haloalkyl or $C_3$-$C_8$halocycloalkyl, $R^4$ is —OH, $C_1$-$C_4$alkoxy or $C_1$-$C_4$alkylthio $R^5$ is $C_1$-$C_6$alkyl, $C_1$-$C_6$haloalkyl or $C_1$-$C_4$haloalkoxy $C_1$-$C_4$haloalkyl, $R^6$ is $C_1$-$C_6$alkyl, —CHO, $C_1$-$C_6$alkylcarbonyl, $C_1$-$C_6$haloalkylcarbonyl, $C_1$-$C_6$alkoxycarbonyl, $C_1$-$C_6$alkylthiocarbonyl, $C_1$-$C_6$alkoxythiocarbonyl, $C_1$-$C_6$alkoxycarbonyl, $C_1$-$C_6$alkylsulfonyl or $C_1$-$C_6$haloalkylsulfonyl, $R^7$ is hydrogen atom or $C_1$-$C_6$alkyl $R^{14}$ is $C_3$-$C_4$cycloalkyl, $C_1$-$C_4$alkoxy or $C_1$-$C_4$alkylthio, $R^{14a}$ is cyano, or —OR$^{23}$, $R^{15}$ is $C_1$-$C_6$alkyl, $C_1$-$C_6$haloalkyl, $C_1$-$C_4$alkoxy $C_1$-$C_4$alkylthio $C_1$-$C_4$alkyl, $C_3$-$C_6$cycloalkyl, or $C_3$-$C_6$alkenyl, and $R^{23}$ is $C_1$-$C_6$alkyl or $C_1$-$C_6$haloalkyl.

4. The isoxazoline compound or the salt thereof according to claim 3, wherein

L is —CH$_2$—, —CH(CH$_3$)— or —CH(CN)—,

X is halogen atom, cyano, nitro, $C_1$-$C_4$alkyl, $C_1$-$C_4$haloalkyl, —OR$^5$ or —S(O)$_nR^5$, when m is 2 or 3, each X may be identical with or different from each other, Y is halogen atom, cyano, nitro, $C_1$-$C_4$alkyl, $C_1$-$C_4$haloalkyl, —OR$^5$, —SR$^5$, —NH$_2$ or —N(R$^7$)R$^6$, $R^1$ is —C(O)R$^{1a}$ or —C(O)NHR$^{1a}$, $R^{1a}$ is $C_1$-$C_4$alkyl, $C_1$-$C_4$haloalkyl, $C_1$-$C_2$alkyl substituted with $R^{14}$, $C_3$-$C_4$cycloalkyl, $C_3$-$C_4$alkynyl, phenyl or phenyl substituted with $(Z)_{p1}$, $R^2$ is hydrogen atom, $C_1$-$C_4$alkyl, $C_1$-$C_2$alkyl substituted with $R^{14a}$, $C_3$-$C_4$alkynyl, $C_1$-$C_4$alkylcarbonyl or $C_1$-$C_4$alkoxycarbonyl, $R^3$ is $C_1$-$C_4$haloalkyl, $R^5$ is $C_1$-$C_4$alkyl or $C_1$-$C_4$haloalkyl, $R^6$ is $C_1$-$C_4$alkyl, —CHO, $C_1$-$C_4$alkylcarbonyl or $C_1$-$C_4$alkoxycarbonyl, $R^{14}$ is $C_3$-$C_4$cycloalkyl or $C_1$-$C_4$alkylthio, $R^{14a}$ is cyano or —OR$^{23}$, and $R^{23}$ is $C_1$-$C_4$alkyl, and n is an integer of 0 or 1.

5. The isoxazoline compound or the salt thereof according to claim 4, wherein $A^1$ is carbon atom, X is halogen atom or $C_1$-$C_4$haloalkyl, when m is 2 or 3, each X may be identical with or different from each other, Y is halogen atom, $C_1$-$C_4$alkyl or $C_1$-$C_4$haloalkyl, $R^1$ is —C(O)R$^{1a}$, $R^{1a}$ is $C_1$-$C_4$alkyl, $C_1$-$C_4$haloalkyl, or $C_3$, $R^2$ is hydrogen atom, and $R^3$ is —CF$_3$ or —CF$_2$Cl.

6. A pesticide containing as an active ingredient one or more selected from the isoxazoline compound and the salt thereof according to claim 1.

7. An agrochemical containing as an active ingredient one or more selected from the isoxazoline compound and the salt thereof according to claim 1.

8. An endo- or ecto-parasiticide for mammals or birds containing as an active ingredient one or more selected from the isoxazoline compound and the salt thereof according to claim 1.

9. An insecticide or acaricide containing as an active ingredient one or more selected from the isoxazoline compound and the salt thereof according to claim 1.

* * * * *

UNITED STATES PATENT AND TRADEMARK OFFICE
CERTIFICATE OF CORRECTION

PATENT NO. : 7,947,715 B2
APPLICATION NO. : 12/230780
DATED : May 24, 2011
INVENTOR(S) : Takeshi Mita et al.

It is certified that error appears in the above-identified patent and that said Letters Patent is hereby corrected as shown below:

Claim 1, Column 385, Line 45,
Delete "M-5, M-20, M-48,"

Claim 1, Column 397, Line 45 to Column 402, Line 15,
Delete chemical formulae M-1 to M-48

Claim 2, Column 404, Line 57,
Delete "cyano,"

Claim 2, Column 405, Line 30,
Delete "cyano,"

Signed and Sealed this
Sixteenth Day of August, 2011

David J. Kappos
*Director of the United States Patent and Trademark Office*